US012297207B2

(12) United States Patent
Nittoli

(10) Patent No.: US 12,297,207 B2
(45) Date of Patent: May 13, 2025

(54) MAYTANSINOID DERIVATIVES, CONJUGATES THEREOF, AND METHODS OF USE

(71) Applicant: Regeneron Pharmaceuticals, Inc., Tarrytown, NY (US)

(72) Inventor: Thomas Nittoli, Pearl River, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/528,144

(22) Filed: Nov. 16, 2021

(65) Prior Publication Data

US 2022/0259225 A1  Aug. 18, 2022

Related U.S. Application Data

(63) Continuation of application No. 16/712,941, filed on Dec. 12, 2019, now abandoned, which is a continuation of application No. 15/081,759, filed on Mar. 25, 2016, now abandoned.

(60) Provisional application No. 62/252,239, filed on Nov. 6, 2015, provisional application No. 62/139,044, filed on Mar. 27, 2015.

(51) Int. Cl.
*A61K 47/68* (2017.01)
*C07D 498/18* (2006.01)

(52) U.S. Cl.
CPC ...... *C07D 498/18* (2013.01); *A61K 47/68033* (2023.08); *A61K 47/6849* (2017.08); *A61K 47/6889* (2017.08)

(58) Field of Classification Search
None
See application file for complete search history.

(56) References Cited

U.S. PATENT DOCUMENTS

| | | | |
|---|---|---|---|
| 4,260,608 A | 4/1981 | Miyashita et al. |
| 4,361,650 A | 11/1982 | Asai et al. |
| 5,208,020 A | 5/1993 | Chari et al. |
| 5,714,586 A | 2/1998 | Kunstmann et al. |
| 6,596,541 B2 | 7/2003 | Murphy et al. |
| 7,595,292 B2 | 9/2009 | Brocchini et al. |
| 7,750,116 B1 | 7/2010 | Doronina et al. |
| 7,939,630 B2 | 5/2011 | Brocchini et al. |
| 8,816,051 B2 | 8/2014 | Brocchini et al. |
| 8,877,706 B2 | 11/2014 | Li et al. |
| 8,889,855 B2 | 11/2014 | Deng |
| 9,005,598 B2 | 4/2015 | Godwin et al. |
| 9,950,076 B2 | 4/2018 | Nittoli et al. |
| 9,951,141 B2 | 4/2018 | Nittoli et al. |
| 10,463,749 B2 | 11/2019 | Nittoli et al. |
| 10,772,972 B2 | 9/2020 | Rudge et al. |
| 2004/0235840 A1 | 11/2004 | Chari et al. |
| 2005/0169933 A1 | 8/2005 | Steeves et al. |
| 2007/0258987 A1 | 11/2007 | Francisco et al. |
| 2008/0171040 A1 | 7/2008 | Ebens et al. |
| 2008/0305044 A1 | 12/2008 | McDonagh et al. |
| 2008/0305497 A1 | 12/2008 | Kosmeder et al. |
| 2009/0068178 A1 | 3/2009 | Crowley et al. |
| 2009/0280056 A1 | 11/2009 | Dennis et al. |
| 2010/0129314 A1 | 5/2010 | Singh et al. |
| 2011/0250133 A1 | 10/2011 | Lattuada et al. |
| 2012/0058892 A1 | 3/2012 | Braun et al. |
| 2012/0096572 A1 | 4/2012 | Macdonald et al. |
| 2012/0276124 A1 | 11/2012 | Bouchard et al. |
| 2013/0029900 A1 | 1/2013 | Widdison |
| 2013/0039900 A1 | 2/2013 | Sunahara et al. |
| 2013/0101546 A1 | 4/2013 | Yurkovetskiy et al. |
| 2014/0178415 A1 | 6/2014 | Li et al. |
| 2014/0179917 A1 | 6/2014 | Deng |
| 2014/0363454 A1 | 12/2014 | Jackson et al. |
| 2014/0369960 A1 | 12/2014 | Brocchini et al. |
| 2015/0056222 A1 | 2/2015 | Papadopoulos et al. |
| 2015/0125473 A1 | 5/2015 | Burt et al. |
| 2015/0157736 A1 | 6/2015 | Rabuka et al. |
| 2015/0216994 A1 | 8/2015 | Godwin et al. |
| 2015/0283259 A1 | 10/2015 | Buet et al. |
| 2016/0058882 A1 | 3/2016 | Chari et al. |
| 2016/0354482 A1 | 12/2016 | Nittoli et al. |
| 2016/0375147 A1 | 12/2016 | Nittoli |
| 2017/0121413 A1 | 5/2017 | Nittoli et al. |
| 2017/0209591 A1 | 7/2017 | Nittoli et al. |
| 2018/0289834 A1 | 10/2018 | Nittoli et al. |
| 2018/0312597 A1 | 11/2018 | Nittoli et al. |
| 2019/0151323 A1 | 5/2019 | Nittoli et al. |
| 2020/0121806 A1 | 4/2020 | Nittoli et al. |
| 2021/0087272 A1 | 3/2021 | Kuhnert et al. |

FOREIGN PATENT DOCUMENTS

| | | |
|---|---|---|
| CN | 103 254 311 A | 8/2013 |
| EP | 0 425 235 A2 | 5/1991 |
| WO | WO 02/094325 A2 | 11/2002 |

(Continued)

OTHER PUBLICATIONS

Reynolds, Fred et al; "A functional proteomic method for biomarker discovery." PLoS One (2011) 6(7) e22471.*
Lowe, Derek; "Not alphafold's fault." Blog "In the Pipeline," entry of Sep. 7, 2022.*
International Search Report and Written Opinion in PCT/US2014/052757, mailed Nov. 28, 2014, 13 pages.
International Search Report and Written Opinion in PCT/US2015/033618 mailed Dec. 21, 2015, 20 pages.
International Search Report and Written Opinion of PCT/US2014/029757 mailed Aug. 28, 2014, 13 pages.
International Search Report and Written Opinion of PCT/US2017/014782 mailed Mar. 20, 2017, 13 pages.

(Continued)

*Primary Examiner* — Fred H Reynolds
(74) *Attorney, Agent, or Firm* — SQUIRE PATTON BOGGS (US)

(57) ABSTRACT

Provided herein are maytansinoid derivatives, conjugates thereof, and methods of treating or preventing proliferative diseases with the same.

8 Claims, 47 Drawing Sheets

(56) References Cited

FOREIGN PATENT DOCUMENTS

| WO | WO 2005/010151 A2 | 2/2005 |
|---|---|---|
| WO | WO 2005/089808 | 9/2005 |
| WO | WO 2006/062779 A2 | 6/2006 |
| WO | WO 2008/122039 | 10/2008 |
| WO | WO 2008/141044 A2 | 11/2008 |
| WO | WO 2009/117277 A2 | 9/2009 |
| WO | WO 2010/010324 | 1/2010 |
| WO | WO 2010/126551 A1 | 11/2010 |
| WO | WO 2011/018611 | 2/2011 |
| WO | WO 2011/039724 A1 | 4/2011 |
| WO | WO 2011/130598 | 10/2011 |
| WO | WO 2012/005982 | 1/2012 |
| WO | WO 2012/058592 A2 | 5/2012 |
| WO | WO 2012/061590 A1 | 5/2012 |
| WO | WO 2012/156918 A1 | 11/2012 |
| WO | WO 2012/166559 | 12/2012 |
| WO | WO 2012/177837 A2 | 12/2012 |
| WO | WO 2013/053872 | 4/2013 |
| WO | WO 2013/053873 | 4/2013 |
| WO | WO 2013/055990 | 4/2013 |
| WO | WO 2013/055993 | 4/2013 |
| WO | WO 2013/068874 | 5/2013 |
| WO | WO 2013/085925 A1 | 6/2013 |
| WO | WO 2013/190272 A1 | 12/2013 |
| WO | WO 2013/190292 A2 | 12/2013 |
| WO | WO 2014/064424 A1 | 5/2014 |
| WO | WO 2014/065661 | 5/2014 |
| WO | WO 2014/080251 | 5/2014 |
| WO | WO 2014/089335 A2 | 6/2014 |
| WO | WO 2014/145090 A1 | 9/2014 |
| WO | WO 2014/194030 A2 | 12/2014 |
| WO | WO 2014/197849 A2 | 12/2014 |
| WO | WO 2014/197854 A1 | 12/2014 |
| WO | WO 2014/197866 A1 | 12/2014 |
| WO | WO 2015/081281 A1 | 6/2015 |
| WO | WO 2015/081282 A1 | 6/2015 |
| WO | WO 2015/081857 | 6/2015 |

OTHER PUBLICATIONS

Invitation together with the Search Report and Written Opinion issued by the Singapore Patent office mailed on Aug. 10, 2016 for the Singapore patent application No. 11201507481W; 11 pages.

Agarwal et al., "A Pictet-Spengler ligation for Protein Chemical Modification", Proc. Natl Acad. Sci., Jan. 2, 2013, vol. 110, No. 1, pp. 46-51.

Akcakanat et al. "Heterogeneous expression of GAGE, NY-ES0-.1, MAGE-A and SSX proteins in esophageal cancer: Implications for immunotherapy", Int. J. Cancer, 2006, vol. 118, pp. 123-128.

Badescu et al., "Bridging Disulfides for Stable and Defined Antibody Drug Conjugates", Bioconjugate Chemistry, May 3, 2014, vol. 25, No. 6, pp. 1124-1136, XP055165403.

Badescu, George: Director Scientific Affairs—Bioconjugation & Protein Engineering, "Producing Better ADCs Using ThioBridge™ Conjugation", ABZENA-Enabling better biopharmaceuticals, World ADC Summit of Oct. 27, 2014, San Diego, 29 pages.

Brocchini Steve et al., "PEGylation of native disulfide bonds in proteins", Nature Protocols, 2006, vol. 1, No. 5, pp. 2241-2252.

Carrico et al., Introducing Genetically Encoded Aldehydes into Proteins, Nature Chemical Biology, Jun. 2007, vol. 3, No. 6, pp. 321-322.

Davis et al., "In Vitro Characterization of the Drug-Drug Interaction Potential of Catabolites of Antibody-Maytansinoid Conjugates", Drug Metabolism And Disposition, Jun. 2012, vol. 40, No. 10, pp. 1927-1934.

Del Rosario et al., "Sulfhydryl Site-Specific Cross-Linking and Labeling of Monoclonal Antibodies by a Fluorescent Equilibrium Transfer Alkylation Cross-Link Reagent", Bioconjugate Chemistry, 1990, vol. 1, No. 1, pp. 51-59.

Dennler et al., "Transglutaminase-Based Chemo-Enzymatic Conjugation Approach Yields Homogeneous Antibody-Drug Conjugates", Bioconjugate Chemistry, 2014, vol. 25, pp. 569-578.

Doronina et al, "Development of potent monoclonal antibody aurostatin conjugates for cancer therapy." Nat. Biotech., 2003, vol. 21, No. 7, pp. 778-785.

Doronina et al., "Enhanced Activity of Monomethylauristatin F through Monoclonal Antibody Delivery: Effects of Linker Technology on Efficacy and Toxicity", Bioconjugate Chem. 2006, vol. 17, pp. 114-124.

Dubowchik et al, "Cathepsin b-labile dipeptide linkers for lysosomal release of doxorubicin from internalizing immunoconjugates: model studies of enzymatic drug release and antigen specific in vitro anticancer activity." Bioconjugate Chem., (2002) vol. 13, pp. 855-869.

Erickson, et al., "Antibody-maytansinoid conjugates are activated in targeted cancer cells by lysosomal degradation and linker-dependent intracellular processing", Cancer Research, American Association For Cancer Research, US, Apr. 15, 2006, vol. 66, No. 8, pp. 4426-4433.

Fishkin et al: "A novel pathway for maytansinoid release from thioether linked antibody-drug conjugates (ADCs) under oxidative conditions"; Chemical Communications; Jan. 1, 2011; vol. 47, No. 38, p. 10752; XP055152687.

Gondi et al., "Cathepsin B as a cancer target", Expert Opinion on Therapeutic Targets, 2013, vol. 17, No. 3, pp. 281-291 DOI: 10.1517/14728222.2013.740461.

Hofer et al., "An Engineered Selenocysteine Defines a Unique Class of Antibody Derivatives", Proc. Natl. Acad. Sci., Aug. 26, 2008, vol. 105, No. 34, pp. 12451-12456.

Hollander et al., Selection of Reaction Additives Used in the Preparation of Monomeric Antibody-Calicheamicin Conjugates, Bioconjugate Chemistry, 2008, vol. 19, pp. 358-361.

Kawai et al., "Chemical Modification Of Ansamitocins 3. Synthesis And Biological Effects Of 3 Acyl Esters of Maytansinol", Chemical And Pharmaceutical Bulletin, Pharmaceutical Society of Japan, vol. 32, No. 9, Jan. 1, 1984, pp. 3441-3451, XP008094318.

Phillips et al., "Targeting HER2-Positive Breast Cancer with Trastuzumab-DM1, an Antibody-Cytotoxic Drug Conjugate", Cancer Research, 2008, No. 62, pp. 9280-9290. http://cancerres.aacrjournals.org/content/68/22/9280.full-text.pdf.

Pillow et al.; "Site-Specific Trastuzumab Maytansinoid Antibody-Drug Conjugates with Improved Therapeutic Activity through Linker and Antibody Engineering", Journal Of Medicinal Chemistry, Oct. 9, 2014, vol. 57, No. 19, pp. 7890-7899, XP055268691.

Rabuka et al., "Site-Specific Chemical Protein Conjugation Using Genetically Encoded Aldehyde Tags", Nat Protocols, Dec. 1, 2012, vol. 7, No. 6, pp. 1052-1067.

Reddy et al., "Folate Receptor-Specific Antitumor Activity of EC131, a Folate-Maytansinoid Conjugate", Cancer Research, Jul. 1, 2007; vol. 67, No. 13; pp. 6376-6382.

Ryan et al., "Polyclonal Antibody Production Against Chito-Oligosaccharides", Food and Agricultural Immunology, 2001, vol. 13, pp. 127-130.

S. C. Jeffrey et al., Dipeptide-Based Highly Potent Doxorubicin Antibody Conjugates, Bioorganic & Medicinal Chemistry Letters, 2006, vol. 16, pp. 358-362.

Salomon et al.; "Sensitive ELISA Method for the Measurement of Catabolites of Antibody-Drug Conjugates (ADCs) in Target Cancer Cells", Molecular Pharmaceutics, Jun. 1, 2015, vol. 12, No. 6, pp. 1752-1761, XP055352192.

Sapra et al., "Monoclonal antibody-based therapies in cancer: Advances and Challenges", Pharmacology & Therapeutics, 2013, vol. 138, pp. 452-469.

Satyanarayanajois et al., "Medicinal chemistry for 2020", Fut. Med. Chem., (Oct. 2011), vol. 3, No. 14, pp. 1765-1786.

Shaunak et al., "Site-specific PEGylation of Native Disulfide Bonds in Therapeutic Proteins", Nature Chemical Biology, Jun. 2006, vol. 2, No. 6, pp. 312-313.

Sun et al., "Design of Antibody-Maytansinoid Conjugates Allows for Efficient Detoxification via Liver Metabolism", Bioconjugate Chemistry; Apr. 20, 2011; vol. 22, No. 4, pp. 728-735, XP055096244.

Trail, "Antibody Drug Conjugates as Cancer Therapeutics", Antibodies, 2013, vol. 2, pp. 113-129; doi:10.3390/antib2010113.

(56) References Cited

OTHER PUBLICATIONS

Widdison et al., "Semisynthetic Maytansine Analogues for the Targeted Treatment of Cancer"; Journal Of Medicinal Chemistry, American Chemical Society, US; Jul. 13, 2006; vol. 49, No. 14; pp. 4392-4408, XP002679529.

Widdison et al., "Development of Anilino-Maytansinoid ADCs that Efficiently Release Cytotoxic Metabolites in Cancer Cells and Induce High Levels of Bystander Killing", Bioconjugate Chemistry 2015, together with Supporting Information Section, 2015, pp. 1-17, Epub ahead of print Sep. 30, 2015.

Wolf Philipp, "Anti-psma antibody-drug conjugates and immunotoxins", Chapter 15 of Antibody-drug conjugates and immunotoxins (2012) Gail Phillips (ed), *ISBN* 978-1-4614-5456-4.

Zhao et al., "Synthesis and Evaluation of Hydrophilic Linkers for Antibody-Maytansinoid Conjugates", Journal of Medicinal Chemistry; May 26, 2011; vol. 54; No. 10; pp. 3606-3623; XP55046274.

Auclair et al. "Strategies for stabilizing superoxide dismutase (SOD1), the protein destabilized in the most common form of familial amyotrophic lateral sclerosis", PNAS, Dec. 14, 2010, vol. 107, No. 50, pp. 21394-21399; www.pnas.org/cgi/doi/10.1073/pnas.1015463107.

Grumbach et al., "Hydrophilic Interaction Chromatography Using Silica Columns for the Retention of Polar Analytes and Enhanced ESI-S Sensitivity", LCGC, North America 2004, An Advanstar Publication, ID No. 7200001048EN.

Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide", Eur. J. Biochem., vol. 101, 1979, pp. 395-399.

Appeal 2021-002841 for U.S. Appl. No. 16/011,118 dated Sep. 15, 2022; 18 pages.

Tang et al., "The Analysis of Key Factors Related to ADCs Structural Design", Apr. 2019, vol. 10, Article 373, doi: 10.3389/fphar.2019.00373.

Nittoli et al., "Antibody drug conjugates of cleavable amino-benzoyl-maytansinoids", Bioorganic & Medicinal Chemistry, vol. 28, 2020, 115785; 5 pages.

\* cited by examiner

MAYTANSINOID DERIVATIVES, CONJUGATES THEREOF, AND METHODS OF USE

US NONPROVISIONAL PATENT APPLICATION

This application claims priority to, and the benefit of, U.S. Provisional Patent Application No. 62/139,044, entitled MAYTANSINOID DERIVATIVES, CONJUGATES THEREOF AND METHODS OF TREATING PROLIFERATIVE DISEASES USING THE SAME, which was filed Mar. 27, 2015, and also claims priority to, and the benefit of U.S. Provisional Patent Application No. 62/252,239, entitled MAYTANSINOID DERIVATIVES, CONJUGATES THEREOF AND METHODS OF TREATING PROLIFERATIVE DISEASES USING THE SAME, which was filed Nov. 6, 2015. The contents of each of these provisional patent applications are herein incorporated by reference in their entirety for all purposes.

FIELD

The present disclosure concerns maytansinoid derivatives, conjugates thereof, and methods of treating or preventing proliferative diseases with the same.

BACKGROUND

Proliferative diseases, for example cancer, are characterized by the uncontrolled growth of abnormal cells. Current treatments of proliferative diseases include surgery, radiation, chemotherapy, hormone-based therapy and/or immunotherapy. A number of these treatments, particularly chemotherapy, utilize anti-proliferative drugs that limit the spread of the abnormal cells. However, these drugs are typically indiscriminate in their ability to kill cells, affecting both normal and abnormal cells. To address this problem, various approaches to targeted drug delivery have been explored, including the use of conjugates of tumor-targeted probes (such as antibodies or growth factors) with toxins, to selectively target abnormal cells. Antibody drug conjugates (ADCs) are compounds composed of an antibody that is linked, via a chemical linker, to a cytotoxic agent. Such compounds leverage the antibody's binding specificity for its target to deliver a cytotoxic agent to an abnormal cell. Thus, there is a need for anti-proliferative compounds and their conjugates.

SUMMARY

Provided herein are compounds of Formula (I):

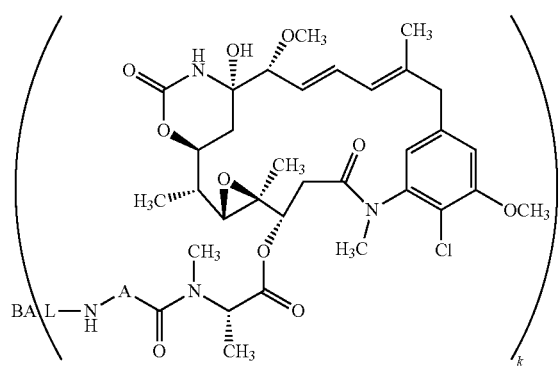

(I)

or a pharmaceutically acceptable salt thereof, wherein:

A is arylene or heteroarylene;

L is a linker;

BA is a binding agent; and k is an integer from 1 to 30. Also provided herein are stereoisomers of compounds of Formula (I).

Provided herein are also compounds of Formula (II):

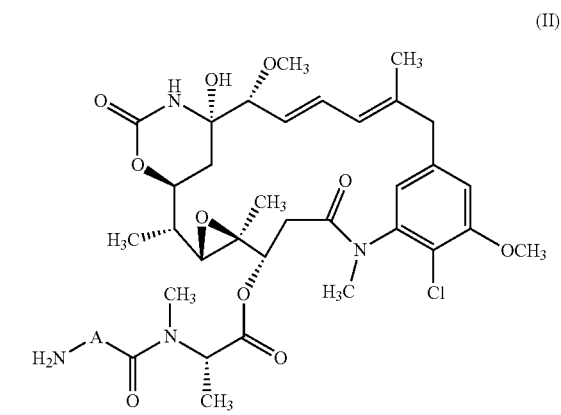

(II)

or a pharmaceutically acceptable salt thereof, wherein A is arylene or heteroarylene. Also provided herein are stereoisomers of compounds of Formula (II).

Provided herein are also compounds of Formula PP5:

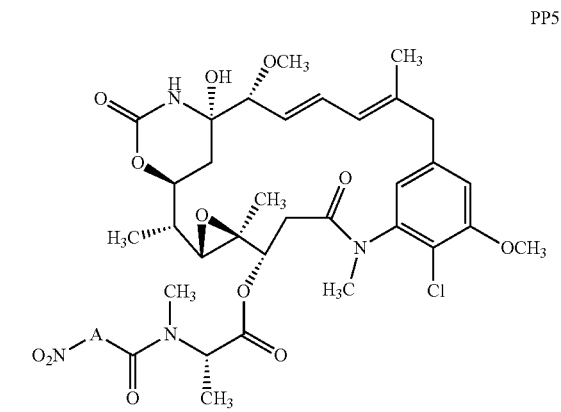

PP5 or a salt thereof, wherein A is arylene or heteroarylene. Also provided herein are stereoisomers of compounds of Formula PP5.

Provided herein are also compounds of Formula PT1:

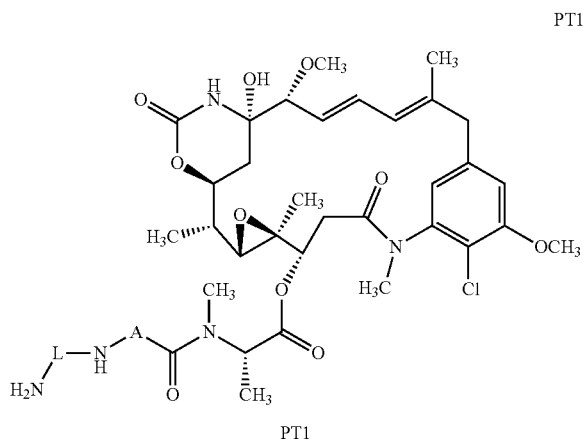

PT1 or a salt thereof, wherein A is arylene or heteroarylene and L is a linker. Also provided herein are stereoisomers of compounds of Formula PT1.

Furthermore, provided herein are methods of treating proliferative diseases comprising administering the compounds described herein.

Furthermore, provided herein are methods of treating proliferative diseases comprising administering the conjugates described herein.

Furthermore, provided herein are of methods of preparing compounds of Formula (I) comprising reacting a deglycosylated antibody or aglycosylated antibody with a compound of Formula (PT1) in the presence of transglutaminase.

BRIEF DESCRIPTIONS OF THE DRAWINGS

DETAILED DESCRIPTION

A. Definitions

Figure 1:
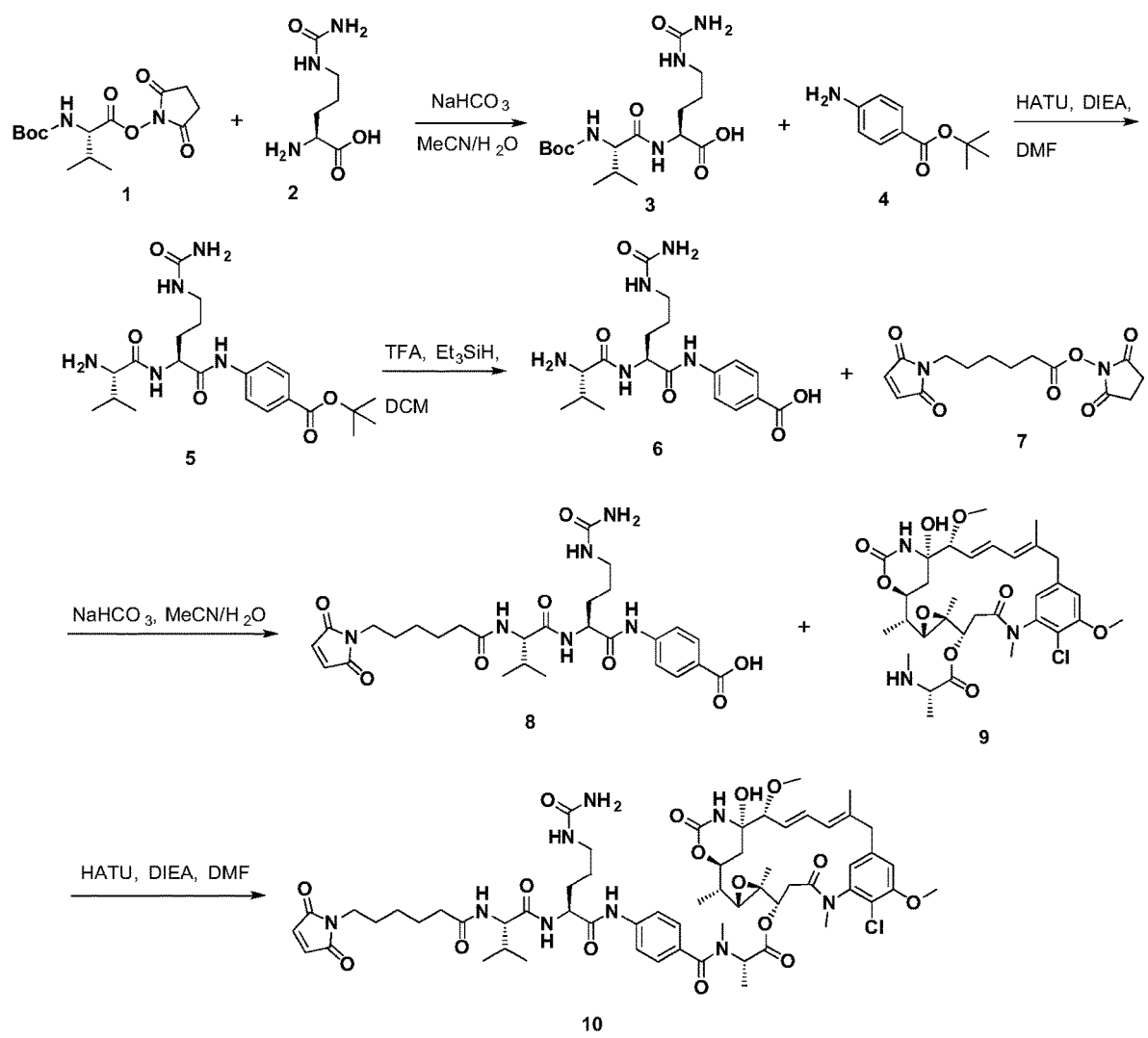
FIG. 1 depicts a synthetic sequence for preparing maytansin-N-methyl-L-alanine-4-aminobenzamido-citrulline-valine-caprolyl-6-maleimidyl.
Figure 2:
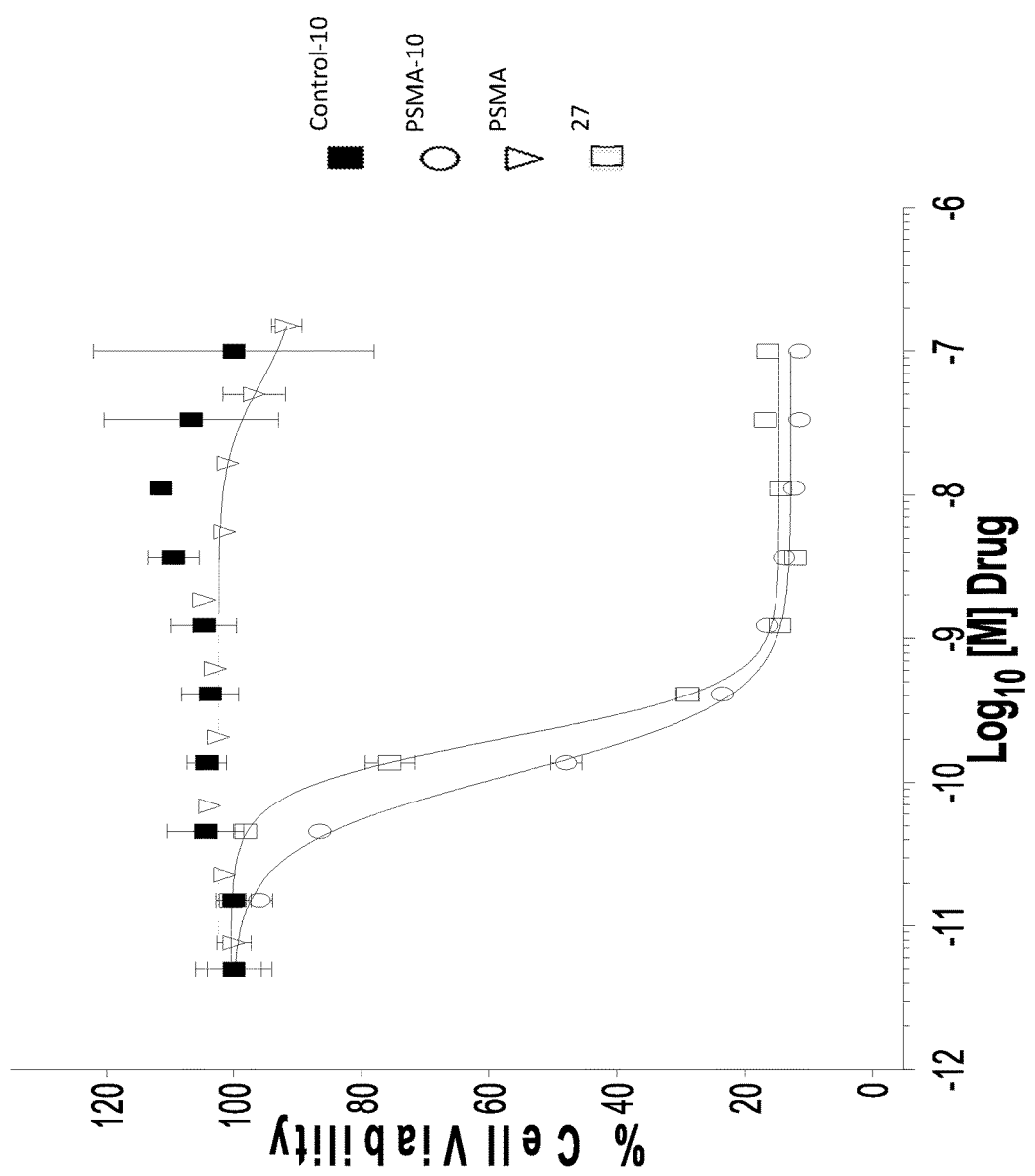
FIG. 2 depicts the plot of % Cell Viability vs. $\log_{10}$ [M] of certain compounds tested in EXAMPLE 41.
Figure 3:
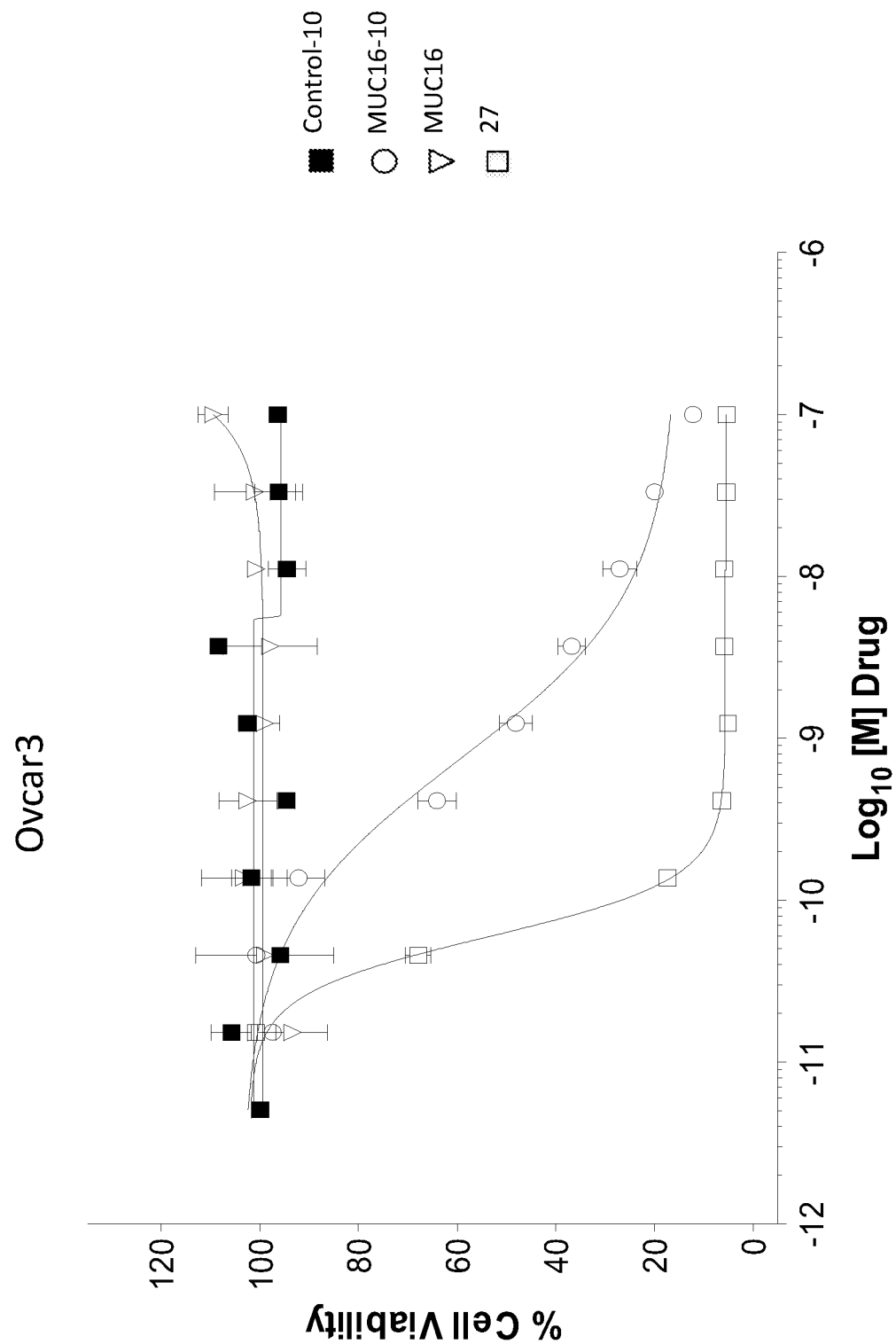
FIG. 3 depicts the plot of % Cell Viability vs. $\log_{10}$ [M] of certain compounds tested in EXAMPLE 41.
Figure 4:
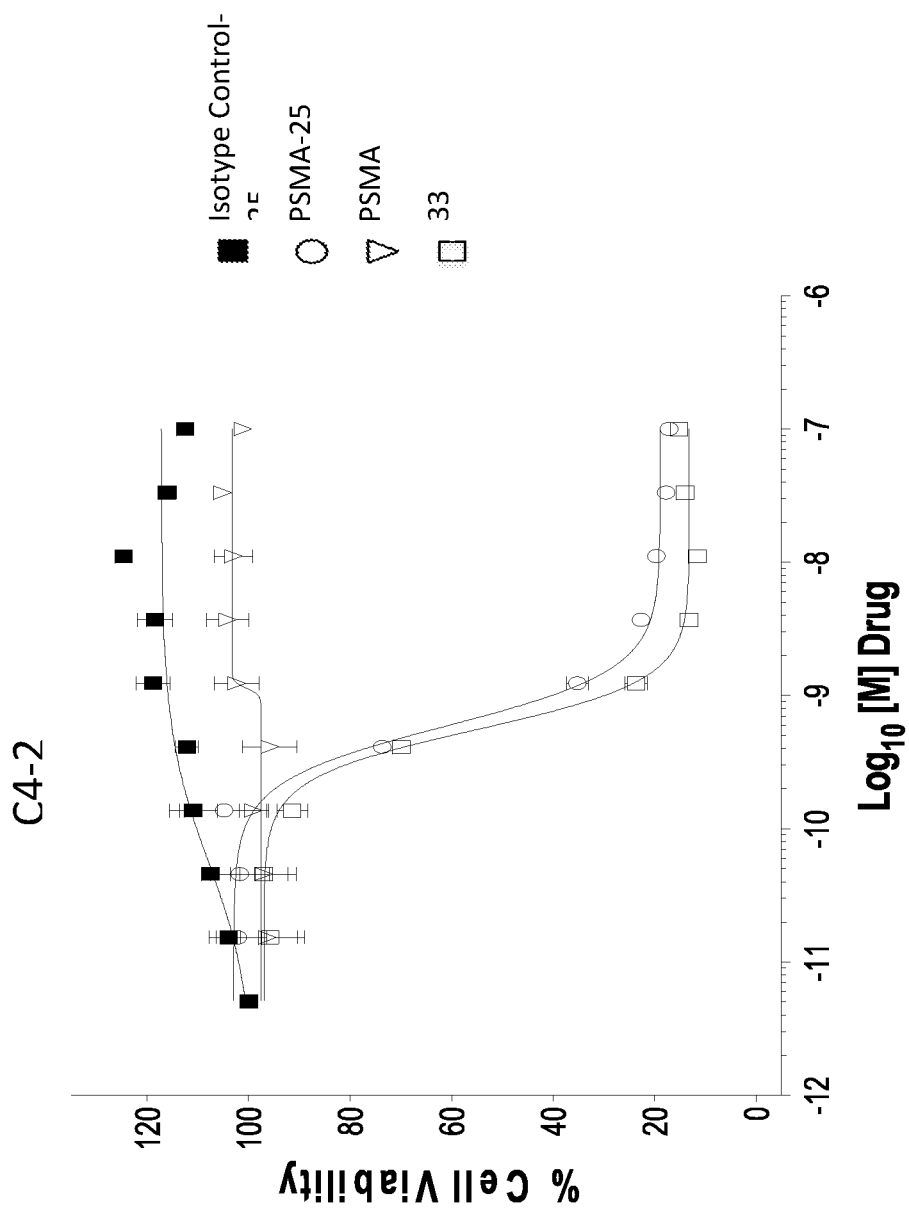
FIG. 4 depicts the plot of % Cell Viability vs. $\log_{10}$ [M] of certain compounds tested in EXAMPLE 41.
Figure 5:
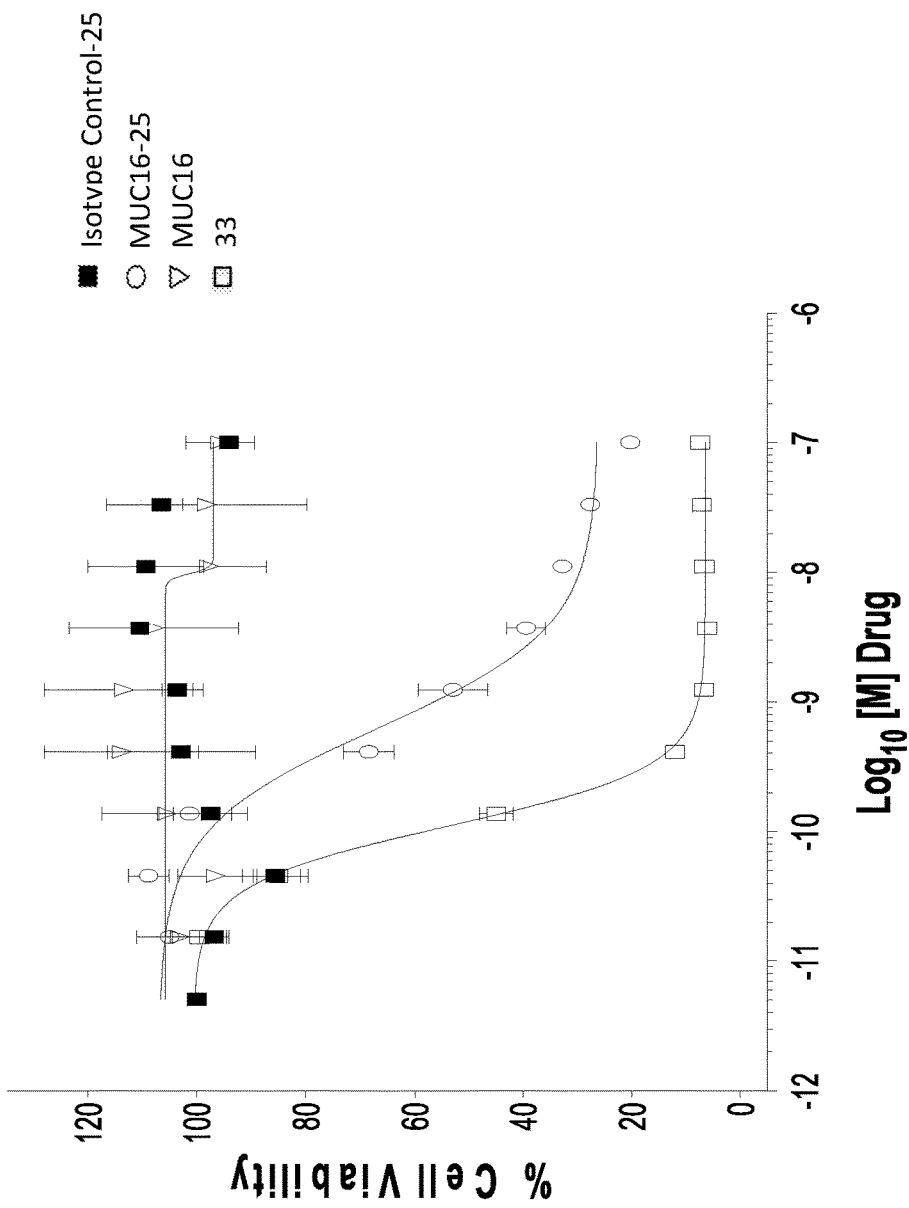
FIG. 5 depicts the plot of % Cell Viability vs. $\log_{10}$ [M] of certain compounds tested in EXAMPLE 41.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl.

As used herein, "haloalkyl" refers to alkyl, as defined above, wherein the alkyl includes at least one substituent selected from a halogen, e.g., F, Cl, Br, or I.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—$O^-$ for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are limited to phenyl, naphthyl, fluorenyl, azulenyl, anthryl, phenanthryl, and pyrenyl.

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of aryl moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "alkaryl" refers to an aryl that is substituted with at least one alkyl. Alkaryl is optionally substituted.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkenyl in which one or more carbon atoms are replaced by heteroatoms. Suitable heteroatoms include, but are not limited to, nitrogen, oxygen, and sulfur atoms. Heteroalkyl is optionally substituted. Examples of heteroalkyl moieties include, but are not limited to, aminoalkyl, sulfonylalkyl, sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to an arylene in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "optionally substituted," when used to describe a radical moiety, e.g., optionally substituted alkyl, means that such moiety is optionally bonded to one or more substituents. Examples of such substituents include, but are not limited to halo, cyano, nitro, haloalkyl, azido, epoxy, optionally substituted heteroaryl, optionally substituted heterocycloalkyl,

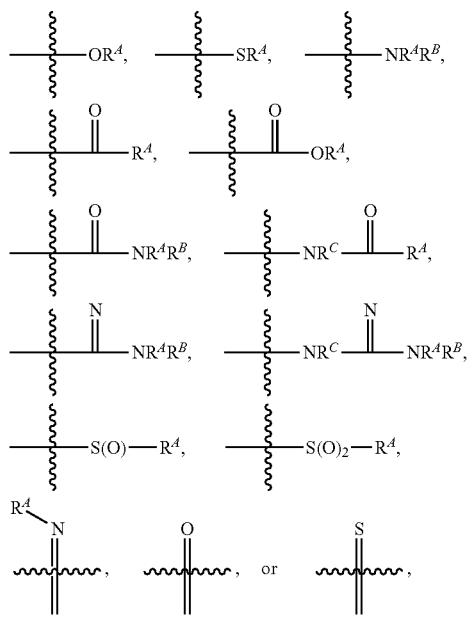

wherein $R^A$, $R^B$, and $R^C$ are, independently at each occurrence, a hydrogen atom, alkyl, alkenyl, alkynyl, aryl, alkaryl, aralkyl, heteroalkyl, heteroaryl, or heterocycloalkyl, or $R^A$ and $R^B$, together with the atoms to which they are bonded, form a saturated or unsaturated carbocyclic ring, wherein the ring is optionally substituted and wherein one or more ring atoms is optionally replaced with a heteroatom. In some embodiments, $R^A$, $R^B$, and $R^C$ are not hydrogen atoms. In some examples, $R^A$ is methyl. In some examples, $R^A$ is methylamino, methylsulfonyl, and methylsulfinyl. In some examples, $R^A$ is methylamino. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "binding agent" refers to any molecule capable of binding with specificity to a given binding partner.

As used herein, "linker" refers to a divalent moiety that covalently links the binding agent to the maytansinoid derivatives described herein.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refers to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b]pyridinium 3-oxid hexafluorophosphate (HATU), 2-Ethoxy-1-ethoxycarbonyl-1,2-dihydroquinoline (EEDQ), 1-Ethyl-3-(3-dimethylaminopropyl)carbodiimide (EDC), 2-Chloro-1,3-dimethylimidazolidinium hexafluorophosphate (CIP), 2-chloro-4,6-dimethoxy-1,3,5-triazine (CDMT), and carbonyldiimidazole (CDI). In some examples, a carboxylic acid is first converted to an activated carboxylic ester before reacting with an amine to form an amide bond. In certain embodiments, the carboxylic acid is reacted with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. For certain carboxylic acids, this activated ester is more susceptible subsequently to nucleophilic attack by an amine than the carboxylic acid is before it is converted. This results in amide bond formation. As such, the carboxylic acid is described as activated. Exemplary reagents include DCC and DIC.

As used herein, "therapeutically effective amount" refers to an amount (of a compound) that is sufficient to provide a therapeutic benefit to a patient in the treatment or management of a disease or disorder, or to delay or minimize one or more symptoms associated with the disease or disorder.

Certain groups, moieties, substituents, and atoms are depicted with a wiggly line that intersects a bond or bonds to indicate the atom through which the groups, moieties, substituents, atoms are bonded. For example, a phenyl group that is substituted with a propyl group depicted as:

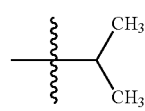

has the following structure:

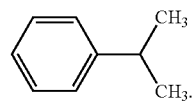

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group, wherein subscript q is an integer from 0 to 4 and in which the positions of substituent $R^1$ are described generically, includes the following groups in which the positions of substituent $R^1$ are described specifically:

-continued

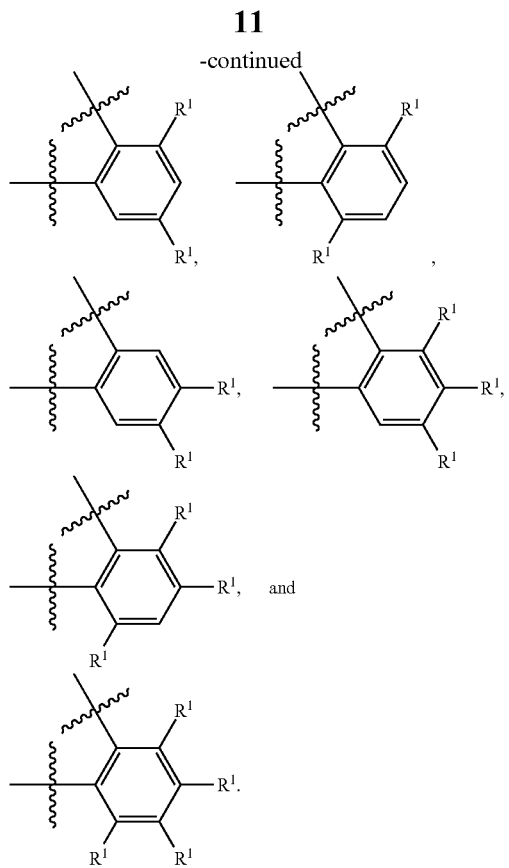

In addition and for example, the group,

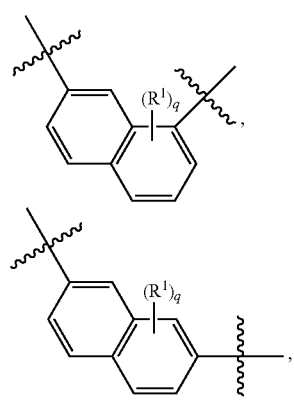

in which the positions of substituents other than R¹ which are bonded to the cyclic group through a bond between ring atoms are described generically, includes the following groups in which the positions of these substituents other than R¹ are described specifically:

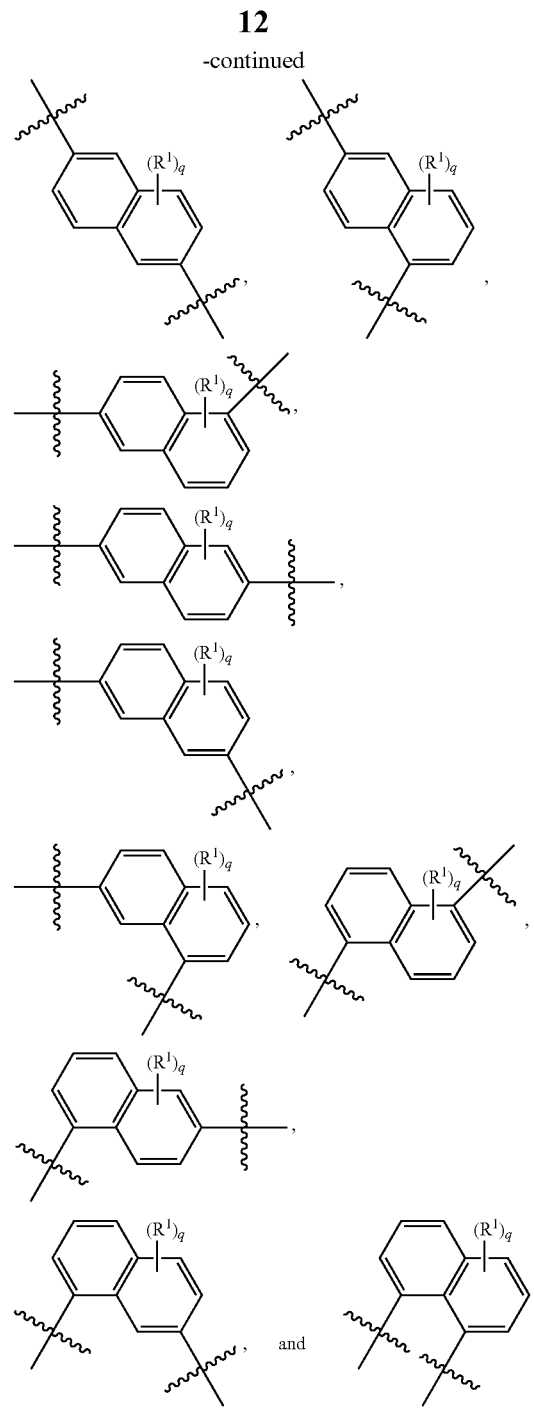

Also, for example, the group, in which the positions of substituents other than R¹ which are bonded to the cyclic group through a bond between ring atoms are described generically, includes the following groups in which the positions of these substituents other than $R^1$ are described specifically:

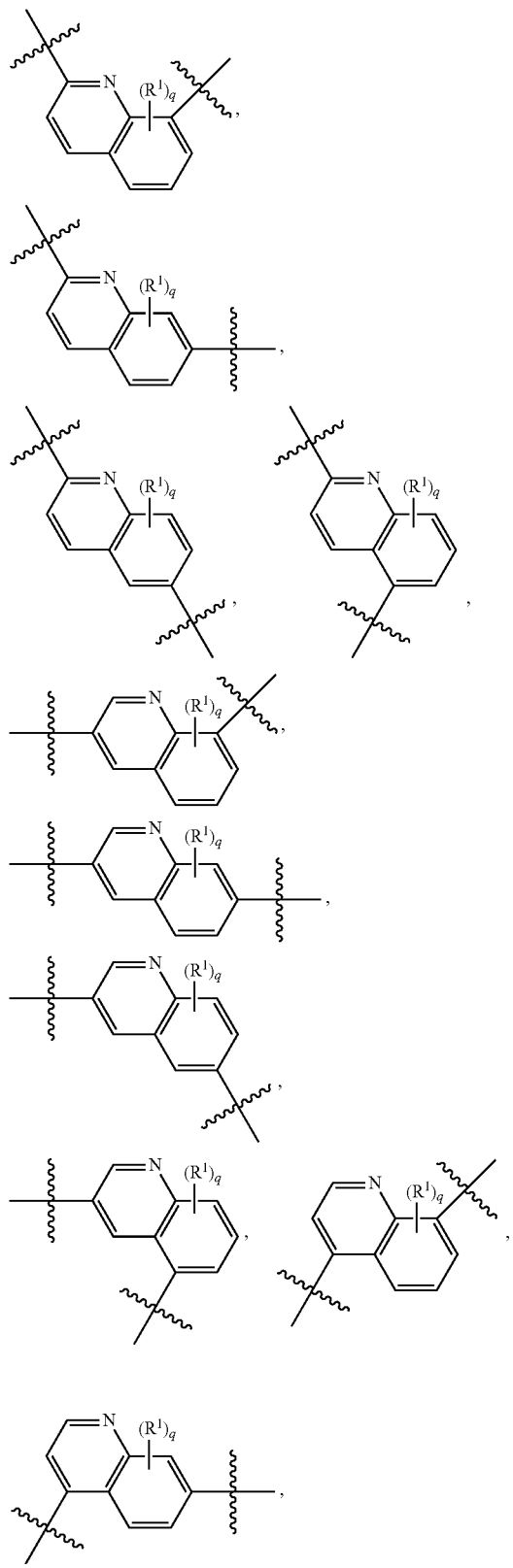

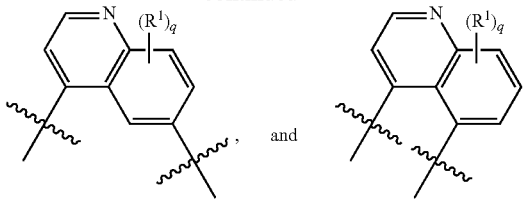

In each of these structures in which the positions of the substituents other than $R^1$ are described specifically, the substituent $R^1$ may be bonded to any ring position in the cyclic group or on any ring in the fused ring group which is not occupied by one of these substituents other than $R^1$. The following non-limiting representative illustrations indicate that the cyclic group can be substituted with the indicated substituent at any ring position or on either ring in the fused ring group:

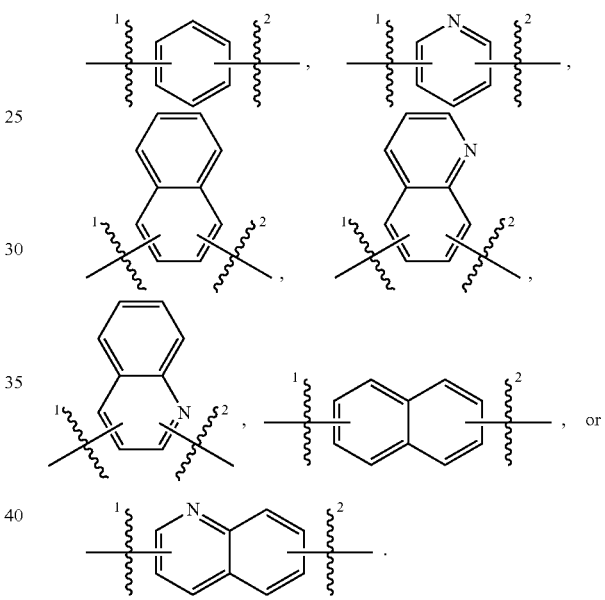

B. Conjugates

Provided herein are compounds of Formula (I):

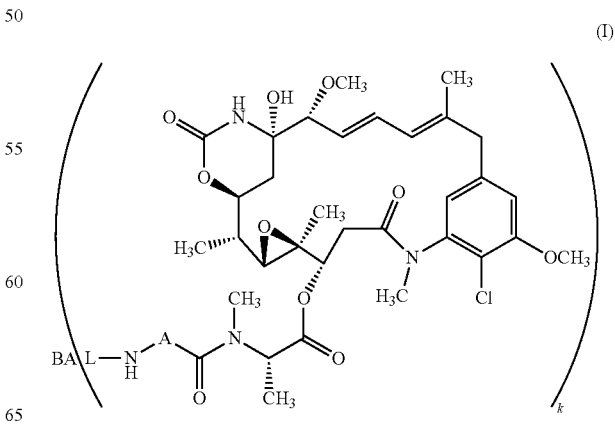

or a pharmaceutically acceptable salt thereof, wherein:
A is arylene or heteroarylene;
L is a linker;
BA is a binding agent; and
k is an integer from 1 to 30.

1. "A" Moieties

In some embodiments, A is arylene. In some embodiments, A is heteroarylene. In some embodiments, the arylene or heteroarylene is substituted with one or more electron withdrawing groups and/or one or more electron donating groups.

In some embodiments, A is a divalent radical of benzene, of pyridine, of naphthalene, or of quinolone, which are optionally substituted.

In some embodiments, A is a divalent radical of benzene which is optionally substituted with a member selected from the group consisting of amino, amido, alkyl, halo, haloalkyl, alkoxy, and haloalkoxy.

In some embodiments, A is:

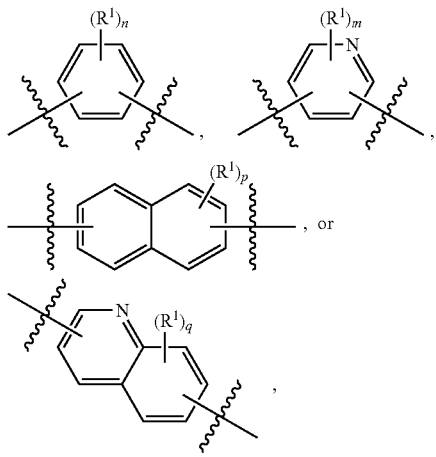

wherein:
R$^1$, independently at each occurrence, is alkyl, alkenyl, alkynyl, aryl, alkaryl, aralkyl, halo, heteroaryl, heterocycloalkyl, hydroxyl, cyano, nitro,

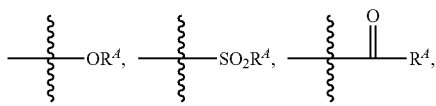

or azido,
wherein R$^A$ is alkyl or heteroalkyl;
n is an integer from 0 to 4;
m is an integer from 0 to 3;
p is an integer from 0 to 6; and
q is an integer from 0 to 5.

In some embodiments, A is:

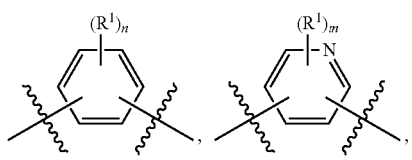

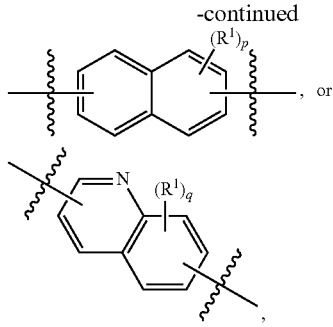

wherein:
R$^1$ is, independently at each occurrence, halo, haloalkyl, haloalkoxy, hydroxyl, alkyl, alkenyl, alkynyl, alkoxy, haloalkoxy, aryl, alkaryl, aralkyl, heteroaryl, heteroalkyl, heterocycloalkyl, cyano, nitro,

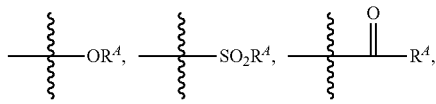

or azido,
wherein R$^A$ is alkyl or heteroalkyl;
n is an integer from 0 to 4;
m is an integer from 0 to 3;
p is an integer from 0 to 6; and
q is an integer from 0 to 5.

In some embodiments, A is:

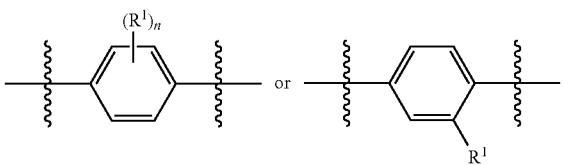

wherein:
R$^1$ is, independently at each occurrence, halo, haloalkyl, hydroxyl, alkyl, alkenyl, alkynyl, alkoxy, aryl, alkaryl, aralkyl, heteroaryl, heteroalkyl, heterocycloalkyl, cyano, nitro,

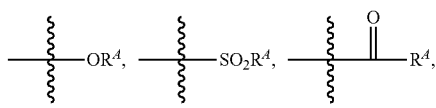

for azido,
wherein R$^A$ is alkyl or heteroalkyl;
n is an integer from 0 to 4;
m is an integer from 0 to 3;
p is an integer from 0 to 6; and
q is an integer from 0 to 5.

In some embodiments, $R^1$ is $C_{1-6}$ alkyl or $C_{1-6}$ alkoxy. In some of these embodiments, $R^1$ is methyl, ethyl, methoxy, or ethoxy. In some of these embodiments, $R^1$ is methoxy.

In some embodiments, $R^1$ is, independently, alkyl or halo. In some embodiments, $R^1$ is, independently, $C_{1-6}$ alkyl, $C_{1-6}$ haloalkyl, or halo. In some embodiments, $R^1$ is, independently, halo. In some embodiments, $R^1$ is, independently, fluoro, chloro, bromo, iodo, or trifluoromethyl. In some embodiments, n, m, p, or q is 0, 1 or 2. In some embodiments, n, m, p, or q is 0 or 1. In some embodiments, n, m, p, or q is 0.

In some embodiments, $R^1$ is

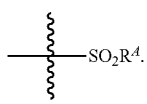

In some embodiments, $R^1$ is

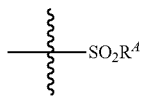

wherein $R^A$ is methyl. In some embodiments, $R^1$ is hydroxyl. In some embodiments, $R^1$ is N-methylformamide. In some embodiments, $R^1$ is morpholinyl.

In some embodiments, $R^1$ is, independently, alkyl, alkoxy, or halo. In some embodiments, $R^1$ is, independently, $C_{1-6}$ alkyl, $C_{1-6}$ alkoxy, $C_{1-6}$ haloalkyl, $C_{1-6}$ haloalkoxy, or halo. In some embodiments, $R^1$ is, independently, halo. In some embodiments, $R^1$ is, independently, fluoro, chloro, bromo, iodo, or trifluoromethyl. In some embodiments, n, m, p, or q is 0, 1 or 2. In some embodiments, n, m, p, or q is 0 or 1. In some embodiments, n, m, p, or q is 0.

In some embodiments, A is:

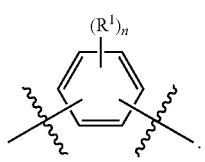

In some embodiments, A is:

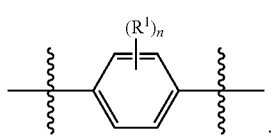

In some embodiments, A is:

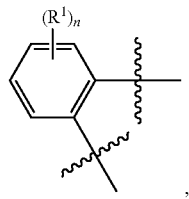

In some embodiments, A is:

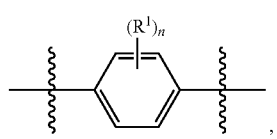

wherein n is 0, 1 or 2.

In some embodiments, A is:

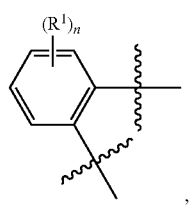

wherein n is 0, 1 or 2.

In some embodiments, A is:

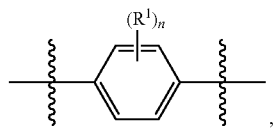

wherein n is 0 or 1; and $R^1$ is alkoxy, halo, or haloalkyl.

In some embodiments, A is:

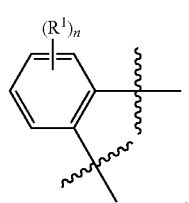

wherein n is 0 or 1; and $R^1$ is alkoxy, halo, or haloalkyl. In some examples, $R^1$ is alkoxy.

In some embodiments, A is:

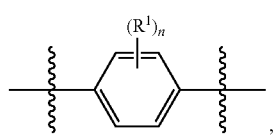

wherein n is 0 or 1; and $R^1$ is $C_{1-6}$ alkoxy, halo, or $C_{1-6}$ haloalkyl.

In some embodiments, A is:

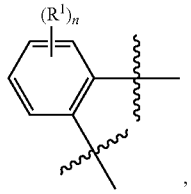

, wherein n is 0 or 1; and $R^1$ is $C_{1-6}$ alkoxy, halo, or $C_{1-6}$ haloalkyl. In some examples, $R^1$ is $C_{1-6}$ alkoxy.

In some embodiments, A is:

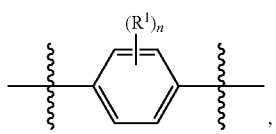

, wherein n is 0 or 1; $R^1$ is $C_{1-6}$ alkoxy, halo, or $C_{1-6}$ haloalkyl; and L is

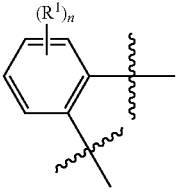

wherein b is an integer from 2 to 8 and

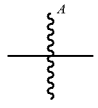

is a bond to the binding agent.

In some embodiments, A is:

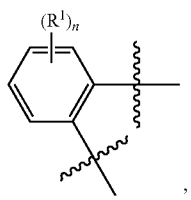

, wherein n is 0 or 1; $R^1$ is $C_{1-6}$ alkoxy, halo, or $C_{1-6}$ haloalkyl; and L is

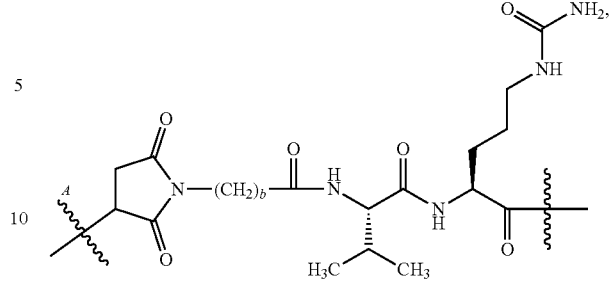

wherein b is an integer from 2 to 8 and

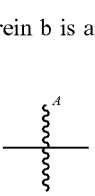

is a bond to the binding agent.

In some embodiments, A is:

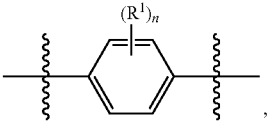

, wherein n is 0, 1, 2, 3, or 4.

In some embodiments, A is:

, wherein n is 0, 1, 2, 3, or 4.

In some embodiments, A is:

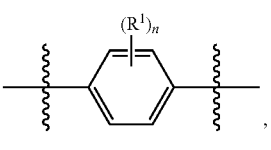

, wherein:
$R^1$ is $C_{1-6}$ alkyl, halo, or $C_{1-6}$ haloalkyl; and
n is 0, 1 or 2.

In some embodiments, A is:

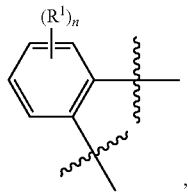

wherein:
R$^1$ is C$_{1-6}$ alkyl, halo, or C$_{1-6}$ haloalkyl; and
n is 0, 1 or 2.

In some embodiments, A is:

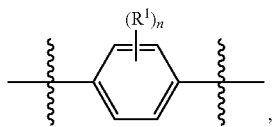

wherein:
R$^1$ is C$_{1-6}$ alkyl, C$_{1-6}$ alkoxy, halo, C$_{1-6}$ haloalkyl, or C$_{1-6}$ haloalkoxy; and
n is 0, 1, 2, 3, or 4.

In some embodiments, A is:

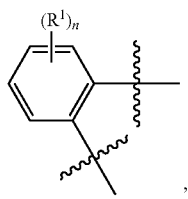

wherein:
R$^1$ is C$_{1-6}$ alkyl, C$_{1-6}$ alkoxy, halo, C$_{1-6}$ haloalkyl, or C$_{1-6}$ haloalkoxy; and
n is 0, 1, 2, 3, or 4.

In some embodiments, A is:

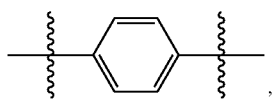

wherein R$^1$ is C$_{1-6}$ alkyl, C$_{1-6}$ alkoxy, halo, or C$_{1-6}$ haloalkyl. In certain of these embodiments, R$^1$ is methoxy or methyl. In some specific embodiments, R$^1$ is methoxy.

In some embodiments, A is:

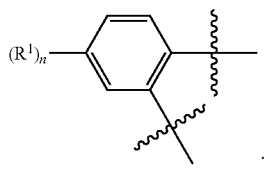

In some embodiments, A is:

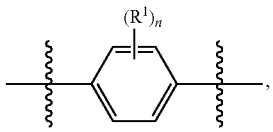

wherein:
R$^1$ is halo or trifluoromethyl; and
n is 0, 1 or 2.

In some embodiments, A is:

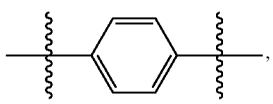

In some embodiments, A is:

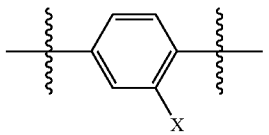

wherein:
X is a hydrogen atom, halo, or trifluoromethyl.

In some embodiments, A is:

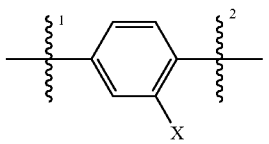

wherein:
X is a hydrogen atom, halo, or trifluoromethyl;

is the bond to the nitrogen atom; and

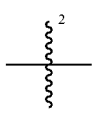

is the bond to the carbonyl.

In some embodiments, A is:

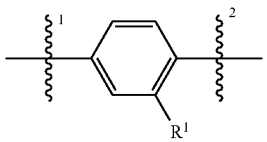

wherein:
R$^1$ is, independently at each occurrence, a hydrogen atom, alkyl, alkoxy, aryl, heteroalkyl, halo, haloalkyl, haloalkoxy or hydroxyl;

is the bond to the nitrogen atom; and

is the bond to the carbonyl. In some embodiments, R$^1$ is 1-methylethyl-thiol, phenyl, 2-fluorophenyl, pyridinyl, 4-pyridinyl, pyrrolidinyl, or 1-pyrrolidinyl. In some embodiments, R$^1$ is trifluoromethyl. In some embodiments, R$^1$ is methoxy. In some embodiments, R$^1$ is fluoro. In some embodiments, R$^1$ is hydrogen. In some embodiments, A is:

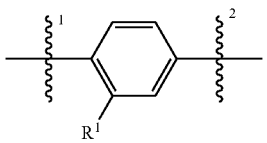

wherein:
R$^1$ is, independently at each occurrence, a hydrogen atom, alkyl, alkoxy, aryl, heteroalkyl, halo, haloalkyl, haloalkoxy, or hydroxyl;

is the bond to the nitrogen atom; and

is the bond to the carbonyl. In some embodiments, R$^1$ is 1-methylethyl-thiol, phenyl, 2-fluorophenyl, pyridinyl, 4-pyridinyl, pyrrolidinyl, or 1-pyrrolidinyl. In some embodiments, R$^1$ is trifluoromethyl. In some embodiments, R$^1$ is methoxy. In some embodiments, R$^1$ is fluoro. In some embodiments, R$^1$ is hydrogen.

In some embodiments, R$^1$ is sulfonyl. In some embodiments, R$^1$ is N-methylformamide. In some embodiments, R$^1$ is hydroxyl. In some embodiments, R$^1$ is morpholinyl.

In some embodiments, A is:

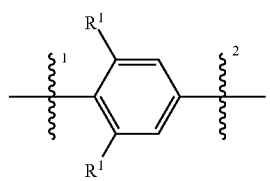

wherein:
R$^1$ is, independently at each occurrence, a hydrogen atom, alkyl, alkoxy, aryl, heteroalkyl, halo, haloalkyl, or haloalkoxy;

is the bond to the nitrogen atom; and

is the bond to the carbonyl. In some embodiments, R$^1$ is alkyl or alkoxy. In some specific embodiments, R$^1$ is propylamino, difluoro-methoxy, phenyl, 2-fluorophenyl. In some embodiments, R$^1$ is trifluoromethyl. In some embodiments, R$^1$ is methoxy. In some embodiments, R$^1$ is fluoro. In some embodiments, R$^1$ is hydrogen.

In some embodiments, A is:

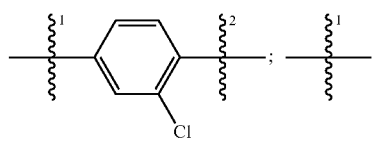

is the bond to the nitrogen atom; and

is the bond to the carbonyl.

In some embodiments, A is:

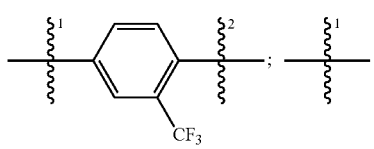

is the bond to the nitrogen atom; and

is the bond to the carbonyl.

In some embodiments, A is:

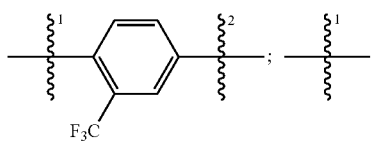

is the bond to the nitrogen atom; and

is the bond to the carbonyl.

In some embodiments, A is:

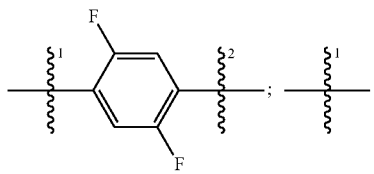

is the bond to the nitrogen atom; and

is the bond to the carbonyl.

In some embodiments, A is:

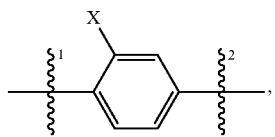

wherein X is F, Cl, Br, CN, methoxy, dimethylamino or cyclopropyl;

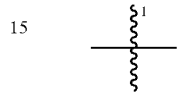

is the bond to the nitrogen atom; and

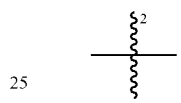

is the bond to the carbonyl.

In some embodiments, A is:

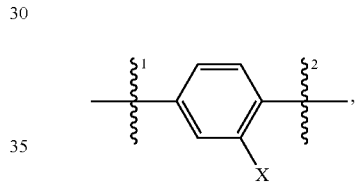

X wherein X is F, Cl, Br, CN, methoxy, dimethylamino, 1-methyl-ethyl-thio or cyclopropyl;

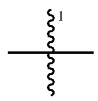

is the bond to the nitrogen atom; and

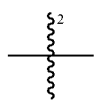

is the bond to the carbonyl.

In some embodiments, A is:

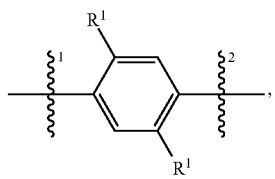

wherein each $R^1$ is independently, at each occurrence, a hydrogen atom, alkyl, alkoxy, halo, haloalkyl, or haloalkoxy;

is the bond to the nitrogen atom; and

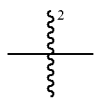

is the bond to the carbonyl. In some embodiments, $R^1$ is hydrogen, fluoro, trifluoromethyl, or methoxy. In some embodiments, $R^1$ is fluoro, chloro, bromo, or iodo.

In some embodiments, A is:

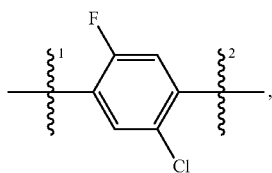 [SMILES: *c1cc(Cl)c(*)cc1F]

wherein

is the bond to the nitrogen atom; and

is the bond to the carbonyl.

In some embodiments, A is:

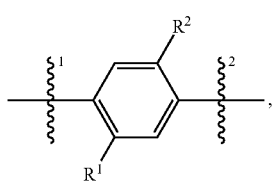

wherein each $R^1$ is independently, at each occurrence, a hydrogen atom, alkyl, alkoxy, halo, haloalkyl, or haloalkoxy,

is the bond to the nitrogen atom; and

is the bond to the carbonyl.
In some embodiments, A is:

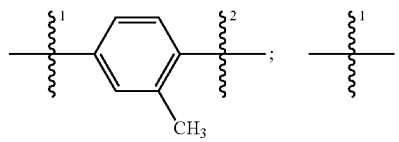

is the bond to the nitrogen atom; and

is bond to the carbonyl.
In some embodiments, A is:

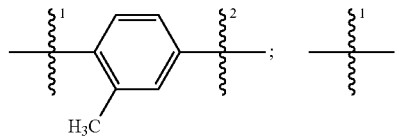

is the bond to the nitrogen atom; and

is the bond to the carbonyl.
In some embodiments, A is:

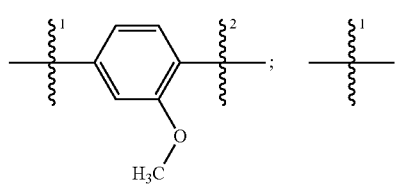

is the bond to the nitrogen atom; and

is the bond to the carbonyl.
In some embodiments, A is:

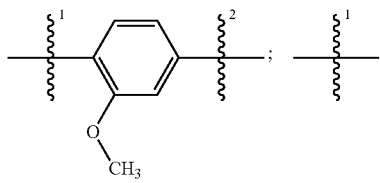

is the bond to the nitrogen atom; and

is the bond to the carbonyl.
In some embodiments, A is:

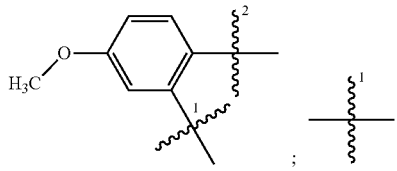

is the bond to the nitrogen atom; and

is the bond to the carbonyl.
In some embodiments, A is:

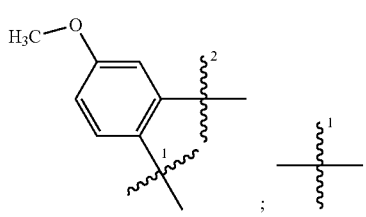

is the bond to the nitrogen atom; and

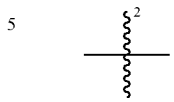

is the bond to the carbonyl.
In some embodiments, A is:

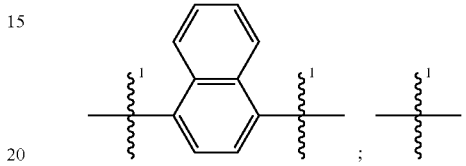

is the bond to the nitrogen atom; and

is the bond to the carbonyl.
In some embodiments, A is:

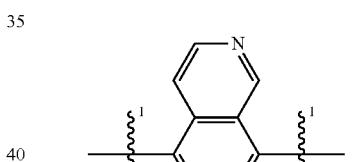

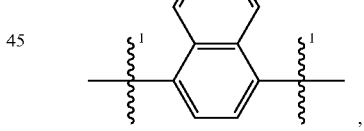

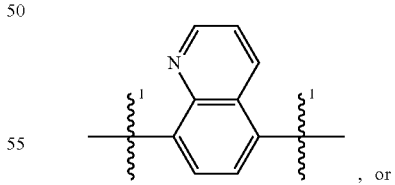, or

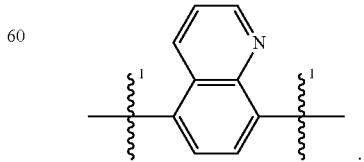.

In some embodiments, A is:

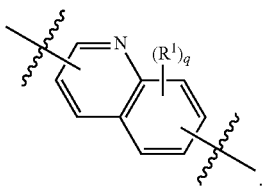

In some embodiments, A is:

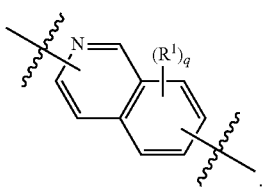

In some embodiments, A is:

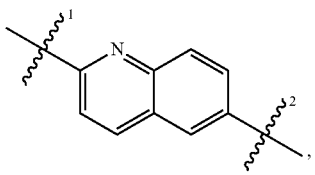 [SMILES: *c1ccc2nc(*)ccc2c1]

wherein:

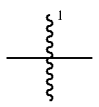

is the bond to the nitrogen atom; and

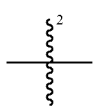

is the bond to the carbonyl.

In some embodiments, A is:

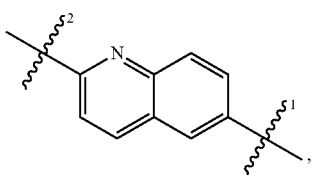 [SMILES: *c1ccc2nc(*)ccc2c1]

wherein:

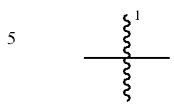

is the bond to the nitrogen atom; and

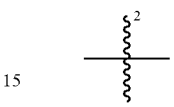

is the bond to the carbonyl.

In some embodiments, A is:

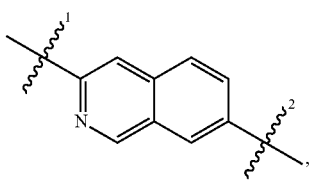 [SMILES: *c1ccc2cc(*)ncc2c1]

wherein:

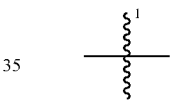

is the bond to the nitrogen atom; and

is the bond to the carbonyl.

In some embodiments, A is:

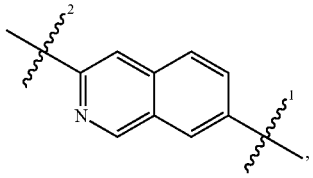 [SMILES: *c1ccc2cc(*)ncc2c1]

wherein:

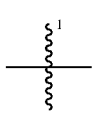

is the bond to the nitrogen atom; and
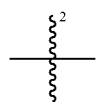
is the bond to the carbonyl.
In some embodiments, A is:
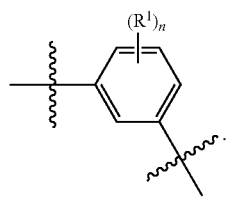
In some embodiments, A is:
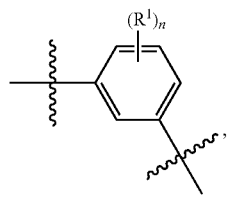
wherein n is 0, 1 2, or 3.
In some embodiments, A is:
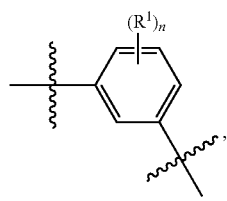
wherein:
R$^1$ is C$_{1-6}$ alkyl, C$_{1-6}$ alkoxy, halo, C$_{1-6}$ haloalkyl, C$_{1-6}$ haloalkoxy, C$_{1-6}$ heteroalkyl; and
n is 0, 1 2, 3 or 4.
In some embodiments, A is:
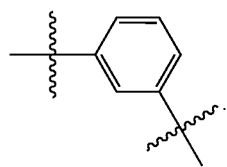 [SMILES: *c1cccc(*)c1]
In some embodiments, A is:
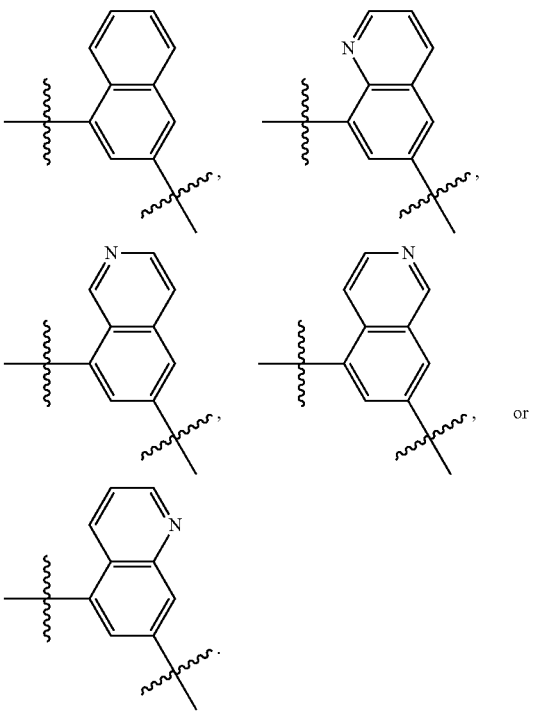
In some embodiments, A is:
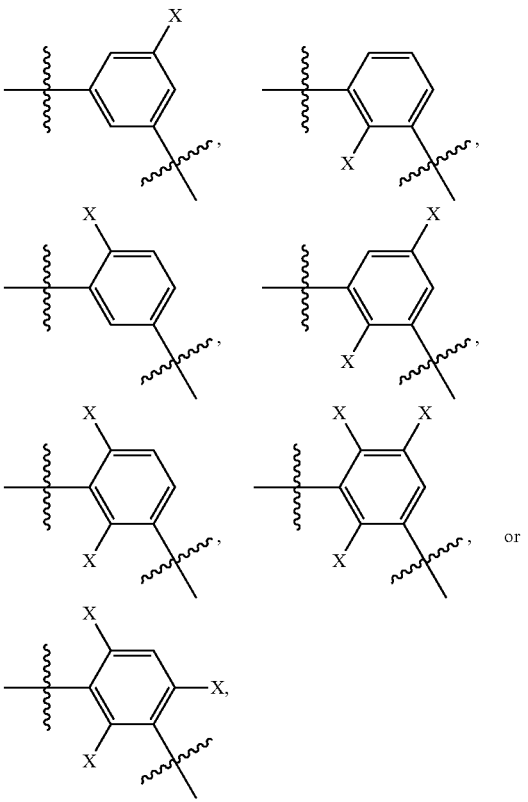

wherein:
X is, independently at each occurrence, a hydrogen atom, alkyl, alkoxy, halo, haloalkoxy, haloalkyl, heteroalkyl. In some embodiments, X is fluoro, chloro, bromo, iodo, dimethylamino, methylamino, methoxy, ethoxy, or trifluoromethyl.

In some embodiments, A is:

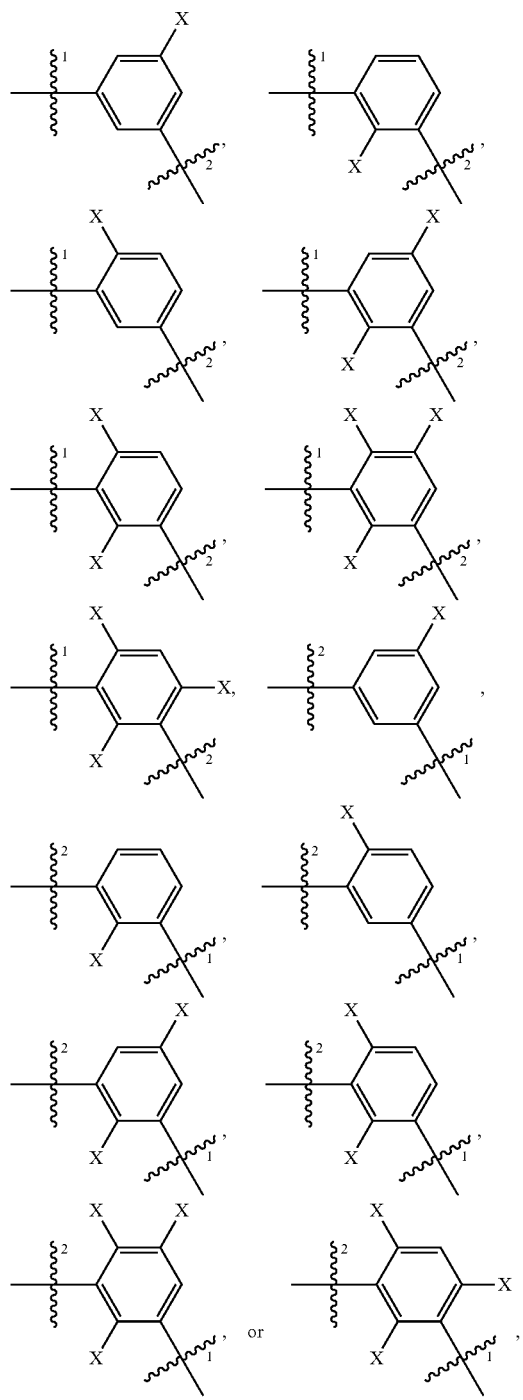

wherein:
X is, independently at each occurrence, a hydrogen atom, alkyl, alkoxy, halo, haloalkoxy, haloalkyl, heteroalkyl. In some embodiments, X is fluoro, chloro, bromo, iodo, dimethylamino, methylamino, methoxy, ethoxy, trifluoromethyl or methoxy;

is the bond to the nitrogen atom; and

is the bond to the carbonyl.

2. Linkers

The linker portion of the conjugates described herein is a divalent moiety that covalently links the binding agent to the maytansinoid derivatives described herein. Suitable linkers include those that release the maytansinoid portion in the presence of an enzyme or at a particular pH range or value.

In some embodiments, the linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety. In some embodiments, the non-cleavable linker is

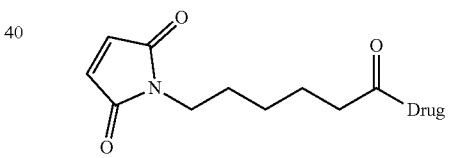

or a residue thereof. In some embodiments, the non-cleavable linker is

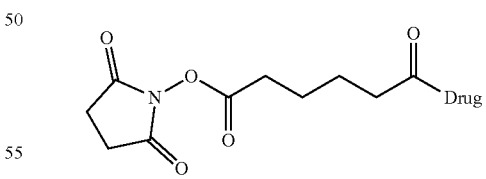

or a residue thereof.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L-, or D-α-amino acids. In some embodiments, the linker comprises alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, or derivative thereof.

In some embodiments, the linker comprises valine and citrulline.

In some embodiments, the linker is:

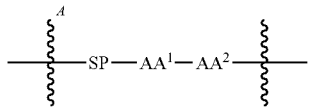

wherein:

SP is a spacer;

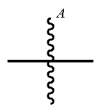

is one or more bonds to the binding agent;

AA$^1$ is an amino acid; and

AA$^2$ is an amino acid.

The spacer is a divalent moiety that connects the AA$^1$-AA$^2$ moiety to the binding agent (BA). Suitable spacers include, but are not limited to, those comprising alkylene or polyethylene glycol. The ends of the spacers, i.e., the portion of the spacer directly bonded to the binding agent or AA$^1$, can be moieties derived from reactive moieties that are used for purposes of coupling the naked antibody or AA$^1$ to the spacer during the chemical synthesis of the conjugate.

In some examples, suitable spacers include, but are not limited to, a primary amine-terminated alkylene or a primary amine-terminated polyethylene glycol. The primary amine-terminating end of the spacer can be directly bonded to a deglycosylated antibody or aglycosylated antibody in the presence of transglutaminase.

In some embodiments, the spacer comprises an alkylene. In some embodiments, the spacer comprises a $C_{5-7}$ alkylene. In some embodiments, the spacer is:

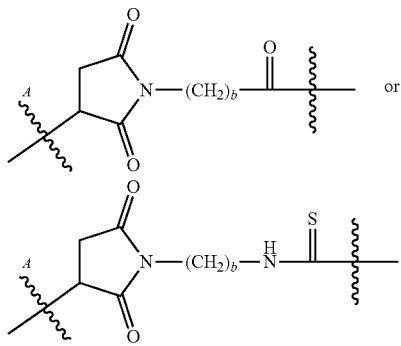

wherein:

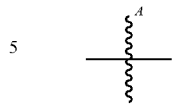

is a bond to the binding agent; and b is an integer from 2 to 8.

In some embodiments, the spacer comprises a primary amine-terminated alkylene. In some embodiments, the spacer comprises a $NH_2$—$C_{5-7}$ alkylene. In some embodiments, the spacer is:

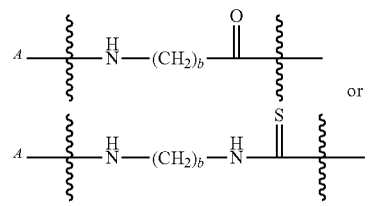

wherein:

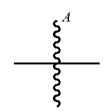

is a bond to the binding agent; and b is an integer from 2 to 8.

In some embodiments, the spacer is:

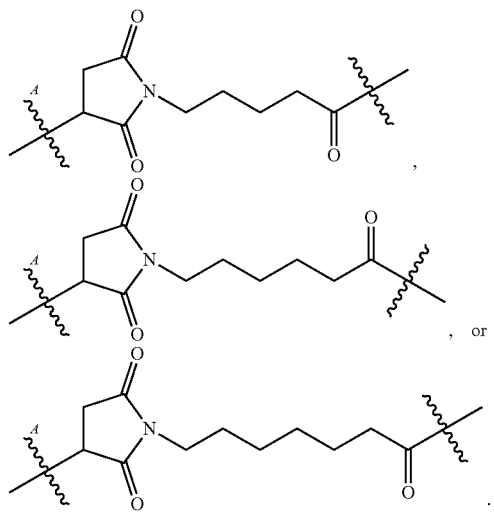

wherein:

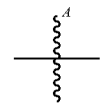

is a bond to the binding agent.

In some embodiments, the spacer is:

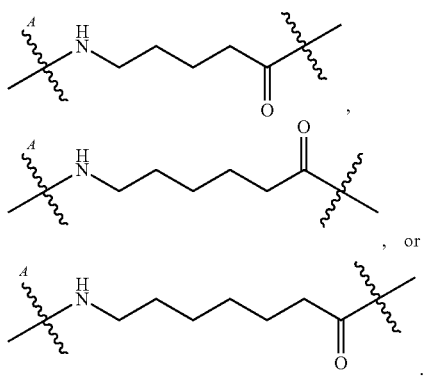

wherein:

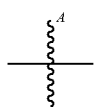

is a bond to the binding agent.

In some embodiments, the spacer is:

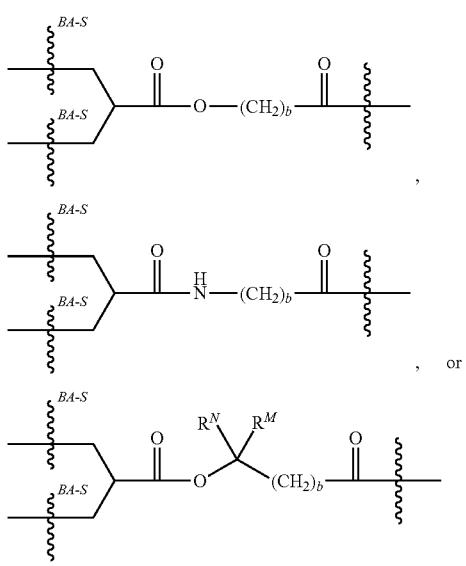

wherein:
$R^N$ is a hydrogen atom or alkyl;
$R^M$ is alkyl;
the two bonds represented by

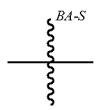

are bonds to cysteines of a binding agent; and
b is an integer from 2 to 8.

In some embodiments, the spacer is:

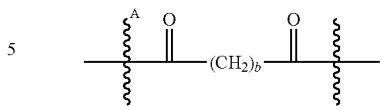

wherein:

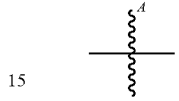

is a bond to the binding agent; and
b is an integer from 2 to 8.

In some embodiments, the spacer is:

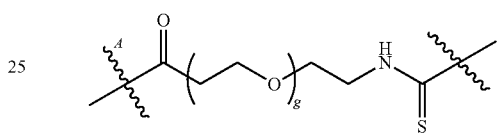

wherein:

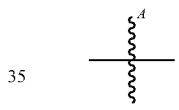

is a bond to the binding agent; and
g is an integer from 2 to 20. In some embodiments, g is 2-8. In some embodiments, g is 2, 4, 6, or 8.

In some embodiments, the spacer is

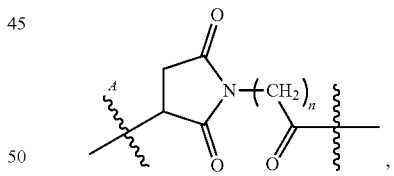

wherein n is an integer from 4 to 10. In some embodiments, n is 4, 5, 6, 7, 8, 9, or 10.

In some embodiments, the spacer is:

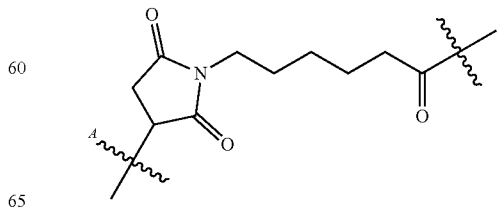

In some embodiments, the spacer is

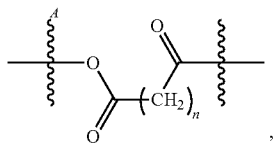

wherein n is an integer from 4 to 10. In some embodiments, n is 4, 5, 6, 7, 8, 9, or 10.

In some embodiments, the spacer is

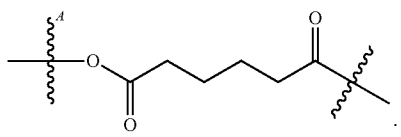

In some embodiments, the spacer is:

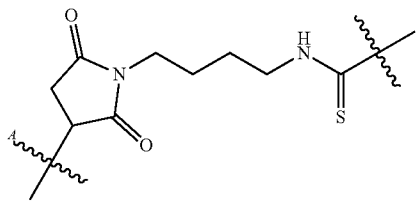

In some embodiments, the spacer is:

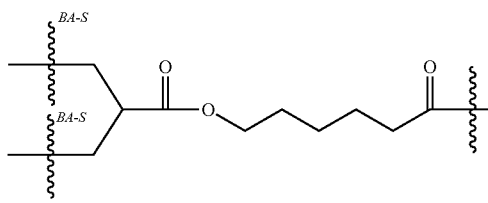

In some embodiments, the spacer is:

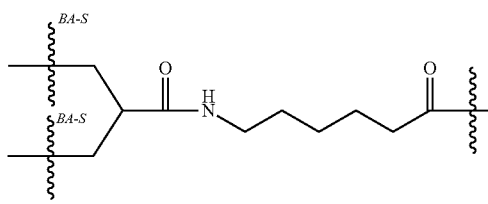

In some embodiments, the spacer is:

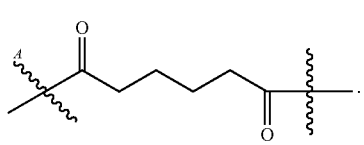

In some embodiments, the spacer is:

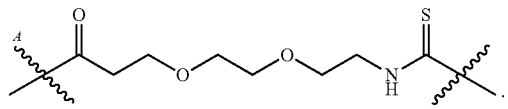

In some embodiments, the spacer is:

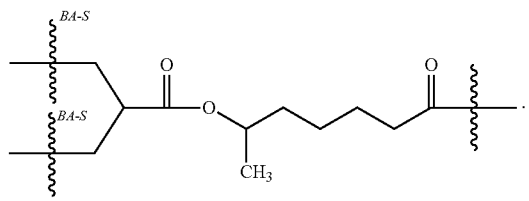

In some embodiments, the spacer is:

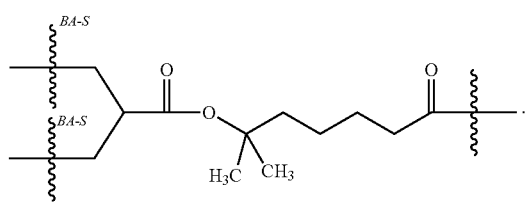

In some embodiments, the spacer is:

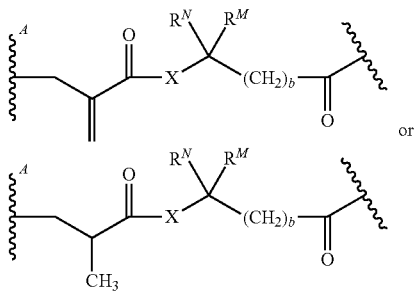

wherein $\xi$ is a bond to the binding agent;

X is N or O; $R^N$ and $R^M$ are each, independently, hydrogen or alkyl; and b is an integer from 1 to 8.

In some embodiments, $AA^1$-$AA^2$ is: valine-citrulline, citrulline-valine, lysine-phenylalanine, phenylalanine-lysine, valine-asparagine, asparagine-valine, threonine-asparagine, asparagine-threonine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some embodiments, $AA^1$-$AA^2$ is: valine-citrulline or citrulline-valine. In some embodiments, $AA^1$-$AA^2$ is: valine-citrulline.

In some embodiments, the linker is:

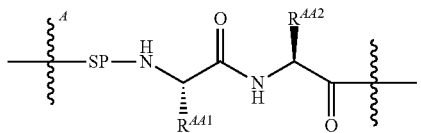

wherein:

SP is a spacer;

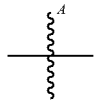

is one or more bonds to the binding agent;

$R^{AA1}$ is an amino acid side chain; and $R^{AA2}$ is an amino acid side chain.

As used herein, "amino acid side chain" refers the monovalent non-hydrogen substituent bonded to the α-carbon of an α-amino acid, including natural and non-natural amino acids. Exemplary amino acid side chains include, but are not limited to, the α-carbon substituent of alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, and citrulline.

In some embodiments, the linker is:

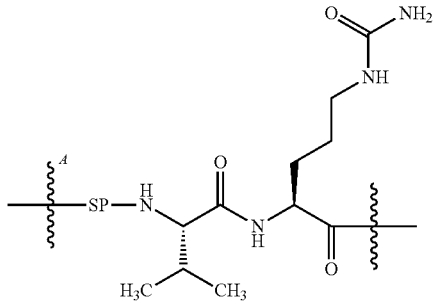

wherein:

SP is a spacer; and

is one or more bonds to the binding agent.

In some embodiments, the linker is:

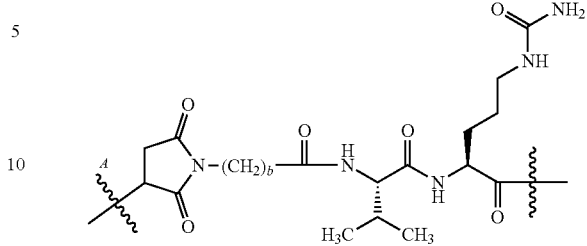

wherein:

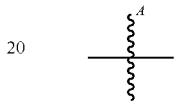

is a bond to the binding agent; and b is an integer from 2 to 8.

In some embodiments, the linker is:

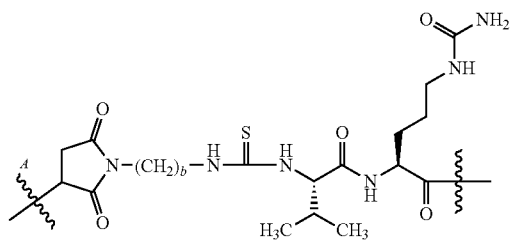

wherein:

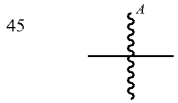

is a bond to the binding agent; and b is an integer from 2 to 8.

In some embodiments, BA is an antibody and the linker is:

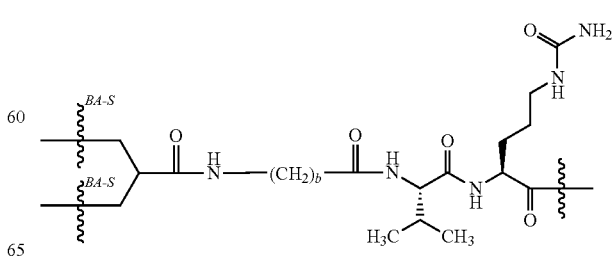

wherein:

the two bonds represented by

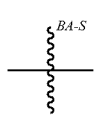

are bonds to cysteines of the antibody; and b is an integer from 2 to 8.

In some embodiments, BA is an antibody and the linker is:

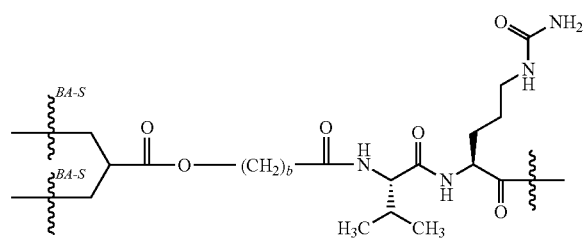

wherein:

the two bonds represented by

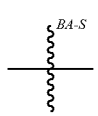

are bonds to cysteines of the antibody; and b is an integer from 2 to 8.

In some embodiments, BA is an antibody and the linker is:

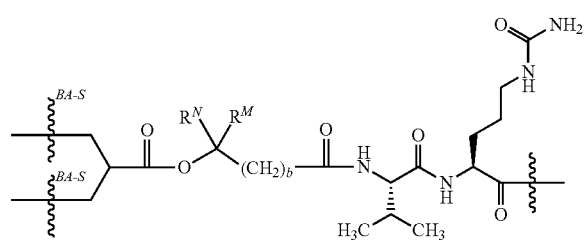

wherein:

$R^N$ is a hydrogen atom or alkyl;

$R^M$ is alkyl;

the two bonds represented by

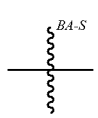

are bonds to cysteines of the antibody; and b is an integer from 2 to 8.

In some embodiments, the linker is:

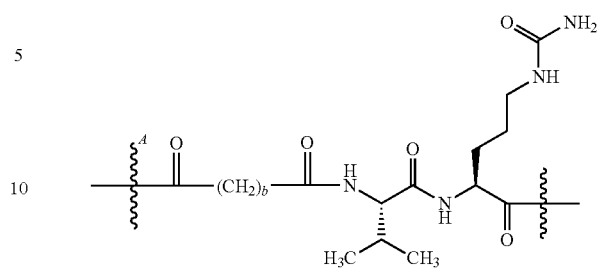

wherein:

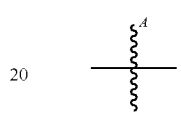

is a bond to the binding agent; and b is an integer from 2 to 8.

In some embodiments, the linker is:

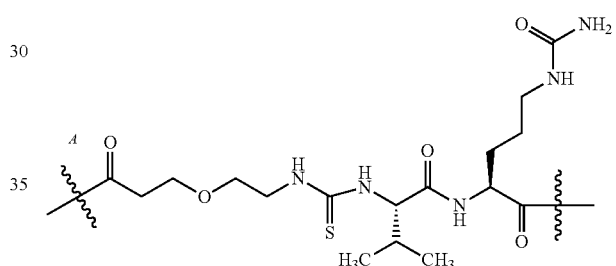

wherein:

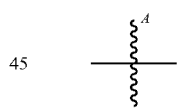

is a bond to the binding agent; and g is an integer from 2 to 20. In some embodiments, g is 2 to 8. In some embodiments, g is 2, 4, 6, or 8.

In some embodiments, the linker is:

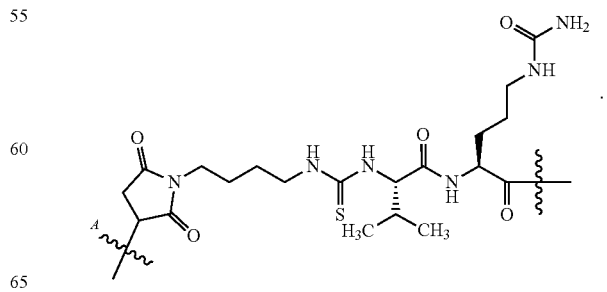

In some embodiments, the linker is:
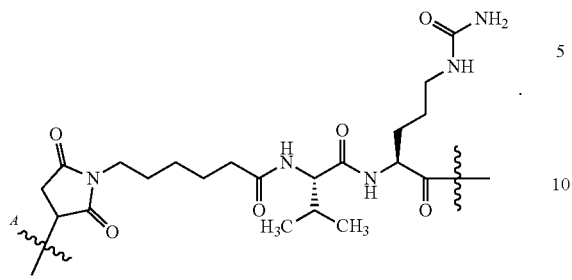
In some embodiments, the linker is:
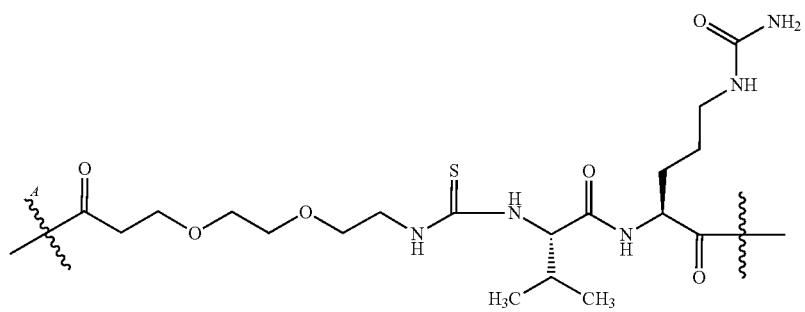
In some embodiments, the linker is:
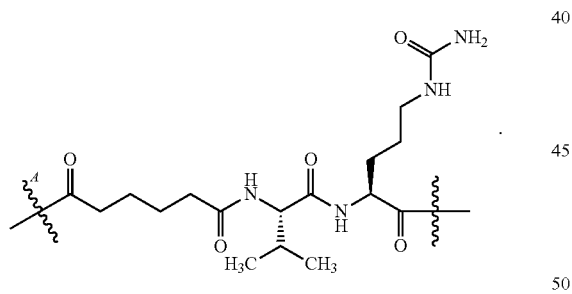
In some embodiments, the linker is:
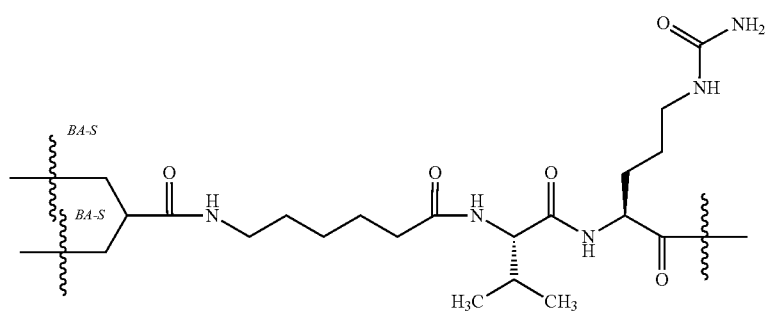

In some embodiments, the linker is:

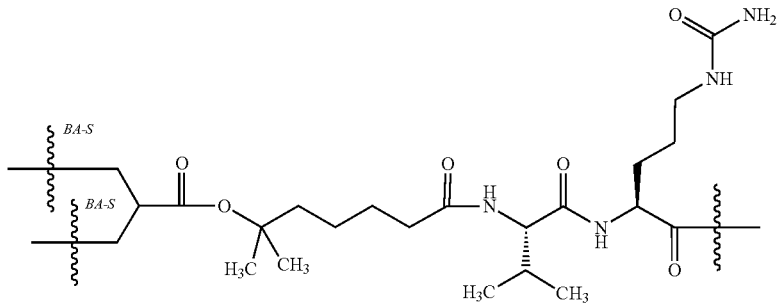

In some embodiments, the linker is:

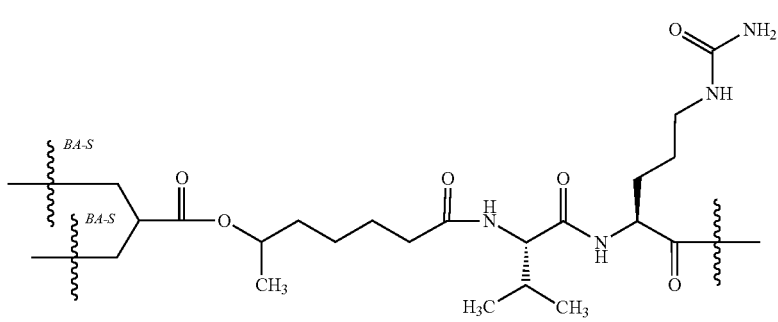

In some embodiments, the linker is:

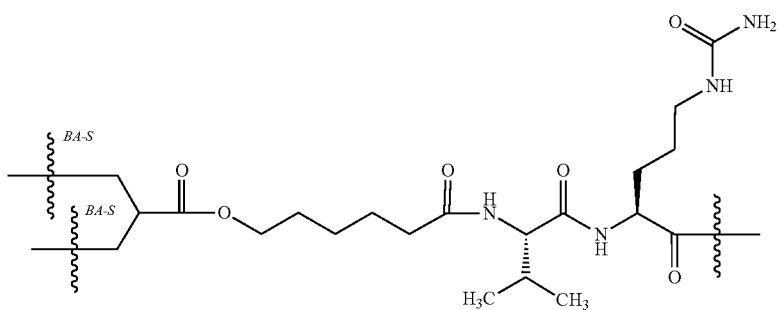

3. Binding Agents

Suitable binding agents include, but are not limited to, antibodies, lymphokines, hormones, growth factors, viral receptors, interleukins, or any other cell binding or peptide binding molecules or substances.

In some embodiments, the binding agent is an antibody. In some embodiments, the antibody is a monoclonal antibody, polyclonal antibody, antibody fragment (Fab, Fab', and F(ab)2, minibody, diabody, tribody, and the like), or bispecific antibody. Antibodies herein can be humanized using methods described in U.S. Pat. No. 6,596,541 and US Publication No. 2012/0096572, each incorporated by reference in their entirety.

Where the binding agent is an antibody, it binds to an antigen binding partner that is a polypeptide and may be a transmembrane molecule (e.g., receptor) or a growth factor that might be glycosylated or phosphorylated. Exemplary antigens include, but are not limited to, molecules such as renin; a growth hormone, including human growth hormone and bovine growth hormone; growth hormone releasing factor; parathyroid hormone; thyroid stimulating hormone; lipoproteins; alpha1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-I-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; 19E; a cytotoxic T-lymphocyte associ ated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-1 and -II (IGF-1 and IGF-II); des(I-3)-IGF-1 (brain IGF-1), insulin-like growth factor binding proteins, EpCAM, GD3, FLT3, PSMA, PSCA, MUC1, MUC16, STEAP, CEA, TENB2, EphA receptors, EphB receptors, folate receptor, FOLRI, mesothelin, cripto, alphavbeta6, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80, CD81, CD103, CD105, CD134, CD137, CD138, CD152, or an antibody which binds to one or more tumor-associated antigens or cell-surface receptors disclosed in US Publication No. 2008/0171040 or US Publication No. 2008/0305044 and incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as AFP, ALK, B7H4, BAGE proteins, β-catenin, brc-abl, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins (e.g., GAGE-1, -2), GD2, GD3, GloboH, glypican-3, GM3, gp100, Her2, HLA/B-raf, HLA/EBNA1, HLA/k-ras, HLA/MAGE-A3, hTERT, IGF1R, LGR5, LMP2, MAGE proteins (e.g., MAGE-1, -2, -3, -4, -6, and -12), MART-1, mesothelin, ML-IAP, Muc1, Muc16 (CA-125), MUM1, NA17, NGEP, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSCA, PSGR, PSMA (FOLH1), RAGE proteins, Ras, RGS5, Rho, SART-1, SART-3, Steap-1, Steap-2, STn, survivin, TAG-72, TGF-β, TMPRSS2, Tn, TNFRSF17, TRP-1, TRP-2, tyrosinase, and uroplakin-3, and fragments of any of the above-listed polypeptides.

Exemplary antigens also include, but are not limited to, BCMA, SLAMF7, B7H4, GPNMB, UPK3A, and LGR5.

In some embodiments, the antigens include prolactin receptor (PRLR) or prostate-specific membrane antigen (PSMA).

Binding agents also include, but are not limited to, ankyrin repeat proteins, interferons, lymphokines such as IL-2 or IL-3, hormones like insulin and glucocorticoids, growth factors such as EGF, transferrin and fibronectin type III.

In some embodiments, the binding agents interact with or bind to tumor antigens, including antigens specific for a type of tumor or antigens that are shared, overexpressed or modified on a particular type of tumor. Examples include, but are not limited to: alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example: BAGE-1, GAGE, GnTV, KK-LC-1, MAGE-A2, NA88-A, TRP2-INT2.

In some embodiments, the binding agent is an antibody. In some embodiments, the binding agent is a monoclonal antibody. In some embodiments, the binding agent is a polyclonal antibody. In some embodiments, the antibody is an anti-PSMA, anti-MUC16, or anti-EGFRvIII, or anti-STEAP-2 antibody.

The linkers can be bonded to the binding agent, e.g., antibody or antigen-binding molecule, through an attachment at a particular amino acid within the antibody or antigen-binding molecule. Exemplary amino acid attachments that can be used in the context of this aspect of the disclosure include, e.g., lysine (see, e.g., U.S. Pat. No. 5,208,020; US 2010/0129314; Hollander et al., Bioconjugate Chem., 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., Proc. Natl. Acad. Sci., USA, 2008, 105:12451-12456), formyl glycine (see, e.g., Carrico et al., Nat. Chem. Biol., 2007, 3:321-322; Agarwal et al., Proc. Natl. Acad. Sci., USA, 2013, 110:46-51, and Rabuka et al., Nat. Protocols, 2012, 10:1052-1067), non-natural amino acids (see, e.g., WO 2013/068874, and WO 2012/166559), and acidic amino acids (see, e.g., WO 2012/05982). Linkers can be conjugated via glutamine via transglutaminase-based chemo-enzymatic conjugation (see, e.g., Dennler et al., Bioconjugate Chem. 2014, 25, 569-578). Linkers can also be conjugated to an antigen-binding protein via attachment to carbohydrates (see, e.g., US 2008/0305497, WO 2014/065661, and Ryan et al., Food & Agriculture Immunol., 2001, 13:127-130) and disulfide linkers (see, e.g., WO 2013/085925, WO 2010/010324, WO 2011/018611, WO 2014/197854, and Shaunak et al., Nat. Chem. Biol., 2006, 2:312-313).

In some embodiments, the binding agent is an antibody, and the antibody is bonded to the linker through a lysine residue. In some embodiments, the antibody is bonded to the linker through a cysteine residue.

4. Illustrative Embodiments

In some embodiments,
A is:

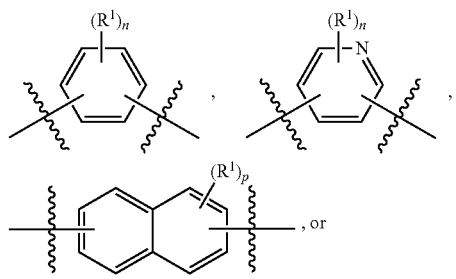

-continued

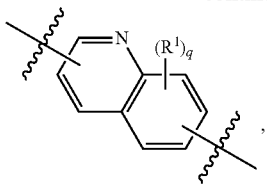

wherein:
R$^1$, independently at each occurrence, is alkyl, alkenyl, alkynyl, aryl, alkaryl, aralkyl, halo, heteroaryl, heterocycloalkyl, hydroxyl, cyano, nitro

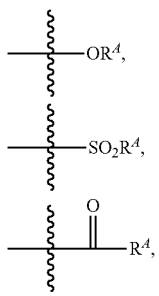

or azido,
wherein R$^A$ is alkyl or heteroalkyl;
n is an integer from 0 to 4;
m is an integer from 0 to 3;
p is an integer from 0 to 6; and
q is an integer from 0 to 5; and
L is:

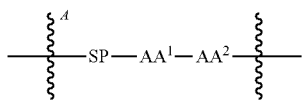

wherein:
SP is a spacer;

is one or more bonds to the binding agent;
AA$^1$ is an amino acid; and
AA$^2$ is an amino acid.
In some embodiments,
A is:

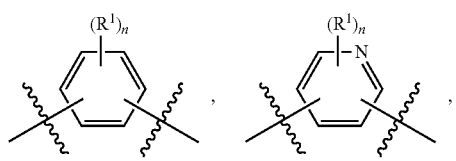

-continued

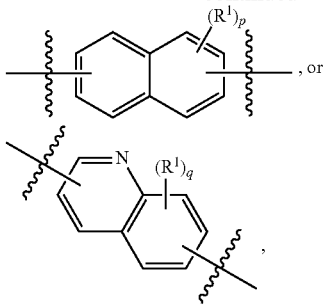

wherein:
R$^1$, independently at each occurrence, is C$_{1-6}$ alkyl, C$_{1-6}$ haloalkyl, or halo;
n is an integer from 0 to 4;
m is an integer from 0 to 3;
p is an integer from 0 to 6; and
q is an integer from 0 to 5; and
L is:

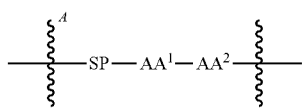

wherein:
SP is a spacer;

is one or more bonds to the binding agent;
AA$^1$ is an amino acid; and
AA$^2$ is an amino acid.
In some embodiments, A is:

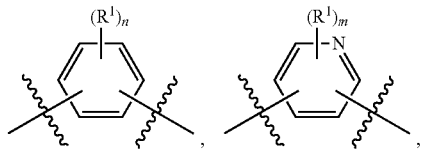

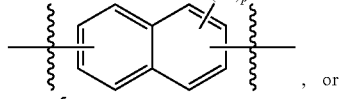

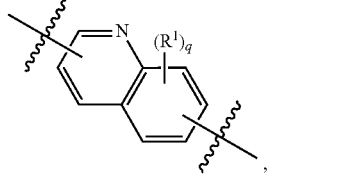

wherein:
R$^1$, independently at each occurrence, is alkyl, alkenyl, alkynyl, alkoxy, aryl, alkaryl, aralkyl, halo, haloalkoxy, haloalkyl, haloalkoxy, heteroaryl, heteroalkyl, heterocycloalkyl, hydroxyl, cyano, nitro,

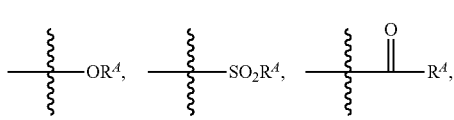

or azido,
wherein $R^A$ is alkyl or heteroalkyl;
n is an integer from 0 to 4;
m is an integer from 0 to 3;
p is an integer from 0 to 6; and
q is an integer from 0 to 5; and
L is:

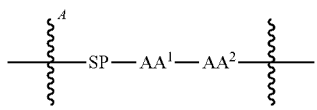

wherein:
SP is a spacer;

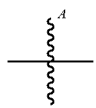

is one or more bonds to the binding agent;
$AA^1$ is an amino acid; and $AA^2$ is an amino acid.
In some embodiments,
A is:

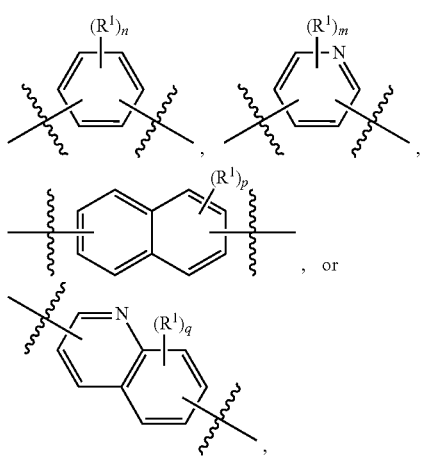

wherein:
$R^1$, independently at each occurrence, is $C_{1-6}$ alkyl, $C_{1-6}$ haloalkyl, or halo;
n is an integer from 0 to 4;
m is an integer from 0 to 3;
p is an integer from 0 to 6; and
q is an integer from 0 to 5;

L is:

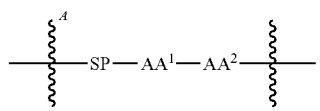

wherein:
SP is:

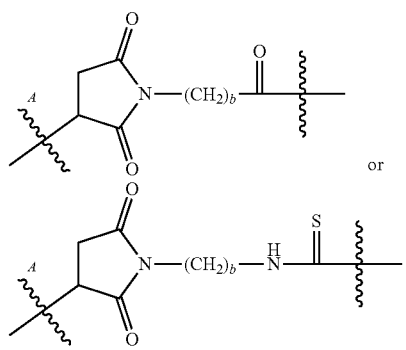

wherein:

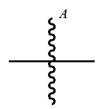

is a bond to the binding agent; and
b is an integer from 2 to 8; and
$AA^1$ is an amino acid; and
$AA^2$ is an amino acid.
In some embodiments, A is:

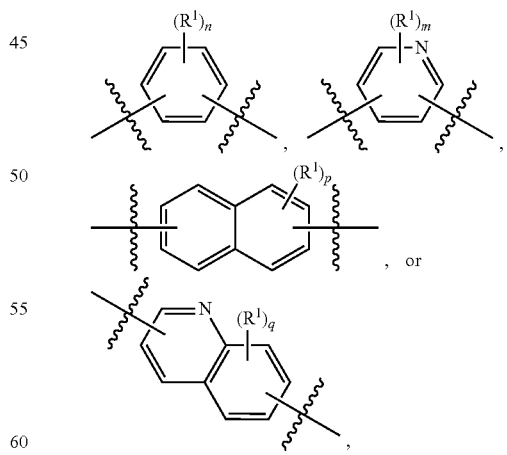

wherein:
$R^1$, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, hydroxyl, cyano, nitro,

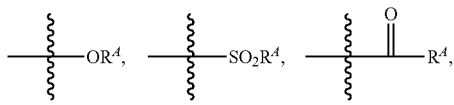

or azido,
wherein $R^A$ is alkyl or heteroalkyl;
n is an integer from 0 to 4;
m is an integer from 0 to 3;
p is an integer from 0 to 6; and
q is an integer from 0 to 5; and
L is:

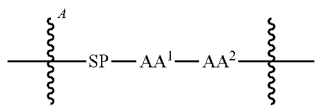

wherein:
SP is:

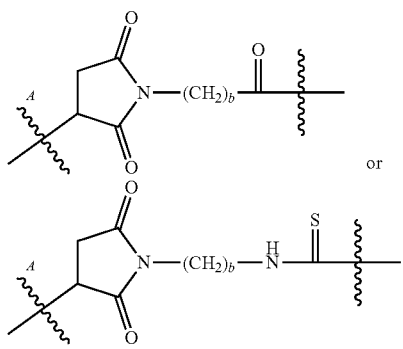

wherein:

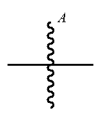

is a bond to the binding agent; and
b is an integer from 2 to 8; and
$AA^1$ is an amino acid; and
$AA^2$ is an amino acid.
In some embodiments,
A is:

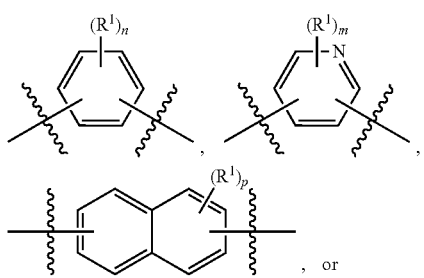

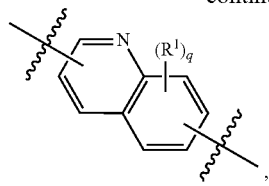

wherein:
$R^1$, independently at each occurrence, is $C_{1-6}$ alkyl, $C_{1-6}$ haloalkyl, or halo;
n is an integer from 0 to 4;
m is an integer from 0 to 3;
p is an integer from 0 to 6; and
q is an integer from 0 to 5; and
L is:

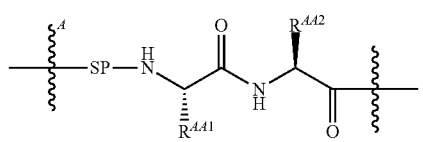

wherein:
SP is a spacer;

is one or more bonds to the binding agent;
$R^{AA1}$ is an amino acid side chain; and
$R^{AA2}$ is an amino acid side chain.
In some embodiments, A is:

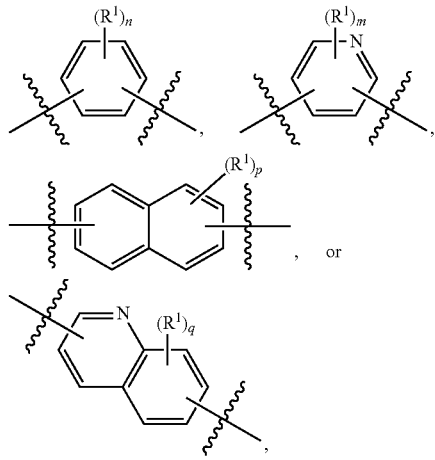

wherein:
$R^1$, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, hydroxyl, cyano, nitro,

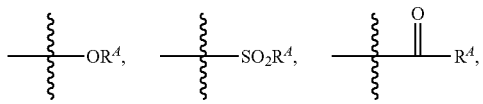

or azido,
wherein $R^A$, is alkyl or heteroalkyl n is an integer from 0 to 4;
m is an integer from 0 to 3;
p is an integer from 0 to 6; and
q is an integer from 0 to 5; and L is:

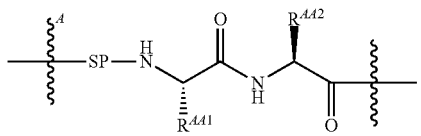

wherein:
SP is a spacer;

is one or more bonds to the binding agent;
$R^{AA1}$ is an amino acid side chain; and
$R^{AA2}$ is an amino acid side chain.

In some embodiments, A is:

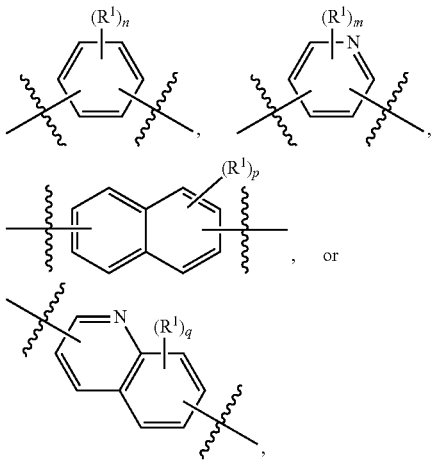

wherein:
$R^1$, independently at each occurrence, is $C_{1-6}$ alkyl, $C_{1-6}$ haloalkyl, or halo;
n is an integer from 0 to 4;
m is an integer from 0 to 3;
p is an integer from 0 to 6; and
q is an integer from 0 to 5; and L is:

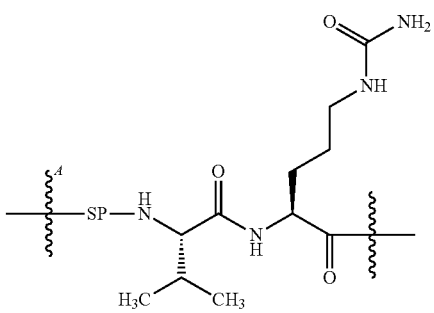

wherein:
SP is a spacer; and

is the one or more bonds to the binding agent.

In some embodiments, A is:

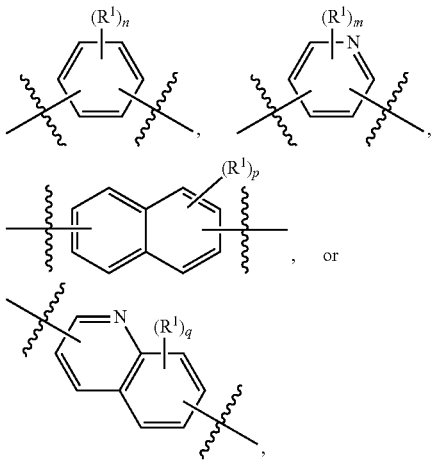

wherein:
$R^1$, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, cyano, nitro,

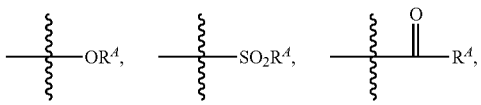

or azido,
wherein $R^A$ is alkyl;
n is an integer from 0 to 4;
m is an integer from 0 to 3;
p is an integer from 0 to 6; and
q is an integer from 0 to 5; and L is:

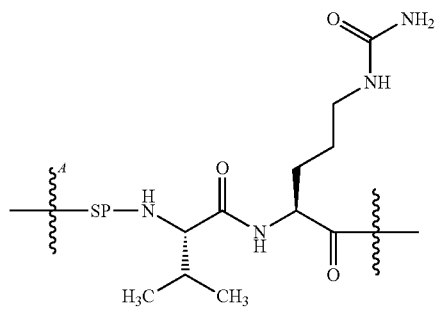

wherein:
SP is a spacer; and

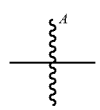

is the one or more bonds to the binding agent.
In some embodiments,
A is:

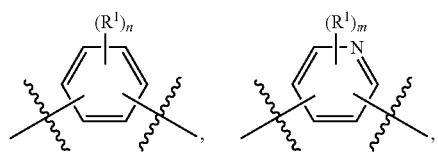

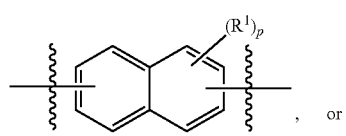, or

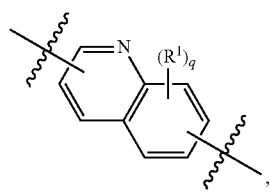, wherein:
$R^1$, independently at each occurrence, is $C_{1-6}$ alkyl, $C_{1-6}$ haloalkyl, or halo;
n is an integer from 0 to 4;
m is an integer from 0 to 3;
p is an integer from 0 to 6; and
q is an integer from 0 to 5; and L is:

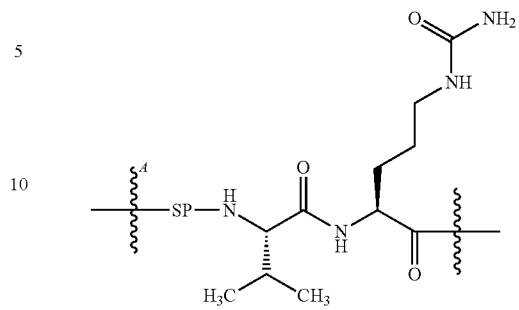

wherein:
SP is:

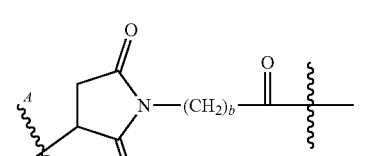

or

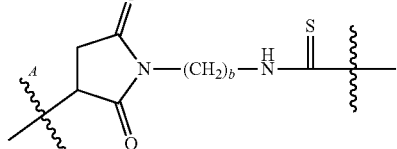

wherein:

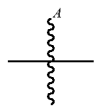

is a bond to the binding agent; and
b is an integer from 2 to 8.
In some embodiments, A is:

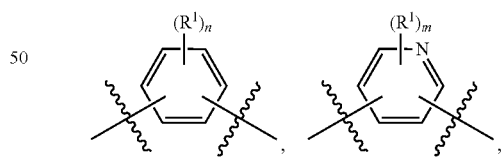

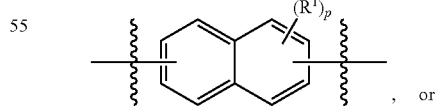, or

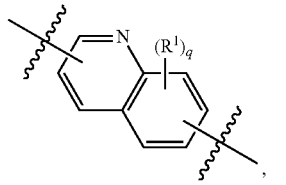, wherein:

R¹, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, hydroxyl, cyano, nitro,

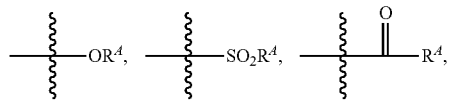

or azido, wherein $R^A$ is alkyl or heteroalkyl;

n is an integer from 0 to 4;

m is an integer from 0 to 3;

p is an integer from 0 to 6; and q is an integer from 0 to 5; and

L is:

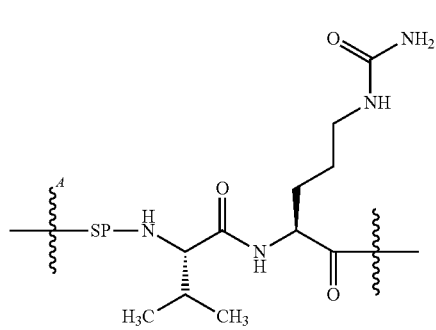

wherein:

SP is:

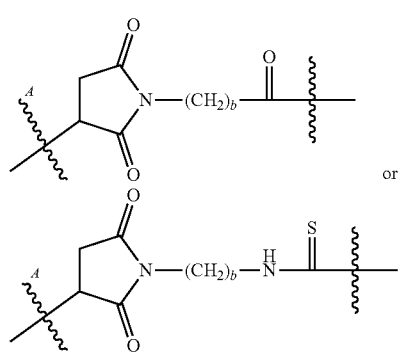

wherein:

is a bond to the binding agent; and
b is an integer from 2 to 8.

In some embodiments, A is:

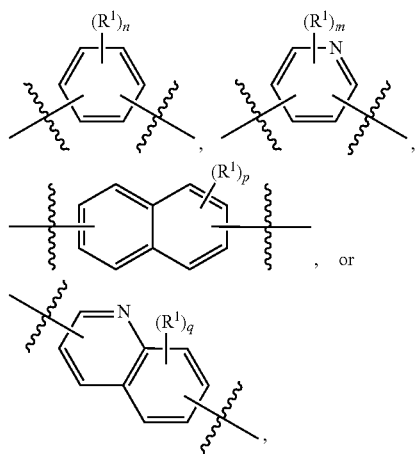

wherein:

R¹, independently at each occurrence, is $C_{1-6}$ alkyl, $C_{1-6}$ haloalkyl, or halo; and n, m, p, and q are 0, 1, or 2; and L is

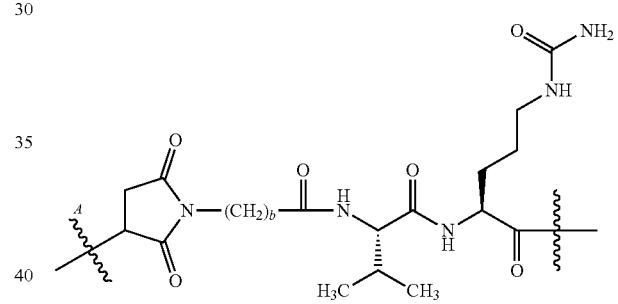

wherein:

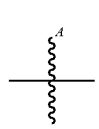

is a bond to the binding agent; and
b is an integer from 2 to 8.

In some embodiments, A is:

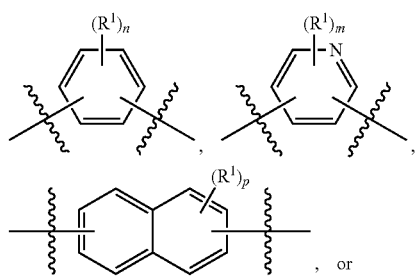

-continued

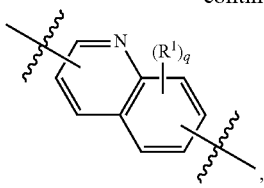

wherein:
R¹, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, cyano, nitro,

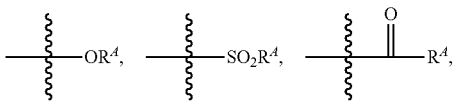

or azido,
wherein $R^A$ is alkyl;
n is an integer from 0 to 4;
m is an integer from 0 to 3;
p is an integer from 0 to 6; and
q is an integer from 0 to 5; and
L is

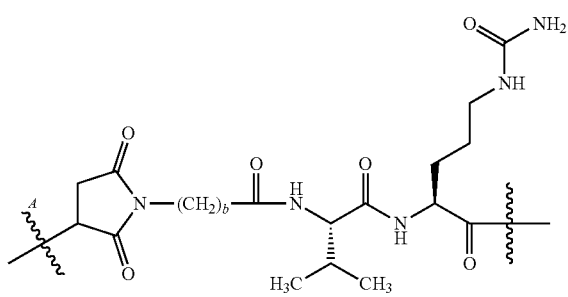

wherein:

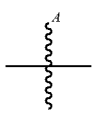

is a bond to the binding agent; and
b is an integer from 2 to 8.
In some embodiments,
A is:

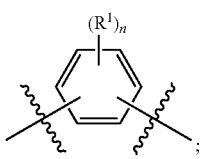

wherein
R¹ is, independently at each occurrence, is $C_{1-6}$ haloalkyl, or halo; and
n is 0, 1, or 2; and L is:

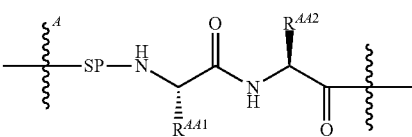

wherein:
SP is a spacer;

is the one or more bonds to the binding agent;
$R^{AA1}$ is an amino acid side chain; and
$R^{AA2}$ is an amino acid side chain.
In some embodiments, A is:

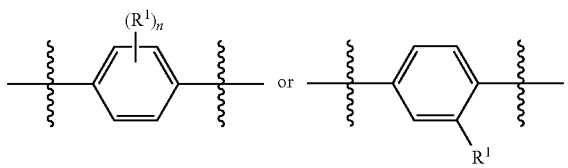

wherein:
R¹, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, hydroxyl, cyano, nitro,

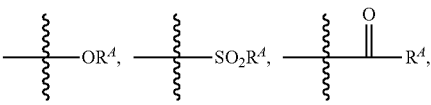

or azido,
wherein $R^A$ is alkyl or heteroalkyl;
wherein n is an integer from 0 to 4;
L is:

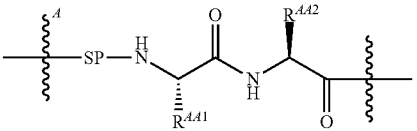

wherein:
SP is a spacer;

is the one or more bonds to the binding agent;
$R^{AA1}$ is an amino acid side chain; and
$R^{AA2}$ is an amino acid side chain.

In some embodiments,
A is:

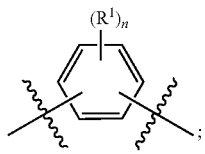

wherein
$R^1$ is, independently at each occurrence, is halo; and
n is 0, 1, or 2; and L is:

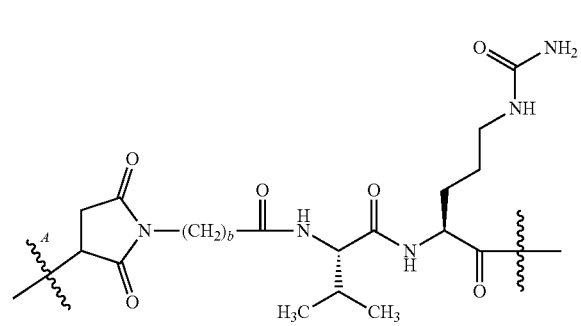

wherein:

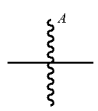

is a bond to the binding agent; and
b is an integer from 2 to 8.

In some embodiments, A is:

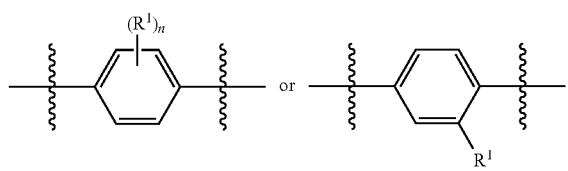

wherein:
$R^1$, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, hydroxyl, cyano, nitro,

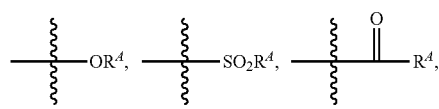

or azido,
wherein $R^A$ is alkyl or heteroalkyl;

L is:

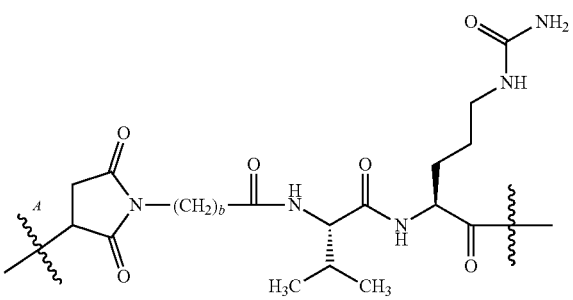

wherein:

is a bond to the binding agent;
wherein n is an integer from 0 to 4; and
b is an integer from 2 to 8.

In some embodiments,
A is:

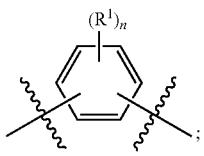

wherein
$R^1$ is, independently at each occurrence, is halo; and
n is 0, 1, or 2; and L is:

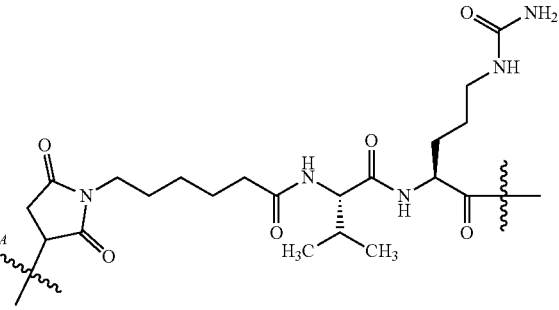

wherein

is a bond to the binding agent.

In some embodiments, A is:

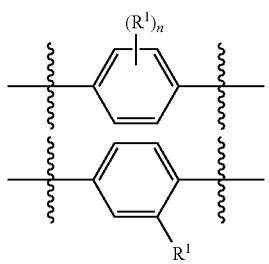

or

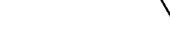

wherein:

$R^1$, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, hydroxyl, cyano, nitro,

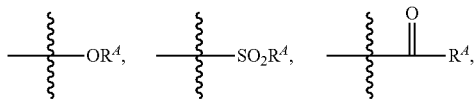

or azido, wherein $R^4$ is alkyl or heteroalkyl;

wherein n is an integer from 0 to 4;

L is:

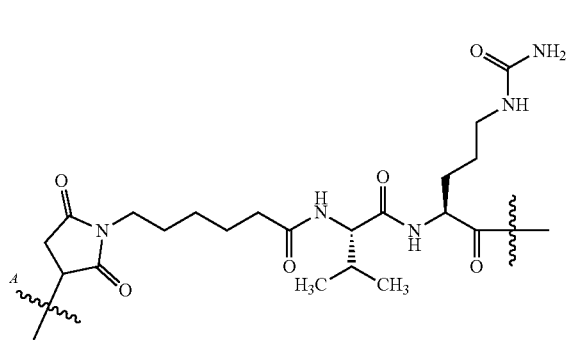

wherein

is a bond to the binding agent.

In some embodiments, A is:

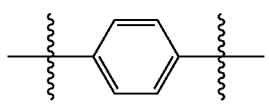

and

L is

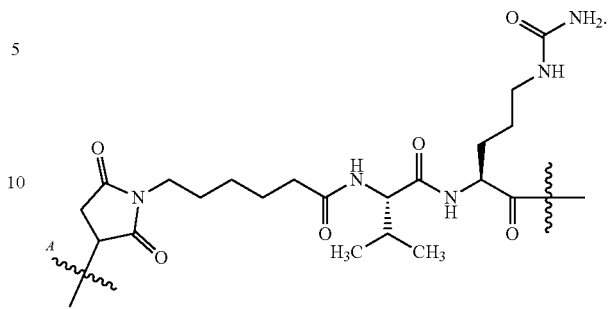

In some embodiments, A is:

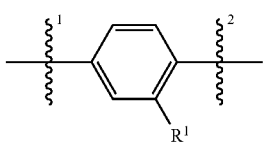

wherein:

$R^1$ is, independently at each occurrence, a hydrogen atom, alkyl, alkoxy, aryl, heteroalkyl, halo, haloalkoxy, haloalkyl, or haloalkoxy;

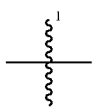

is the bond to the nitrogen atom; and

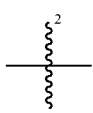

is the bond to the carbonyl. In some embodiments, $R^1$ is 1-methylethyl-thiol, phenyl, 2-fluorophenyl, pyridinyl, 4-pyridinyl, pyrrolidinyl, or 1-pyrrolidinyl. In some embodiments, $R^1$ is trifluoromethyl. In some embodiments, $R^1$ is methoxy. In some embodiments, $R^1$ is fluoro. In some embodiments, $R^1$ is hydrogen.

In some embodiments, A is:

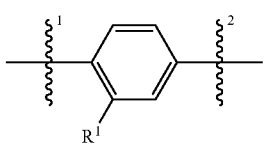

wherein:

$R^1$ is, independently at each occurrence, a hydrogen atom, alkyl, alkoxy, aryl, heteroalkyl, halo, haloalkyl, haloalkoxy;

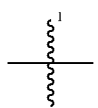

is the bond to the nitrogen atom; and

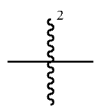

is the bond to the carbonyl. In some embodiments, $R^1$ is 1-methylethyl-thiol, phenyl, 2-fluorophenyl, pyridinyl, 4-pyridinyl, pyrrolidinyl, or 1-pyrrolidinyl. In some embodiments, $R^1$ is trifluoromethyl. In some embodiments, $R^1$ is methoxy. In some embodiments, $R^1$ is fluoro. In some embodiments, $R^1$ is hydrogen.

In some embodiments,

A is:

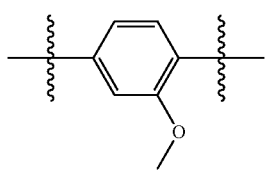

and

L is

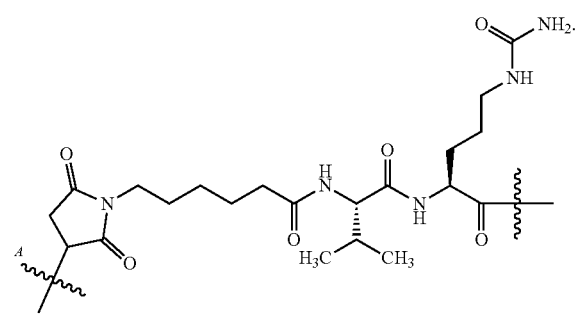

In some embodiments,

BA is an antibody,

A is:

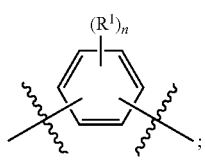

wherein $R^1$ is, independently at each occurrence, is halo; and n is 0, 1, or 2; and L is:

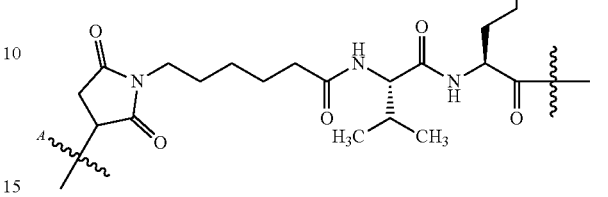

wherein

is a bond to the binding agent.

In some embodiments,

A is:

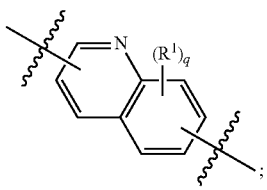

wherein $R^1$, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, cyano, nitro,

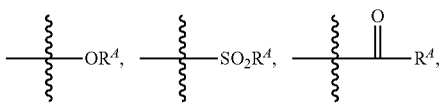

or azido; and q is an integer from 0 to 5; and

L is:

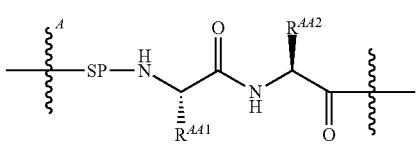

wherein:

SP is a spacer;

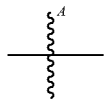

is the one or more bonds to the binding agent;
$R^{AA1}$ is an amino acid side chain; and
$R^{AA2}$ is an amino acid side chain.

In some embodiments, A is:

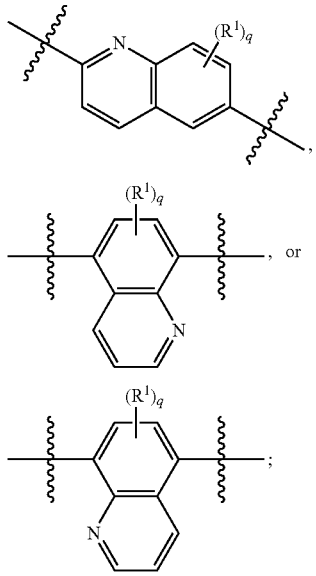

wherein:

$R^1$, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, cyano, nitro,

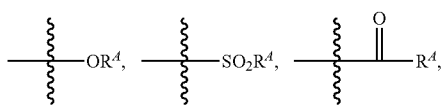

or azido;
wherein q is an integer from 0 to 5;
L is:

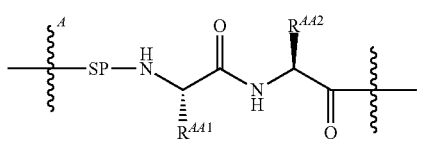

wherein:

SP is a spacer;

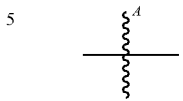

is the one or more bonds to the binding agent;
$R^{AA1}$ is an amino acid side chain; and
$R^{AA2}$ is an amino acid side chain.

In some embodiments,
A is:

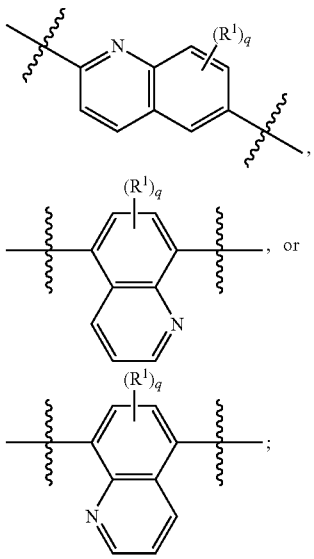

wherein:

$R^1$, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, cyano, nitro,

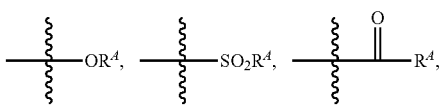

or azido;
wherein q is an integer from 0 to 5; and
L is:

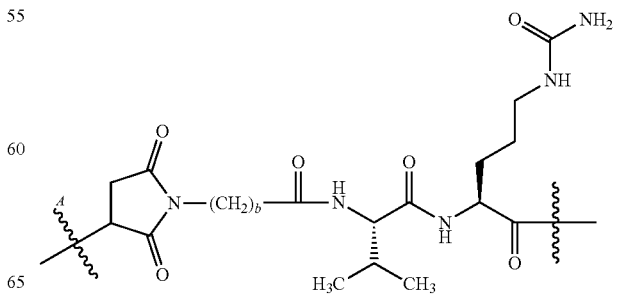

wherein:

is a bond to the binding agent; and
b is an integer from 2 to 8.
In some embodiments,
A is:

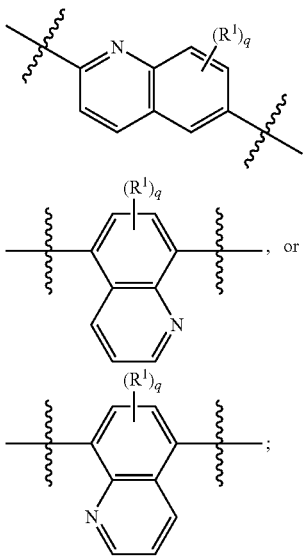

wherein:
R¹, independently at each occurrence, is alkyl, alkenyl, alkynyl, alkoxy, aryl, alkaryl, aralkyl, halo, haloalkoxy, haloalkyl, heteroaryl, heteroalkyl, heterocycloalkyl, cyano, nitro,

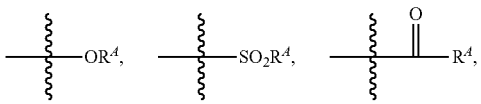

or azido; and
q is an integer from 0 to 5; and
L is:

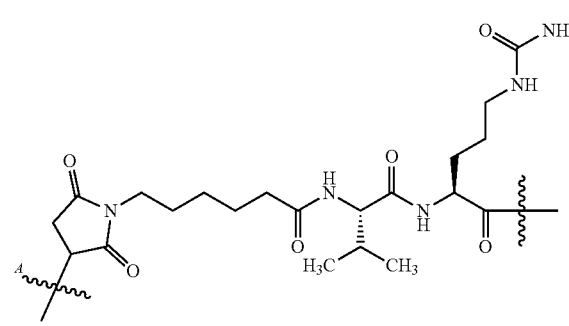

wherein

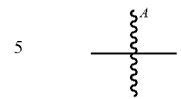

is a bond to the binding agent.
In some embodiments, A is:

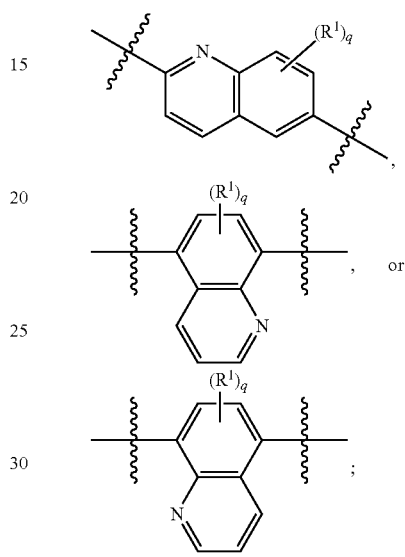

wherein:
R¹, independently at each occurrence, is alkyl, alkenyl, alkynyl, alkoxy, aryl, alkaryl aralkyl, halo, haloalkoxy, haloalkyl, heteroaryl, heteroalkyl, heterocycloalkyl, cyano, nitro,

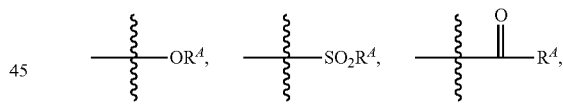

or azido;
wherein q is an integer from 0 to 5;
L is:

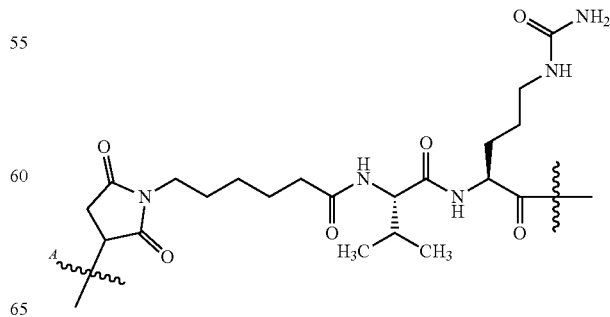

wherein

is a bond to the binding agent.
In some embodiments,
A is:

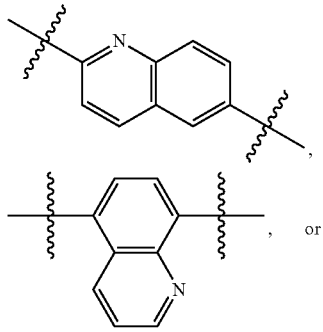, or

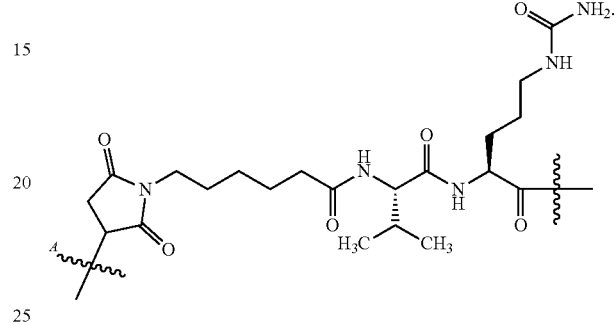

and
L is

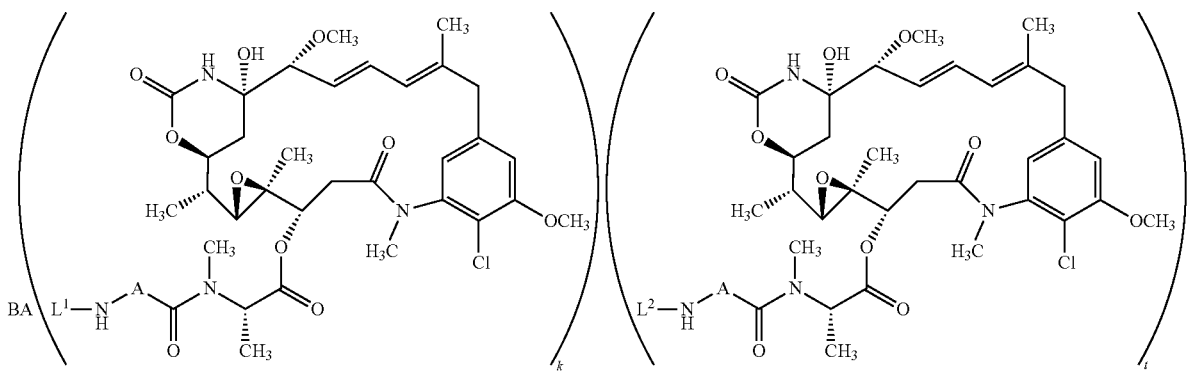

In some embodiments, the compound of Formula I is:

wherein A is arylene or heteroarylene, $L^1$ and $L^2$ are linkers, BA is a binding agent, k is an integer from 0 to 30, and t is an integer from 0 to 8. In some of these embodiments, $L^1$ is a linker which binds to the BA through a lysine residue. In some of these embodiments, the subscript, k, represents the number of linkers, $L^1$, bonded to the BA through lysine residues on the BA. In some of these embodiments, $L^2$ is a linker which binds to the BA through a cysteine residue. In some of these embodiments, the subscript, t, represents the number of linkers, $L^2$, bonded to the BA through cysteine residues on the BA. In some embodiments, when the linker, $L^2$, is a monodentate linker, t is an integer from 0 to 8. In some embodiments, when the linker, $L^2$, is a bidentate linker, t is an integer from 0 to 4. In some of these examples, the sum of k+t is equal to 1-8.

In some embodiments, the compound of Formula I is:

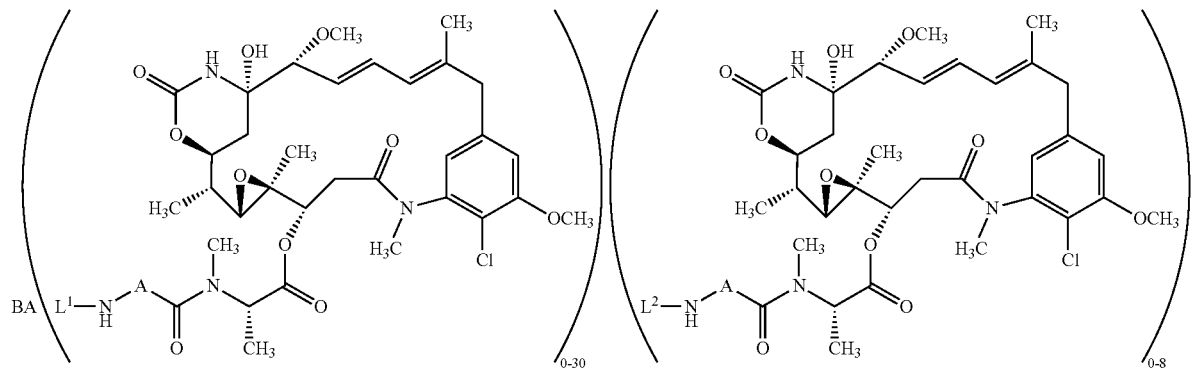

wherein A is arylene or heteroarylene, $L^1$ and $L^2$ are linkers, and BA is a binding agent. In some of these embodiments, $L^1$ is a linker which binds to the BA through a lysine residue. In some of these embodiments, $L^2$ is a linker which binds to the BA through a cysteine residue.

In some embodiments, the compound of Formula I is:

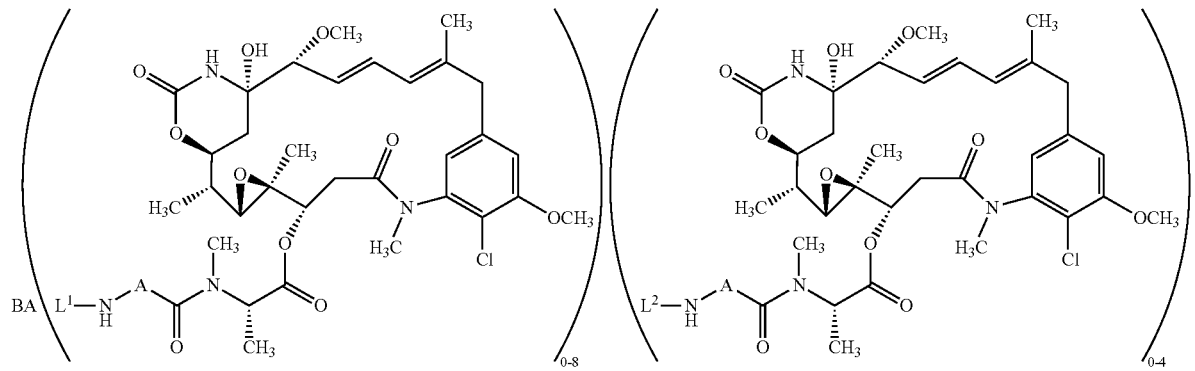

wherein A is arylene or heteroarylene, $L^1$ and $L^2$ are linkers, and BA is a binding agent. In some of these embodiments, $L^1$ is a linker which binds to the BA through a lysine residue. In some of these embodiments, $L^2$ is a linker which binds to the BA through a cysteine residue.

In some embodiments, A is:

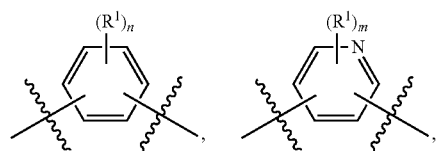

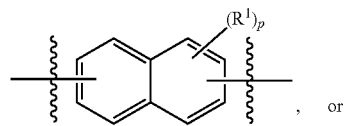, or

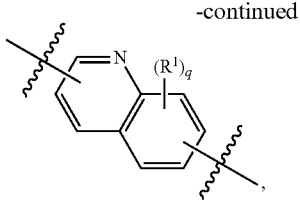, wherein:

$R^1$ is, independently at each occurrence, halo, haloalkyl, haloalkoxy, hydroxyl, alkyl, alkenyl, alkynyl, alkoxy, haloalkoxy, aryl, alkaryl, aralkyl, heteroaryl, heteroalkyl, heterocycloalkyl, cyano, nitro,

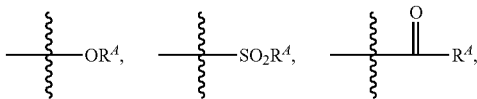

or azido, wherein $R^A$ is alkyl or heteroalkyl;

n is an integer from 0 to 4;
m is an integer from 0 to 3;
p is an integer from 0 to 6; and
q is an integer from 0 to 5.
In some embodiments, the linker is:

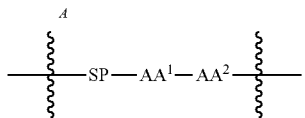

wherein:
SP is a spacer;

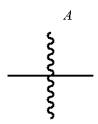

is one or more bonds to the binding agent;
$AA^1$ is an amino acid; and
$AA^2$ is an amino acid.

The spacer is a divalent moiety that connects the $AA^1$-$AA^2$ moiety to the binding agent (BA). Suitable spacers include, but are not limited to, those comprising alkylene or polyethylene glycol. The ends of the spacers, i.e., the portion of the spacer directly bonded to the binding agent or $AA^1$, can be moieties derived from reactive moieties that are used for purposes of coupling the antibody or $AA^1$ to the spacer during the chemical synthesis of the conjugate.

In some embodiments, the spacer comprises an alkylene. In some embodiments, the spacer comprises a $C_{5-7}$ alkylene. In some embodiments, the spacer is:

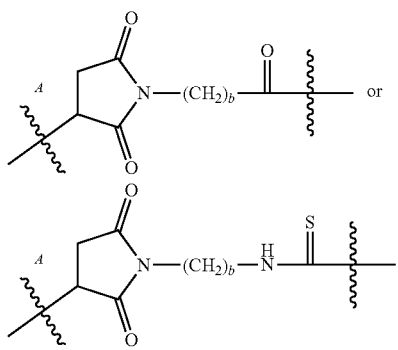

wherein:

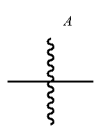

is a bond to the binding agent; and
b is an integer from 2 to 8.

In some embodiments, the spacer is:

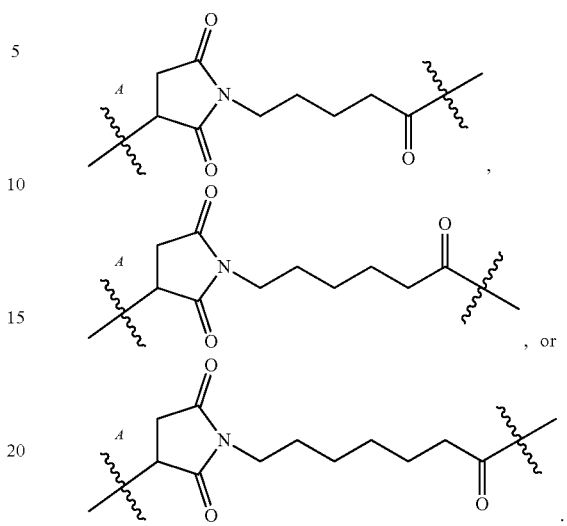

wherein:

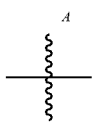

is a bond to the binding agent.
In some embodiments, the spacer is:

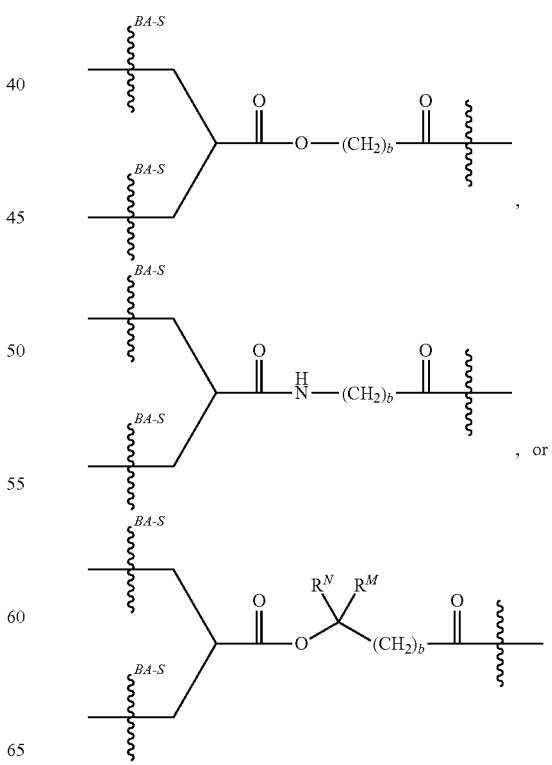

wherein:
$R^N$ is a hydrogen atom or alkyl;
$R^M$ is alkyl;
the two bonds represented by

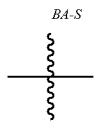

are bonds to cysteines of a binding agent; and
b is an integer from 2 to 8.
In some embodiments, the spacer is:

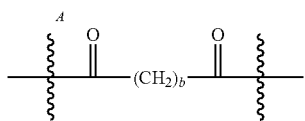

wherein:

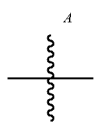

is a bond to the binding agent; and
b is an integer from 2 to 8.
In some embodiments, the spacer is:

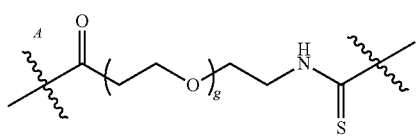

wherein:

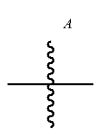

is a bond to the binding agent; and
g is an integer from 2 to 20. In some embodiments, g is 2-8. In some embodiments, g is 2, 4, 6, or 8.
In some embodiments, the spacer is:

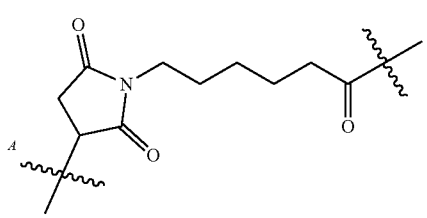

In some embodiments, the spacer is:

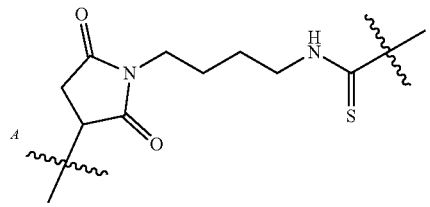

In some embodiments, the spacer is:

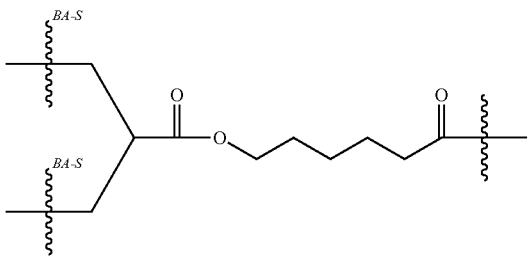

In some embodiments, the spacer is:

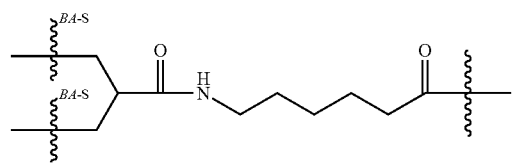

In some embodiments, the spacer is:

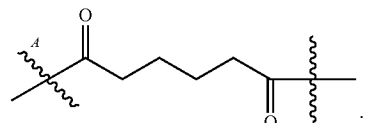

In some embodiments, the spacer is:

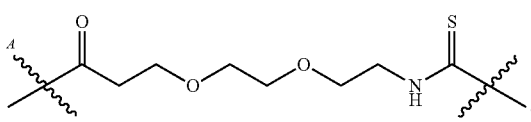

In some embodiments, the spacer is:

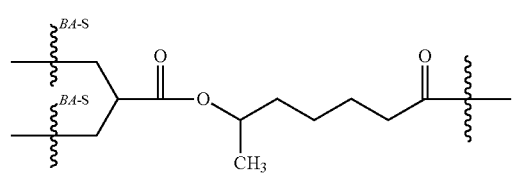

85

In some embodiments, the spacer is:

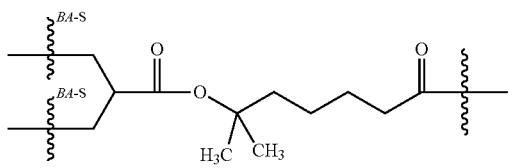

In some embodiments, the spacer is:

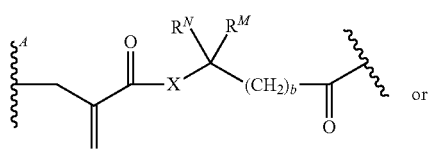 or

86

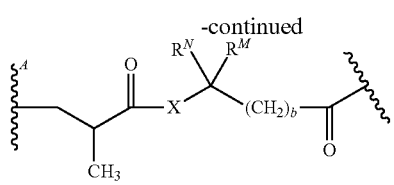

wherein $\xi^A$ is a bond to the binding agent;
X is N or O; $R^N$ and $R^M$ are each, independently, hydrogen or alkyl; and b is an integer from 1 to 8.

In some embodiments, $AA^1\text{-}AA^2$ is: valine-citrulline, citrulline-valine, lysine-phenylalanine, phenylalanine-lysine, valine-asparagine, asparagine-valine, threonine-asparagine, asparagine-threonine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some embodiments, $AA^1\text{-}AA^2$ is: valine-citrulline or citrulline-valine. In some embodiments, $AA^1\text{-}AA^2$ is: valine-citrulline.

In some embodiments, the compound of Formula I is:

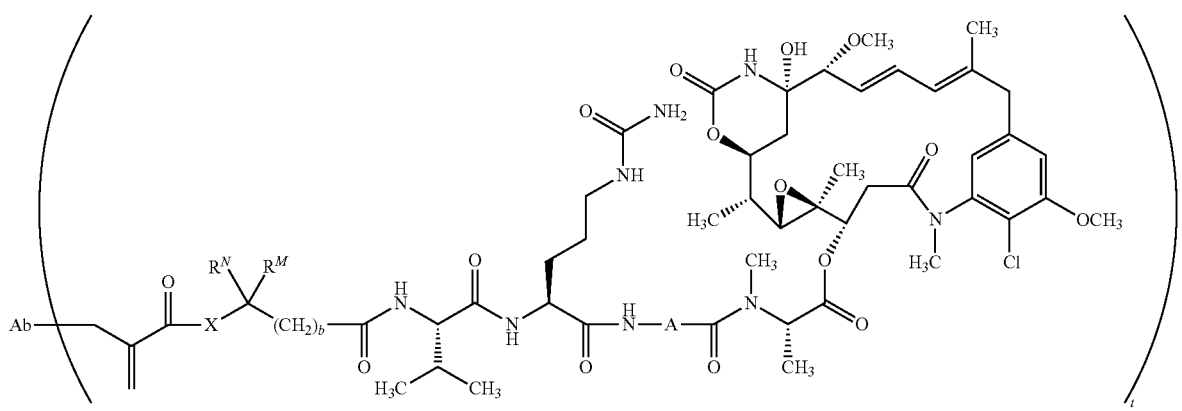

or

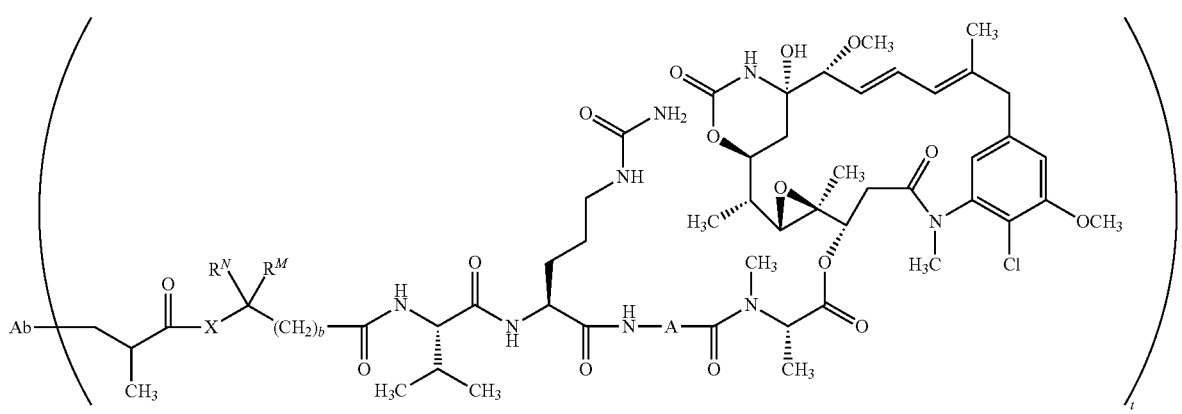

wherein X is N or O,
$R^N$ and $R^M$ are each, independently, hydrogen or aryl,
b is an integer from 1 to 8,
A is aryl or heteroaryl, and
t is an integer from 1-8.

In some embodiments, the compound of Formula I is:
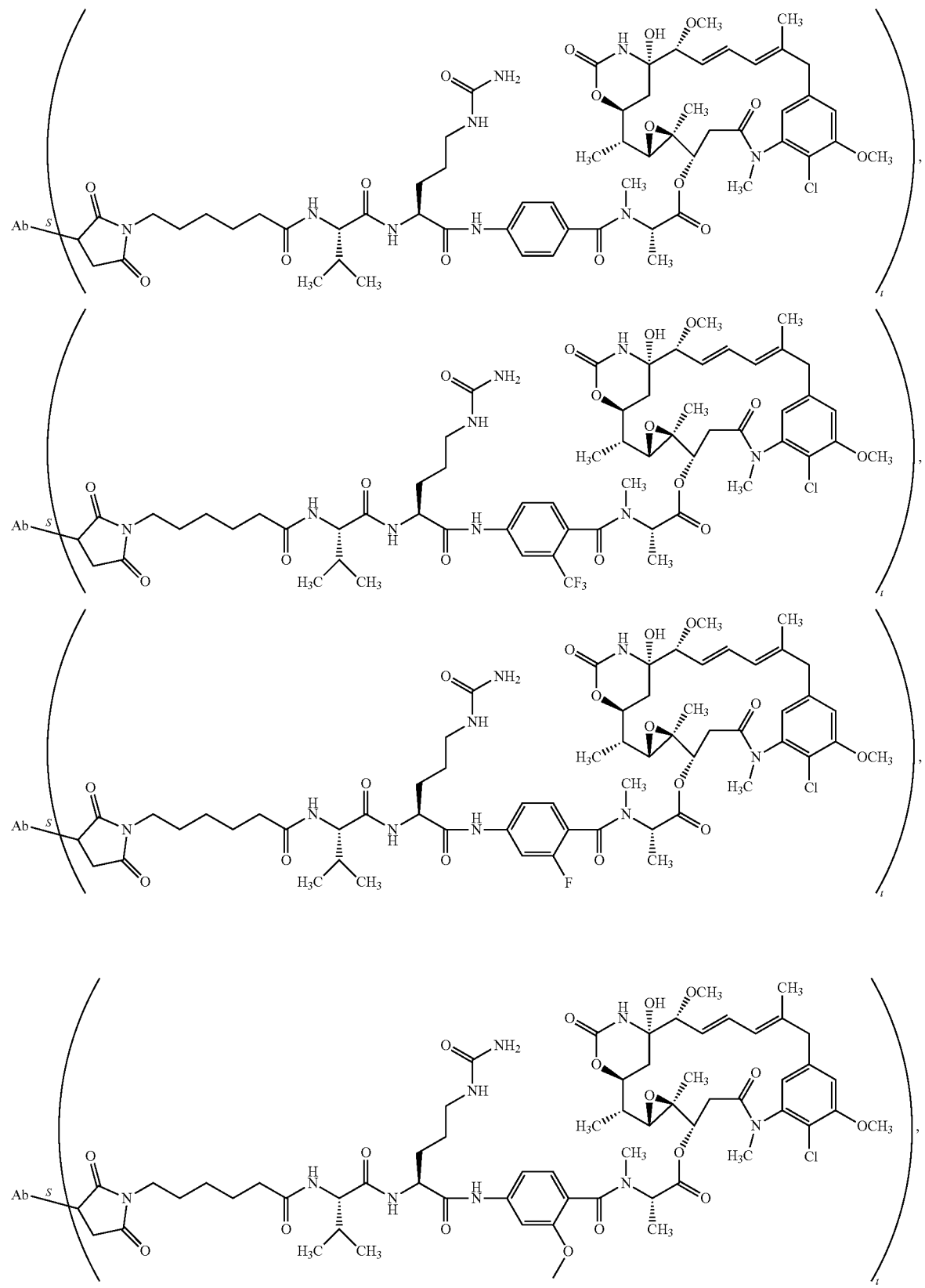

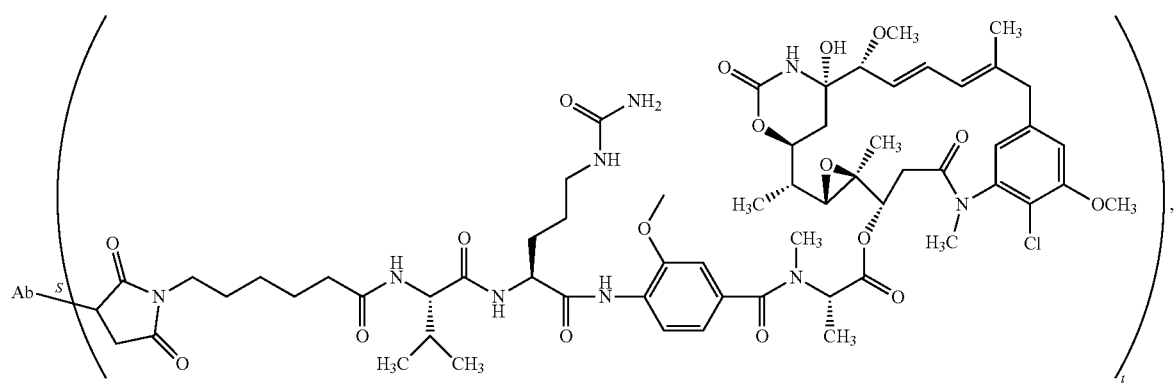
,
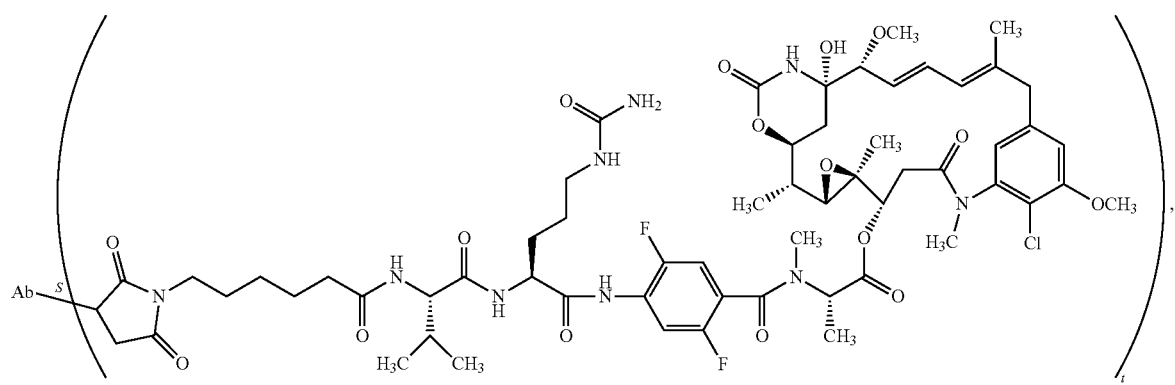
,
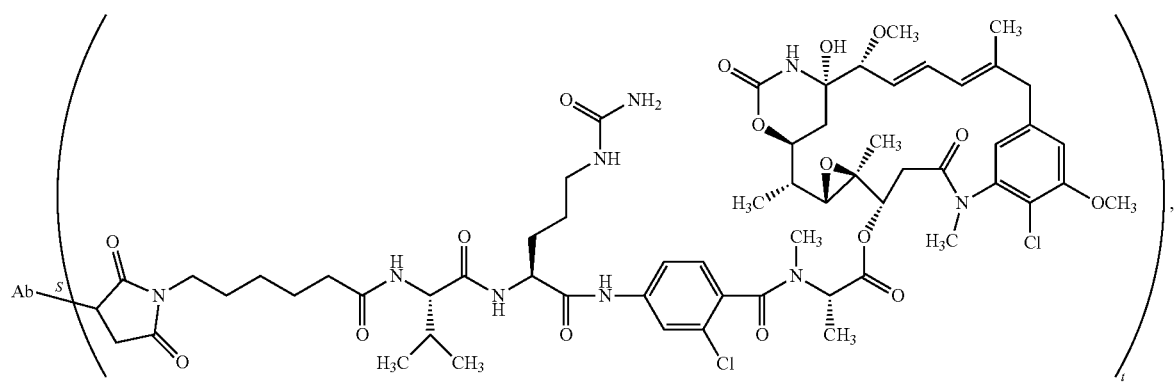
,
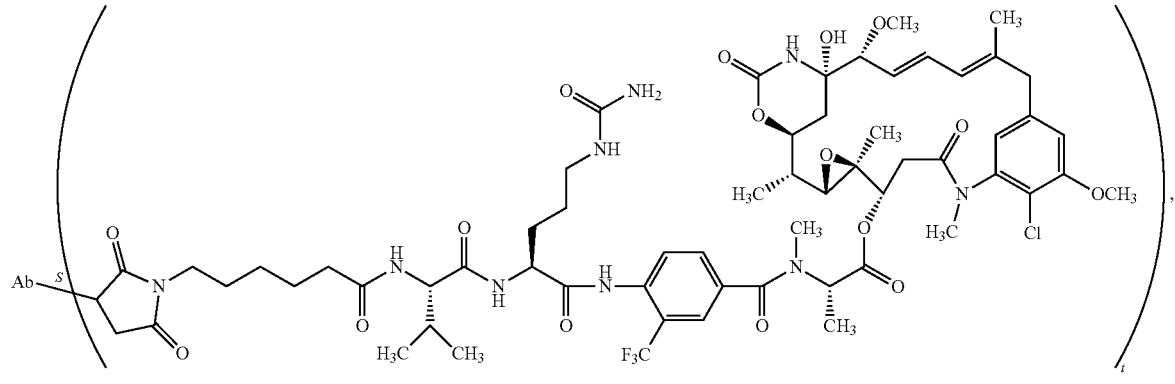
,

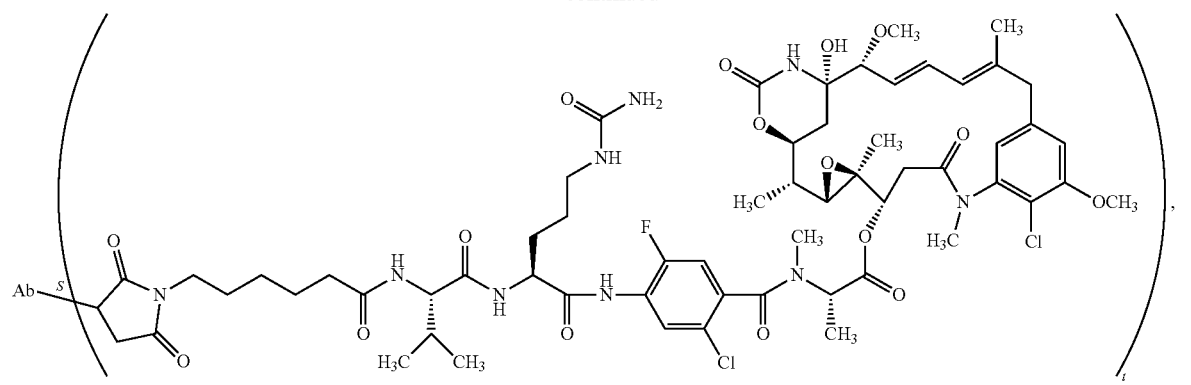,
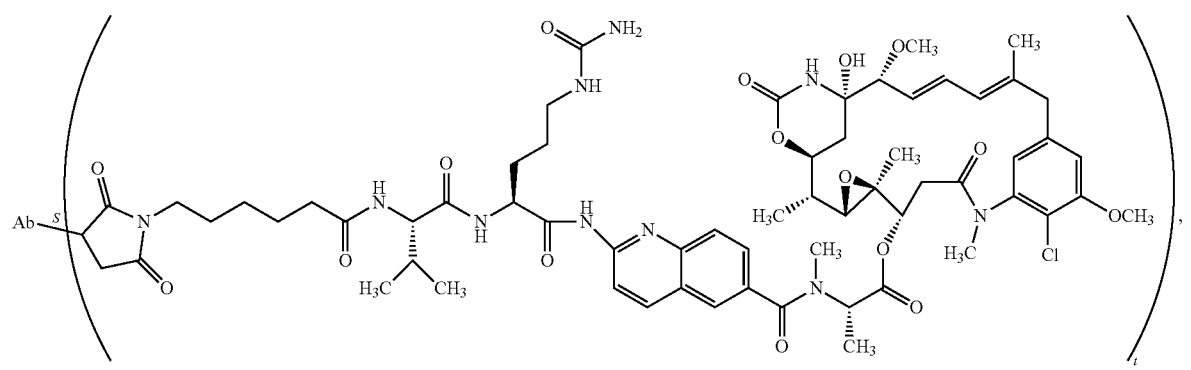,
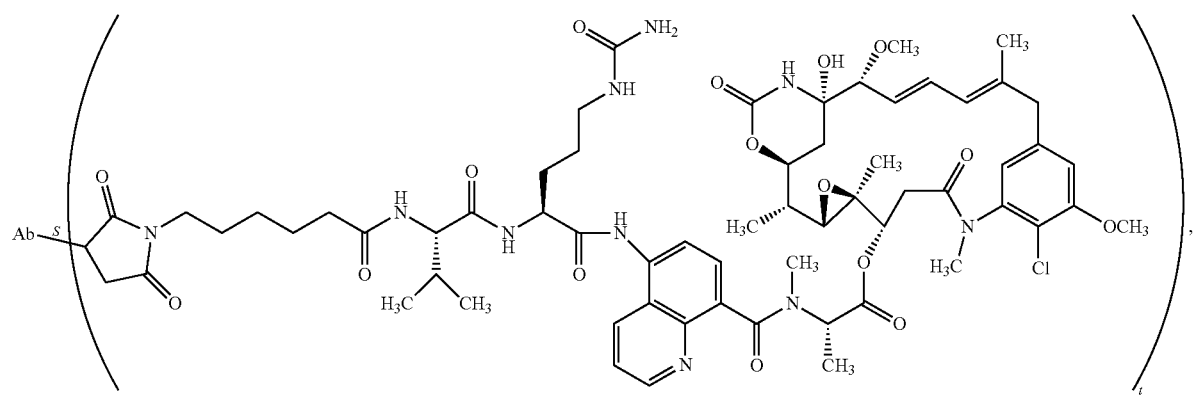,
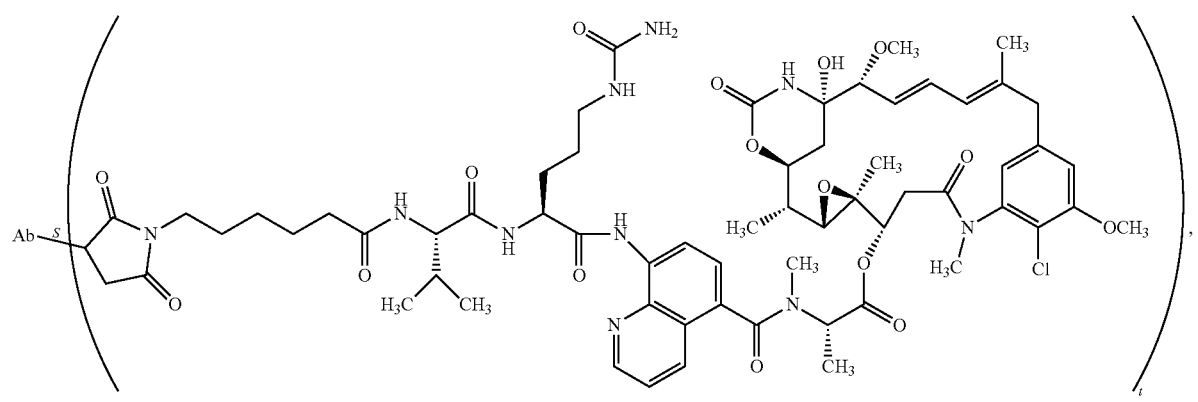,

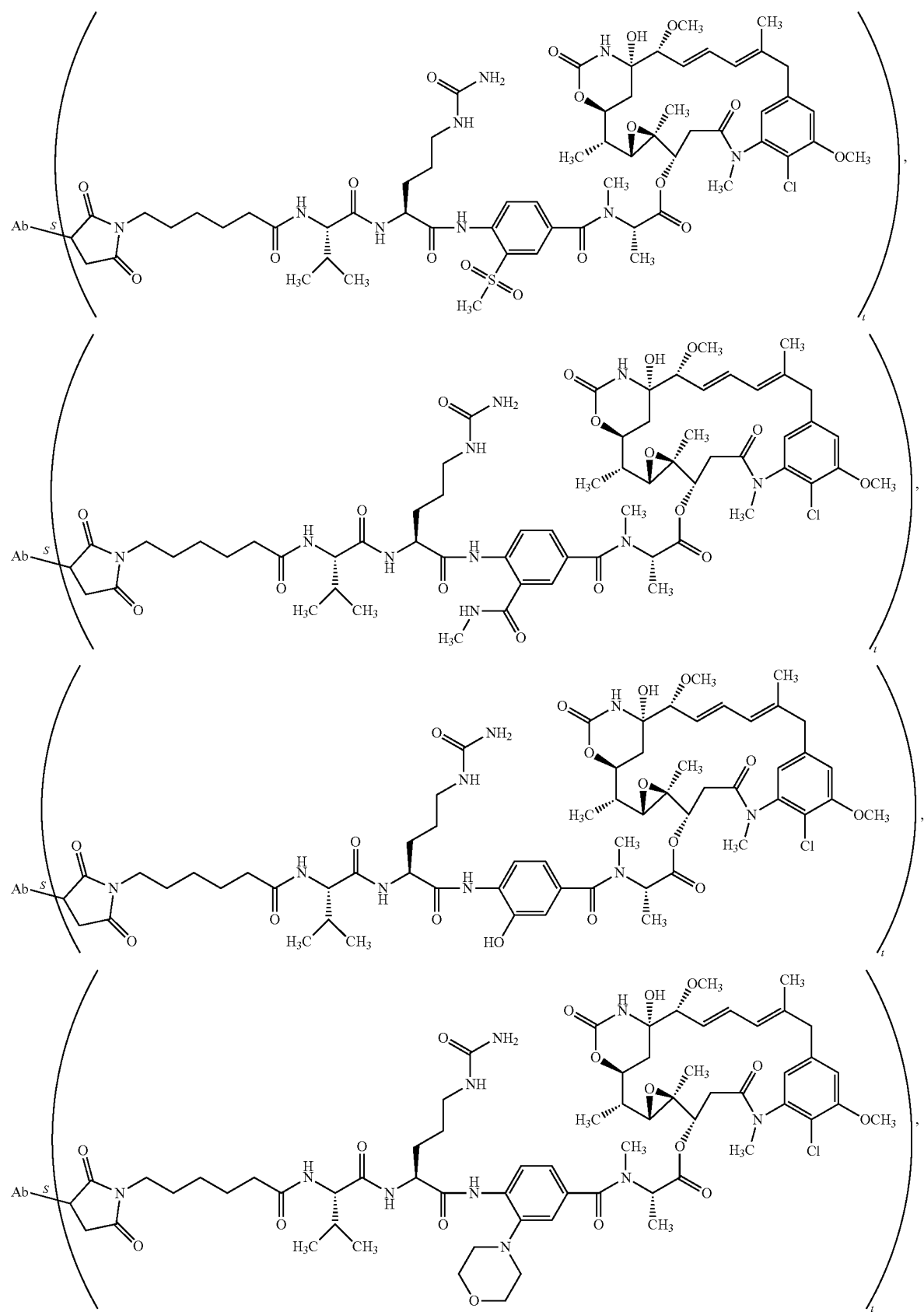

-continued
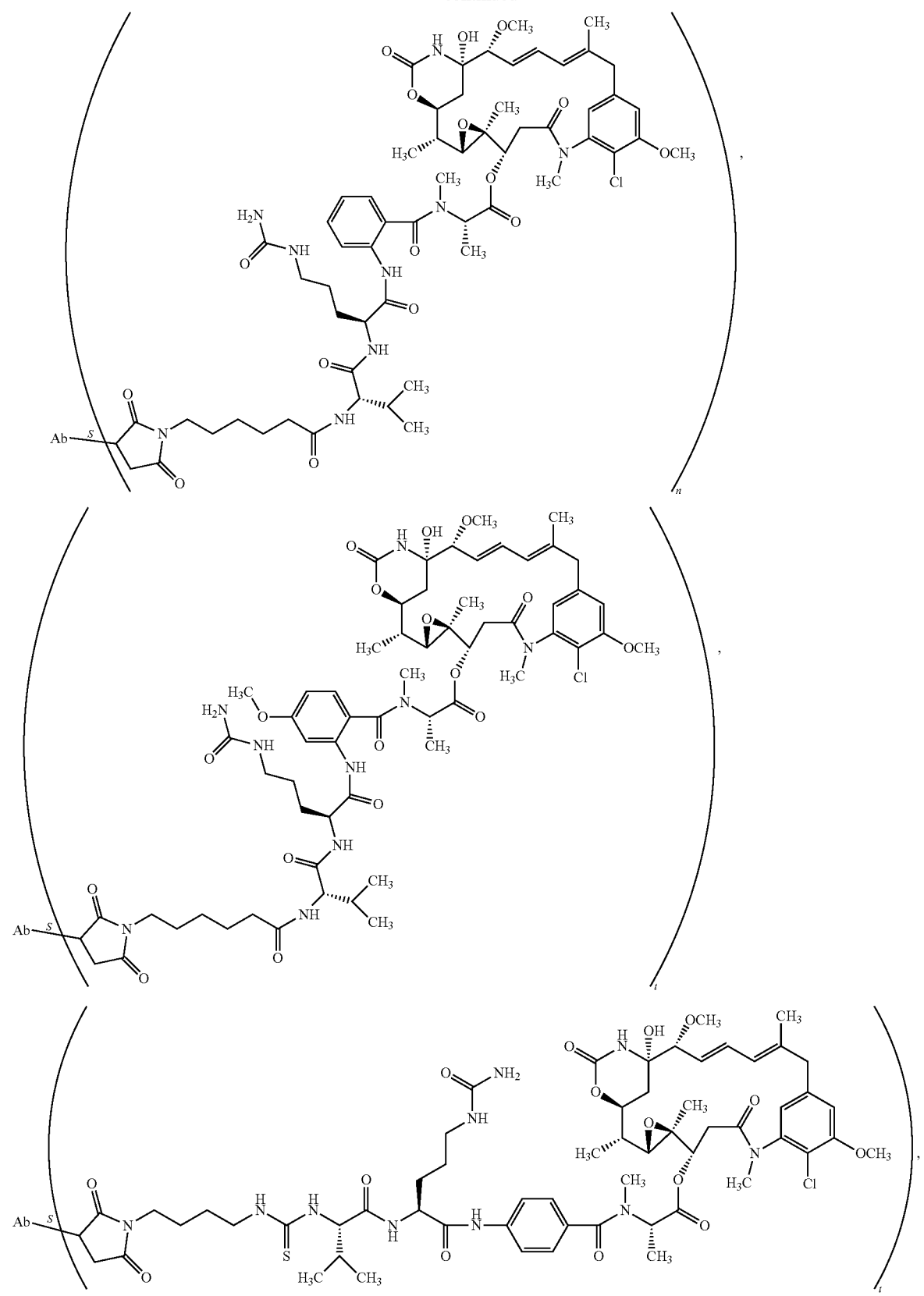

-continued
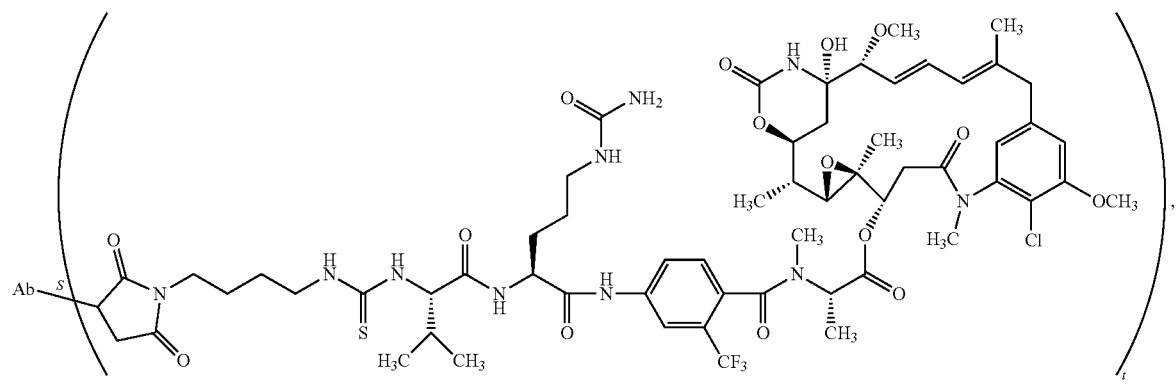
,
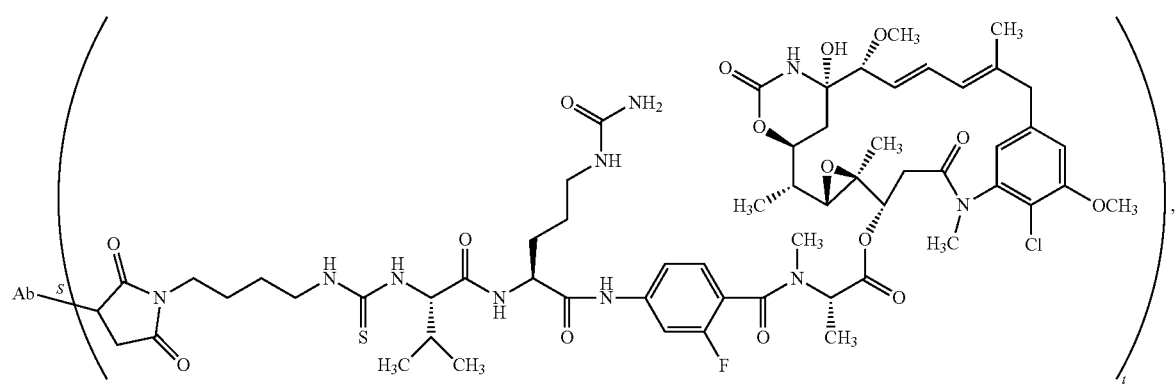
,
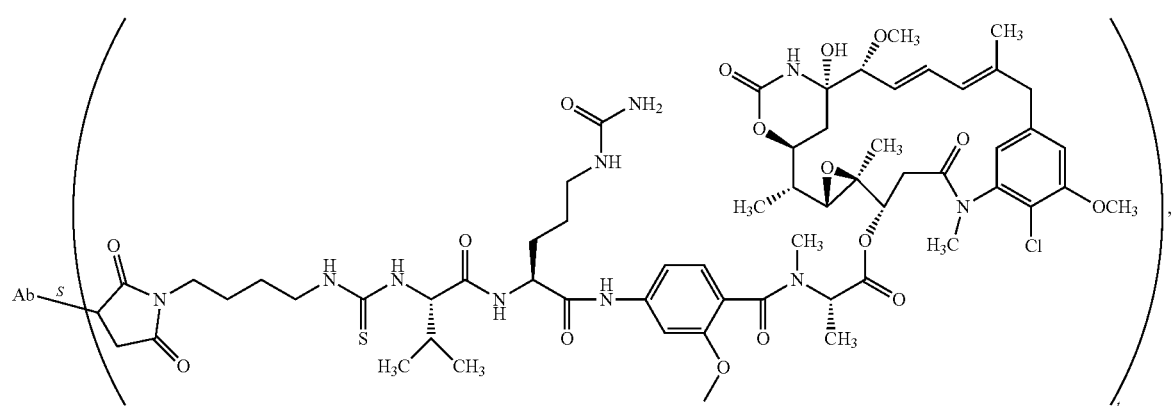
,
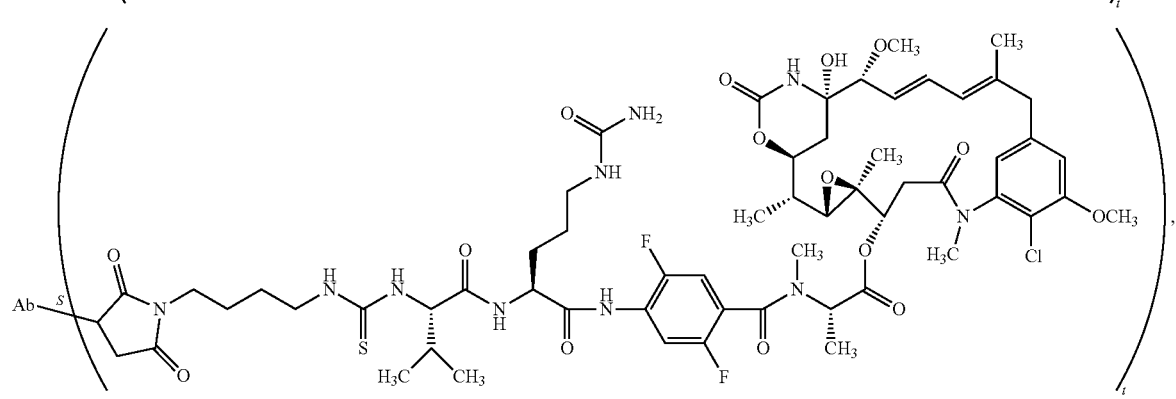
,

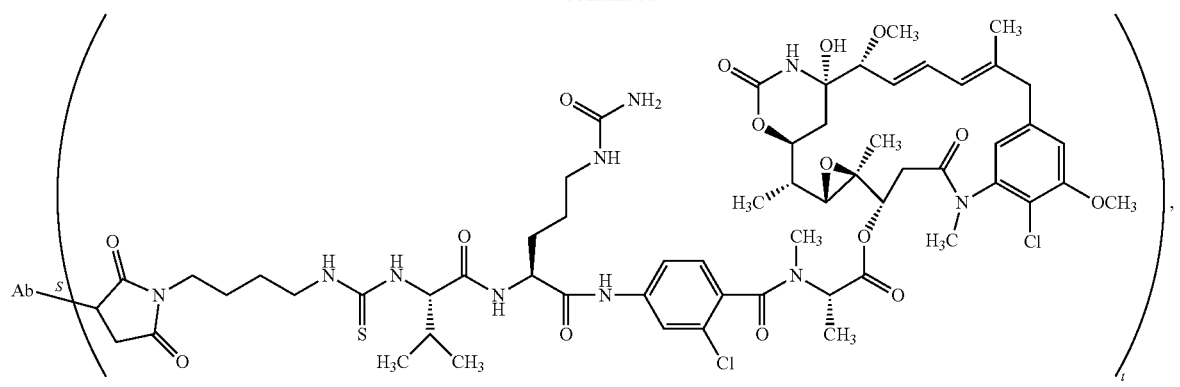
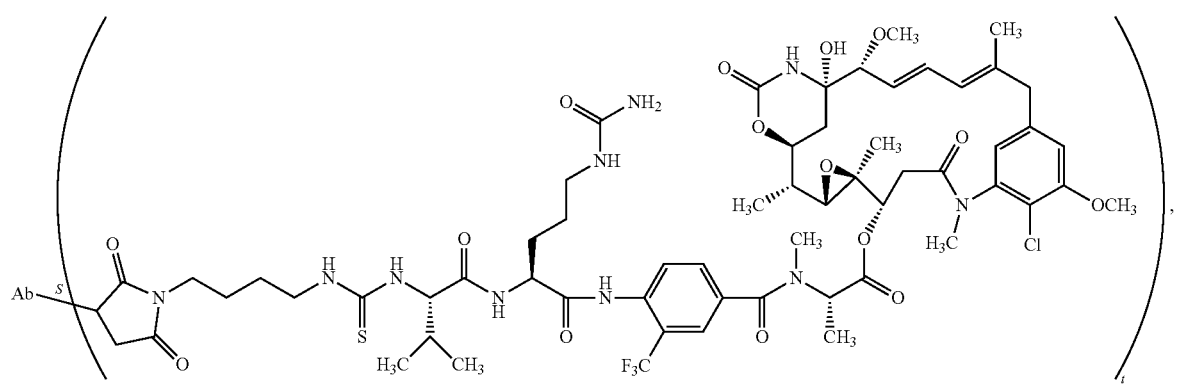
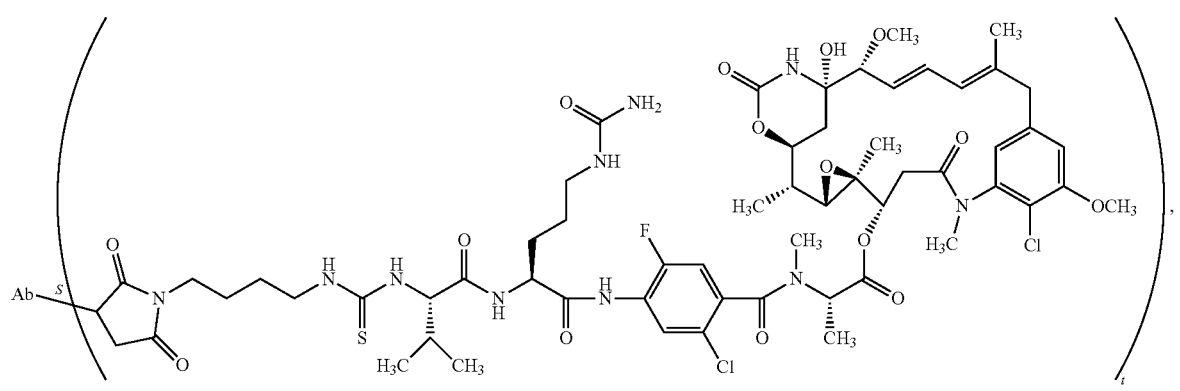
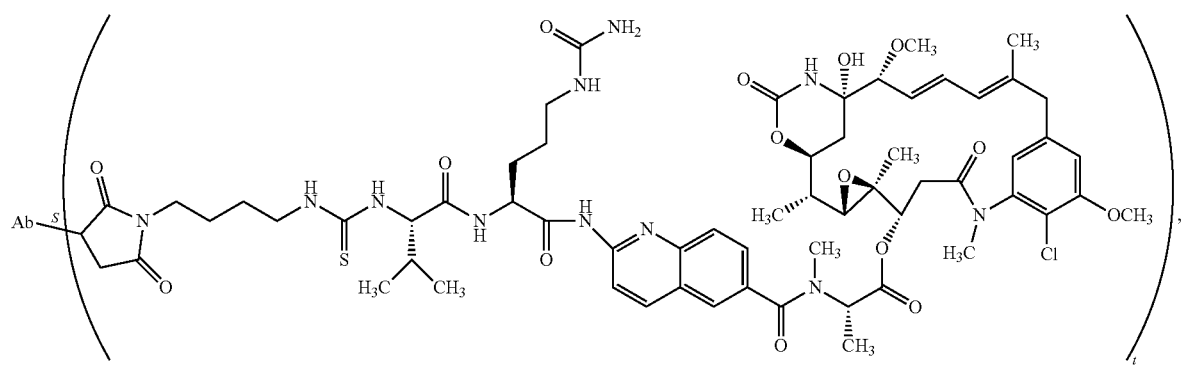

101 102
-continued
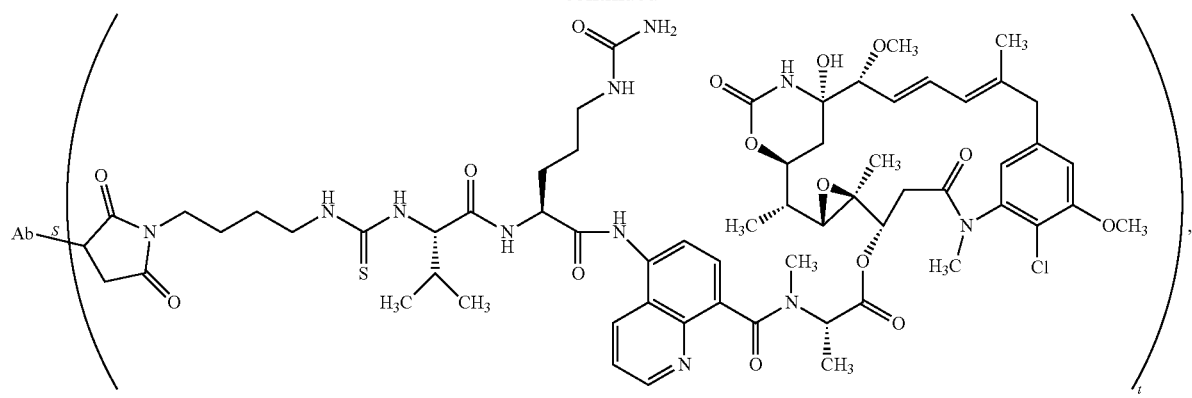
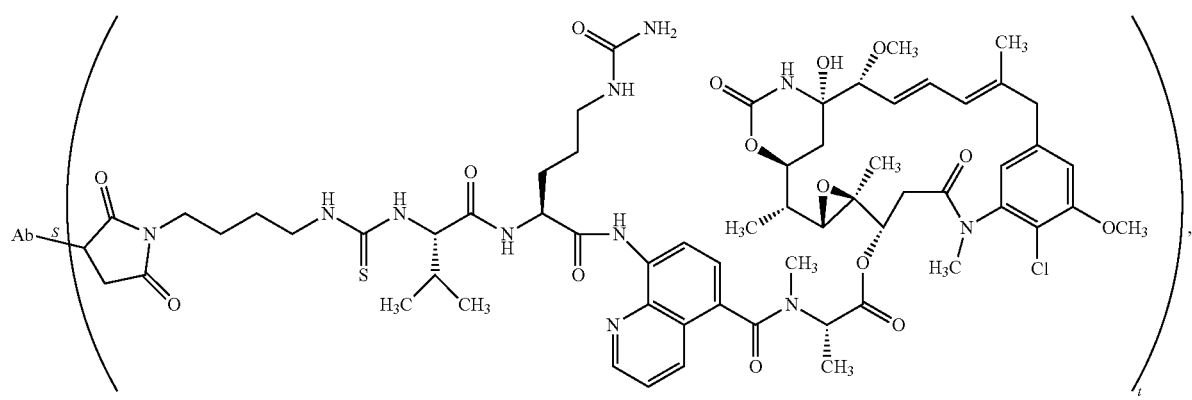
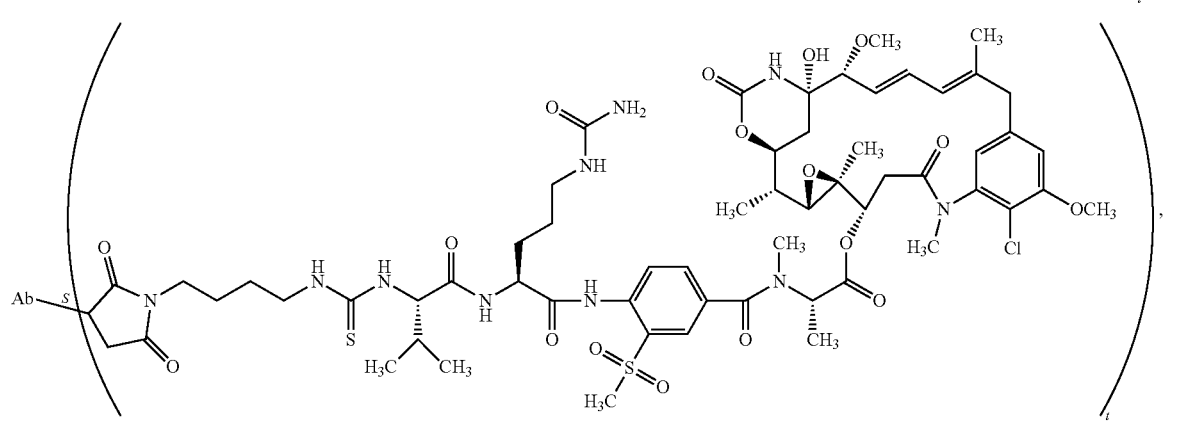
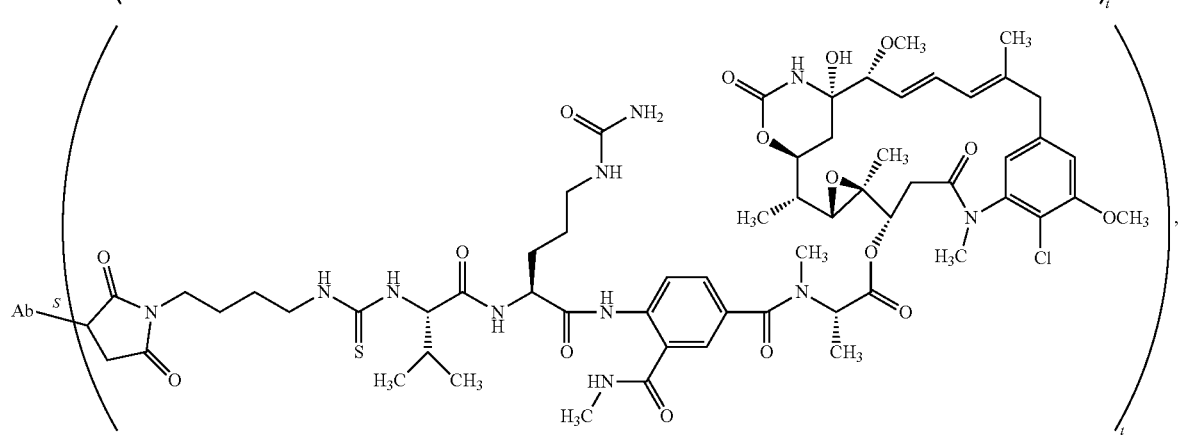

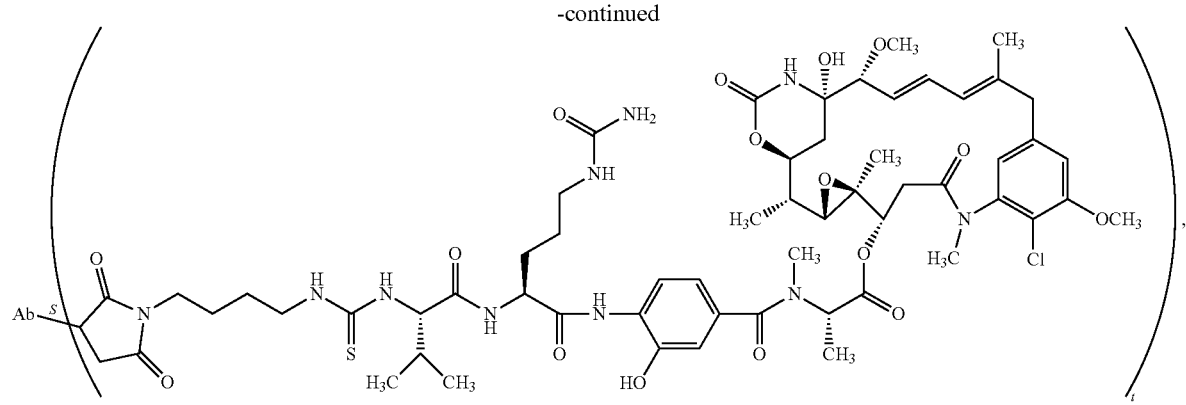
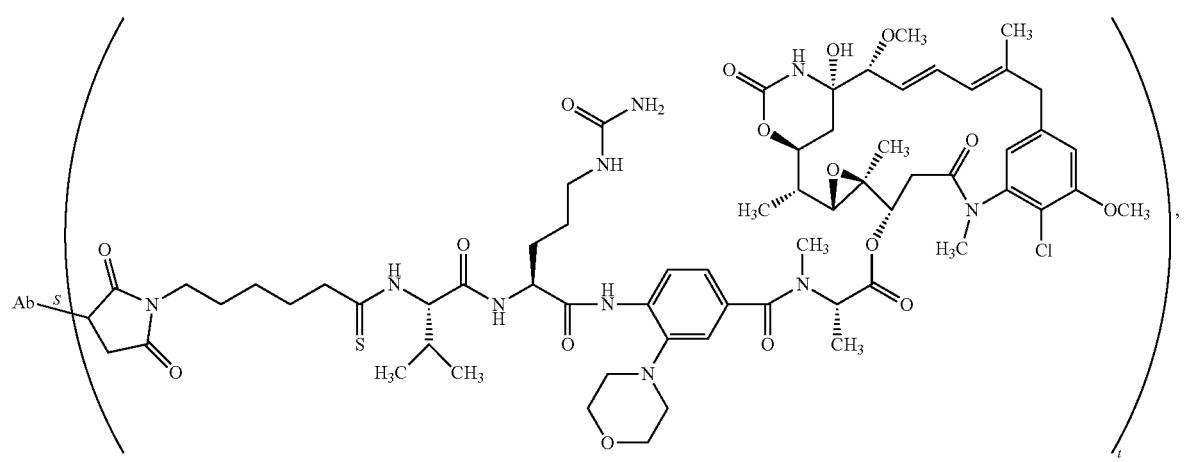
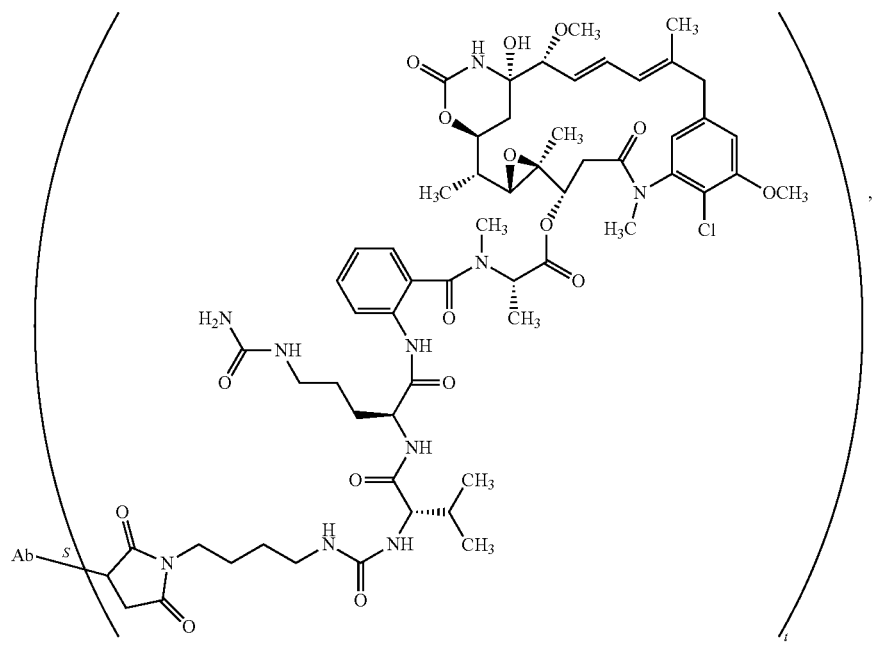

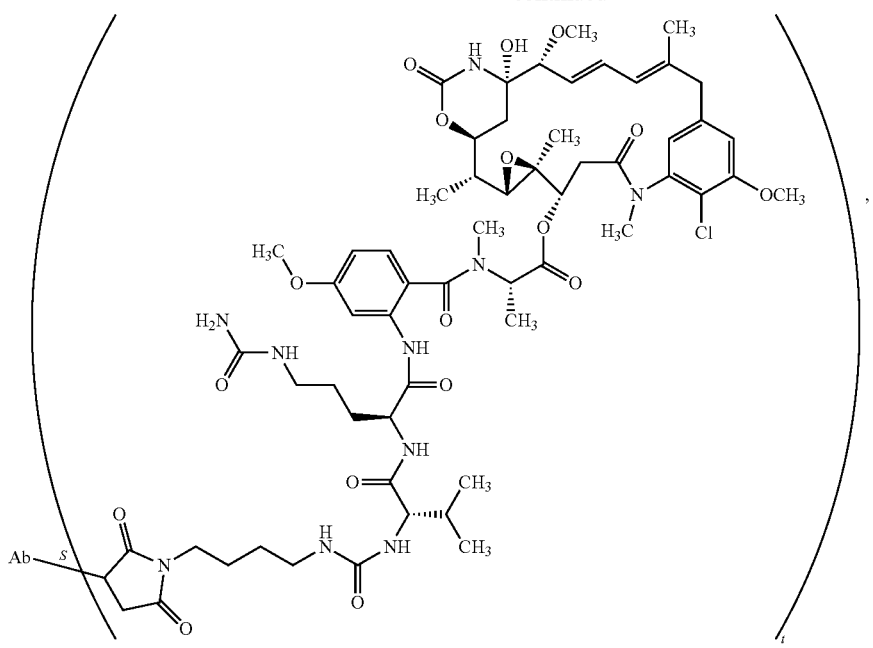
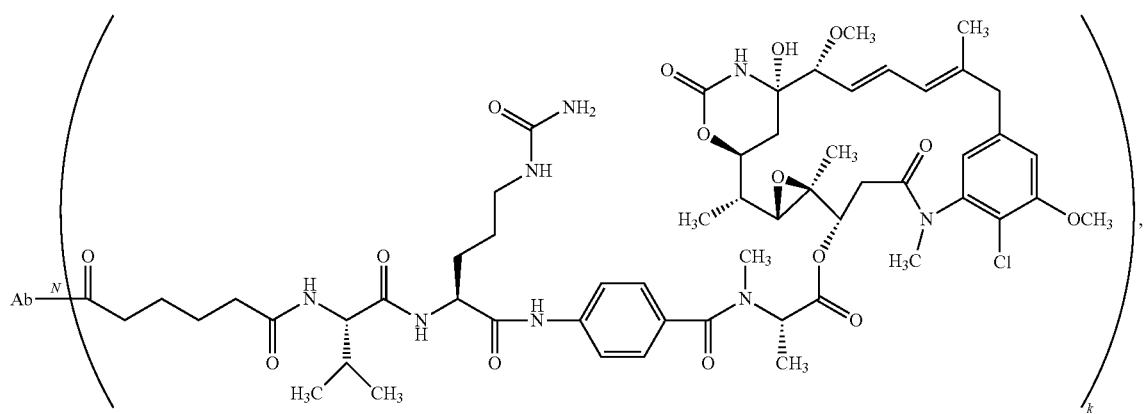
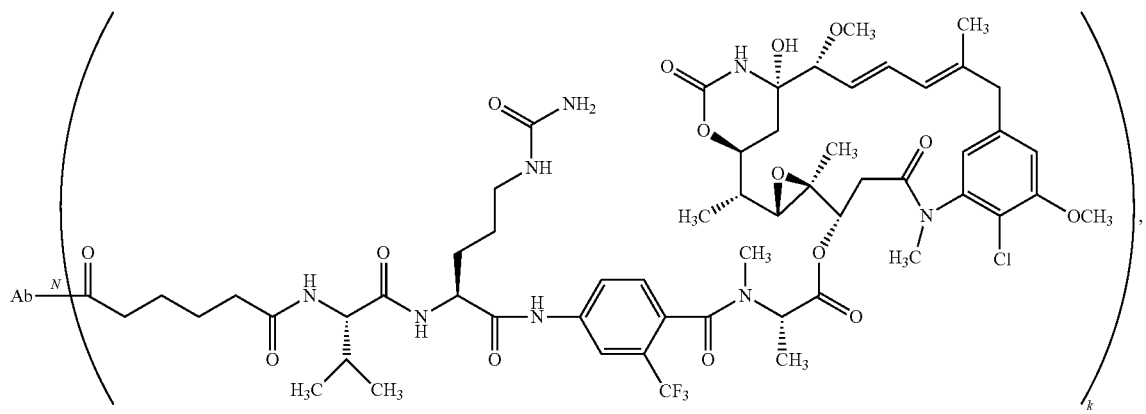

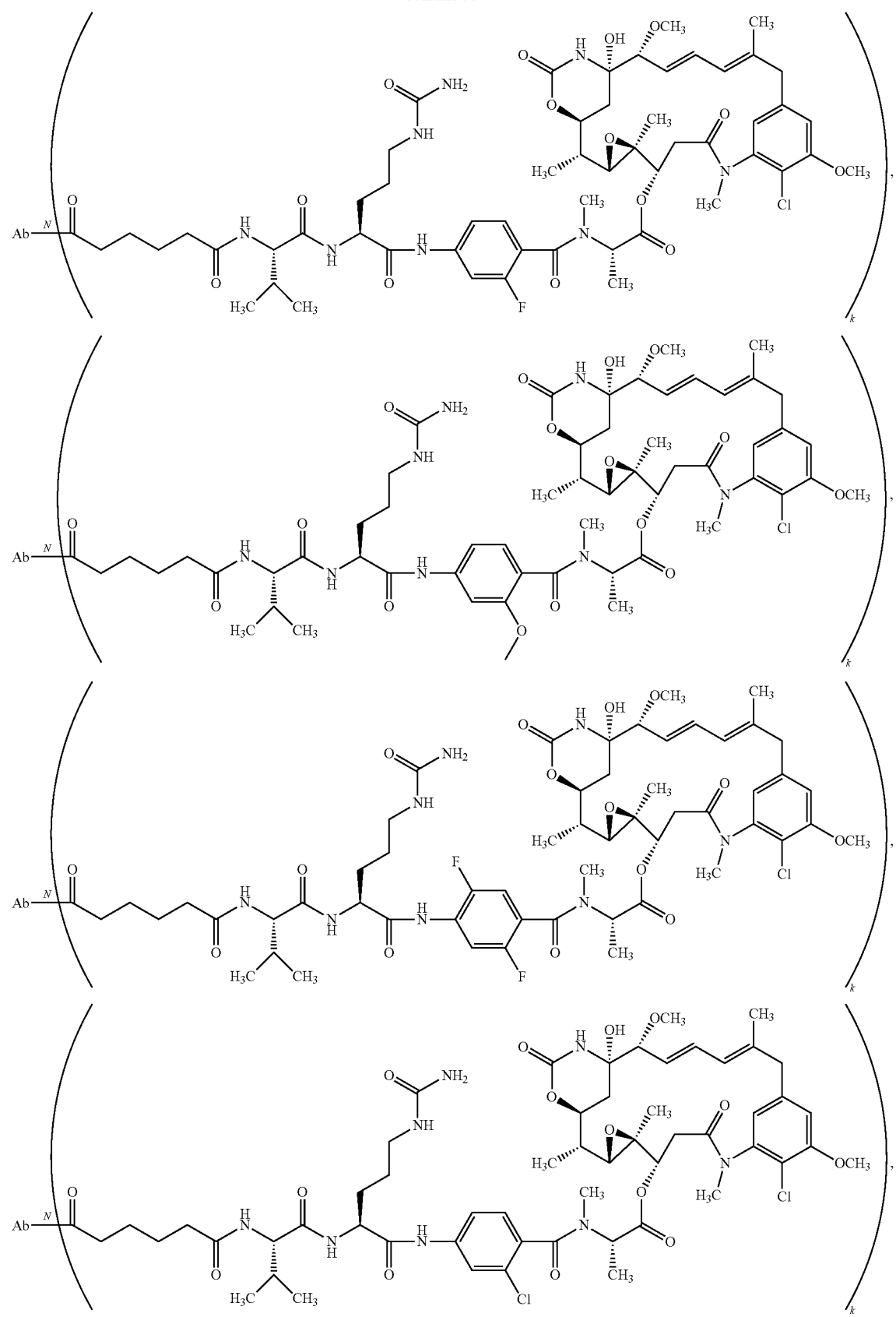

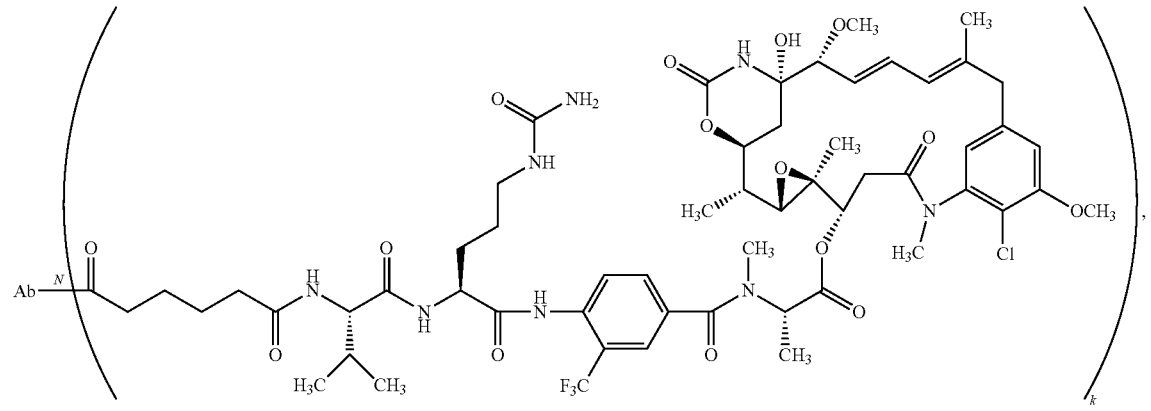
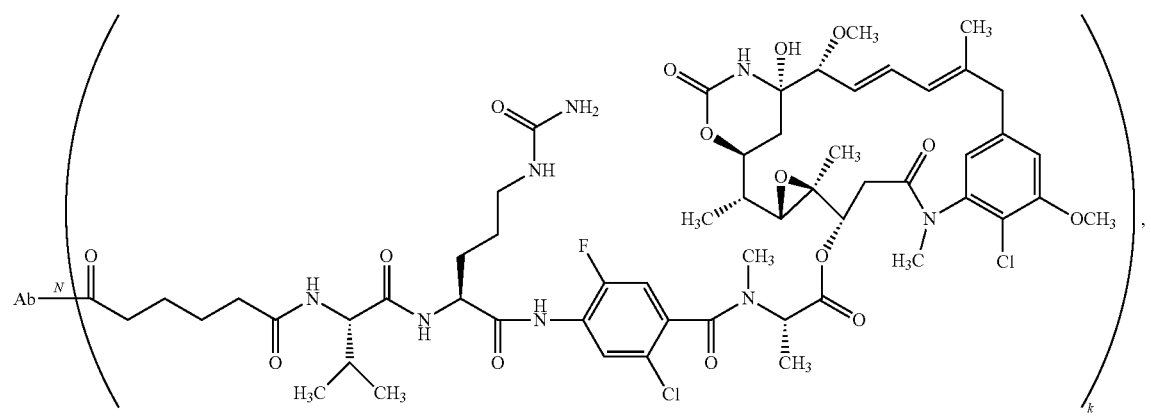
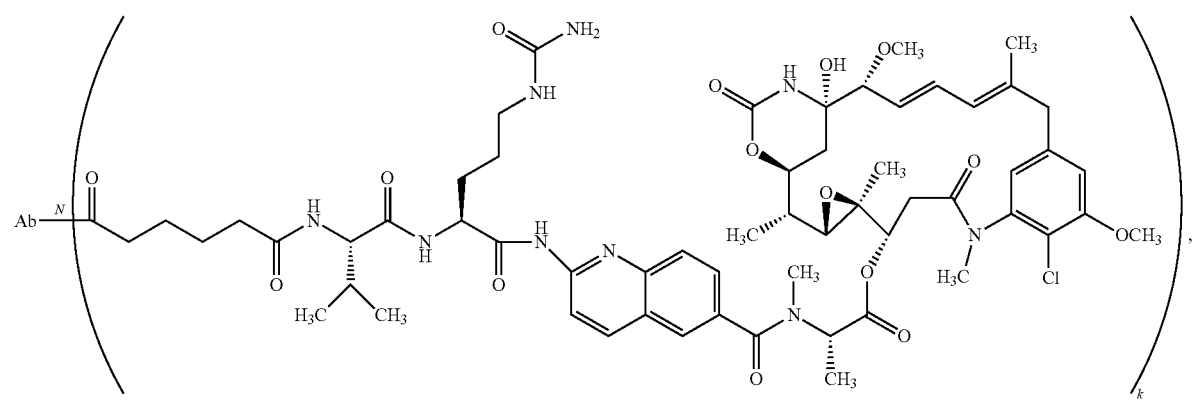
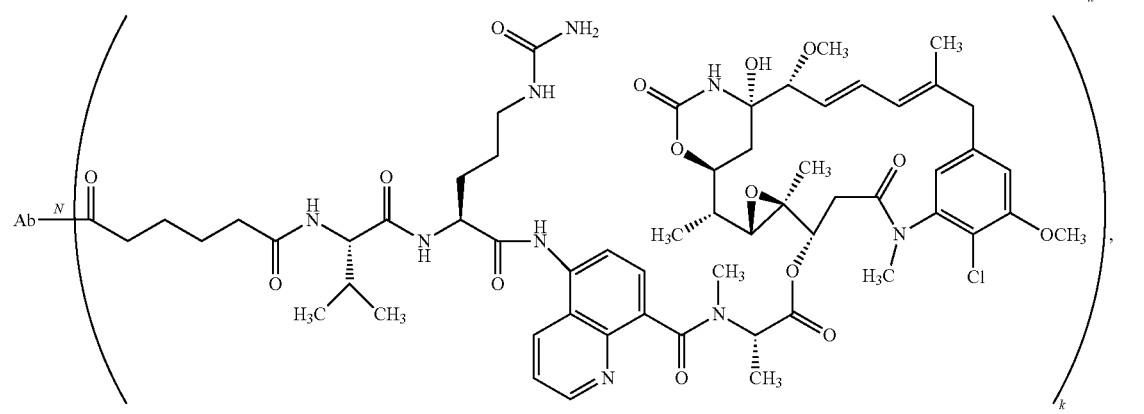

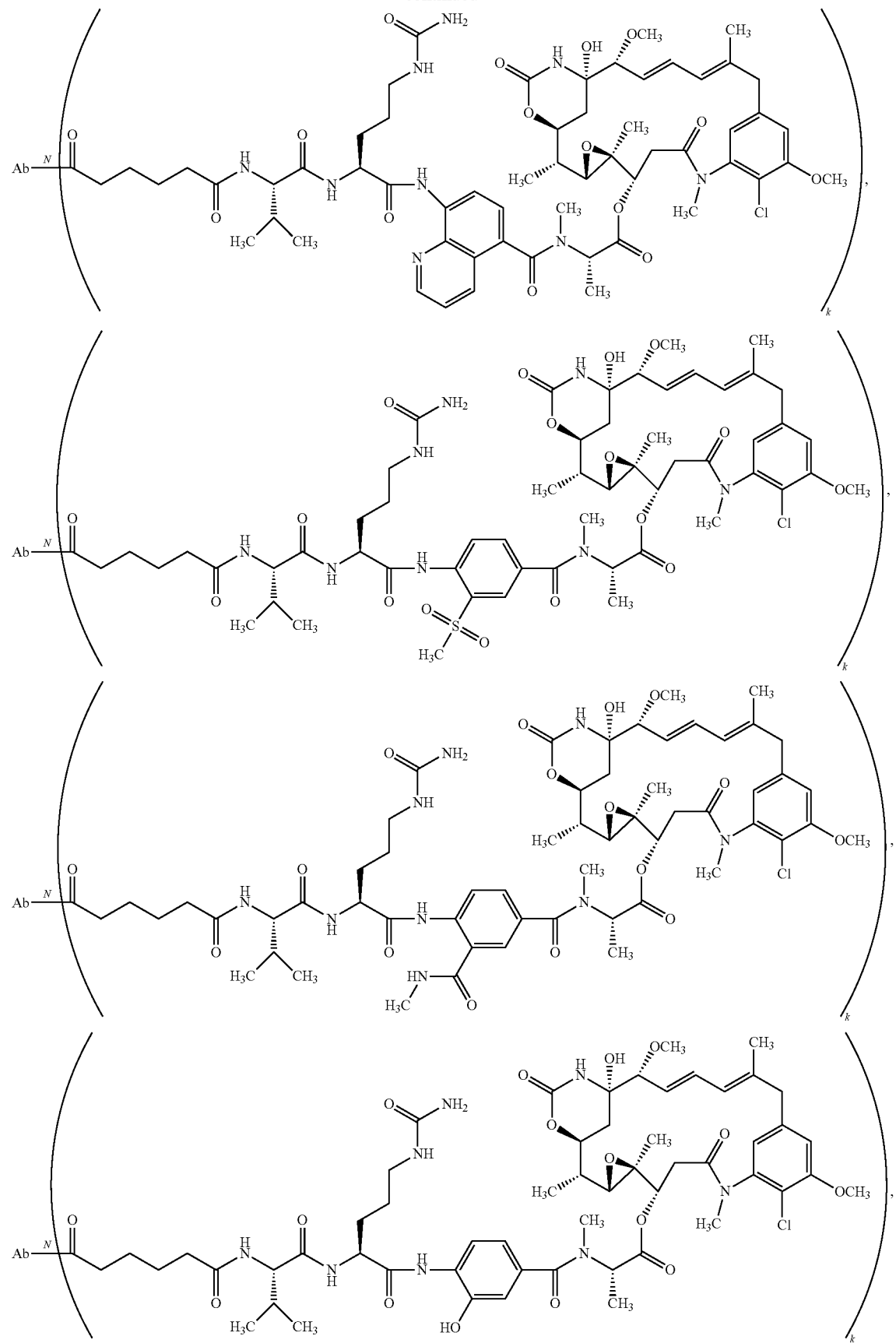

113
114
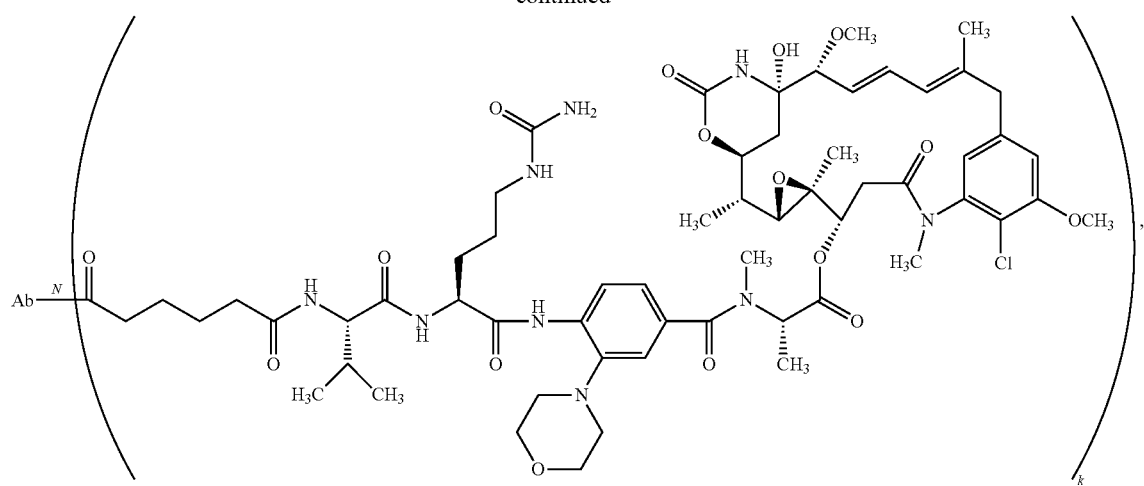
,
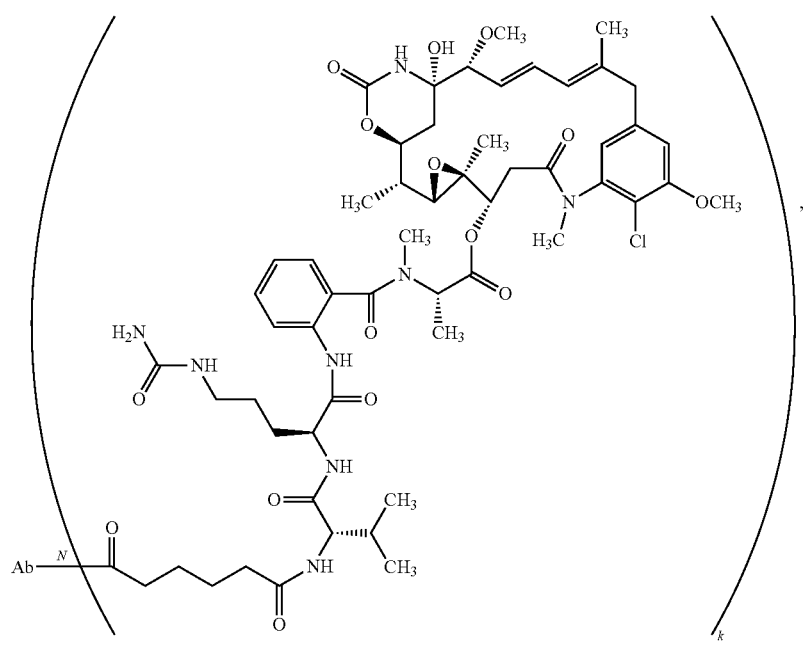
,

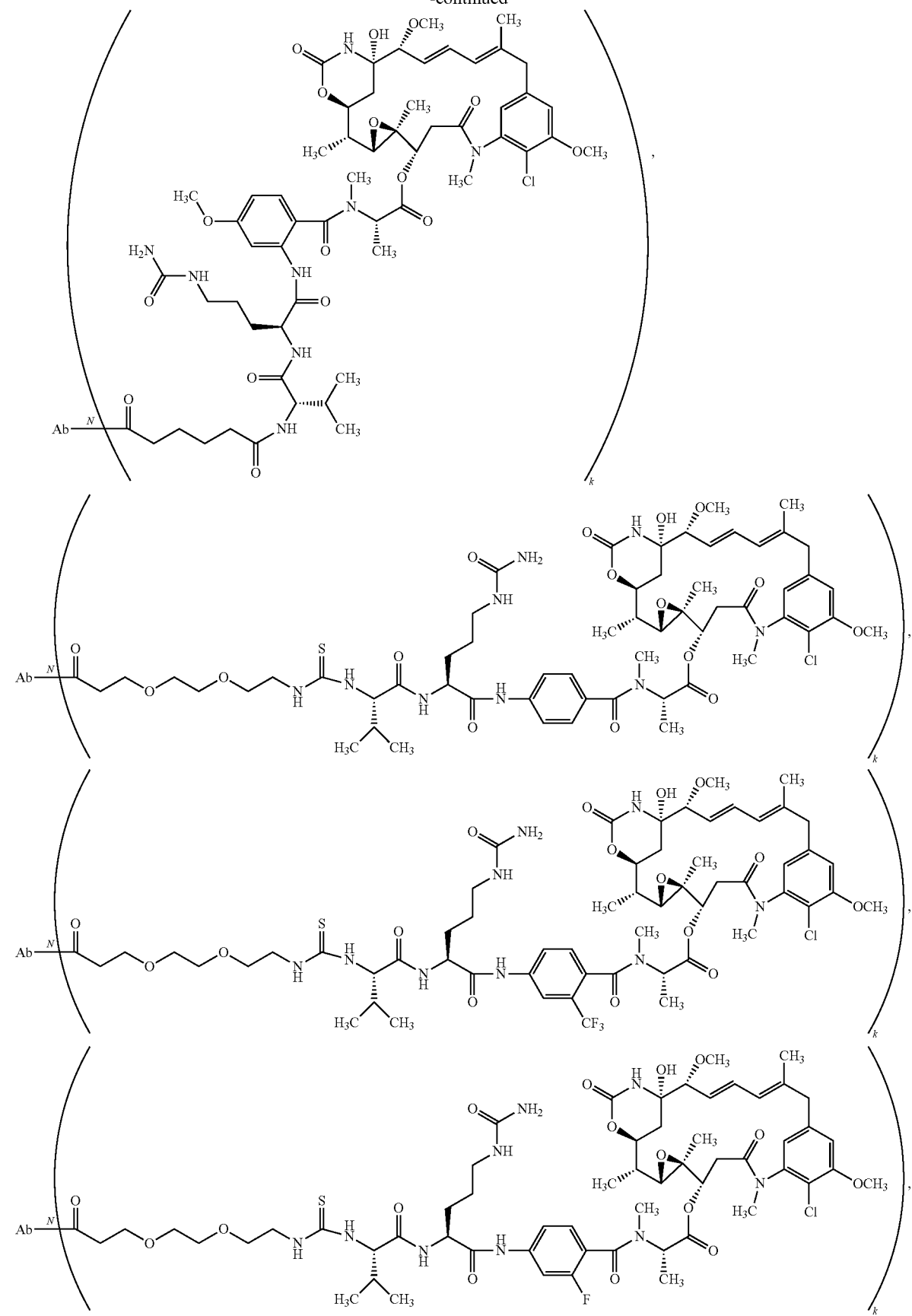

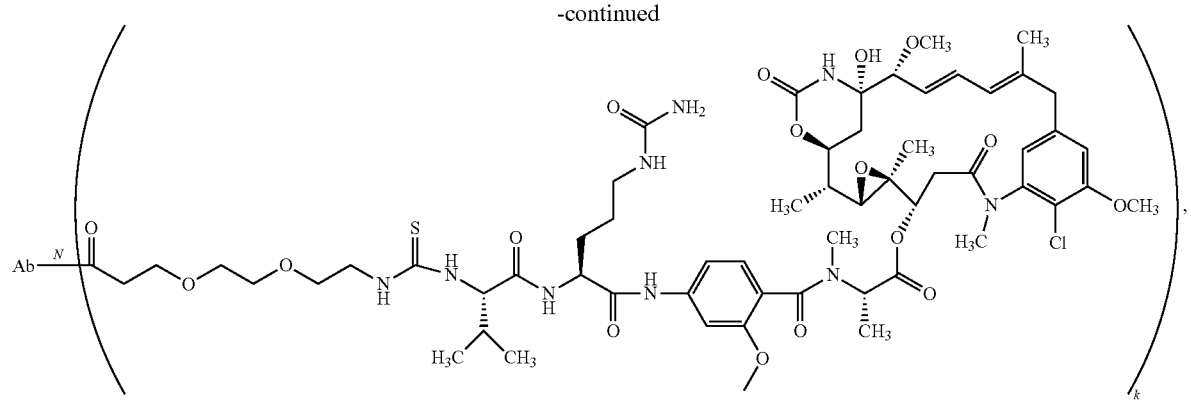
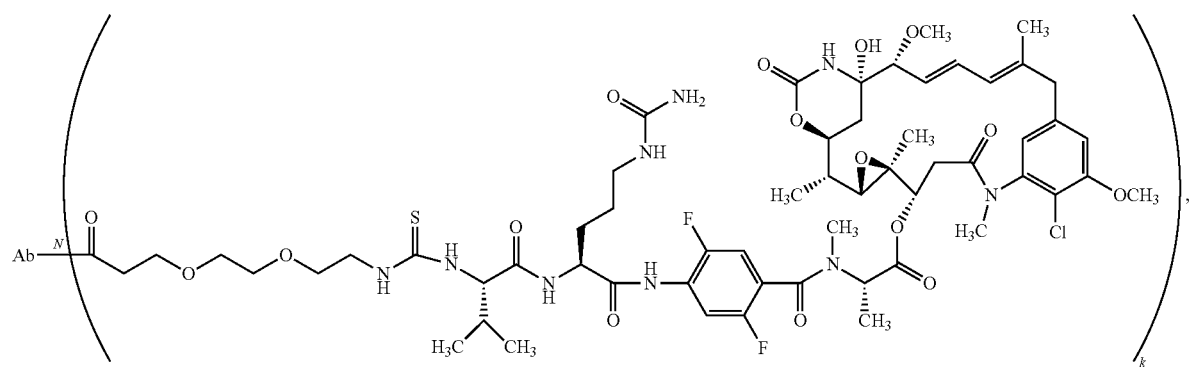
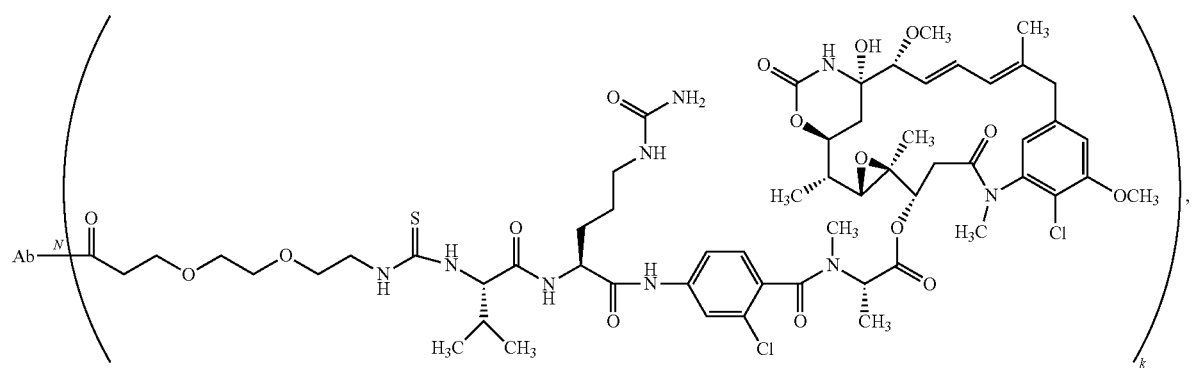
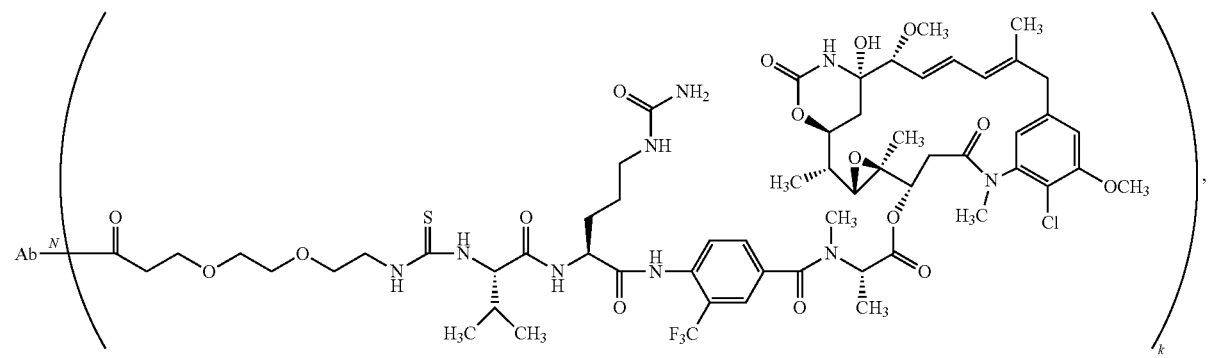

-continued
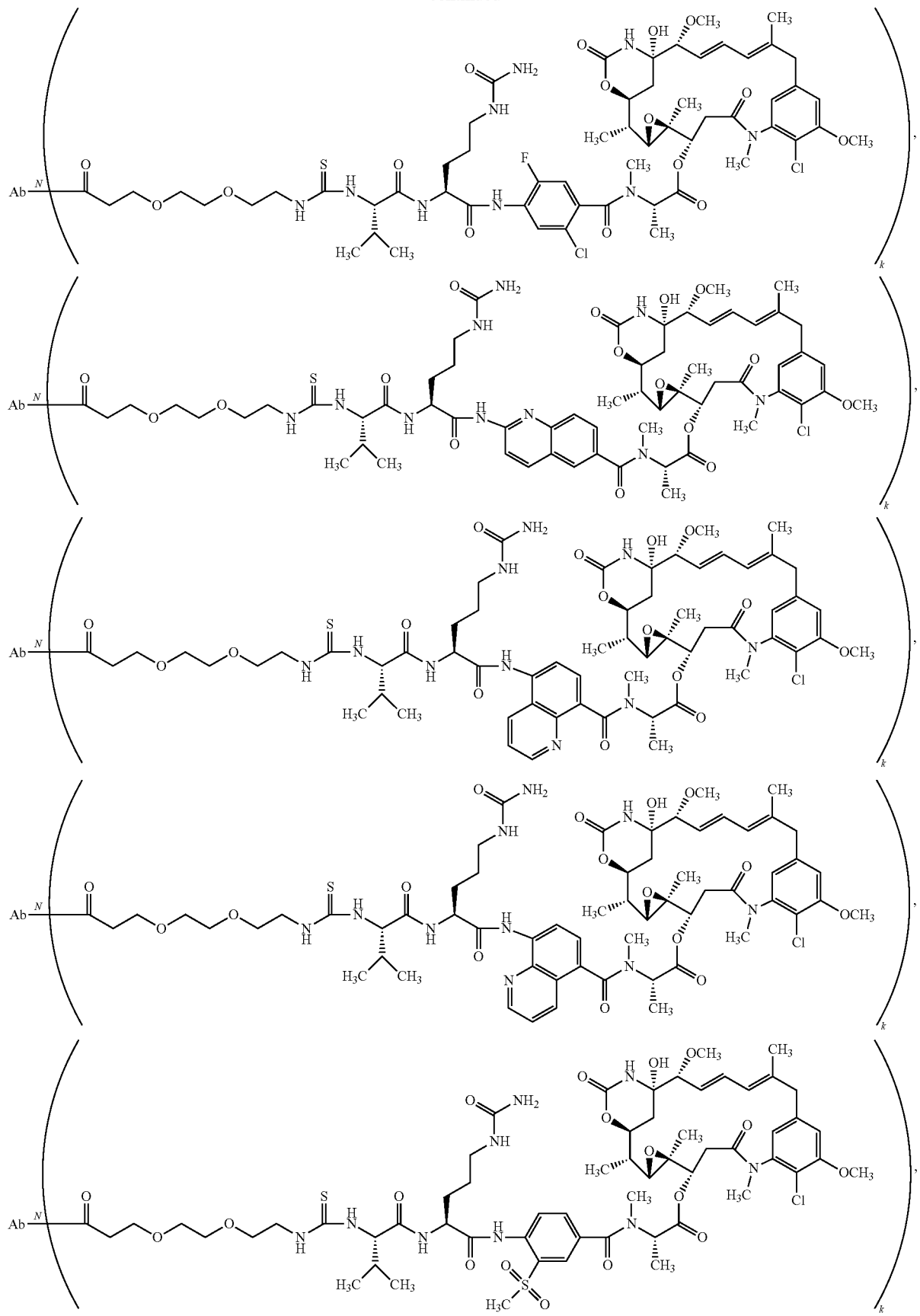

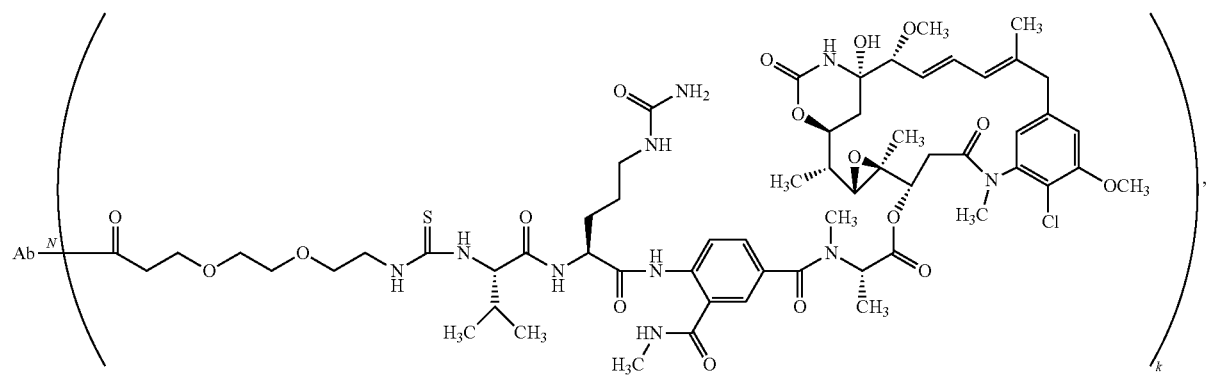
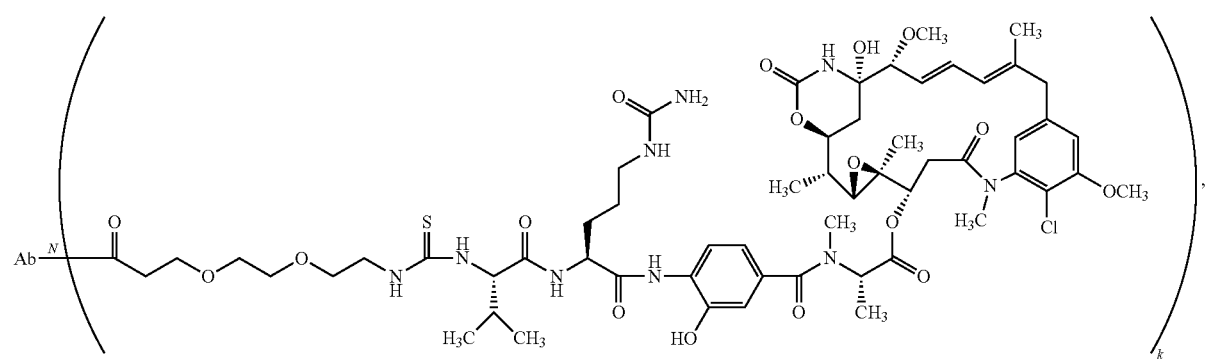
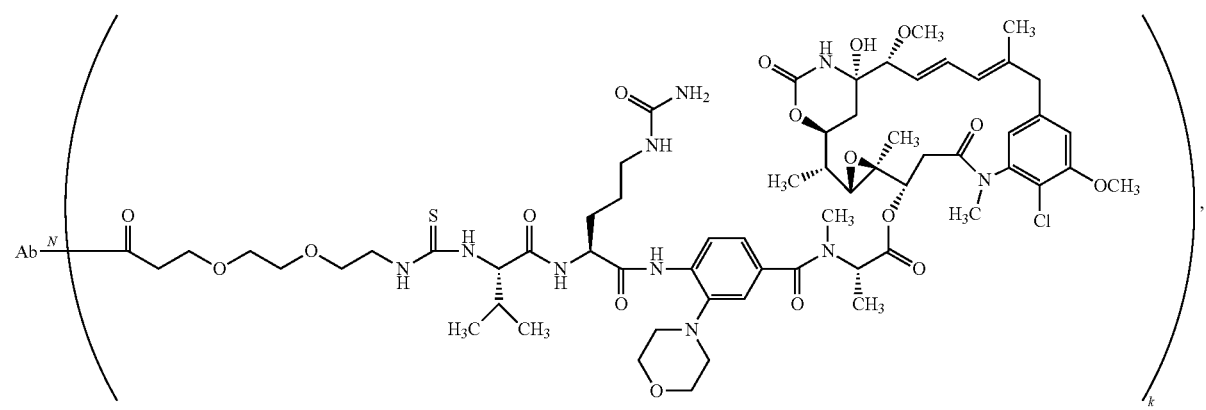

-continued
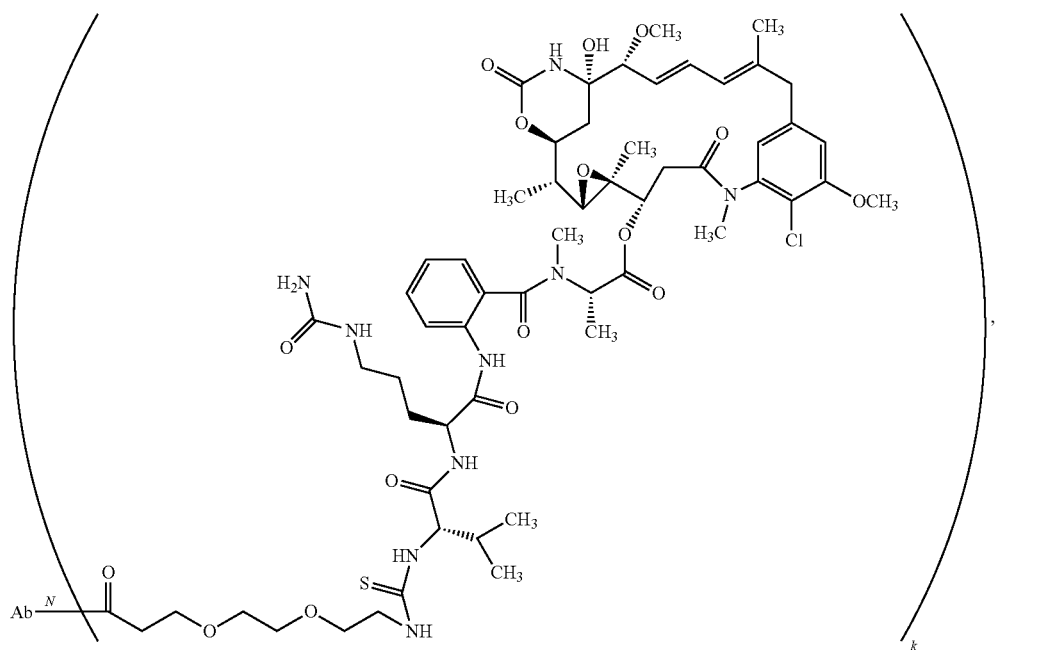
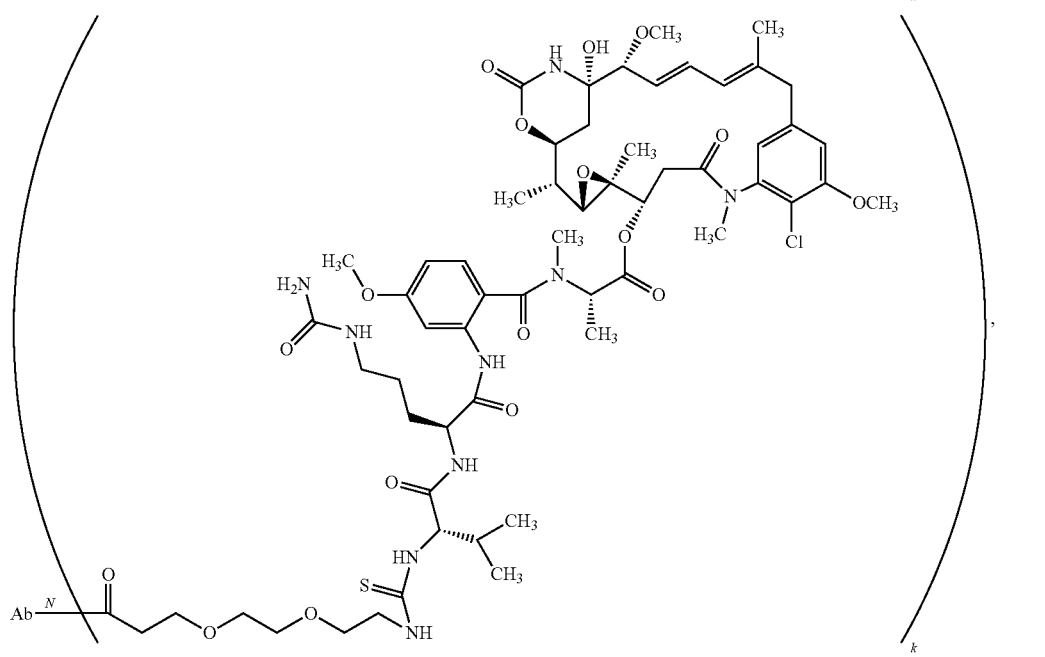
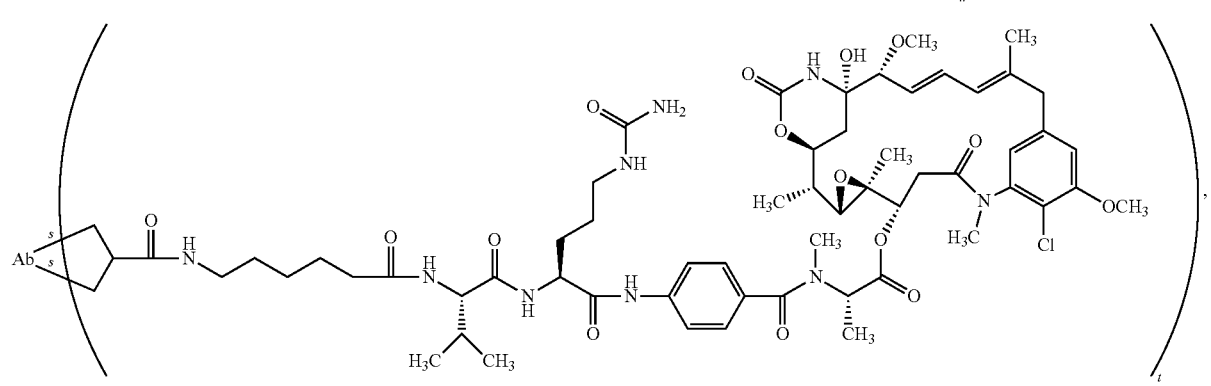

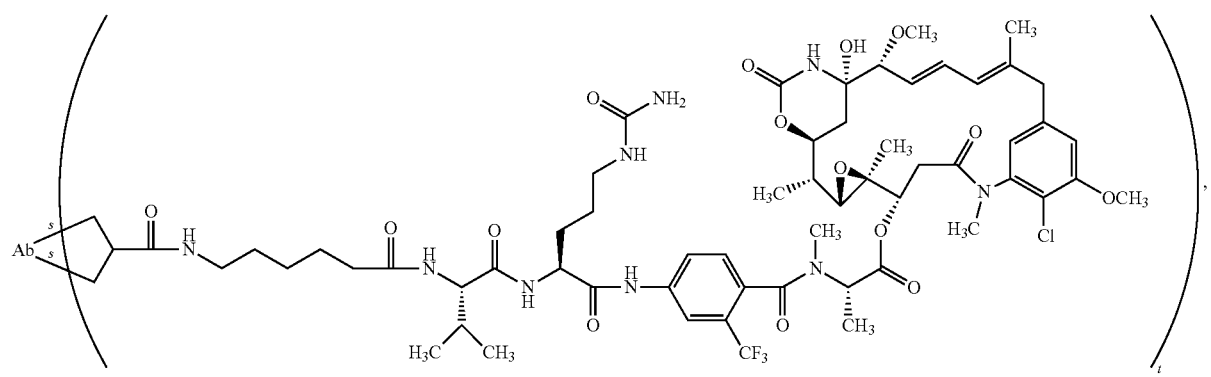
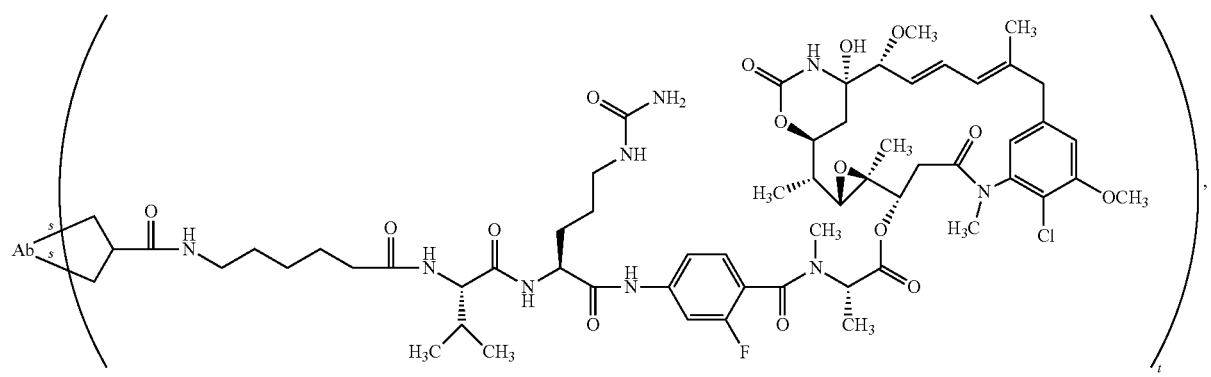
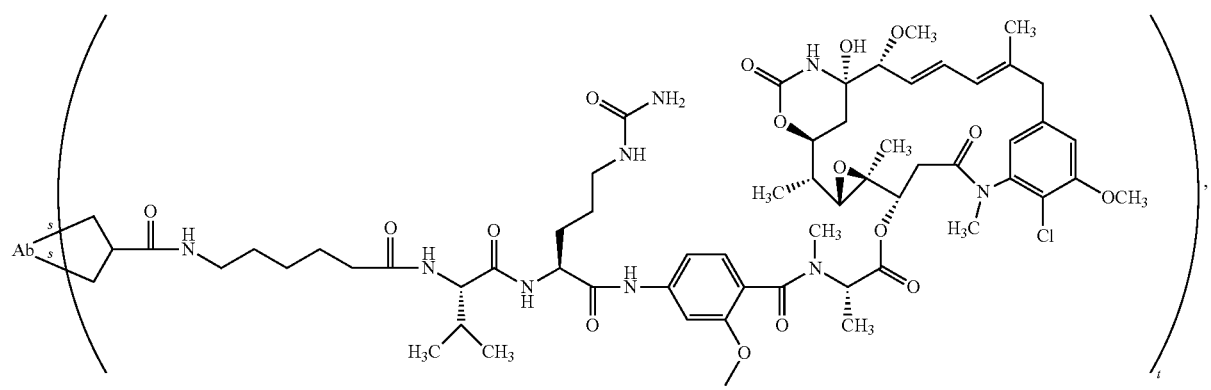
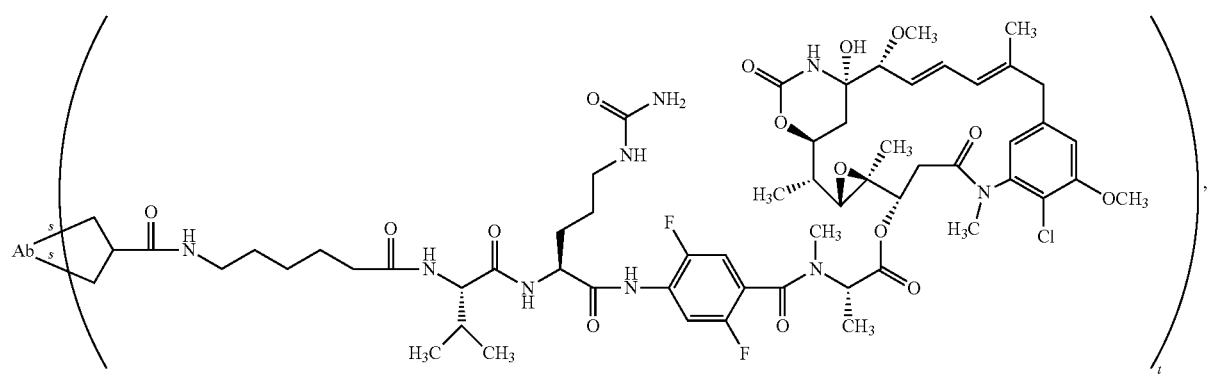

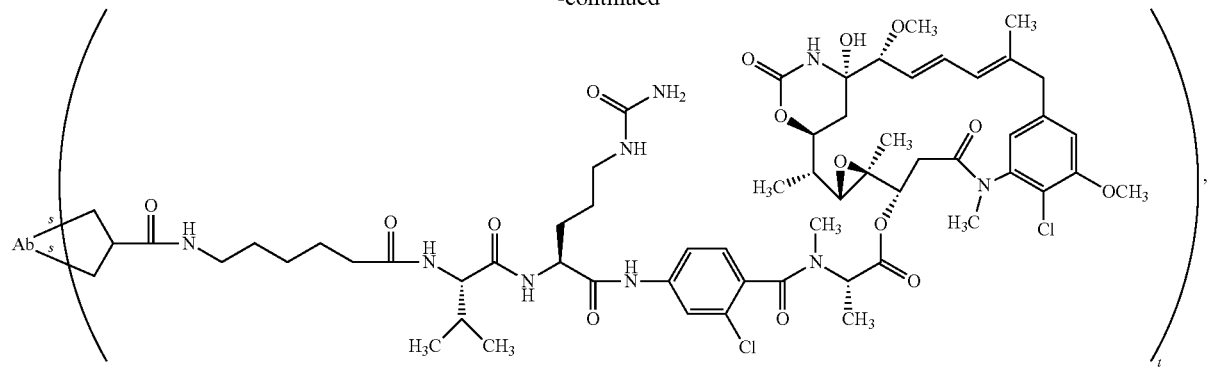
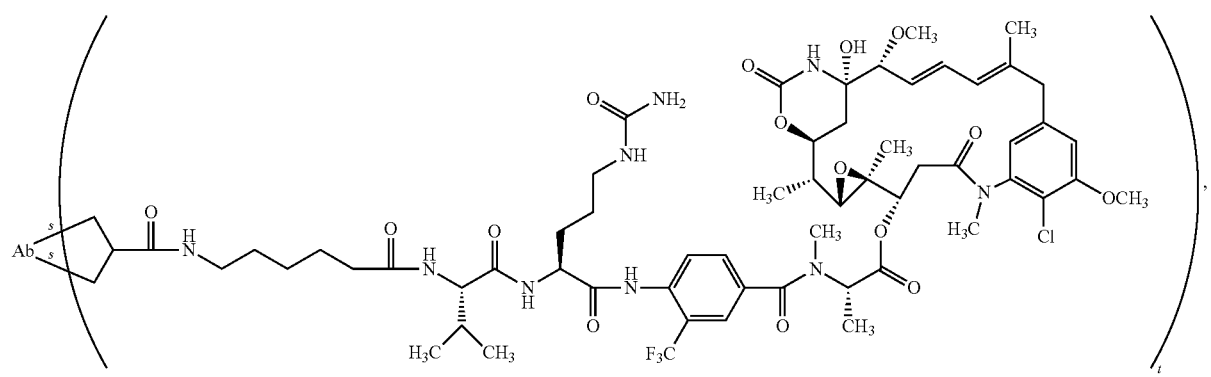
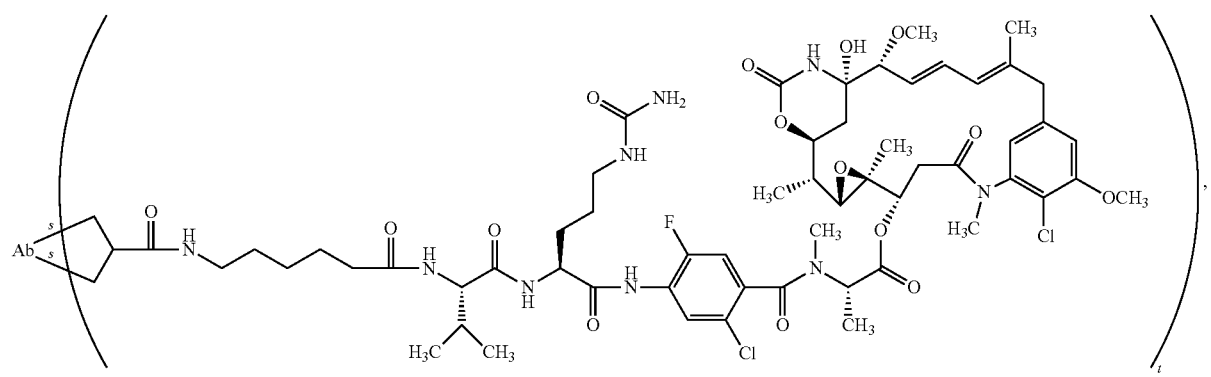
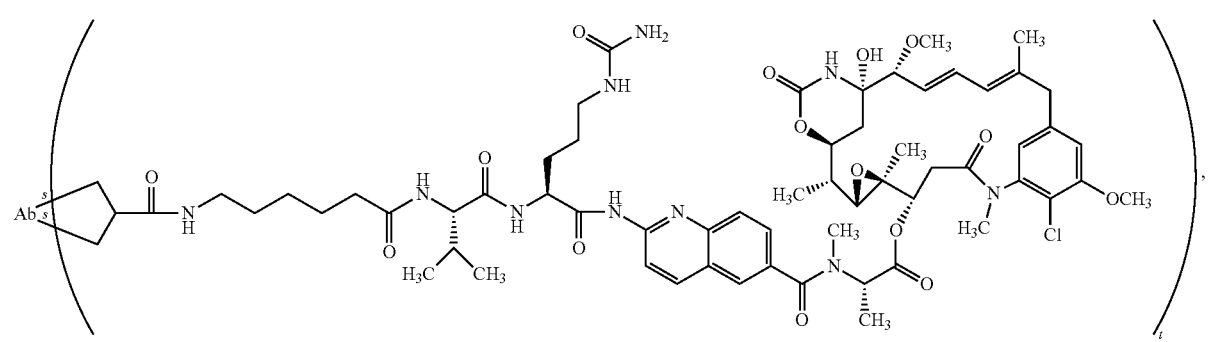

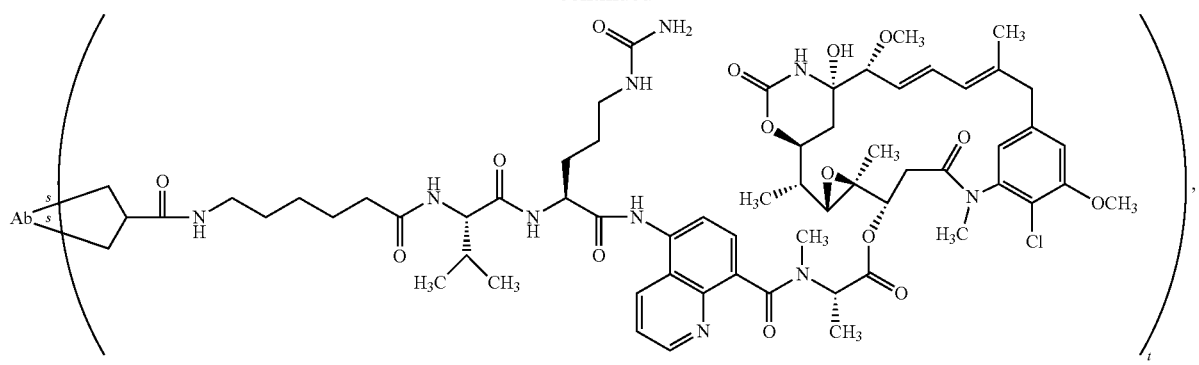
,
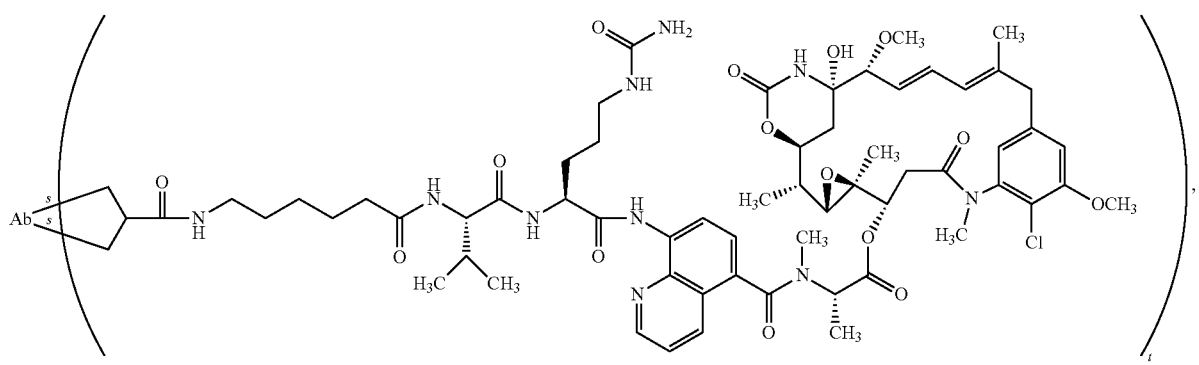
,
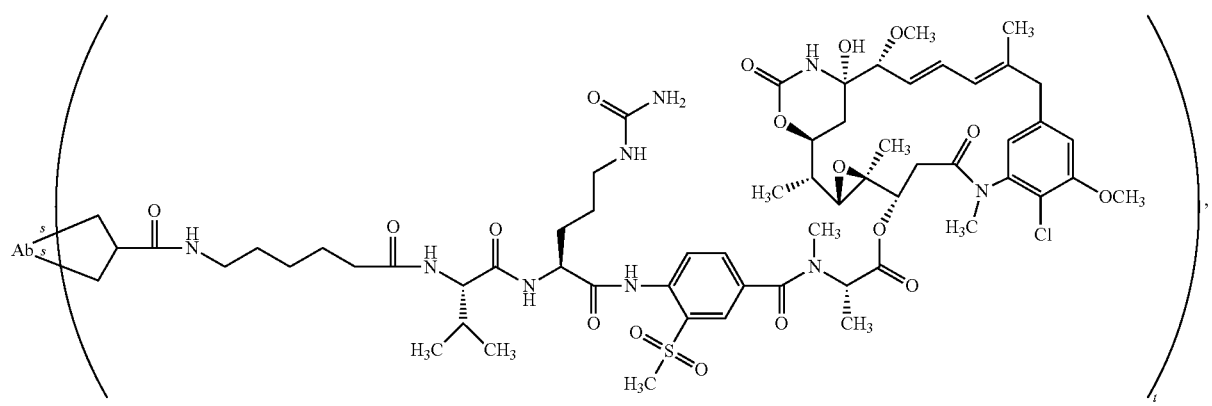
,
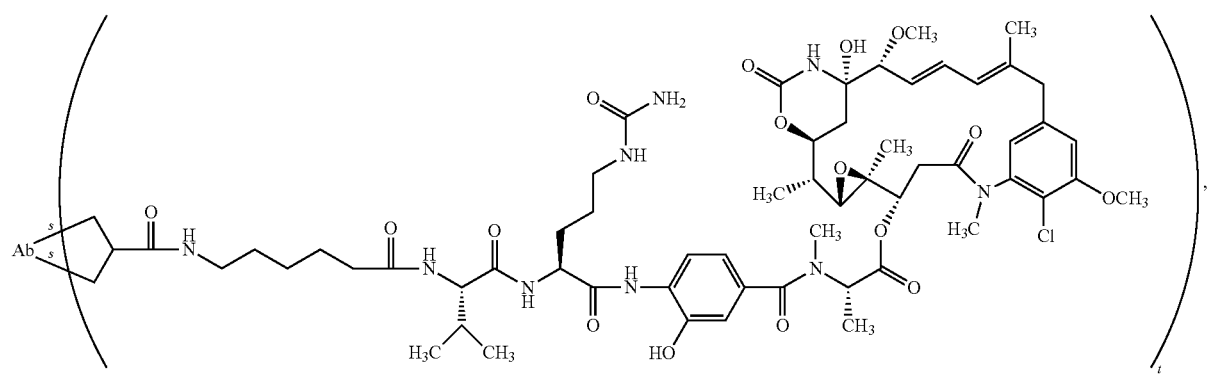
,

-continued
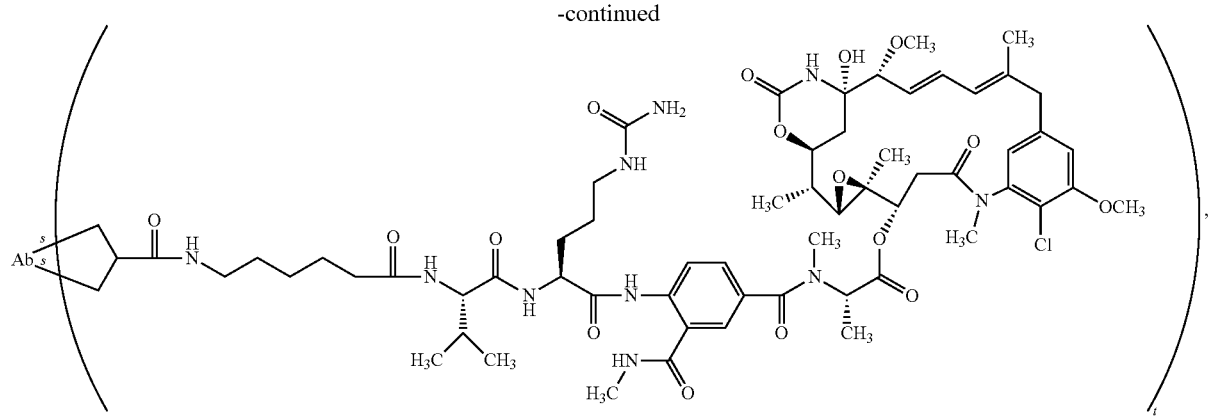
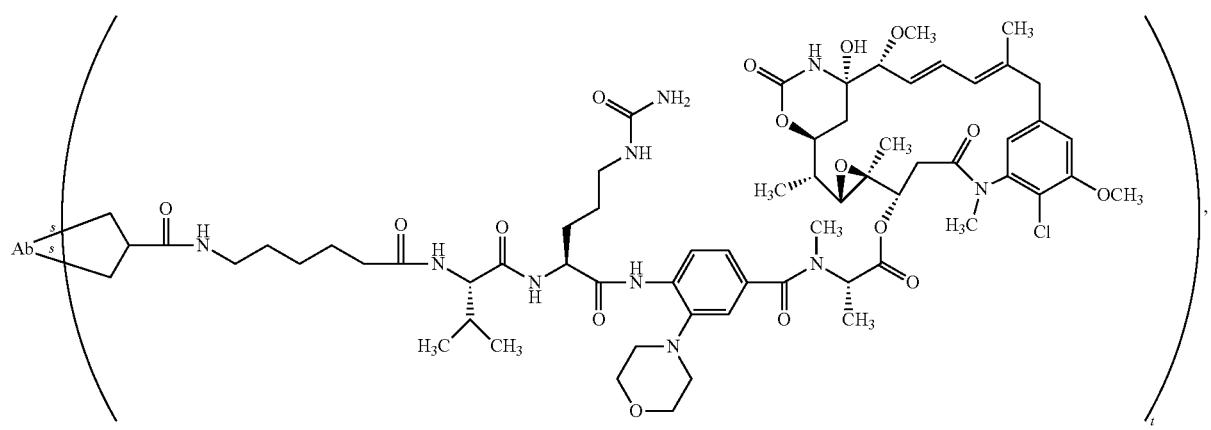
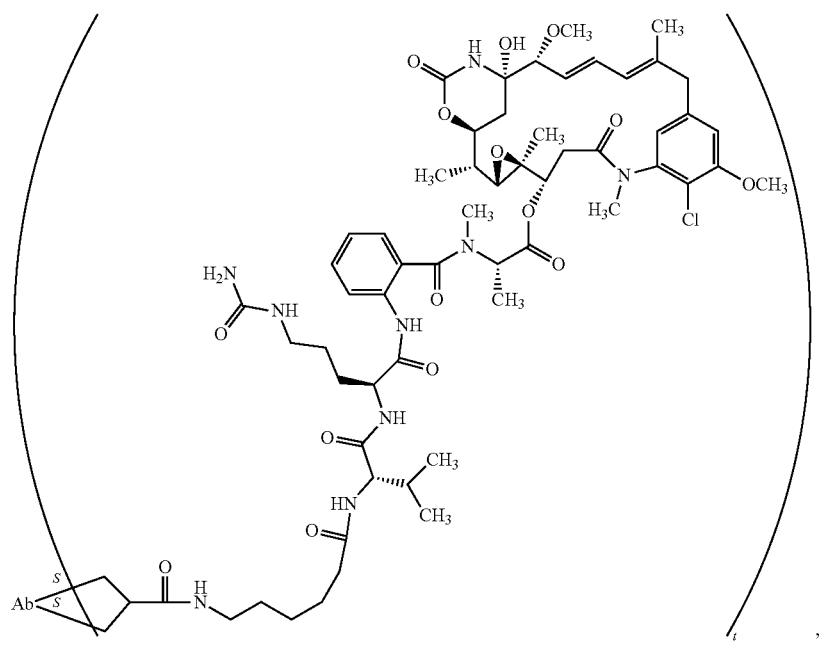

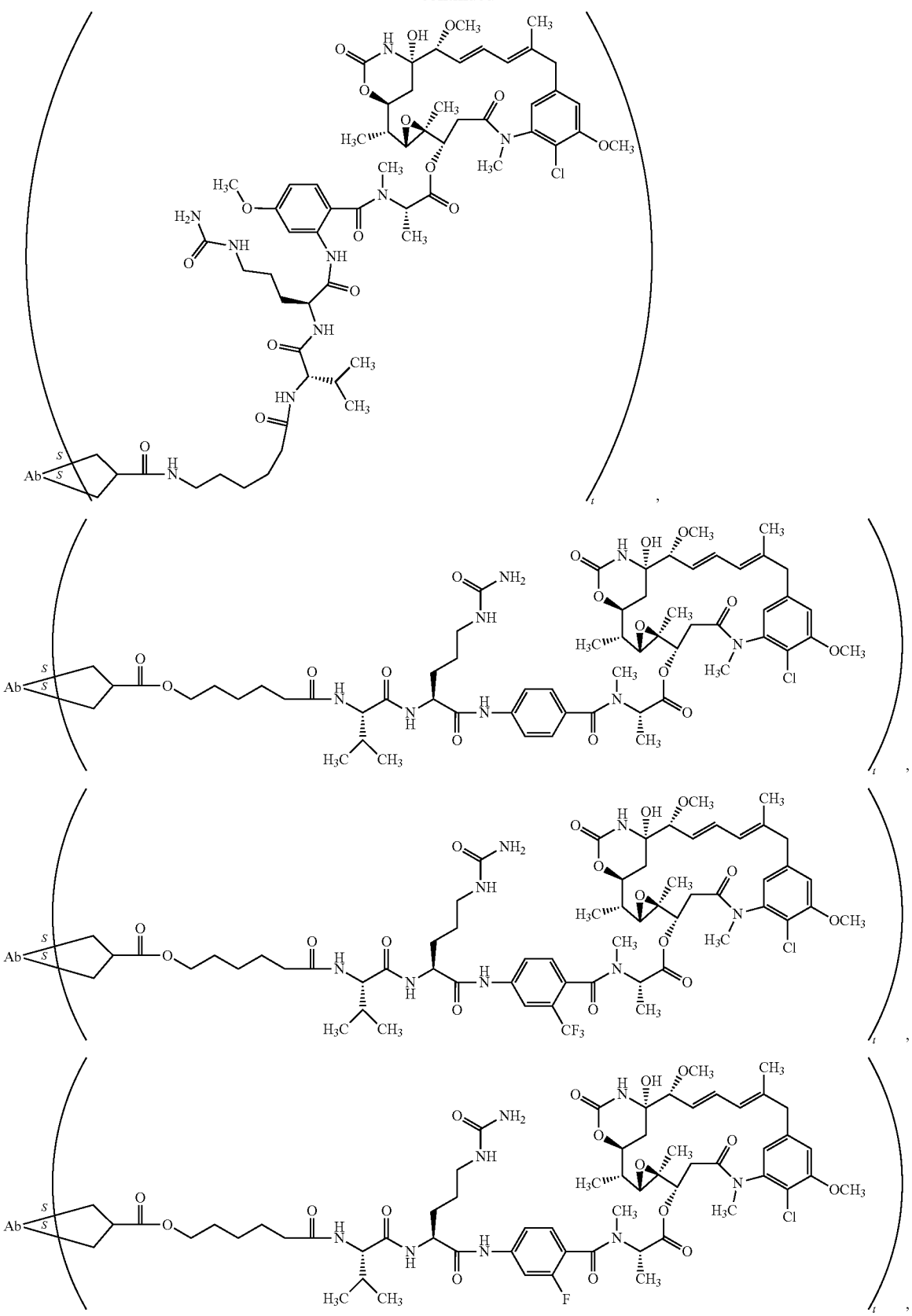

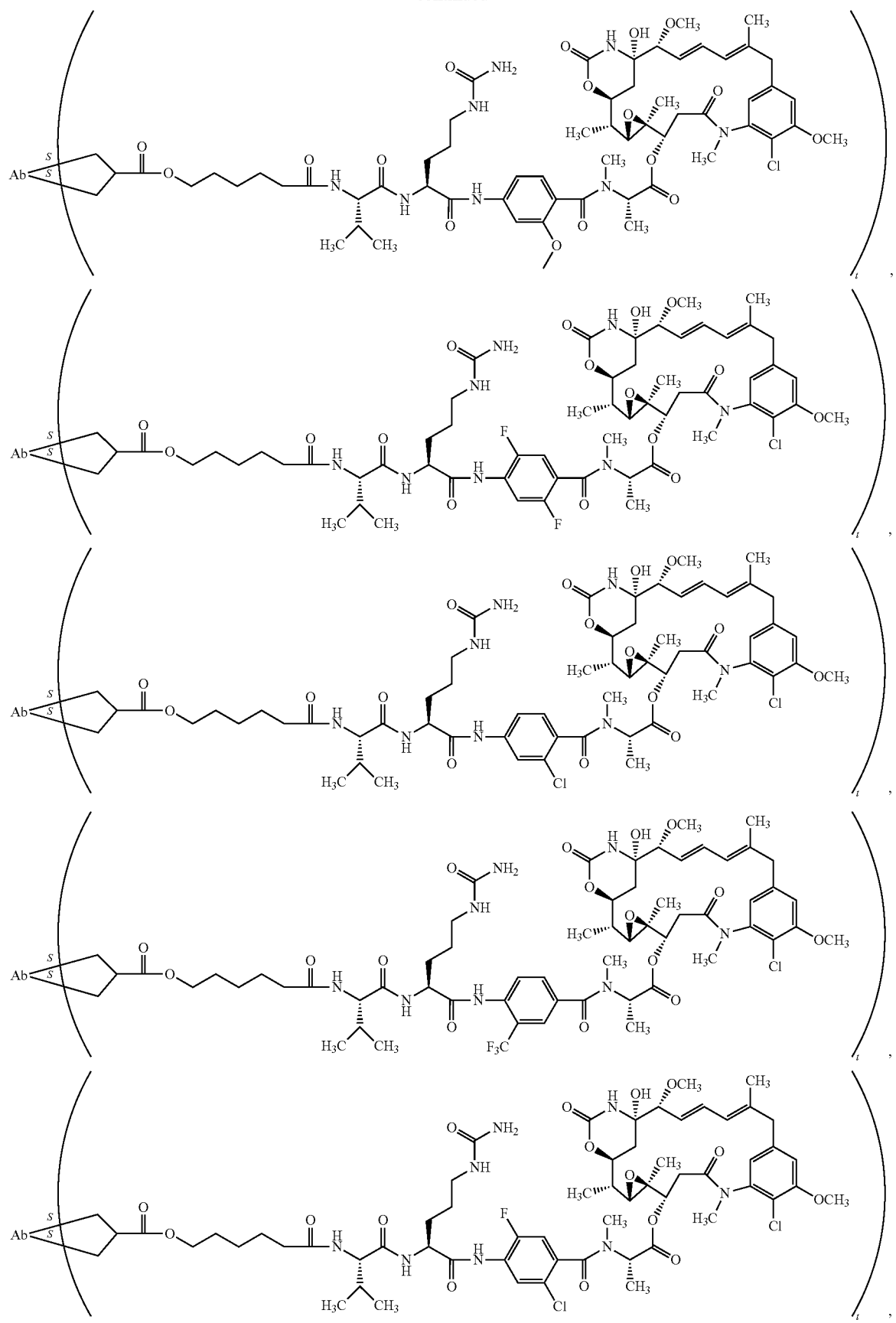

-continued
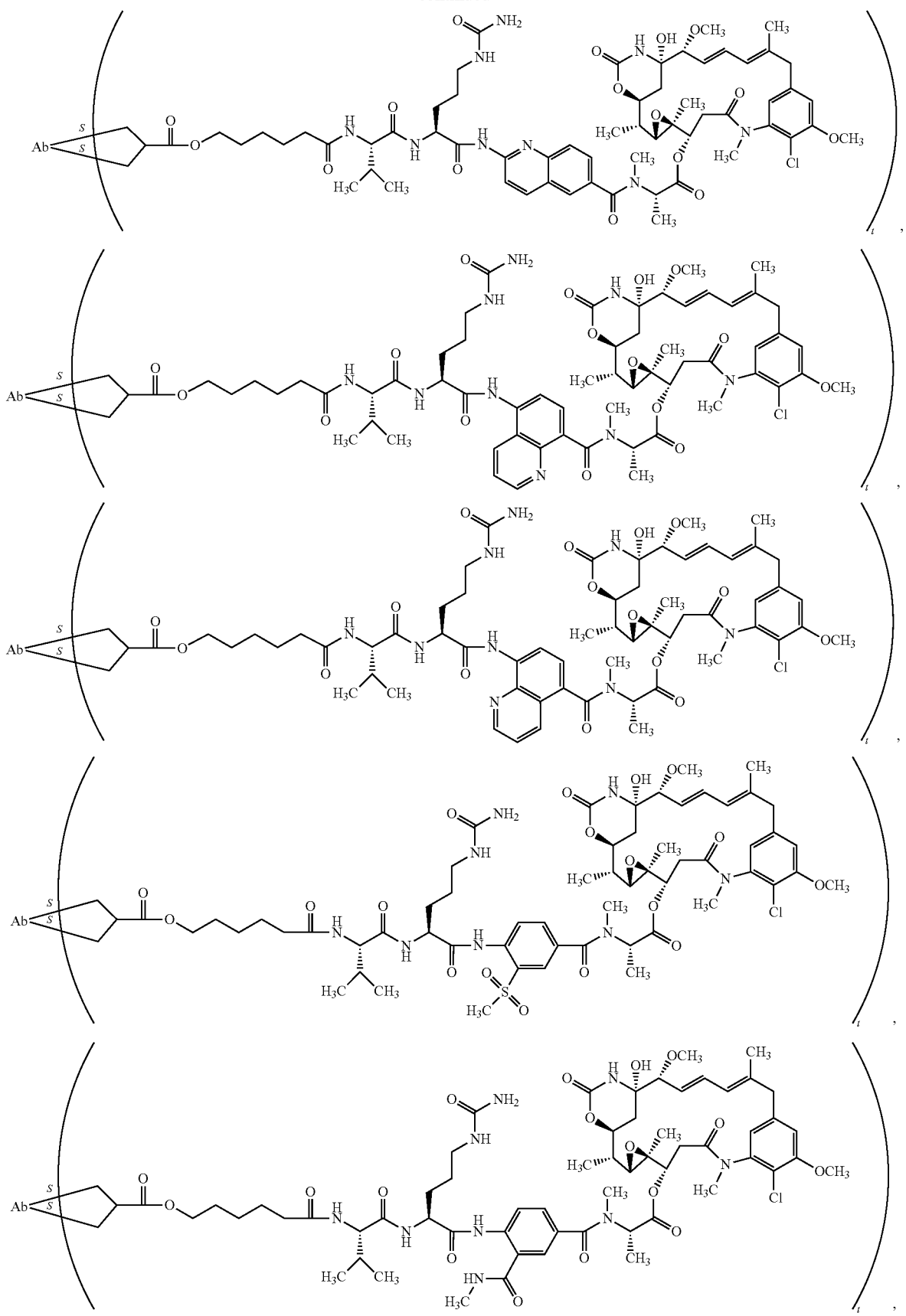

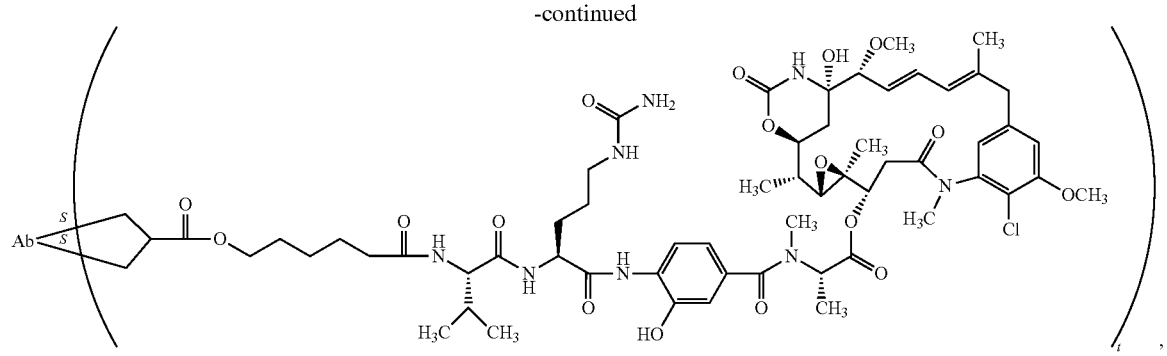
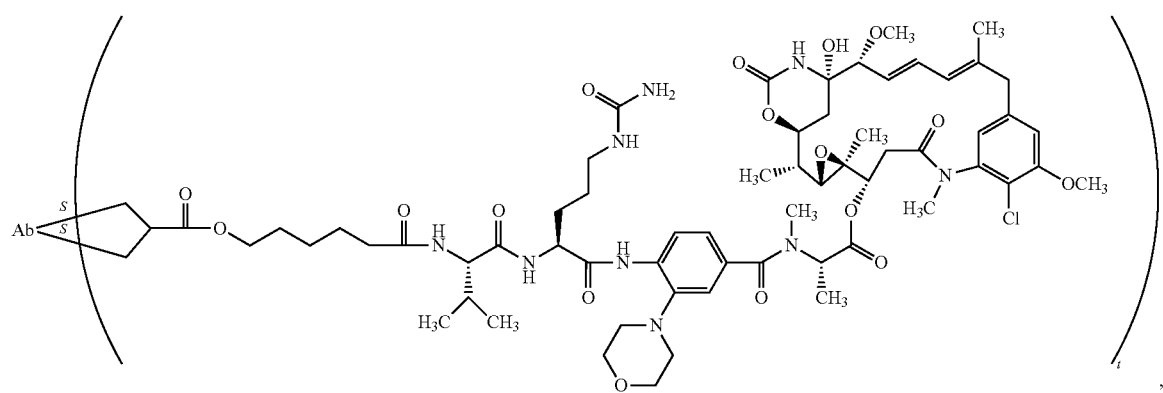
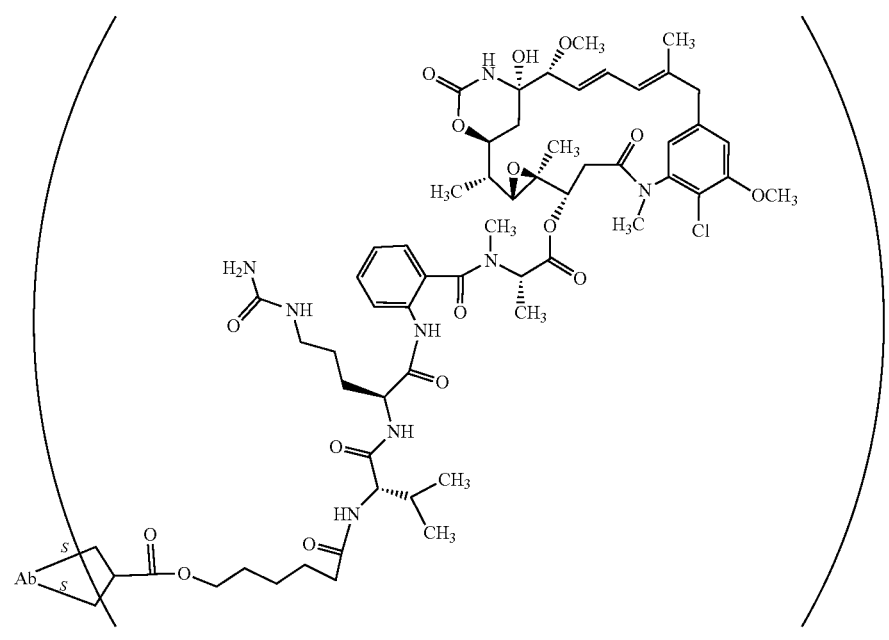

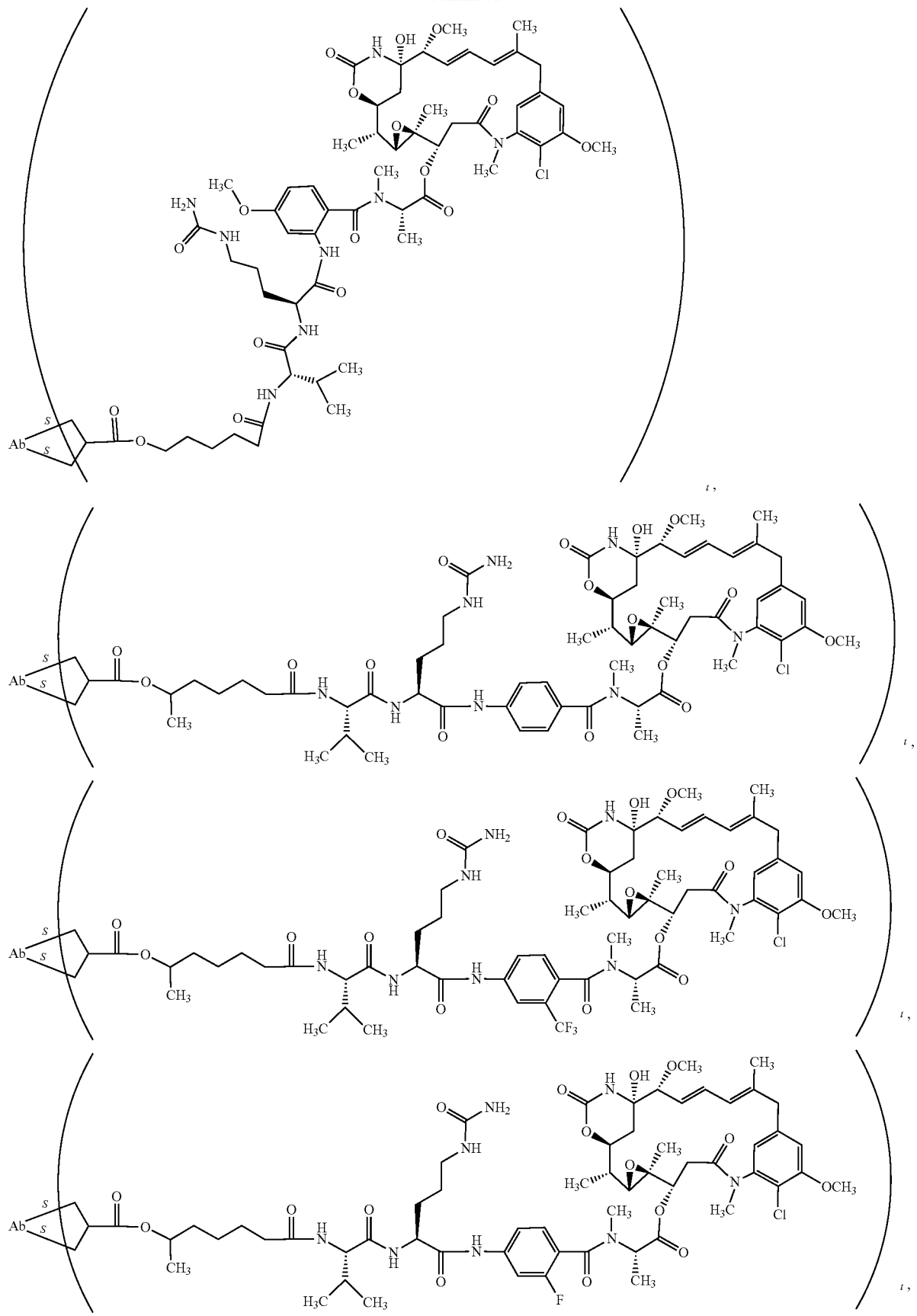

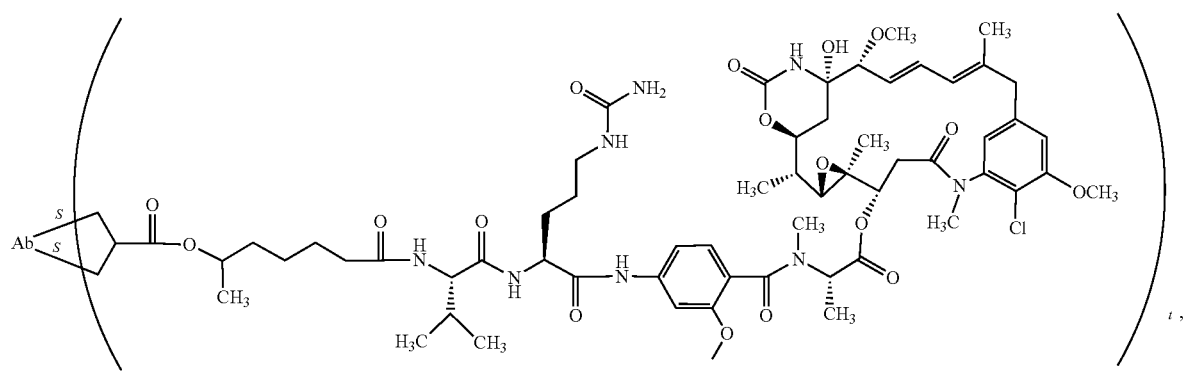
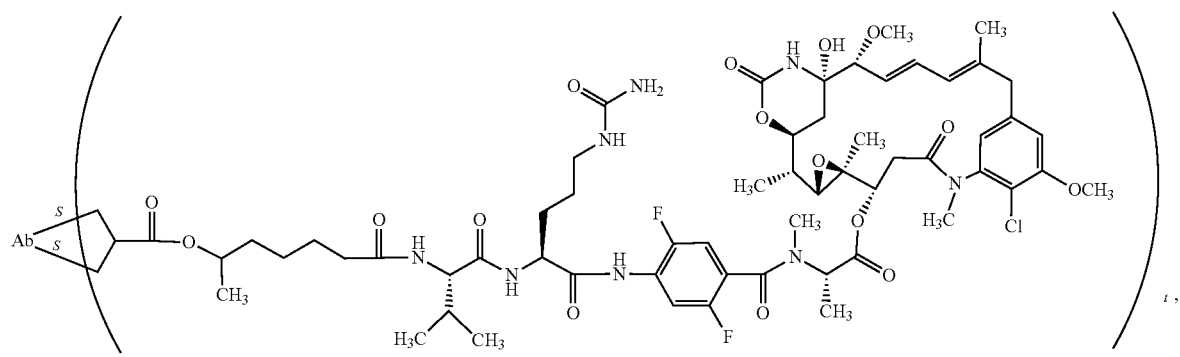
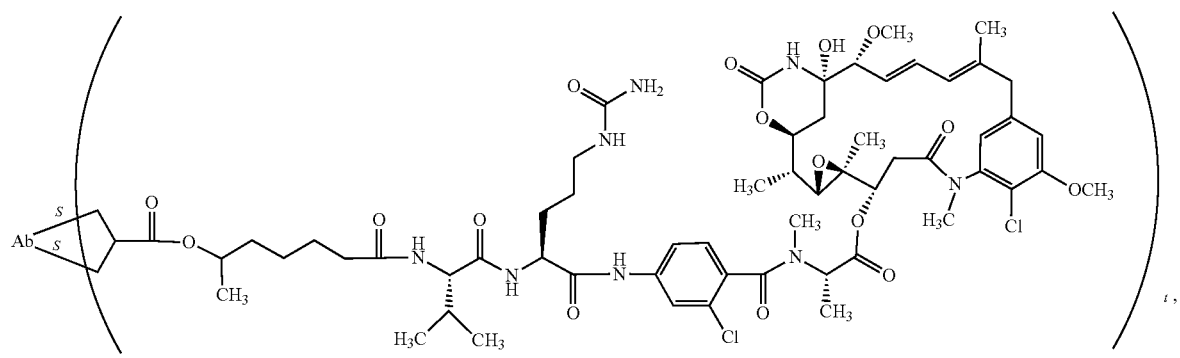
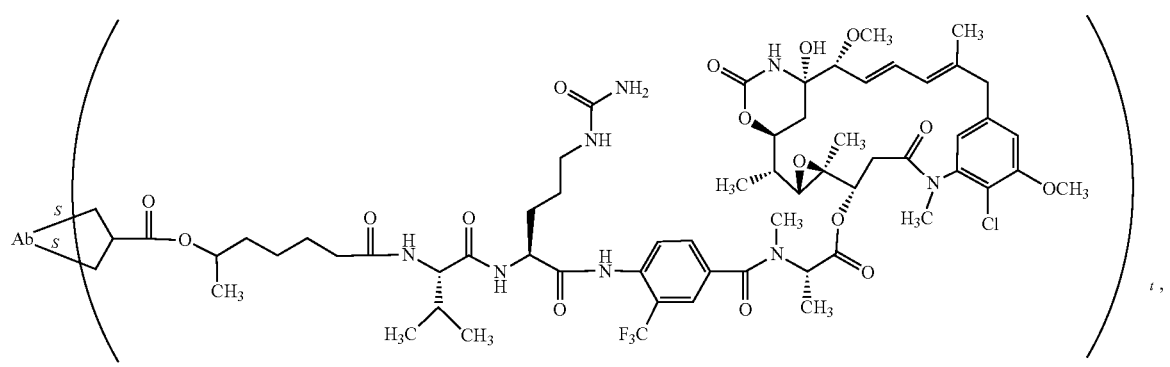

-continued
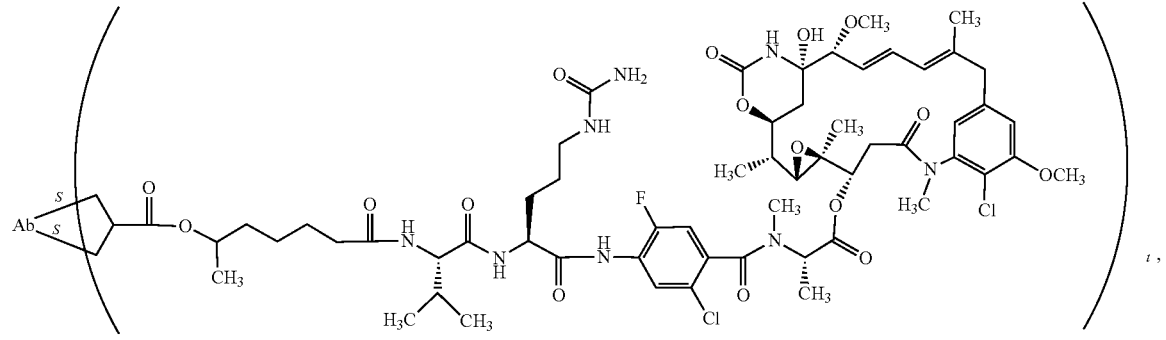
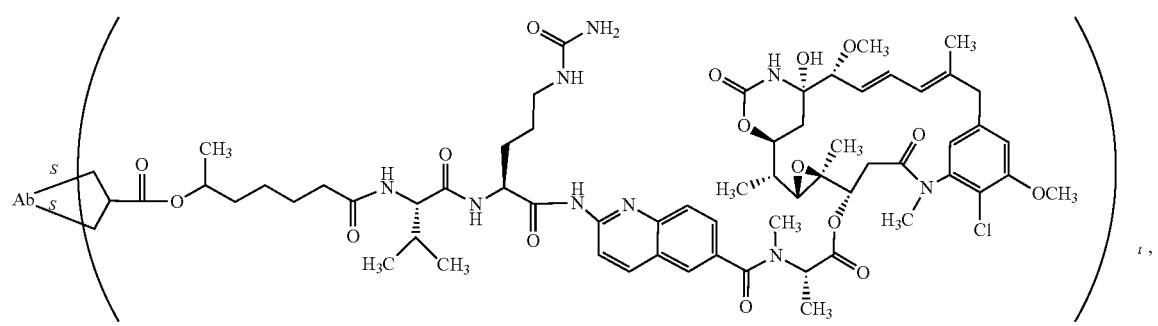
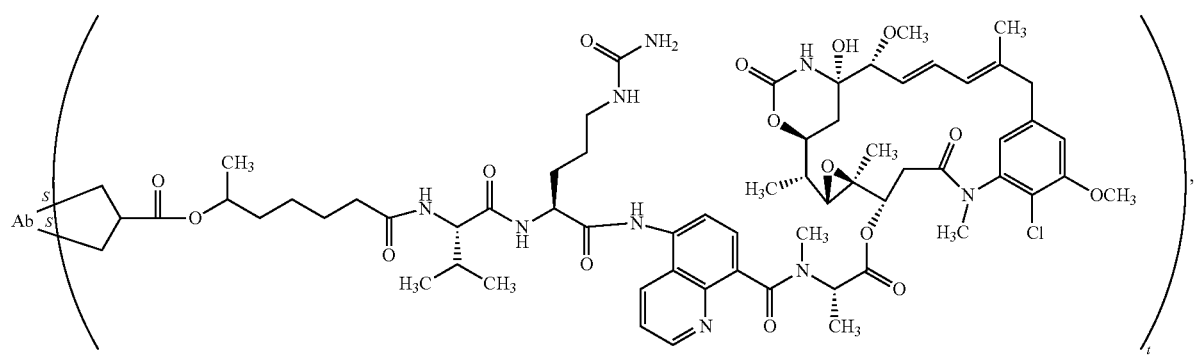
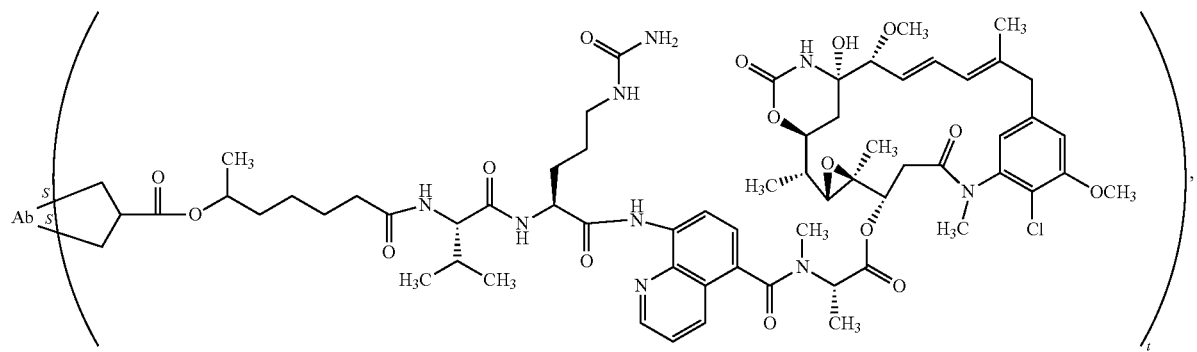

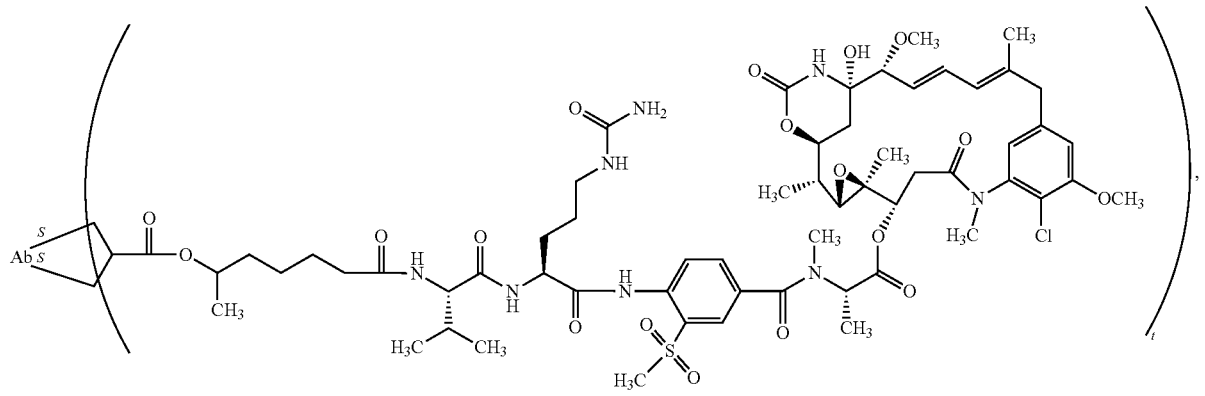
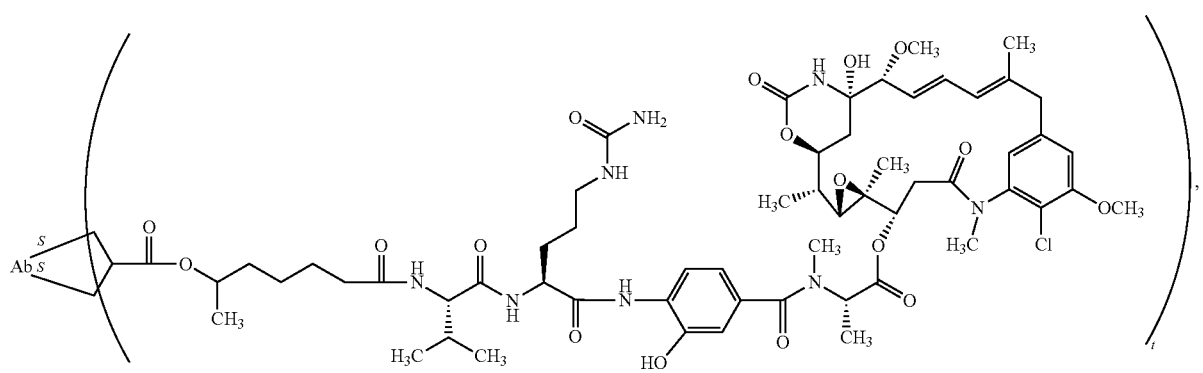
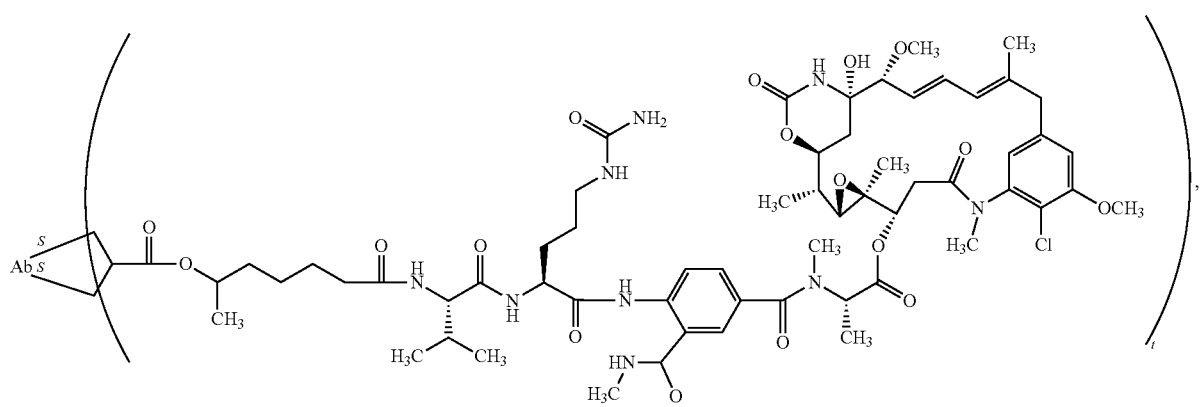
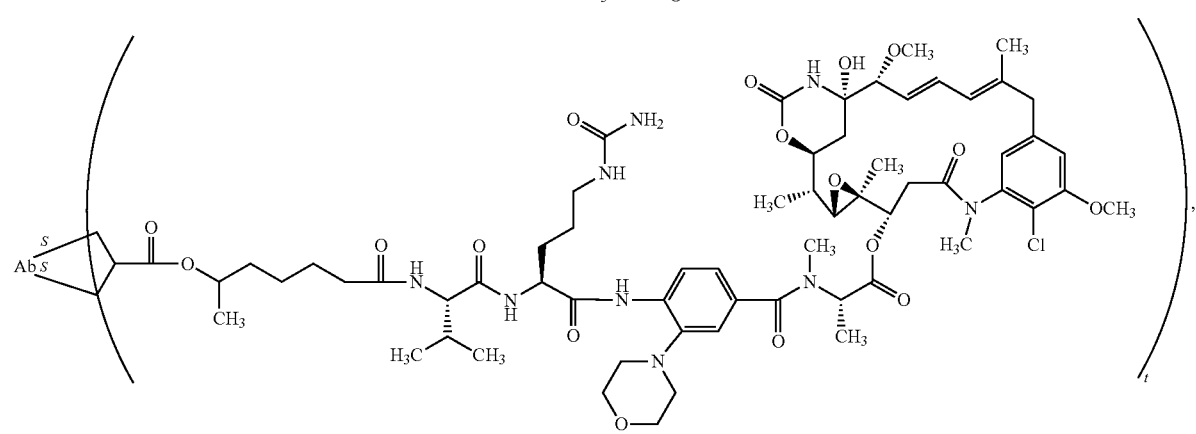

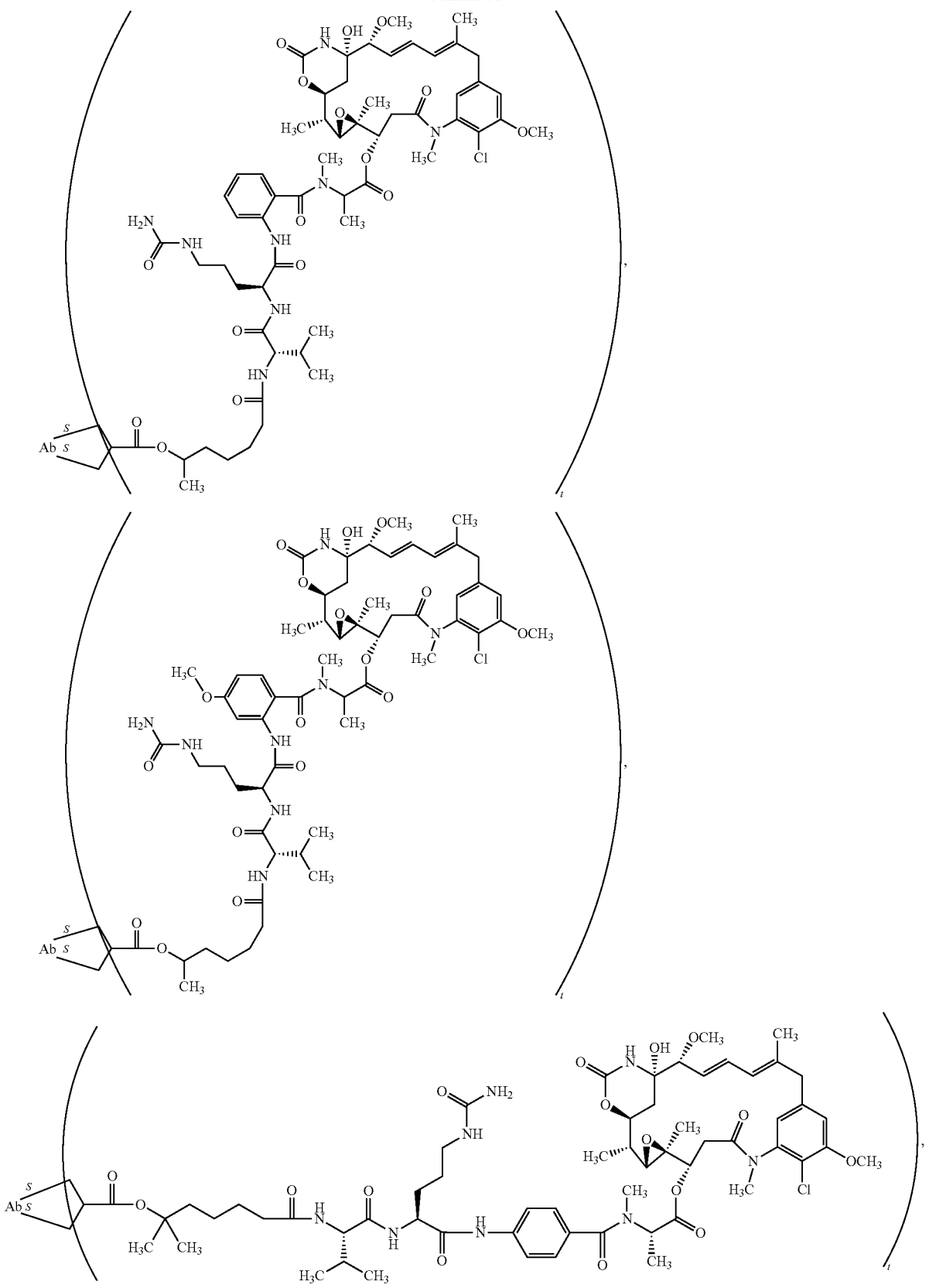

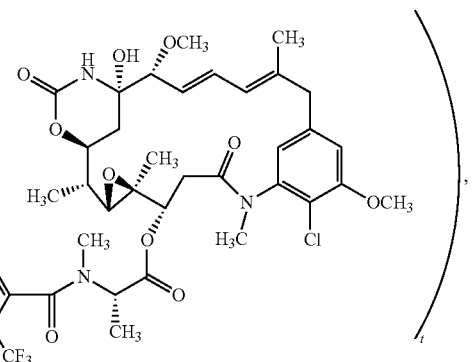
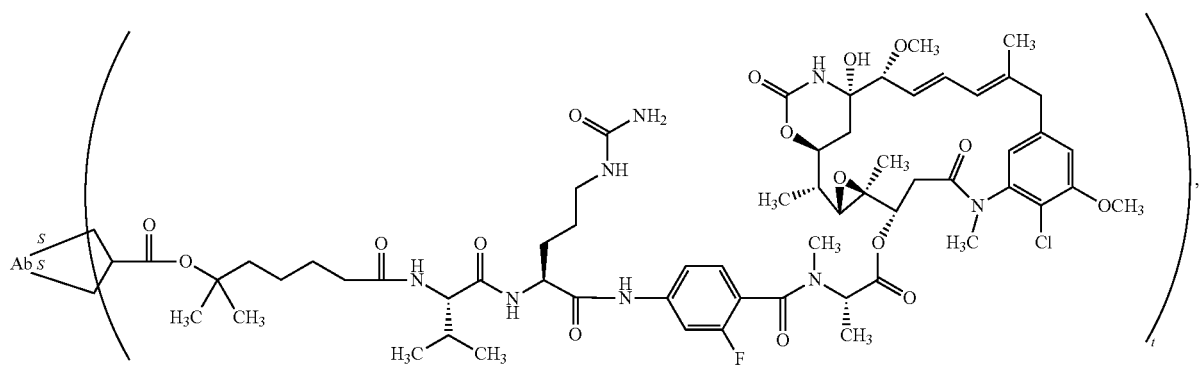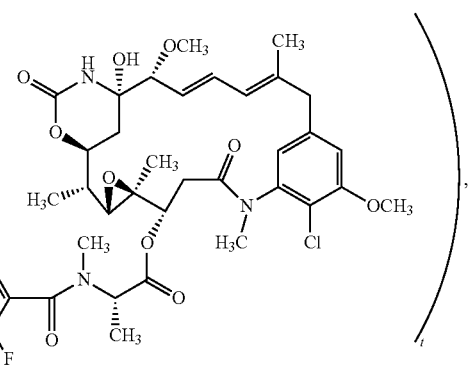
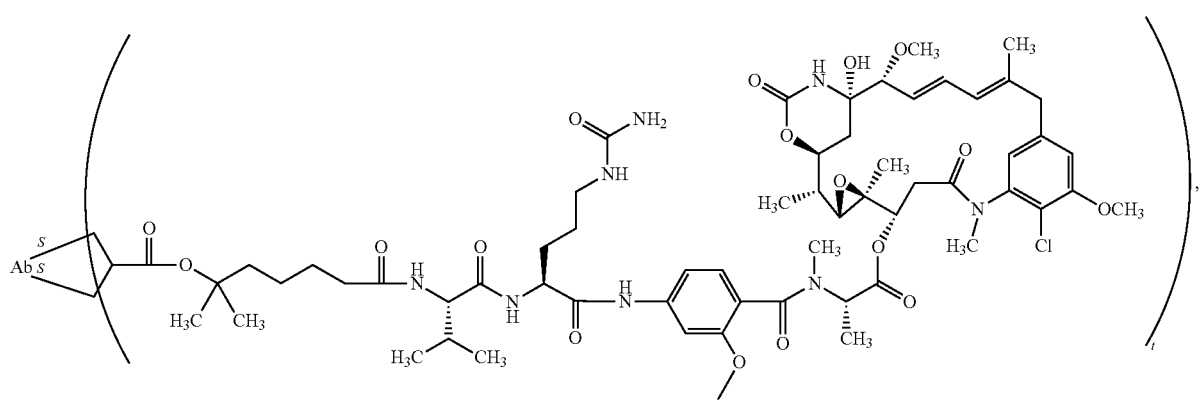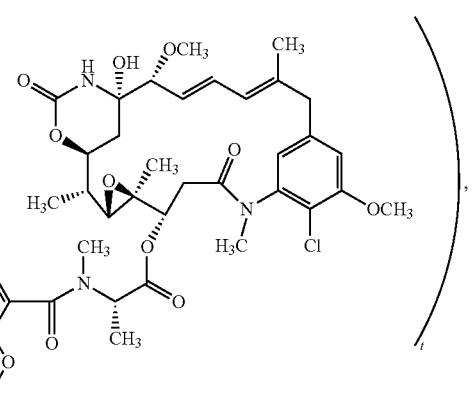
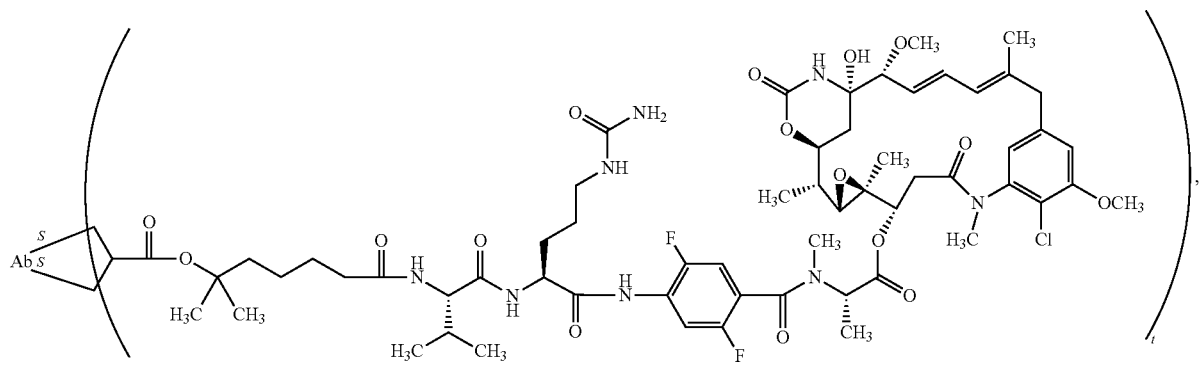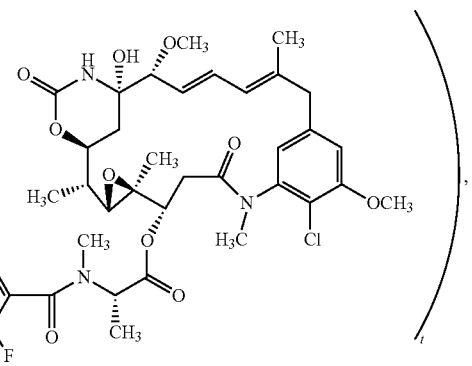

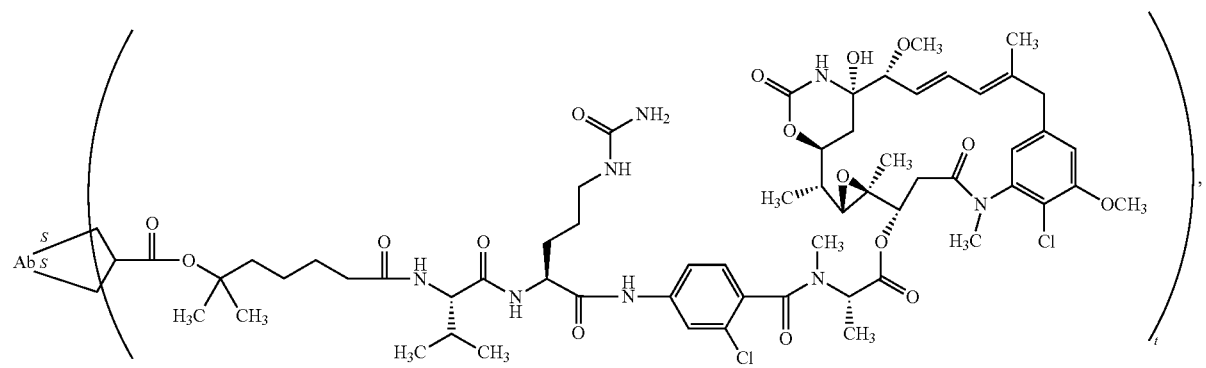
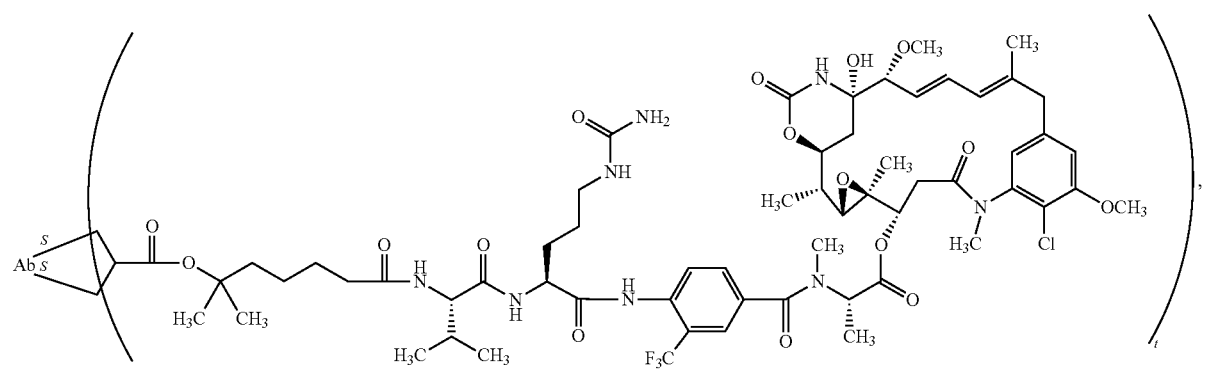
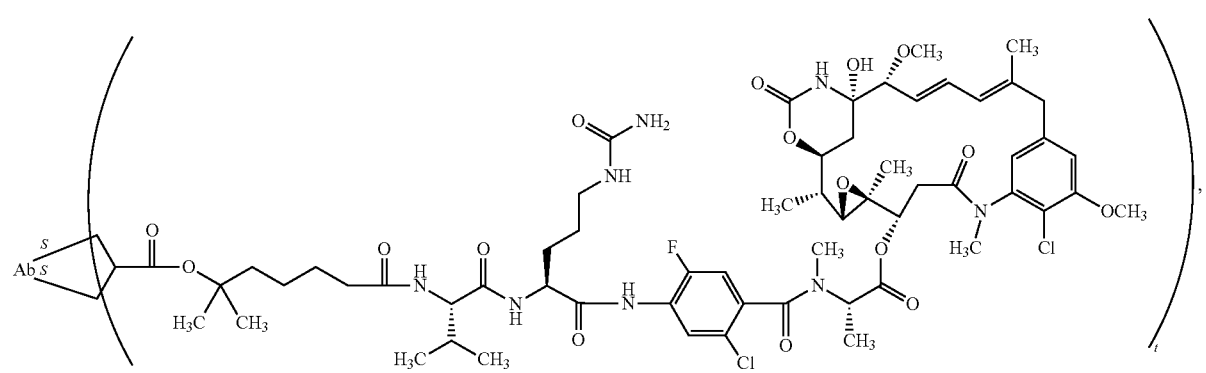
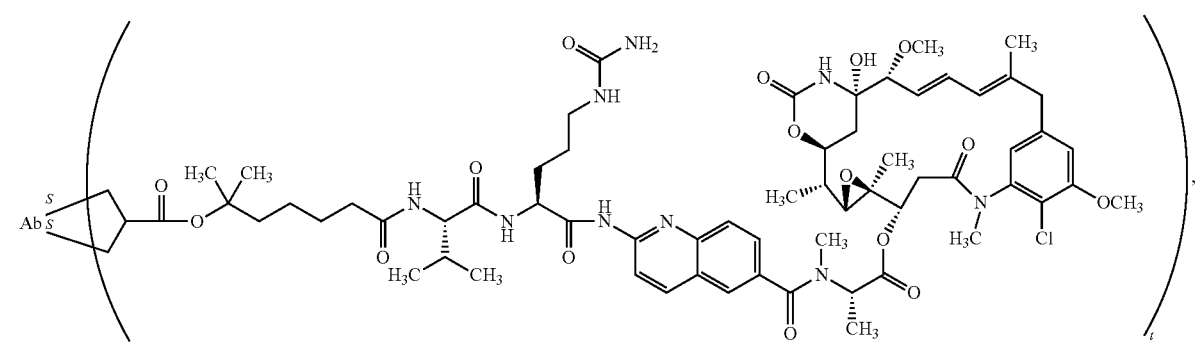

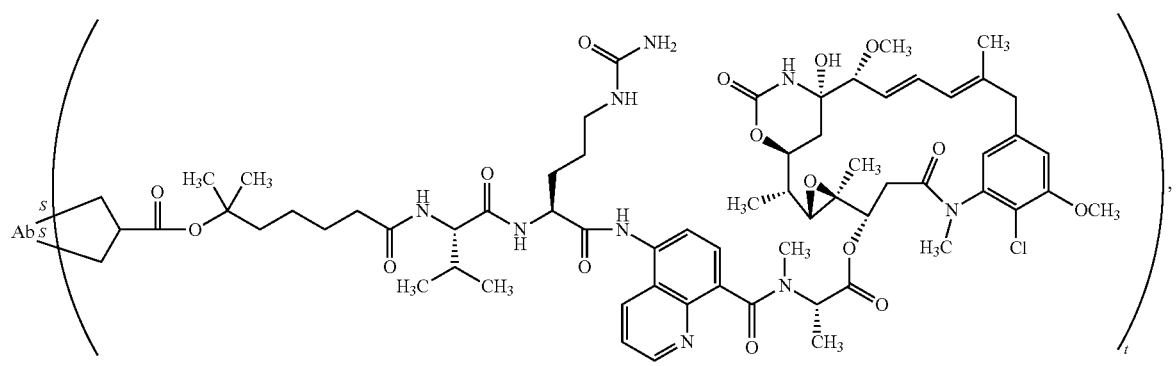
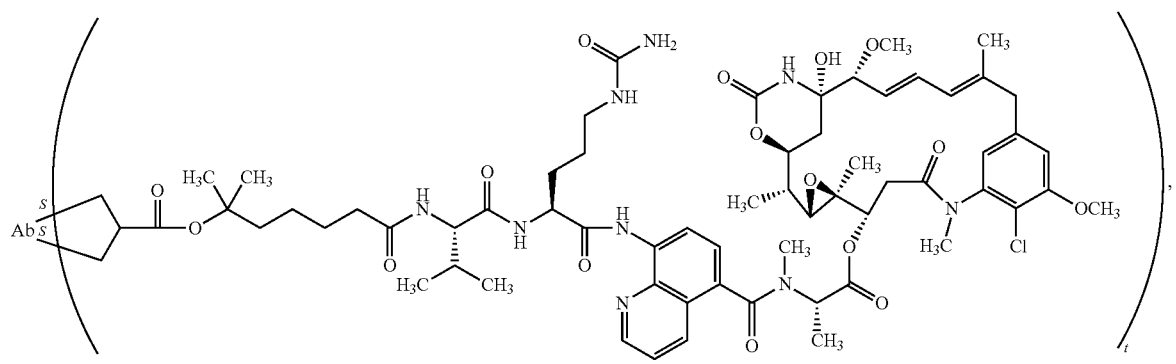
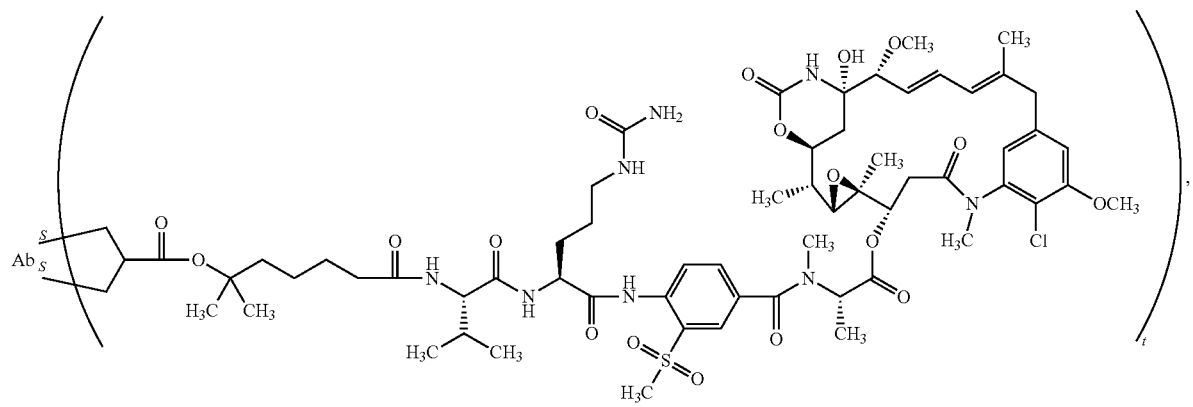
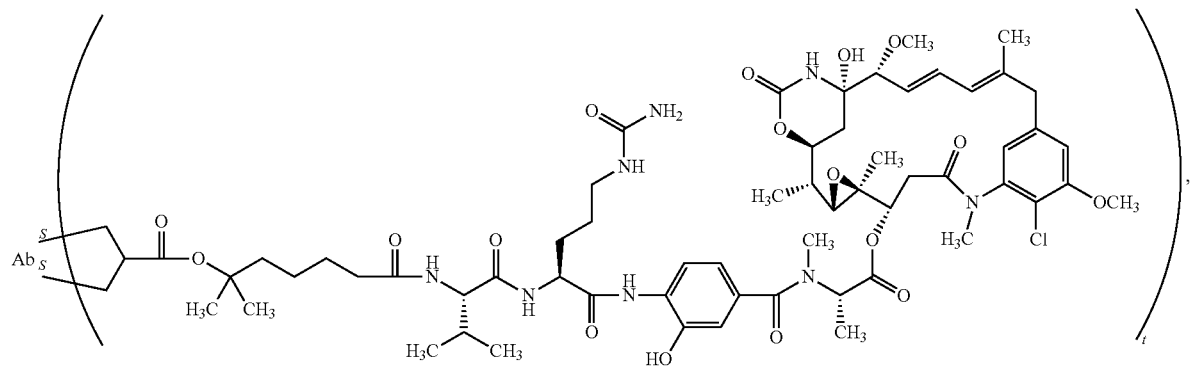

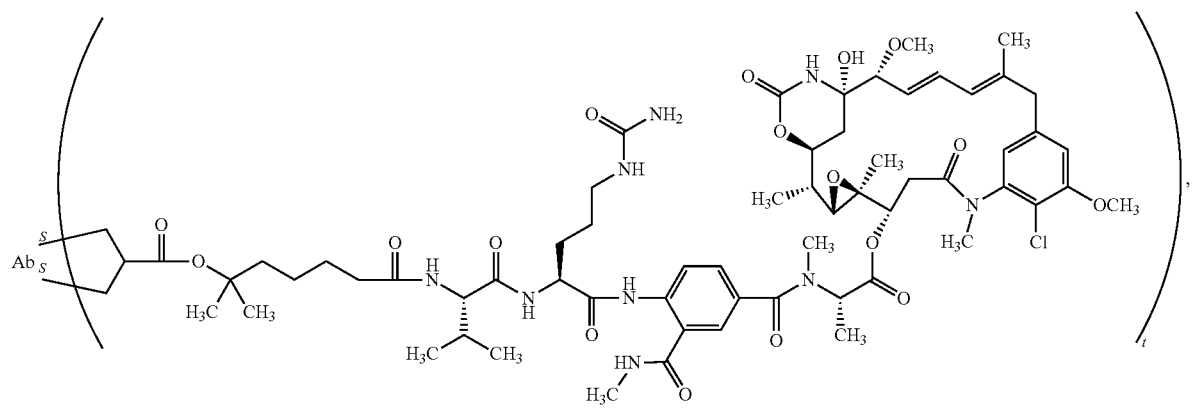
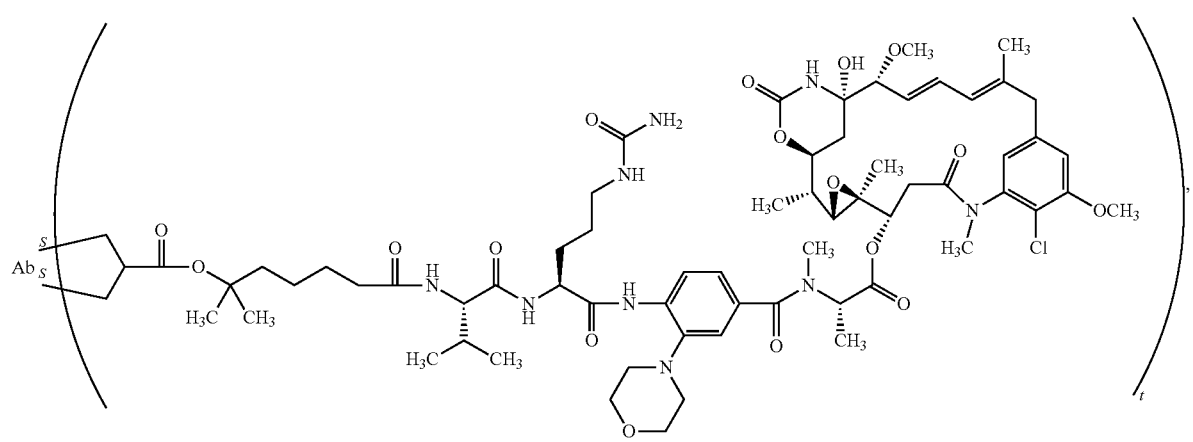
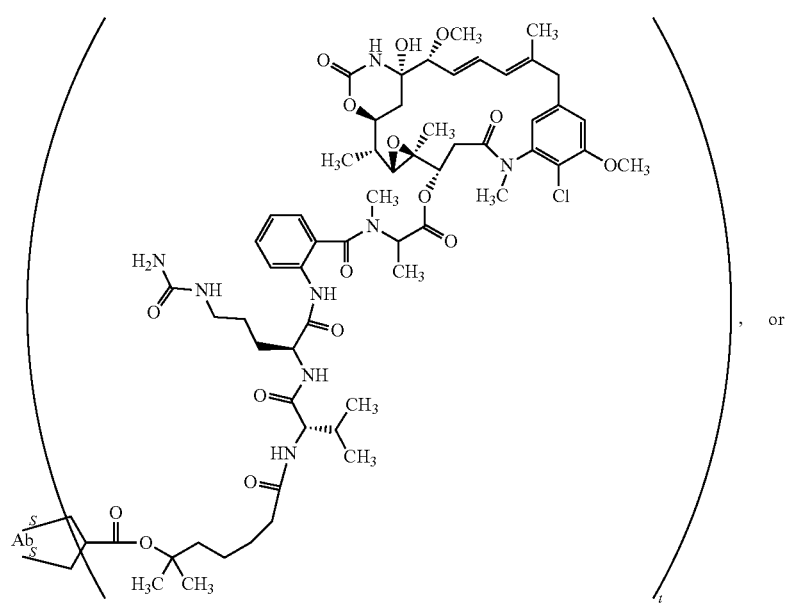
, or

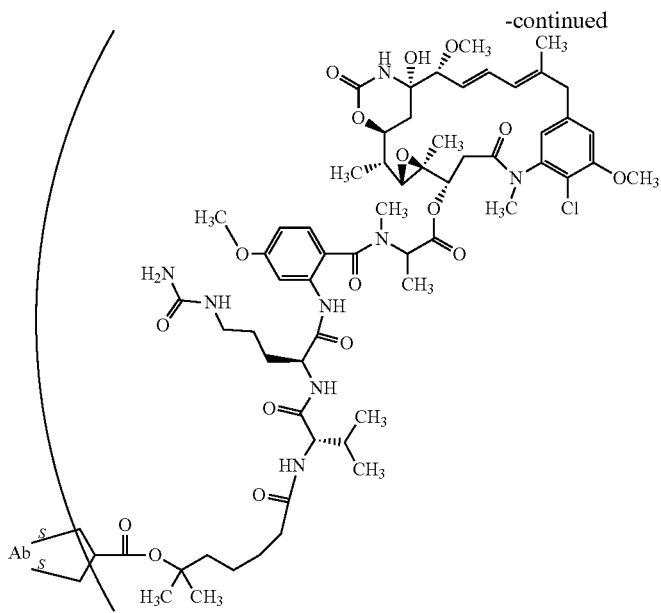

wherein:
  Ab is an antibody;
  S is a bond to a cysteine of the antibody;
  N is a bond to a lysine of the antibody;
  k is an integer from 1 to 30; and
  t is an integer from 1 to 8. In some examples, k is an integer from 1 to 8. In some examples, t is an integer from 1 to 4. In some examples, when S is a bond to a cysteine of the antibody, up to 8 conjugates set forth herein may be bonded to the antibody. In some examples, when N is a bond to a lysine of the antibody, up to 30 conjugates set forth herein may be bonded to the antibody.

In some embodiments, the compound of Formula I is:

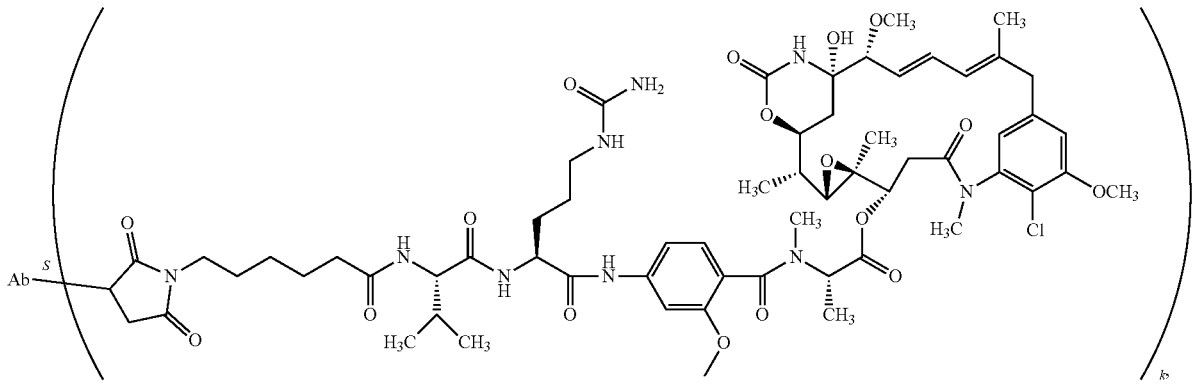

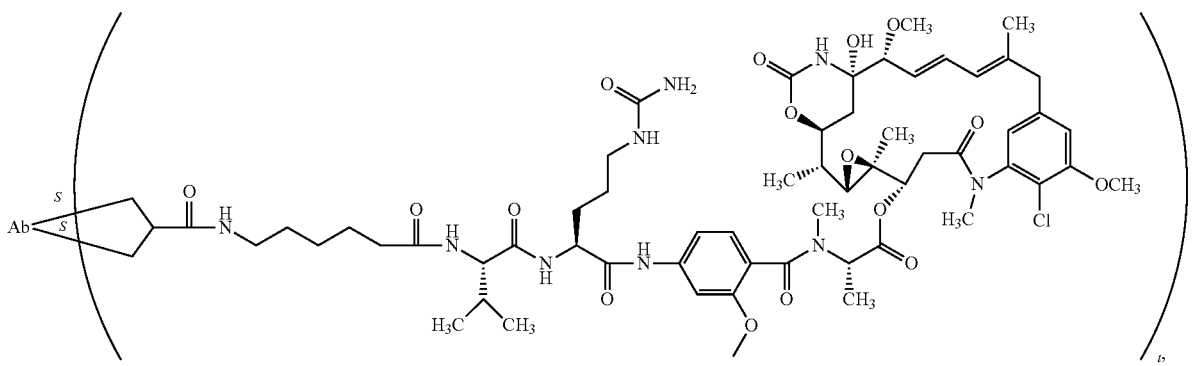

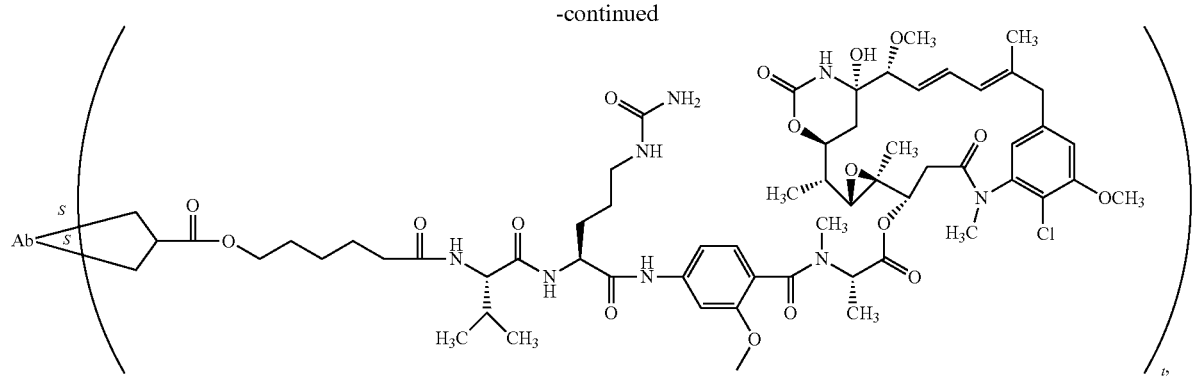
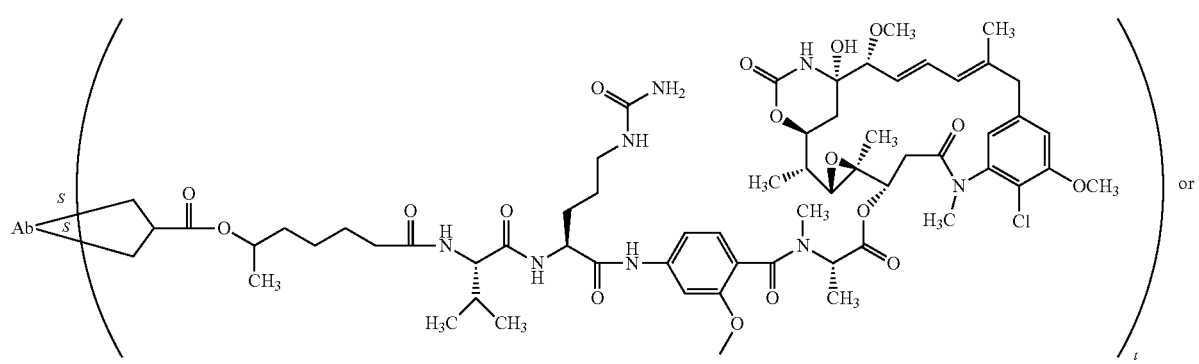
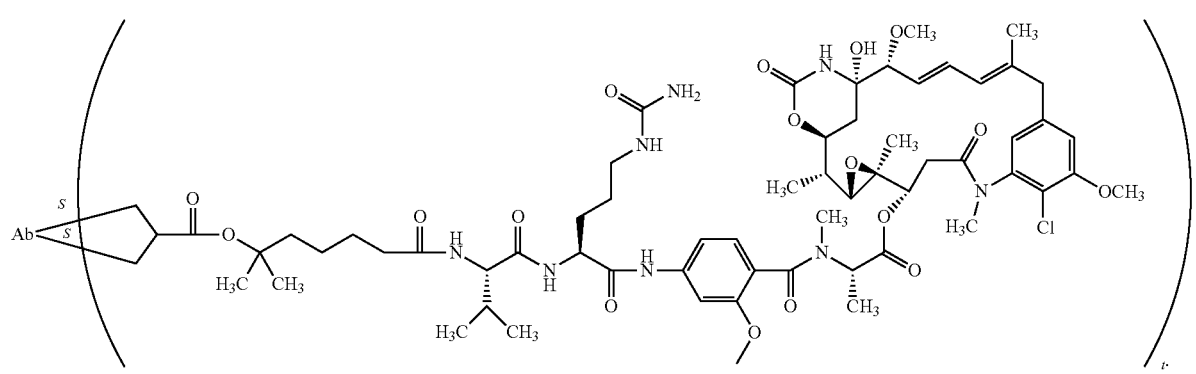
In some embodiment, k is an integer from 1 to 30. In some embodiment, k is an integer from 1 to 8. In some embodiment, k is an integer from 1 to 6. In some embodiments, k is an integer from 1 to 4. In some embodiments, k is an integer from 1 to 3. In some embodiments, the drug-antibody ratio (DAR) of the conjugate is from 1.0 to 3.0.

C. Maytansinoid Derivatives

Provided herein are compounds of Formula (II):

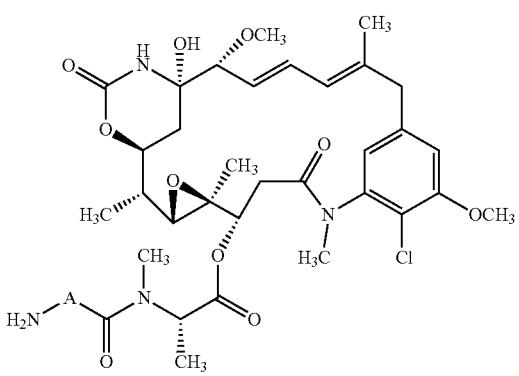

(II)

or a pharmaceutically acceptable salt thereof,
wherein A is arylene or heteroarylene.

In certain embodiments, these compounds represent the payload portion of the conjugates described herein and are released, e.g., by enzyme proteolysis, following internalization of the conjugate into a cell. The methods provided herein include methods of treating a proliferative disease, e.g., cancer, comprising administering to a patient a therapeutically effective amount of a conjugate, e.g., antibody-drug conjugate that releases a compound of Formula (II) following internalization of said conjugate into a cell in said patient.

In some embodiments, these compounds represent the metabolic product of the conjugates described herein, e.g., enzyme proteolysis product. In some embodiments, these compounds represent the catabolic product of the conjugates described herein. In some embodiments, these compounds represent the cellular product of the conjugates described herein.

In some embodiments, A is a divalent radical of benzene, of pyridine, of naphthalene, or of quinolone, which are optionally substituted.

In some embodiments, A is arylene.

In some embodiments, A is:

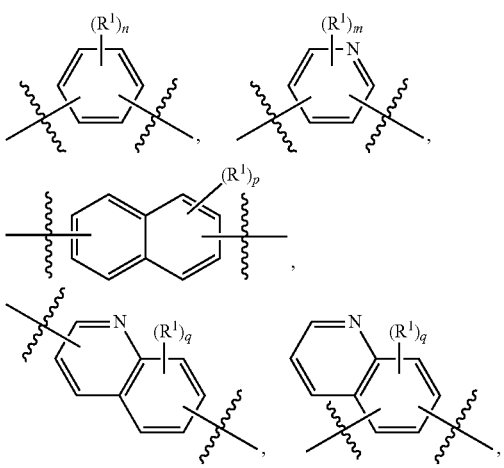

wherein:

$R^1$ is, independently at each occurrence, alkyl, alkenyl, alkynyl, aryl, alkaryl, aralkyl, halo, heteroaryl, heterocycloalkyl, hydroxyl, cyano, nitro,

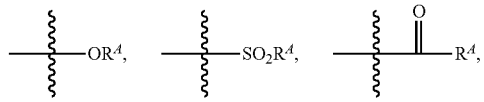

or azido,
wherein $R^A$ is alkyl or heteroalkyl;
n is an integer from 0 to 4;
m is and integer from 0 to 3;
p is an integer from 0 to 6; and
q is an integer from 0 to 5.

In some embodiments, the compound of Formula (II) is a compound of the Formula (IIA):

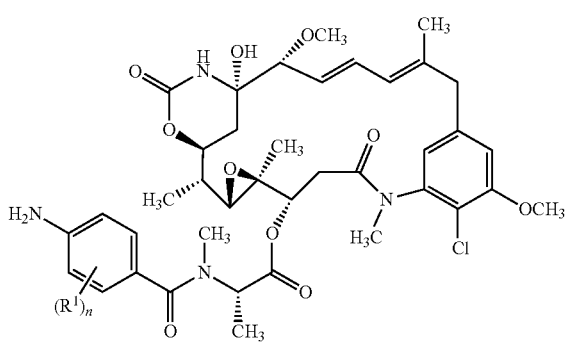

(IIA)

wherein $R^1$ and n are as defined herein.

In some embodiments, the compound of Formula (II) is a compound of the Formula (IIB):

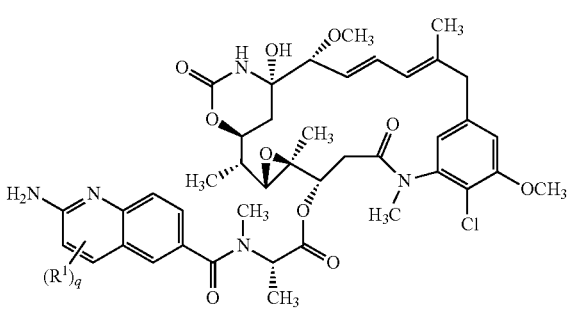

(IIB)

wherein $R^1$ and q are as defined herein.

In some embodiments, the compound of Formula (II) is a compound of the Formula (IIB2):

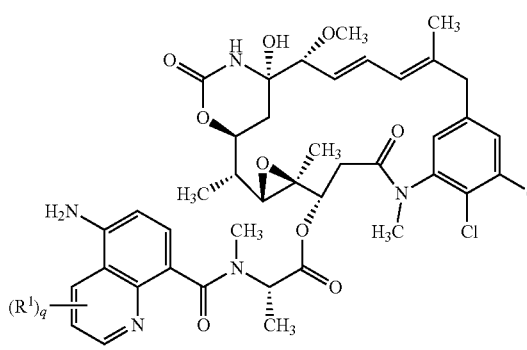

(IIB2)

wherein R¹ and q are as defined herein.

In some embodiments, the compound of Formula (II) is a compound of the Formula (IIB3):

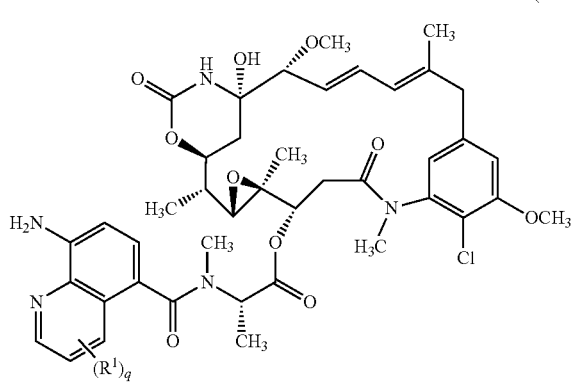

(IIB3)

wherein R¹ and q are as defined herein.

In some embodiments, the compound of Formula (II) is a compound of the Formula (IIC):

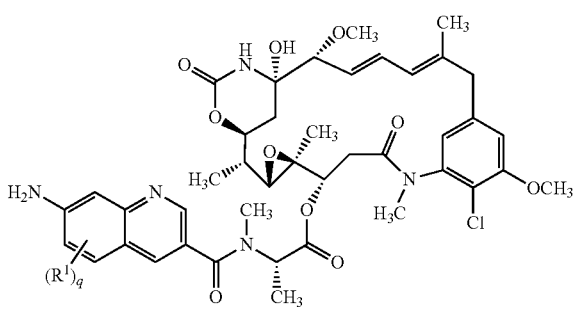

(IIC)

wherein R¹ and q are as defined herein.

In some embodiments, the compound of Formula (II) is a compound of the Formula (IID):

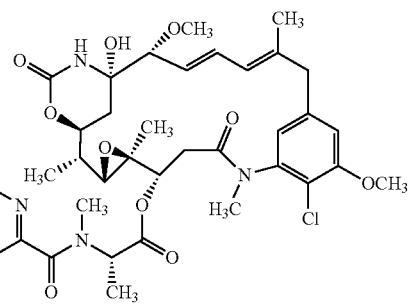

(IID)

wherein R¹ and q are as defined herein.

In some embodiments, the compound of Formula (II) is a compound of the Formula (IIE):

(IIE)

wherein R¹ and q are as defined herein.

In some embodiments, the compound of Formula (II) is a compound of the Formula (IIF):

(IIF)

wherein R¹ and q are as defined herein.

In some embodiments, the compound of Formula (II) is a compound of the Formula (IIG):

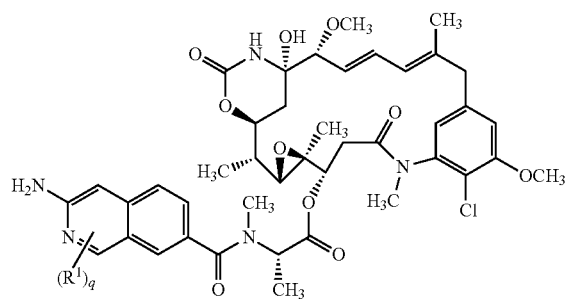
(IIG)

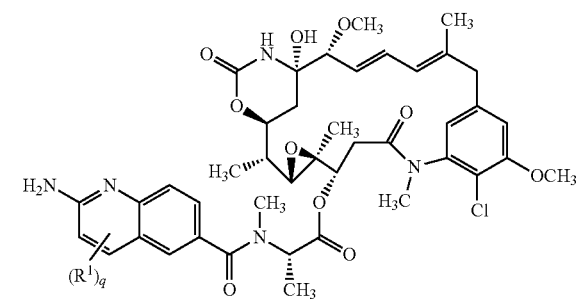
(IIB)

wherein R¹ and q are as defined herein.

In some embodiments, R¹ is, independently, alkyl or halo. In some embodiments, R¹ is, independently, $C_{1-6}$ alkyl, $C_{1-6}$ haloalkyl, or halo. In some embodiments, R¹ is, independently, $C_{1-6}$ haloalkyl or halo. In some embodiments, R¹ is, independently, halo. In some embodiments, R¹ is, independently, fluoro, chloro, bromo, iodo, or trifluoromethyl. In some embodiments, n, m, p, or q is 0, 1 or 2. In some embodiments, n, m, p, or q is 0 or 1. In some embodiments, n, m, p, or q is 0.

In some embodiments, R¹ is, independently, alkyl, alkoxy, heteroalkyl, halo, haloalkyl, or haloalkoxy. In some embodiments, R¹ is, independently, $C_{1-6}$ alkyl, $C_{1-6}$ alkoxy, $C_{1-6}$ haloalkyl, $C_{1-6}$ haloalkoxy, or halo. In some embodiments, R¹ is, independently, $C_{1-6}$ alkyl or $C_{1-6}$ alkoxy. In some embodiments, R¹ is, independently, alkoxy. In some embodiments, R¹ is, independently, methoxy, ethoxy, propoxy. In some embodiments, n, m, p, or q is 0, 1 or 2. In some embodiments, n, m, p, or q is 0 or 1. In some embodiments, n, m, p, or q is 0. In some embodiments, the compound of Formula (II) is a compound of Formula (IIA):

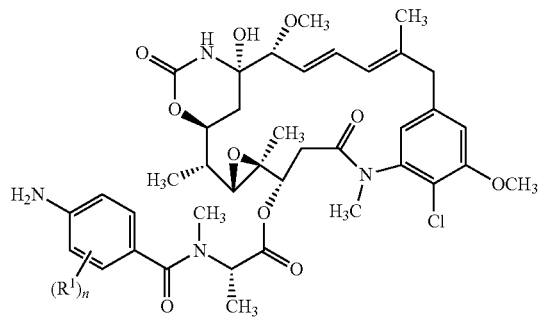
(IIA)

wherein:
R¹ is, independently at each occurrence, halo or trifluoromethyl; and
n is 0, 1, or 2.

In some embodiments, the compound of Formula (II) is a compound of Formula (IIB):

wherein:
R¹ is, independently at each occurrence, halo or trifluoromethyl; and
q is 0, 1, or 2.

In some embodiments, the compound of Formula (II) is:

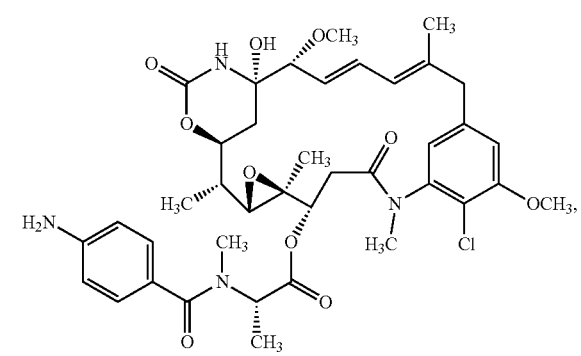

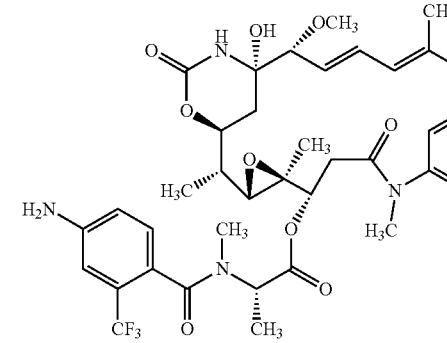

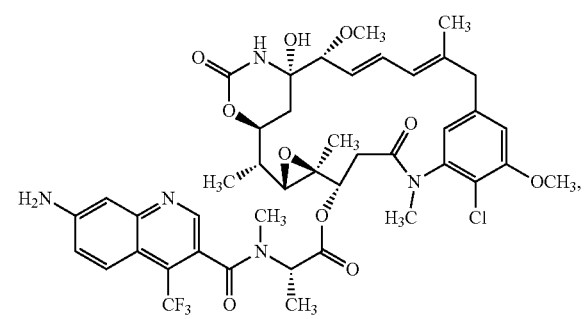

169
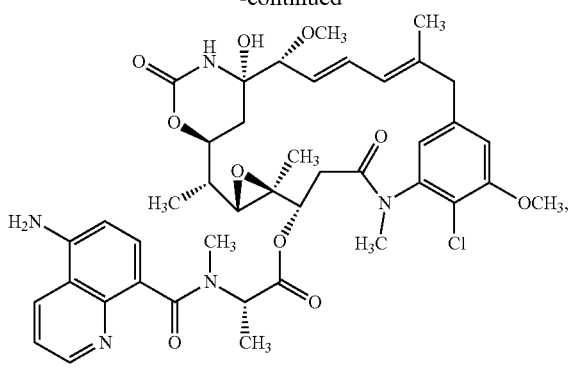
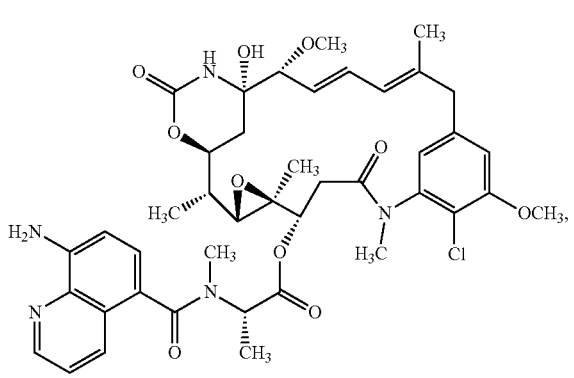
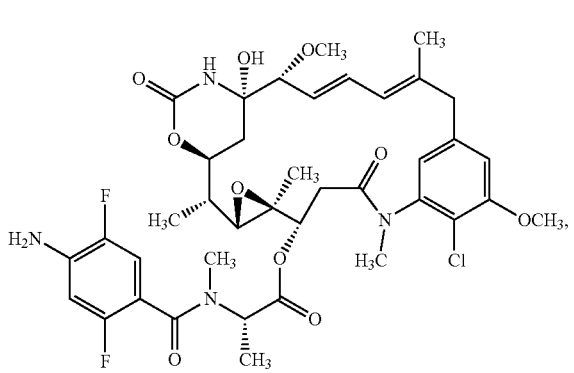
or
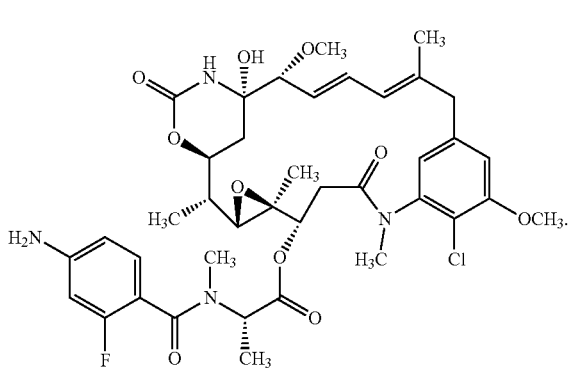
In some embodiments, the compound of Formula (II) is a compound selected from
170
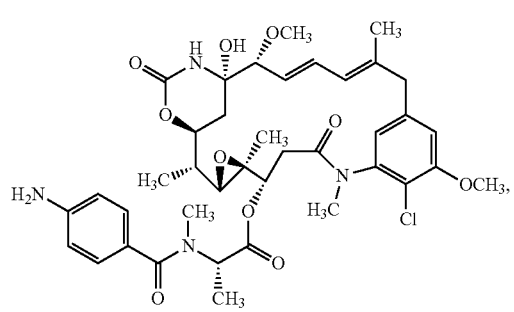
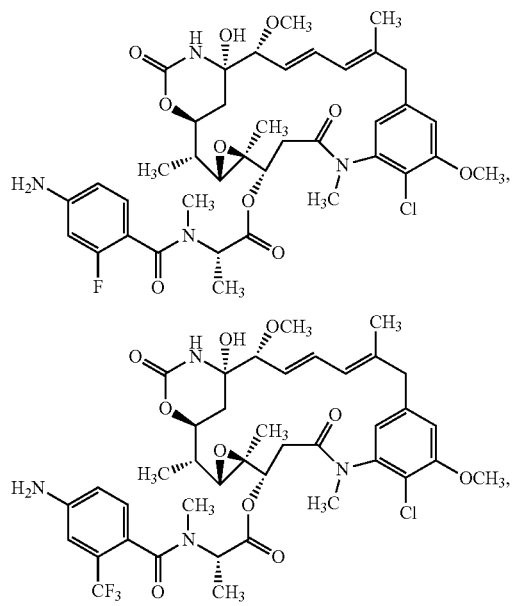
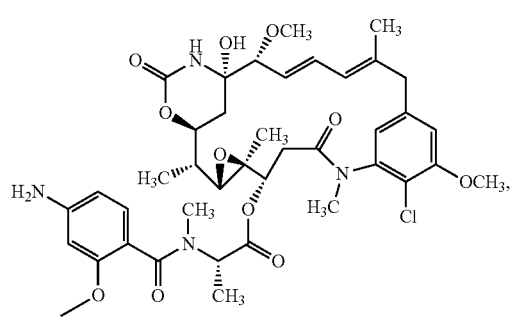
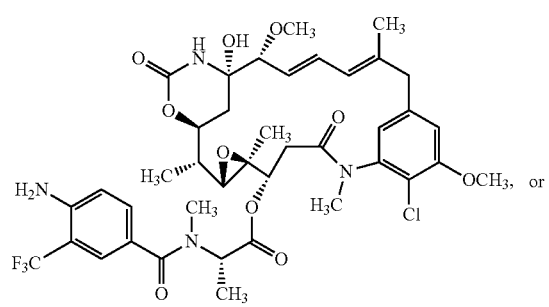

-continued

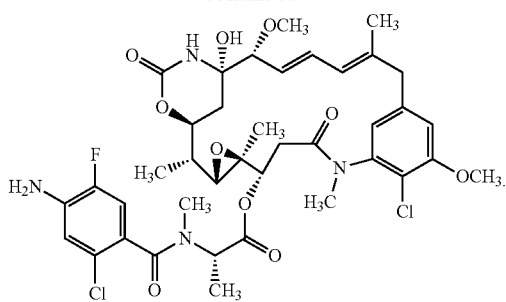

In some embodiments, the compound of Formula (II) is:

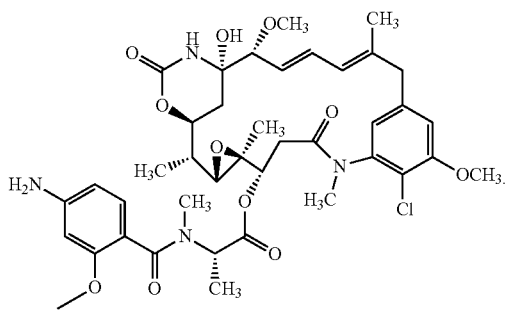

In certain embodiments, these compounds represent the payload portion of the conjugates described herein and are released, e.g., by enzyme proteolysis, following internalization of the conjugate into a cell. The methods provided herein include methods of treating a proliferative disease, e.g., cancer, comprising administering to a patient a therapeutically effective amount of a conjugate, e.g., antibody-drug conjugate that releases a compound of Formula (II) following internalization of said conjugate into a cell in said patient.

In some embodiments, these compounds represent the metabolic product of the conjugates described herein, e.g., enzyme proteolysis product.

In some embodiments, A is a divalent radical of benzene, of pyridine, of naphthalene, or of quinolone, which are optionally substituted.

In some embodiments, A is arylene.

In some embodiments, A is:

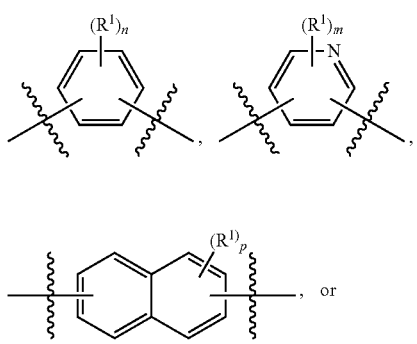

-continued

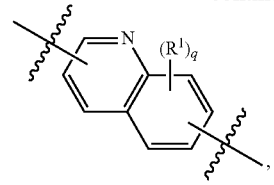

wherein:
R$^1$ is, independently at each occurrence, alkyl, alkenyl, alkynyl, aryl, alkaryl, aralkyl halo, haloalkoxy, heteroaryl, heterocycloalkyl, hydroxyl, cyano, nitro,

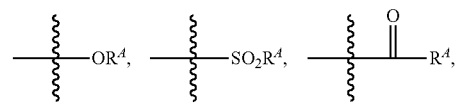

or azido,
wherein R$^A$ is alkyl or heteroalkyl;
n is an integer from 0 to 4;
m is and integer from 0 to 3;
p is an integer from 0 to 6; and
q is an integer from 0 to 5.
In some embodiments, the compound of Formula (II) is a compound of the Formula (IIA):

(IIA)

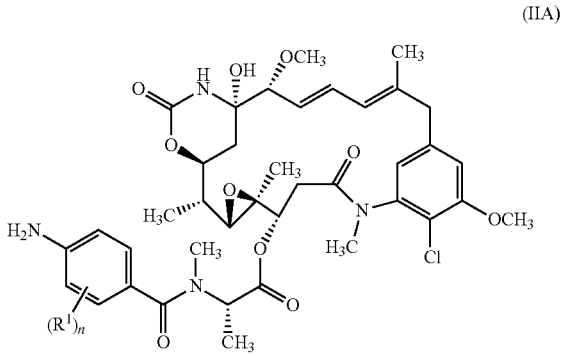

wherein R$^1$ is, independently at each occurrence, methoxy, halo or trifluoromethyl; and
n is 0, 1, or 2.
In some embodiments, the compound of Formula (II) is a compound of the Formula (IIB):

(IIB)

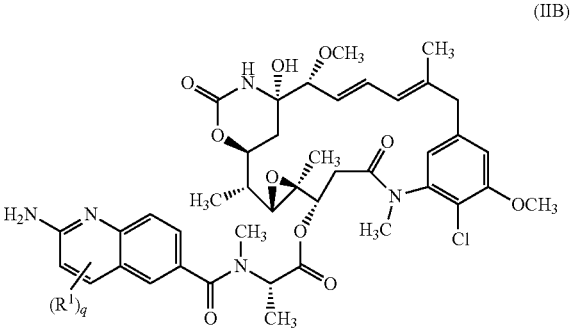

wherein R¹ is, independently at each occurrence, methoxy, halo or trifluoromethyl; and q is 0, 1, or 2.

In some embodiments, the compound of Formula (II) is a compound of the Formula (IIB2):

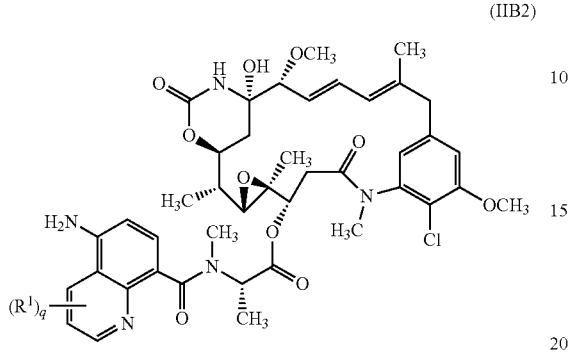

(IIB2)

wherein R¹ is, independently at each occurrence, methoxy, halo or trifluoromethyl; and q is 0, 1, or 2.

In some embodiments, the compound of Formula (II) is a compound of the Formula (IIB3):

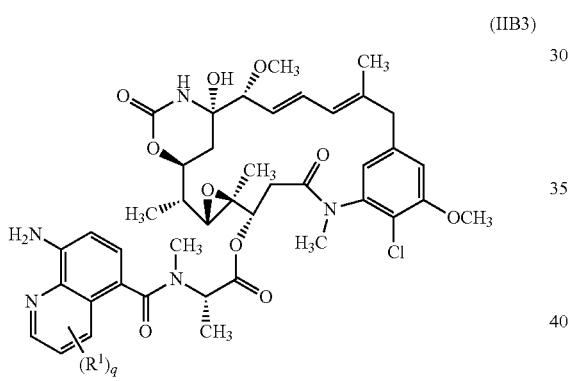

(IIB3)

wherein R¹ is, independently at each occurrence, methoxy, halo or trifluoromethyl; and q is 0, 1, or 2. In some embodiments, R¹ is, independently, alkyl or halo. In some embodiments, R¹ is, independently, $C_{1-6}$ alkyl, $C_{1-6}$ haloalkyl, or halo. In some embodiments, R¹ is, independently, $C_{1-6}$ haloalkyl or halo. In some embodiments, R¹ is, independently, halo. In some embodiments, R¹ is, independently, fluoro, chloro, bromo, iodo, or trifluoromethyl. In some embodiments, n, m, p, or q is 0, 1 or 2. In some embodiments, n, m, p, or q is 0 or 1. In some embodiments, n, m, p, or q is 0.

In some embodiments, R¹ is, independently, alkyl, alkoxy, heteroalkyl, halo, haloalkyl, or haloalkoxy. In some embodiments, R¹ is, independently, $C_{1-6}$ alkyl, $C_{1-6}$ alkoxy, $C_{1-6}$ haloalkyl, $C_{1-6}$ haloalkoxy, or halo. In some embodiments, R¹ is, independently, $C_{1-6}$ alkyl or $C_{1-6}$ alkoxy. In some embodiments, R¹ is, independently, alkoxy. In some embodiments, R¹ is, independently, methoxy, ethoxy, propoxy. In some embodiments, n, m, p, or q is 0, 1 or 2. In some embodiments, n, m, p, or q is 0 or 1. In some embodiments, n, m, p, or q is 0.

In some embodiments, the compound of Formula (II) is:

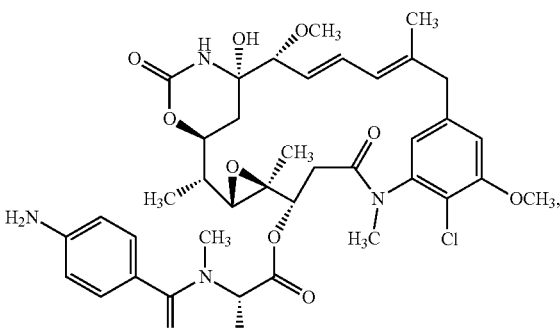

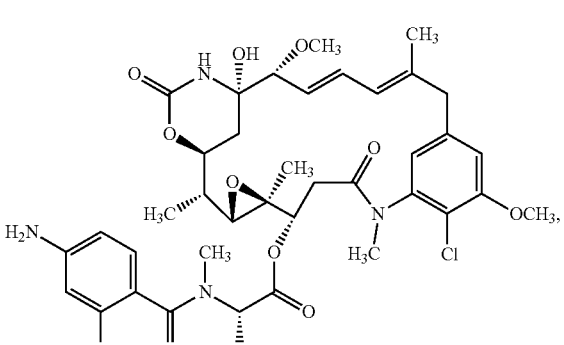

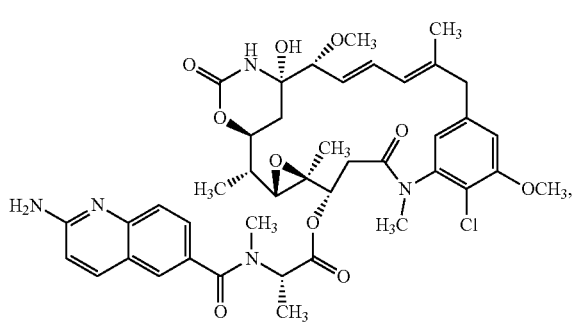

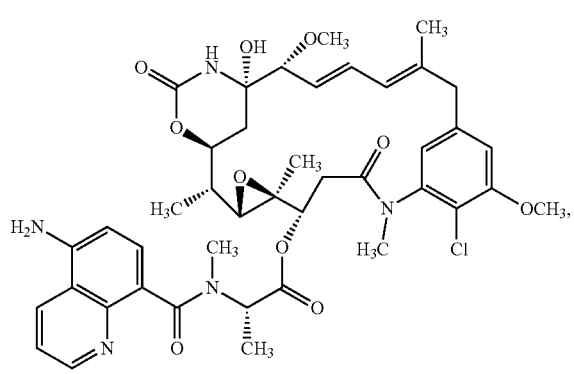

-continued
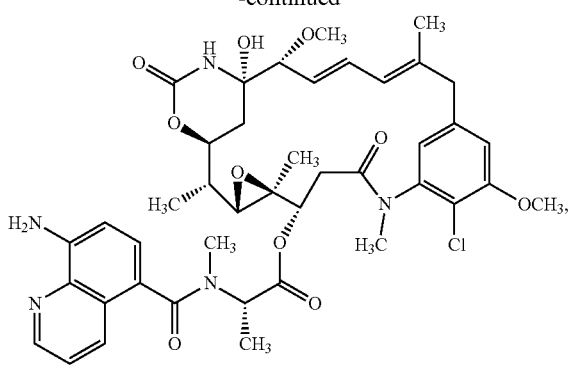
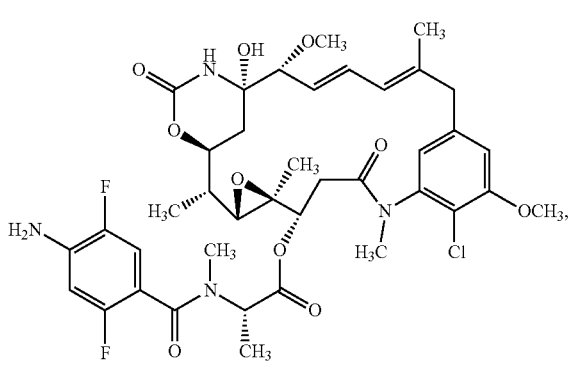
or
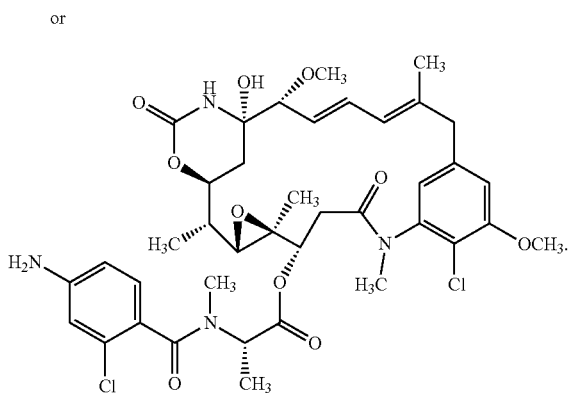
In some embodiments, the compound of Formula (II) is a compound of the Formula (IIH).
(IIH)
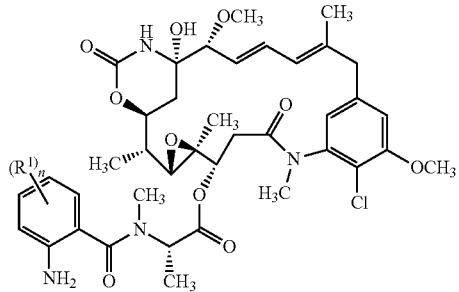
wherein R¹ and n are as defined herein.
In some embodiments, the compound of Formula (II) is a compound selected from
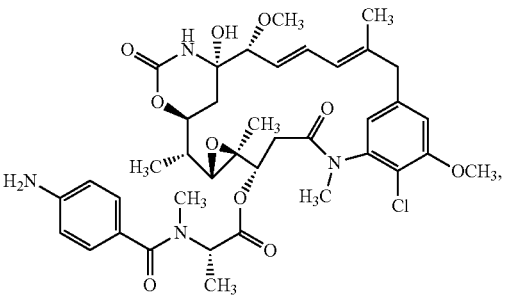
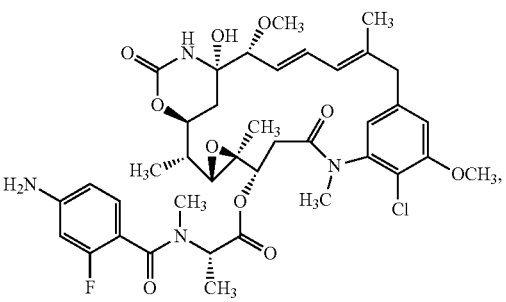
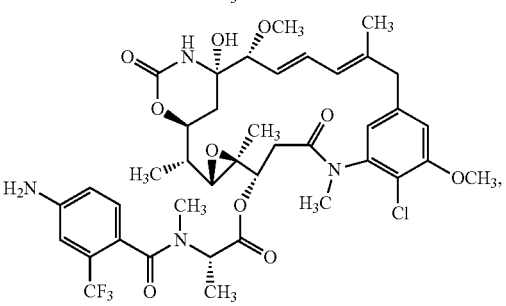
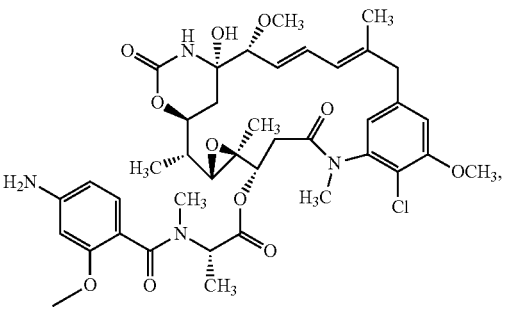 [SMILES: COc1cc(N)ccc1C(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]
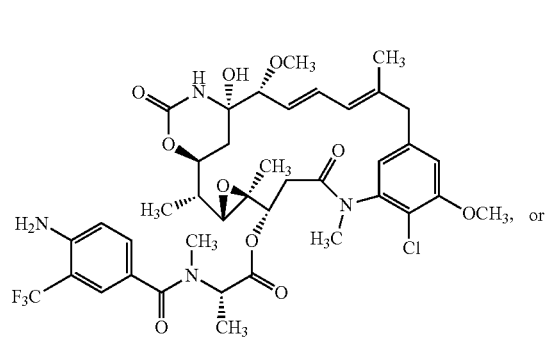

-continued

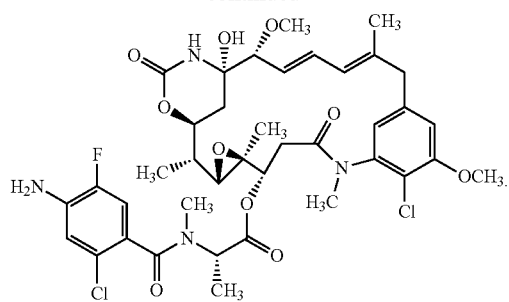

In some embodiments, the compound of Formula (II) is a compound selected fro

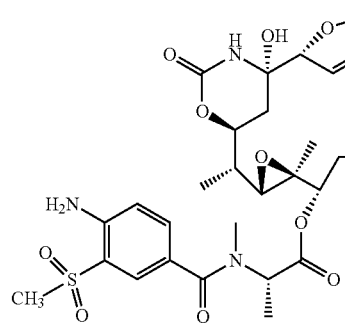

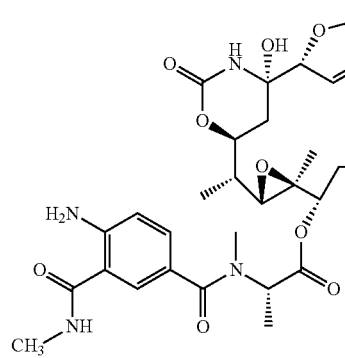

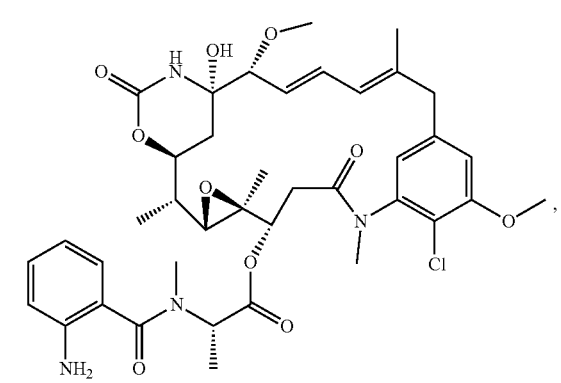

-continued

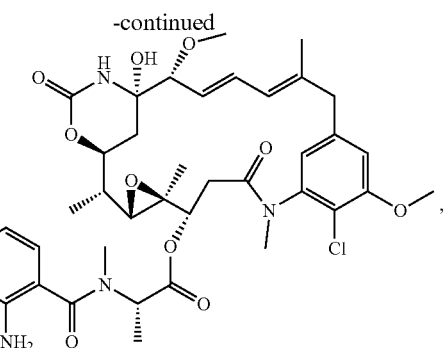

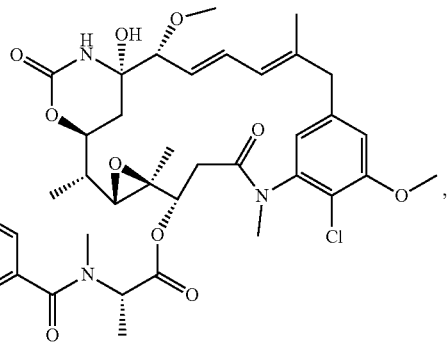

or

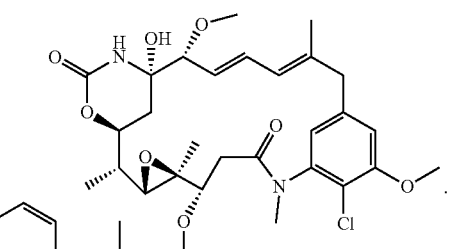

D. Preparation of Compounds

Compounds of Formula I can be synthesized by coupling compounds of Formula P1 with a binding agent, e.g., antibody under standard conjugation conditions (see, e.g, Doronina et al., *Nature Biotechnology* 2003, 21, 7, 778, which is incorporated herein by reference). When the binding agent is an antibody, the antibody can be coupled to a compound of Formula P1 via one or more cysteine or lysine residues of the antibody. Compounds of Formula P1 can be coupled to cysteine residues, for example, by subjecting the antibody to a reducing agent, e.g., dithiotheritol, to cleave the disulfide bonds of the antibody, purifying the reduced antibody, e.g., by gel filtration, and subsequently reacting the antibody with a compound of formula P1 containing a reactive moiety, e.g., a maleimido group. Suitable solvents include, but are not limited to water, DMA, DMF, and DMSO. Compounds of formula P1 containing a reactive moiety, e.g., activated ester or acid halide group, can be coupled to lysine residues. Suitable solvents include, but are not limited to water, DMA, DMF, and DMSO. The compounds of Formula I can be purified using known protein techniques, including, for example, size exclusion chromatography, dialysis, and ultrafiltration/diafiltration.

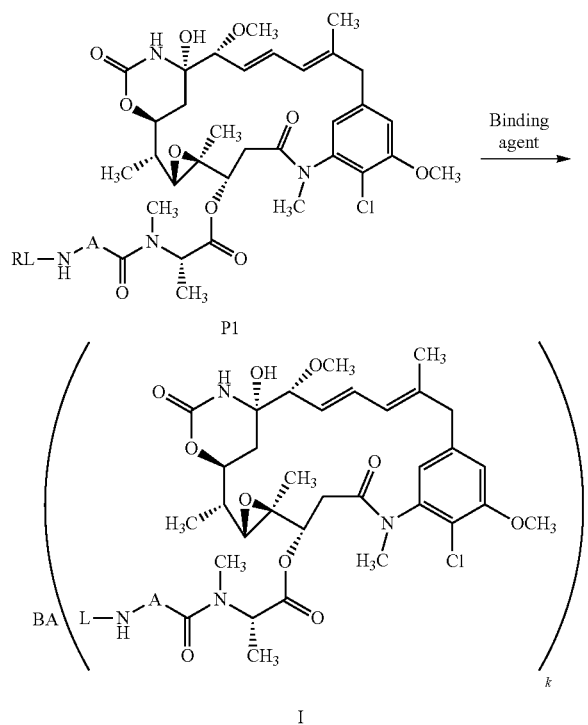

P1

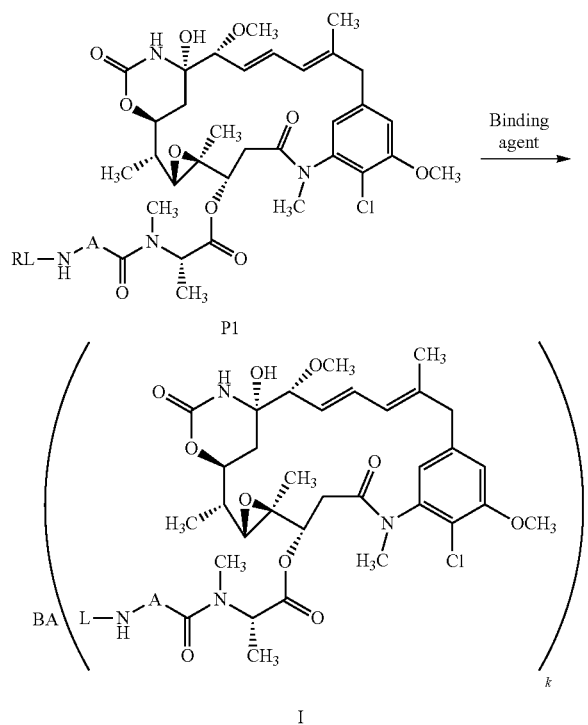

I wherein RL is a reactive linker, A is arylene or heteroarylene, L is a linker, and BA is a binding agent.

In some embodiments, the compound of formula P1 includes A, wherein A is:

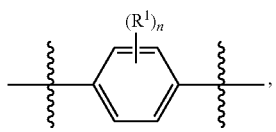

wherein n is 0 or 1; and $R^1$ is alkoxy, halo, or haloalkyl.

In some embodiments, the compound of formula P1 includes A, wherein A is:

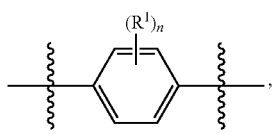

wherein n is 0 or 1; and $R^1$ is $C_{1-6}$ alkoxy, halo, or $C_{1-6}$ haloalkyl.

In some embodiments, the compound of formula P1 includes A, wherein A is:

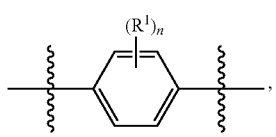

wherein n is 0 or 1; $R^1$ is $C_{1-6}$ alkoxy, halo, or $C_{1-6}$ haloalkyl; and RL is

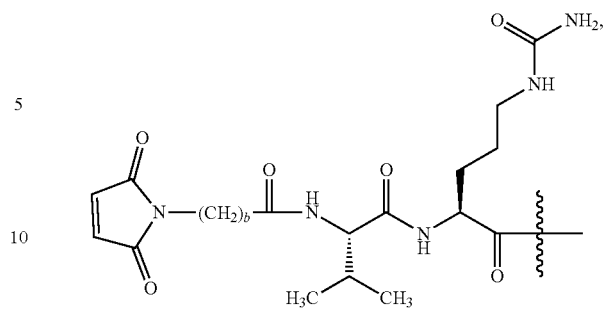

wherein b is an integer from 2 to 8 and

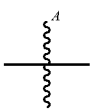

is a bond to the binding agent.

The reactive linker is a moiety comprising a portion in its structure that is capable of reacting with the binding agent (e.g., reacting with an antibody at its cysteine or lysine residues) to form the compound of Formula I. Following conjugation to the binding agent, the reactive linker becomes the linker (L) moiety of the compound of Formula I. Illustrative reactive linkers include, but are not limited to, those that comprise haloacetyl, isothiocyanate, or maleimide portions that are capable of reacting with the binding agent. Reactive portions also include moieties having the following structure:

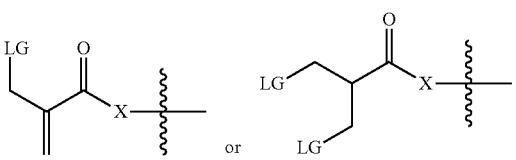

wherein X is —O— or —NH— and LG is a leaving group, e.g., Br.

In some embodiments, the reactive linker is:

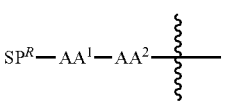

wherein:
SP$^R$ is a reactive spacer;
AA$^1$ is an amino acid; and
AA$^2$ is an amino acid.

The reactive spacer is a moiety that contains the above-described reactive linker portion that is capable of reacting with the binding agent and connects this portion to AA$^1$. Suitable spacers include, but are not limited to, those comprising alkylene or polyethylene glycol connecting the AA$^1$ to the portion capable of reacting with binding agent (e.g., haloacetyl, isothiocyanate, or maleimide).

In some embodiments, the reactive spacer comprises a non-cleavable moiety selected from

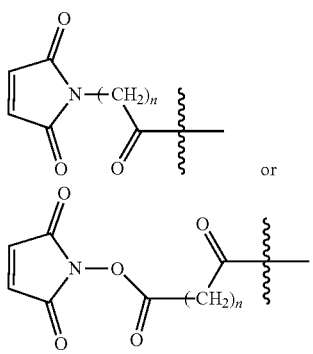

wherein

represents one or more bonds to the maytansinoid derivative; and wherein n is an integer from 4 to 10. In some examples, n is 4, 5, 6, 7, 8, 9, or 10. In some embodiments, the reactive spacer is

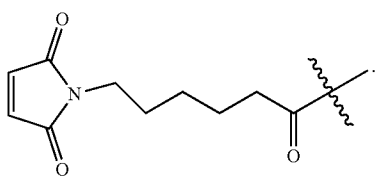 [SMILES: *C(=O)CCCCCN1C(=O)C=CC1=O]

In some embodiments, the reactive spacer is

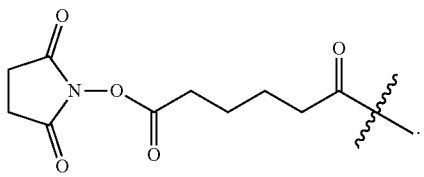 [SMILES: *C(=O)CCCCC(=O)ON1C(=O)CCC1=O]

In some embodiments, the reactive spacer is:

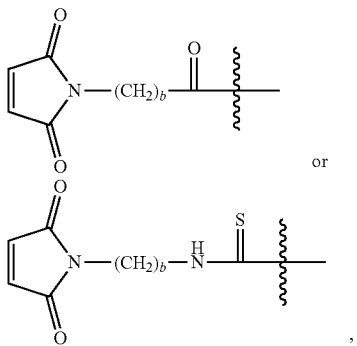

wherein b is an integer from 2 to 8.

In some embodiments, the reactive spacer is:

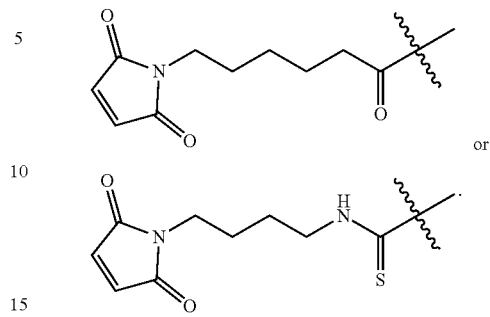

In some embodiments, the spacer is

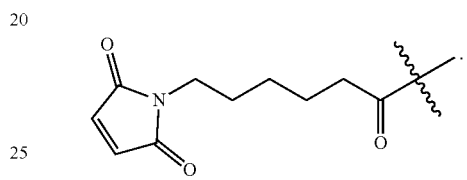

In some embodiments, the spacer is

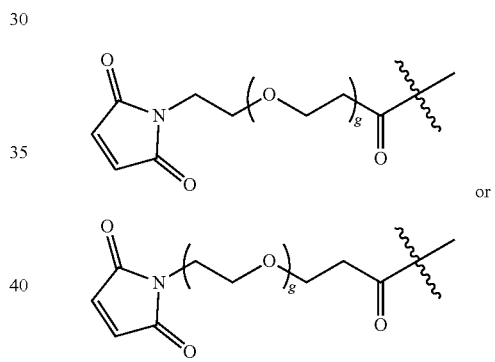

wherein g is an integer from 1 to 24.

In some embodiments, the reactive spacer is:

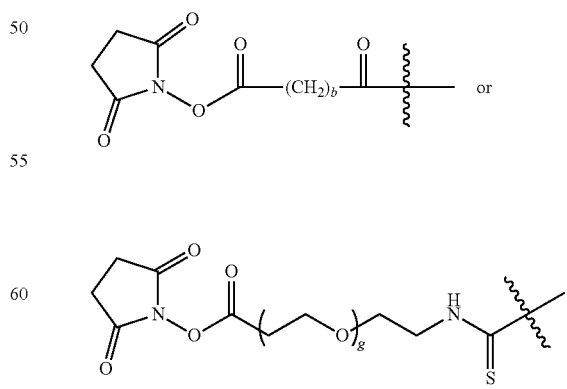

wherein b is an integer from 2 to 8 and g is an integer from 2 to 20.

In some embodiments, the reactive spacer is:

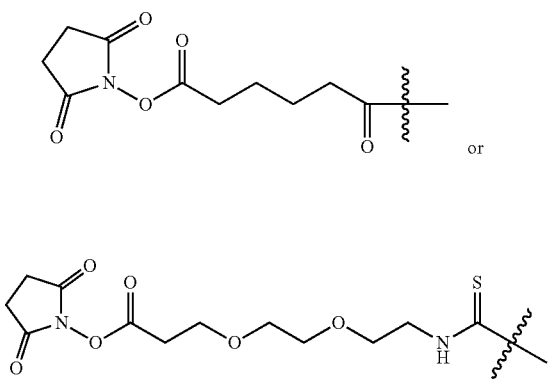

or

In some embodiments, AA$^1$-AA$^2$ is: valine-citrulline, citrulline-valine, lysine-phenylalanine, phenylalanine-lysine, valine-asparagine, asparagine-valine, threonine-asparagine, asparagine-threonine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some embodiments, AA$^1$-AA$^2$ is: valine-citrulline or citrulline-valine. In some embodiments, AA$^1$-AA$^2$ is: valine-citrulline.

In some embodiments, the reactive linker is:

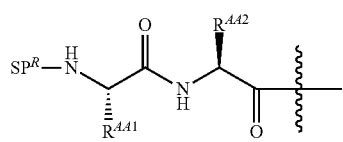

wherein:
SP$^R$ is a reactive spacer;
R$^{AA1}$ is an amino acid side chain; and
R$^{AA2}$ is an amino acid side chain.

In some embodiments, the reactive linker is:

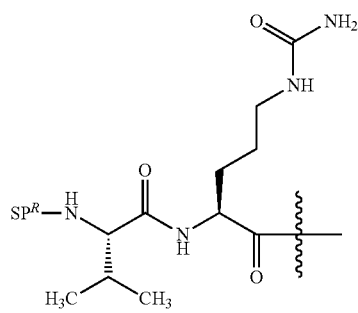

wherein:
SP is a reactive spacer.

In some embodiments, the reactive linker is:

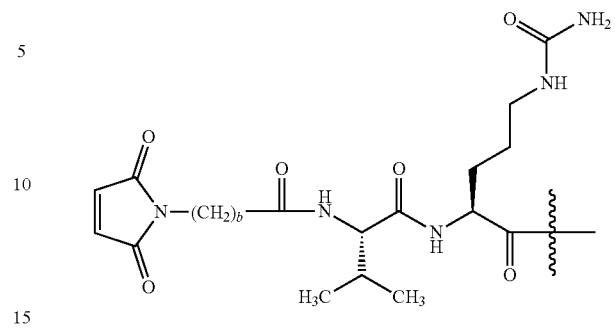

wherein b is an integer from 2 to 8.

In some embodiments, the reactive linker is:

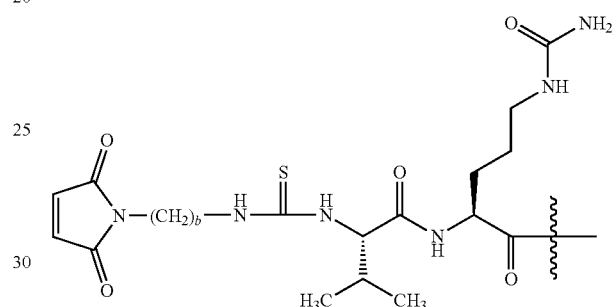

wherein b is an integer from 2 to 8.

In some embodiments, the reactive linker is:

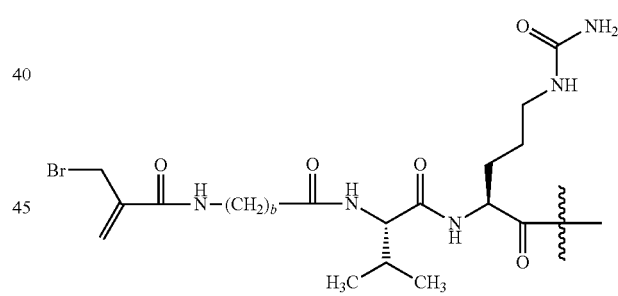

wherein b is an integer from 2 to 8.

In some embodiments, the reactive linker is:

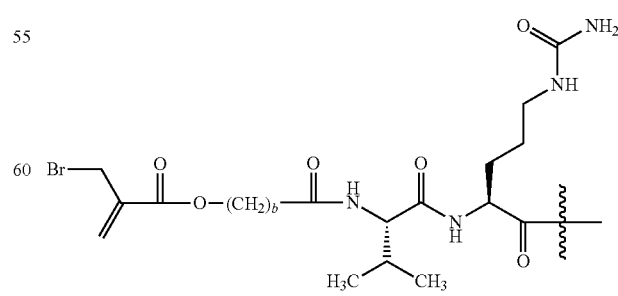

wherein b is an integer from 2 to 8.

In some embodiments, the reactive linker is:

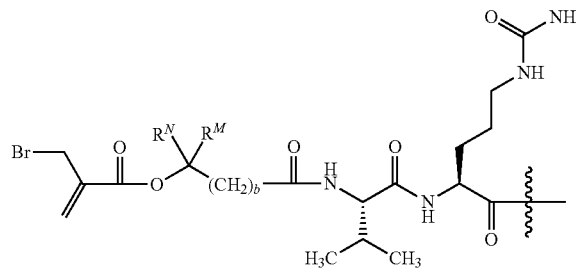

wherein b is an integer from 2 to 8, $R^N$ is a hydrogen atom or alkyl, and $R^M$ is alkyl.

In some embodiments, the reactive linker is:

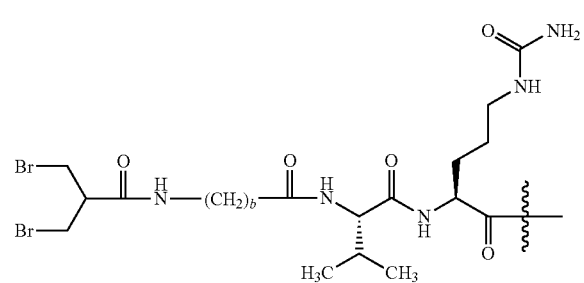

wherein b is an integer form 2 to 8.

In some embodiments, the reactive linker is:

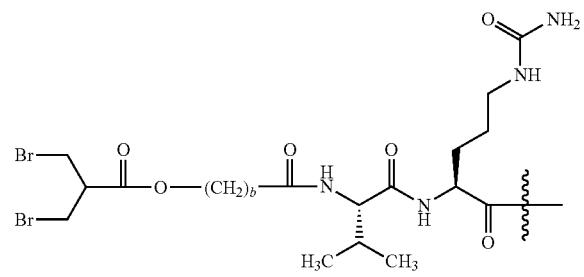

wherein b is an integer from 2 to 8.

In some embodiments, the reactive linker is:

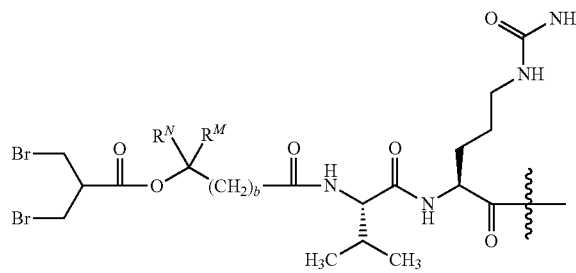

wherein b is an integer from 2 to 8; $R^N$ is a hydrogen atom or alkyl; and $R^M$ is alkyl.

In some embodiments, the reactive linker is:

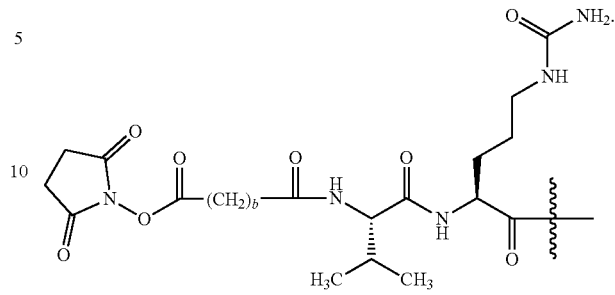

wherein b is an integer from 2 to 8.

In some embodiments, the reactive linker is:

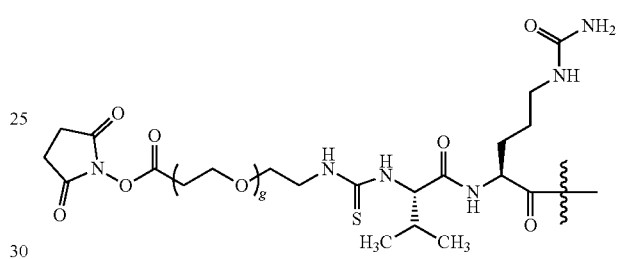

wherein g is an integer from 2 to 8.

In some embodiments, the reactive linker is:

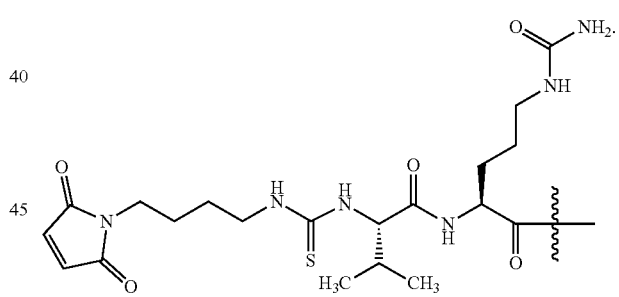

In some embodiments, the reactive linker is:

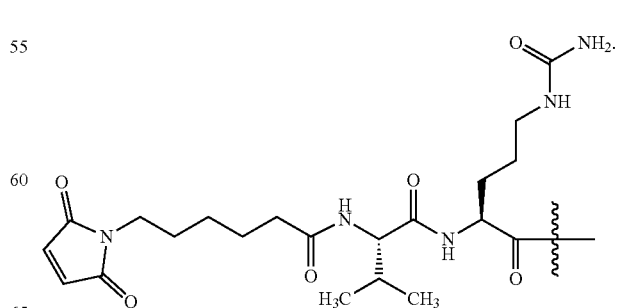

187
In some embodiments, the reactive linker is:
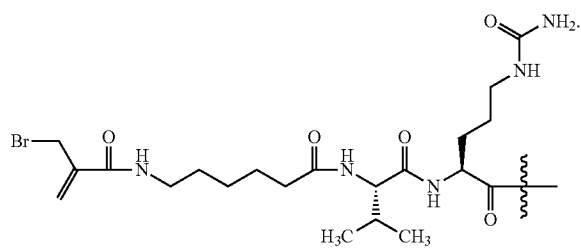 [SMILES: *C(=O)[C@H](CCCNC(N)=O)NC(=O)[C@@H](NC(=O)CCCCCNC(=O)C(=C)CBr)C(C)C]
In some embodiments, the reactive linker is:
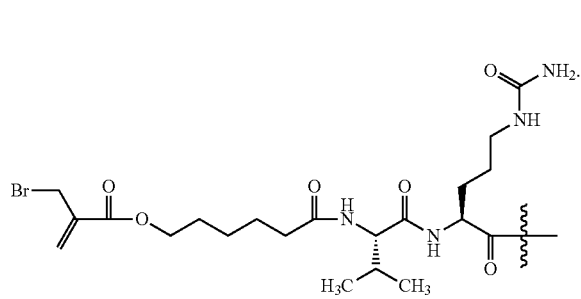 [SMILES: *C(=O)[C@H](CCCNC(N)=O)NC(=O)[C@@H](NC(=O)CCCCCOC(=O)C(=C)CBr)C(C)C]
In some embodiments, the reactive linker is:
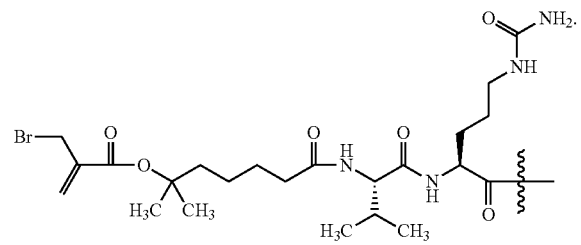 [SMILES: *C(=O)[C@H](CCCNC(N)=O)NC(=O)[C@@H](NC(=O)CCCCC(C)(C)OC(=O)C(=C)CBr)C(C)C]
In some embodiments, the reactive linker is:
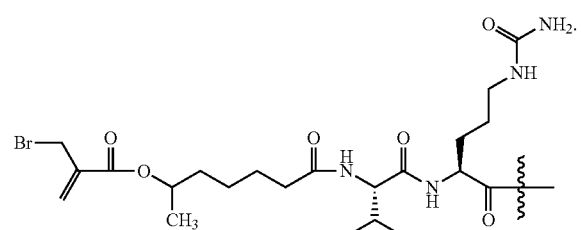
188
In some embodiments, the reactive linker is:
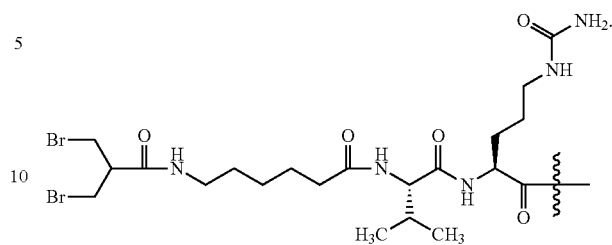
In some embodiments, the reactive linker is:
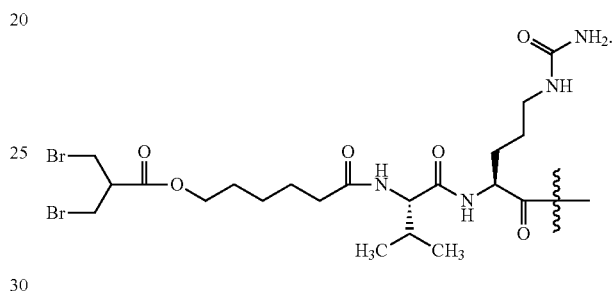
In some embodiments, the reactive linker is:
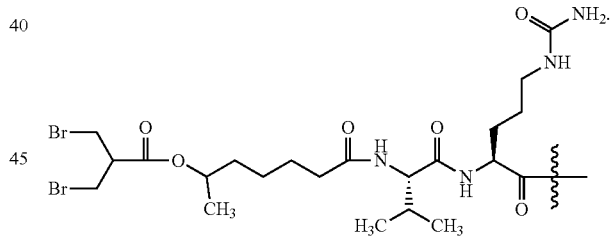
In some embodiments, the reactive linker is:
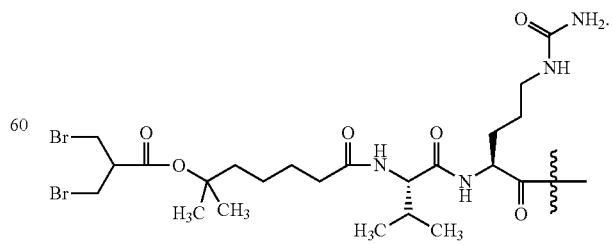

In some embodiments, the reactive linker is:

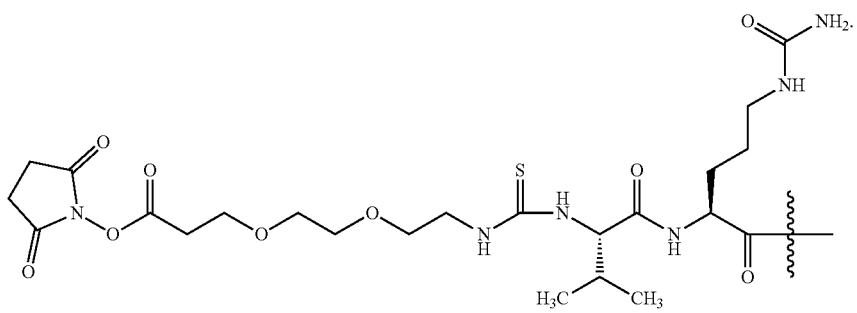 [SMILES: *C(=O)[C@H](CCCNC(N)=O)NC(=O)[C@@H](NC(=S)NCCOCCOCCC(=O)ON1C(=O)CCC1=O)C(C)C]

In some embodiments, the reactive linker is:

[structure 20]

In some embodiments, the compound of Formula P1 is a compound of Formula P1A:

P1A

[structure with SP^R—AA^1—AA^2 attached to maytansinoid core through A]

wherein:

A is:

[three structures shown: substituted phenyl with (R^1)_n, substituted pyridyl with (R^1)_m, substituted naphthyl with (R^1)_p, or]

-continued

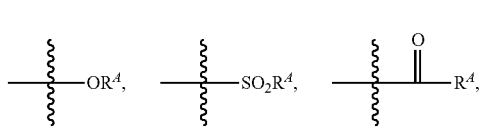

wherein:

R^1 is alkyl, alkenyl, alkynyl, alkoxy, aryl, alkaryl, aralkyl, halo, haloalkoxy, haloalkyl, heteroaryl, heterocycloalkyl, hydroxyl, cyano, nitro,

[three substituent structures: —OR^A, —SO_2R^A, —C(O)R^A]

or azido, wherein R^A is alkyl or heteroalkyl;

n is an integer from 0 to 4;

m is an integer from 0 to 3;

p is an integer from 0 to 6; and q is an integer from 0 to 5;

SP^R is a reactive spacer;

AA^1 is an amino acid; and

AA^2 is an amino acid.

In some embodiments, the compound of Formula P1A is a compound which includes A wherein A is:

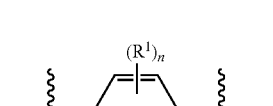

wherein n is 0 or 1; and R^1 is alkoxy, halo, or haloalkyl. In some examples, R^1 is methylsulfonyl, N-methylformamide, hydroxyl, or morpholinyl.

In some embodiments, the compound of Formula P1A is a compound which includes A wherein A is:

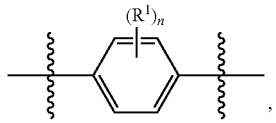

wherein n is 0 or 1; and $R^1$ is $C_{1-6}$ alkoxy, halo, or $C_{1-6}$ haloalkyl.

In some embodiments, the compound of Formula P1A is a compound which includes A wherein A is:

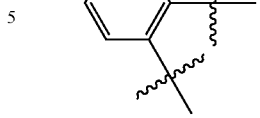

wherein n is 0 or 1; and $R^1$ is alkoxy, halo, or haloalkyl. In some examples, $R^1$ is methylsulfonyl, N-methylformamide, hydroxyl, or morpholinyl.

In some embodiments, the compound of Formula P1 is a compound of Formula P1B:

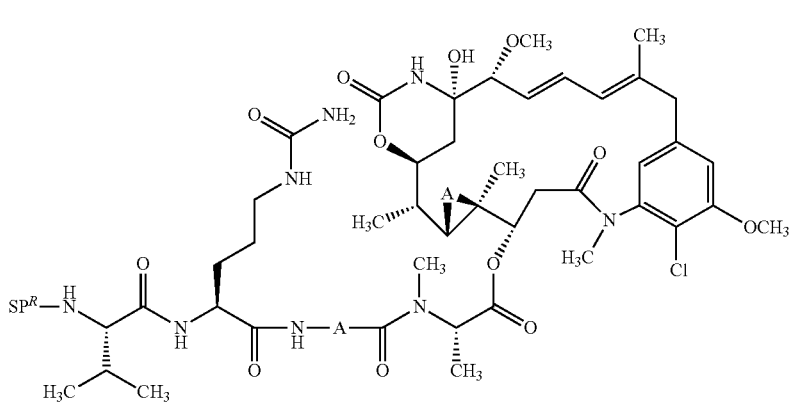

P1B wherein A is:

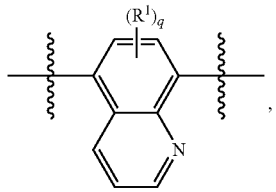

wherein q is an integer from 0 to 5; and $R^1$ is $C_{1-6}$ alkoxy, halo, or $C_{1-6}$ haloalkyl.

In some embodiments, the compound of Formula P1A is a compound which includes A wherein A is:

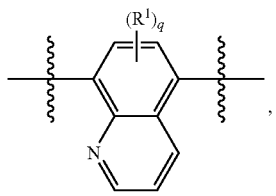

wherein q is an integer from 0 to 5; and $R^1$ is $C_{1-6}$ alkoxy, halo, or $C_{1-6}$ haloalkyl.

In some embodiments, the compound of Formula P1A is a compound which includes A wherein A is:

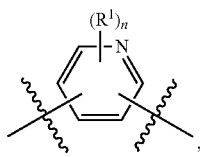

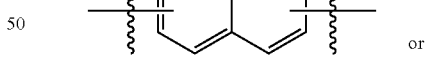

or

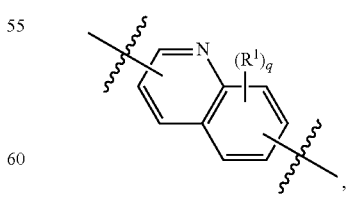

wherein:

$R^1$ is alkyl, alkenyl, alkynyl, alkoxy, aryl, alkaryl, aralkyl, halo, haloalkoxy, haloalkyl, heteroaryl, heterocycloalkyl, hydroxyl, cyano, nitro,

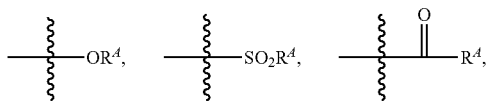

or azido, wherein $R^A$ is alkyl or heteroalkyl;
n is an integer from 0 to 4;
m is an integer from 0 to 3;
p is an integer from 0 to 6; and
q is an integer from 0 to 5; and
$SP^R$ is a reactive spacer.

In some embodiments, the compound of Formula P1 is a compound of Formula P1C:

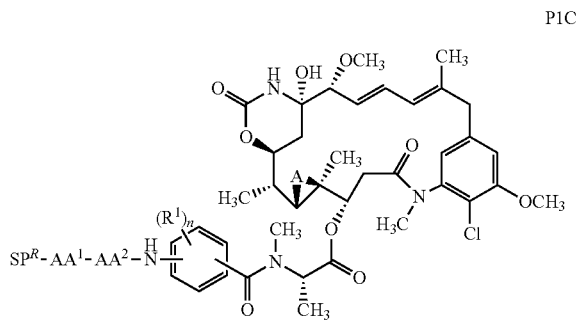

wherein:
$SP^R$ is a reactive spacer;
$AA^1$ is an amino acid;
$AA^2$ is an amino acid;
$R^1$ is, independently at each occurrence, alkyl, alkoxy, halo, haloalkoxy, haloalkyl, or trifluoromethyl, and
n is 0, 1, or 2.

In some embodiments, the compound of Formula P1 is a compound of Formula P1D:

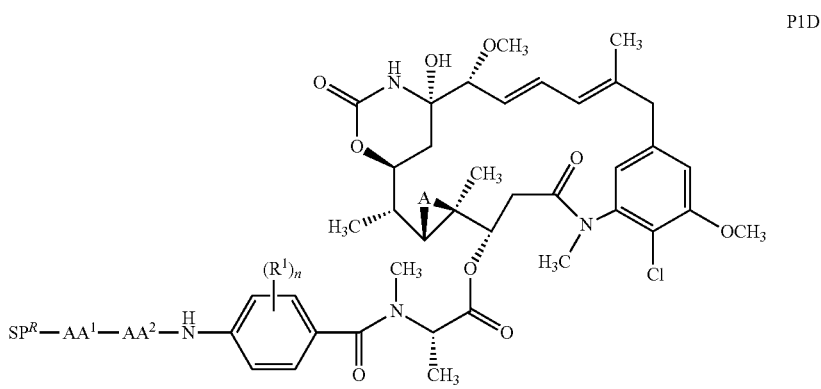

wherein:
$SP^R$ is a reactive spacer;
$AA^1$ is an amino acid;
$AA^2$ is an amino acid;
$R^1$ is, independently at each occurrence, alkyl, alkoxy, halo, haloalkoxy, haloalkyl, or trifluoromethyl, and
n is 0, 1, or 2. In some embodiments, n is 0. In some embodiments, n is 1. In some embodiments, n is 2.

In some embodiments, the compound of Formula P1 is a compound of Formula P1D, wherein $R^1$ is alkoxy, halo, or haloalkyl. In some embodiments, $R^1$ is $C_{1-6}$ alkoxy, halo, or $C_{1-6}$ haloalkyl. In some embodiments, n is 0. In some embodiments, n is 1. In some embodiments, n is 2.

In some embodiments, the compound of Formula P1 is a compound of Formula P1D, wherein $R^1$ is $C_{1-6}$ alkoxy, halo, or $C_{1-6}$ haloalkyl; and $SP^R$-$AA^1$-$AA^2$ is

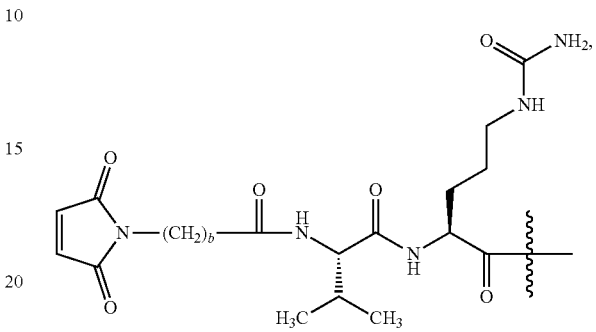

wherein b is an integer from 2 to 8 and

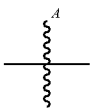

is a bond to the binding agent. In some embodiments, n is 0. In some embodiments, n is 1. In some embodiments, n is 2. In some embodiments b is 2. In some embodiments b is 3. In some embodiments b is 4. In some embodiments b is 5. In some embodiments b is 6. In some embodiments b is 7. In some embodiments b is 8.

In some embodiments, the compound of Formula P1 is a compound of Formula P1E:

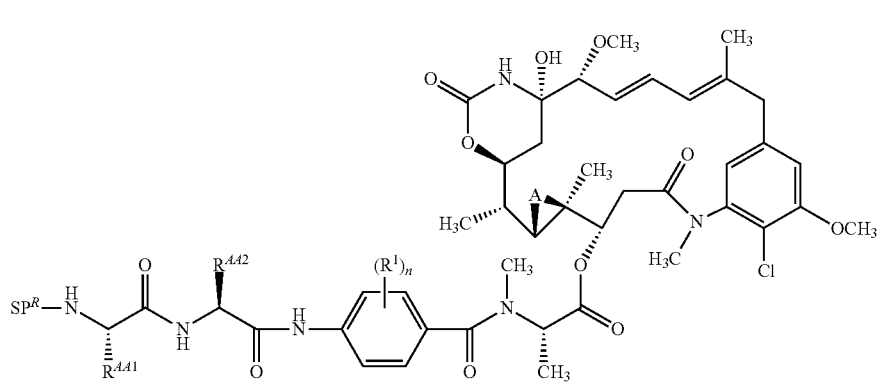

P1E wherein:
SP$^R$ is a reactive spacer;
R$^{AA1}$ is an amino acid side chain;
R$^{AA2}$ is an amino acid side chain;
R$^1$ is, independently at each occurrence, alkyl, alkoxy, halo, haloalkoxy, haloalkyl, or trifluoromethyl, and
n is 0, 1, or 2.

In some embodiments, the compound of Formula P1 is a compound of Formula P1F:

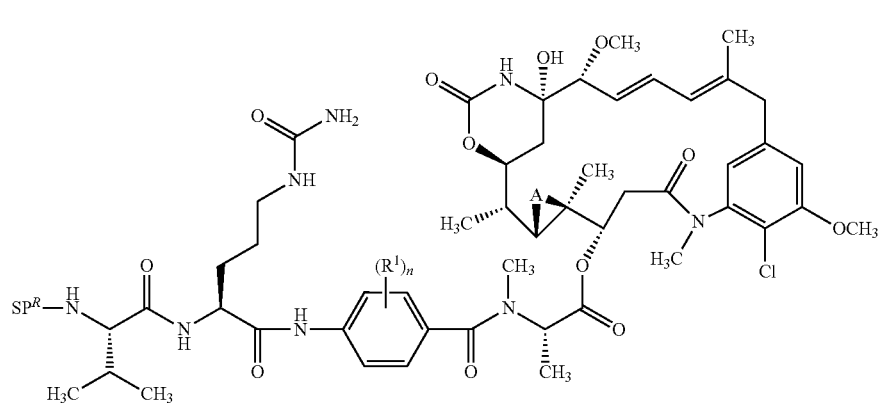

P1F wherein:
SP$^R$ is a reactive spacer;
R$^1$ is, independently at each occurrence, alkyl, alkoxy, halo, haloalkoxy, haloalkyl, or trifluoromethyl, and
n is 0, 1, or 2.

In some embodiments, the compound of Formula P1 is a compound of Formula P1G:

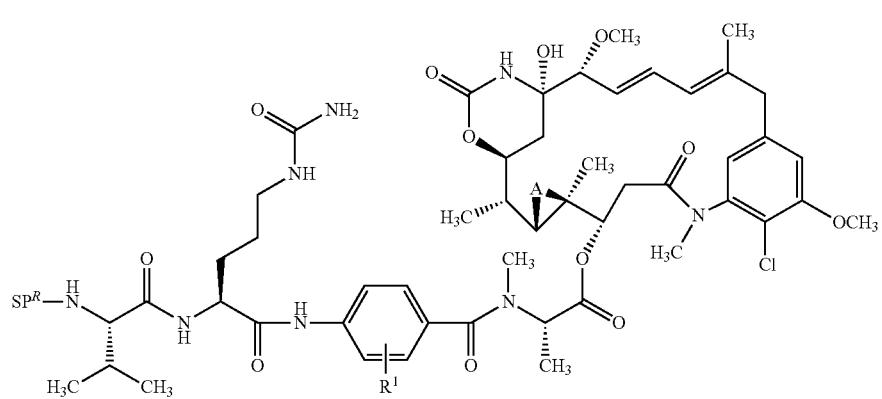

P1G wherein:
SP^R is a reactive spacer; and
R¹ is a hydrogen atom, alkyl, alkoxy, halo, haloalkoxy, haloalkyl, or trifluoromethyl.

In some embodiments, the compound of Formula P1 is a compound of Formula P1H:

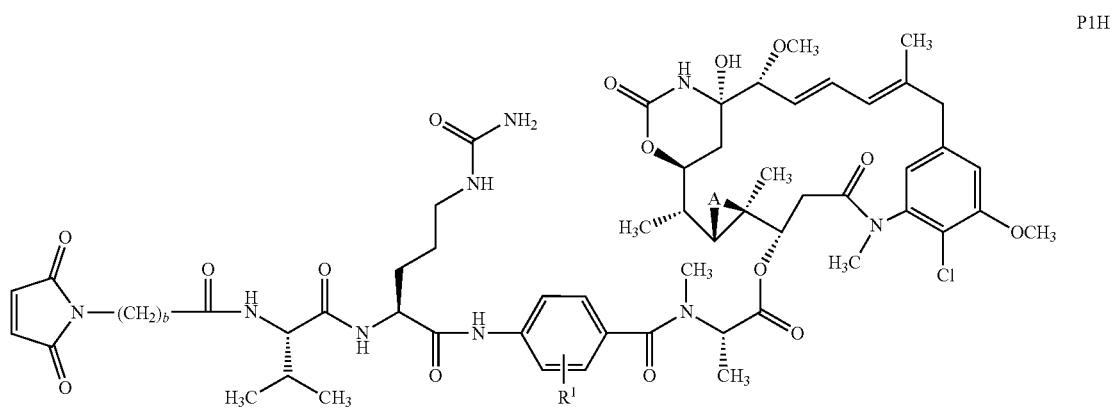

P1H wherein:
R¹ is hydrogen atom, alkyl, alkoxy, halo, haloalkoxy, haloalkyl, or trifluoromethyl; and
b is an integer from 2 to 8.

In some embodiments, the compound of Formula P1 is a compound of Formula P1I:

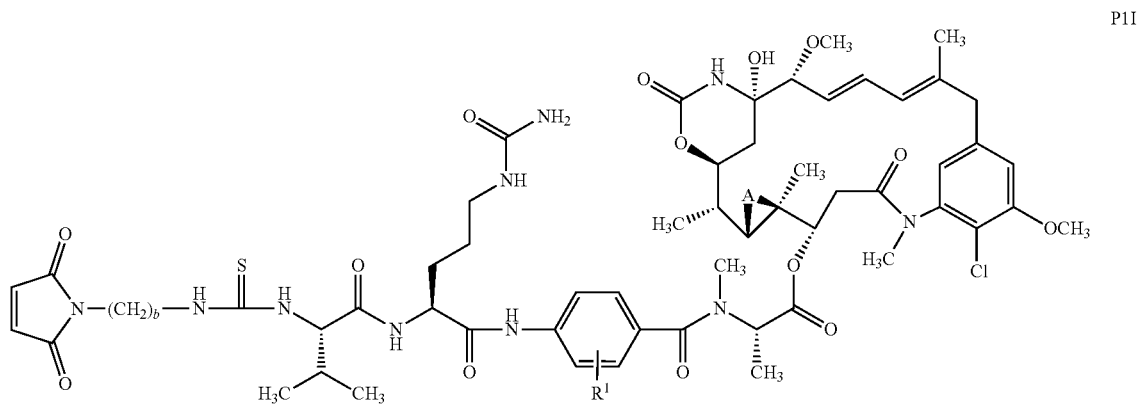

P1I wherein:
R¹ is a hydrogen atom, alkyl, alkoxy, halo, haloalkoxy, haloalkyl, or trifluoromethyl; and
b is an integer from 2 to 8.

In some embodiments, the compound of Formula P1 is a compound of Formula P1J:

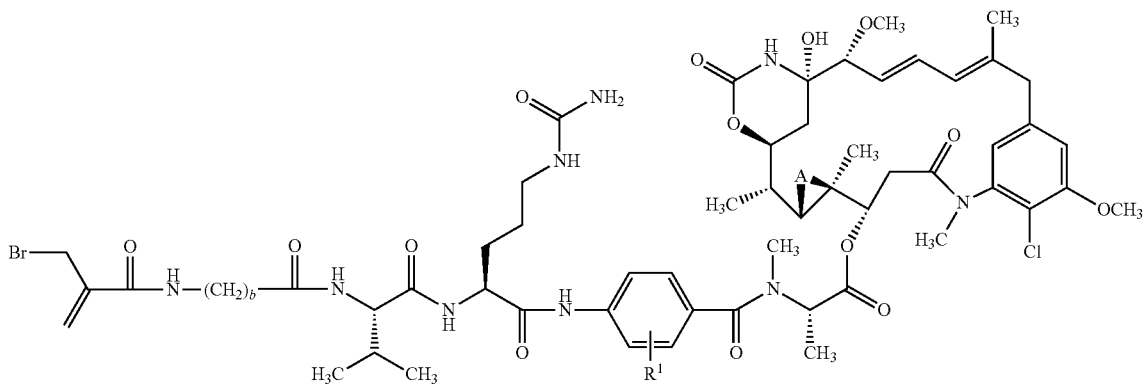
P1J
wherein:
R[1] is a hydrogen atom, alkyl, alkoxy, halo, haloalkoxy, haloalkyl, or trifluoromethyl; and
b is an integer from 2 to 8.
In some embodiments, the compound of Formula P1 is a compound of Formula P1K:
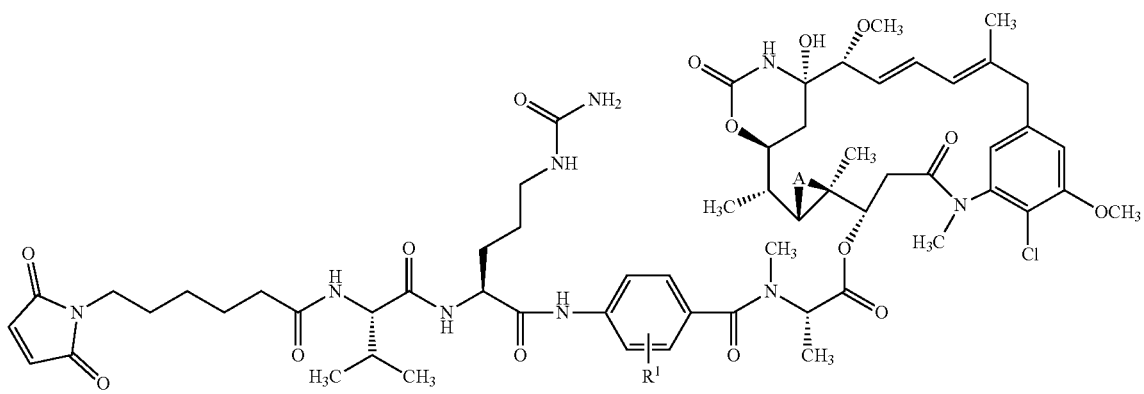
P1K
wherein R[1] is a hydrogen atom, alkyl, alkoxy, halo, haloalkoxy, haloalkyl, or trifluoromethyl.
In some embodiments, the compound of Formula P1 is a compound of Formula P1L:
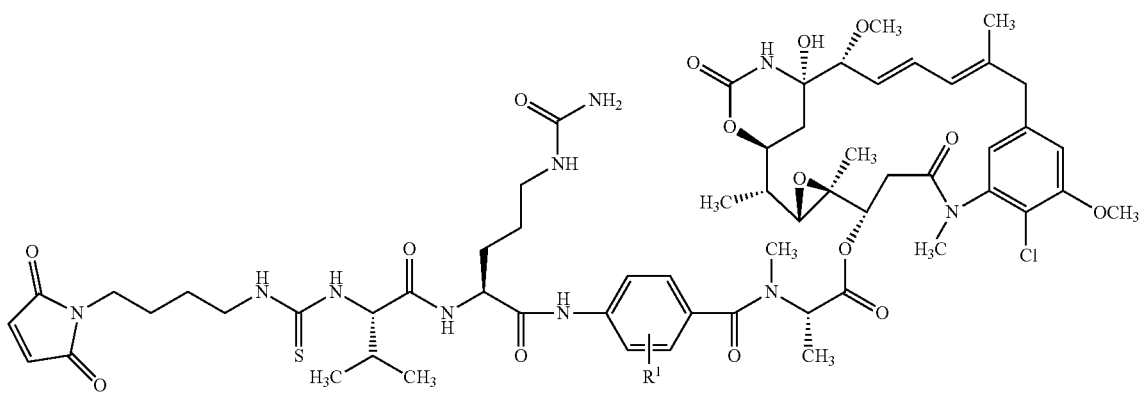
P1L wherein R¹ is a hydrogen atom, alkyl, alkoxy, halo, haloalkoxy, haloalkyl, or trifluoromethyl.

In some embodiments, the compound of Formula P1 is a compound of Formula P1M:

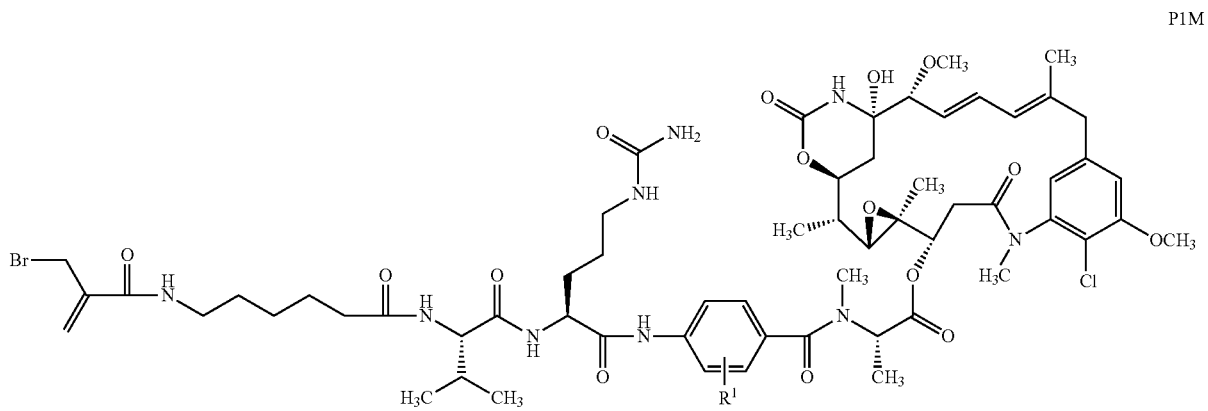

P1M wherein R¹ is a hydrogen atom, alkyl, alkoxy, halo, haloalkoxy, haloalkyl, or trifluoromethyl.

In some embodiments, the compound of Formula P1 is a compound of Formula P1N:

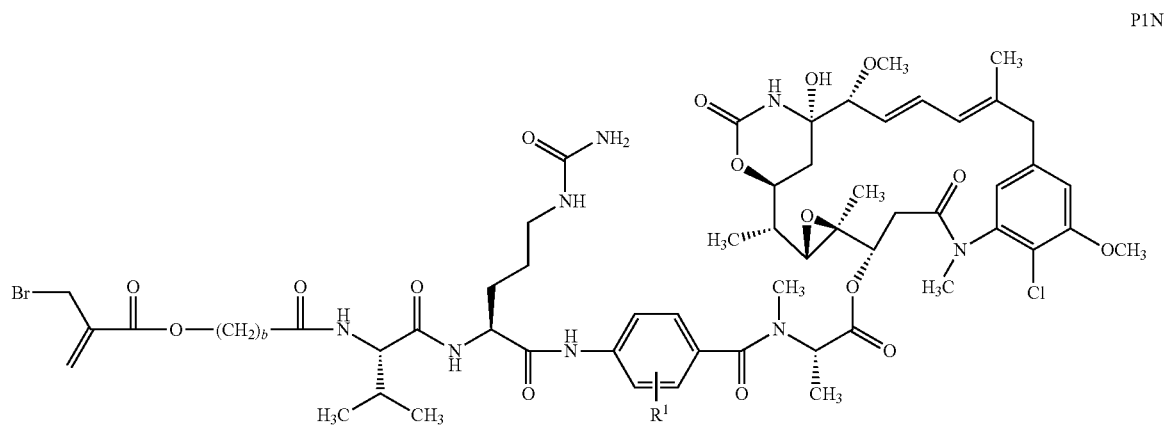

P1N wherein R¹ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1O:

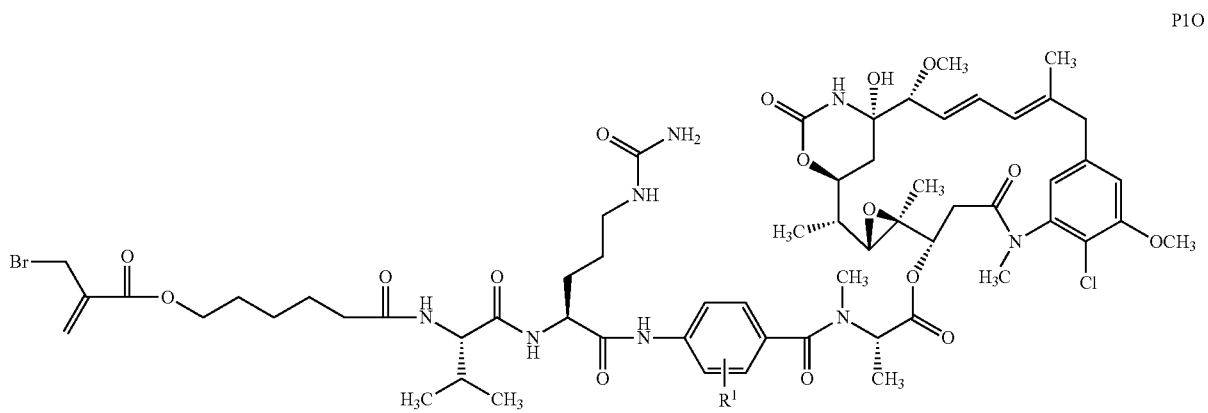

P1O wherein R¹ is a hydrogen atom, alkyl, alkoxy, halo, haloalkoxy, haloalkyl, or trifluoromethyl.

In some embodiments, the compound of Formula P1 is a compound of Formula P1P:

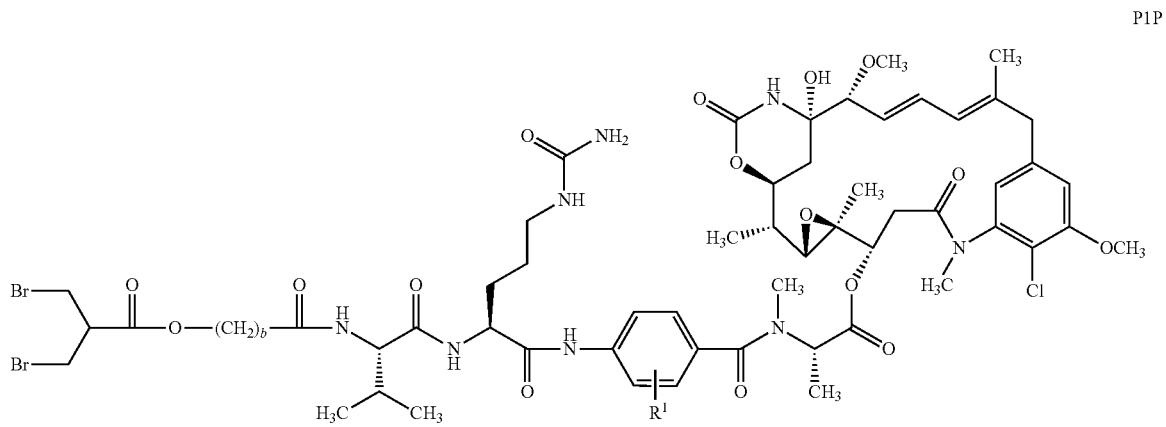

P1P wherein R¹ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1Q:

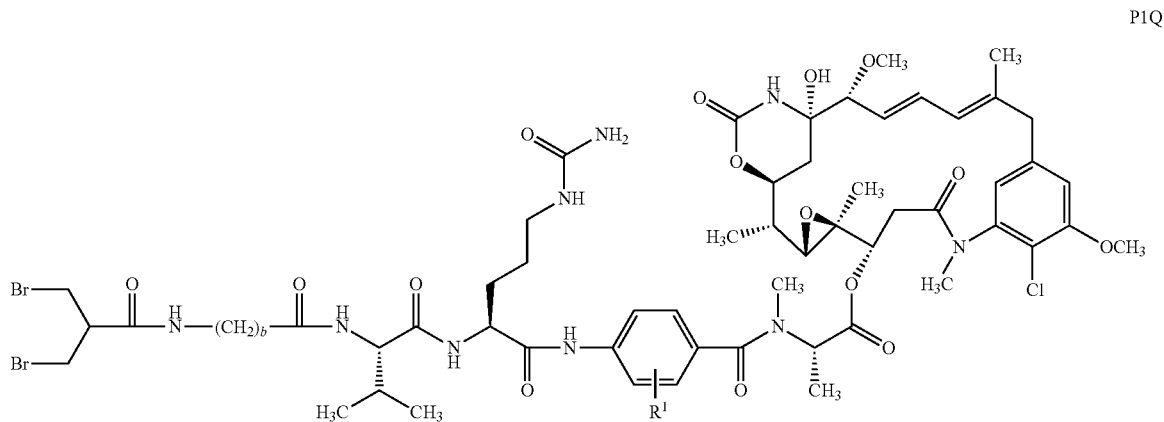

P1Q wherein R¹ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1R:

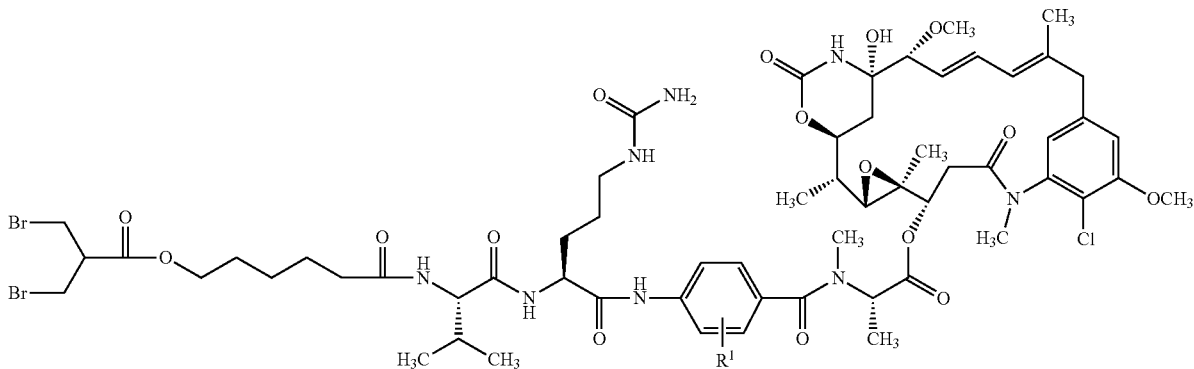

wherein $R^1$ is a hydrogen atom, alkyl, alkoxy, halo, haloalkoxy, haloalkyl, or trifluoromethyl.

In some embodiments, the compound of Formula P1 is a compound of Formula P1S:

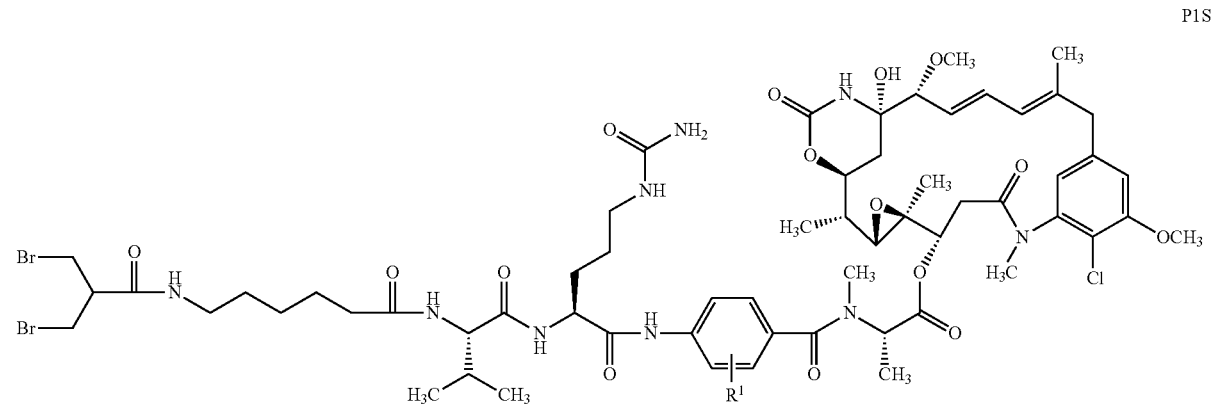

P1S wherein $R^1$ is a hydrogen atom, alkyl, alkoxy, halo, haloalkoxy, haloalkyl, or trifluoromethyl.

In some embodiments, the compound of Formula P1 is a compound of Formula P1T:

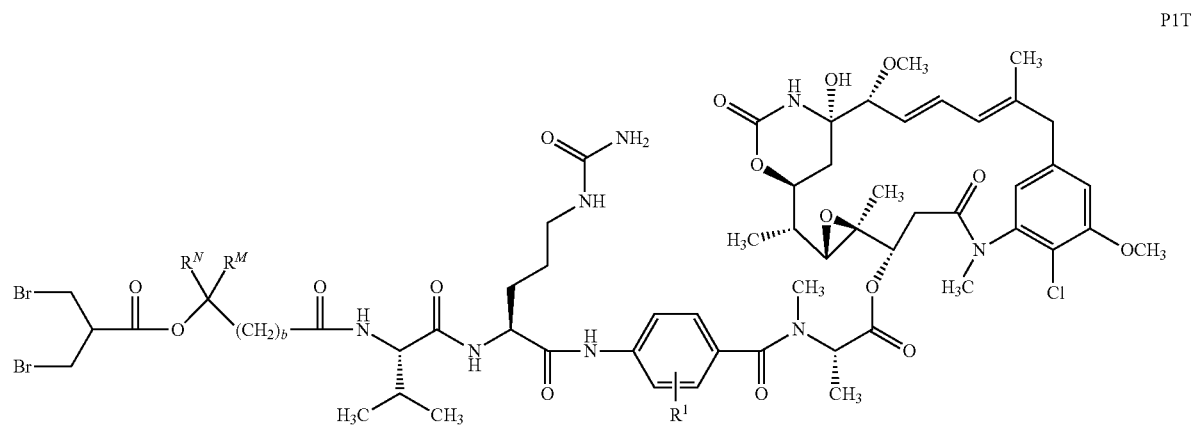

P1T wherein $R^N$ is a hydrogen atom or alkyl, $R^M$ is alkyl, $R^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1U:

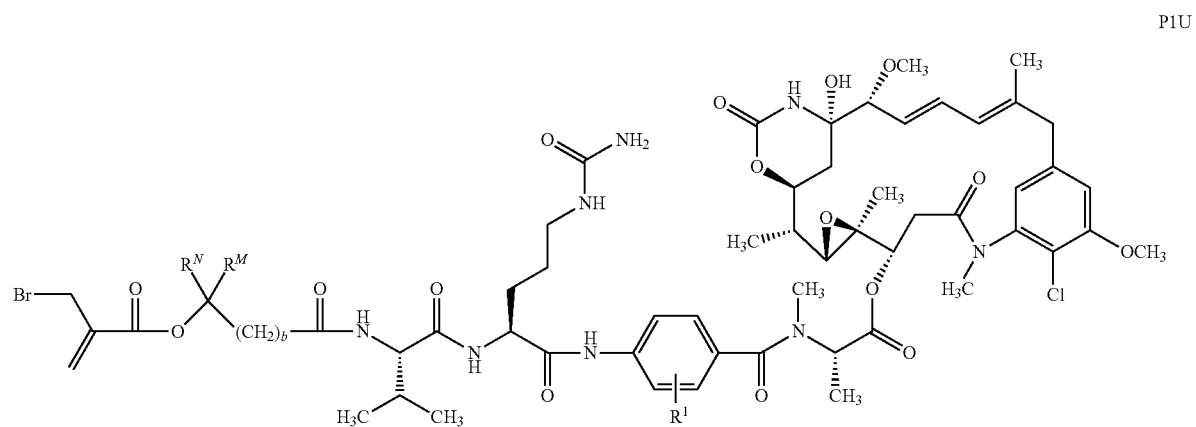

P1U wherein $R^N$ is a hydrogen atom or alkyl, $R^M$ is alkyl, $R^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1V:

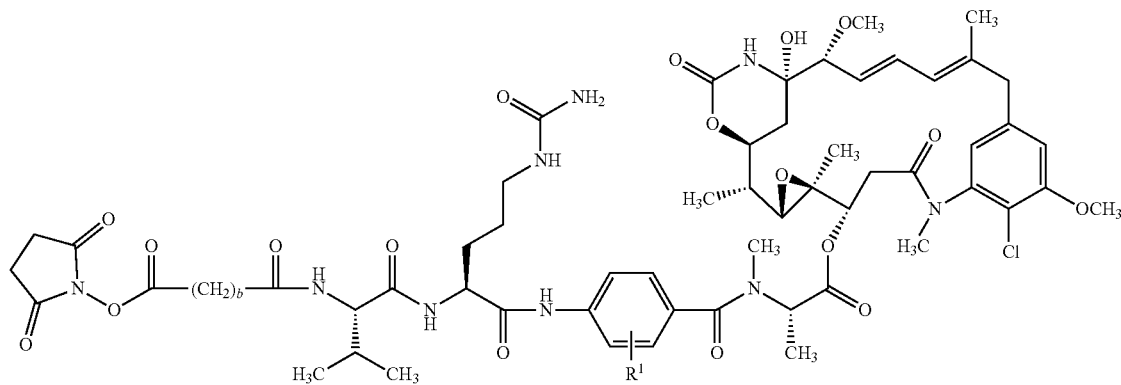

P1V wherein $R^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1W:

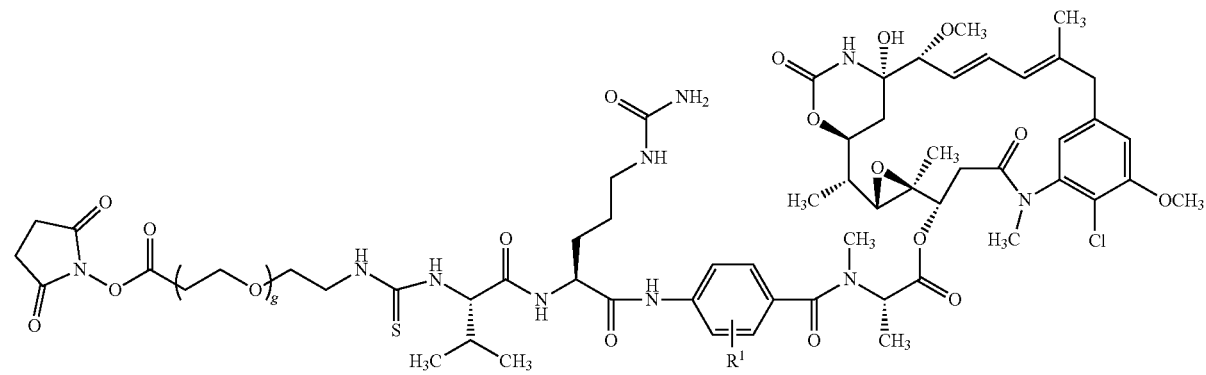

P1W wherein $R^1$ is a hydrogen atom, alkyl, alkoxy, halo, haloalkoxy, haloalkyl, or trifluoromethyl, g is an integer from 2 to 20; and b is an integer from 2 to 8.

In some embodiments, the compound of Formula P1 is a compound of Formula P1X:

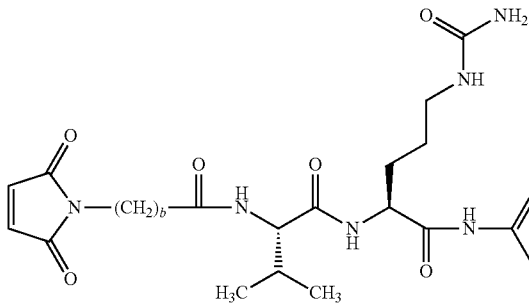
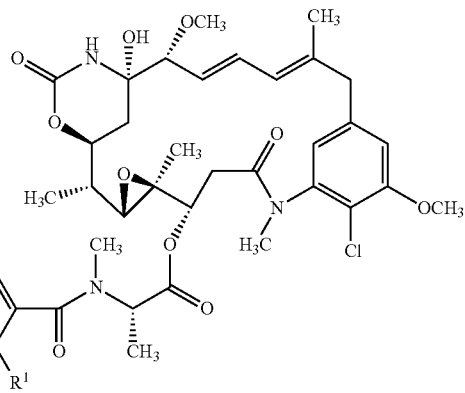

wherein:
R¹ is alkyl, alkenyl, alkynyl, alkoxy, heteroalkyl, halo, haloalkyl, or haloalkoxy; and b is an integer from 2 to 8. In some embodiments, R¹ is methyl, ethyl, methoxy, or ethoxy. In some of these embodiments, R¹ is methoxy. In some embodiments, R¹ is 1-methylethyl-thiol, phenyl, 2-fluorophenyl, pyridinyl, 4-pyridinyl, pyrrolidinyl, or 1-pyrrolidinyl. In some embodiments, R¹ is trifluoromethyl. In some embodiments, R¹ is fluoro. In some embodiments, R¹ is hydrogen.

In some embodiments, the compound of Formula P1 is a compound of Formula P1Y:

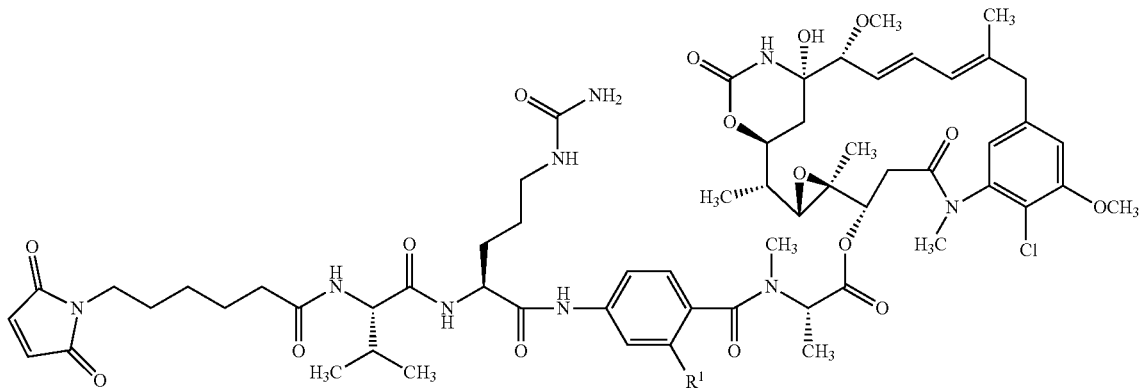

wherein R¹ is alkyl, alkenyl, alkynyl, alkoxy, heteroalkyl, halo, haloalkyl, haloalkoxy. In some embodiments, R¹ is methyl, ethyl, methoxy, or ethoxy. In some of these embodiments, R¹ is methoxy. In some embodiments, R¹ is 1-methylethyl-thiol, phenyl, 2-fluorophenyl, pyridinyl, 4-pyridinyl, pyrrolidinyl, or 1-pyrrolidinyl. In some embodiments, R¹ is trifluoromethyl. In some embodiments, R¹ is fluoro. In some embodiments, R¹ is hydrogen.

In some embodiments, the compound of Formula P1 is a compound of Formula P1Z:

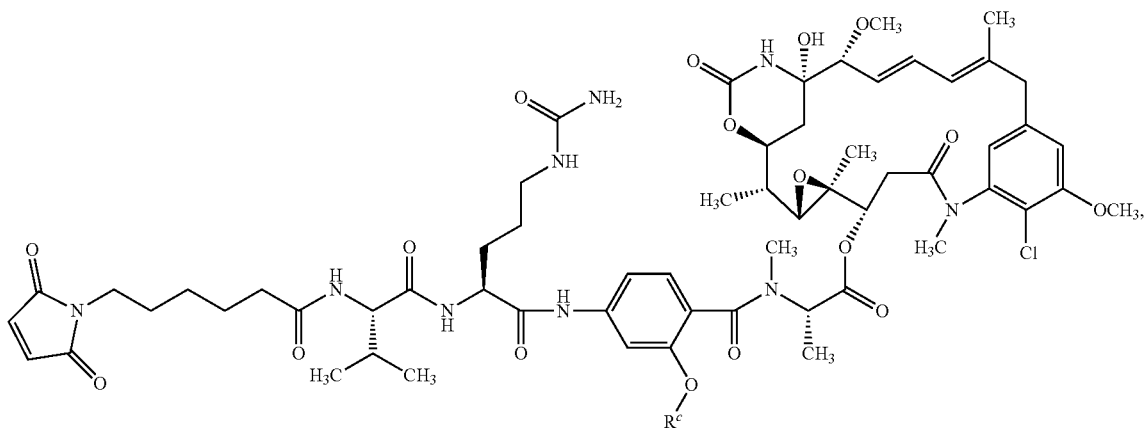
wherein R[c] is selected from alkyl or haloalkyl and wherein the alkyl or haloalkyl is linear, branched, or cyclic.
In some embodiments, the compound of Formula P1 is a compound having one of the following structures:
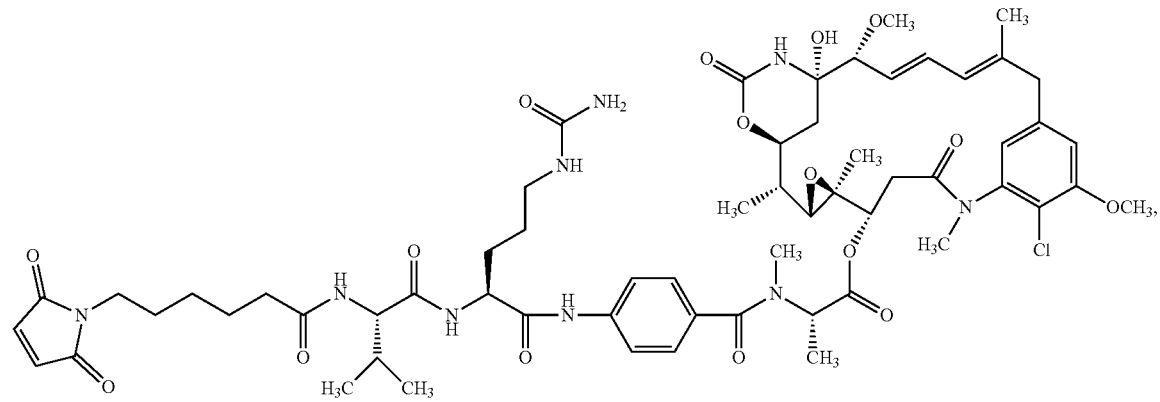
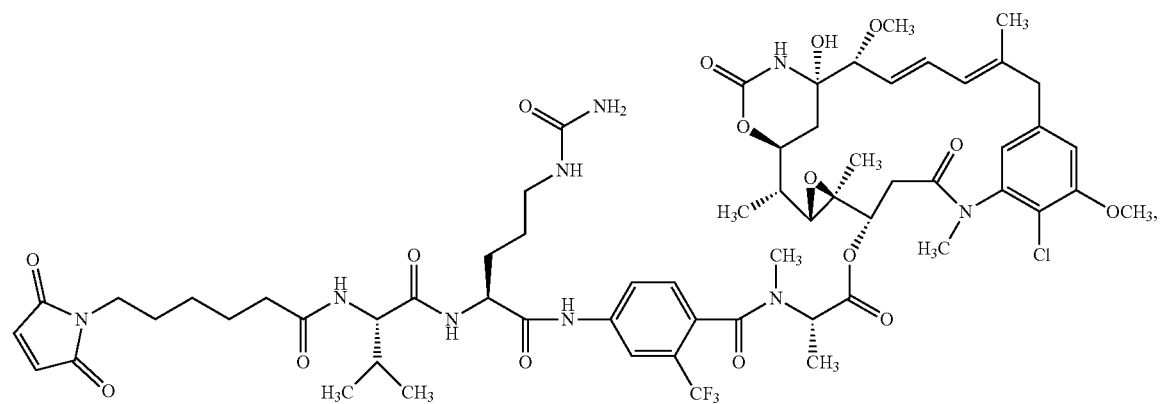

213 214
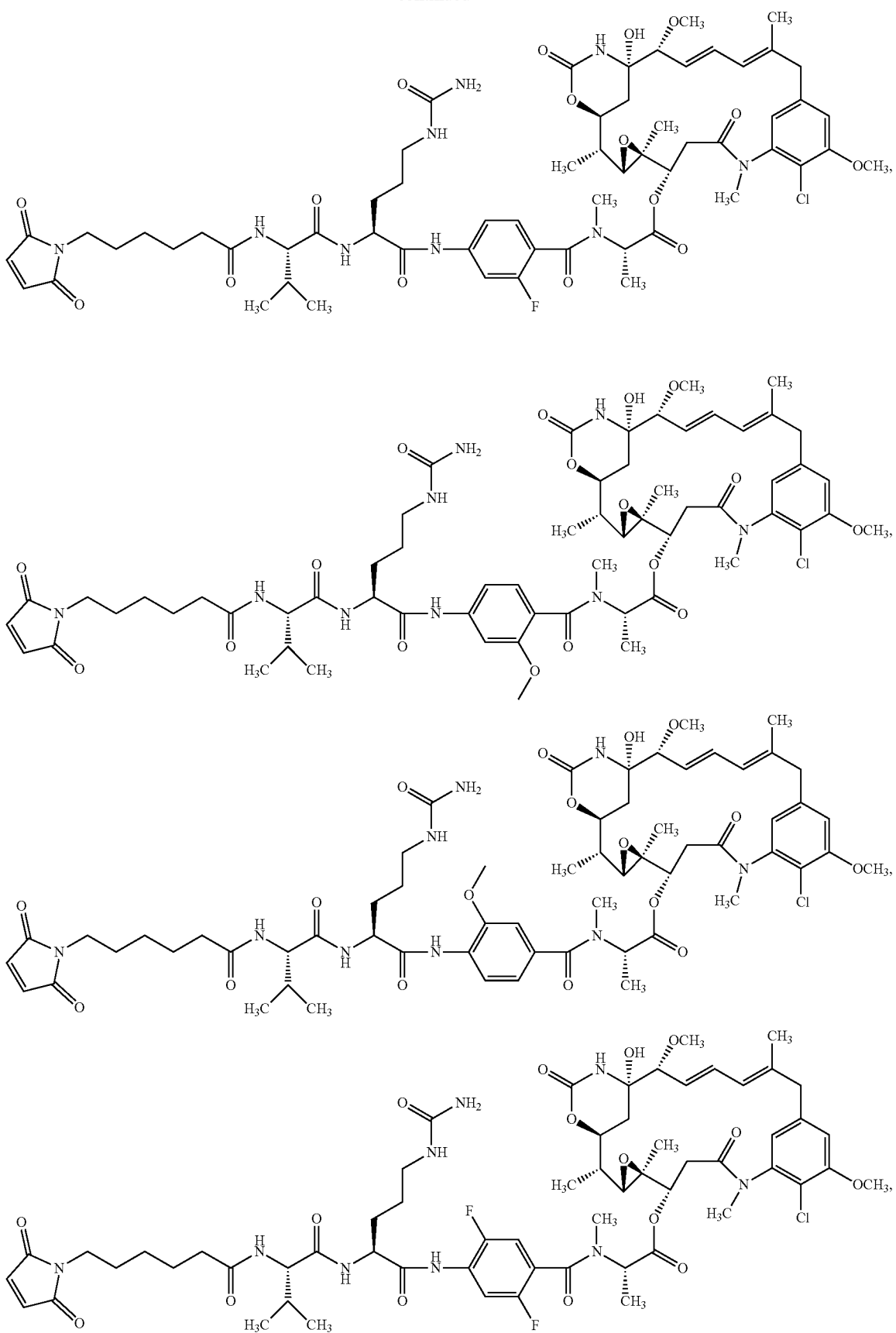
-continued

215
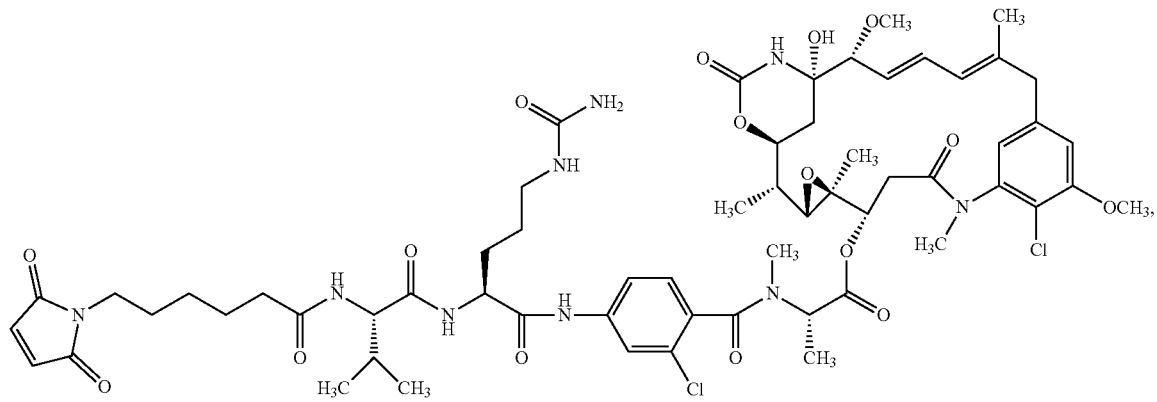
216
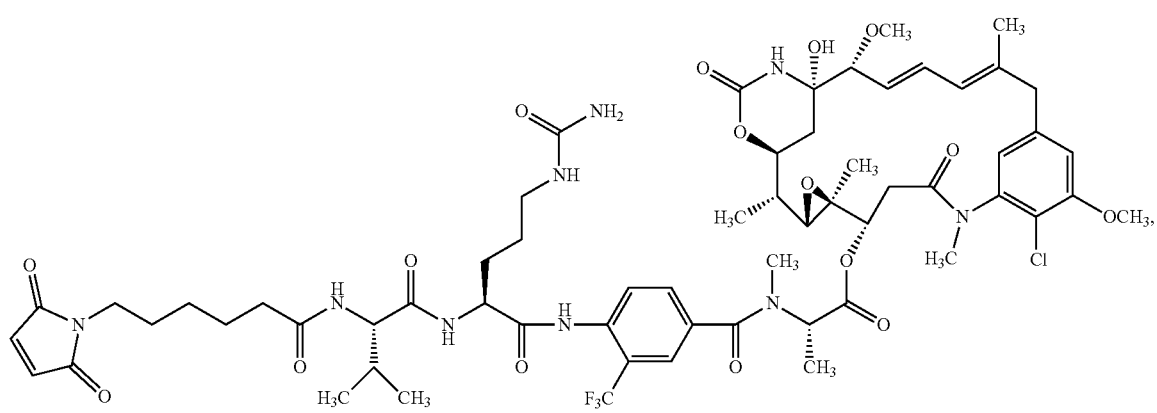
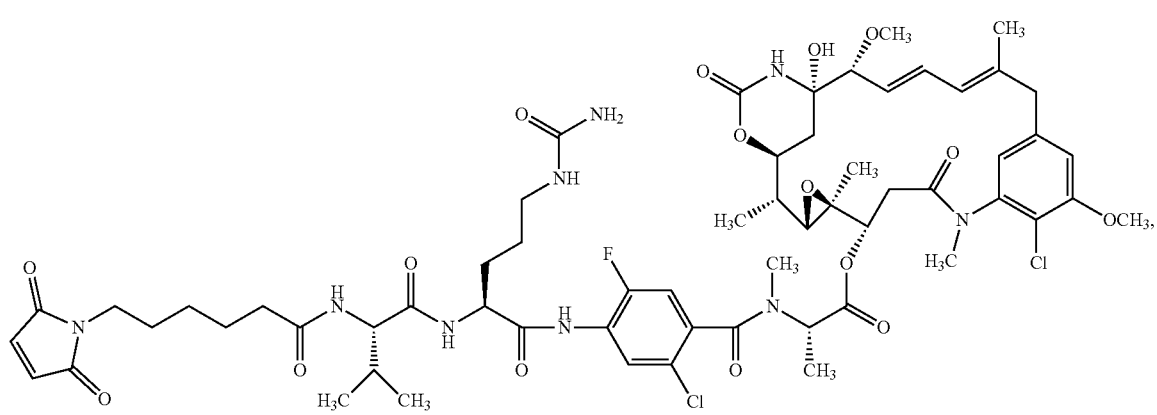
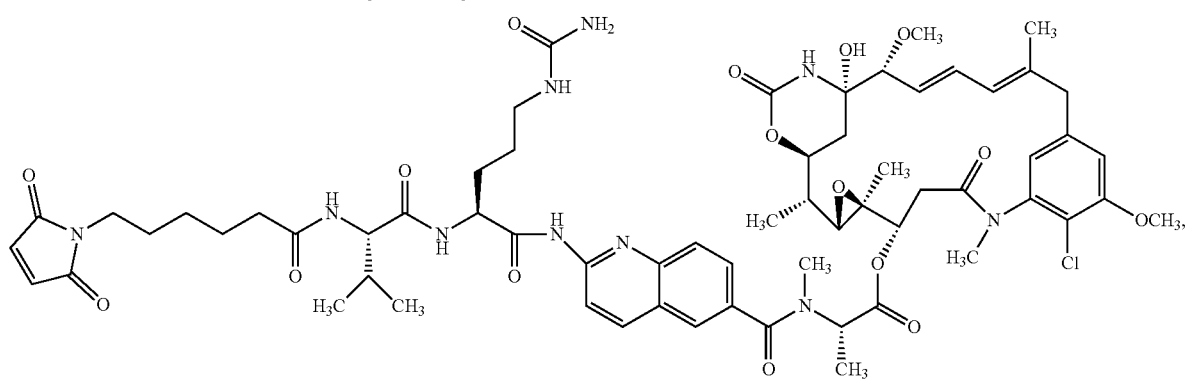

-continued
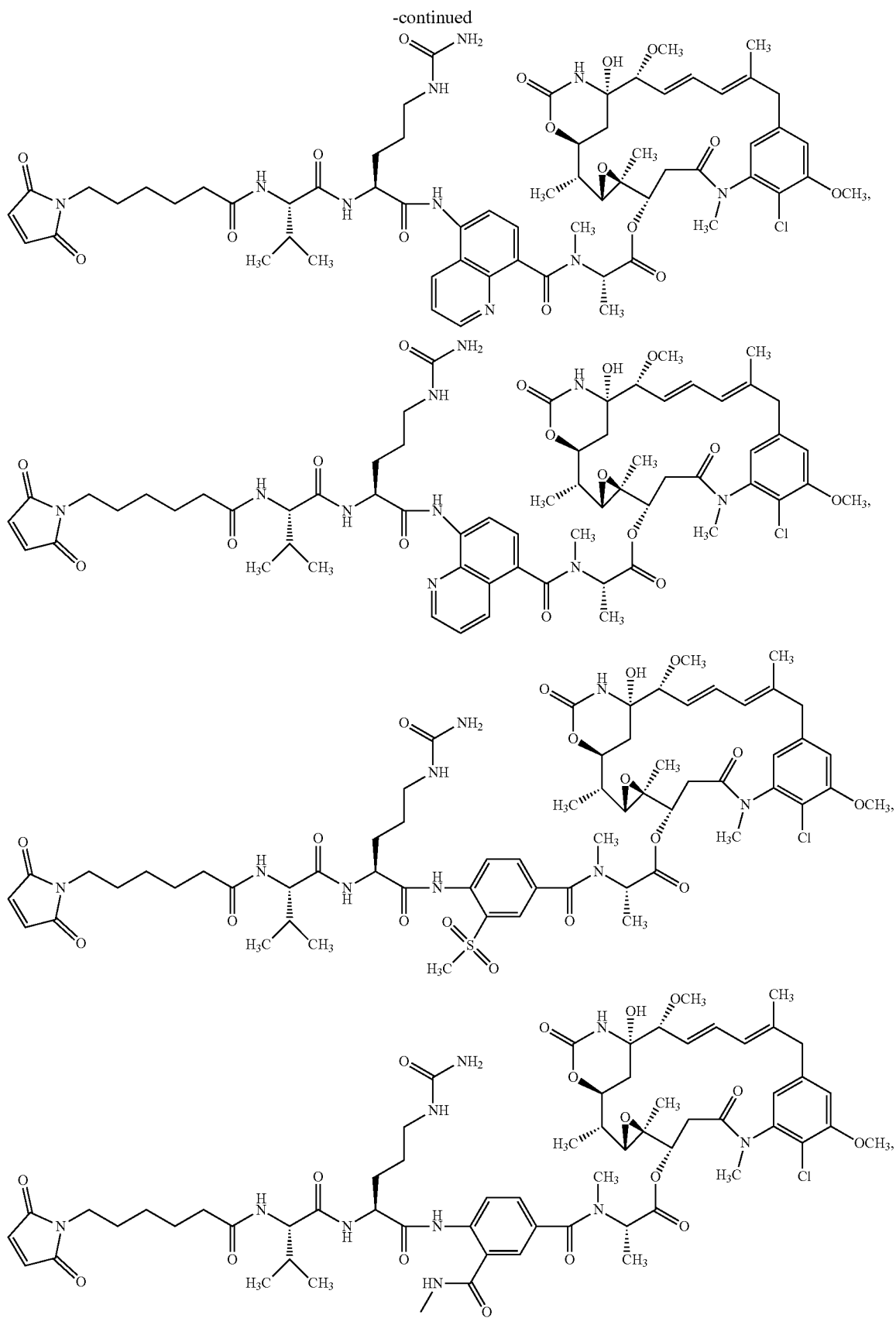

219 220
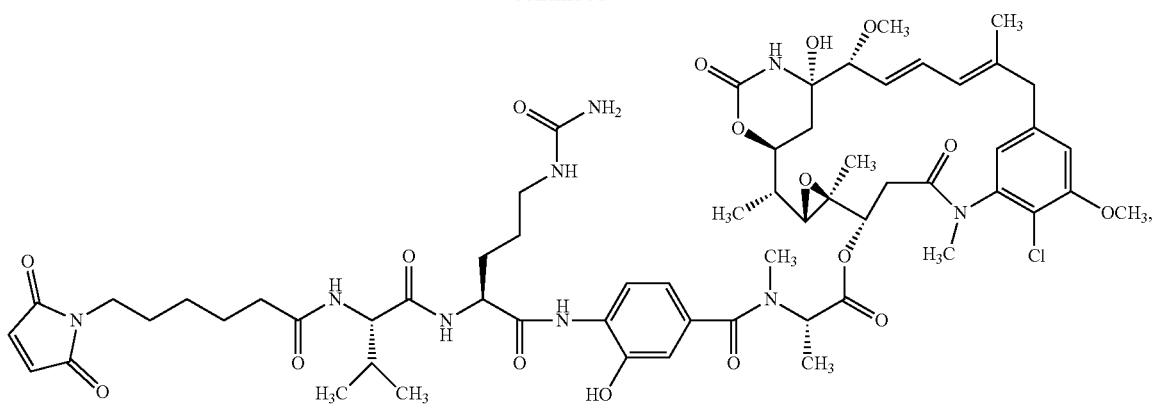
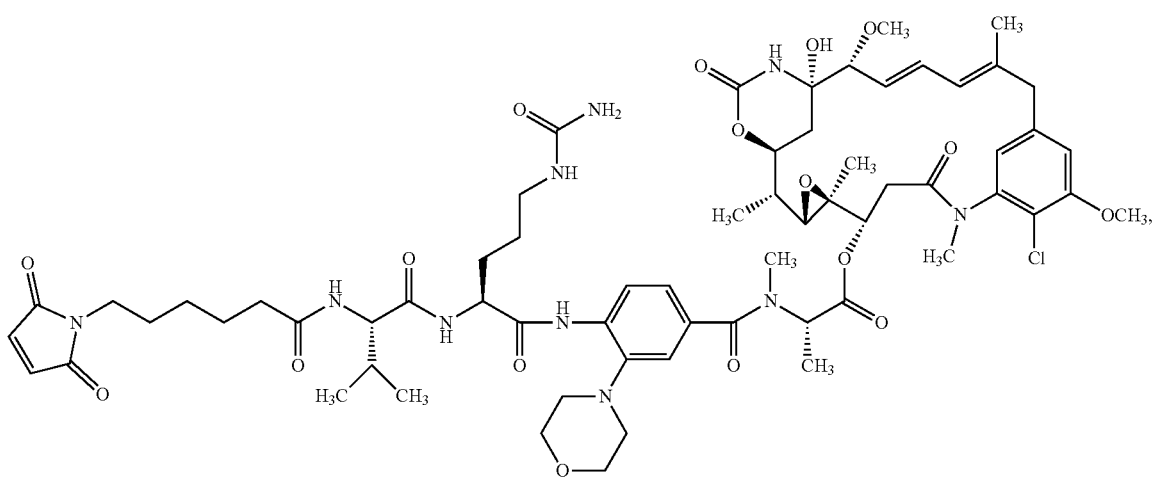
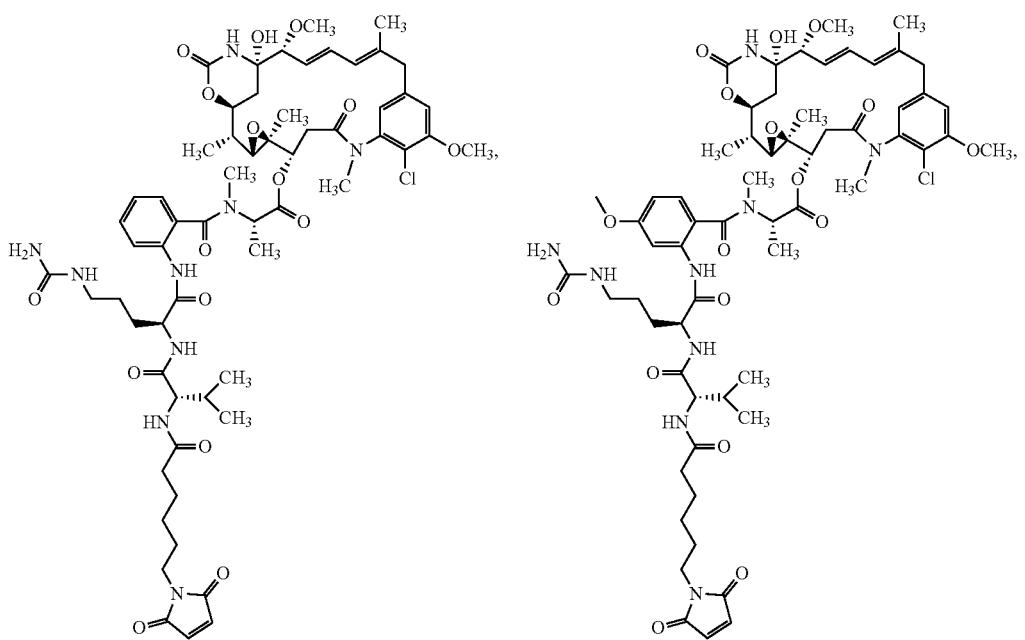

-continued
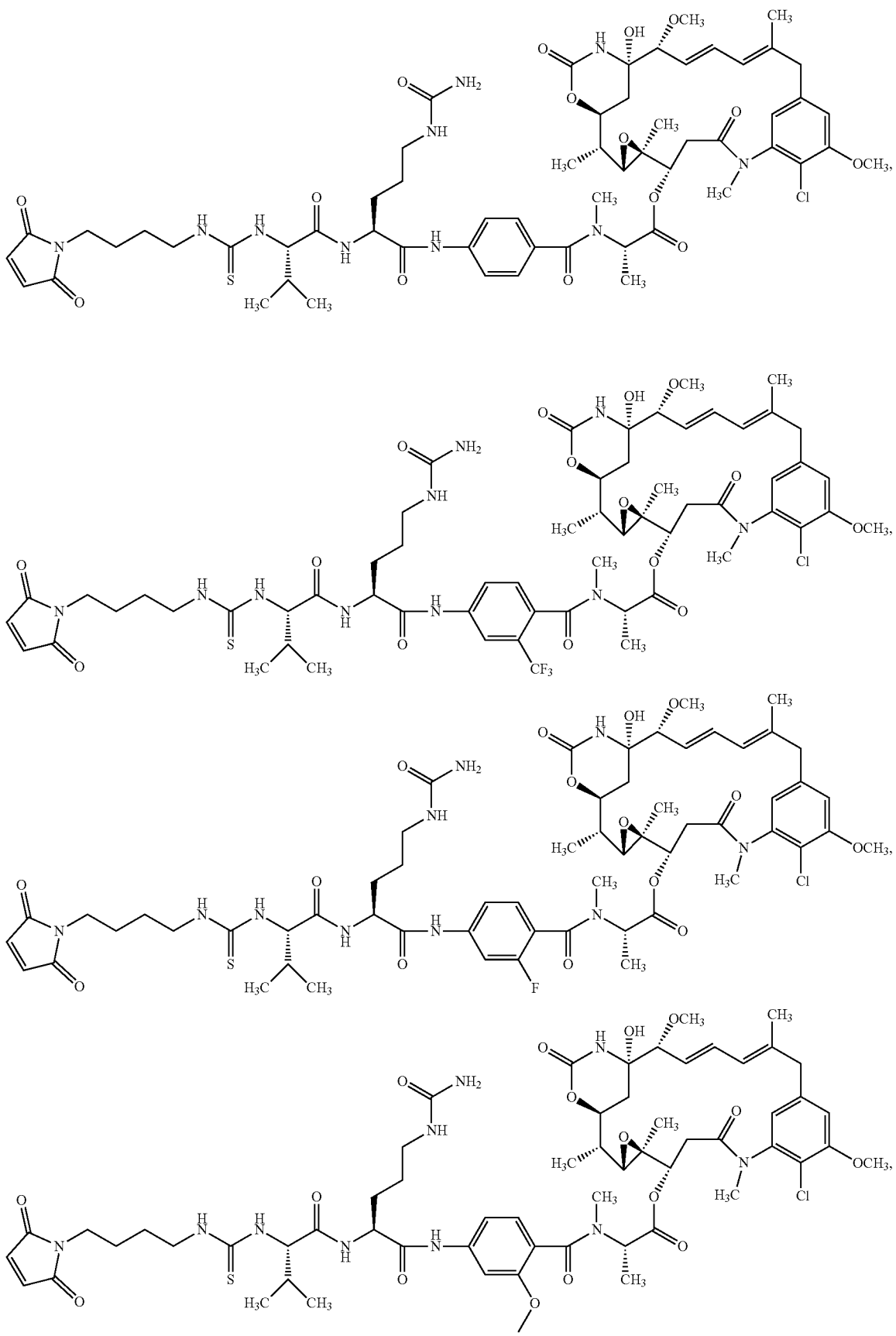

223 224
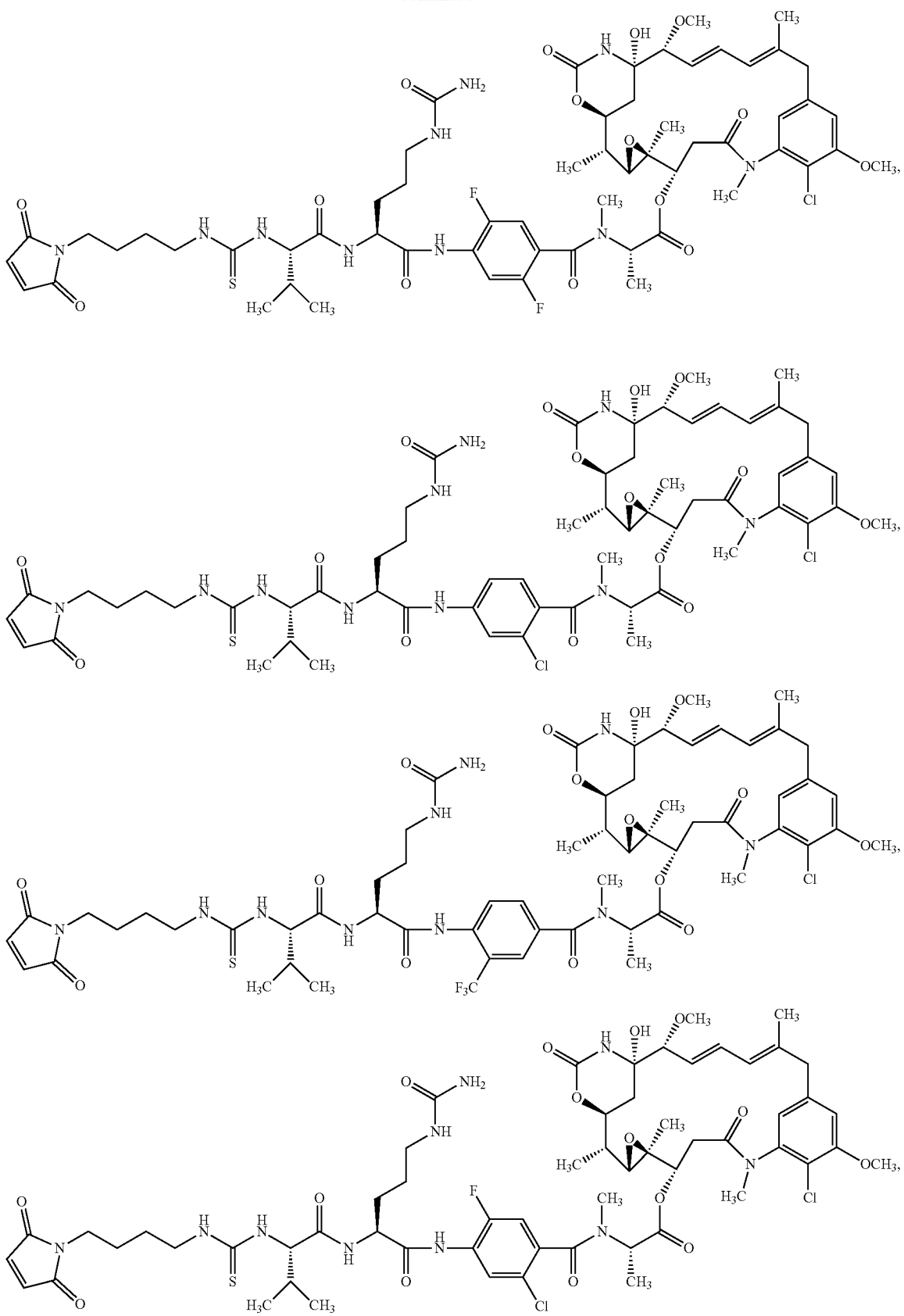
-continued

225
-continued
226
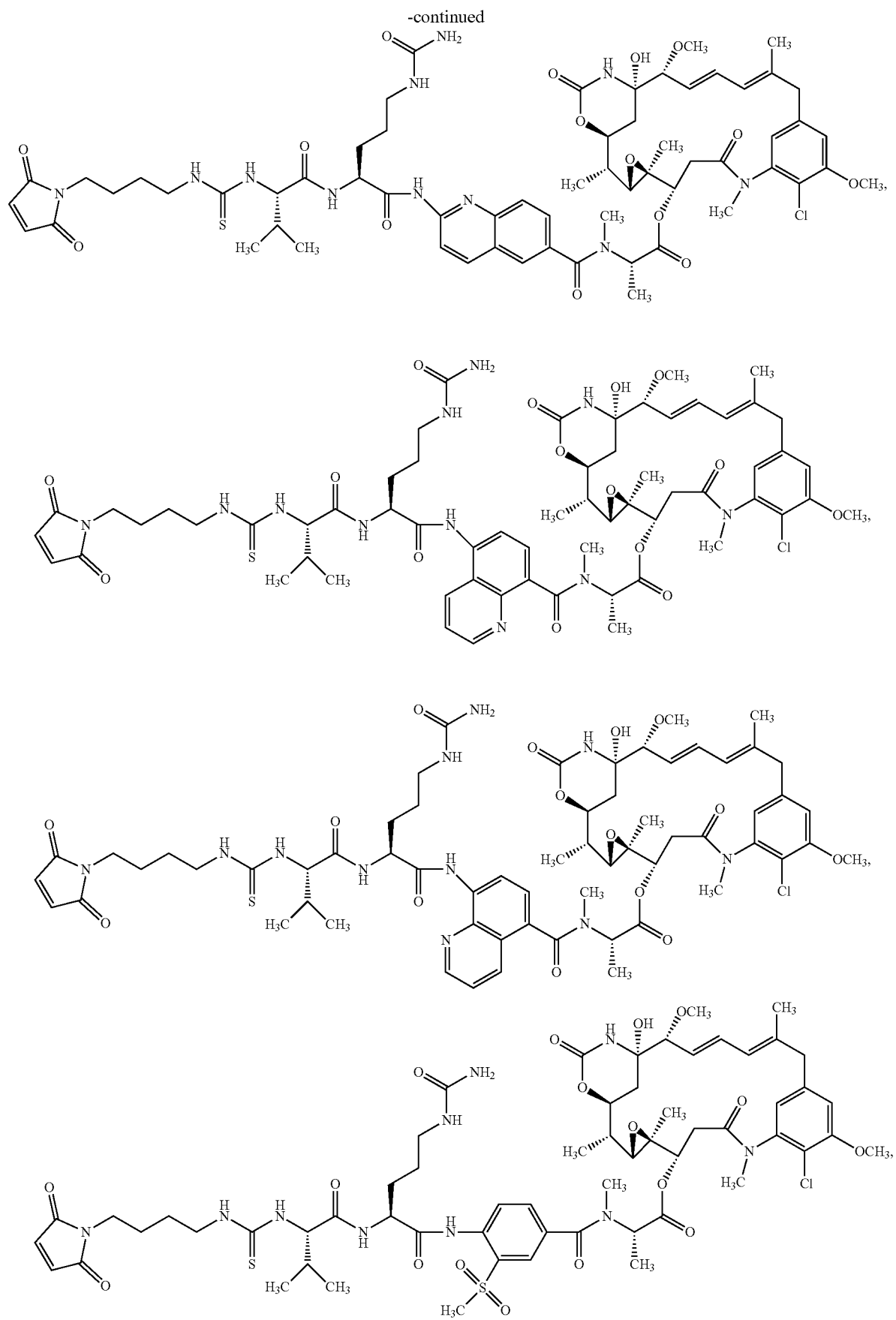

227
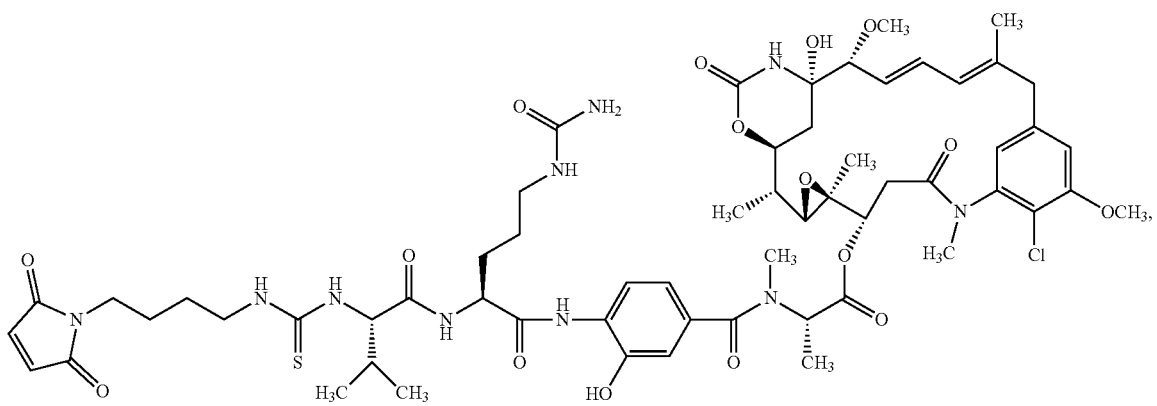
228
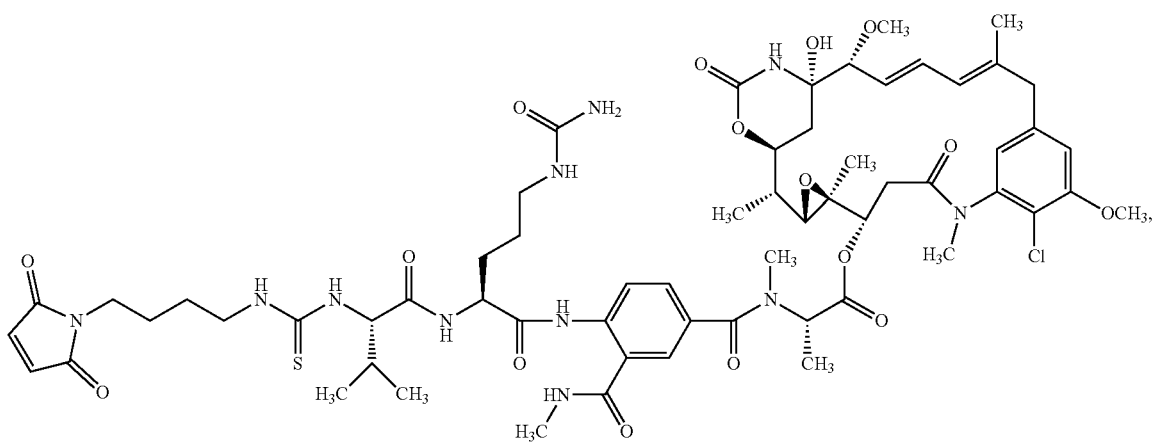
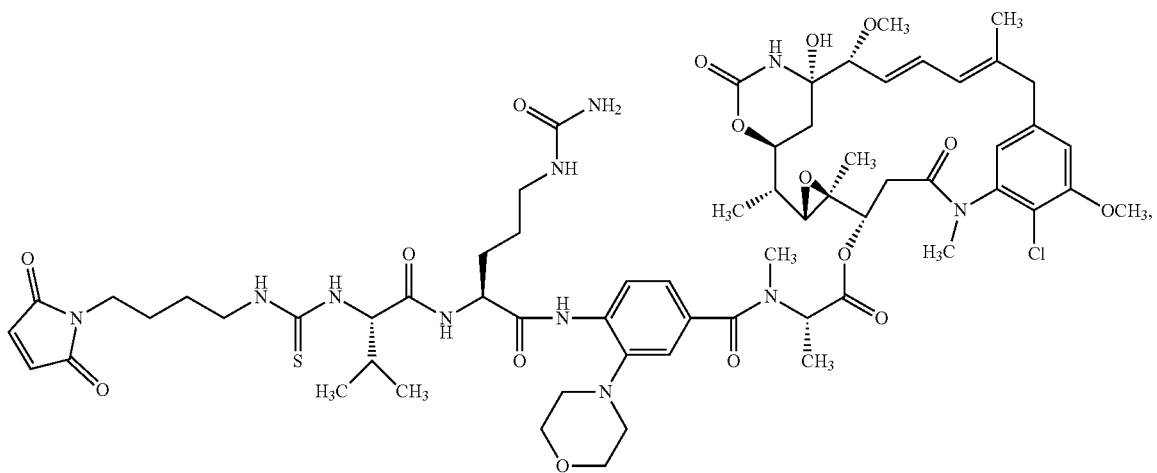

229
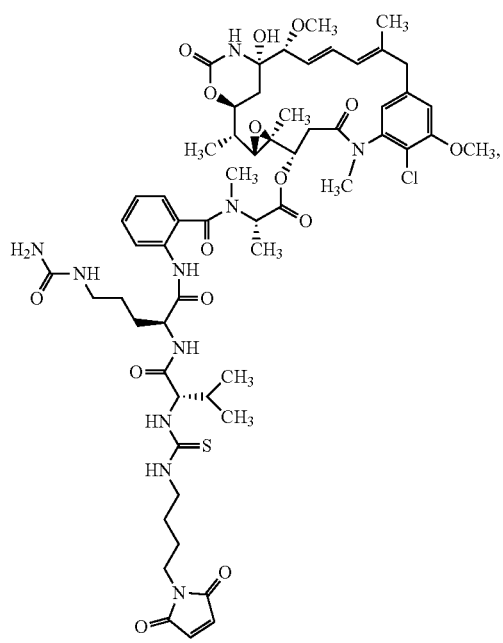
230
-continued
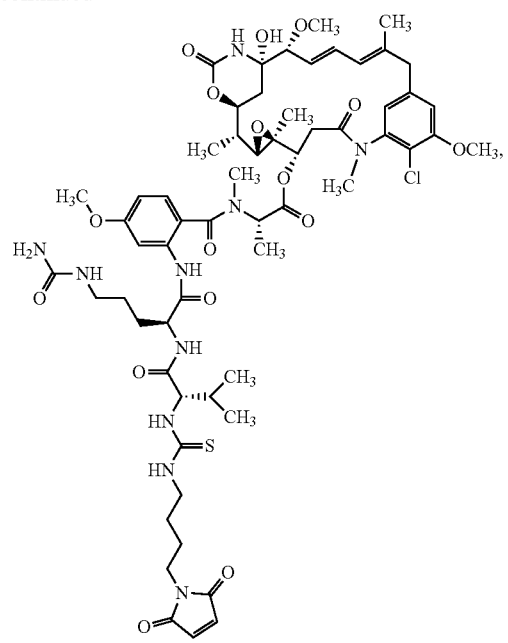
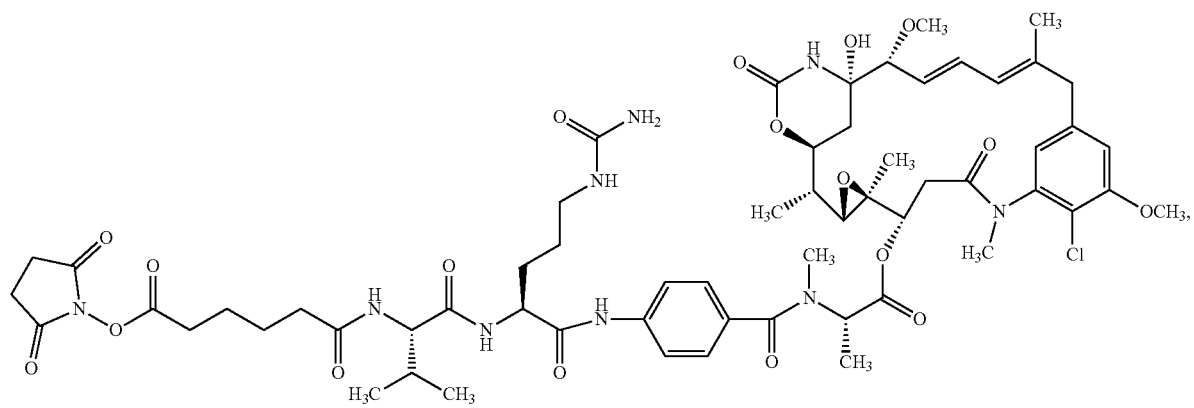
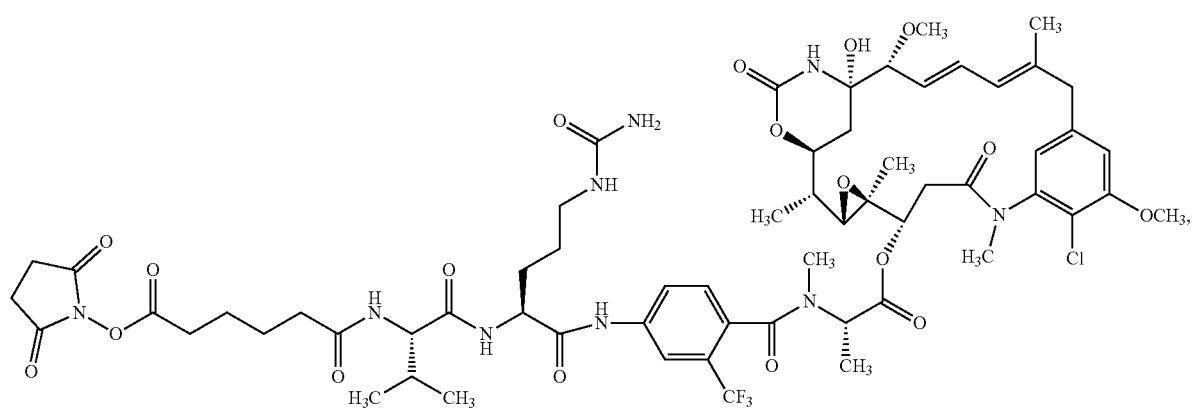

-continued
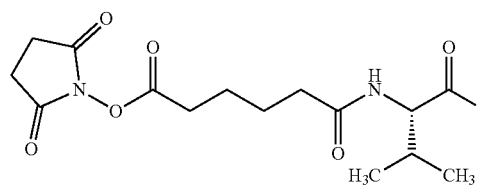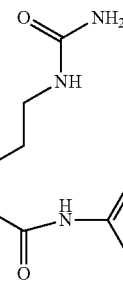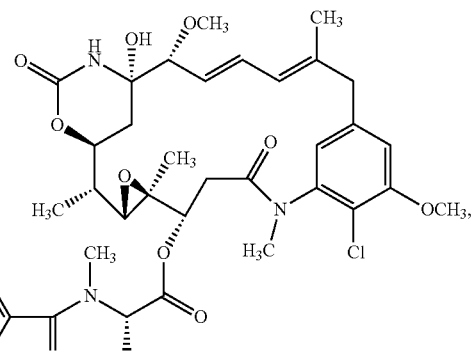
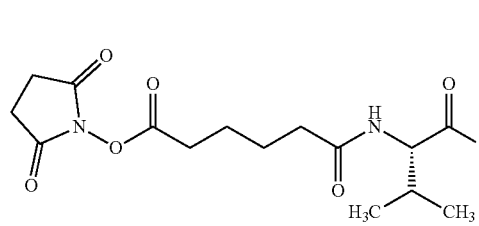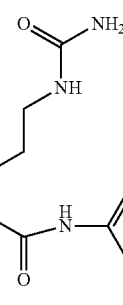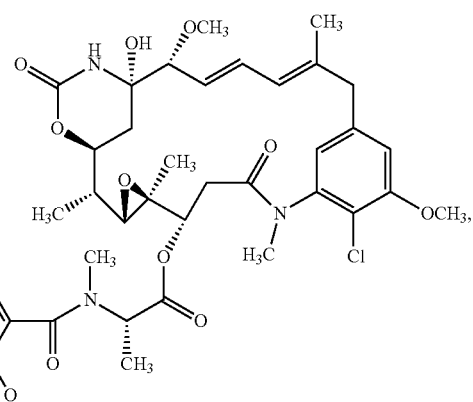
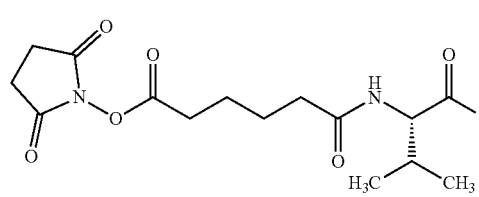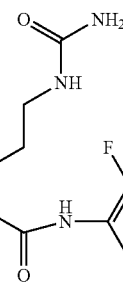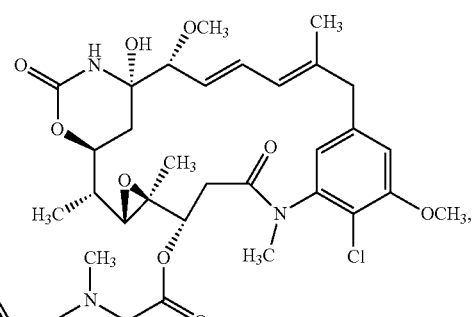
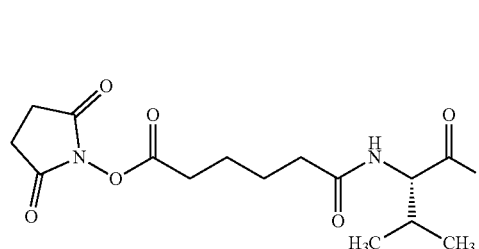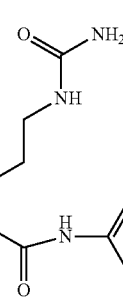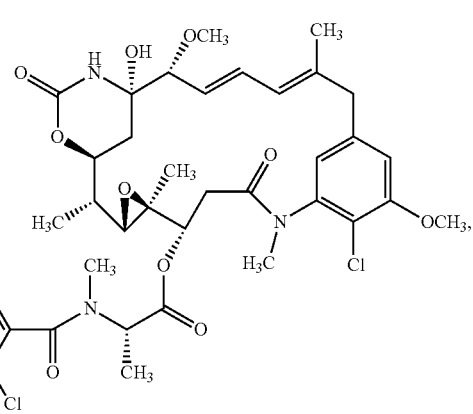

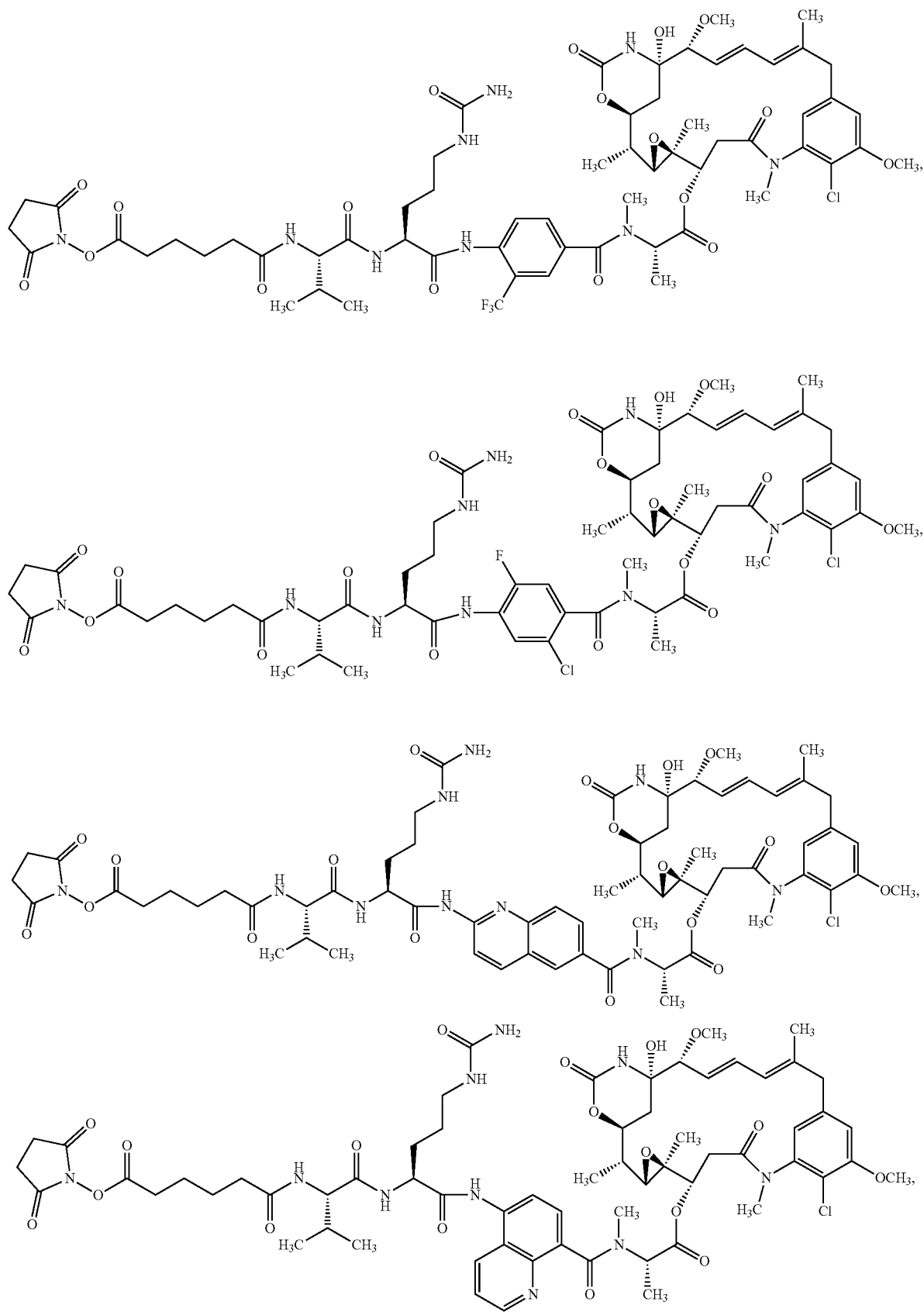

235 236
-continued
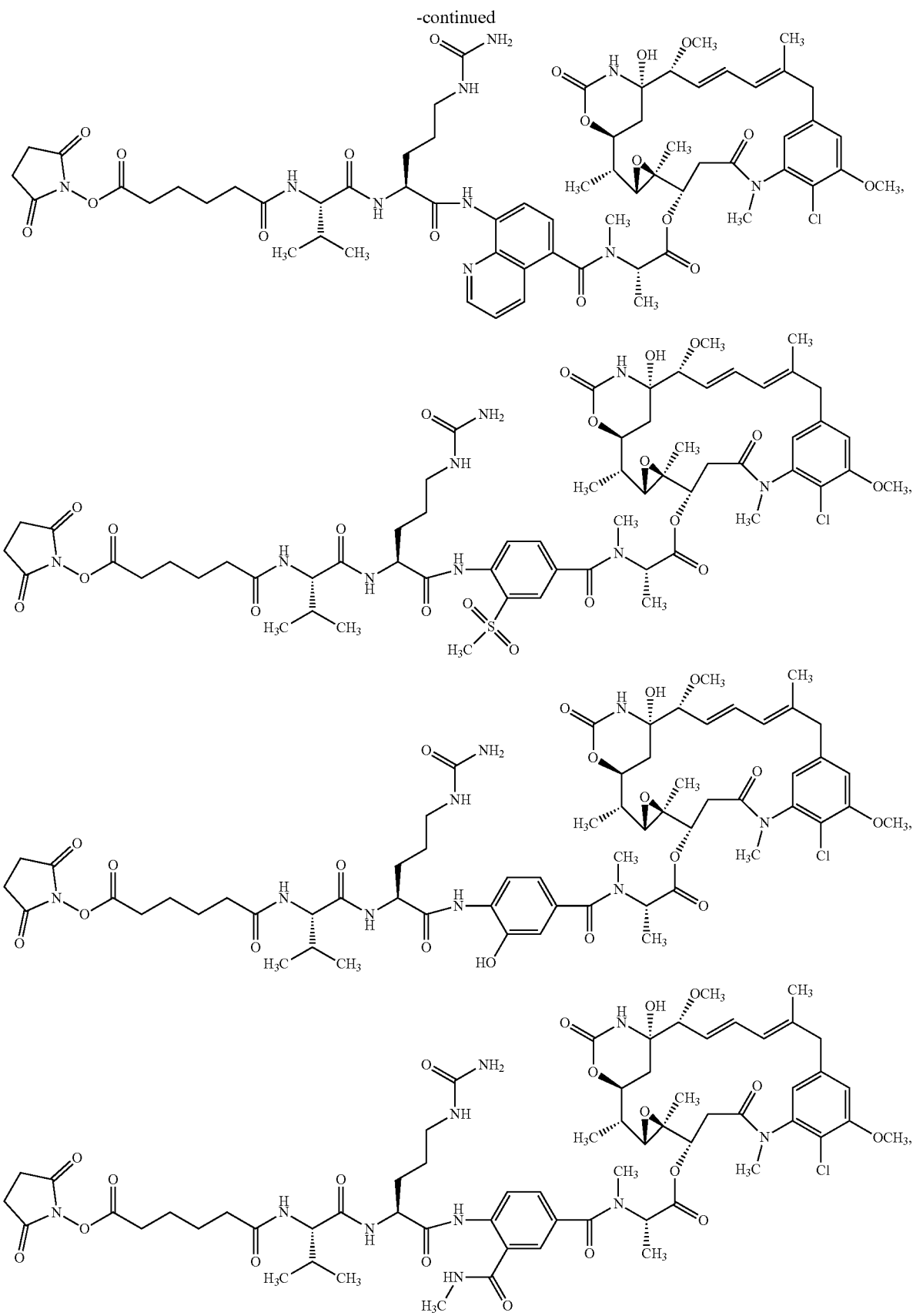

237
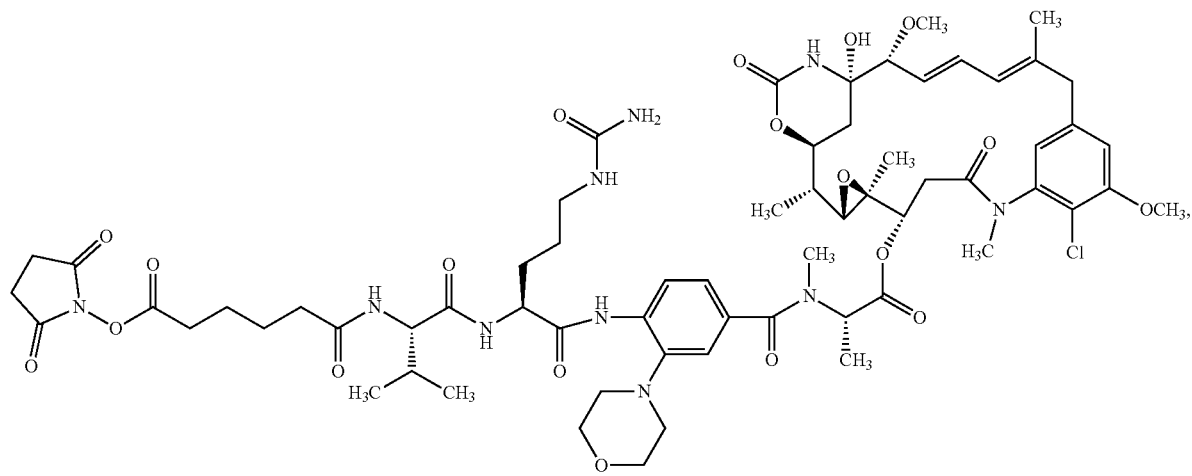
-continued
238
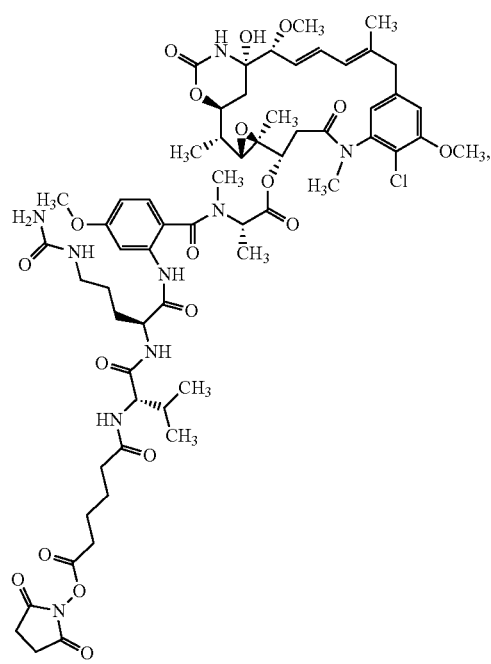
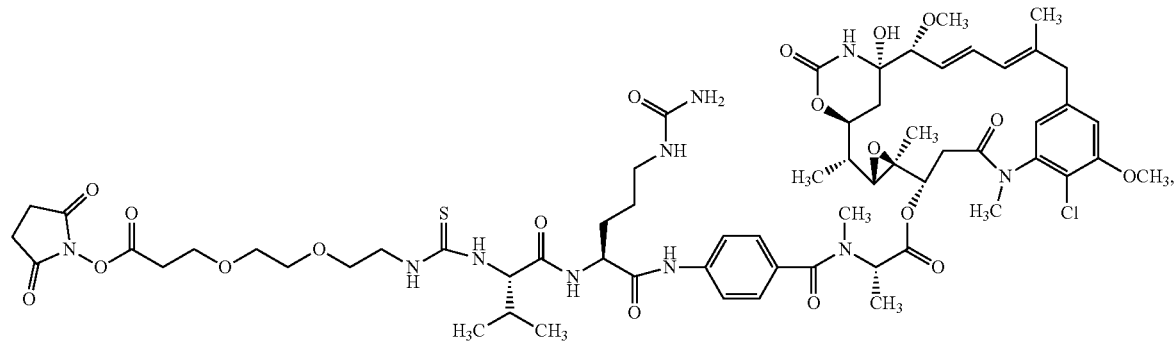

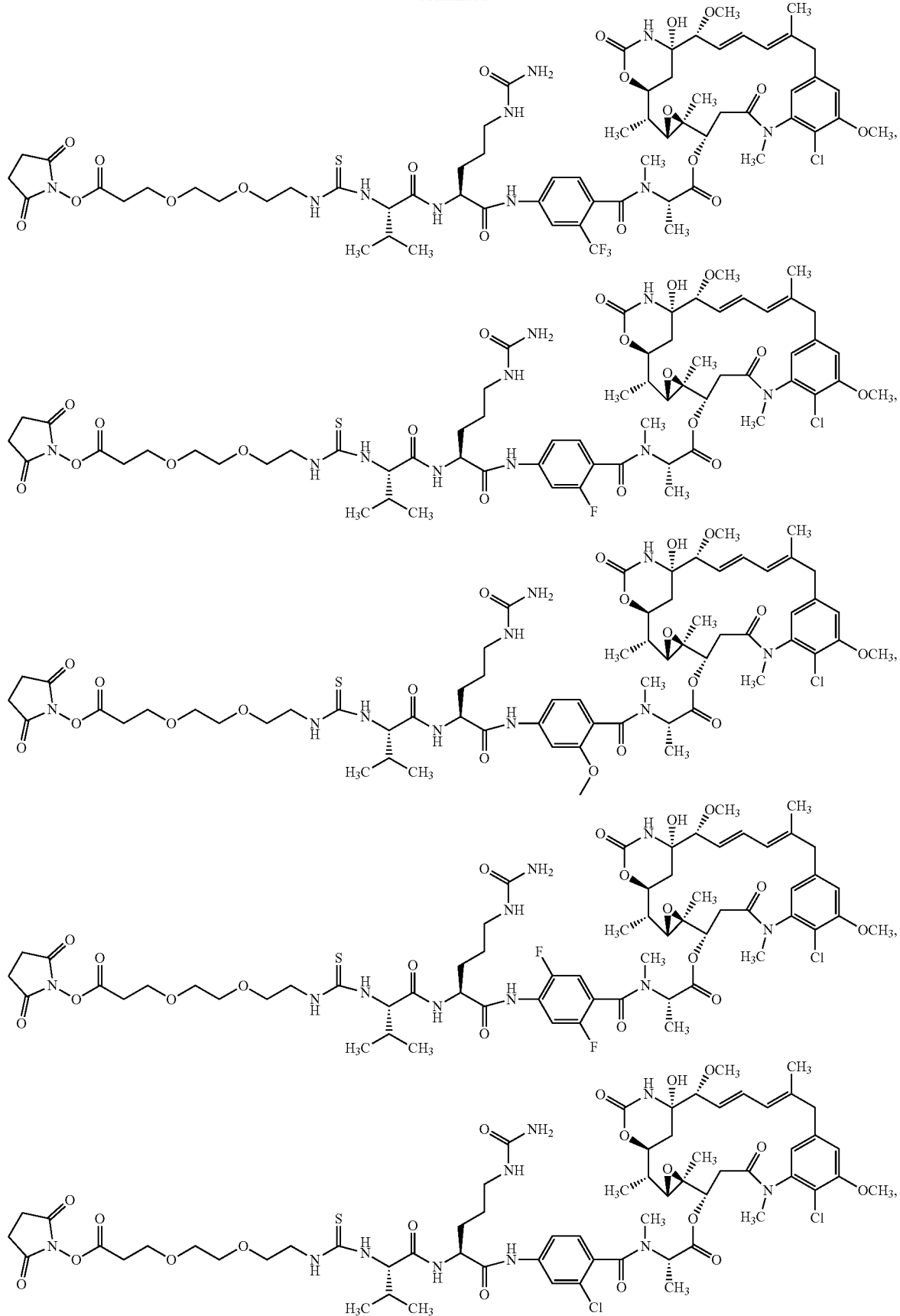

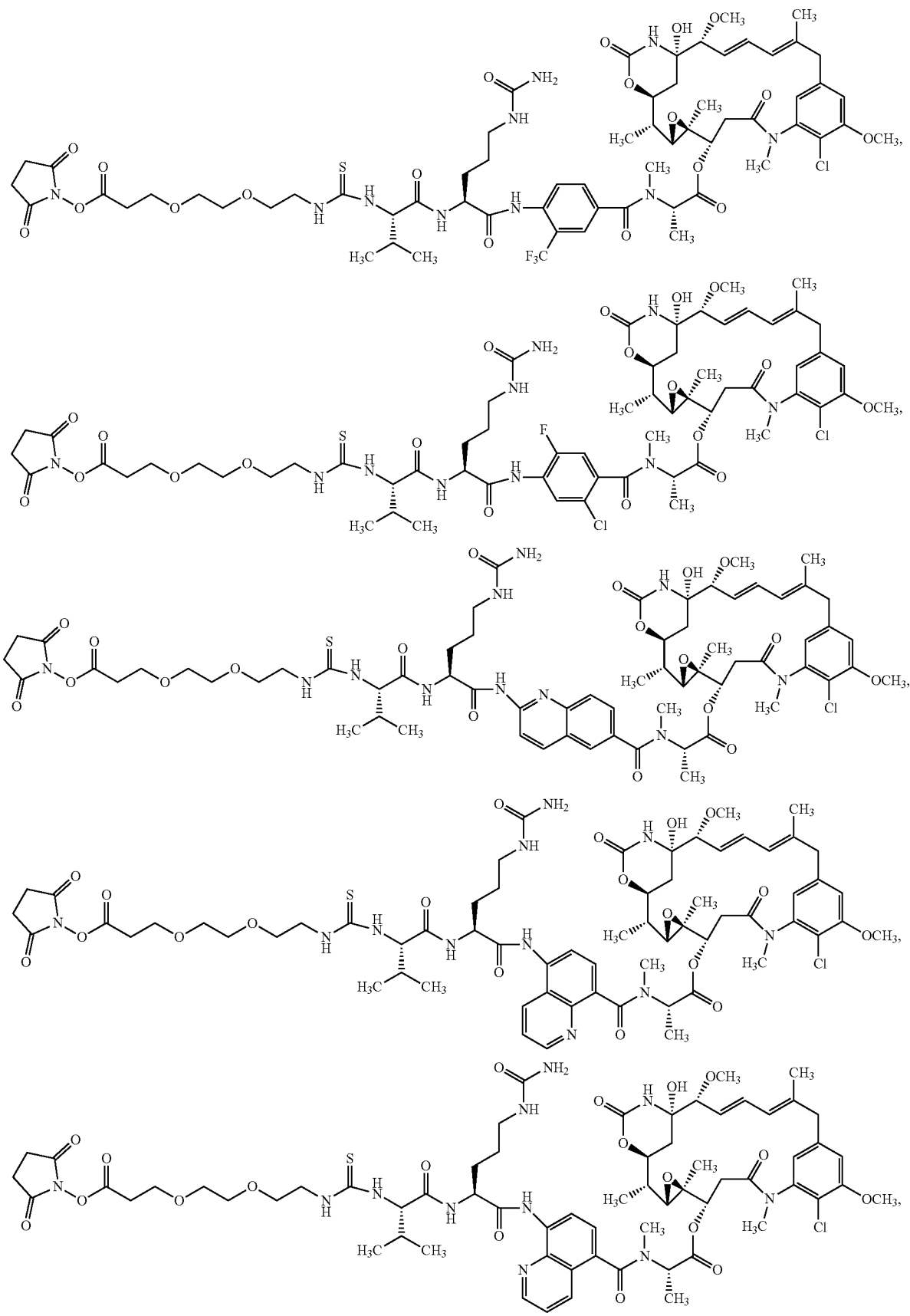

243 244
-continued
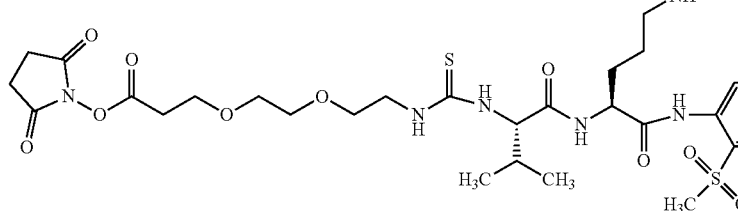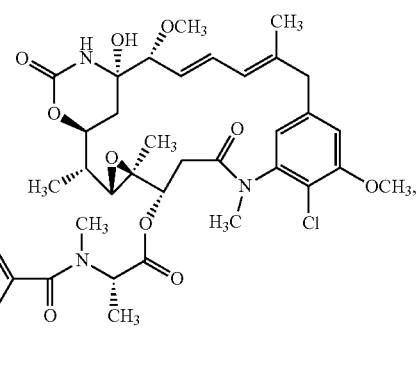
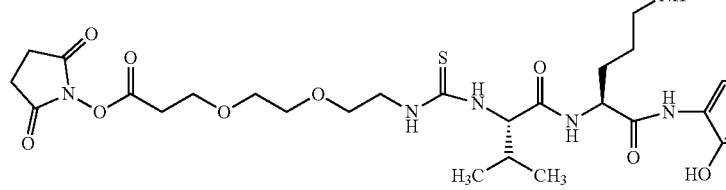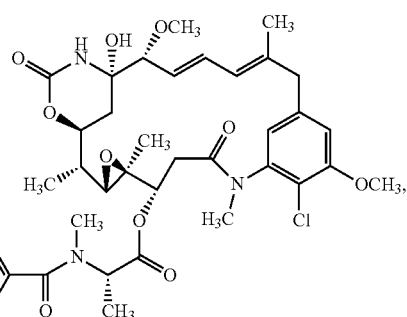
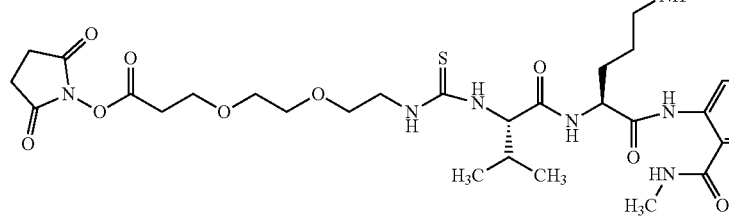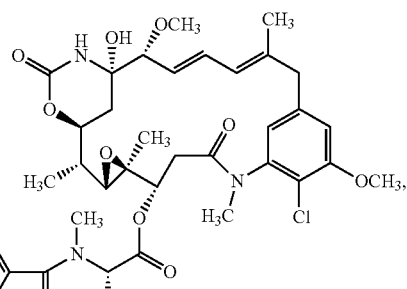
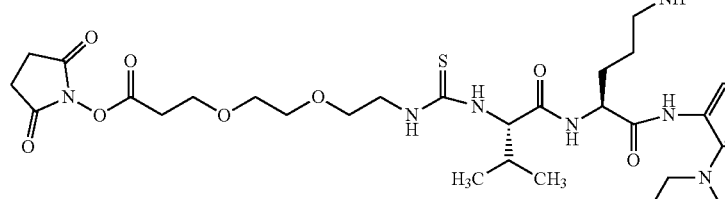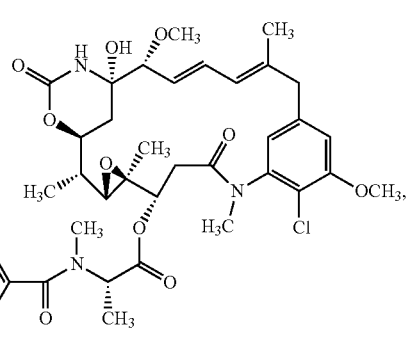

245
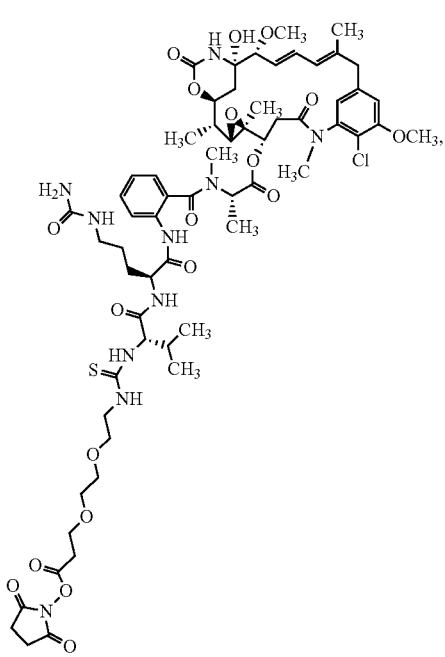
246
-continued
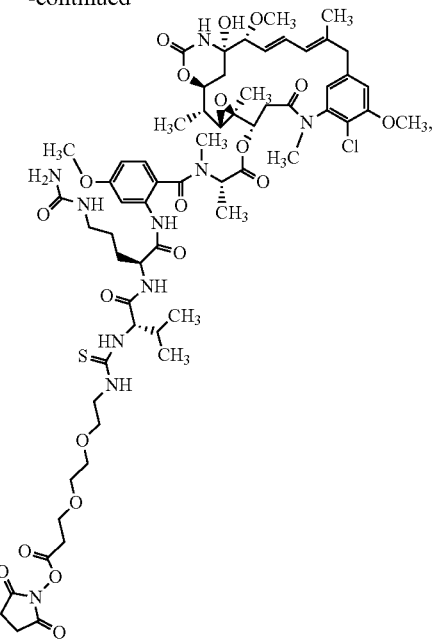
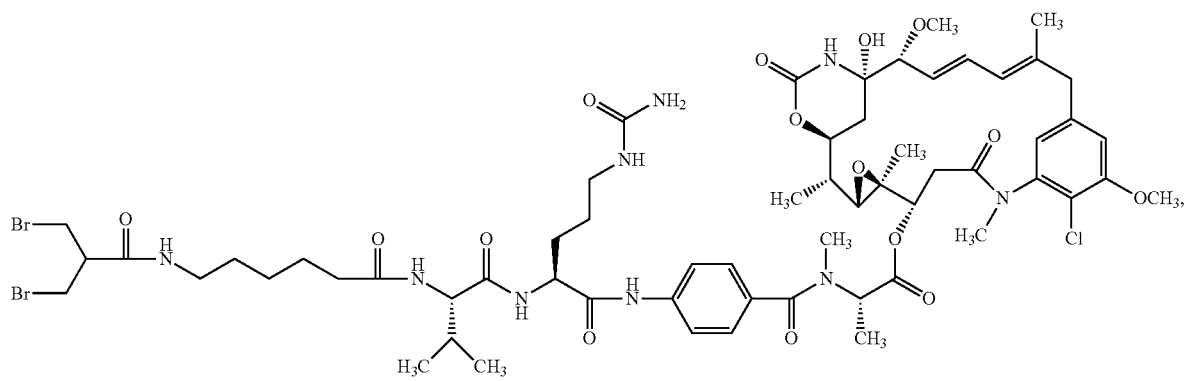
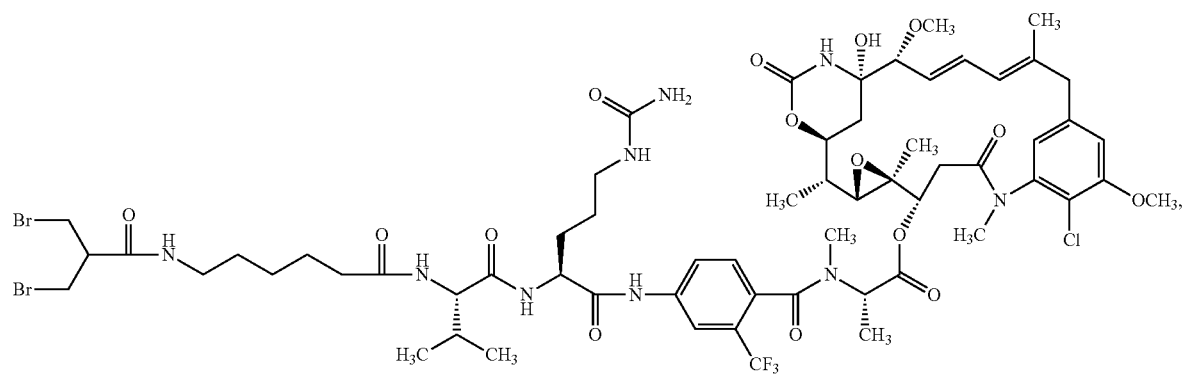

247 248
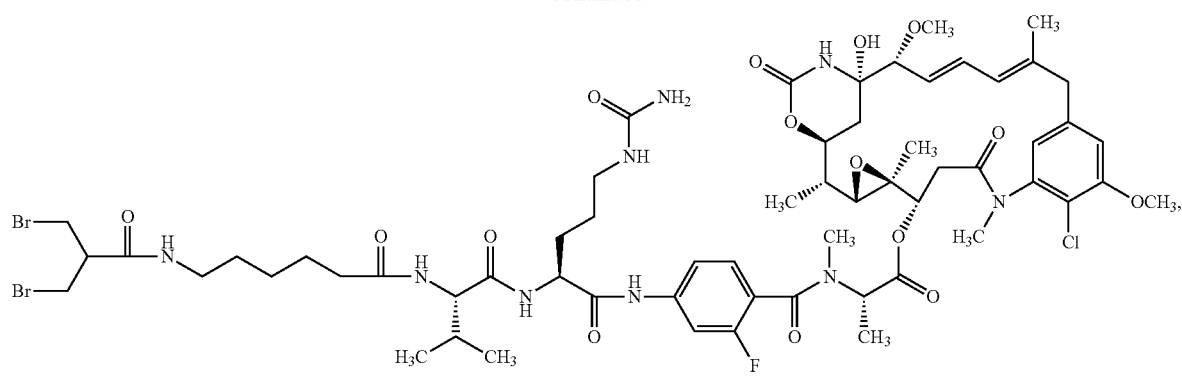
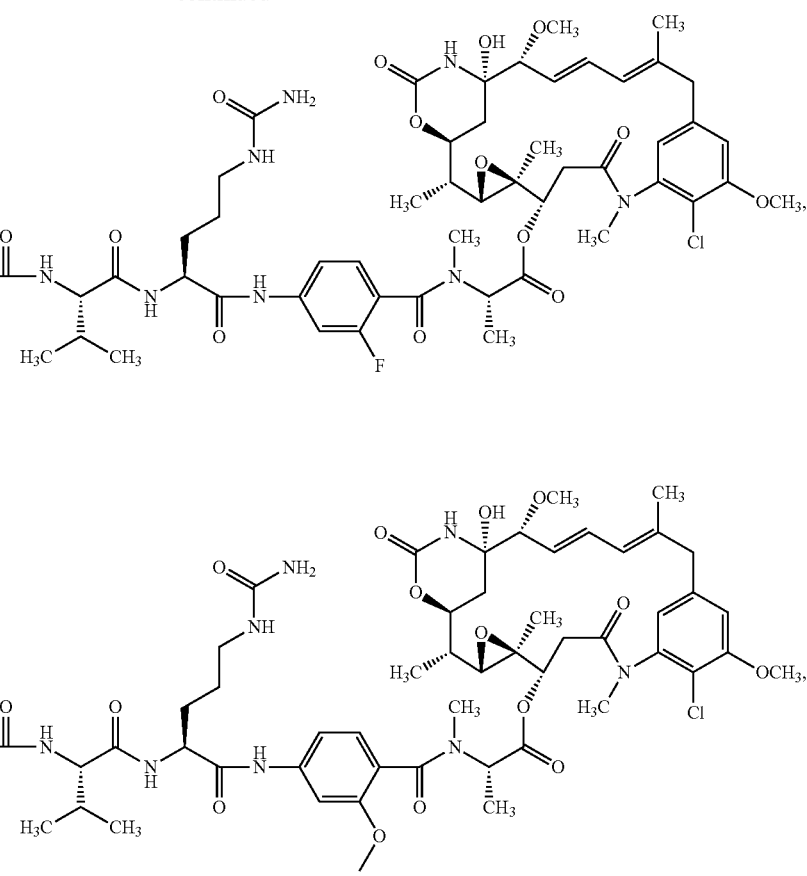
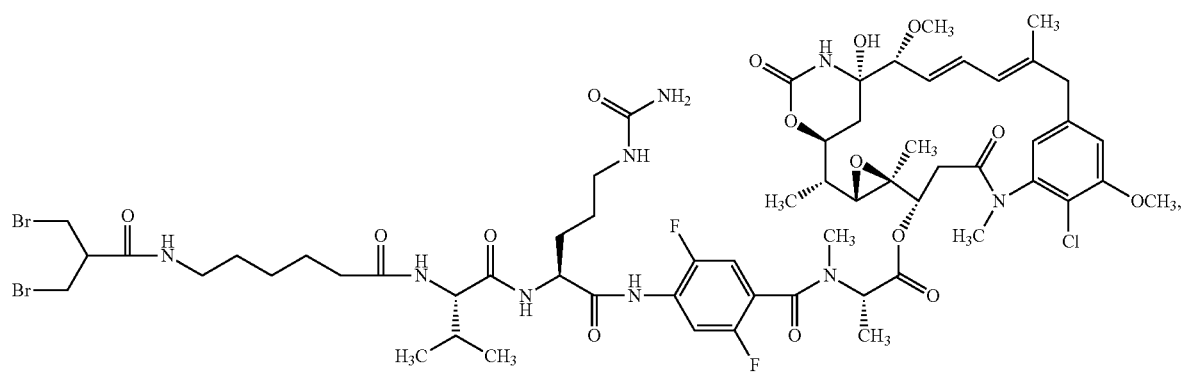
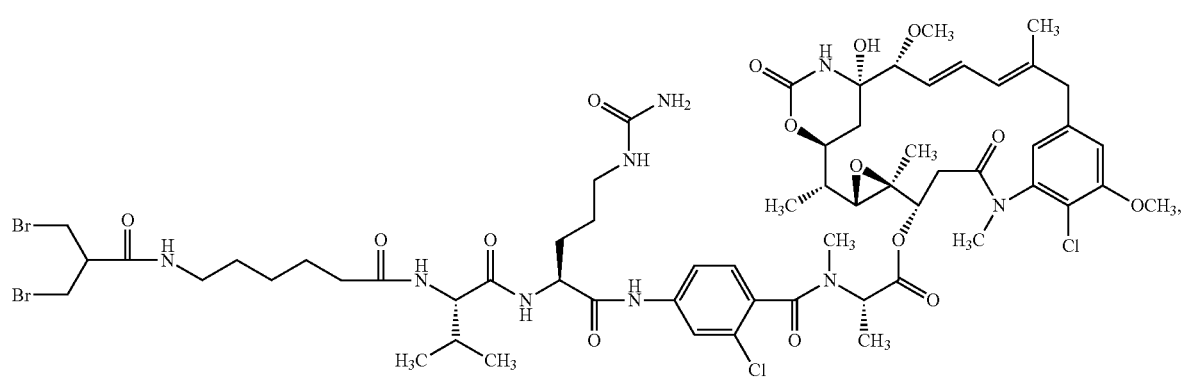

249 250
-continued
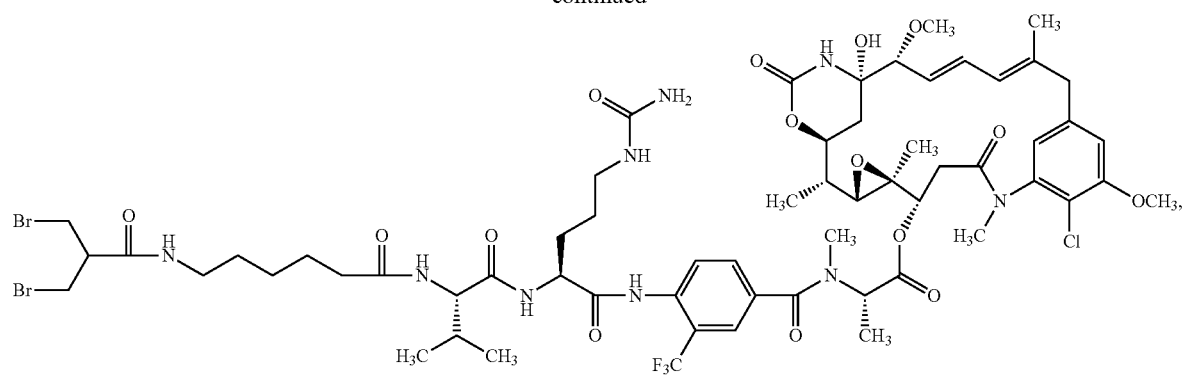
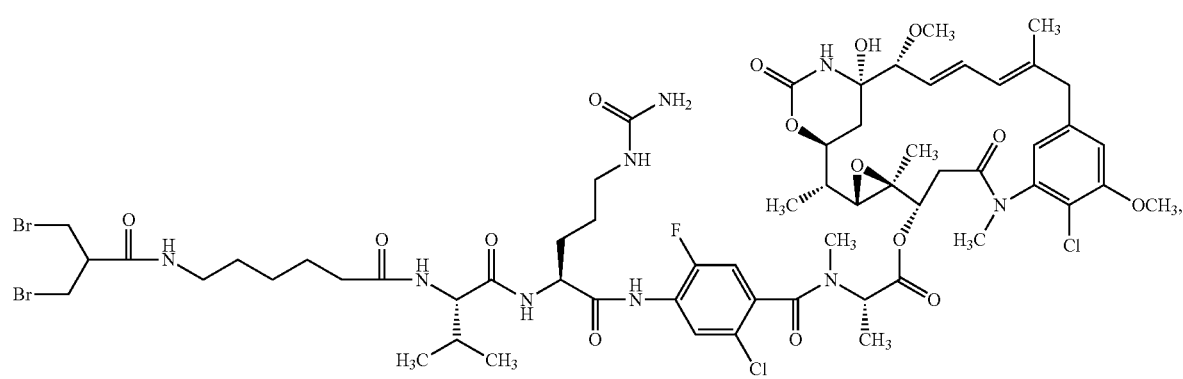
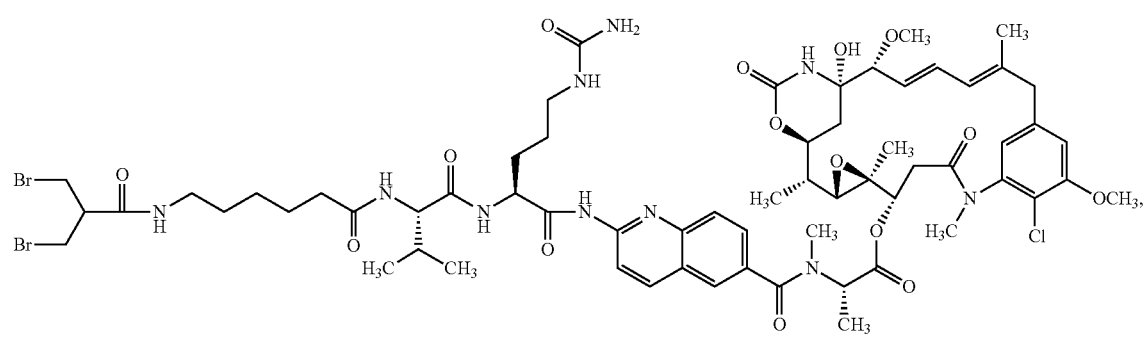
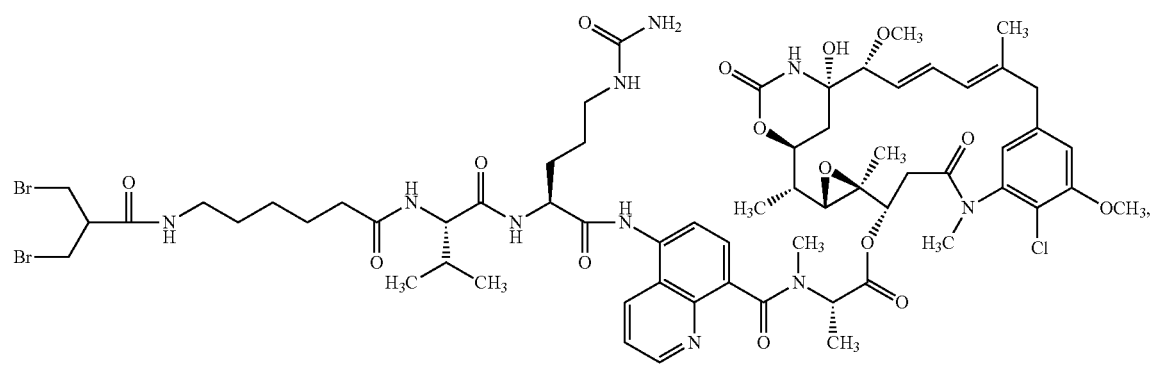

-continued
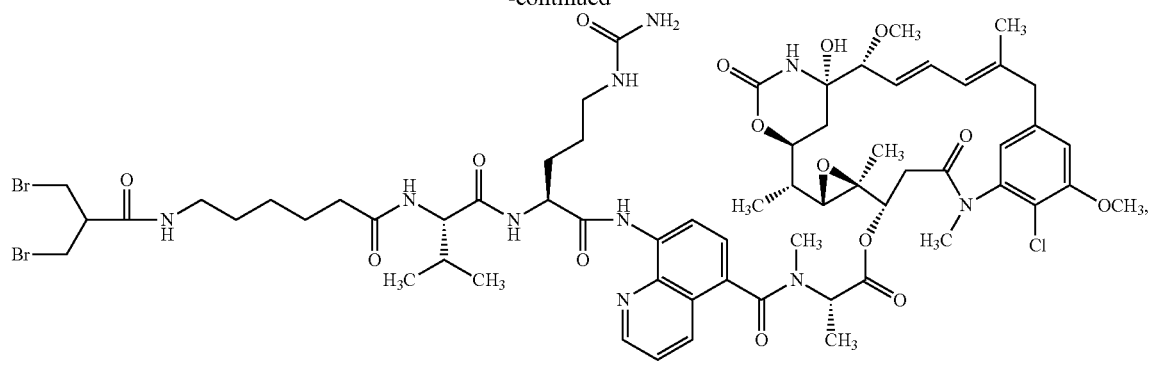
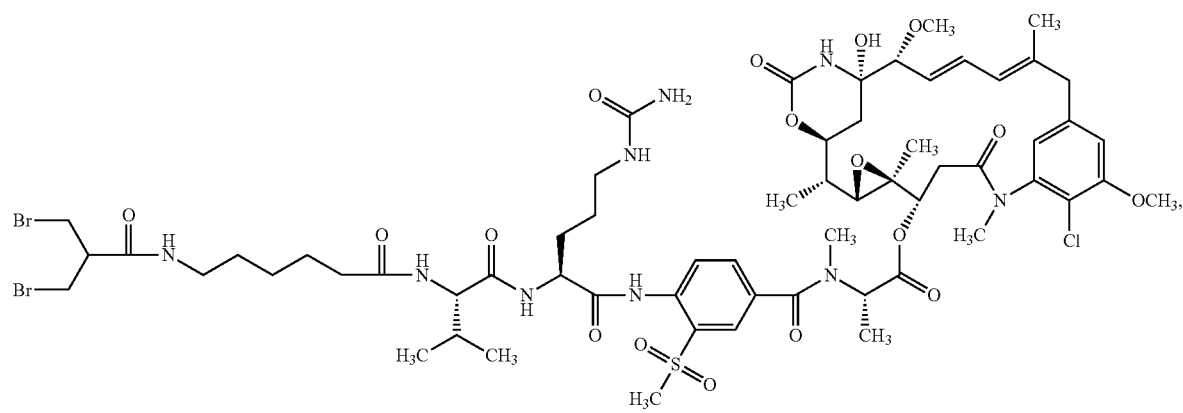
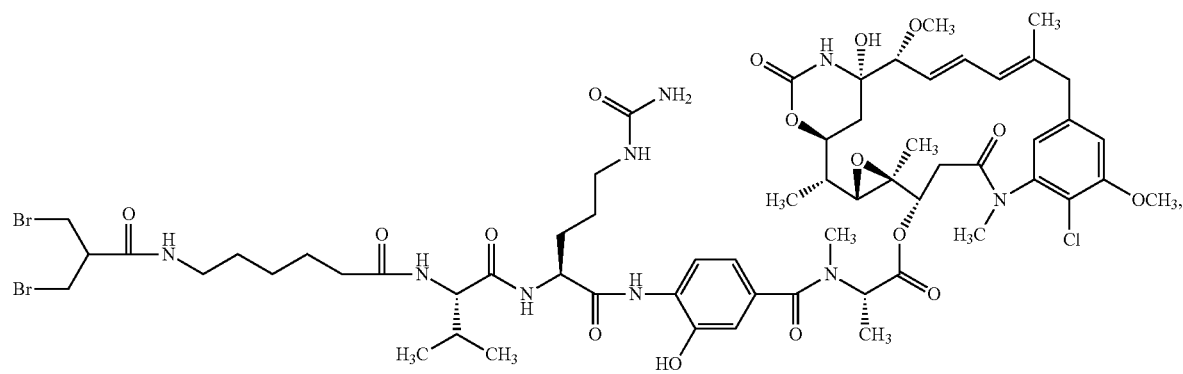
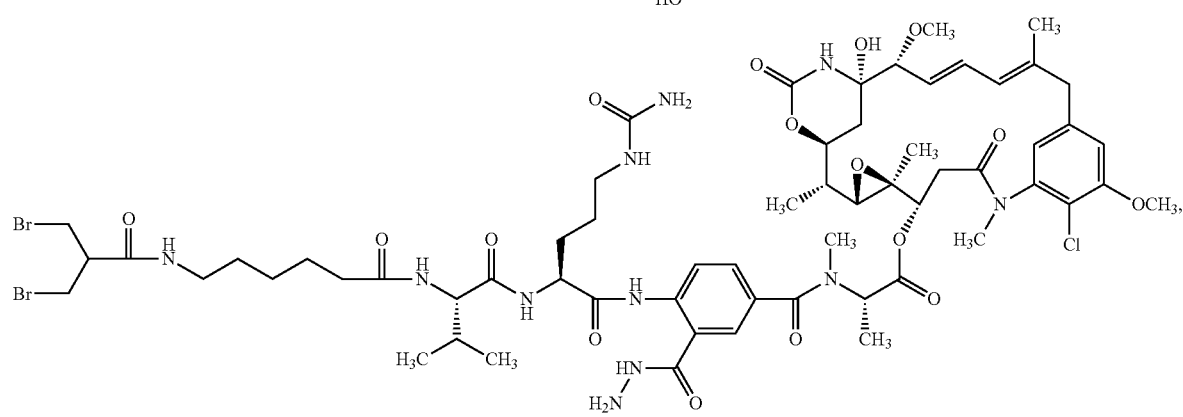

253
254
-continued
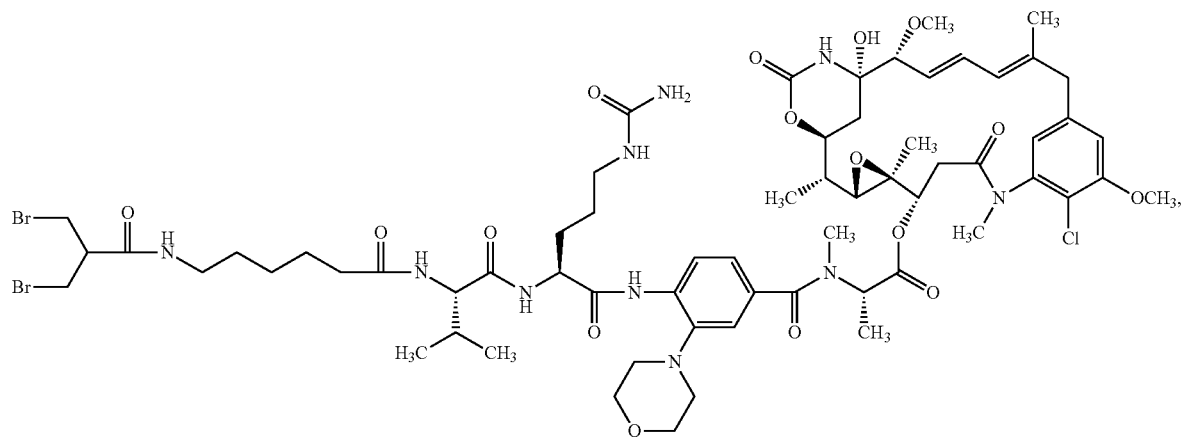
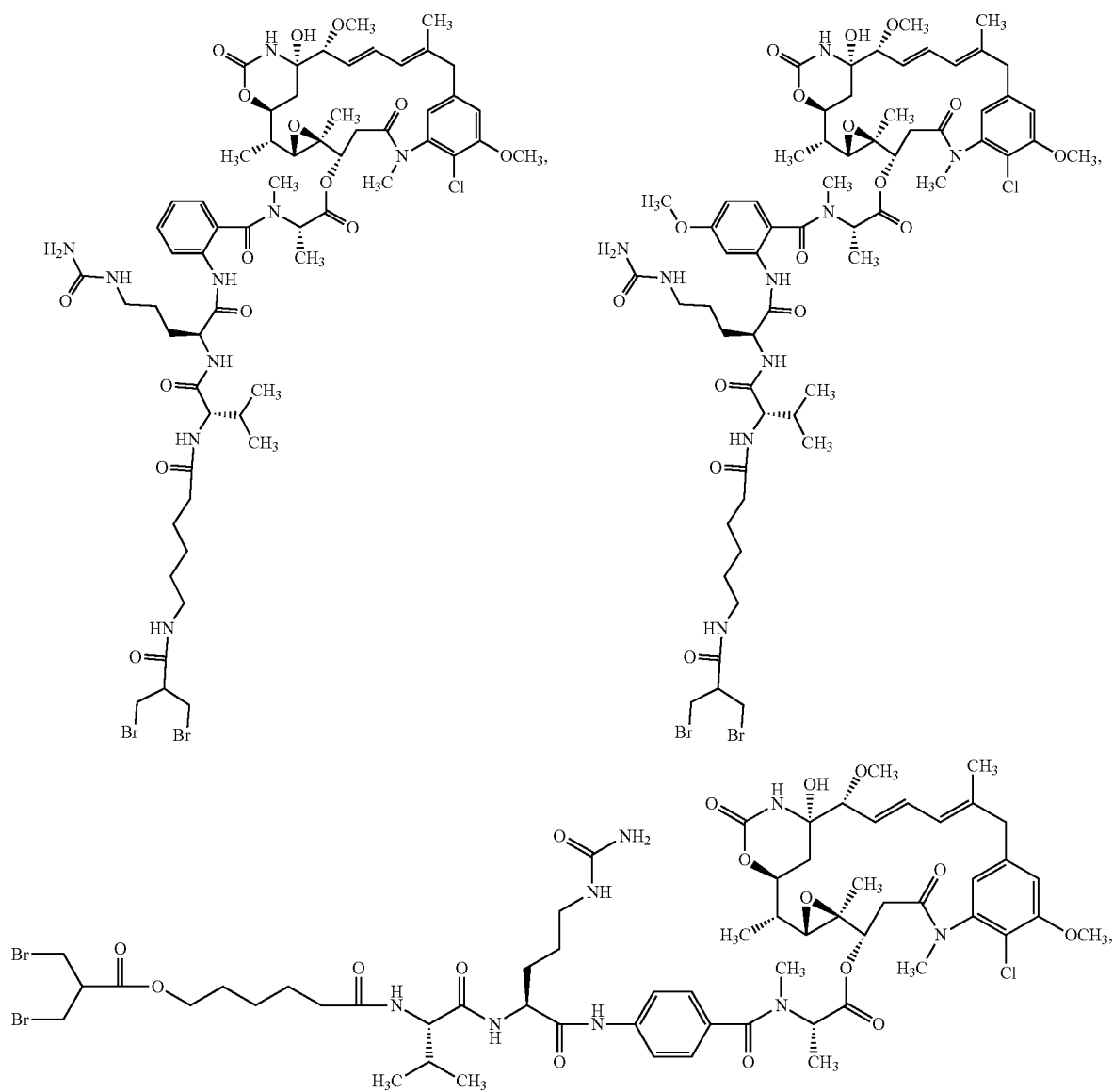

255
256
-continued
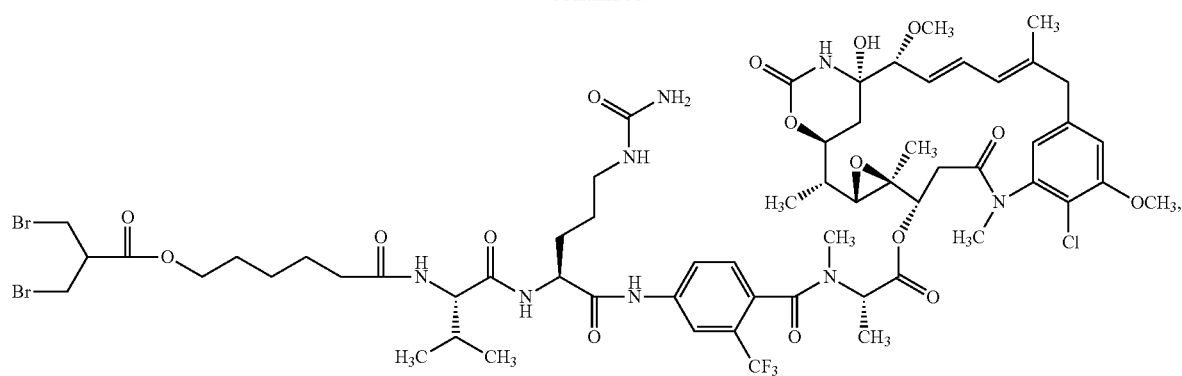
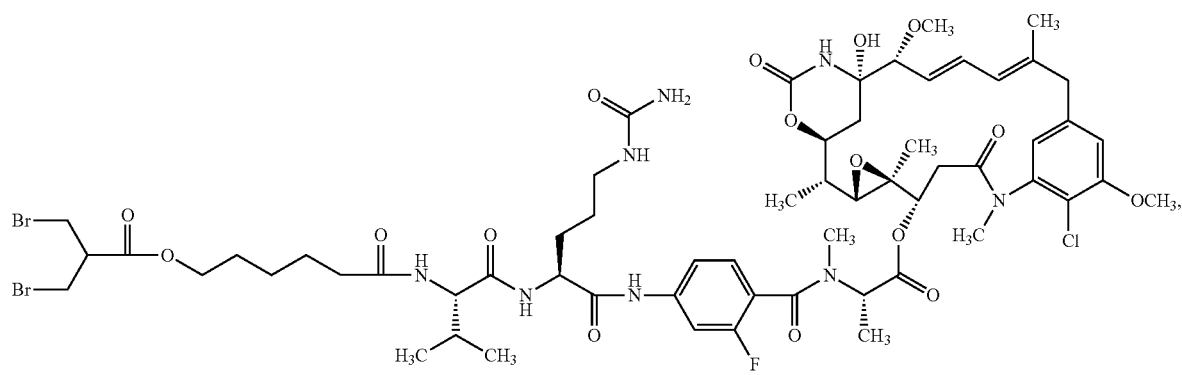
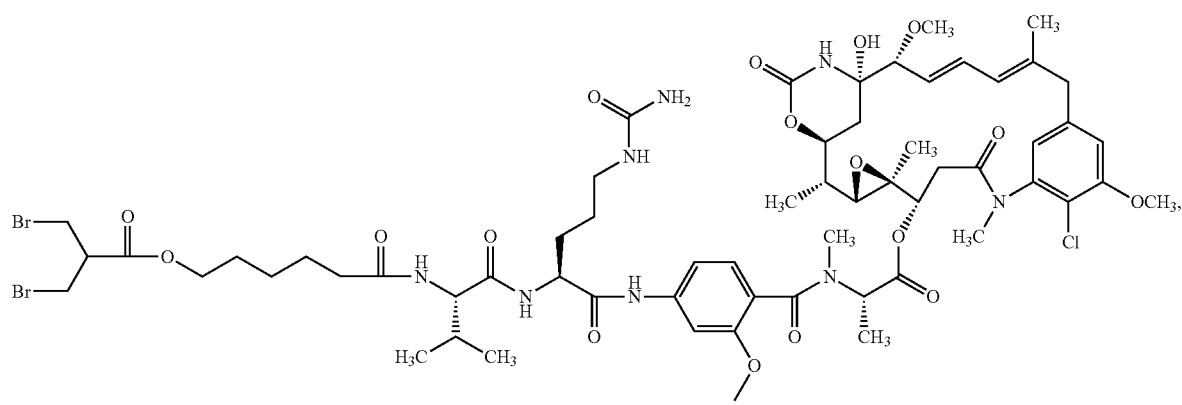
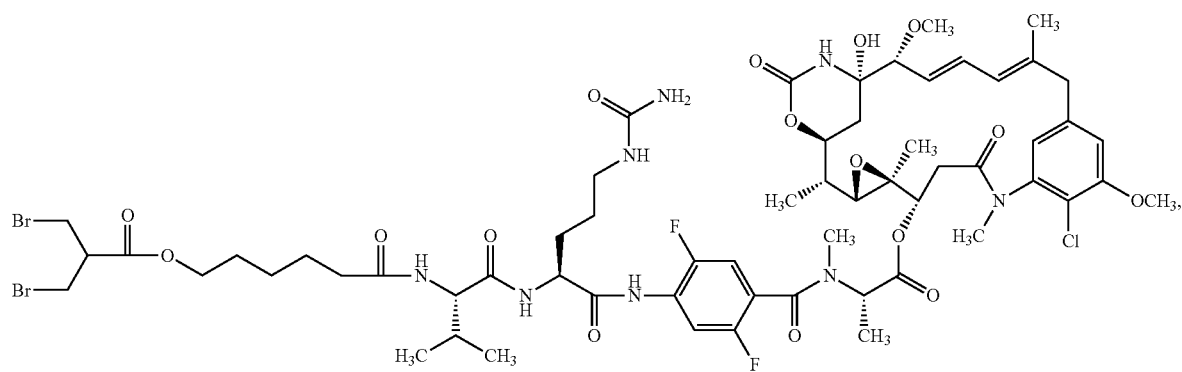

257 258
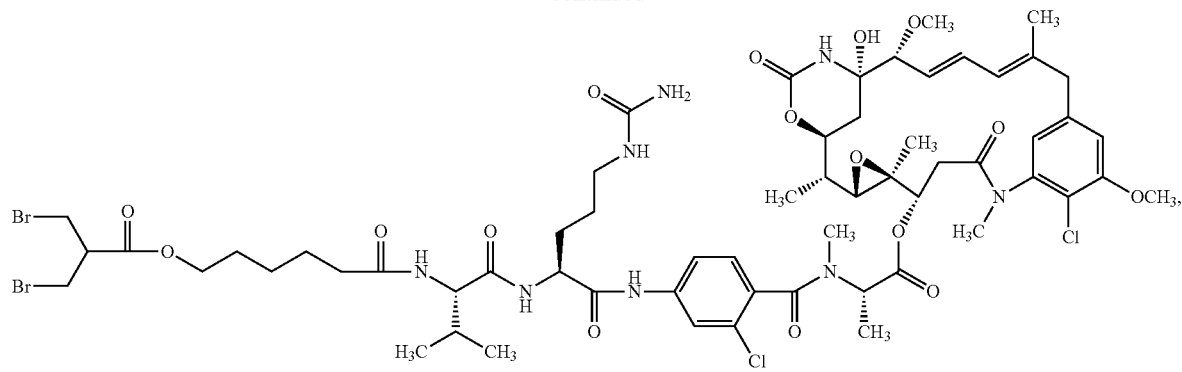
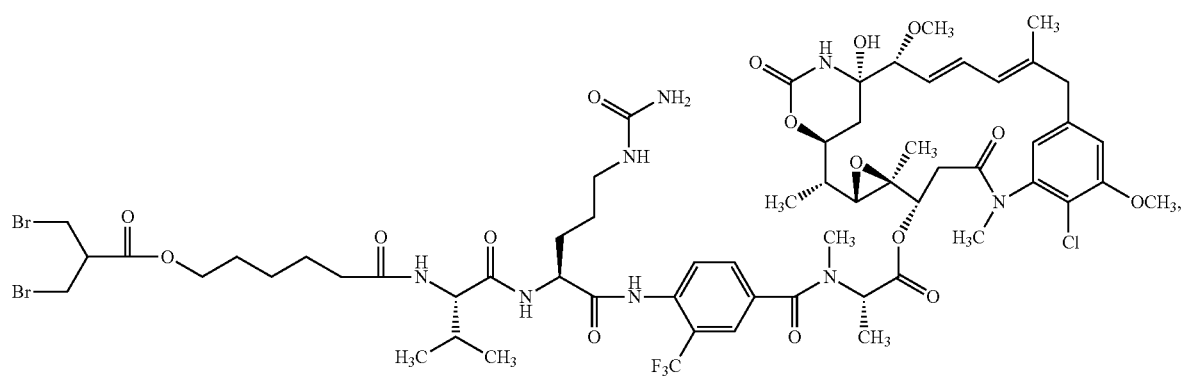
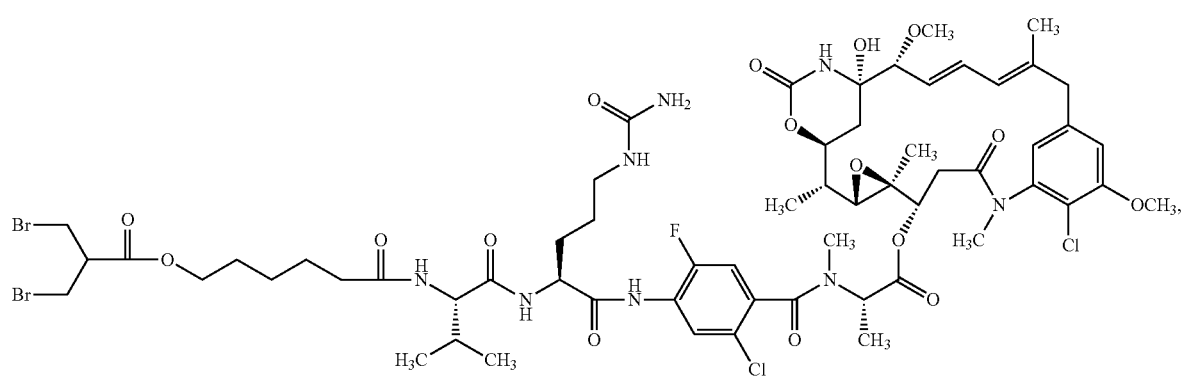
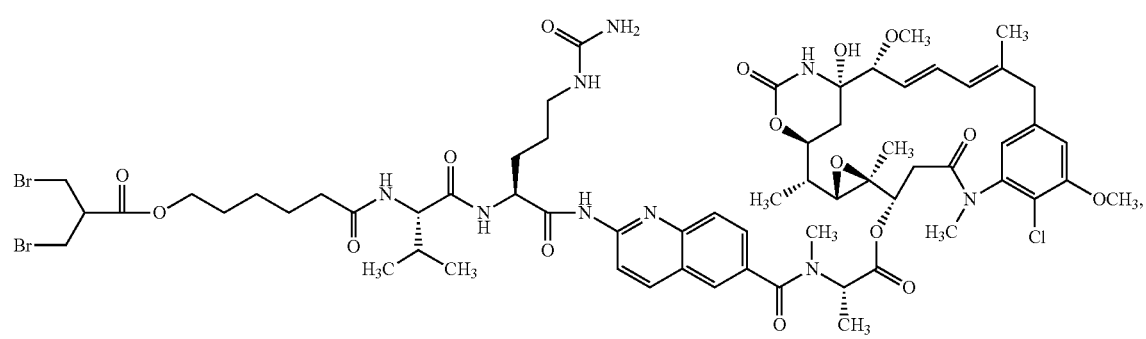

259
260
-continued
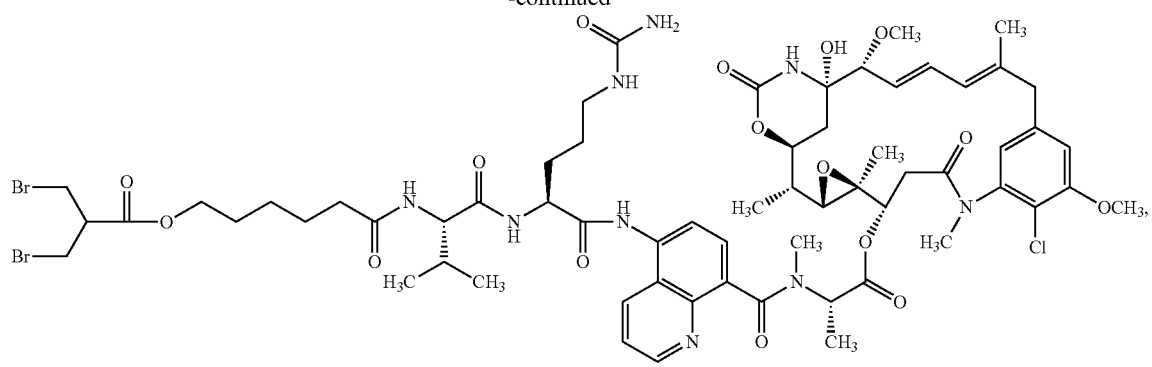
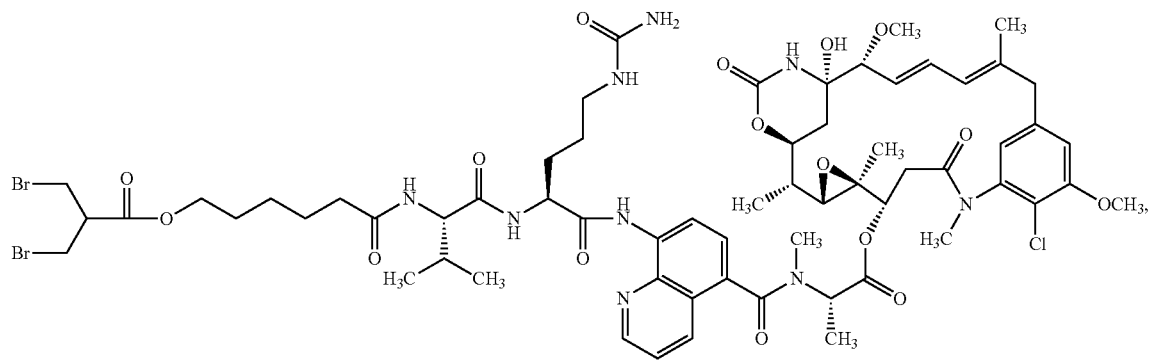
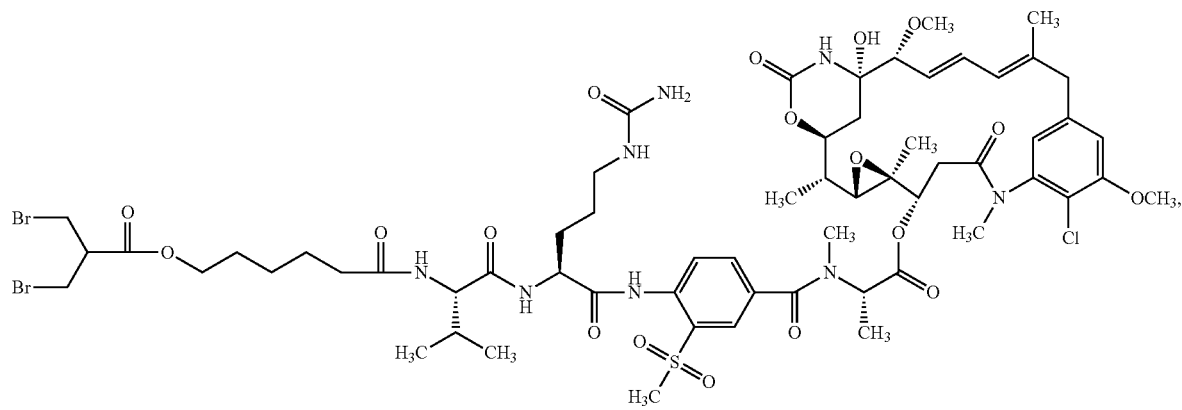
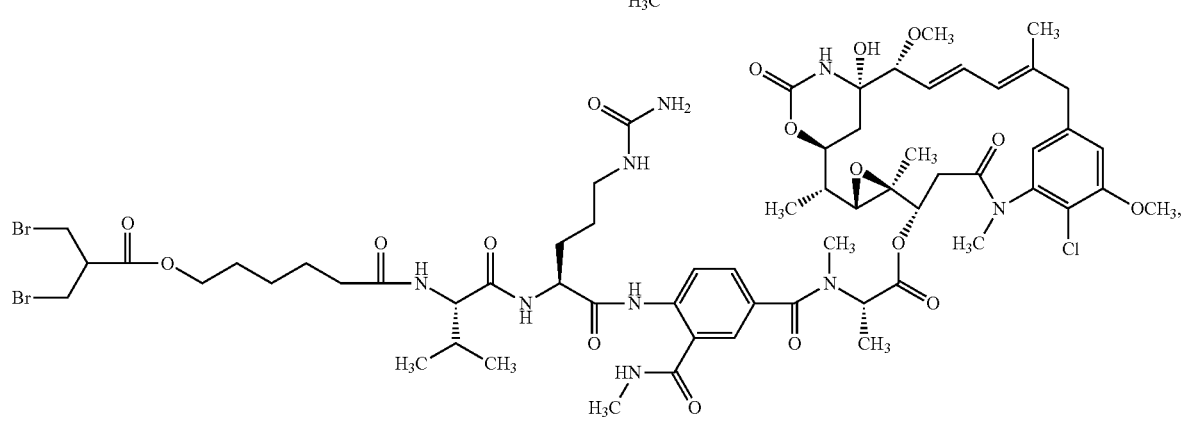

261
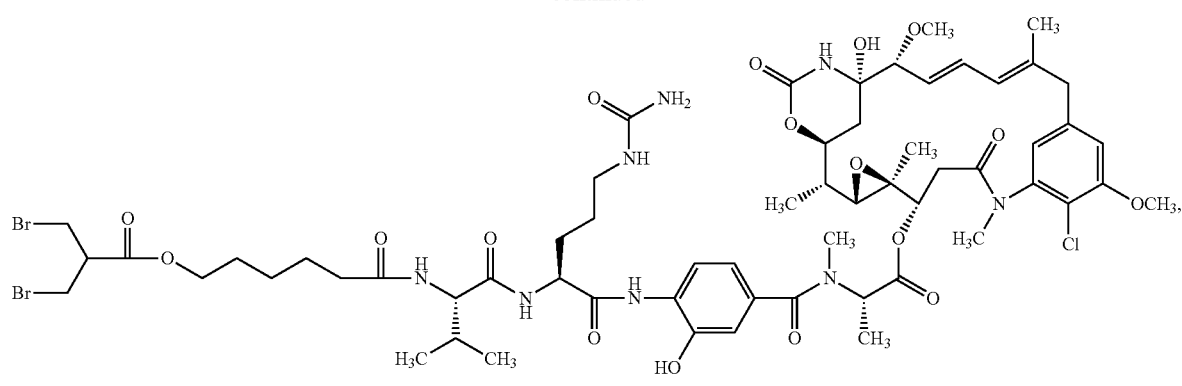
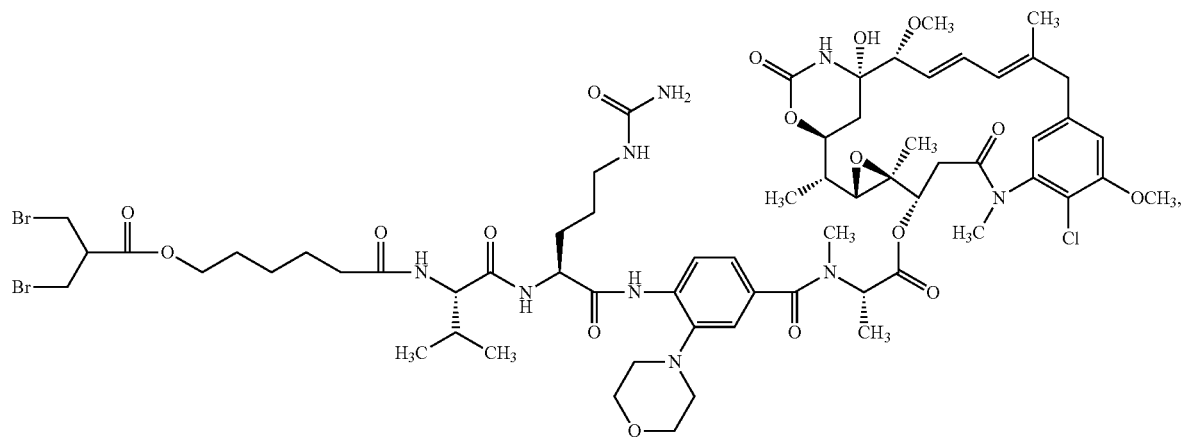
262
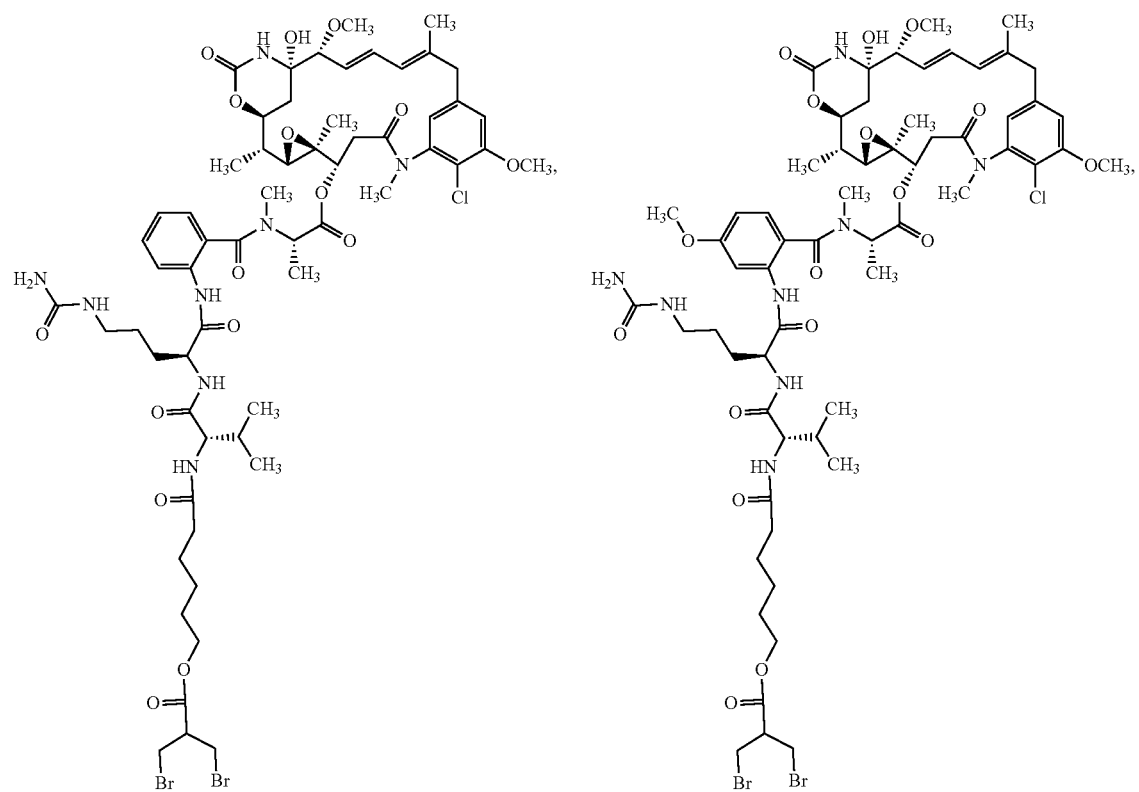

263
264
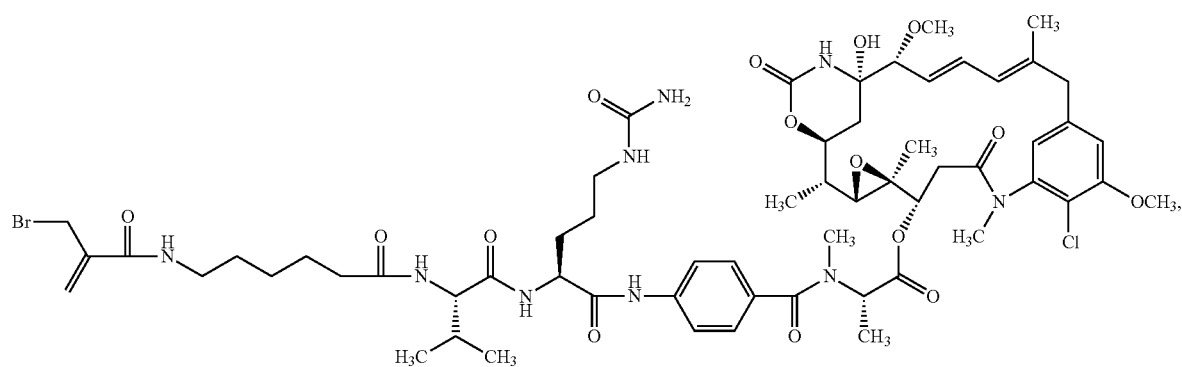 [SMILES: C=C(CBr)C(=O)NCCCCCC(=O)N[C@H](C(=O)N[C@@H](CCCNC(N)=O)C(=O)Nc1ccc(C(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)cc1)C(C)C]
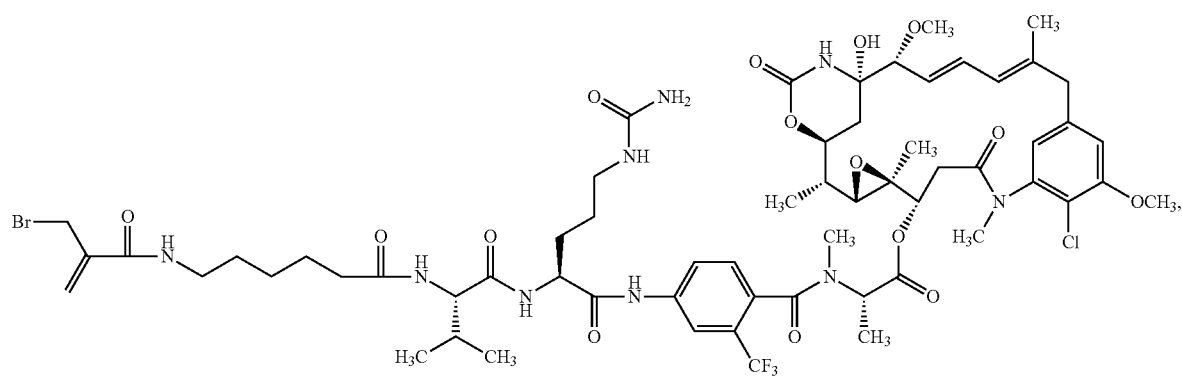
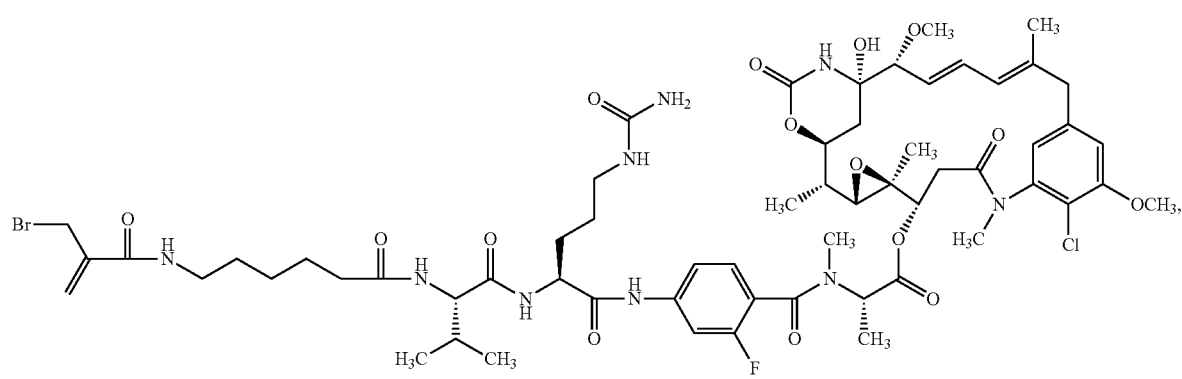
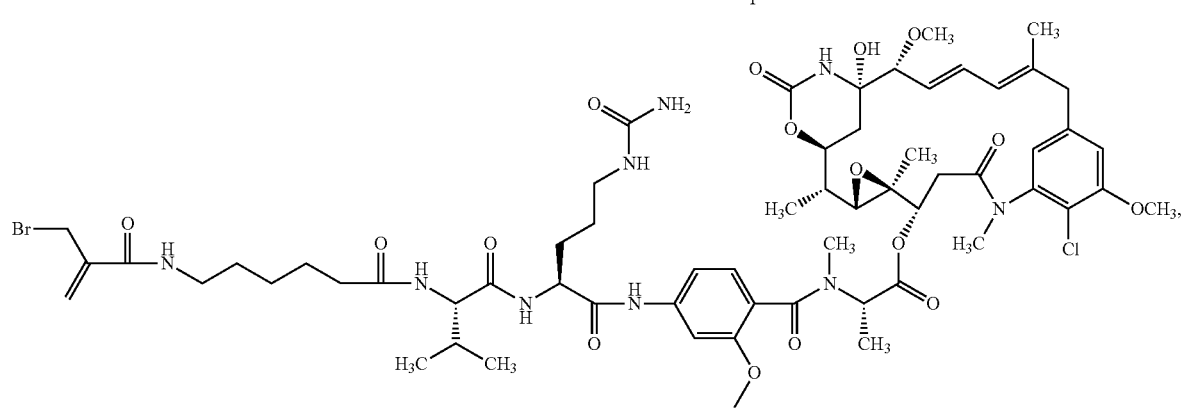

-continued
265
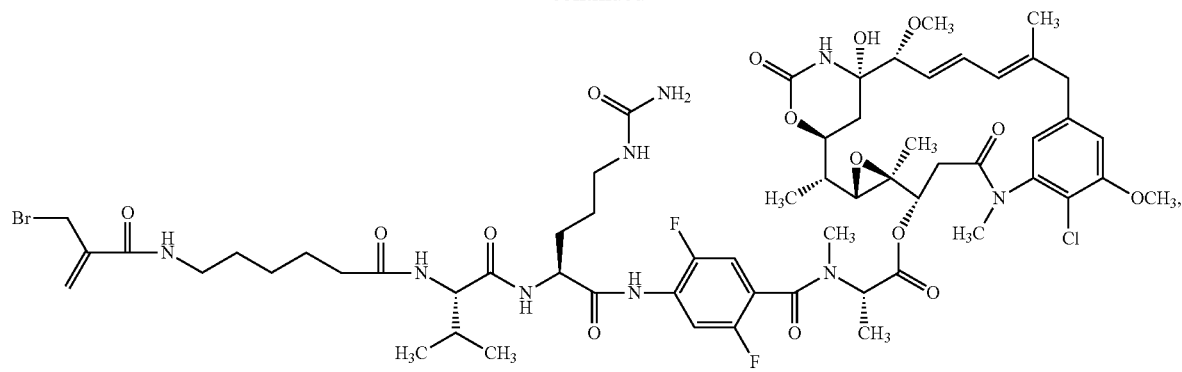
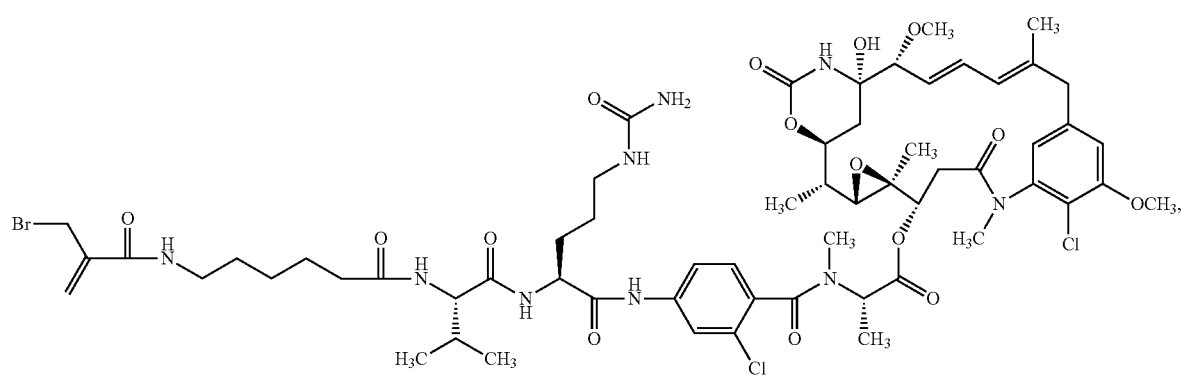
266
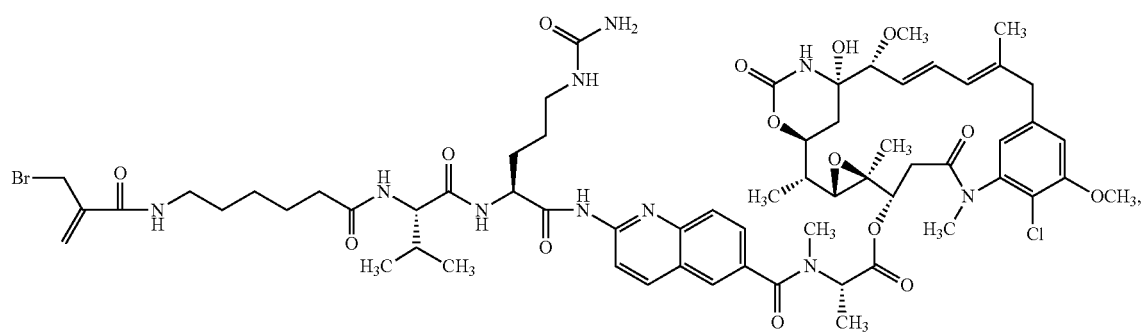
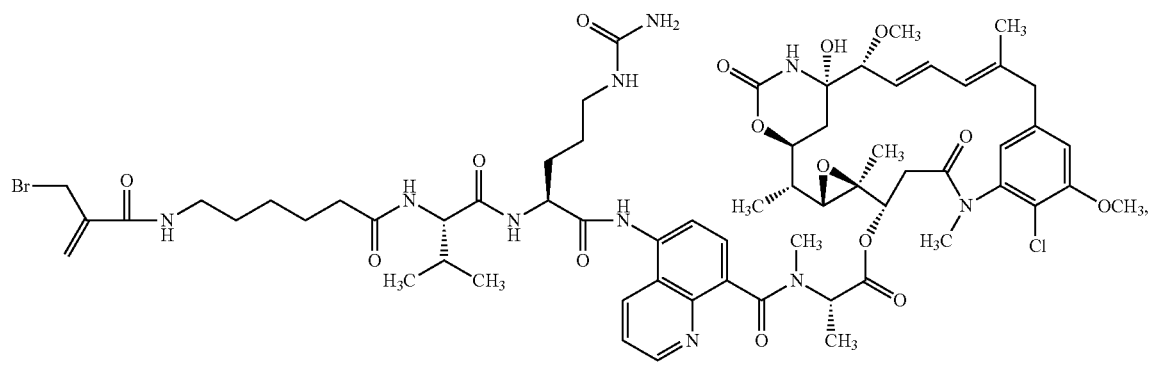

-continued
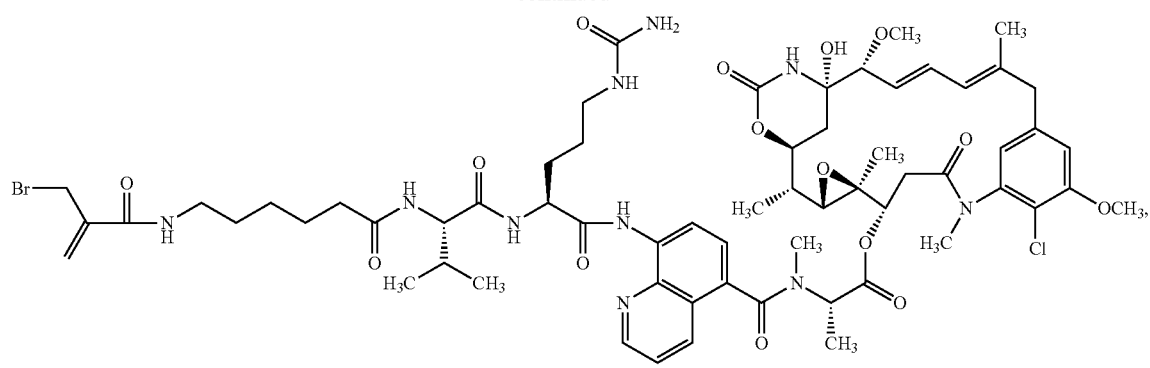
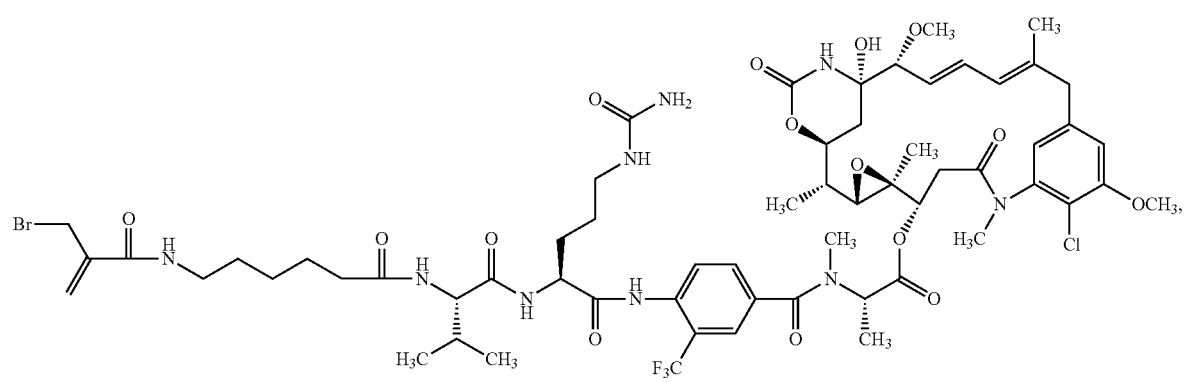
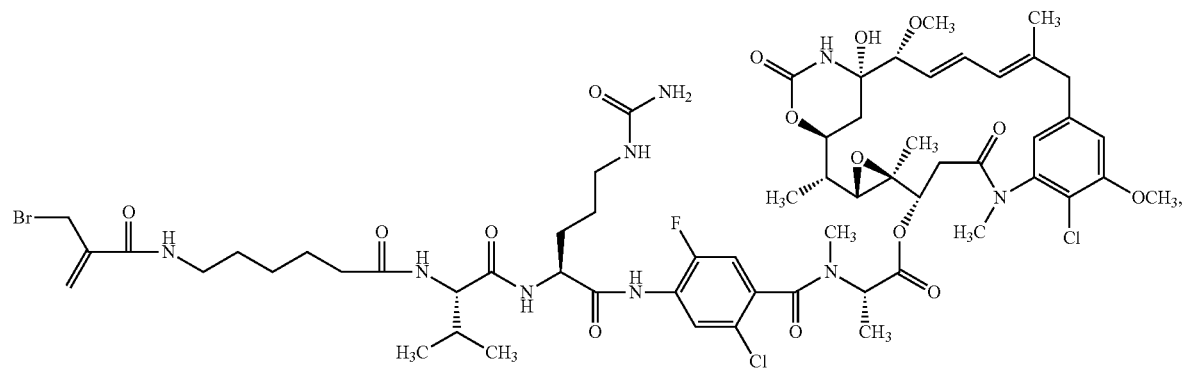
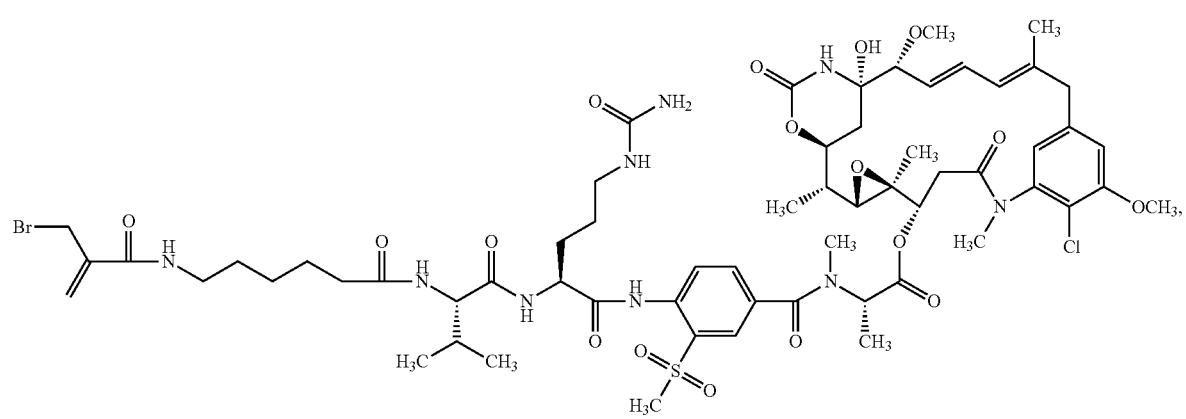

269
270
-continued
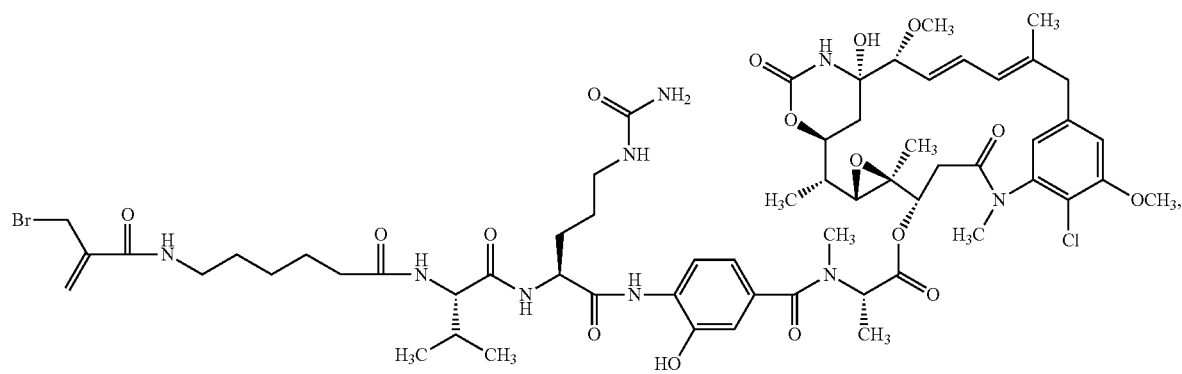
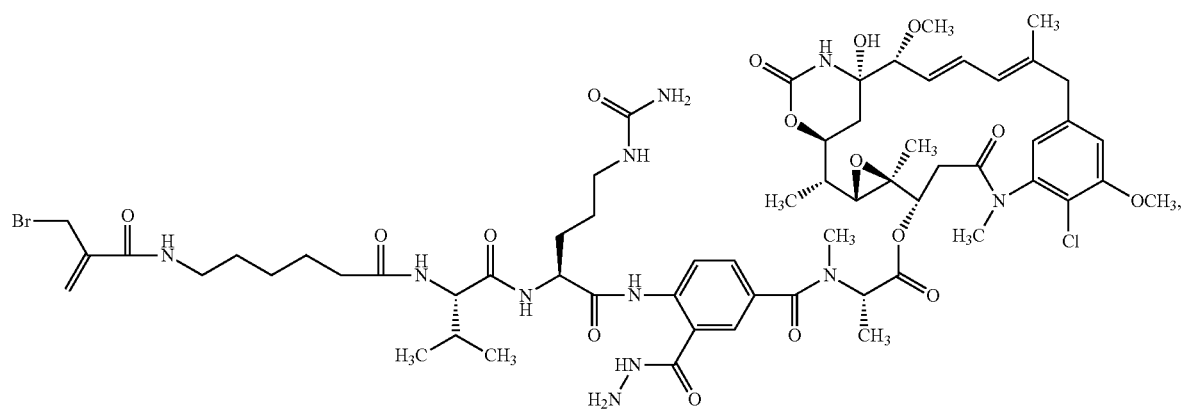
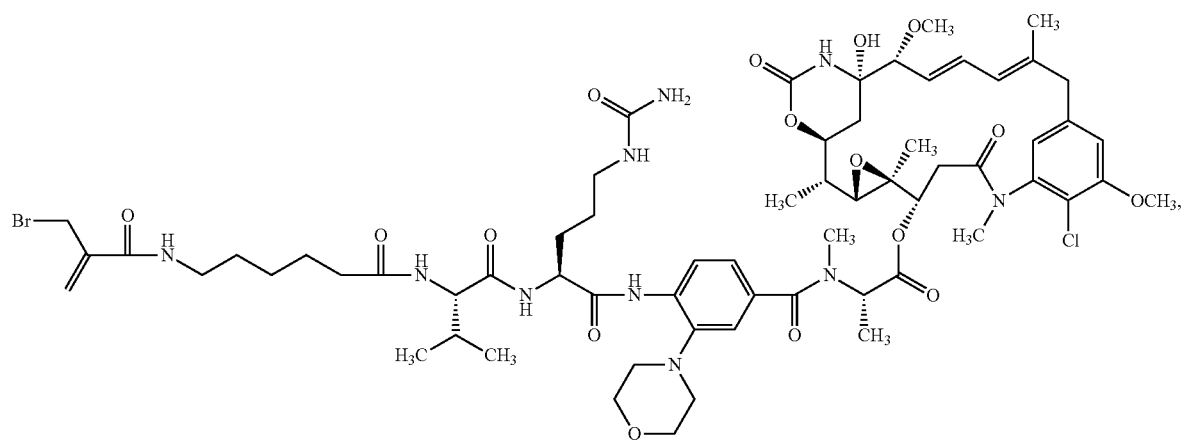

271
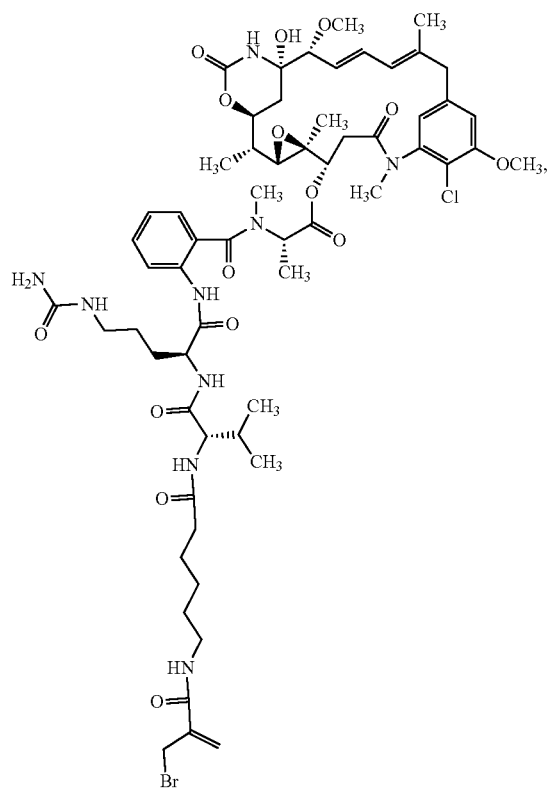
272
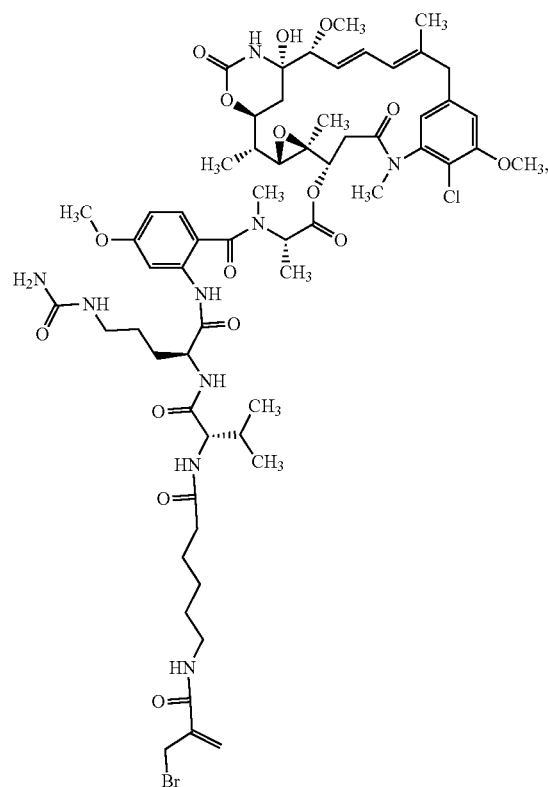
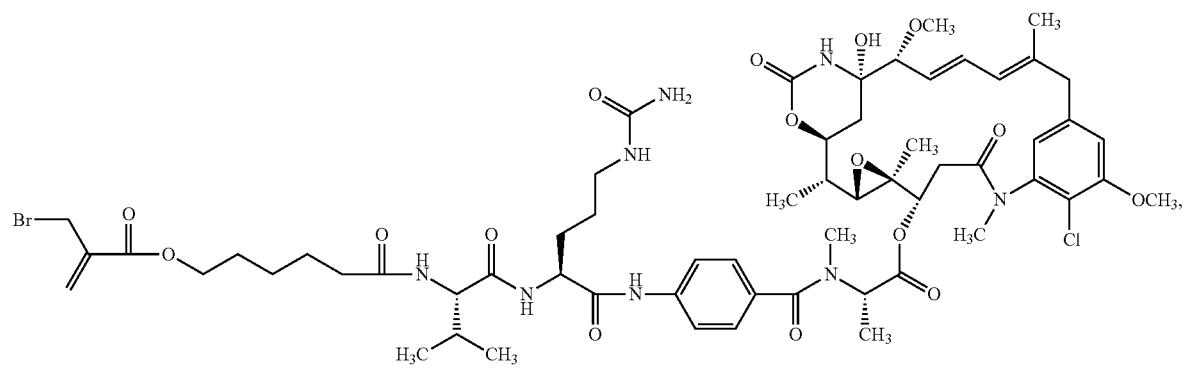
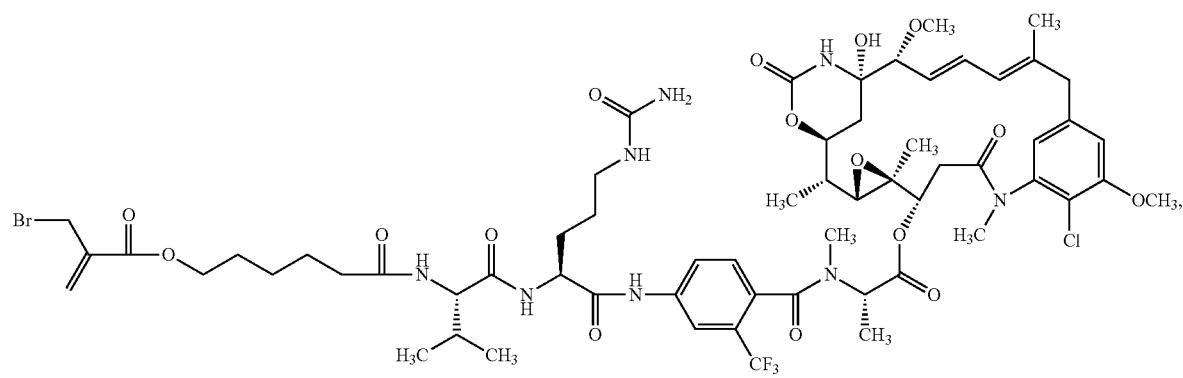

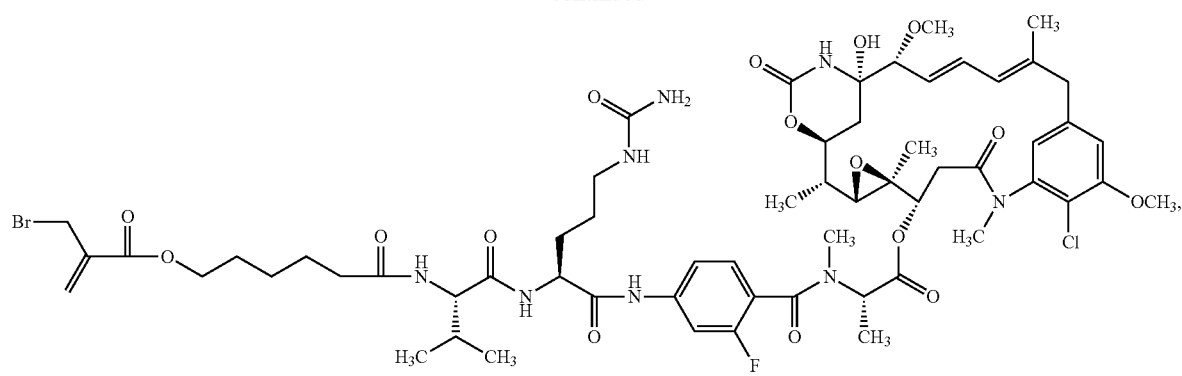
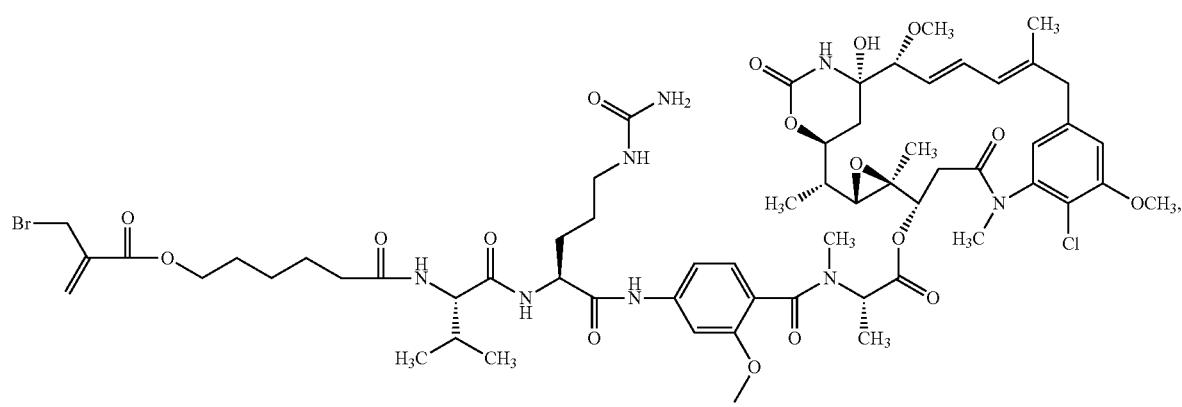
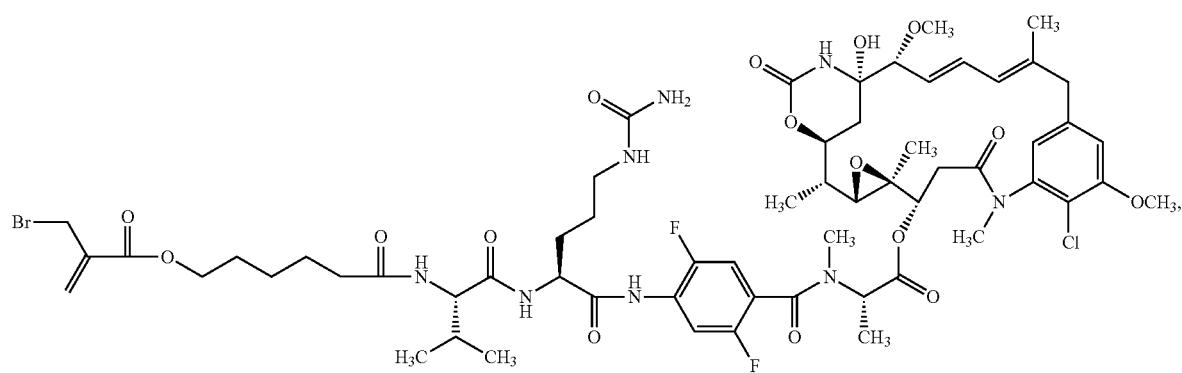
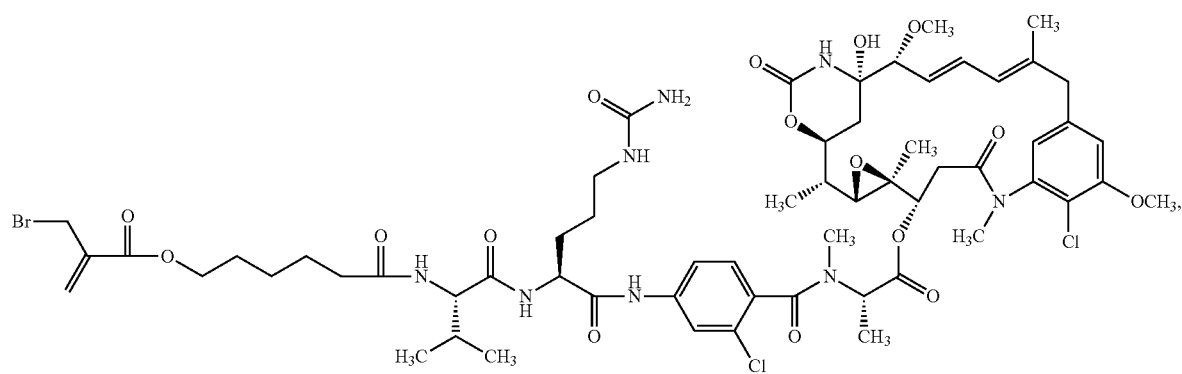

275 276
-continued
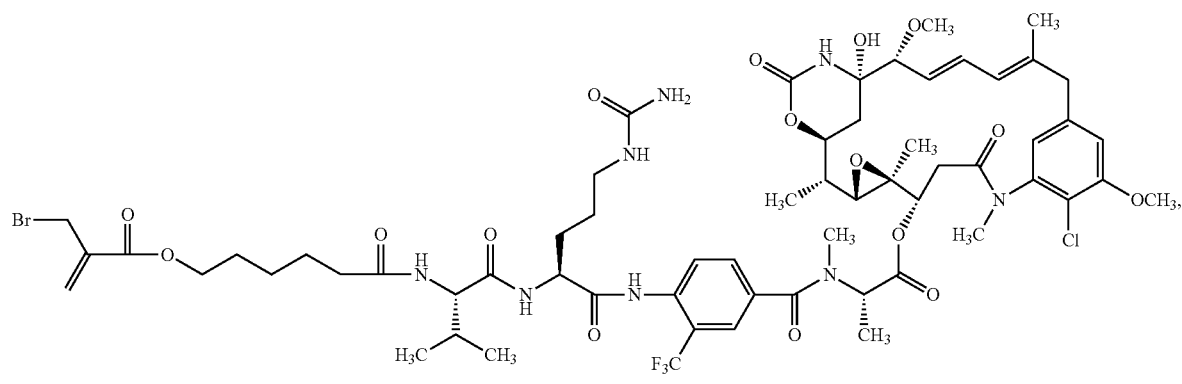
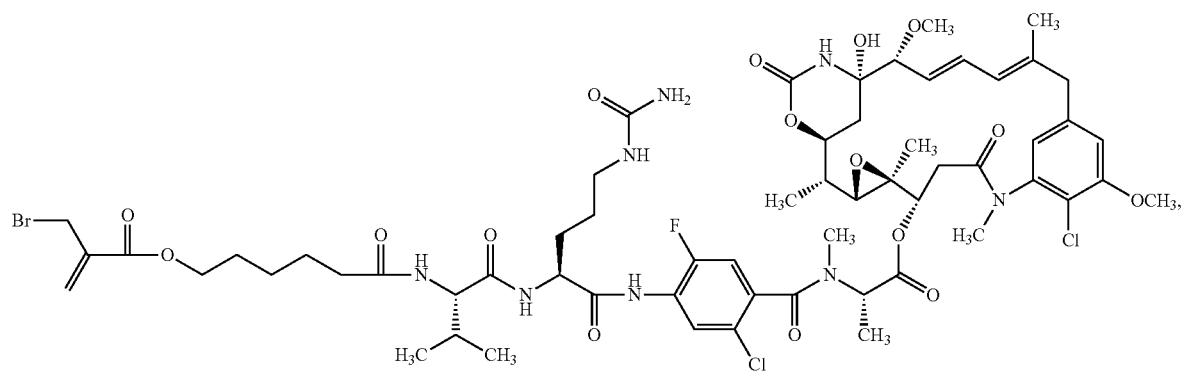
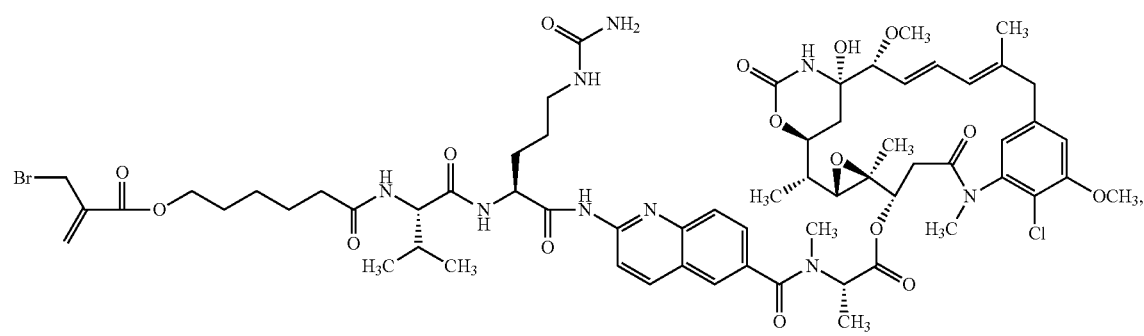
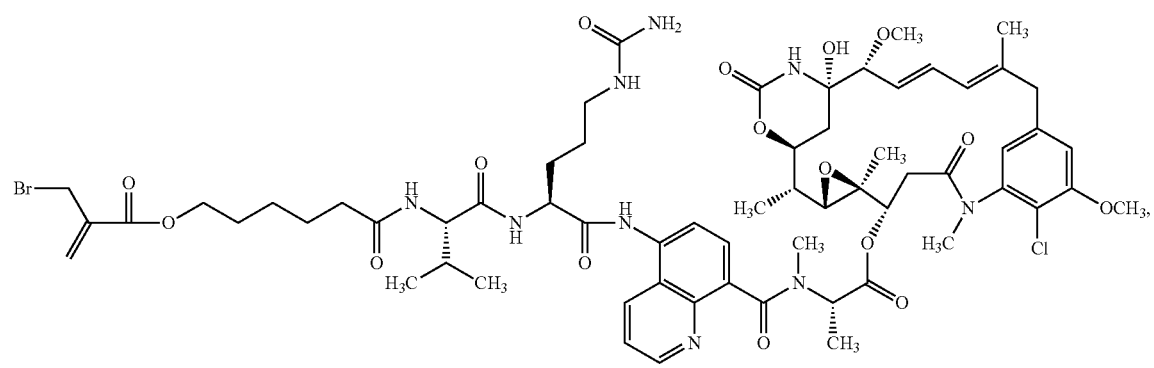

-continued
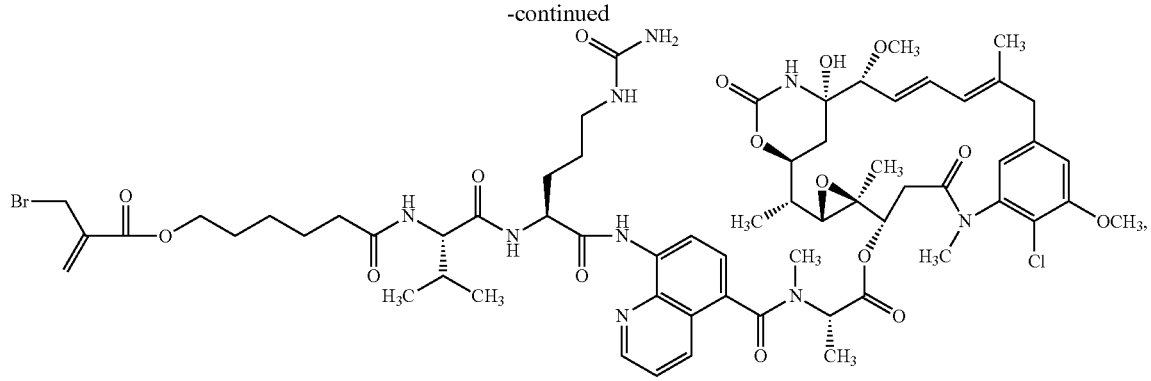
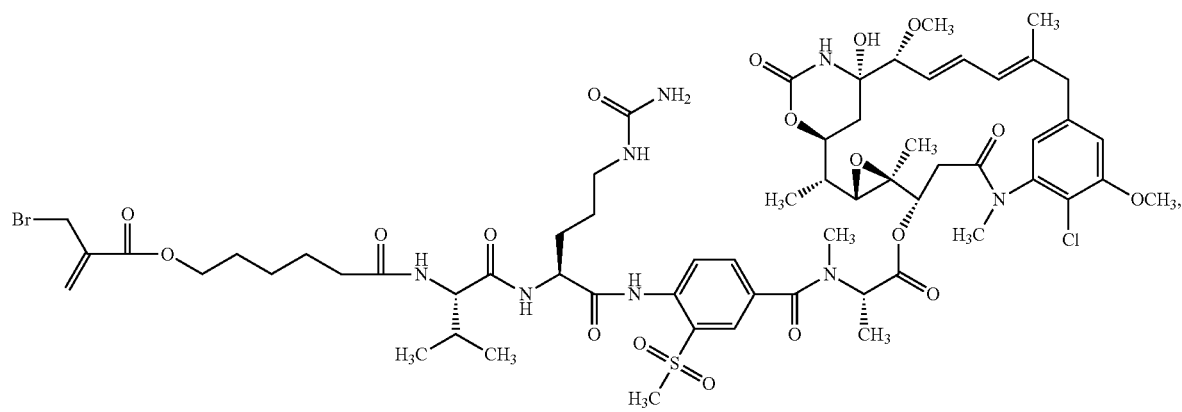
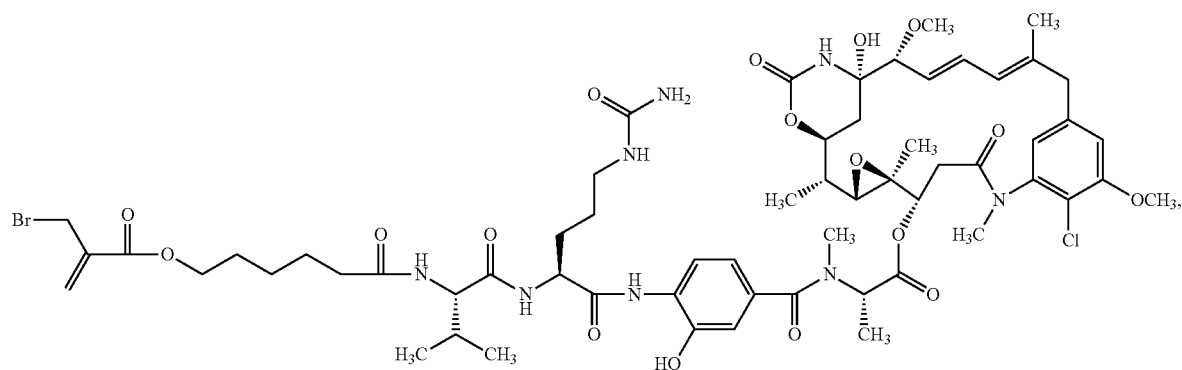
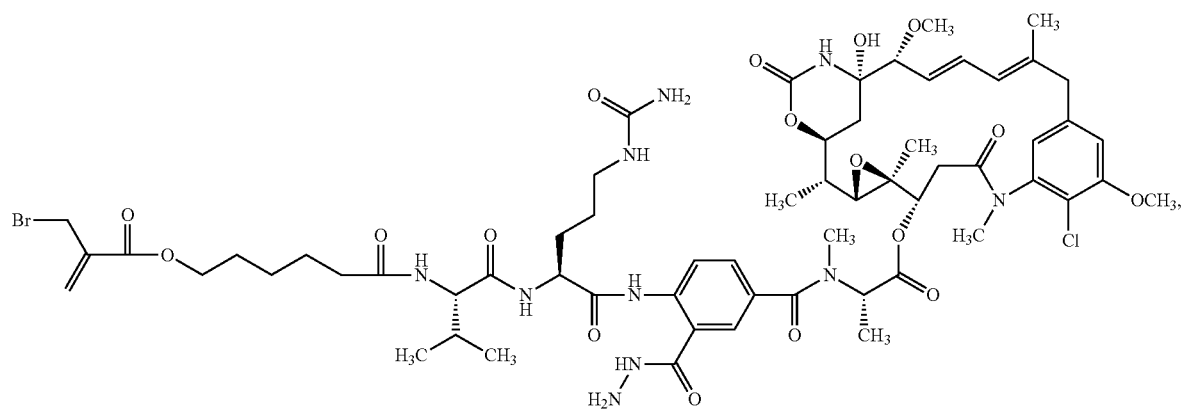

279 280
-continued
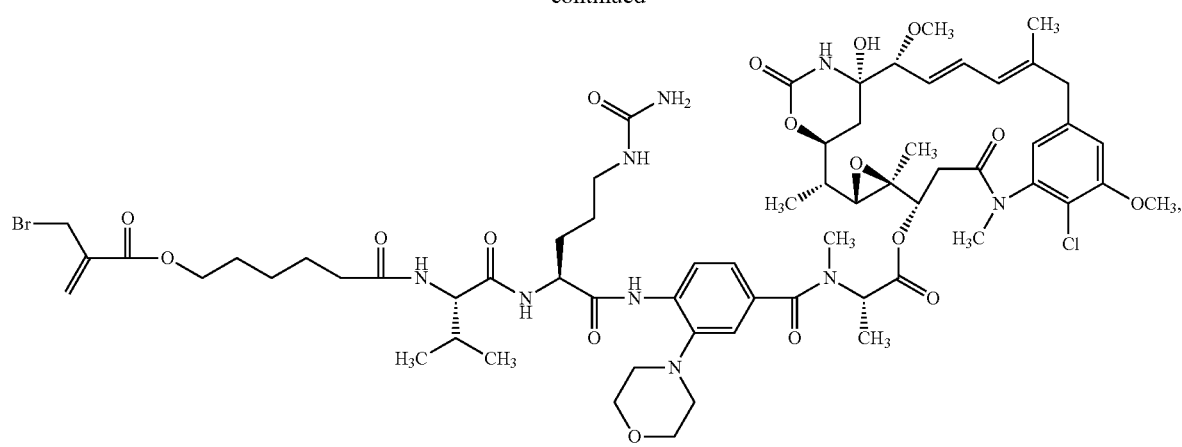
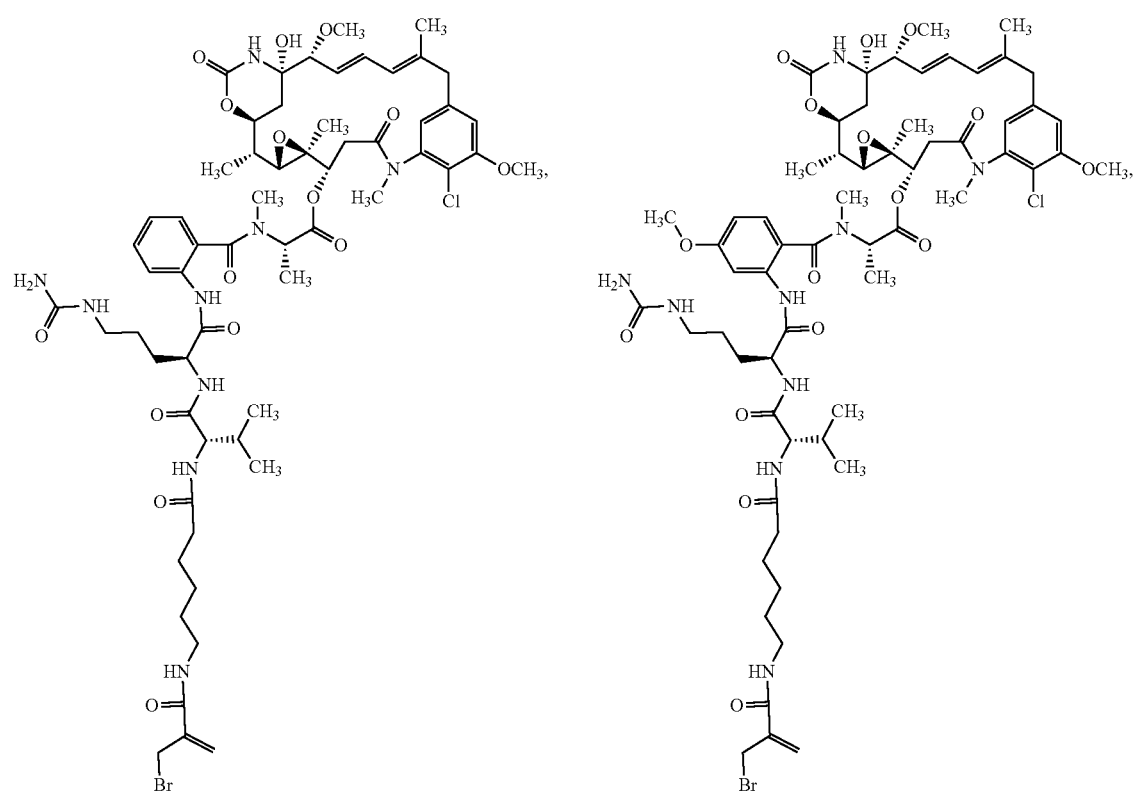
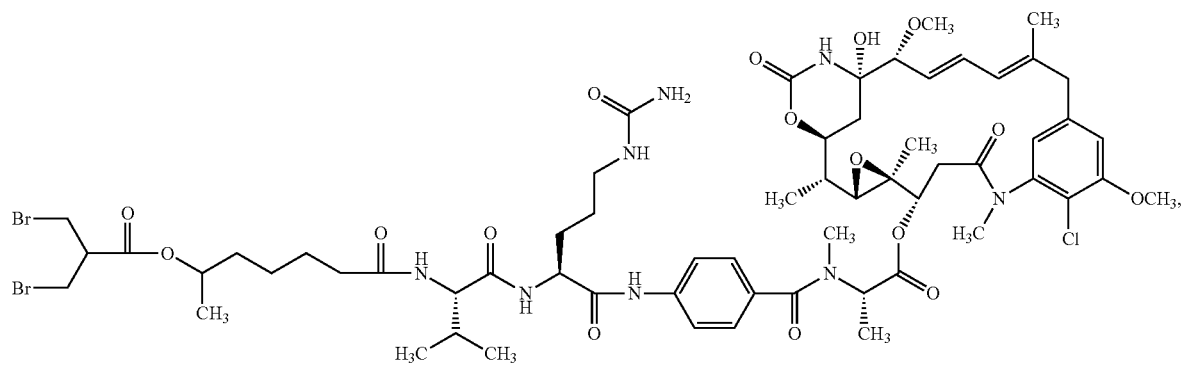 [SMILES: COc1cc2cc(c1Cl)N(C)C(=O)C[C@H](OC(=O)[C@H](C)N(C)C(=O)c1ccc(NC(=O)[C@H](CCCNC(N)=O)NC(=O)[C@@H](NC(=O)CCCCC(C)OC(=O)C(CBr)CBr)C(C)C)cc1)[C@]1(C)O[C@H]1[C@H](C)[C@@H]1C[C@@](O)(NC(=O)O1)[C@H](OC)/C=C/C=C(\C)C2]

281 282
-continued
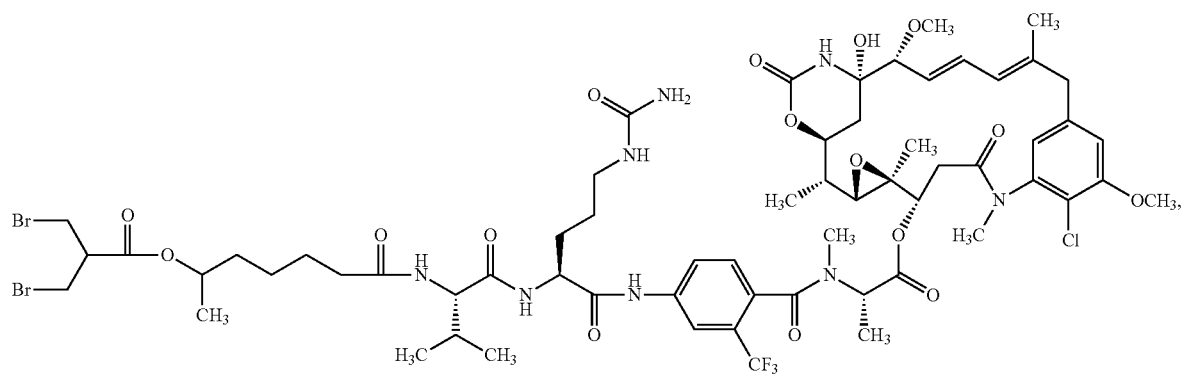
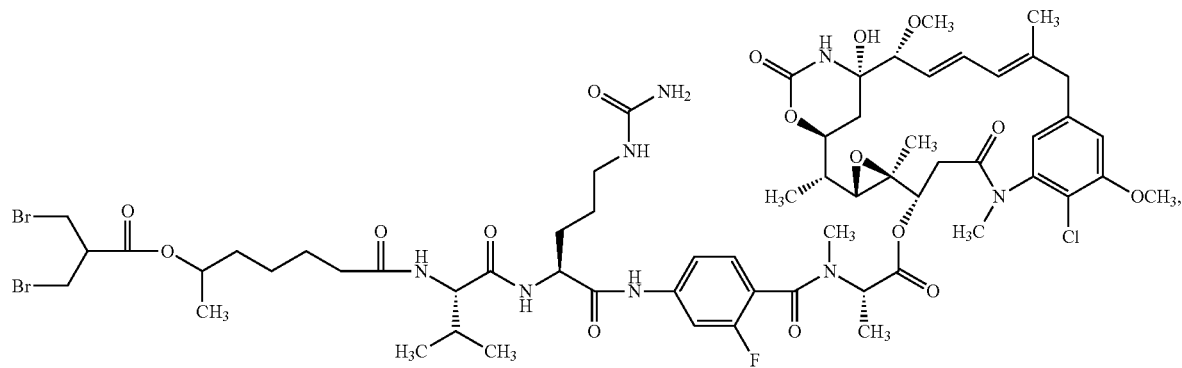
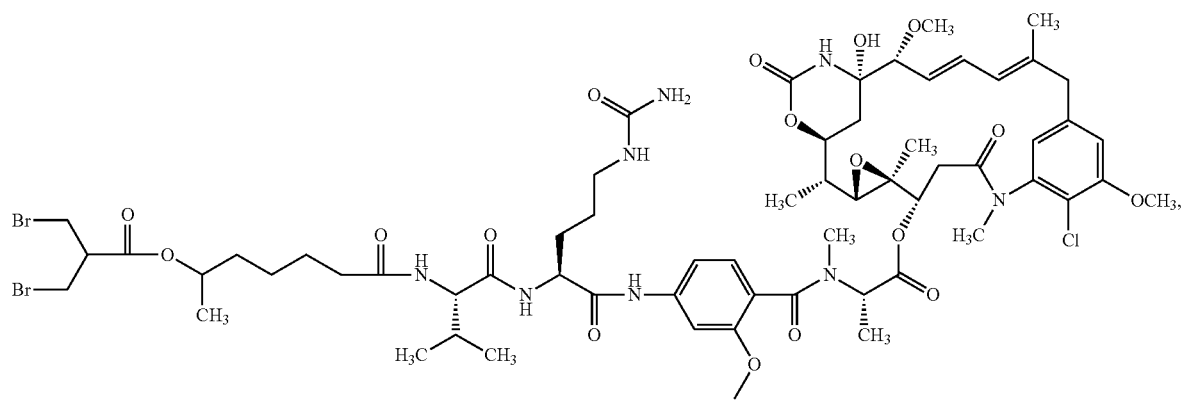
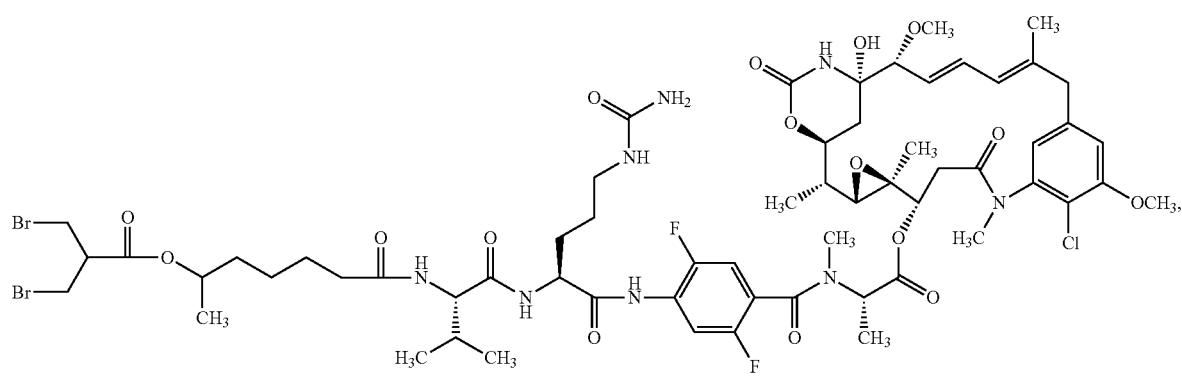

283  284
-continued
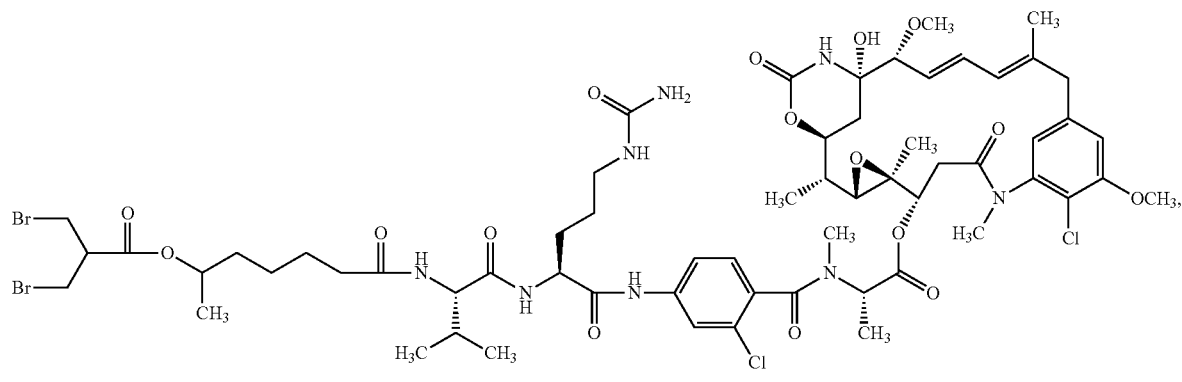
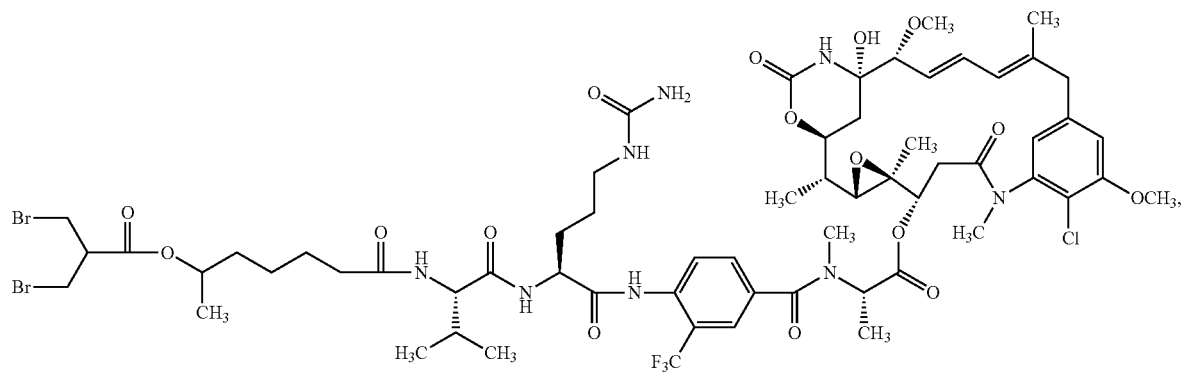
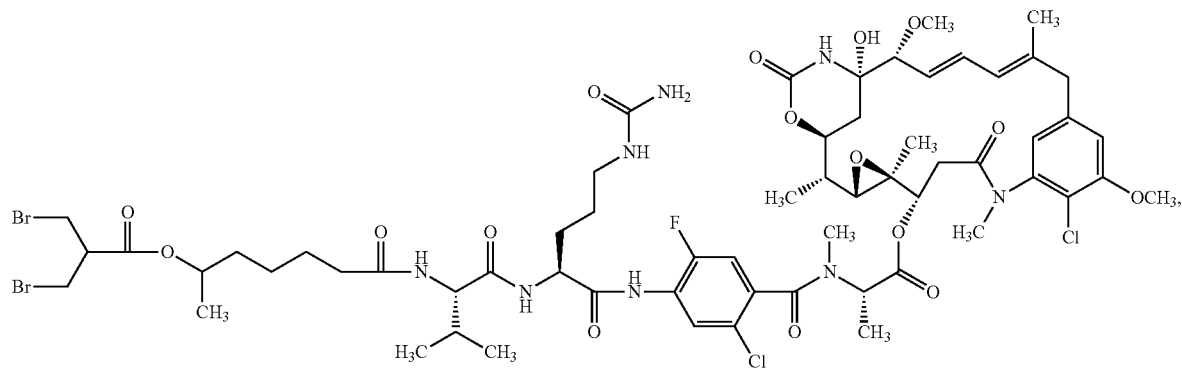
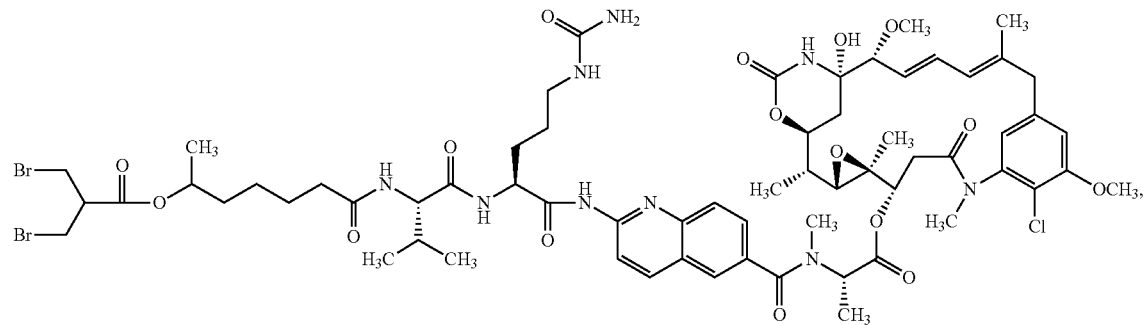

-continued
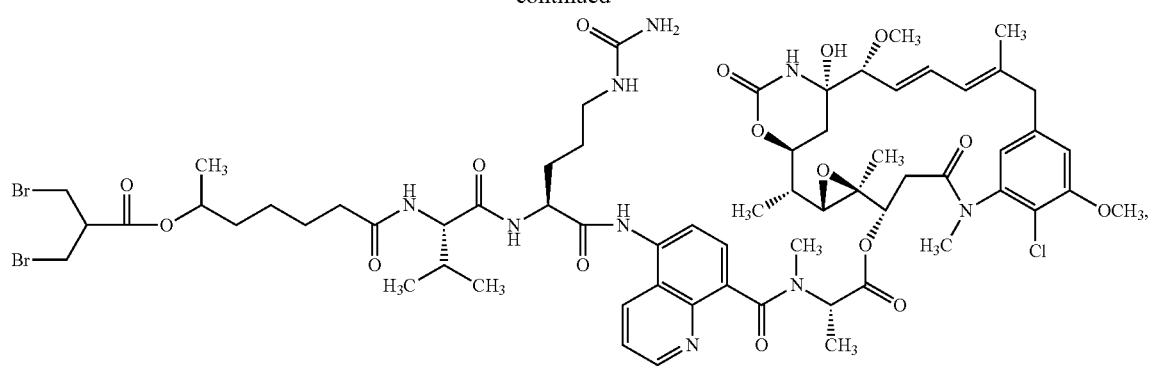
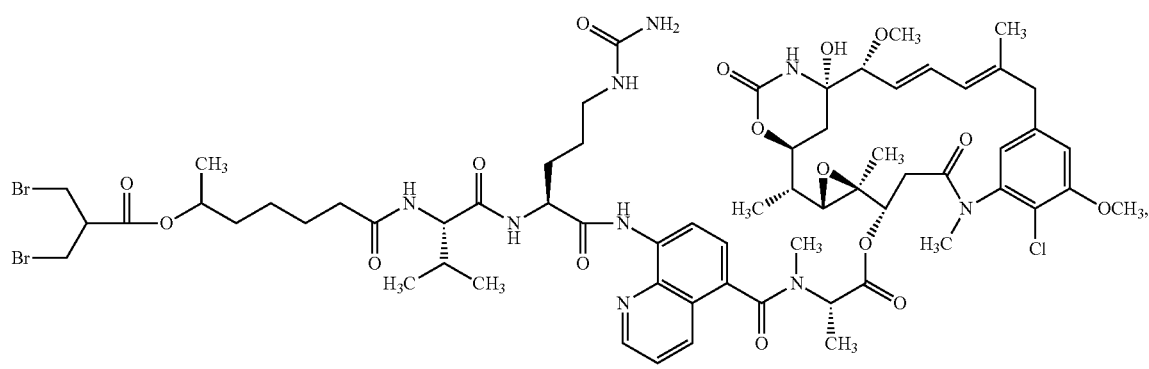
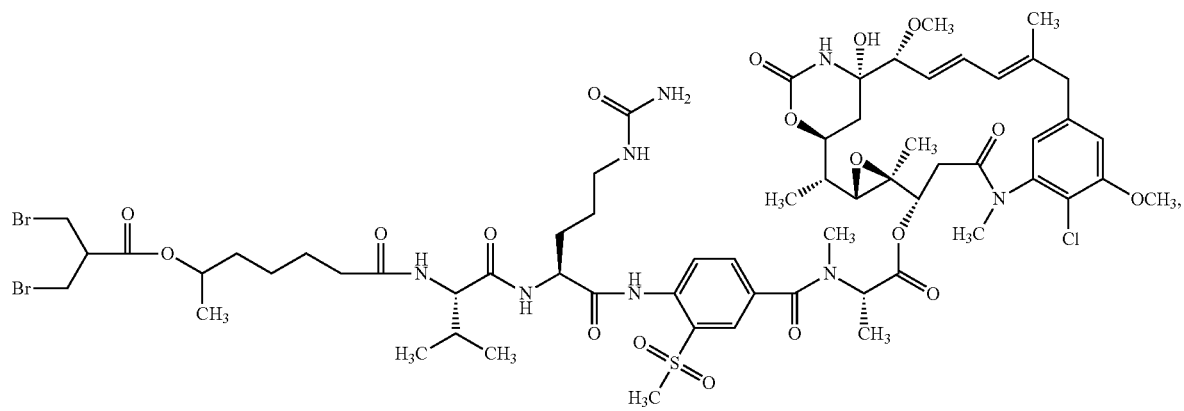
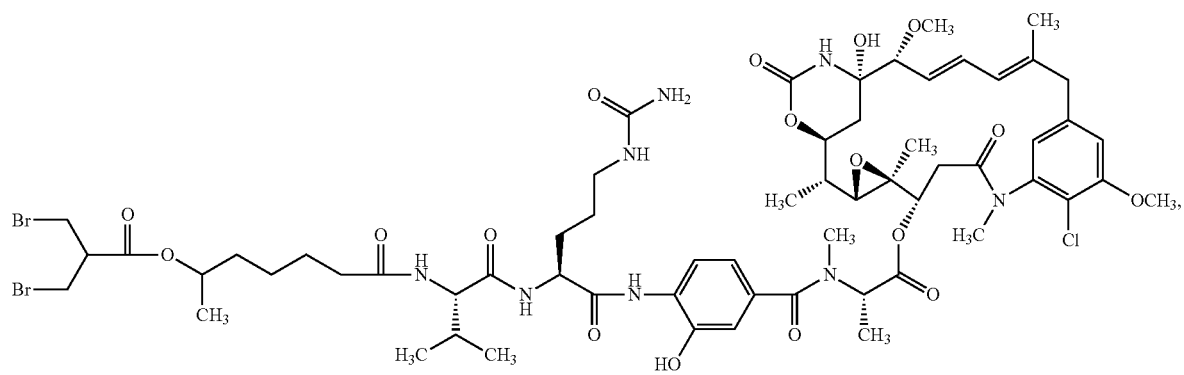

287
288
-continued
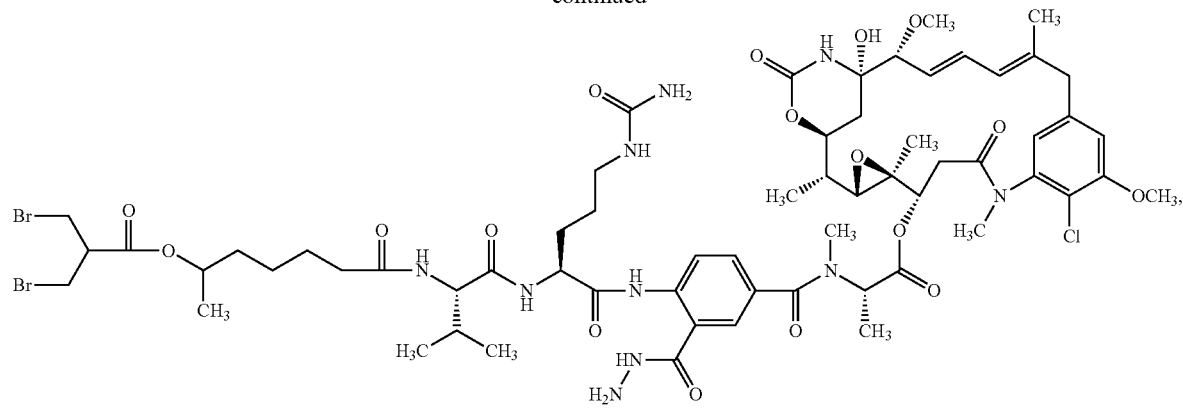
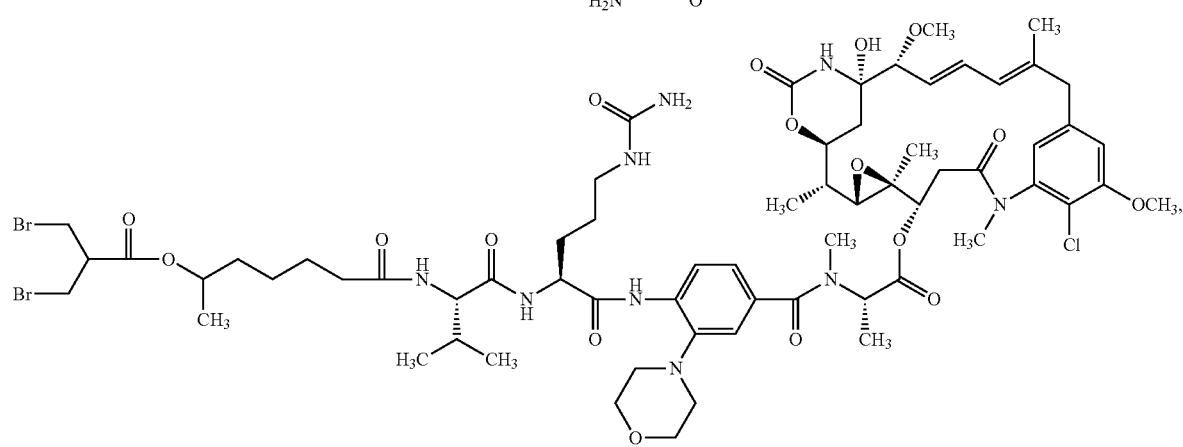
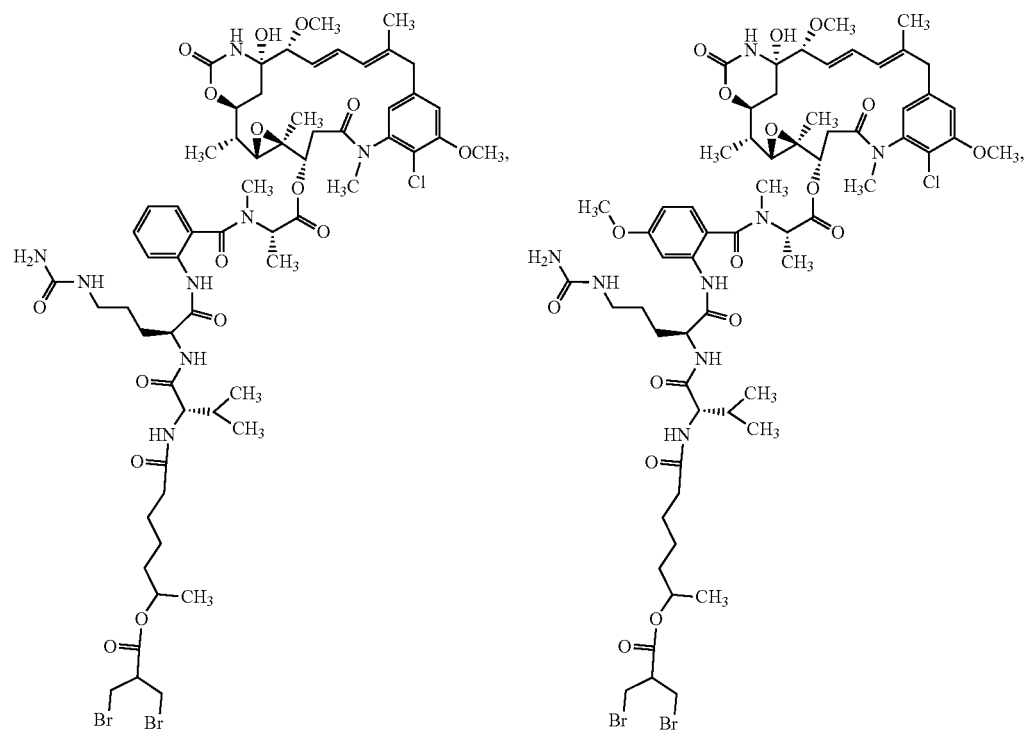

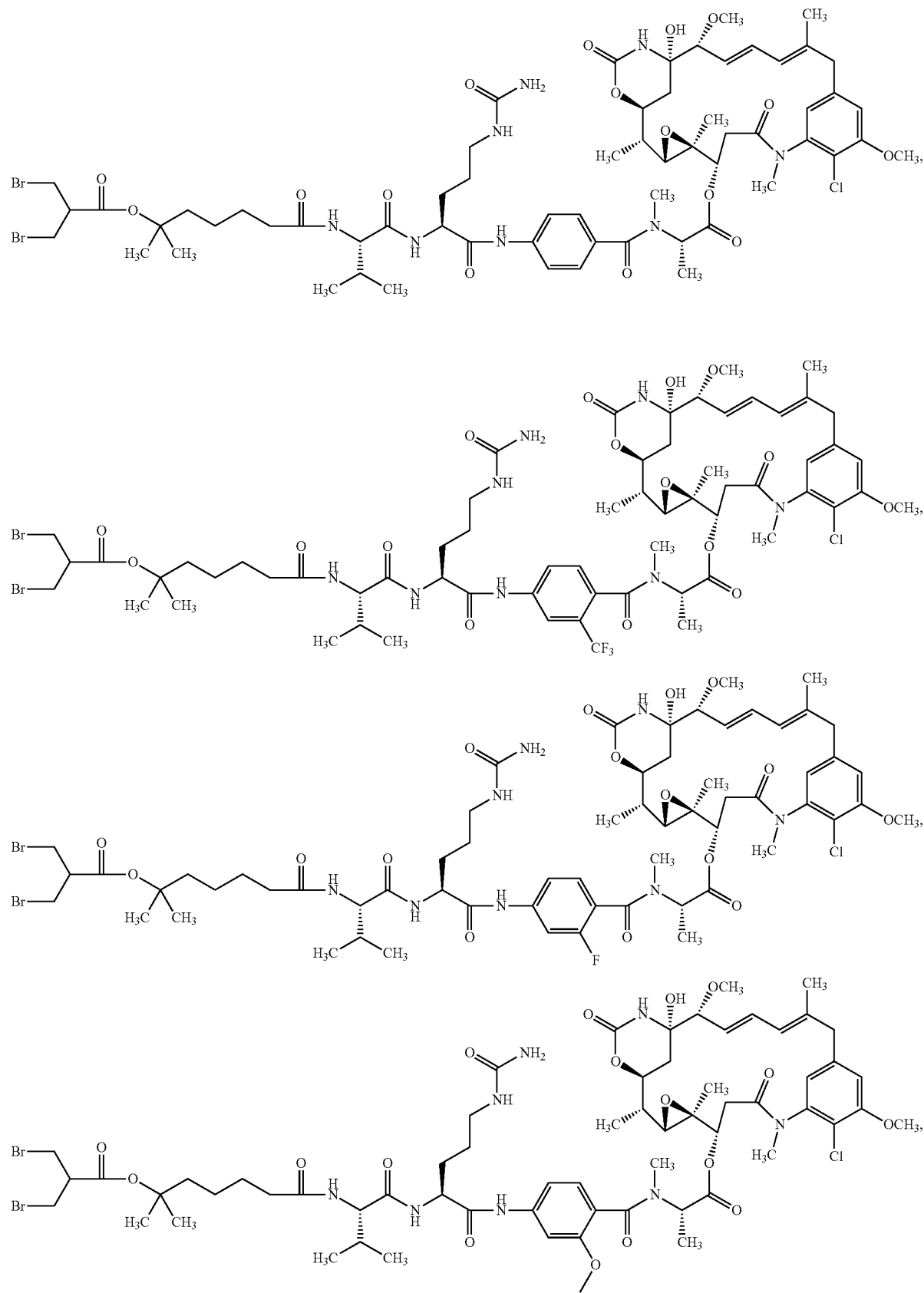

291 292
-continued
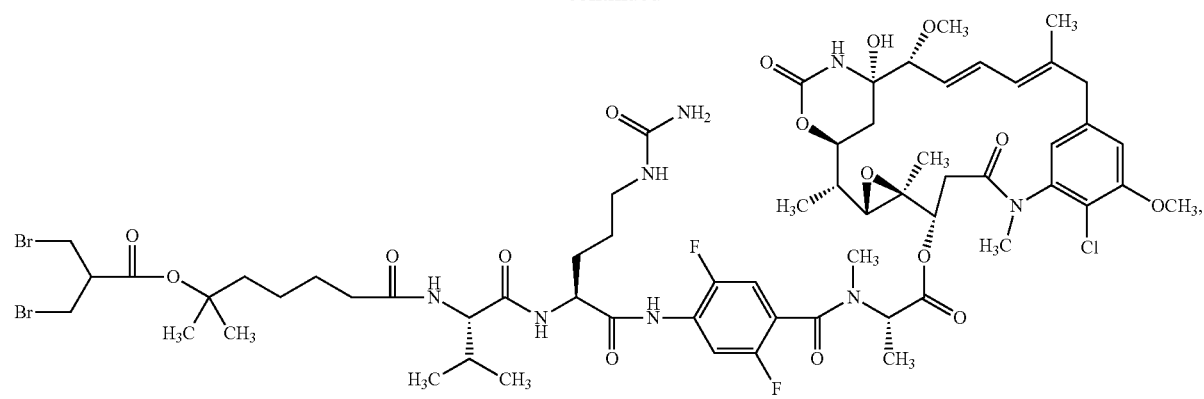
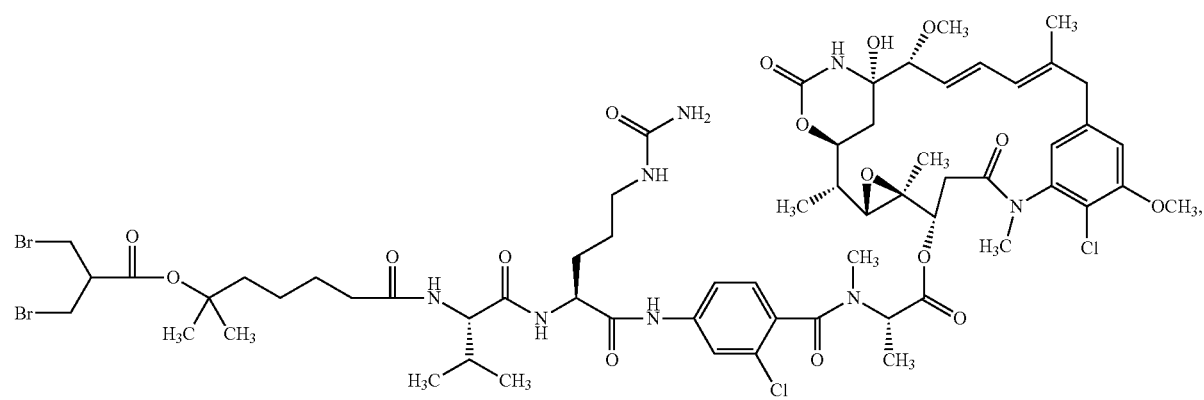
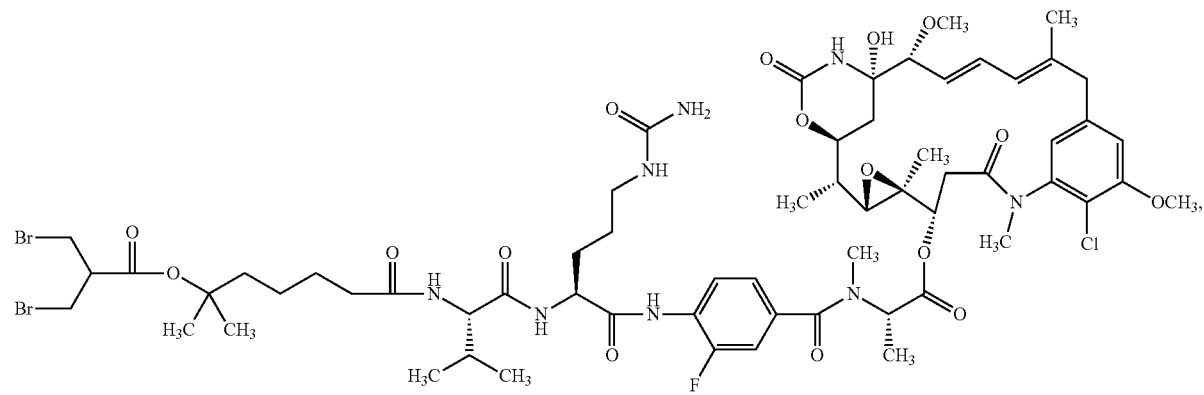
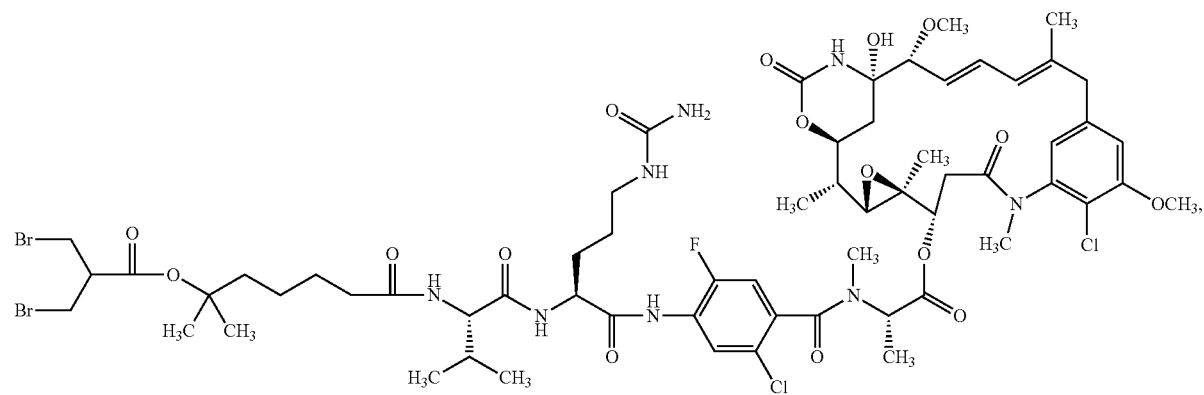

293 294
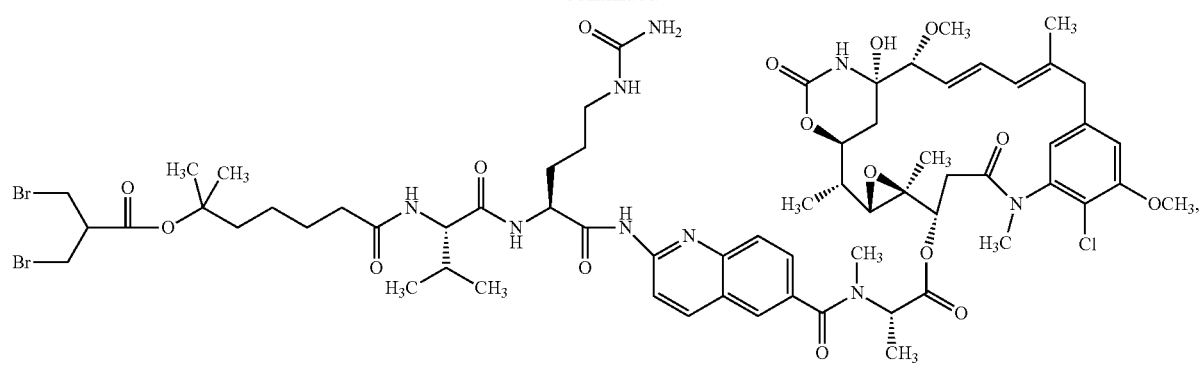
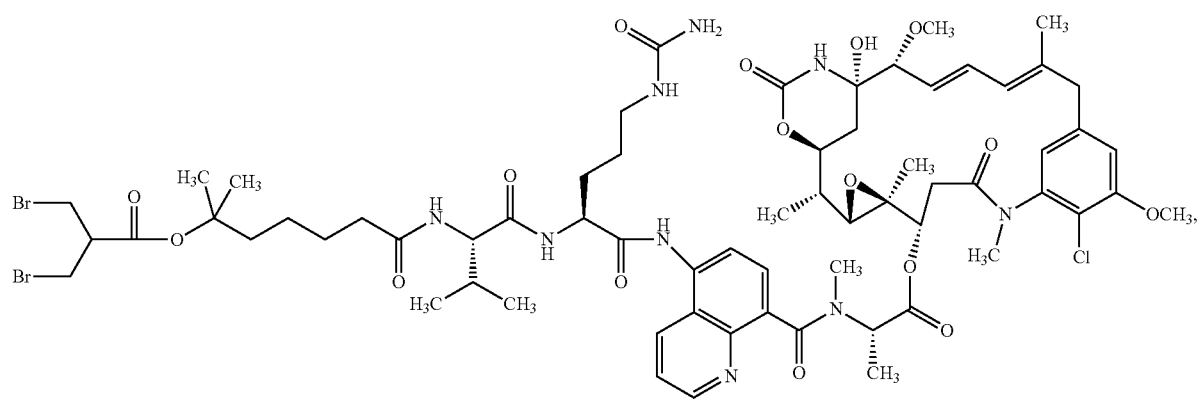
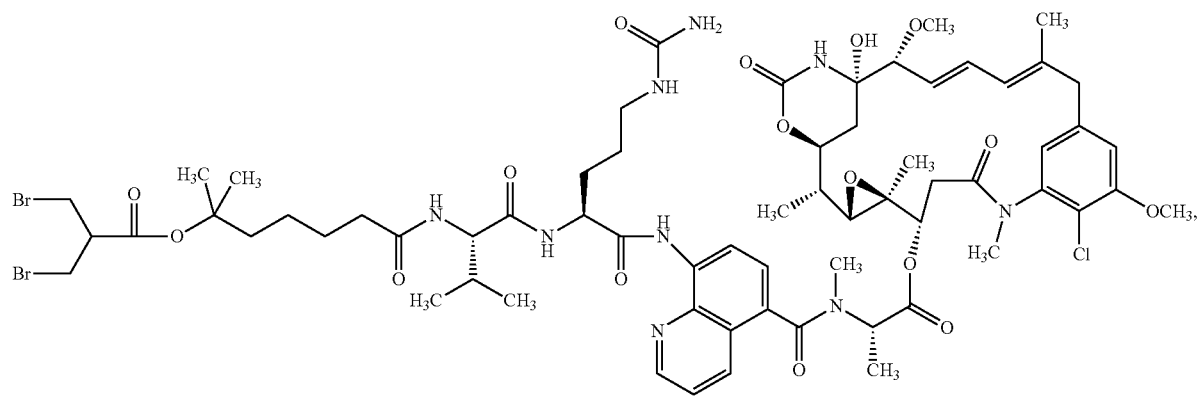
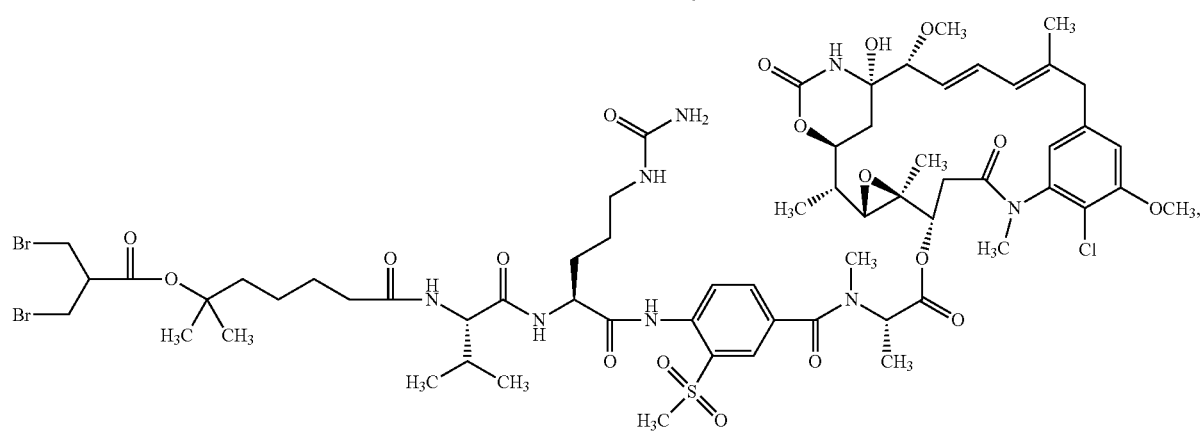

295
296
-continued
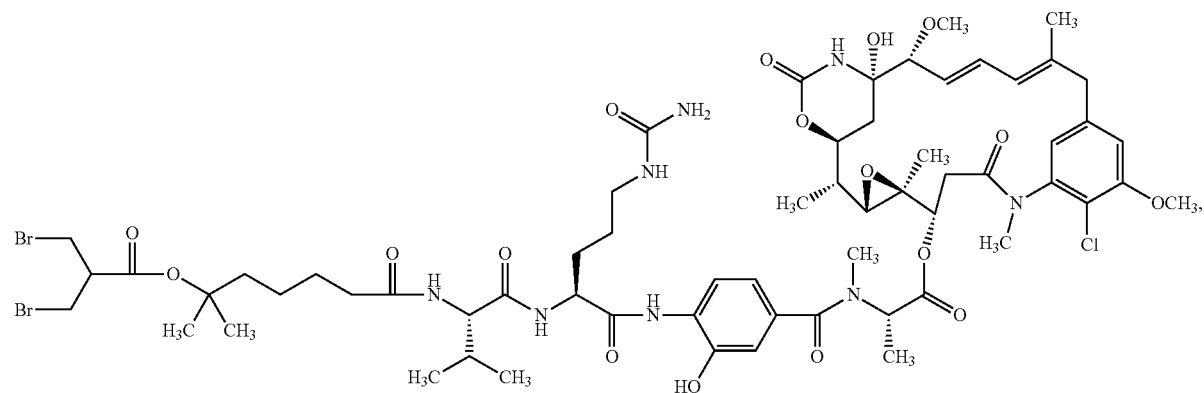
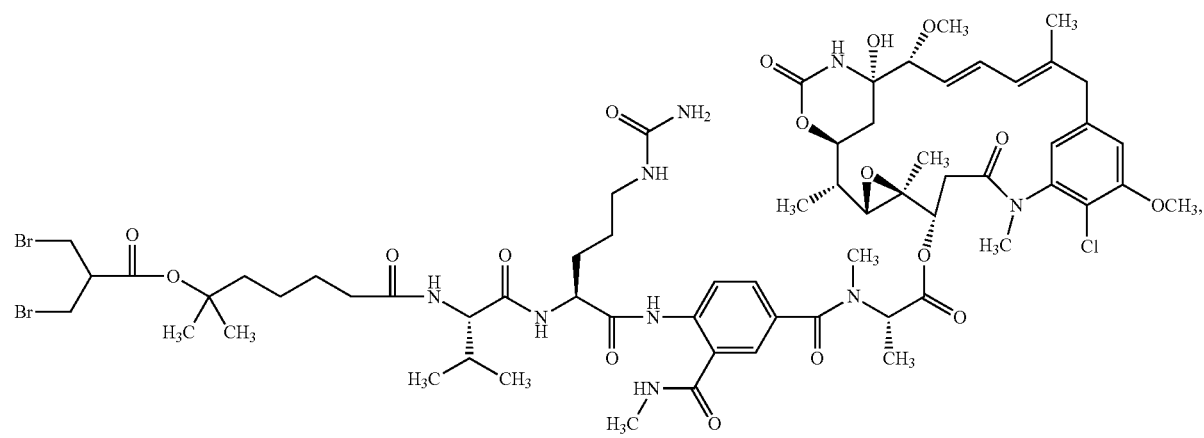
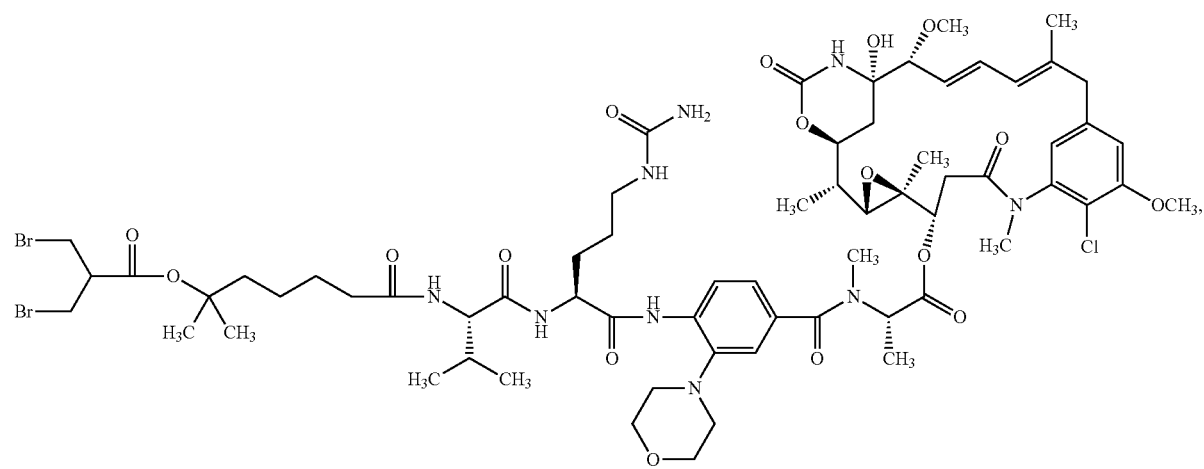

297
298
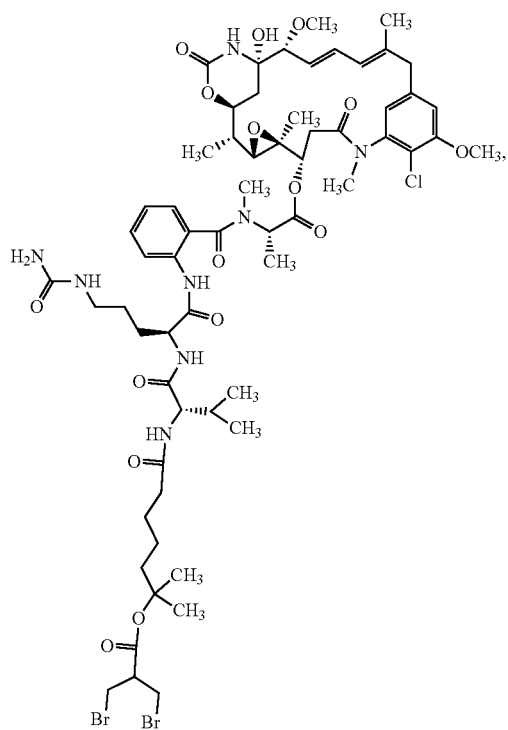
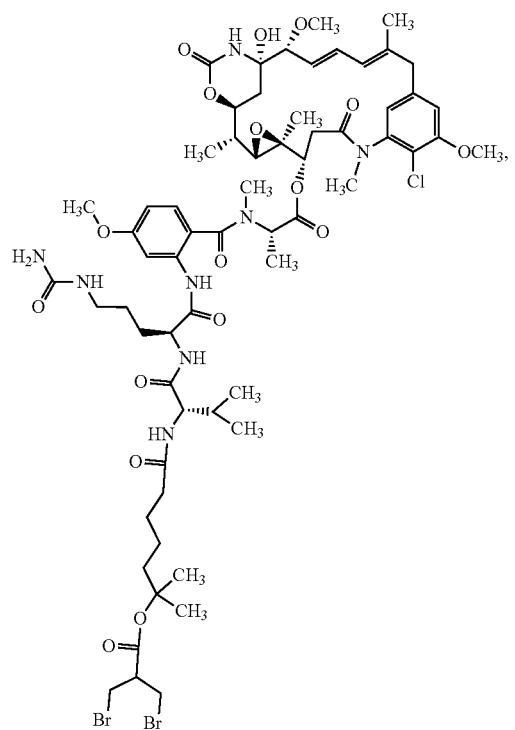
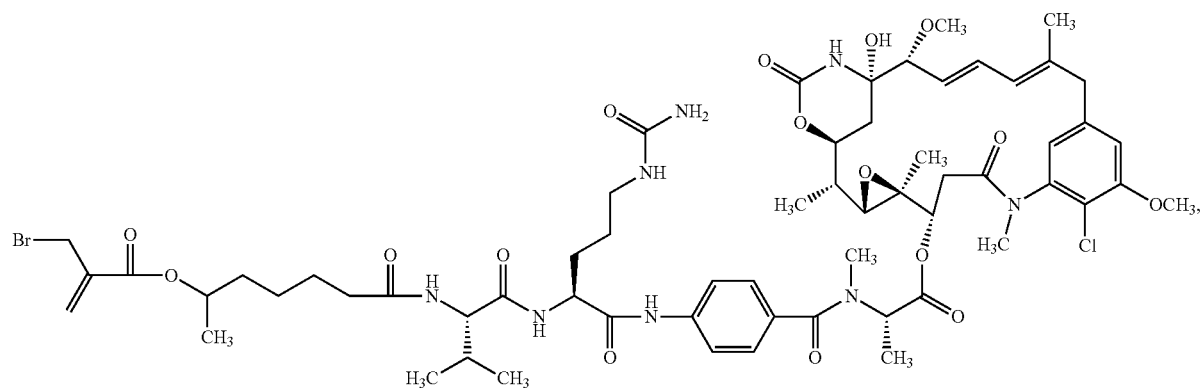
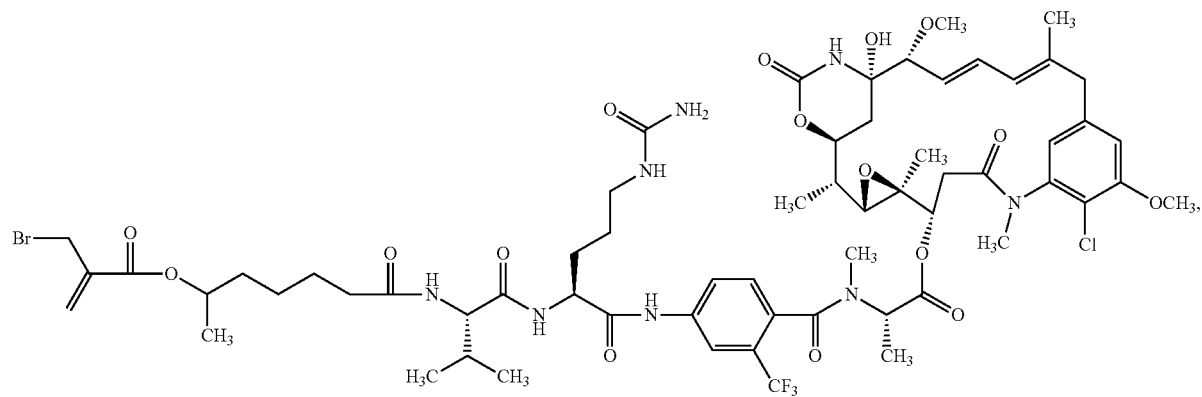

-continued
299
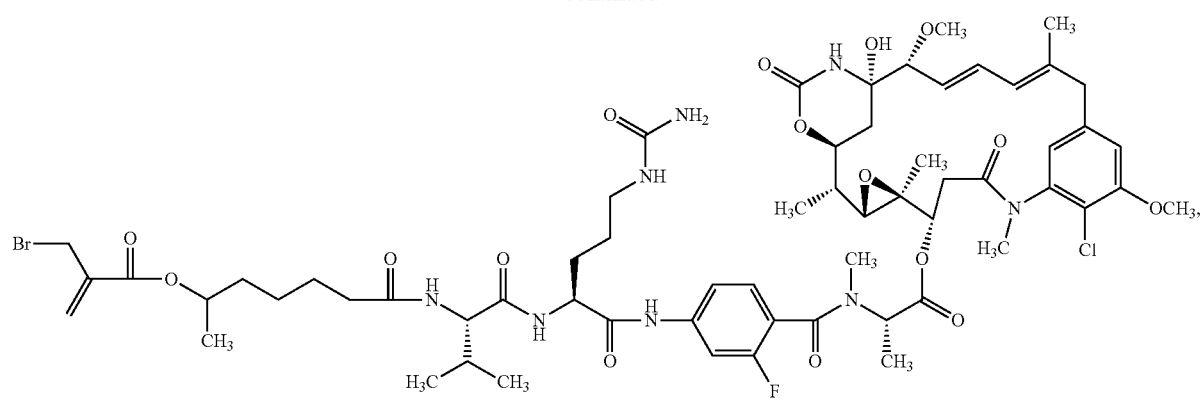
300
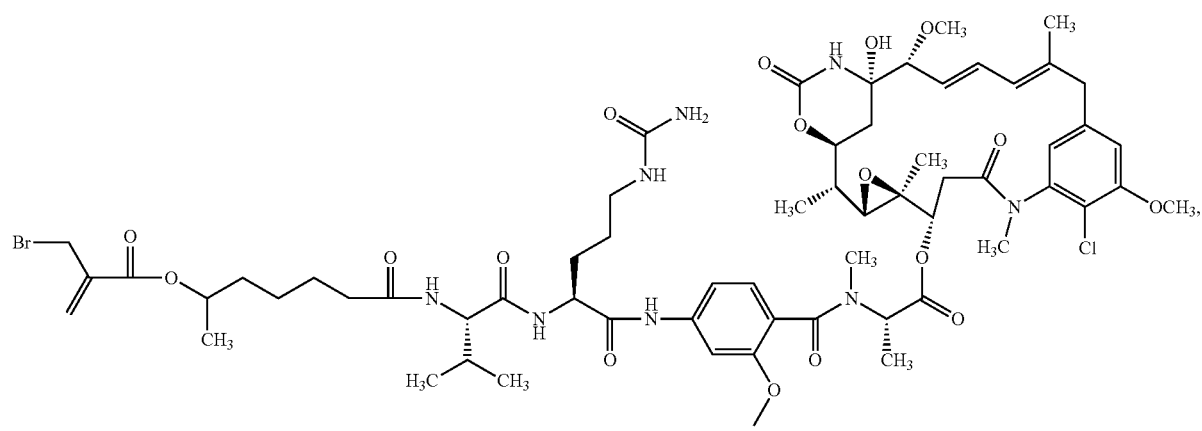
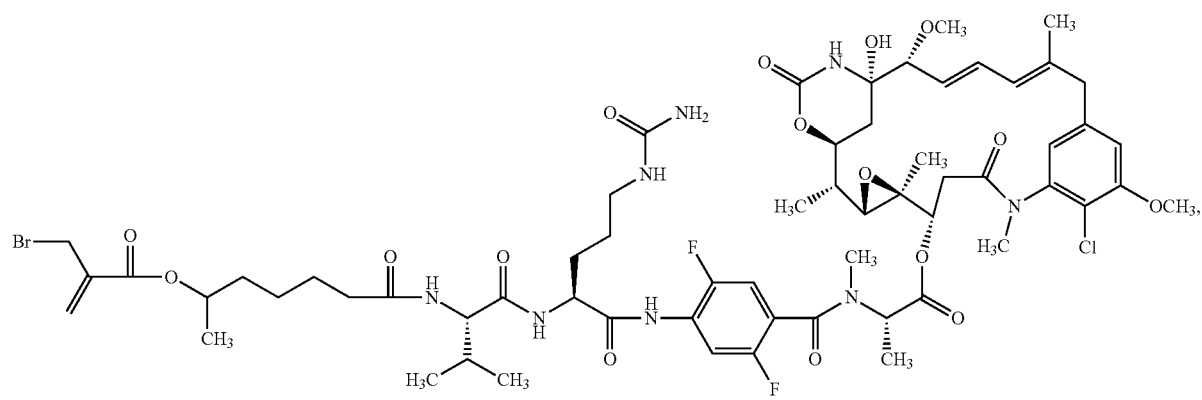
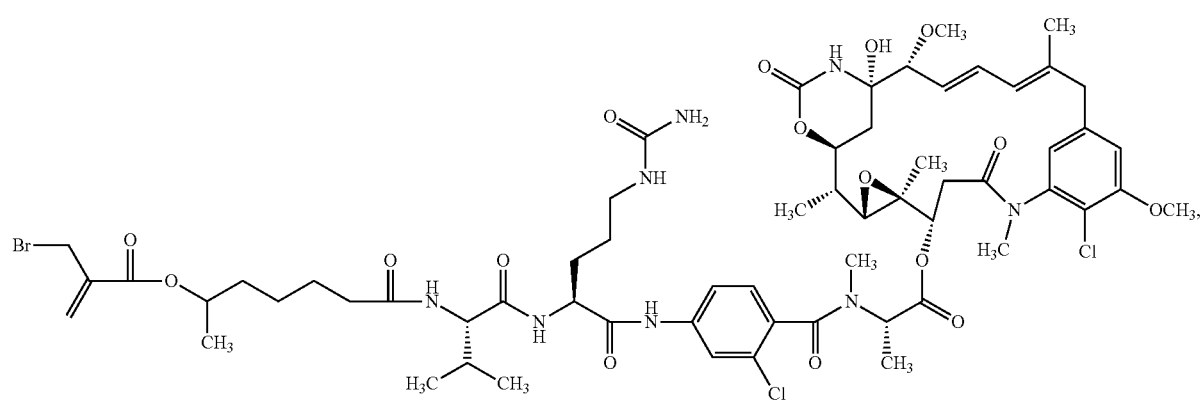

-continued
301 302
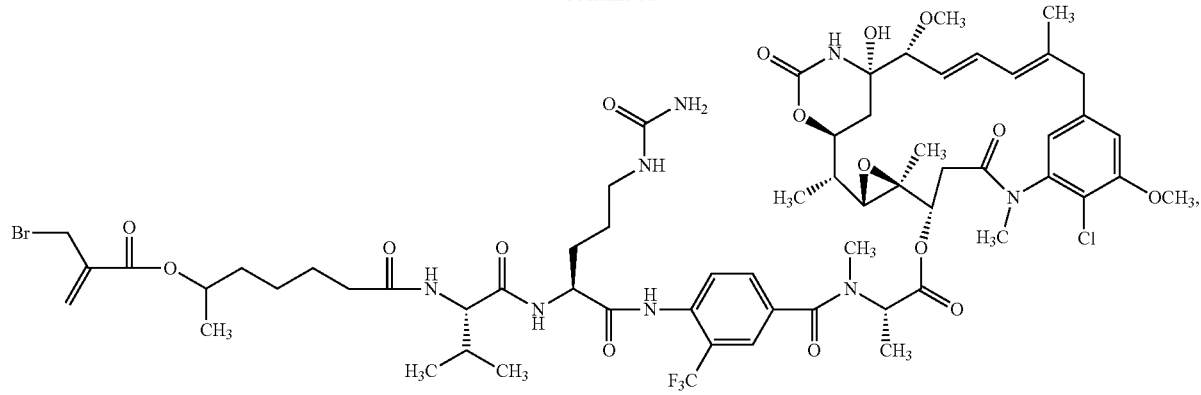
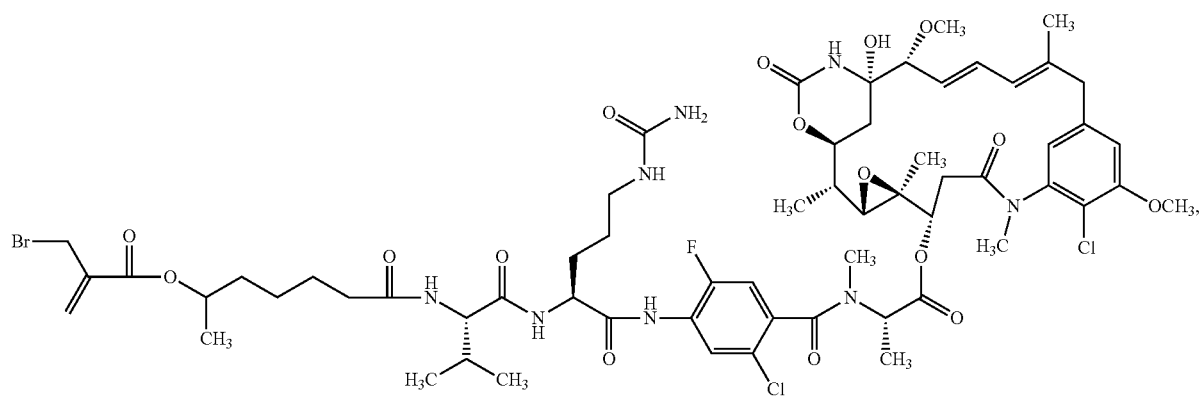
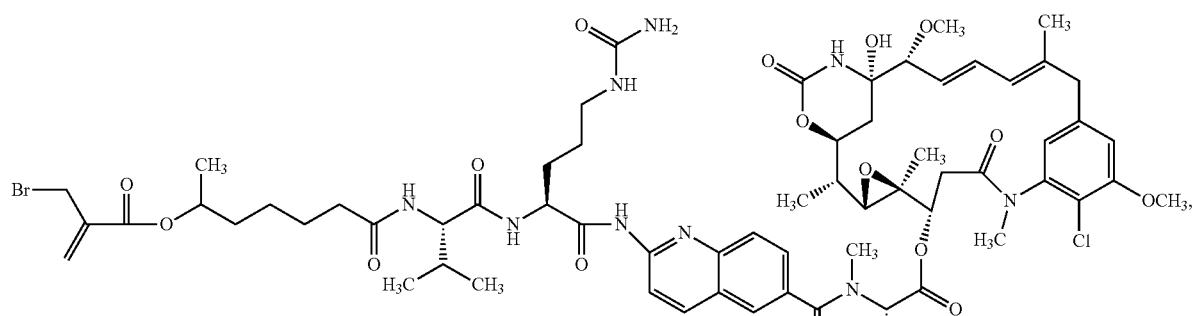
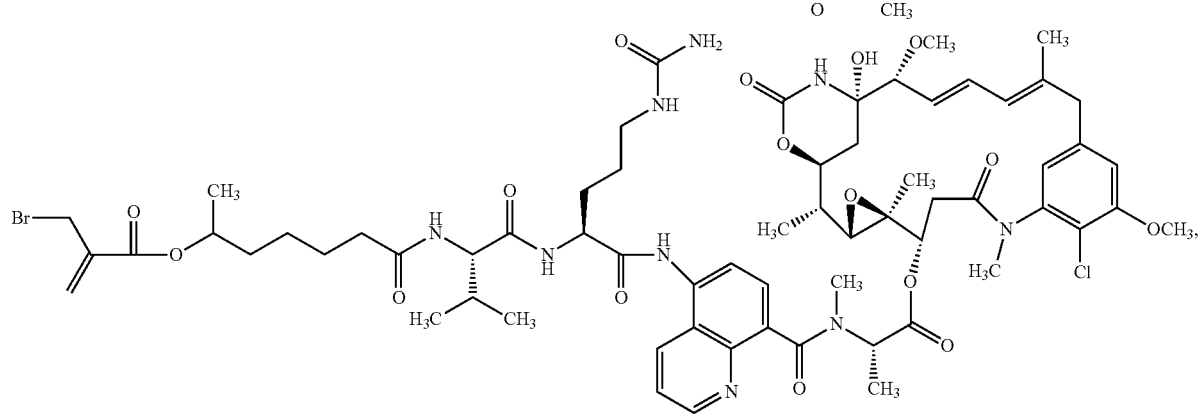

303
304
-continued
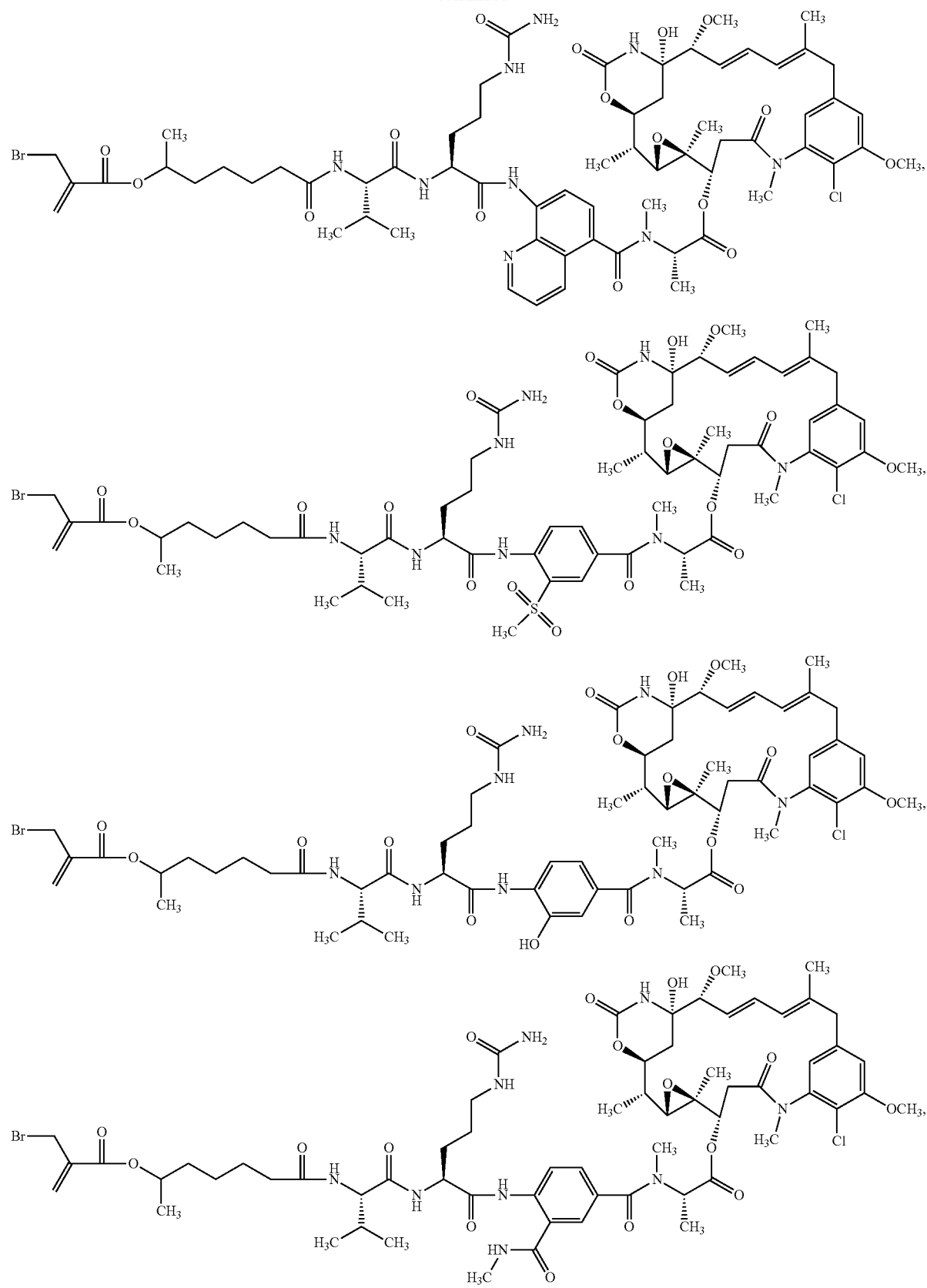

305
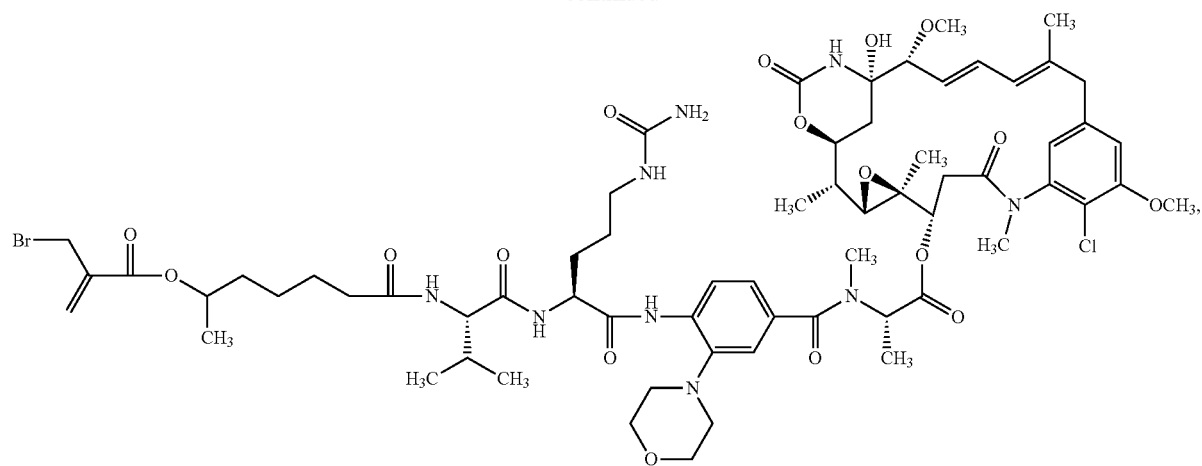
306
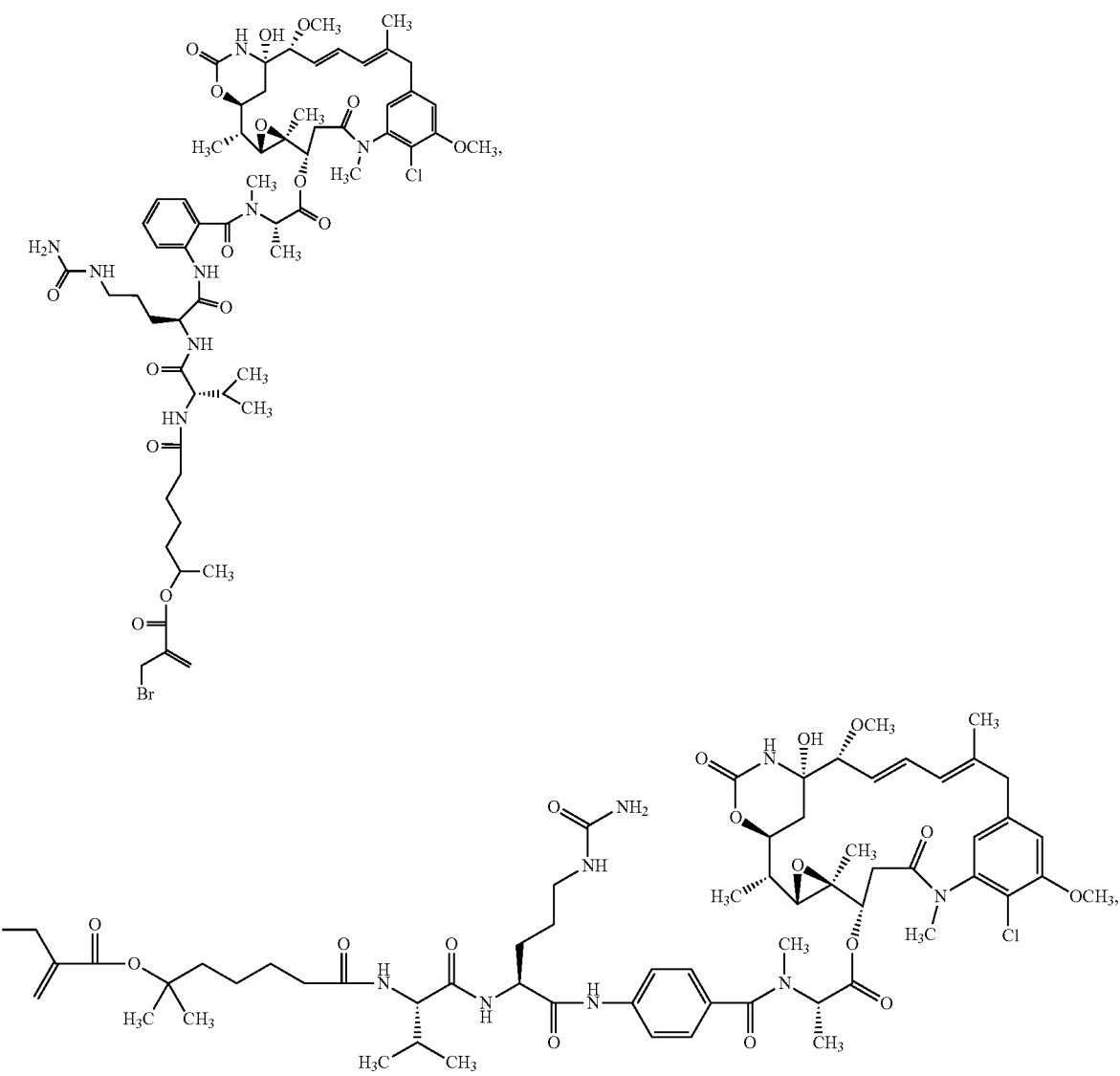

307
308
-continued
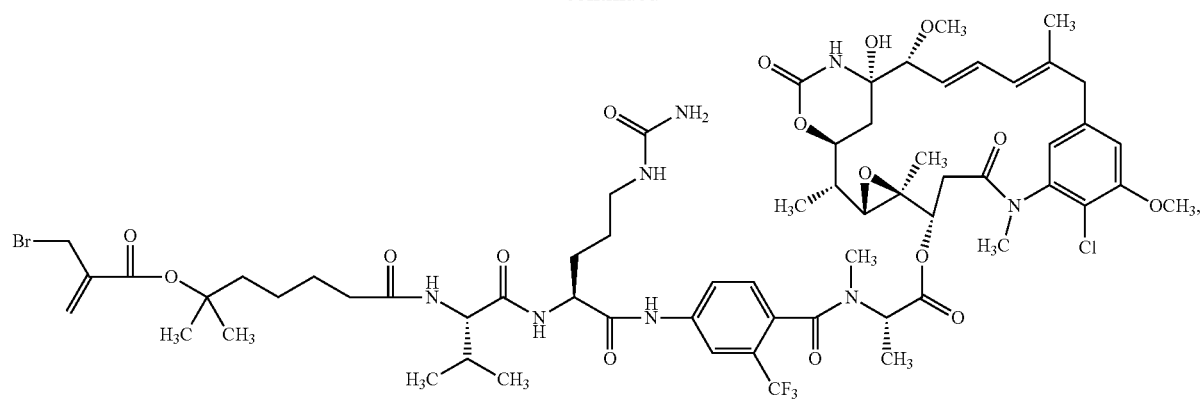
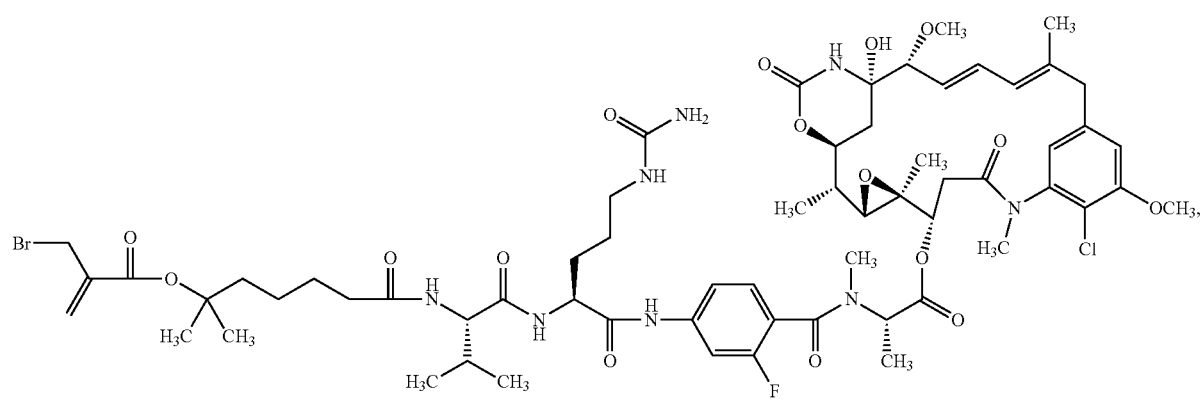
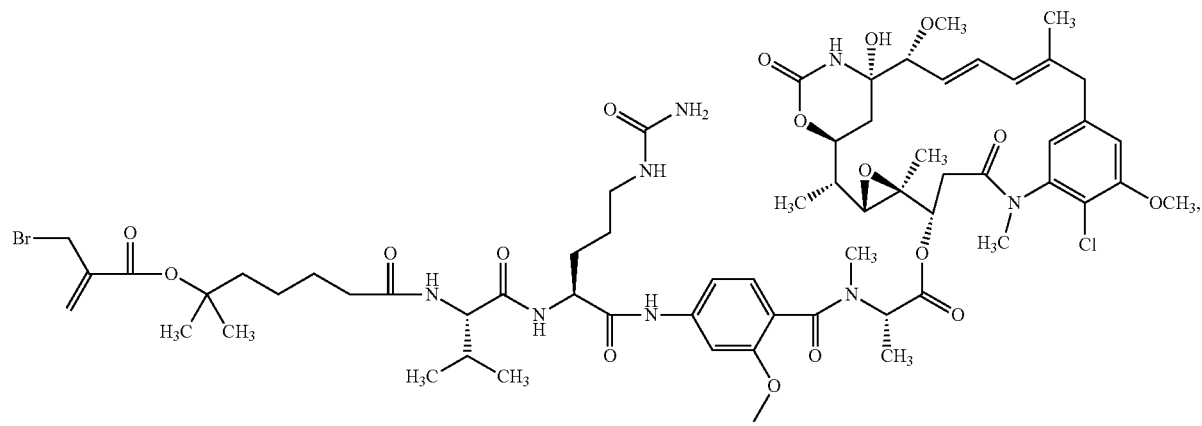
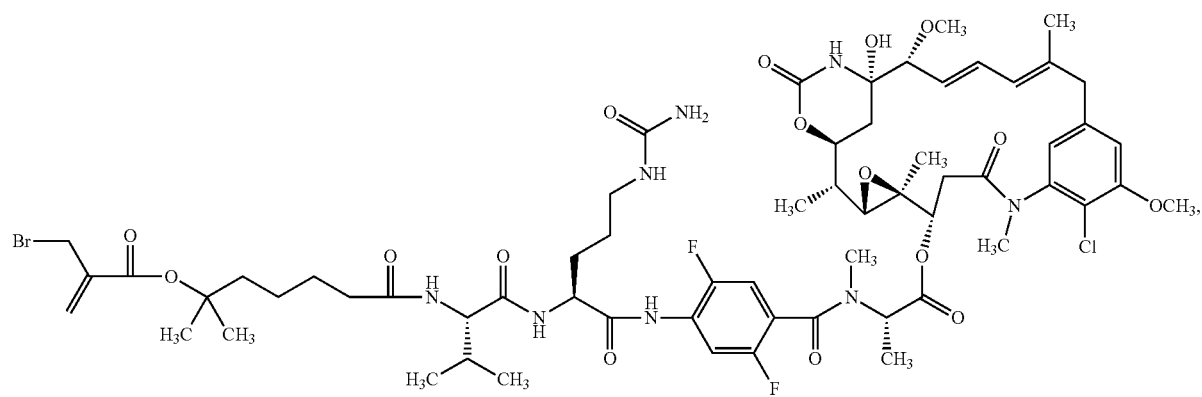

309
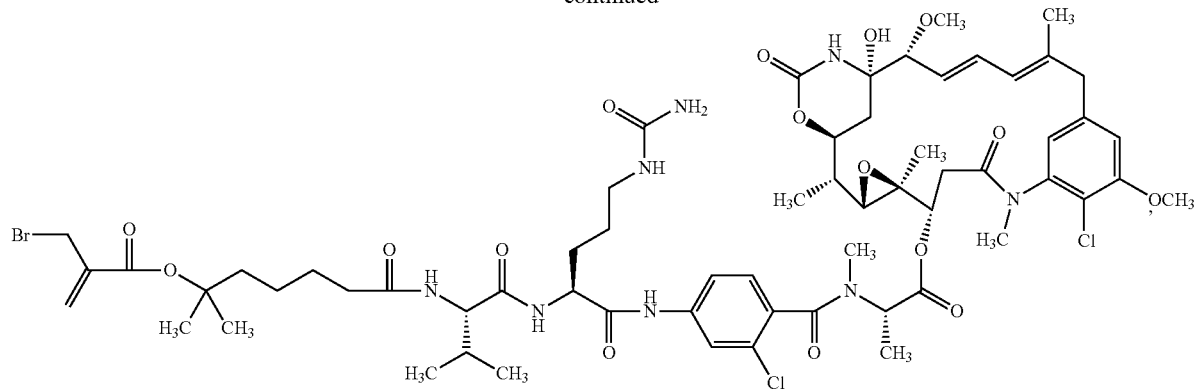
-continued
310
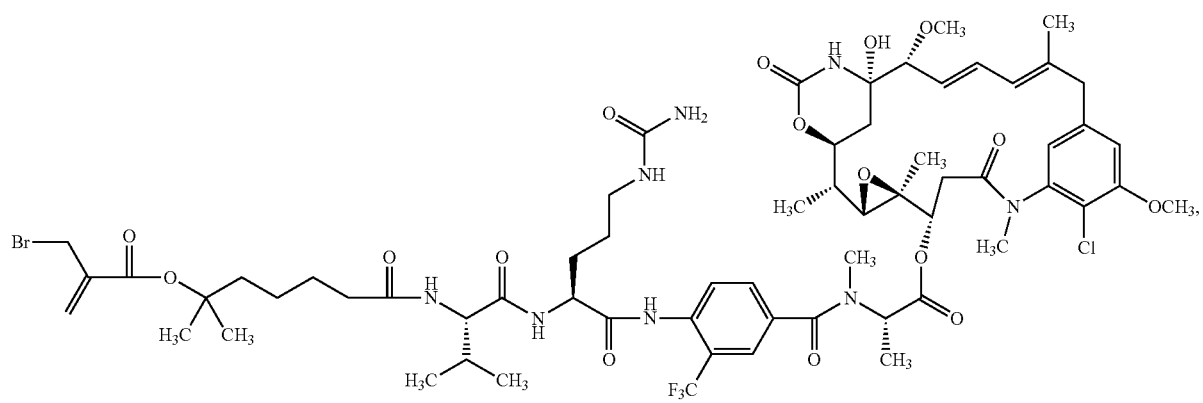
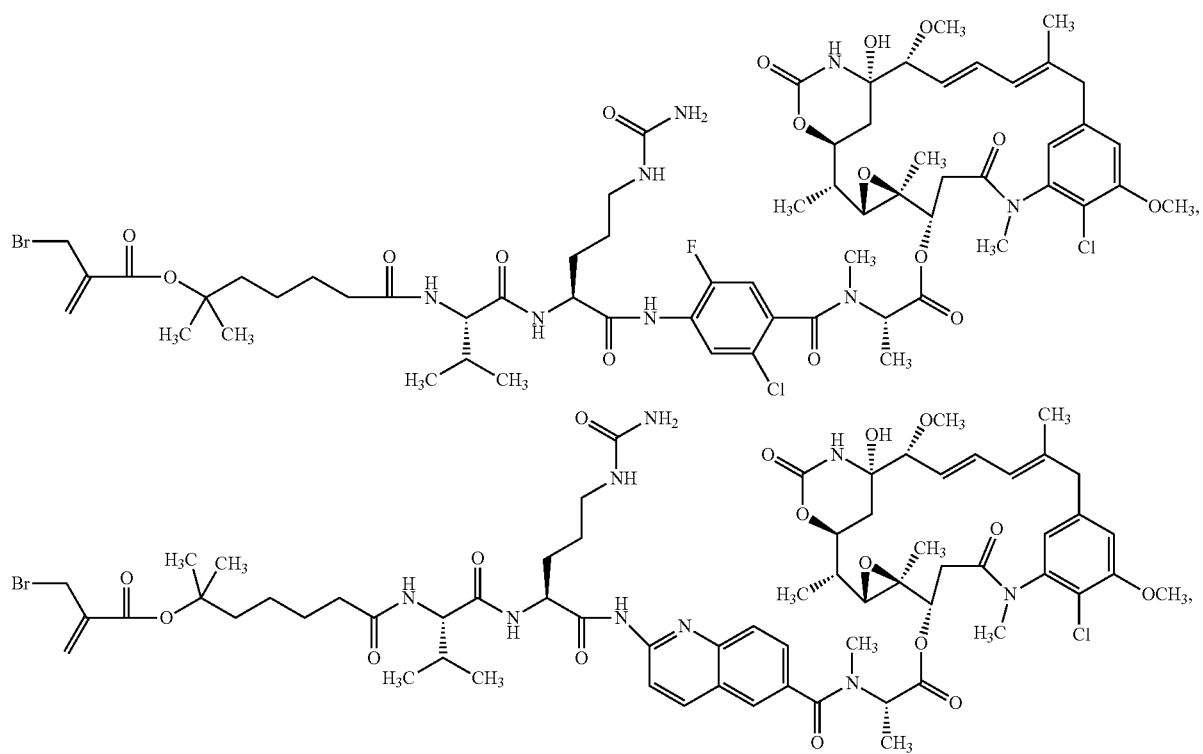

311                                                                 312
-continued
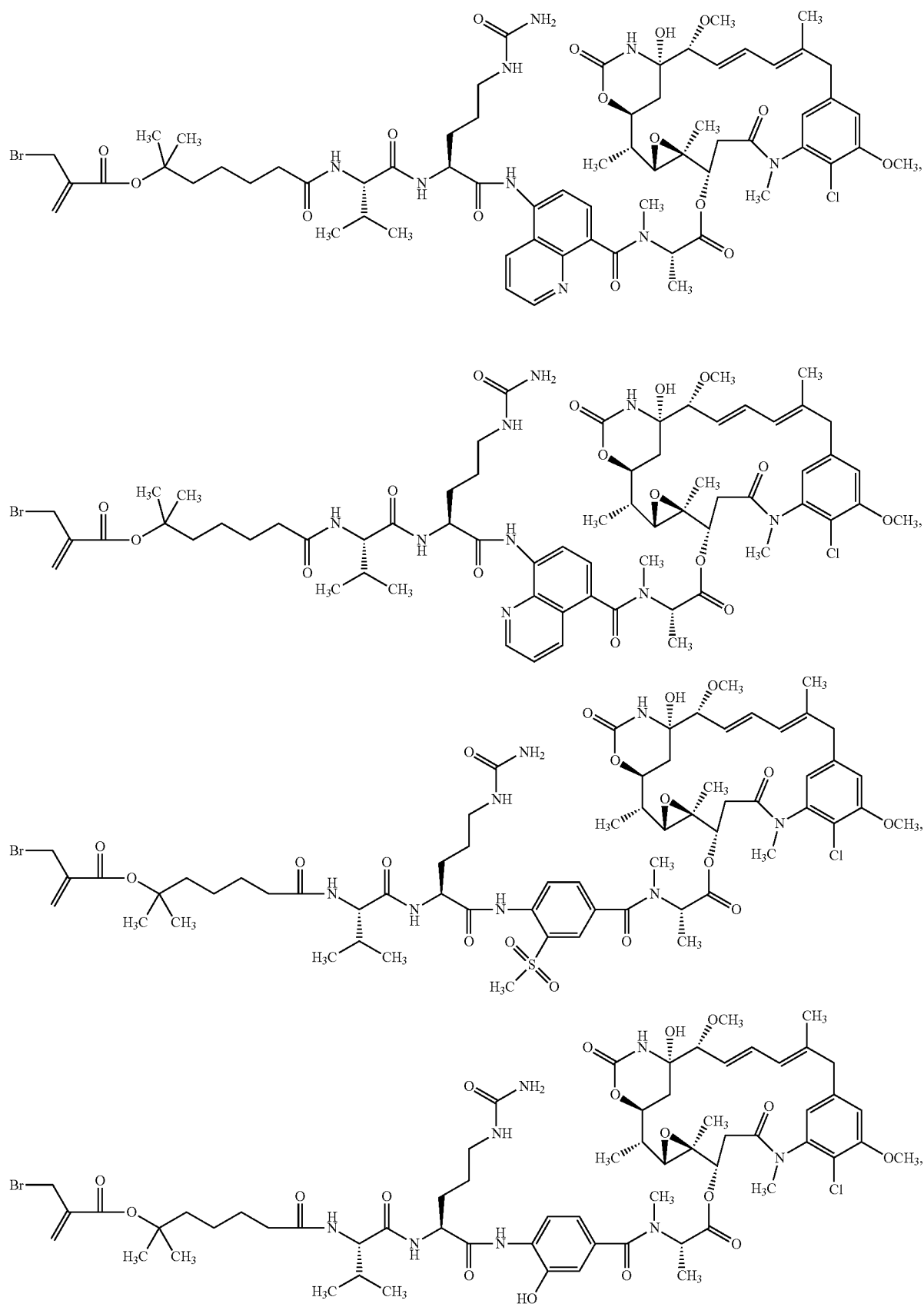

313
-continued
314
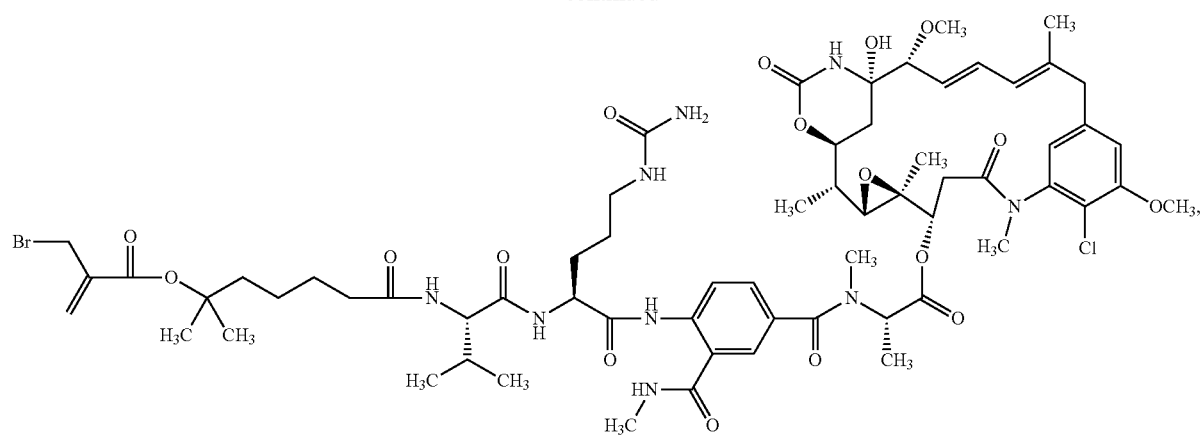
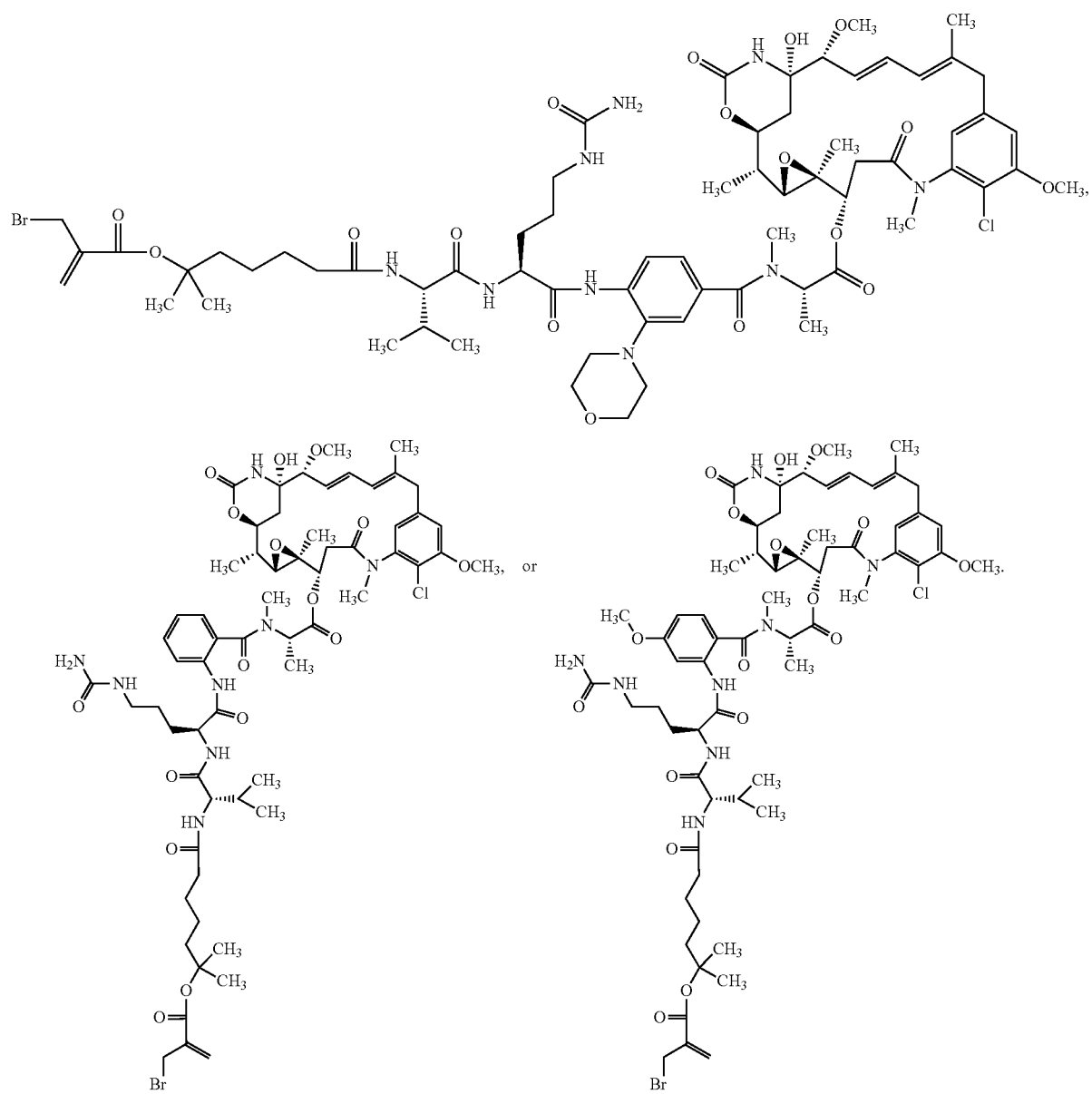

In some embodiments, the compound of Formula P1 is a compound having one of the following structures:
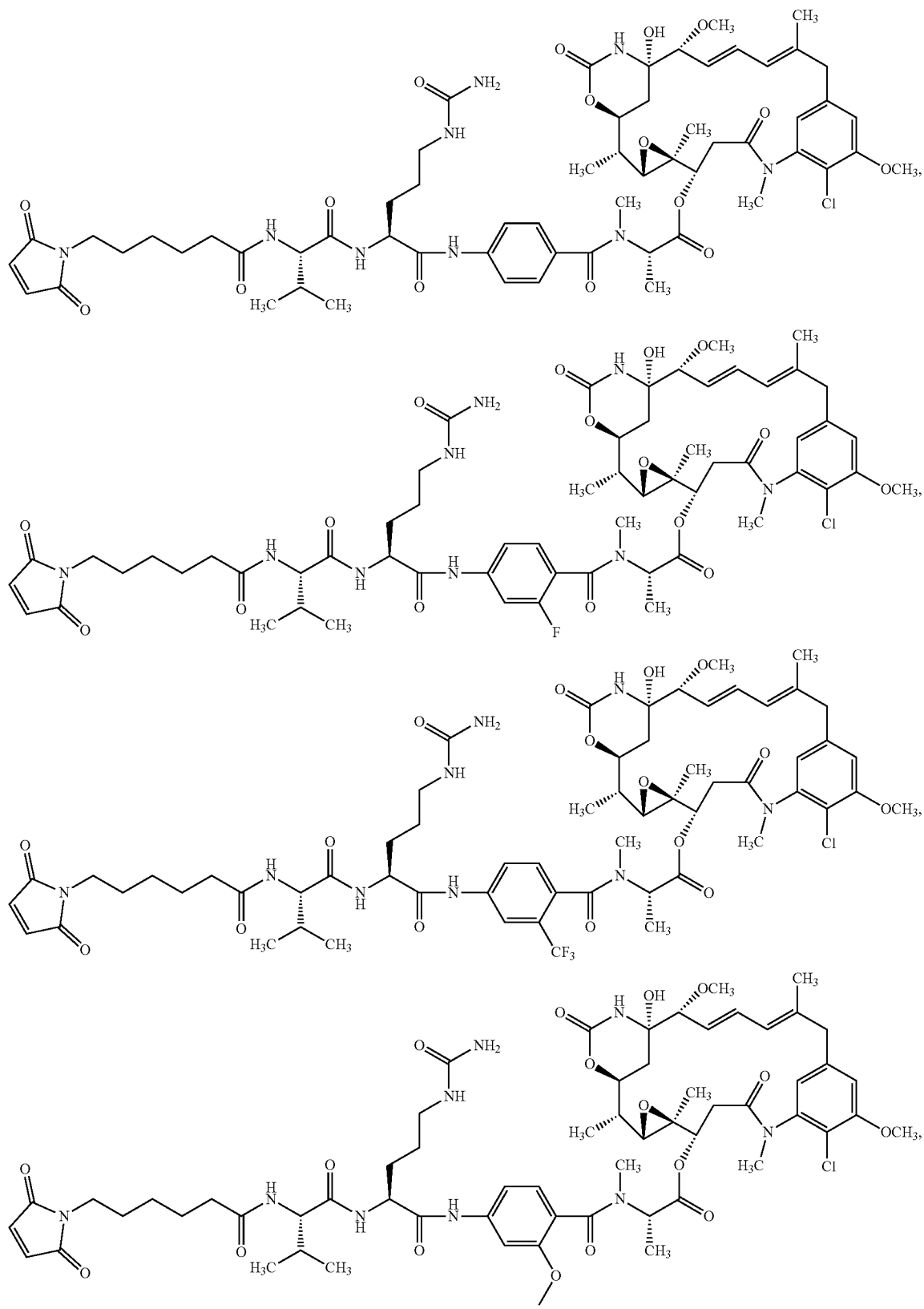

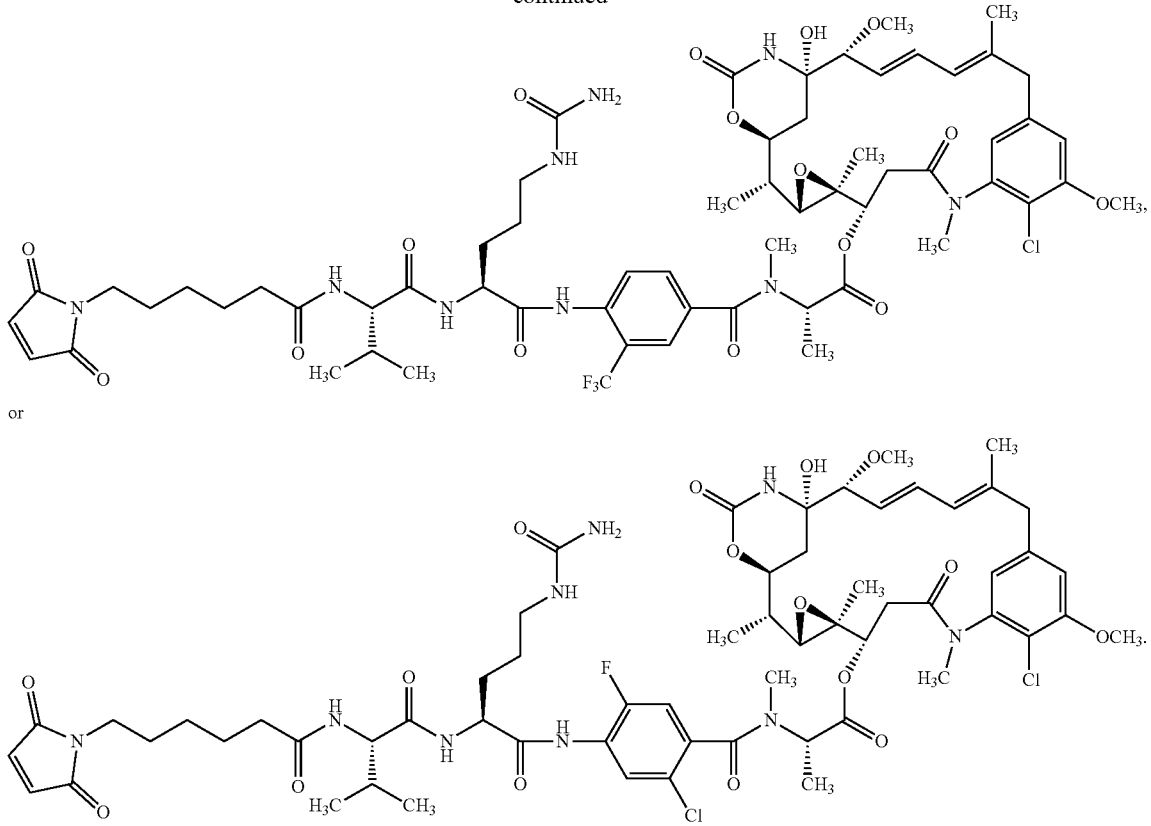

or

Compounds of Formula P1 can by synthesized by reacting compounds of Formula P2 with the compound of Formula P3 under amide synthesis conditions. Suitable amide synthesis conditions include, but are not limited to, contacting the compound of Formula P2 in the presence of a carboxylic acid activating agent and base. Suitable activating agents include, but are not limited to EDC, HATU, HBTU, DCC, BOP, and EEDQ. Suitable bases include, but are not limited to DIEA, DBU, Tributylamine, and 2,6-Lutidine.

The compound of Formula P2 can be synthesized directly from maytansinol and alanine using known techniques (see, e.g., U.S. Pat. No. 4,308,269, which is incorporated herein by reference).

Compounds of Formula I can be synthesized by coupling compounds of Formula PP3:

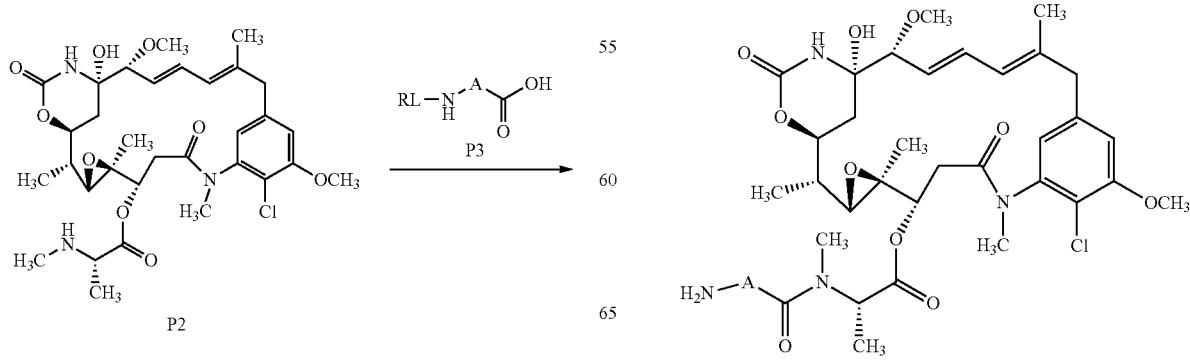

with compounds of Formula PP4 under amide synthesis conditions:

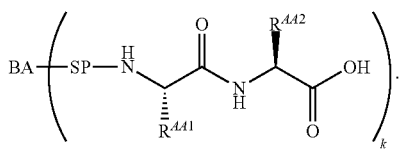

wherein:
BA is a binding agent;
SP is a spacer;
$R^{AA1}$ is an amino acid side chain;
$R^{AA2}$ is an amino acid side chain;
A is arylene or heteroarylene; and
k is an integer from 1 to 10.

Compounds of Formula PP3 can be synthesized by contacting compounds of Formula PP5 with a suitable reducing agent:

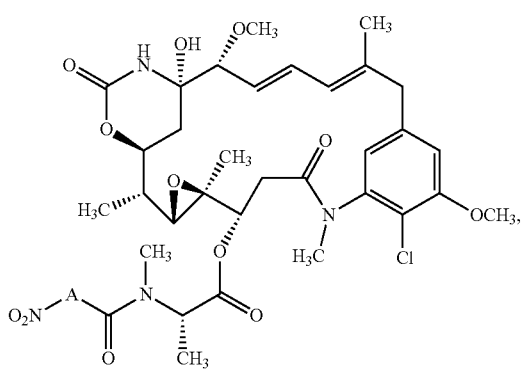

wherein A is arylene or heteroarylene.

In some embodiments, the suitable reducing agent includes a metal, a metal foil, a metal powder, a metal amalgam, or metal filings. In certain embodiments, the metal is selected from zinc, iron, aluminum, palladium, or Raney nickel.

For example, in some embodiments, the following reducing agent conditions are employed. With respect to the amount of compound PP5, for example, in some of the methods herein about twenty (20) equivalents of zinc dust and forty (40) equivalents of acetic acid were combined. In some examples, the reducing reaction was conducted at room temperature for about from 1 to 20 hours. In some of these examples, the aforementioned acetic acid is substituted with another suitable mild acid or proton donor. Examples of suitable mild acids or proton donors include, but are not limited to formic acid, pTsOH, and $NH_4Cl$. In some of these examples, the reducing metal is substituted with a suitable reducing agent selected from iron, aluminum, palladium, or Raney nickel. In some of these examples, suitable solvents includes those solvents having 10-50% water (by volume) in a miscible organic solvent. Example miscible organic solvents include, but are not limited to THF, Dioxane, and diethyl ether. In some examples, the reducing reactions set forth herein are conducted at reaction temperatures which range from 0 to 50° C. In some examples, the reducing reactions set forth herein are conducted at reaction times which range from 1 to 40 hours.

Suitable acids include, but are not limited to, acetic acid.
In some embodiments, A is:

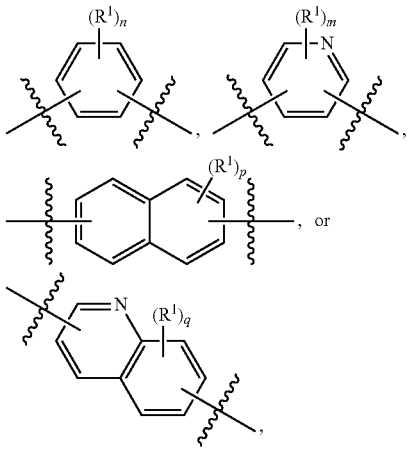

wherein:
$R^1$ is, independently at each occurrence, alkyl, alkenyl, alkynyl, aryl, alkaryl, aralkyl, halo, heteroaryl, heterocycloalkyl, hydroxyl, cyano, nitro,

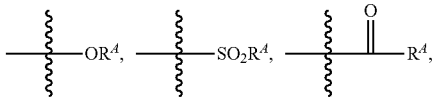

or azido,
wherein $R^A$ is alkyl or heteroalkyl;
n is an integer from 0 to 4;
m is and integer from 0 to 3;
p is an integer from 0 to 6; and
q is an integer from 0 to 5.

In some embodiments, the compound of Formula PP5 is a compound of the Formula PP5A:

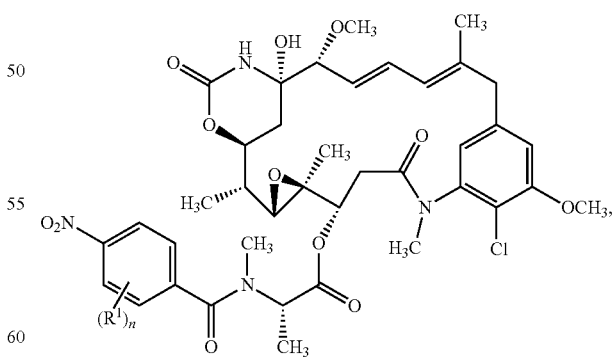

wherein $R^1$ and n are as defined herein.

In some embodiments, $R^1$ is, independently, alkyl, alkoxy, heteroalkyl, halo, haloalkyl, or haloalkoxy. In some embodiments, $R^1$ is, independently, $C_{1-6}$ alkyl, $C_{1-6}$ alkoxy, $C_{1-6}$ haloalkyl, $C_{1-6}$ haloalkoxy, or halo. In some embodiments, $R^1$ is, independently, $C_{1-6}$ alkyl or $C_{1-6}$ alkoxy. In some embodiments, $R^1$ is, independently, alkoxy. In some embodiments, $R^1$ is, independently, methoxy, ethoxy, propoxy. In some embodiments, n, m, p, or q is 0, 1 or 2. In some embodiments, n, m, p, or q is 0 or 1. In some embodiments, n, m, p, or q is 0.

In some embodiments, the compound of Formula PP5 is a compound of the Formula PP5A:

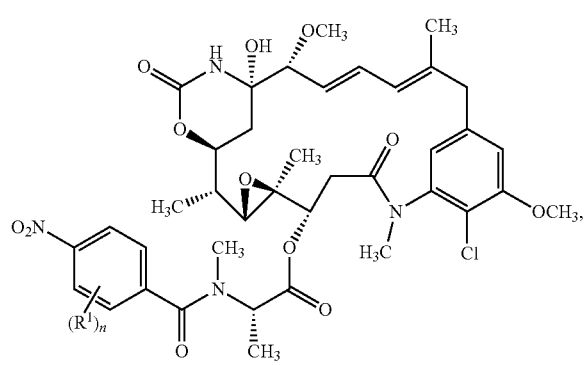

PP5A wherein:
  $R^1$ is, independently at each occurrence, halo or trifluoromethyl; and
  n is 0, 1, or 2.

In some embodiments, the compound of Formula PP5 is a compound of the Formula PP5A2:

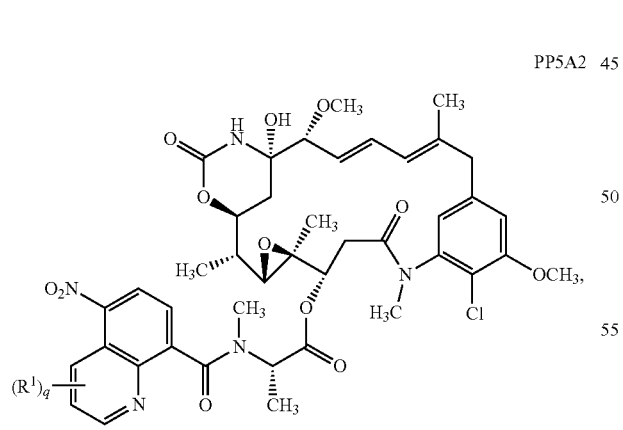

PP5A2 wherein:
  $R^1$ is, independently at each occurrence, halo or trifluoromethyl; and
  q is an integer from 0 to 5

In some embodiments, the compound of Formula PP5 is a compound of the Formula PP5A3:

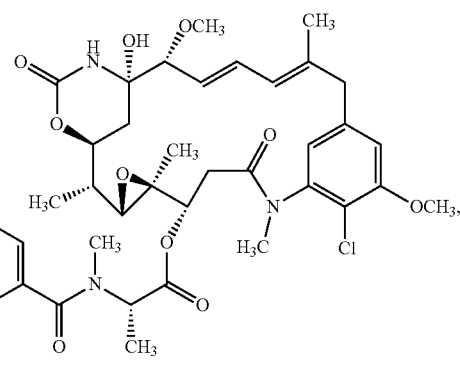

PP5A3 wherein:
  $R^1$ is, independently at each occurrence, halo or trifluoromethyl; and q is an integer from 0 to 5. In some embodiments, $R^1$ is 1-methylethyl-thiol, phenyl, 2-fluorophenyl, pyridinyl, 4-pyridinyl, pyrrolidinyl, or 1-pyrrolidinyl. In some embodiments, $R^1$ is trifluoromethyl. In some embodiments, $R^1$ is methoxy. In some embodiments, $R^1$ is fluoro. In some embodiments, $R^1$ is hydrogen.

In some embodiments, the compound of Formula PP5 is a compound of the Formula PP5A4:

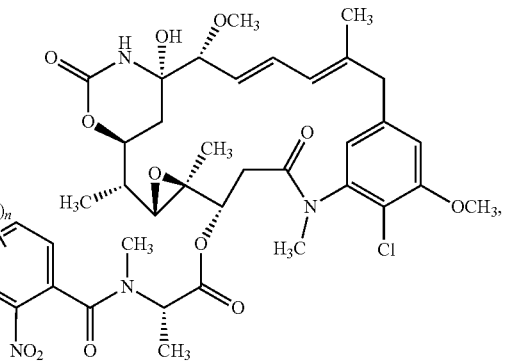

PP5A4 wherein $R^1$ and n are as defined herein.

Compounds of Formula PP5 can be synthesized by contacting compounds of Formula P2 with compounds of Formula PP6 under amide synthesis conditions:

323

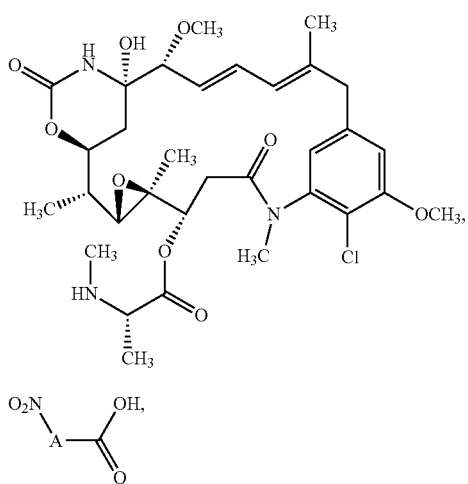

P2

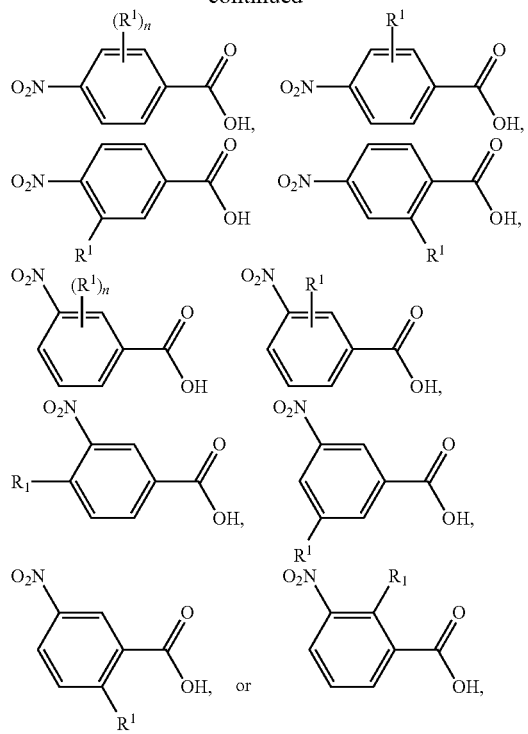

PP6

Suitable compounds of Formula PP6 include, but are not limited to, 3-nitro-benzoic acid, 3-chloro-5-nitro-benzoic acid, 3-fluoro-5-nitro-benzoic acid, 3-nitro-1-naphthalenecarboxylic acid, 2-fluoro-5-nitro-benzoic acid, 3-(dimethylamino)-5-nitro-benzoic acid, 3-ethoxy-5-nitro-benzoic acid, 2-methoxy-5-nitro-benzoic acid, 4-methoxy-3-nitro-benzoic acid, 2,6-difluoro-3-nitro-benzoic acid, 2-chloro-6-fluoro-3-nitro-benzoic acid, 6-chloro-2-fluoro-3-nitro-benzoic acid, 2-chloro-4-fluoro-5-nitro-benzoic acid, 4-chloro-2-fluoro-5-nitro-benzoic acid, 2-ethoxy-5-nitro-benzoic acid, 2-(methylamino)-3-nitro-benzoic acid, 6-nitro-8-quinolinecarboxlic acid, 4-(dimethylamino)-3-nitro-benzoic acid hydrochloride (1:1), 2-methyl-nitro-benzoic acid, 3-methyl-4-nitro-benzoic acid, 4-nitro-1-naphthalenecarboxylic acid, 4-nitro-1-naphthalenecarboxylic acid, 2,6-dimethyl-4-nitro-benzoic acid, 3-fluoro-4-nitro-benzoic acid, 3-chloro-4-nitro-benzoic acid, 3-bromo-4-nitro-benzoic acid, 3-cyano-4-nitro-benzoic acid, 3-cyclopropyl-4-nitro-benzoic acid, 3-methoxy-4-nitro-benzoic acid, 2-methoxy-4-nitro-benzoic acid, 5-chloro-2-methyl-4-nitro-benzoic acid, 8-nitro-5-isoquinolinecarboxylic acid, 5-nitro-8-quinolinecarboxylic acid, 8-nitro-5-quinolinecarboxylic acid, 2,5-difluoro-4-nitro-benzoic acid, 2-(dimethylamino)-4-nitro-benzoic acid, 2-chloro-5-fluoro-4-nitro-benzoic acid, 3-(dimethylamino)-4-nitro-benzoic acid, 2-[(1-methylethyl)thio]-4-nitro-benzoic acid, 4-nitro-3-(trifluoromethyl)-benzoic acid, 4-nitro-2-(trifluoromethyl)-benzoic acid, 3,5-dimethoxy-4-nitro-benzoic acid, 4-nitro-2-(propylamino)-benzoic acid, 3-(difluoromethoxy)-4-nitro-benzoic acid, 2-(2-fluoro-phenyl)-4-nitro-benzoic acid, 4-nitro-2-(4-pyridinyl)-benzoic acid, 4-nitro-3-(4-pyridinyl)-benzoic acid, or 4-nitro-2-(1-pyrrolidinyl)-benzoic acid.

Suitable compounds of Formula PP6 include compounds having any one of the following formula:

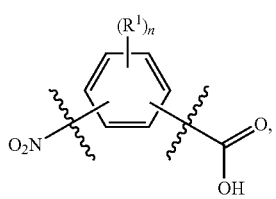

324

-continued

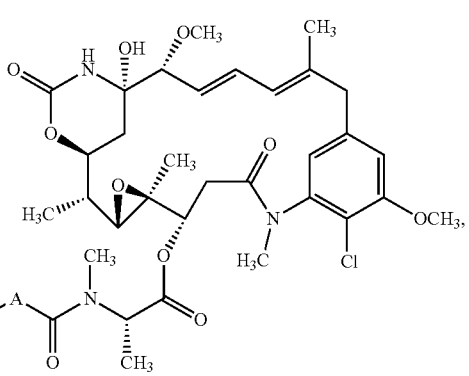

wherein $R^1$ is, independently at each occurrence, $C_{1-6}$ alkyl, $C_{1-6}$ alkoxy, halo, $C_{1-6}$ haloalkyl, or $C_{1-6}$ haloalkoxy, wherein n is 0, 1, 2, 3, or 4. In certain of these embodiments, $R^1$ is methoxy or methyl. In some specific embodiments, $R^1$ is methoxy, fluoro, or trifluoromethyl. In certain embodiments, n is 1 or 2. In some of these embodiments, n is 1. In some embodiments, $R^1$ is fluoro, chloro, bromo, or iodo.

In some embodiments, $R^1$ is 1-methylethyl-thiol, phenyl, 2-fluorophenyl, pyridinyl, 4-pyridinyl, pyrrolidinyl, or 1-pyrrolidinyl. In some embodiments, $R^1$ is trifluoromethyl. In some embodiments, $R^1$ is methoxy. In some embodiments, $R^1$ is fluoro. In some embodiments, $R^1$ is hydrogen.

In some embodiments, provided herein are compounds of Formula PP5:

PP5 wherein A is arylene or heteroarylene.

In some embodiments, the compound of Formula PP5 is a compound selected from

325
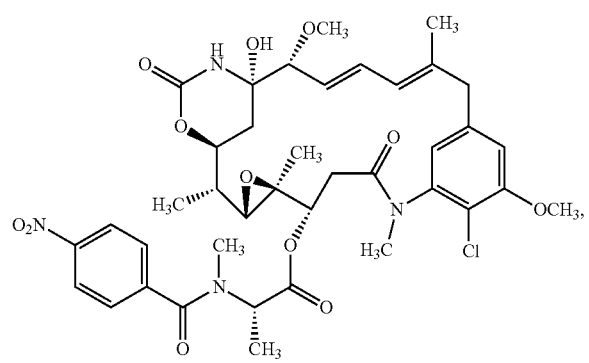
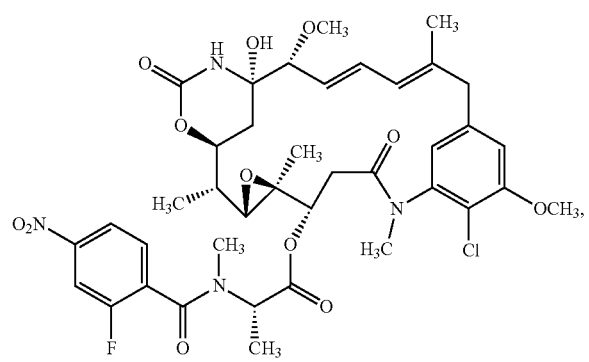
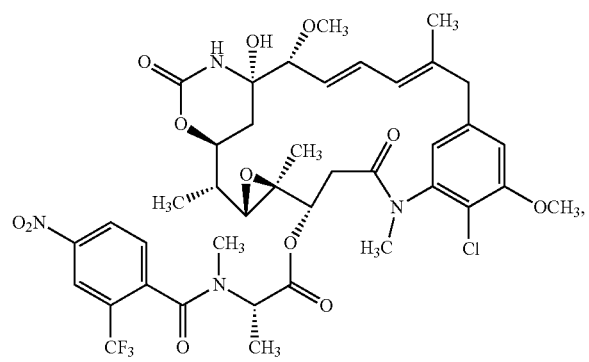 [SMILES: COc1cc2cc(c1Cl)N(C)C(=O)C[C@H](OC(=O)[C@H](C)N(C)C(=O)c1cc(F)c([N+](=O)[O-])cc1Cl)[C@]1(C)O[C@H]1[C@H](C)[C@@H]1C[C@@](O)(NC(=O)O1)[C@H](OC)/C=C/C=C(\C)C2]
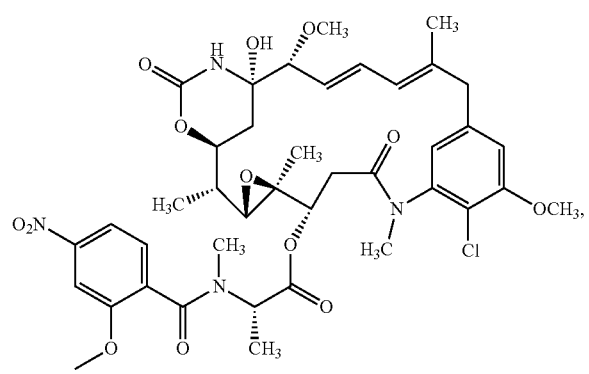 [SMILES: COc1cc([N+](=O)[O-])ccc1C(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]
326
-continued
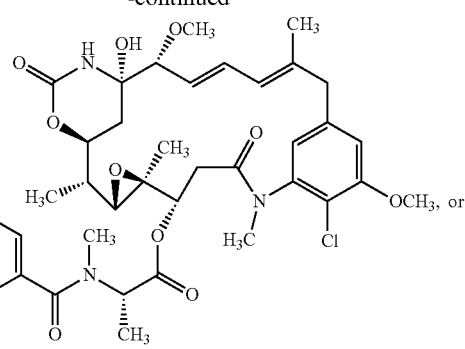
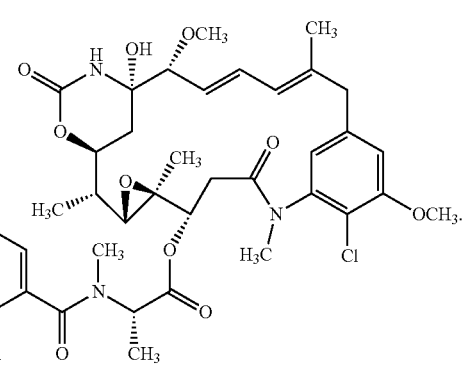
In some embodiments, the compound of Formula PP5 is:
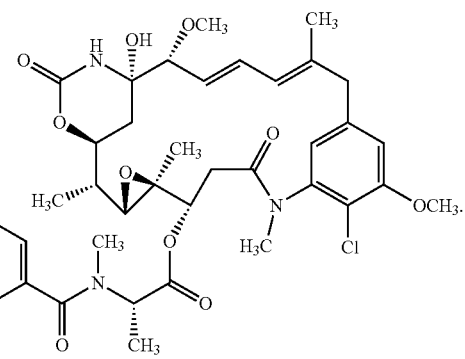

Compounds of Formula III:

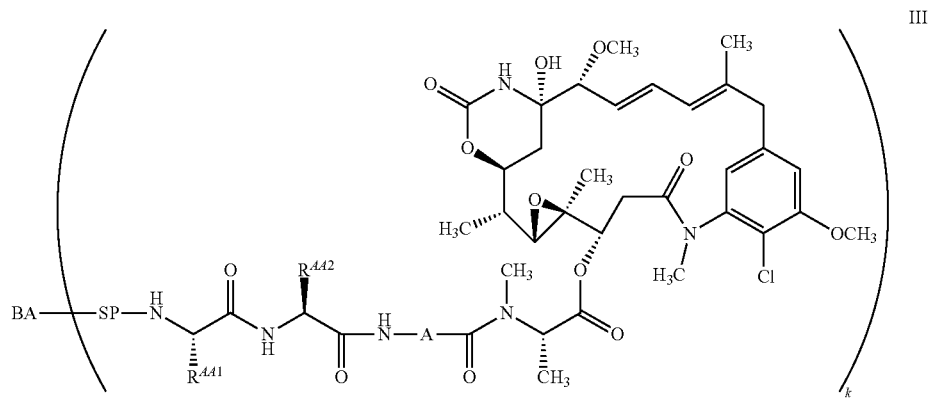

can be synthesized by contacting compounds of Formula PP1:

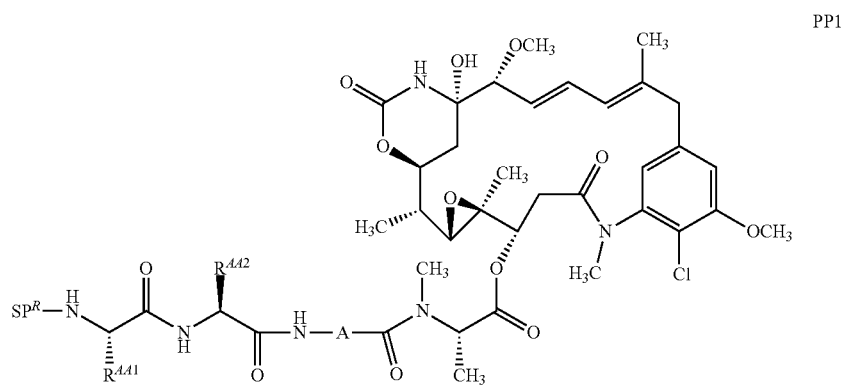

with a binding agent under conjugation conditions, wherein:
BA is a binding agent;
SP is a spacer;
$SP^R$ is a reactive spacer;
$R^{AA1}$ is an amino acid side chain;
$R^{AA2}$ is an amino acid side chain;
A is arylene or heteroarylene; and
k is an integer from 1 to 30.

Compounds of Formula PP1 can be prepared by contacting a compound of Formula PP2 with the compound of Formula P2:

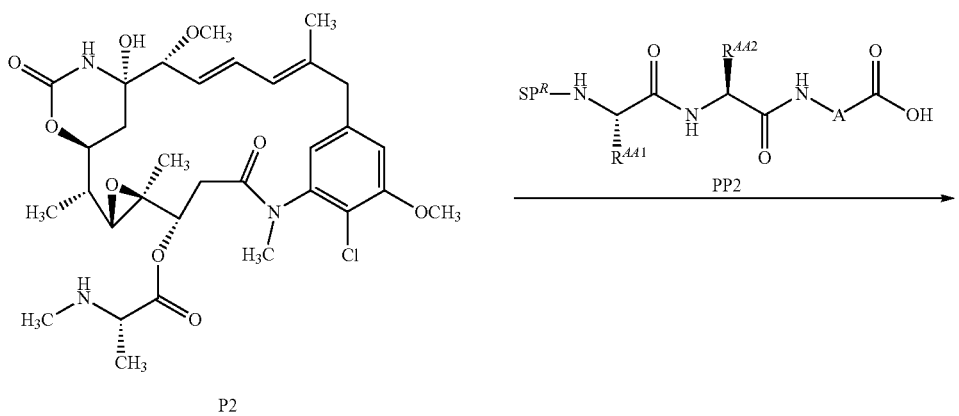

-continued

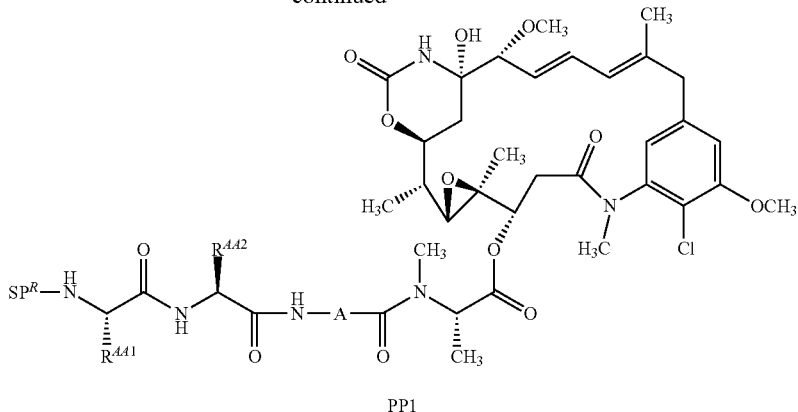

PP1 wherein:
SP$^R$ is a reactive linker;
R$^{AA1}$ is an amino acid side chain;
R$^{AA1}$ is an amino acid side chain; and
A is arylene or heteroarylene.

Compounds of Formula PP1 can be prepared by contacting a compound of Formula PP3 with the compound of Formula PP7:

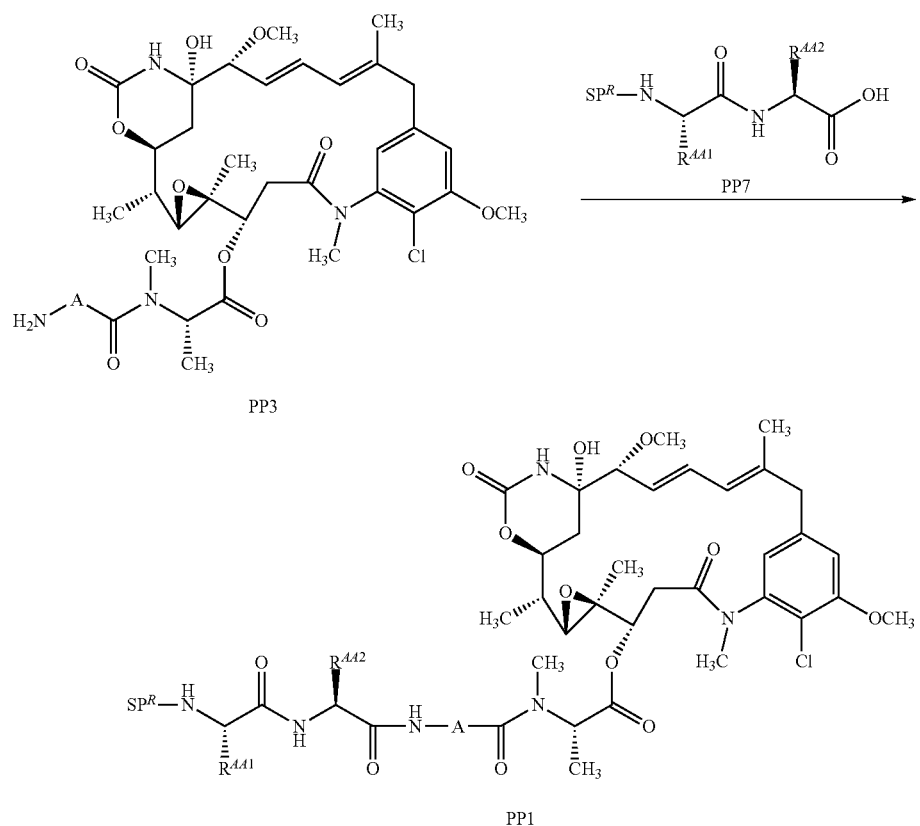

wherein:
SP$^R$ is a reactive linker;
R$^{AA1}$ is an amino acid side chain;
R$^{AA1}$ is an amino acid side chain; and
A is arylene or heteroarylene.

Compounds of Formula PP2 can be prepared by contacting a compound of Formula PP8 with a bifunctional spacer:

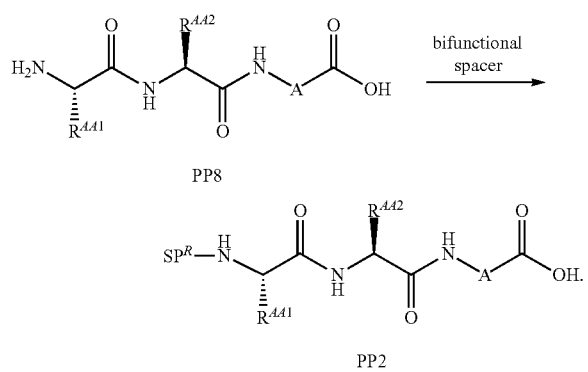

PP8 → PP2

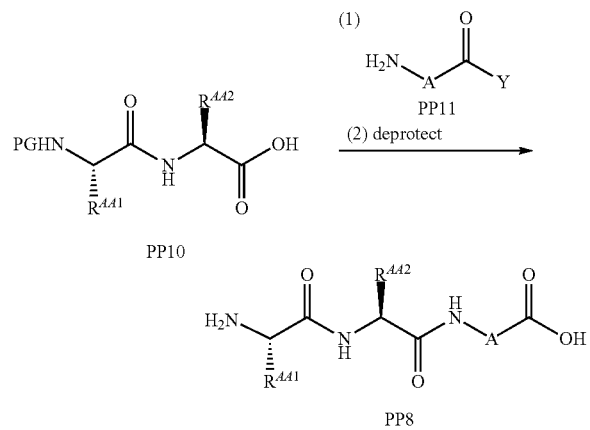

PP10 + PP11 → PP8 wherein PG is an amine protecting group and Y is a moiety that renders the carbonyl to which it is attached electrophilic. Compound of Formula PP10 can be prepared by coupling its corresponding amino acids using standard amino acid coupling techniques, including, for example, active ester formation using HATU, BOP/HOBt, or EDC/N-hydroxysuccinamide in the presence of DIEA, DBU, or tributylamine.

Bifunctional spacers are compounds that react with the compound of Formula PP9 to append the SP$^R$ moiety present in the compounds of Formula PP7. Illustrative bifunctional spacers include, but are not limited to:

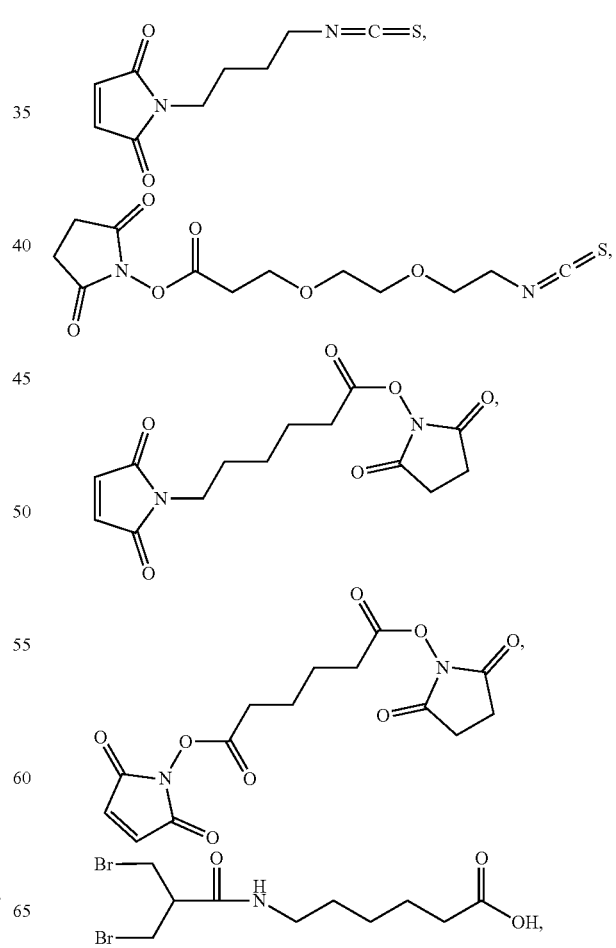

Compounds of Formula PP7 can be prepared by contacting a compound of Formula PP9 with a bifunctional spacer:

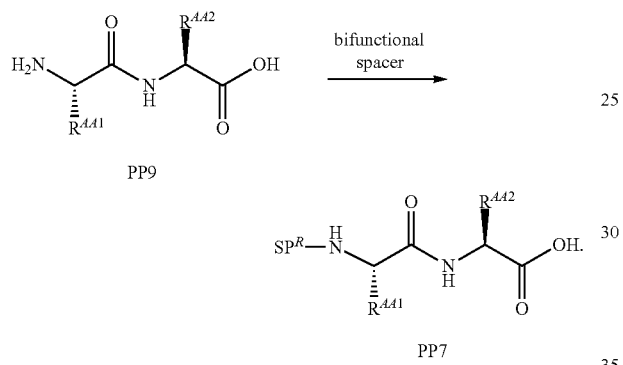

Bifunctional spacers are compounds that react with the compound of Formula PP3 to append the SP$^R$ moiety present in the compounds of Formula PP2. Illustrative bifunctional spacers include, but are not limited to:

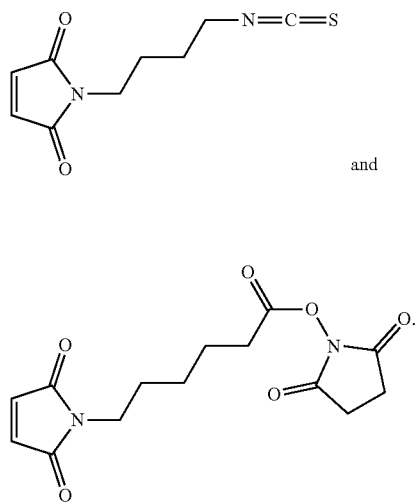

Compounds of Formula PP8 can be prepared by contacting a compound of Formula PP10 with a compound of Formula PP11, following by removal of the protecting group:

-continued

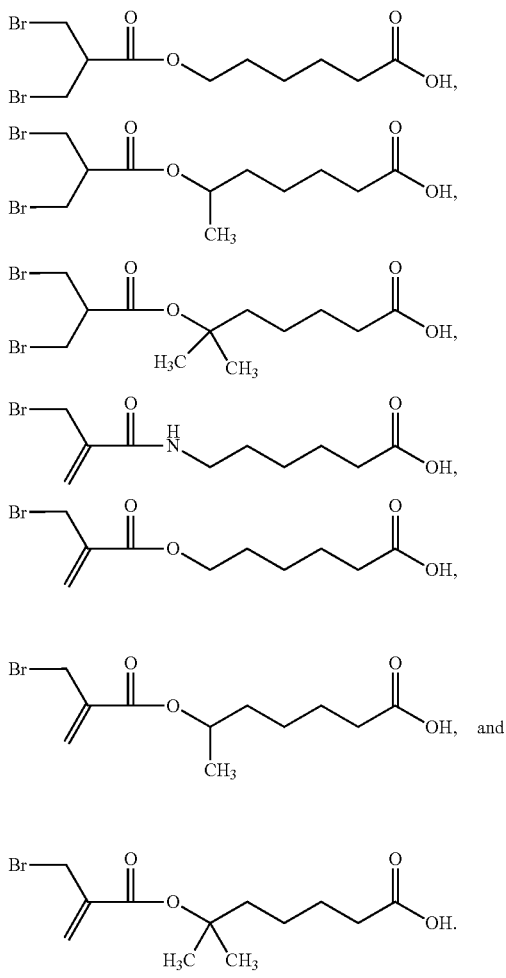

Antibody drug conjugate compounds of Formula (I) can also be prepared by reacting a suitable antibody, e.g., deglycosylated antibody or aglycosylated antibody with a compound of Formula (PT1) in the presence of transglutaminase:

PT1

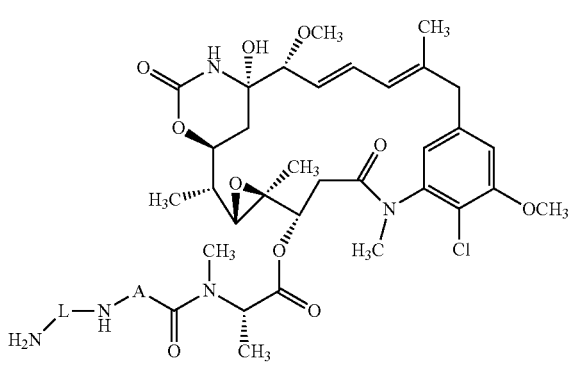

wherein:
A is arylene or heteroarylene; and
L is a linker.

In some embodiments, A is:

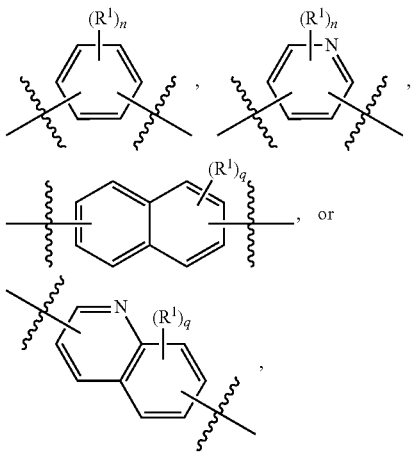

wherein:
R$^1$ is, independently at each occurrence, halo, haloalkyl, haloalkoxy, hydroxyl, alkyl, alkenyl, alkynyl, alkoxy, haloalkoxy, aryl, alkaryl, aralkyl, heteroaryl, heteroalkyl, heterocycloalkyl, cyano, nitro,

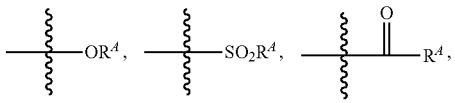

or azido,
wherein R$^A$ is alkyl or heteroalkyl;
n is an integer from 0 to 4;
m is an integer from 0 to 3;
p is an integer from 0 to 6; and
q is an integer from 0 to 5.
In some embodiments, A is:

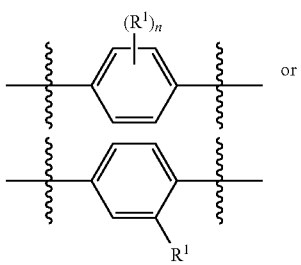

wherein:
R$^1$ is, independently at each occurrence, halo, haloalkyl, hydroxyl, alkyl, alkenyl, alkynyl, alkoxy, aryl, alkaryl, aralkyl, heteroaryl, heteroalkyl, heterocycloalkyl, cyano, nitro,

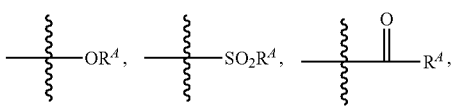

or azido,
wherein R$^A$ is alkyl or heteroalkyl;
n is an integer from 0 to 4;

m is an integer from 0 to 3;
p is an integer from 0 to 6; and
q is an integer from 0 to 5.

In some embodiments, $R^1$ is, independently, alkyl or halo. In some embodiments, $R^1$ is, independently, $C_{1-6}$ alkyl, $C_{1-6}$ haloalkyl, or halo. In some embodiments, $R^1$ is, independently, halo. In some embodiments, $R^1$ is, independently, fluoro, chloro, bromo, iodo, or trifluoromethyl. In some embodiments, n, m, p, or q is 0, 1 or 2. In some embodiments, n, m, p, or q is 0 or 1. In some embodiments, n, m, p, or q is 0.

In some embodiments, $R^1$ is

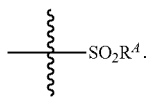

In some embodiments, $R^1$ is

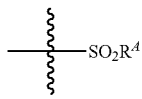

wherein $R^A$ is methyl. In some embodiments, $R^1$ is hydroxyl. In some embodiments, $R^1$ is N-methylformamide. In some embodiments, $R^1$ is morpholinyl.

In some embodiments, the linker comprises one or more amino acids. Suitable amino acids include natural, non-natural, standard, non-standard, proteinogenic, non-proteinogenic, and L-, or D-α-amino acids. In some embodiments, the linker comprises alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, or derivative thereof.

In some embodiments, the linker comprises valine and citrulline.

In some embodiments, the linker is:

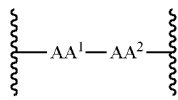

wherein:
one

is one or more bonds to the payload;
the other

is one or more bonds to the —NH$_2$ of PT1;
$AA^1$ is an amino acid; and
$AA^2$ is an amino acid.

The linker may further comprise a divalent moiety that connects the $AA^1$-$AA^2$ moiety to the —NH$_2$ of PT1. Suitable divalent moieties include, but are not limited to, those comprising alkylene or polyethylene glycol. The divalent moiety may comprise one or more reactive groups to facilitate bonding to the rest of the compound, or one or more residues of such reactive groups.

PT1 includes a primary amine-terminated alkylene or a primary amine-terminated polyethylene glycol. The primary amine-terminating moiety can be directly bonded to a deglycosylated antibody or aglycosylated antibody in the presence of transglutaminase.

In some embodiments, the compound comprises a primary amine-terminated alkylene. In some embodiments, the compound comprises a NH$_2$—C$_{5-7}$ alkylene. In some embodiments, the compound comprises:

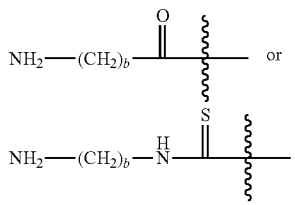

wherein:

is a bond to the payload; and
b is an integer from 2 to 8.

In some embodiments, the compound comprises:

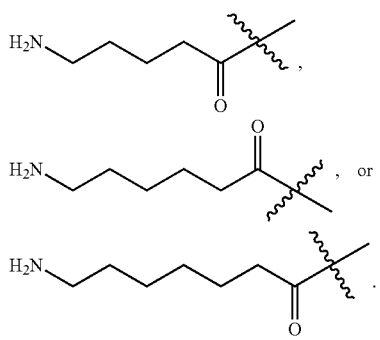

wherein:

is a bond to the payload.

In some embodiments, the compound of PT1 is

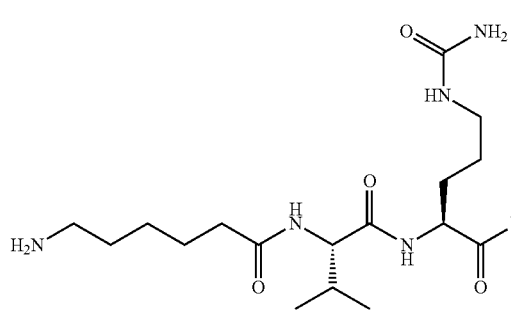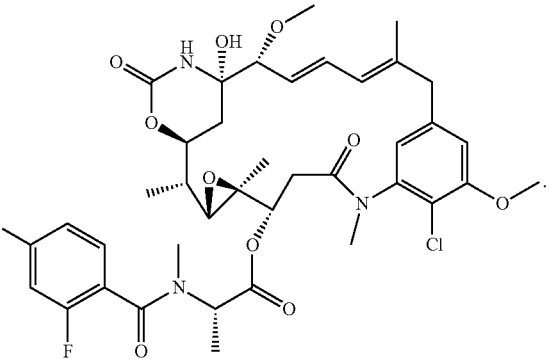

In some embodiments, the compound of Formula (I) is prepared by contacting a binding agent with PT1 in the presence of transglutaminase under conditions suitable for a transglutamination reaction. In some embodiments, the transglutaminase reaction is at a pH between about 7 and about 8 for at least 4 hr. In some examples, the pH is 7.2, 7.3, 7.4, 7.5, 7.6, 7.8, or 8.

In some embodiments, the compound of Formula (I) is prepared by a transglutaminase reaction wherein the concentration of the compound of Formula (PT1) is at a concentration of at least 30 molar equivalents compared to the deglycosylated antibody or aglycosylated antibody. In some embodiments, the compound of Formula (I) is prepared by a transglutaminase reaction wherein the concentration of the compound of Formula (PT1) is at a concentration of 30 to 150 molar equivalents compared to the deglycosylated antibody or aglycosylated antibody.

In some embodiments, the compound of Formula (I) is prepared by a transglutaminase reaction wherein the concentration of the compound of Formula (PT1) is 1 to 30 U per milligram of deglycosylated antibody or aglycosylated antibody.

In some embodiments, the antibody is deglycosylated with peptide N-glycosidase F (PNGaseF) prior to the transglutaminase reaction.

In some embodiments, the antibody is aglycosylated. An aglycosylated antibody can be prepared by mutagenesis techniques to remove one or more amino acid sequences that are necessary for glycosylation of the antibody. In certain embodiments the antibody comprises a heavy chain with a mutation that substitutes another amino acid for N180. In certain embodiments, the aglycosylated antibody comprises one or more N180Q heavy chain polypeptides.

In some embodiments, the compound of Formula (I) is prepared by a transglutaminase reaction which is conducted in one or more solvent(s) selected from the group consisting of water, buffered water, saline water, buffered saline water, and an organic.

In some embodiments, the compound of Formula (I) is prepared by a transglutaminase reaction which is conducted in water buffered with phosphate, HEPES, or MOPS.

In some embodiments, the compound of Formula (I) is prepared by a transglutaminase reaction which includes reacting the glutaminyl-modified antibody with a reactive spacer compound to form an antibody-spacer conjugate; and then reacting the antibody-spacer conjugate with a reactive payload compound to form an antibody-spacer-payload conjugate.

In some embodiments, provided herein is a glutaminyl-modified antibody produced by a method set forth herein.

In some embodiments, provided herein is a pharmaceutical composition comprising a glutaminyl-modified antibody produced by a method set forth herein.

In some embodiments, provided herein is a method of treating a condition in a subject in need thereof comprising administering to the subject a pharmaceutically acceptable amount of the antibody or antibody-drug-conjugate provided herein.

In some embodiments, provided herein is an antibody or antibody-drug-conjugate described herein for therapy.

In some embodiments, provided herein is an antibody or antibody-drug-conjugate described herein for the treatment of cancer.

E. Methods of Use and Pharmaceutical Compositions

The present disclosure includes methods of treating or preventing diseases, conditions, or disorders e.g., proliferative diseases such as cancer, comprising administering a therapeutically effective amount or one or more of the compounds disclosed herein, e.g., one or more of the compounds of Formula (I) or (II). Diseases, disorders, and/or conditions include, but are not limited to, those associated with the antigens listed herein. In some embodiments, the antigen is PSMA, MUC16, or EGFRvIII.

The compounds disclosed herein can be used for treating primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the compounds provided herein are used to treat one or more of the following cancers: renal cell carcinoma, pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, or melanoma. In some embodiments, the cancer is breast cancer.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET antagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody or small molecule kinase inhibitor such as, e.g., imatinib mesylate or sunitinib malate), a PDGF ligand inhibitor (e.g., anti-PDGF-A, —B, —C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), etc. Other agents that may be beneficially administered in combination with compounds of the disclosure include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

Suitable therapeutic agents also include, but are not limited to chemotherapeutic agents, including alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The compounds described herein can also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

In some embodiments of the methods described herein, multiple doses of a compound described herein (or a pharmaceutical composition comprising a combination of an compound described herein and any of the additional therapeutic agents mentioned herein) may be administered to a subject over a defined time course. The methods according to this aspect of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks or months). The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all contain the same amount the compound described herein, but generally can differ from one another in terms of frequency of administration. In certain embodiments, the amount of the compound contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this aspect of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., the compounds of Formula (I) and (II), e.g., compositions comprising a compound described herein, a salt, stereoisomer, polymorph thereof, and a pharmaceutically acceptable carrier, diluent, and/or excipient. Examples of suitable carriers, diluents and excipients include, but are not limited to: buffers for maintenance of proper composition pH (e.g., citrate buffers, succinate buffers, acetate buffers, phosphate buffers, lactate buffers, oxalate buffers and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

F. EXAMPLES

Proton NMR spectra were acquired on Varian Inova 300 or 500 MHz instruments, while mass spectra were collected on an Agilent 1100 or 1200 series LC/MSD with electrospray ionization source and either single-quad or ion trap analyzer. Certain linker payloads in enzymatic assays were analyzed by a Waters Xevo TQ-S mass spectrometer. All starting materials and solvents were purchased commercially and used without purification, unless otherwise noted.

Example 1

Compound 10 was synthesized from Compound 1 as described below and as depicted in FIG. 1.

Maytansin-N-methyl-L-alanine-4-aminobenzamido-Cit-Val-Cap-Mal (10)

Step A: To a round-bottom flask was weighed Boc-L-valine (1.03 g, 4.74 mmol), N-hydroxysuccinimide (1.22 g, 10.6 mmol), and EDC (1.60 g, 8.35 mmol). The reagents were dissolved in dry DCM (30 mL), the flask sealed via rubber septum, purged with argon, and the reaction stirred at ambient temperature. After 3 days no Boc-valine remained by TLC (after staining with ninhydrin), so the reaction was washed with water and sat. aq. NaHCO$_3$, the aqueous layer extracted with DCM, combined organic layers washed with brine, dried over Na$_2$SO$_4$, and filtered. The filtrate was then evaporated and dried in vacuo giving Boc-L-valine-succinate as a white solid (1.52 g, 100%). $^1$H-NMR (300 MHz, CDCl$_3$): δ 4.98 (br d, 1H), 4.58 (dd, 1H), 2.82 (m, 4H), 2.27 (m, 1H), 1.44 (s, 9H), 1.03 (dd, 6H).

Boc-L-valine-L-citrulline (3)

Boc-L-valine-succinate (1) of the preceding step (1.50 g, 4.77 mmol) was dissolved in acetonitrile (MeCN, 15 mL), treated with a solution of L-citrulline (2, 1.07 g, 6.11 mmol)

in water (9 mL) and sat. aq. NaHCO$_3$ (6 mL), the flask sealed with a vented septum, and the reaction stirred at ambient temperature. The reaction was incomplete after 18 h, so additional sat. aq. NaHCO$_3$ (3 mL) was added to bring the pH up to ca. 7 and the reaction stirred another 36 h. The reaction was partially concentrated in vacuo to remove MeCN and washed once with ethyl acetate (EtOAc) to remove any nonpolar impurities. The aqueous layer was then acidified to pH 3 with 10% v/v HCl, saturated with NaCl, and extracted 4 times with 9:1 EtOAc/isopropanol. The combined organic extracts were washed with brine, dried over Na$_2$SO$_4$, and filtered. The filtrate was then evaporated and dried in vacuo giving the title compound as a white solid (1.56 g, 87%). MS (ESI, pos.): calc'd for C$_{16}$H$_{30}$N$_4$O$_6$, 374.2; found 375.2 (M+H), 397.2 (M+Na).

Boc-L-valine-L-citrulline-p-aminobenzoic acid t-butyl ester (5)

Step B: The product of the preceding step (3, 152 mg, 0.406 mmol), tert-butyl-4-aminobenzoate (4, 150 mg, 0.776 mmol), and 1-[Bis(dimethylamino)methylene]-1H-1,2,3-triazolo[4,5-b]pyridinium 3-oxid hexafluorophosphate (HATU, 488 mg, 1.28 mmol) were weighed into a round-bottom flask and dissolved in anhydrous N,N-dimethylformamide (DMF, 3 mL). N,N-Diisopropylethylamine (DIEA, 0.25 mL, 1.44 mmol) was added to the reaction, the flask sealed via rubber septum, purged with argon, and the reaction stirred at ambient temperature. After 18 h the reaction was purified directly on a 100 g C18 RediSep Gold column via ISCO system (gradient elution: 20-80% MeCN in water, 0.05% acetic acid in both, over 20 min). The product-containing fractions were combined, partially concentrated in vacuo, frozen on dry ice, and lyophilized overnight giving an impure white solid (115 mg). This was dissolved in DCM and repurified on a 12 g silica gel RediSep column via ISCO (gradient elution: 0-10% methanol in DCM over 12 min), and the slower-running product fractions evaporated and dried in vacuo giving the title compound as a pale yellow solid (65 mg, 29%). MS (ESI, pos.): calc'd for C$_{27}$H$_{43}$N$_5$O$_7$, 549.3; found 450.3 (M-Boc+H), 572.3 (M+Na), 1099.5 (2M+H), 1121.5 (2M+Na).

L-valine-L-citrulline-p-aminobenzoic acid (6)

Step C: The title compound was prepared using the method of Mehta et al. (*Tet. Lett.* 1992, 33, 5441-5444). The product of the preceding step (5, 61 mg, 0.111 mmol) was dissolved in dry DCM (3 mL) in a round-bottom flask, and treated with trifluoroacetic acid (TFA, 110 uL, 1.44 mmol) and triethylsilane [TES (Et$_3$SiH), 50 uL, 0.313 mmol]. The flask was sealed via septum, purged with argon, and stirred at ambient temperature for 18 h. The reaction was incomplete by LCMS, so additional TFA (90 uL) and TES (25 uL) were added and the reaction stirred another 6 h. The reaction was still incomplete so it was capped and stored at −20° C. for 3 d. After warming to ambient temperature and stirring another 24 h it was concentrated in vacuo to an oil, triturated twice with diethyl ether, and dried under high vacuum giving the title compound as an off-white solid (55 mg, 98%). MS (ESI, pos.): calc'd for C$_{18}$H$_{27}$N$_5$O$_5$, 393.2; found 394.0 (M+H), 787.2 (2M+H). $^1$H-NMR (500 MHz, DMSO-d$_6$) showed a mixture of amide rotamers: δ 10.52 (s, 0.5H), 10.46 (s, 0.5H), 8.83 (d, 0.5H), 8.71 (d, 0.5H), 8.06 (br s, 3H), 7.89 (m, 2H), 7.72 (m, 2H), 6.03 (m, 1H), 4.55 (m, 1H), 3.05 (m, 1H), 2.97 (m, 1H), 2.10 (m, 1H), 1.73 (m, 1H), 1.63 (m, 1H), 1.5-1.3 (m, 2H), 0.95 (m, 6H).

6-(Maleimidyl-caprolyl)-L-valine-L-citrulline-p-aminobenzoic acid (8)

Step D: The product of the preceding step (6, 55 mg, 0.108 mmol) was dissolved in water (3 mL), treated with sat. aq. NaHCO$_3$, then with a solution of 6-maleimidyl-caproic acid succinate ester (56 mg, 0.182 mmol) in MeCN (3 mL). The flask was capped under argon and the reaction stirred at ambient temperature for 22 h. The reaction was complete by LCMS, so it was partially concentrated in vacuo and purified directly on a 30 g C18 Aq RediSep Gold column via ISCO (gradient elution: 20-80% MeCN in water, 0.05% acetic acid in both, over 12 min). The major product fractions were combined, partially concentrated in vacuo, frozen on dry ice, and lyophilized overnight giving an impure pale yellow solid (92 mg). This was found to be impure by LCMS so it was dissolved in MeCN/water and repurified on a 100 g C18 Aq Gold column (gradient elution: 0-50% MeCN in water, 0.05% acetic acid in both, over 20 min). The cleanest product fractions were combined, partially concentrated in vacuo, frozen on dry ice, and lyophilized giving the title compound as a white solid (34 mg, 53%). MS (ESI, pos.): calc'd for C$_{28}$H$_{38}$N$_6$O$_8$, 586.3; found 587.3 (M+H), 609.3 (M+Na). $^1$H-NMR (500 MHz, DMSO-d$_6$) showed a mixture of amide rotamers: δ 10.26 (s, 0.6H), 10.11 (s, 0.4H), 8.43 (d, 0.4H), 8.13 (d, 0.6H), 7.93-7.70 (m, 4H), 6.99 (m, 2H), 5.97 (m, 1H), 5.41 (m, 2H), 4.38 (m, 1H), 4.21-4.12 (m, 1H), 3.36 (m, 2H), 3.02 (m, 1H), 2.95 (m, 1H), 2.17 (m, 1H), 2.12 (m, 1H), 1.95 (m, 1H), 1.78-1.58 (m, 2H), 1.48 (m, 6H), 1.36 (m, 1H), 1.18 (m, 2H), 0.85 (m, 6H).

Maytansin-N-methyl-L-alanine-4-aminobenzamide-citrulline-valine-caproyl-6-maleimidyl (10)

Step E: The product of the preceding step (8, 33 mg, 0.056 mmol), HATU (33 mg, 0.087 mmol), and maytansin-N-methyl-L-alanine (9, prepared as a gold solid from maytansinol using the methods described in U.S. Patent Application 2007/0037972 A1, 25 mg, 0.038 mmol), were weighed into a round-bottom flask, dissolved in anhydrous DMF (2 mL), and treated with DIEA (20 uL, 0.115 mmol). The flask was sealed via rubber septum, purged with argon, and the reaction stirred at ambient temperature for 20 h. The reaction was diluted with water (1 mL) and purified directly on a 50 g C18 Aq RediSep Gold column via ISCO (gradient elution: 20-80% MeCN in water, 0.05% acetic acid in both, over 12 min). The product fractions were combined, partially concentrated in vacuo, frozen on dry ice, and lyophilized overnight giving the title compound as a white solid (8 mg, 17%). MS (ESI, pos.): calc'd for C$_{60}$H$_{80}$N$_9$O$_{16}$Cl, 1217.5; found 1218.6 (M+H), 1200.7 (M−H$_2$O+H), 1240.7 (M+Na). $^1$H-NMR (500 MHz, CDCl$_3$): δ 9.25 (s, 1H), 7.68-7.61 (m, 2H), 7.33 (d, 2H), 6.91 (s, 1H), 6.84 (s, 1H), 6.75 (d, 1H), 6.67 (s, 2H), 6.45 (dd, 1H), 6.27 (br s, 1H), 6.21 (d, 1H), 5.74 (dd, 1H), 5.44 (m, 1H), 4.98 (m, 1H), 4.88 (d, 1H), 4.77 (t, 1H), 4.53 (br s, 1H), 4.33-4.25 (m, 2), 4.00 (s, 3H), 3.65 (d, 1H), 3.48 (m, 4H), 3.56 (s, 3H), 3.20 (m, 1H), 3.11 (d, 1H), 3.05 (m, 3H), 2.88 (s, 3H), 2.69 (t, 1H), 2.26-2.19 (m, 3H), 2.10 (m, 2H), 1.94 (m, 1H), 1.70-1.55 (m, 6H), 1.66 (s, 3H), 1.46 (d, 3H), 1.33-1.26 (m, 7H), 0.96 (m, 6H), 0.85 (s, 3H).

Example 2

Figure 6:
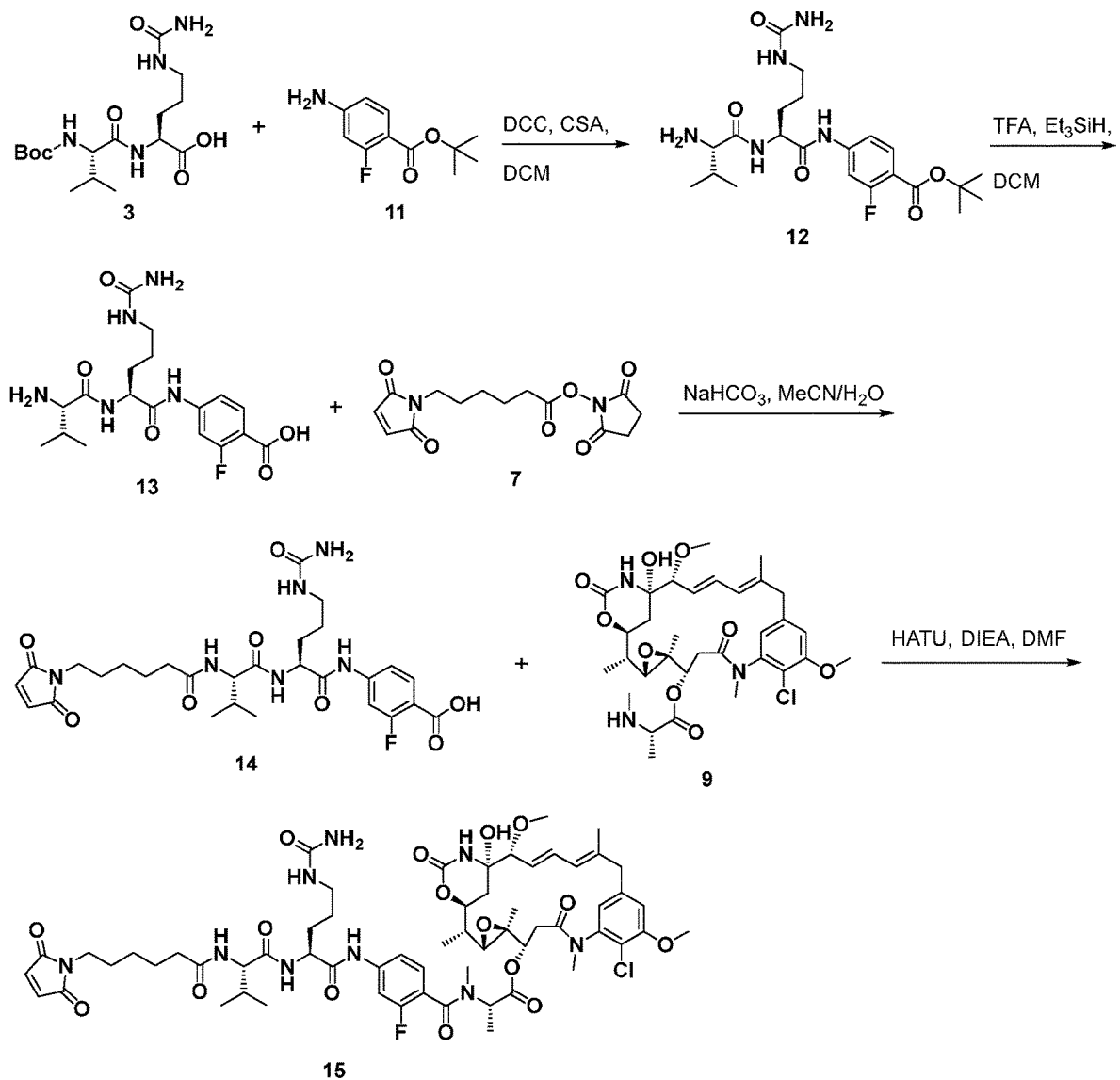
FIG. 6 depicts a synthetic sequence for preparing maytansin-N-methyl-L-alanine-(4-amino-2-fluoro)benzamido-Cit-Val-Cap-Mal.

Compound 15 was synthesized as described below and as depicted in FIG. 6.

Maytansin-N-methyl-L-alanine-(4-amino-2-fluoro)benzamido-Cit-Val-Cap-Mal (15)

Boc-L-valine-L-citrulline-(4-amino-2-fluoro)benzoic acid t-butyl ester (12)

Step A: Following the procedure of Wipf & Heimgartner (*Helv. Chim. Acta,* 1998, 71, 140-154), Boc-L-valine-L-citrulline (3, 155 mg, 0.414 mmol) and dicyclohexylcarbodiimide (DCC, 95 mg, 0.460 mmol) were dissolved in dry dichloromethane (DCM, 3 mL), cooled to 0° C., and stirred for 5 min. (+)-Camphor-10-sulfonic acid (CSA, 15 mg, 0.065 mmol) and tert-butyl-4-amino-2-fluorobenzoate (99 mg, 0.469 mmol) were then added dry and the reaction allowed to slowly warm to ambient temperature while stirring for 3 d. LCMS analysis showed a large new peak with m/z 566 (ESI, neg.). The reaction was diluted with DCM and washed with 10% v/v HCl, water, and saturated NaHCO$_3$. The aqueous layers were each extracted once with DCM, and the combined organic layers washed with brine, dried over Na$_2$SO$_4$, and filtered. The filtrate was then evaporated and dried in vacuo giving a pale gold solid which was purified on a 24 g RediSep Gold column via ISCO (gradient elution: Ethyl Acetate—5:5:1 EtOAc/DCM/methanol over 12 min). The cleanest product fractions were combined, concentrated in vacuo, and dried under high vacuum giving the title compound as a white solid (95 mg, 40%). MS (ESI, pos.): calc'd for C$_{27}$H$_{42}$N$_5$O$_7$F, 567.3; found 568.3 (M+H), 590.4 (M+Na).

L-valine-L-citrulline-(4-amino-2-fluoro)benzoic acid trifluoroacetate salt (13)

Step B: The title compound was prepared from the product of the preceding step (12, 94 mg, 0.166), using Step C, Example 1, to give an off-white solid (112 mg). MS (ESI, pos.): calc'd for C$_{18}$H$_{26}$N$_5$O$_5$F, 411.2; found 412.2 (M+H), 395.2 (M–H$_2$O+H).

6-(Maleimido)-caproamidyl-L-valine-L-citrulline-(4-amino-2-fluoro)benzoic acid (14)

Step C: The title compound was prepared from the product of the preceding step (13, 106 mg, 0.166 mmol), using Step D, Example 1, to give a white solid (92 mg) that was only 70% pure by LCMS but used without further purification. MS (ESI, pos.): calc'd for C$_{28}$H$_{37}$N$_6$O$_8$F, 604.3; found 605.2 (M+H), 627.2 (M+Na).

Maytansin-N-methyl-L-alanine-(4-amino-2-fluoro)benzamido-Cit-Val-Cap-Mal (15)

Step D: The title compound was prepared from the product of the preceding step (14, 50 mg, 0.077 mmol) and maytansin-N-methyl-L-alanine (9, 50 mg, 0.077 mmol), using Step E, Example 1, to give a white solid (18 mg) that was only 55% pure by LCMS. Purifying twice by HPLC using a Phenomenex Gemini C18 5 u, 30×150 mm column (20-80%, then 40-60%, MeCN in water, 0.1% HOAc both phases, over 20 min, 30 mL/min) gave the title compound as a white solid (3 mg, 3%). MS (ESI, pos.): calc'd for C$_{60}$H$_{79}$N$_9$O$_{16}$ClF, 1235.5; found 1236.5 (M+H), 1258.5 (M+Na). $^1$H-NMR (500 MHz, CDCl$_3$): δ 9.40 (s, 1H), 7.64 (d, 1H, J=12 Hz), 7.42 (s, 1H), 7.14 (t, 1H, J=8 Hz), 6.90 (s, 1H), 6.86 (s, 1H), 6.77 (m, 1H), 6.68 (s, 2H), 6.46 (dd, 1H, J=15 Hz, 11 Hz), 6.25 (br s, 1H), 6.19 (br m, 1H), 5.75 (dd, 1H, J=15 Hz, 9 Hz), 5.48 (br m, 1H), 4.88 (d, 1H, J=12 Hz), 4.76 (m, 1H), 4.29 (t, 1H, J=11 Hz), 4.23 (t, 1H, J=7 Hz), 4.01 (s, 2H), 3.99 (m, 1H), 3.70 (m, 1H), 3.53-3.47 (m, 4H), 3.36 (s, 3H), 3.20 (m, 1H), 3.13 (d, 1H, J=12 Hz), 3.03 (m, 3H), 2.81 (s, 2H), 2.67 (dd, 1H, J=15 Hz, 12 Hz), 2.25 (t, 1H, J=7 Hz), 2.21 (m, 2H), 2.10 (m, 1H), 1.70-1.64 (m, 2H), 1.67 (s, 3H), 1.46-1.41 (m, 6H), 1.33-1.25 (m, 10H), 0.99-0.95 (m, 6H), 0.89-0.80 (m, 1H), 0.85 (s, 3H).

Example 3

Figure 7:
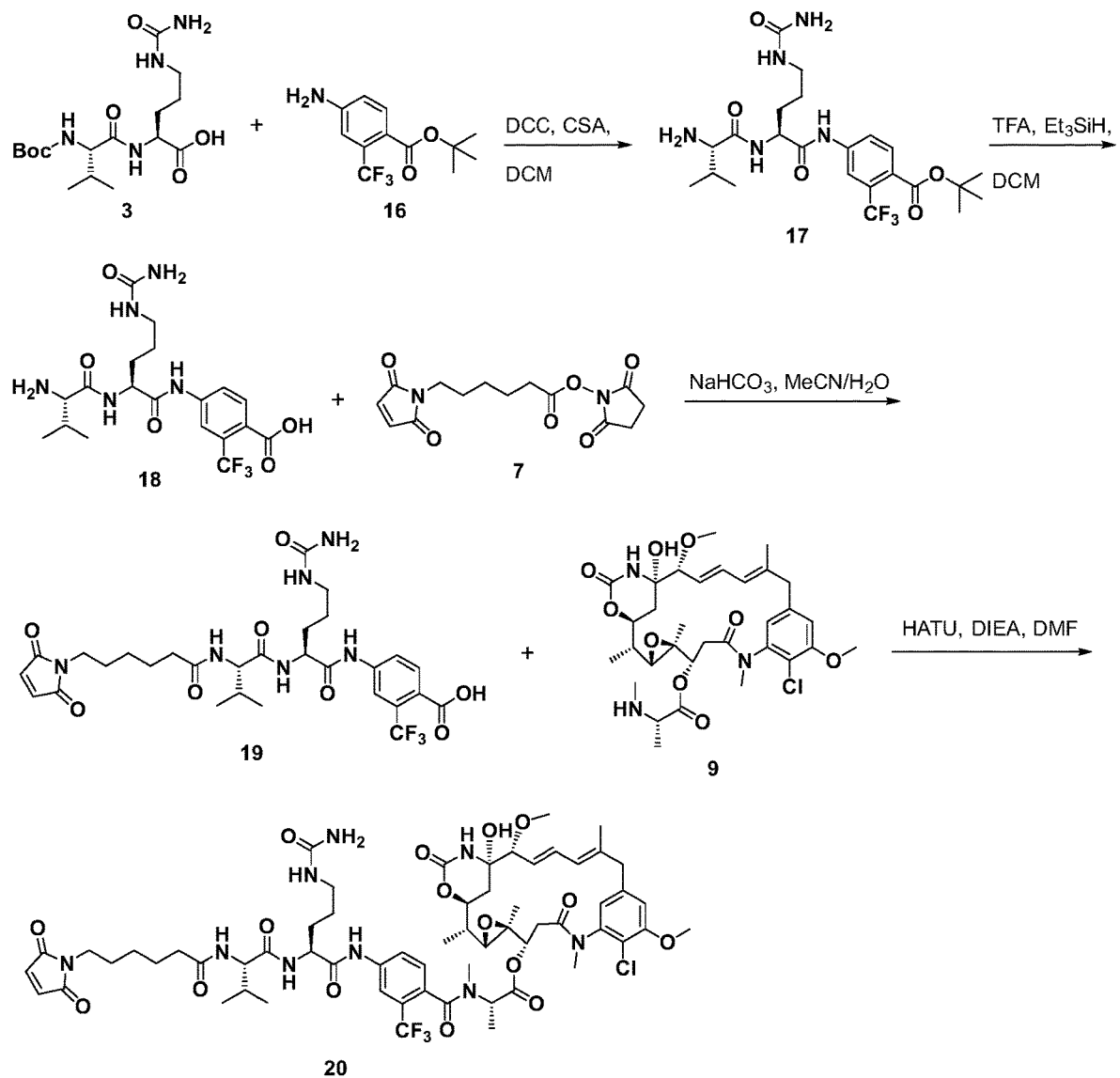
FIG. 7 depicts a synthetic sequence for preparing maytansin-N-methyl-L-alanine-(4-amino-2-trifluoromethyl)benzamido-Cit-Val-Cap-Mal.

Compound 20 was synthesized as described below and as depicted in FIG. 7.

Maytansin-N-methyl-L-alanine-(4-amino-2-trifluoromethyl)benzamido-Cit-Val-Cap-Mal (20)

Boc-L-valine-L-citrulline-(4-amino-2-trifluoromethyl)benzoic acid t-butyl ester (17)

Step A: The title compound was prepared from Boc-L-valine-L-citrulline (3, 175 mg, 0.467 mmol) and tert-butyl-4-amino-2-trifluoromethylbenzoate (150 mg, 0.574 mmol), using the method of Wipf & Heimgartner (*Helv. Chim. Acta,* 1998, 71, 140-154) to give a white solid (77 mg, 27%). MS (ESI, neg.): calc'd for C$_{28}$H$_{42}$N$_5$O$_7$F$_3$, 617.3; found 616.4 (M–H).

L-valine-L-citrulline-(4-amino-2-trifluoromethyl)benzoic acid trifluoroacetate salt (18)

Step B: The title compound was prepared from the product of the preceding step (17, 67 mg, 0.108), using Step C, Example 1, to give an off-white solid (77 mg). MS (ESI, pos.): calc'd for C$_{19}$H$_{26}$N$_5$O$_5$F$_3$, 461.2; found 462.3 (M+H), 445.2 (M–H$_2$O+H).

6-(Maleimido)-caproamidyl-L-valine-L-citrulline-(4-amino-2-trifluoromethyl)benzoic acid (19)

Step C: The title compound was prepared from the product of the preceding step (18, 75 mg, 0.108 mmol), using Step D, Example 1, to give a white solid (47 mg, 66%). MS (ESI, pos.): calc'd for C$_{29}$H$_{37}$N$_6$O$_8$F$_3$, 654.3; found 655.3 (M+H).

Maytansin-N-methyl-L-alanine-(4-amino-2-trifluoromethyl)benzamido-Cit-Val-Cap-Mal (20)

Step D: The title compound was prepared from the product of the preceding step (19, 34 mg, 0.052 mmol) and maytansin-N-methyl-L-alanine (9, 34 mg, 0.052 mmol), using Step E, Example 1, to give a white solid (11 mg, 16%) after a second ISCO purification (100 g C18 Aq Gold column, 30-70% MeCN in water, 0.05% HOAc both, over 15 min, 50 mL/min). MS (ESI, pos.): calc'd for C$_{61}$H$_{79}$N$_9$O$_{16}$ClF$_3$, 1285.5; found 1287.4 (M+H), 1268.4 (M–H$_2$O+H), 1308.4 (M+Na). $^1$H-NMR (500 MHz, DMSO-d$_6$): δ 10.4 (s, 1H), 8.16 (d, 1H, J=7 Hz), 8.13 (s, 1H), 7.80 (d, 1H, J=8 Hz), 7.25 (s, 1H), 7.12 (m, 1H), 6.99 (s, 2H), 6.93 (s, 1H), 6.84 (s, 1H), 6.63-6.55 (m, 2H), 6.01 (s, 1H), 5.95 (m, 1H), 5.58 (dd, 1H, J=15 Hz, 9 Hz), 5.38 (m, 3H), 4.64 (dd, 1H, J=12 Hz, 3 Hz), 4.30 (m, 1H), 4.17-4.08

(m, 2H), 3.96 (s, 2H), 3.93 (m, 1H), 3.53 (d, 1H, J=9 Hz), 3.40 (br m, 1H), 3.36 (m, 1H), 3.27 (s, 3H), 3.25 (m, 1H), 3.04 (s, 3H), 3.03-2.92 (m, 2H), 2.84-2.70 (m, 2H), 2.53 (m, 2H), 2.20-2.09 (m, 3H), 1.94 (m, 1H), 1.70 (m, 1H), 1.64 (s, 3H), 1.60-1.53 (m, 3H), 1.51-1.44 (m, 6H), 1.40 (m, 1H), 1.37-1.32 (m, 3H), 1.30-1.24 (m, 2H), 1.20-1.12 (m, 5H), 0.89 (m, 1H), 0.86 (s, 3H), 0.84-0.80 (m, 6H).

Example 4

Figure 8:
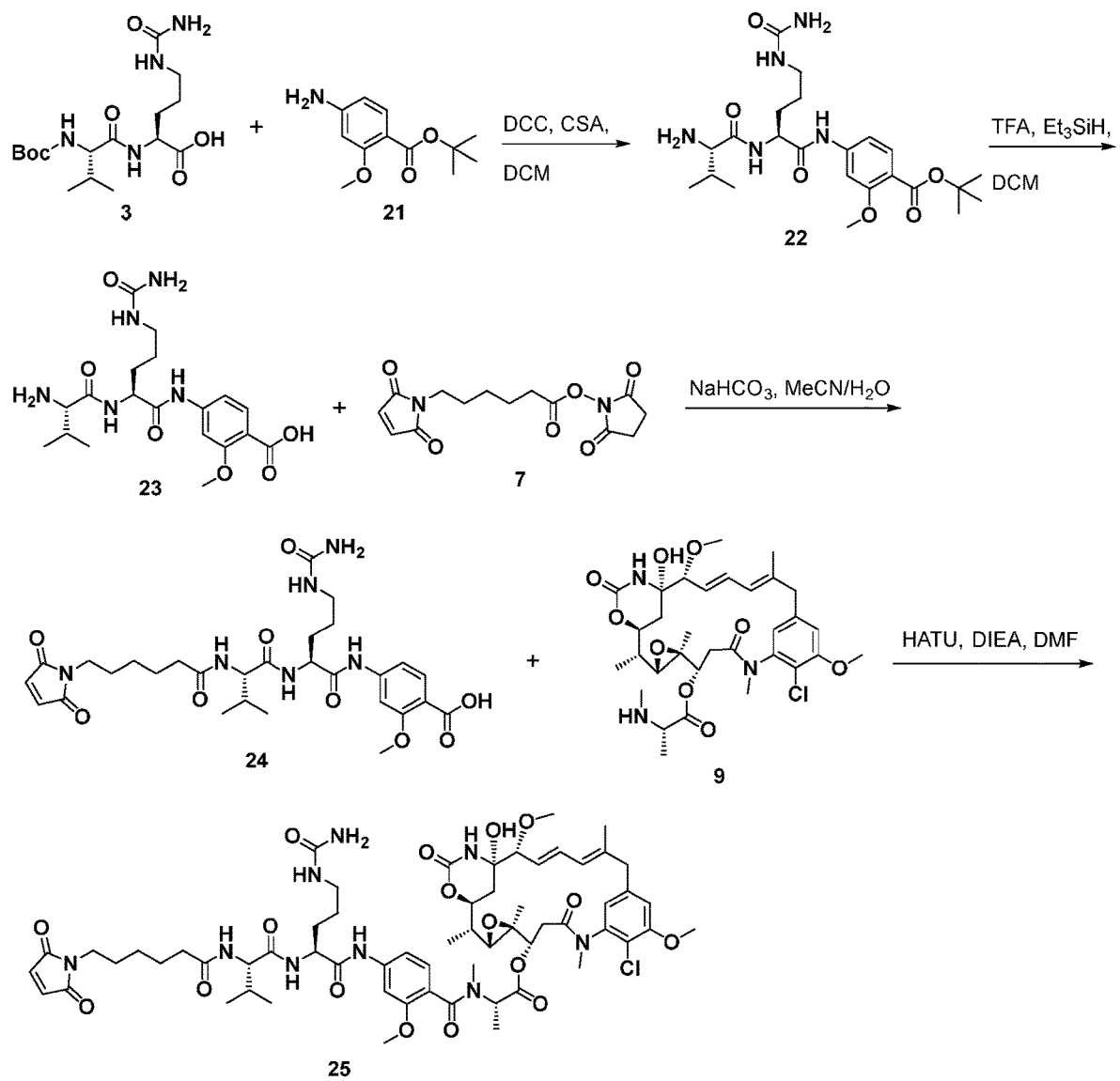
FIG. 8 depicts a synthetic sequence for preparing maytansin-N-methyl-L-alanine-(4-amino-2-methoxy)benzamido-Cit-Val-Cap-Mal.

Compound 25 was synthesized as described below and as depicted in FIG. 8.

Maytansin-N-methyl-L-alanine-(4-amino-2-methoxy)benzamido-Cit-Val-Cap-Mal (25)

Boc-L-valine-L-citrulline-(4-amino-2-methoxy)benzoic acid t-butyl ester (22)

Step A: The title compound was prepared from Boc-L-valine-L-citrulline (3, 143 mg, 0.382 mmol) and tert-butyl-4-amino-2-methoxybenzoate (109 mg, 0.488 mmol), using the method of Wipf & Heimgartner (*Helv. Chim. Acta,* 1998, 71, 140-154) to give a white solid (92 mg, 42%). MS (ESI, neg.): calc'd for $C_{28}H_{45}N_5O_8$, 579.3; found 580.3 (M–H), 602.3 (M+Na).

L-valine-L-citrulline-(4-amino-2-methoxy)benzoic acid trifluoroacetate salt (23)

Step B: The title compound was prepared from the product of the preceding step (22, 90 mg, 0.155), using Step C, Example 1, to give a pale solid (99 mg) that was triturated twice with DCM, dissolved in MeCN and THF, filtered, and the solvent evaporated in vacuo to give the title compound as an off-white solid (79 mg, 95%). MS (ESI, pos.): calc'd for $C_{19}H_{29}N_5O_6$, 423.2; found 424.2 (M+H), 407.2 (M–H$_2$O+H), 446.2 (M+Na).

6-(Maleimido)-caproamidyl-L-valine-L-citrulline-(4-amino-2-methoxy)benzoic acid (24)

Step C: The title compound was prepared from the product of the preceding step (23, 76 mg, 0.141 mmol), using Step D, Example 1, to give a white solid (50 mg, 57%). MS (ESI, pos.): calc'd for $C_{29}H_{40}N_6O_9$, 616.3; found 617.2 (M+H).

Maytansin-N-methyl-L-alanine-(4-amino-2-methoxy)benzamido-Cit-Val-Cap-Mal (25)

Step D: The title compound was prepared from the product of the preceding step (24, 49 mg, 0.079 mmol) and maytansin-N-methyl-L-alanine (9, 34 mg, 0.052 mmol), using Step E, Example 1, to give a white solid (34 mg, 34%). MS (ESI, pos.): calc'd for $C_{61}H_{82}N_9O_{17}Cl$, 1247.6; found 1248.5 (M+H), 1230.5 (M–H$_2$O+H), 1270.5 (M+Na). $^1$H-NMR (500 MHz, DMSO-d$_6$): δ 9.26 (br s, 1H), 7.49 (br m, 1H), 6.99 (m, 1H), 6.95 (s, 1H), 6.87 (s, 1H), 6.85 (m, 1H), 6.69 (s, 2H), 6.45 (dd, 1H, J=15 Hz, 11 Hz), 6.29 (br s, 1H), 5.73 (dd, 1H, J=16 Hz, 10 Hz), 4.84 (d, 1H, J=12 Hz), 4.70 (br m, 1H), 4.30 (t, 1H, J=12 Hz), 4.01 (s, 3H), 3.74 (br m, 4H), 3.55-3.47 (m, 5H), 3.35 (s, 3H), 3.14 (m, 2H), 3.02 (m, 4H), 2.83 (br s, 3H), 2.71 (s, 3H), 2.65 (m, 1H), 2.60 (t, 1H, J=8 Hz), 2.24-2.18 (m, 3H), 2.09 (m, 1H), 1.77 (pentet, 1H, J=8 Hz), 1.70-1.61 (m, 6H), 1.67 (s, 3H), 1.51-1.40 (m, 6H), 1.30-1.26 (m, 5H), 0.94 (m, 6H), 0.85 (s, 3H).

Example 5

Figure 9:
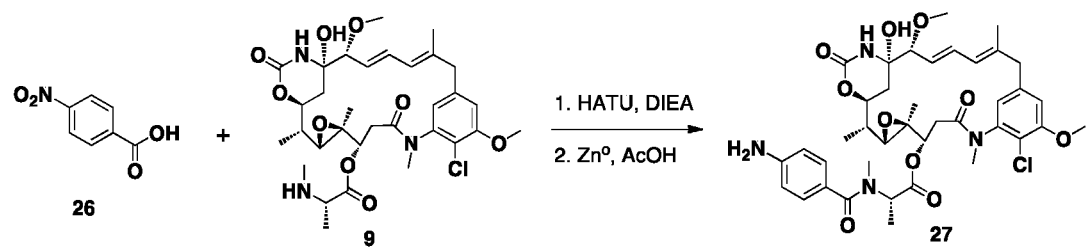
FIG. 9 depicts a synthetic sequence for preparing maytansin-N-methyl-L-alanine-4-aminobenzamide.

Compound 27 was synthesized from Compound 26 as described below and as depicted in FIG. 9.

Maytansin-N-methyl-L-alanine-4-aminobenzamide (27)

Step A:
Maytansin-N-methyl-L-alanine-(4-nitro)benzamide

To a dry, round-bottom flask was weighed maytansin-N-methyl-L-alanine (9, 96 mg, 0.15 mmol), 4-nitrobenzoic acid (26) (42 mg, 0.25 mmol), and HATU (0.12 g, 0.31 mmol). The reagents were dissolved in anhydrous DMF (3.0 mL), treated with DIEA (0.10 mL, 0.57 mmol), and the flask purged with argon and sealed with a rubber septum. The reaction was stirred at ambient temperature for 3 d, after which LCMS showed complete conversion of Maytan-NMA, so it was diluted with a few mL of water and purified directly on a 100 g C18 Aq Gold column (gradient elution: 20-80% MeCN in water, 0.05% acetic acid in both, over 15 min). The cleanest product fractions were combined, partially concentrated in vacuo, frozen on dry ice, and lyophilized overnight giving the title compound as a yellow solid (64 mg, 54%). MS (ESI, pos.): calc'd for $C_{39}H_{47}N_4O_{12}Cl$, 798.3; found 798.4 (M+H).

Step B: Maytan-NMA-(4-amino)benzamide (27)

The product of the preceding step (63 mg, 0.079 mmol) and zinc dust (<10 um, 98+% pure, 108 mg, 1.65 mmol) were dissolved/suspended in a mixture of THF (4 mL) and water (1 mL). Acetic acid (0.180 mL, 3.14 mmol) was added to the mixture, the flask sealed with a rubber septum, and the reaction stirred at ambient temperature for 1 h. LCMS of the crude mixture showed complete conversion, so the reaction was filtered over Celite, washed off with MeCN, and the filtrate concentrated in vacuo. The crude product was purified directly on a 50 g C18 Aq Gold column (gradient elution: 20-80% MeCN in water, 0.05% acetic acid in both, over 12 min). The cleanest product fractions were combined, partially concentrated in vacuo, frozen on dry ice, and lyophilized overnight giving 46 mg of white solid that was only 88% pure by LCMS. This was dissolved in 1:1 MeCN/water (3 mL) and repurified by HPLC using a Phenomenex Gemini C18 5 u, 30×150 mm column in two injections (40-80% and 30-70% MeCN in water, 0.05% HOAc both phases, over 20 min, 30 mL/min), and the cleanest fraction were concentrated, frozen, and lyophilized as above giving the title compound as a white solid (31 mg, 48%). MS (ESI, pos.): calc'd for $C_{41}H_{53}N_4O_{12}Cl$, 768.3; found 751.2 (M–H$_2$O+H), 769.2 (M+H). $^1$H-NMR (500 MHz, CDCl$_3$): δ 7.24 (d, 2H, J=9 Hz), 6.93 (s, 1H), 6.82 (s, 1H), 6.76 (d, 1H, J=12 Hz), 6.57 (d, 2H, J=9 Hz), 6.45 (dd, 1H, J=16 Hz, 12 Hz), 6.23 (s, 1H), 5.74 (dd, 1H, J=16 Hz, 9 Hz), 5.43 (br m, 1H), 4.87 (dd, 1H, J=12 Hz, 3 Hz), 4.32 (m, 1H), 3.99 (s, 3H), 3.85 (s, 2H), 3.65 (d, 1H, J=13 Hz), 3.51 (d, 1H, J=9 Hz), 3.47 (br s, 1H), 3.36 (s, 3H), 3.10 (d, 1H, J=13 Hz), 3.07 (s, 3H), 3.04 (d, 1H, J=9 Hz), 2.93 (s, 3H), 2.67 (m, 1H), 2.20 (dd, 1H, J=14 Hz, 3 Hz), 1.67 (m, 1H), 1.66 (s, 3H), 1.51-1.47 (m, 2H), 1.44 (d, 3H, J=7 Hz), 1.31 (d, 3H, J=7 Hz), 1.27 (m, 1H), 0.84 (s, 3H).

Example 6

Figure 10:
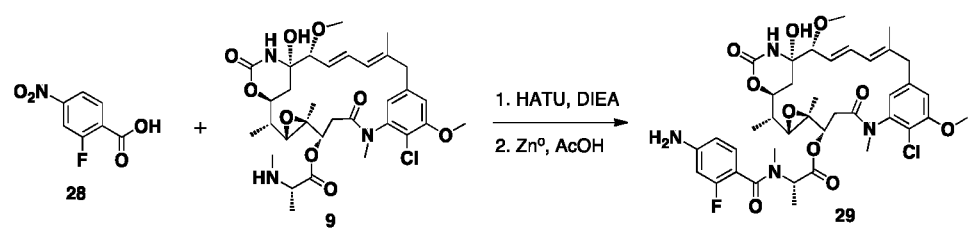
FIG. 10 depicts a synthetic sequence for preparing maytansin-N-methyl-L-alanine-(2-fluoro-4-amino)benzamide

Compound 29 was synthesized from Compound 28 as described below and as depicted in FIG. 10.

Maytansin-N-methyl-L-alanine-(2-fluoro-4-amino)benzamide (29)

Step A: Maytansin-N-methyl-L-alanine-(2-fluoro-4-nitro)benzamide

The title compound was prepared from maytansin-N-methyl-L-alanine (9, 40 mg, 0.056 mmol) and 2-fluoro-4-nitrobenzoic acid (28) (26 mg, 0.140 mmol), using Step A of Example 5, to give a light yellow solid (16 mg, 35%). MS (ESI, pos.): calc'd for $C_{39}H_{46}N_4O_{12}ClF$, 816.3; found 817.2 (M+H), 839.2 (M+Na).

Step B: Maytan-NMA-(2-fluoro-4-amino)benzamide (29)

The title compound was prepared from the product of the preceding step (15 mg, 0.018 mmol), using Step B of Example 5, to give a white solid (8 mg, 50%). MS (ESI, pos.): calc'd for $C_{39}H_{48}N_4O_{10}ClF$, 786.3; found 769.2 (M–H$_2$O+H), 787.2 (M+H), 809.3 (M+Na). $^1$H-NMR (500 MHz, CDCl$_3$): δ 7.05-6.99 (m, 2H), 6.92 (s, 1H), 6.85 (s, 1H), 6.81 (d, 1H, J=11 Hz), 6.47 (dd, 1H, J=15 Hz, 11 Hz), 6.36-6.29 (m, 2H), 6.22 (s, 1H), 5.73 (dd, 1H, J=16 Hz, 9 Hz), 5.48 (m, 1H), 4.87 (dd, 1H, J=12 Hz, 3 Hz), 4.30 (m, 1H), 4.00 (s, 3H), 3.93 (s, 2H), 3.73 (d, 1H, J=13 Hz), 3.51 (d, 1H, J=9 Hz), 3.41 (br m, 1H), 3.36 (s, 3H), 3.13 (d, 1H, J=12 Hz), 3.04 (s, 3H), 3.02 (m, 1H), 2.83 (s, 3H), 2.66 (dd, 1H, J=15 Hz, 13 Hz), 2.19 (dd, 1H, J=15 Hz, 3 Hz), 1.67 (s, 3H), 1.63 (m, 1H), 1.51-1.45 (m, 2H), 1.43 (d, 3H, J=7 Hz), 1.30 (d, 3H, J=7 Hz), 1.27 (m, 1H), 0.84 (s, 3H).

Example 7

Figure 11:
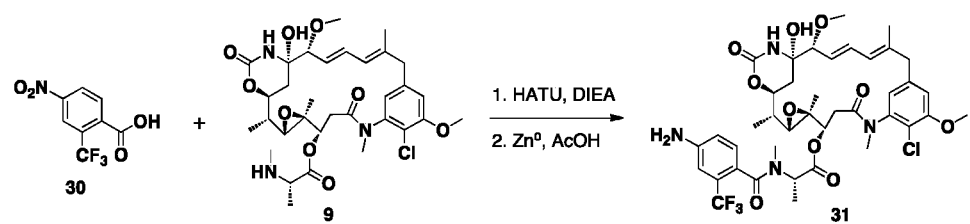
FIG. 11 depicts a synthetic sequence for preparing maytansin-N-methyl-L-alanine-(2-trifluoromethyl-4-amino)benzamide.

Compound 31 was synthesized as described below and as depicted in FIG. 11.

Maytansin-N-methyl-L-alanine-(2-trifluoromethyl-4-amino)benzamide (31)

Step A: Maytansin-N-methyl-L-alanine-(2-trifluoromethyl-4-nitro)benzamide

The title compound was prepared from maytansin-N-methyl-L-alanine (9, 68 mg, 0.105 mmol) and 2-trifluoromethyl-4-nitrobenzoic acid (30) (37 mg, 0.157 mmol), using Step A of Example 5, to give a pale yellow solid (82 mg, 90%). MS (ESI, pos.): calc'd for $C_{40}H_{46}N_4O_{12}ClF_3$, 866.3; found 867.1 (M+H), 889.1 (M+Na).

Step B: Maytan-NMA-(2-trifluoromethyl-4-amino)benzamide (31)

The title compound was prepared from the product of the preceding step (79 mg, 0.091 mmol), using Step B of Example 5, to give a white solid (29 mg, 35%). MS (ESI, pos.): calc'd for $C_{40}H_{48}N_4O_{10}ClF_3$, 836.3; found 818.8 (M–H$_2$O+H), 836.8 (M+H), 858.0 (M+Na). $^1$H-NMR (500 MHz, CDCl$_3$): δ 7.00-6.91 (m, 3H), 6.85 (d, 1H, J=3 Hz), 6.75 (br d, 1H, J=18 Hz), 6.63 (d, 1H, J=11 Hz), 6.45 (dd, 1H, J=26 Hz, 19 Hz), 6.23 (s, 1H), 5.73 (dd, 1H, J=26 Hz, 15 Hz), 4.88 (dd, 1H, J=20 Hz, 5 Hz), 4.31 (m, 1H), 4.01 (s, 3H), 3.96 (m, 1H), 3.66 (d, 1H, J=22 Hz), 3.52 (d, 1H, J=15 Hz), 3.37 (s, 3H), 3.14 (s, 3H), 3.11 (m, 1H), 3.03 (d, 1H, J=16 Hz), 2.72 (m, 1H), 2.66 (s, 3H), 2.23 (dd, 1H, J=24 Hz, 5 Hz), 1.66 (s, 3H), 1.51-1.45 (m, 2H), 1.43 (d, 3H, J=12 Hz), 1.31 (d, 3H, J=11 Hz), 1.27 (m, 1H), 0.87 (s, 3H).

Example 8

Figure 12:
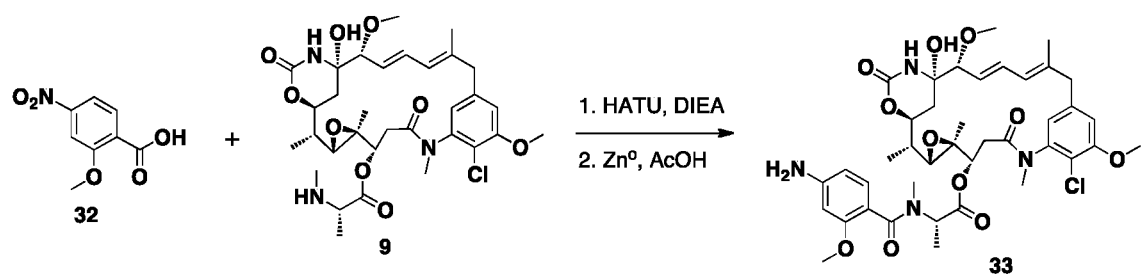
FIG. 12 depicts a synthetic sequence for preparing maytansin-N-methyl-L-alanine-(2-methoxy-4-amino)benzamide.

Compound 33 was synthesized as described below and as depicted in FIG. 12.

Maytansin-N-methyl-L-alanine-(2-methoxy-4-amino)benzamide (33)

Step A: Maytansin-N-methyl-L-alanine-(2-methoxy-4-nitro)benzamide

The title compound was prepared from maytansin-N-methyl-L-alanine (9, 68 mg, 0.105 mmol) and 2-methoxy-4-nitrobenzoic acid (32) (32 mg, 0.162 mmol), using Step A of Example 5, to give a pale yellow solid (78 mg, 90%). MS (ESI, pos.): calc'd for $C_{40}H_{49}N_4O_{13}Cl$, 828.3; found 811.1 (M–H$_2$O+H), 829.2 (M+H), 851.2 (M+Na).

Step B: Maytan-NMA-(2-methoxy-4-amino)benzamide (33)

The title compound was prepared from the product of the preceding step (75 mg, 0.090 mmol), using Step B of Example 5, to give a white solid (62 mg, 79%). MS (ESI, pos.): calc'd for $C_{40}H_{51}N_4O_{11}Cl$, 798.3; found 781.2 (M–H$_2$O+H), 799.2 (M+H), 821.2 (M+Na). $^1$H-NMR (500 MHz, CDCl$_3$): δ 7.03 (d, 1H, J=14 Hz), 6.99 (s, 1H), 6.94 (d, 1H, J=12 Hz), 6.86 (s, 1H), 6.81 (d, 1H, J=8 Hz), 6.46 (dd, 1H, J=16 Hz, 11 Hz), 6.24 (s, 1H), 6.17 (s, 1H), 6.11 (d, 1H, J=8 Hz), 5.73 (dd, 1H, J=15 Hz, 9 Hz), 5.54 (m, 1H), 4.81 (m, 1H), 4.31 (t, 1H, J=11 Hz), 4.00 (s, 3H), 3.81 (d, 1H, J=13 Hz), 3.79 (m, 1H), 3.52 (d, 1H, J=9 Hz), 3.36 (s, 3H), 3.12 (d, 1H, J=13 Hz), 3.04 (m, 1H), 3.02 (s, 3H), 2.72 (s, 3H), 2.64 (t, 1H, J=12 Hz), 2.18 (dd, 1H, J=14 Hz, 3 Hz), 1.66 (s, 3H), 1.63 (m, 2H), 1.51-1.45 (m, 2H), 1.41 (d, 3H, J=7 Hz), 1.30 (d, 3H, J=7 Hz), 1.26 (m, 1H), 0.84 (s, 3H).

Example 9

Figure 13:
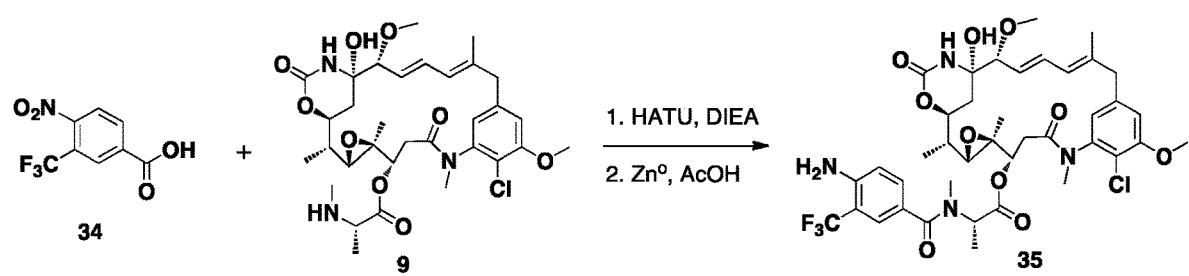
FIG. 13 depicts a synthetic sequence for preparing maytansin-N-methyl-L-alanine-N-(3-trifluoromethyl-4-amino)benzamide.

Compound 35 was synthesized as described below and as depicted in FIG. 13.

Maytansin-N-methyl-L-alanine-N-(3-trifluoromethyl-4-amino)benzamide (35)

Step A: Maytansin-N-methyl-L-alanine-(3-trifluoromethyl-4-nitro)benzamide

The title compound was prepared from maytansin-N-methyl-L-alanine (9, 46 mg, 0.071 mmol) and 3-trifluoromethyl-4-nitrobenzoic acid (34) (25 mg, 0.106 mmol), using the method from Step A of Example 5, to give a light yellow solid (37 mg, 61%). MS (ESI, pos.): calc'd for $C_{40}H_{46}N_4O_{12}ClF_3$, 866.3; found 849.2 (M–H$_2$O+H), 867.2 (M+H), 889.2 (M+Na).

Step B: Maytansin-N-methyl-L-alanine-N-(3-trifluoromethyl-4-amino)benzamide (35)

The title compound was prepared from the product of the preceding step (36 mg, 0.042 mmol), using the method from Step B of Example 5, to give a white solid (17 mg, 46%). MS (ESI, pos.): calc'd for $C_{40}H_{48}N_4O_{10}ClF_3$, 836.3; found 819.2 (M–H$_2$O+H), 837.2 (M+H), 859.2 (M+Na). $^1$H-NMR (500 MHz, CDCl$_3$): d 7.54 (s, 1H), 7.37 (d, 1H, J=8 Hz), 6.91 (br s, 1H), 6.83 (s, 1H), 6.70 (d, 1H, J=11 Hz), 6.66 (d, 1H, J=8 Hz), 6.45 (dd, 1H, J=15 Hz, 11 Hz), 6.28 (s, 1H), 5.73 (dd, 1H, J=16 Hz, 9 Hz), 5.44 (m, 1H), 4.88 (dd, 1H, J=12 Hz, 3 Hz), 4.40 (s, 2H), 4.30 (t, 1H, J=11 Hz), 3.99 (s, 3H), 3.63 (d, 1H, J=13 Hz), 3.52 (d, 1H, J=9 Hz), 3.36 (s, 3H), 3.12 (d, 1H, J=13 Hz), 3.03 (m, 4H), 2.92 (s, 3H), 2.69 (m, 1H), 2.21 (dd, 1H, J=14 Hz, 3 Hz), 1.65 (m, 4H), 1.52-1.44 (m, 4H), 1.31 (d, 3H, J=6 Hz), 1.26 (m, 2H), 0.85 (s, 3H).

Example 10

Figure 14:
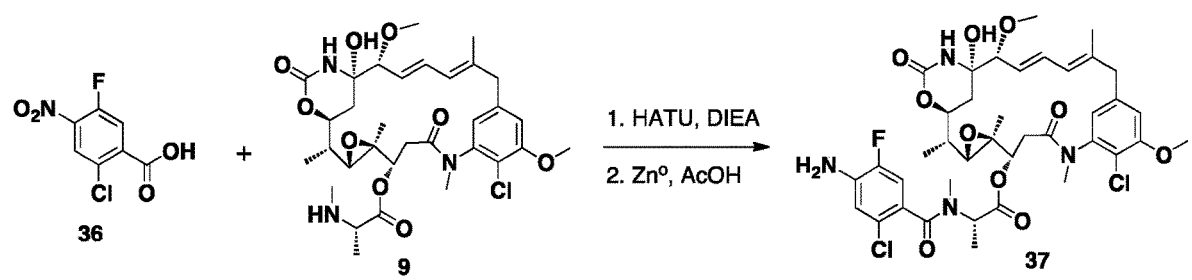
FIG. 14 depicts a synthetic sequence for preparing maytansin-N-methyl-L-alanine-N-(2-chloro-4-amino-5-fluoro)benzamide.
Figure 15:
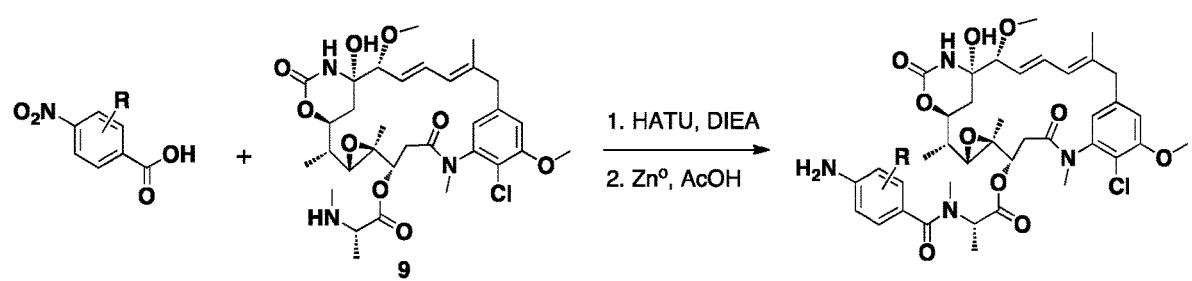
FIG. 15 depicts a general synthetic sequence for preparing compounds of Formula (II) wherein substituent R is defined herein and below.

Compound 37 was synthesized as described below and as depicted in FIG. 14.

Maytansin-N-methyl-L-alanine-N-(2-chloro-4-amino-5-fluoro)benzamide (37)

Step A: Maytansin-N-methyl-L-alanine-(2-chloro-4-nitro-5-fluoro)benzamide

The title compound was prepared from maytansin-N-methyl-L-alanine (9, 46 mg, 0.071 mmol) and 3-trifluoromethyl-4-nitrobenzoic acid (36.26 mg, 0.118 mmol), using the method from Step A of Example 5, to give a white solid (33 mg, 55%). MS (ESI, pos.): calc'd for $C_{39}H_{45}N_4O_{12}Cl_2F$, 850.2; found 833.1 (M–H$_2$O+H), 851.1 (M+H), 873.1 (M+Na).

Step B: Maytansin-N-methyl-L-alanine-N-(2-chloro-4-amino-5-fluoro)benzamide (37)

The title compound was prepared from the product of the preceding step (36 mg, 0.042 mmol), using the method from Step B of Example 5, to give a white solid (17 mg, 46%). MS (ESI, pos.): calc'd for $C_{39}H_{47}N_4O_{10}Cl_2F$, 820.3; found 803.2 (M–H$_2$O+H), 821.2 (M+H), 843.2 (M+Na). $^1$H-NMR (500 MHz, CDCl$_3$): d 6.88 (d, 2H, J=13 Hz), 6.83 (d, 1H, J=11 Hz), 6.77 (d, 1H, J=8 Hz), 6.72 (d, 1H, J=10 Hz), 6.46 (dd, 1H, J=15 Hz, 11 Hz), 6.25 (s, 1H), 5.71 (dd, 1H, J=16 Hz, 10 Hz), 5.52 (m, 1H), 4.85 (dd, 1H, J=12 Hz, 3 Hz), 4.30 (t, 1H, J=11 Hz), 4.01 (s, 3H), 3.92 (s, 2H), 3.73 (d, 1H, J=13 Hz), 3.52 (d, 1H, J=9 Hz), 3.37 (s, 3H), 3.15 (d, 1H, J=13 Hz), 3.10 (s, 3H), 3.03 (d, 1H, J=10 Hz), 2.75 (s, 3H), 2.68 (dd, 1H, J=14 Hz, 12 Hz), 2.22 (dd, 1H, J=15 Hz, 3 Hz), 1.67 (s, 3H), 1.61 (m, 1H), 1.50-1.43 (m, 5H), 1.31 (d, 3H, J=6 Hz), 1.27-1.24 (m, 1H), 0.86 (s, 3H).

Example 11

Figure 16:
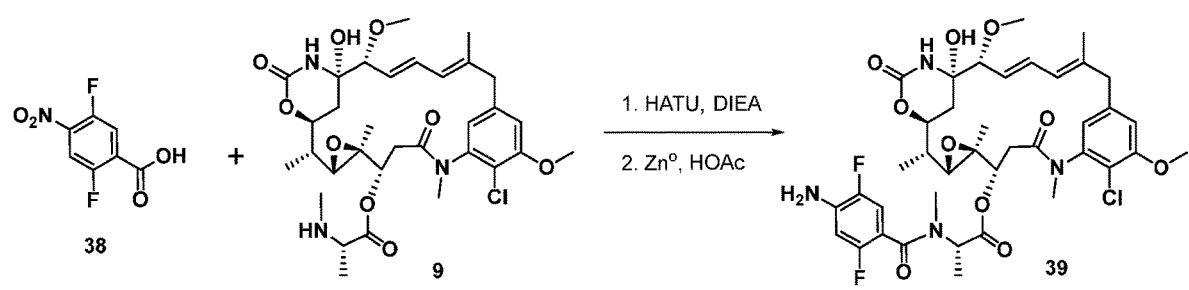
FIG. 16 depicts a synthetic sequence for preparing maytansin-N-methyl-L-alanine-N-(2,5-difluoro-4-amino)benzamide.

Compound 39 was synthesized as described below and as depicted in FIG. 16.

Maytansin-N-methyl-L-alanine-N-(2,5-difluoro-4-amino)benzamide (39)

Step A: Maytansin-N-methyl-L-alanine-(2,5-difluoro-4-nitro)benzamide

The title compound was prepared from maytansin-N-methyl-L-alanine (9, 48 mg, 0.074 mmol) and 2,5-difluoro-4-nitrobenzoic acid (38, 27 mg, 0.133 mmol), using the method from Step A of Example 5, to give a yellow solid (37 mg, 60%). MS (ESI, pos.): calc'd for $C_{39}H_{45}N_4O_{12}ClF_2$, 834.3; found 817.2 (M–H$_2$O+H), 835.2 (M+H), 857.2 (M+Na).

Step B: Maytansin-N-methyl-L-alanine-(2,5-difluoro-4-amino)benzamide (39)

The title compound was prepared from the product of the preceding step (36 mg, 0.043 mmol), using the method from Step B of Example 5, to give a white solid (22 mg, 59%). MS (ESI, pos.): calc'd for $C_{39}H_{47}N_4O_{10}ClF_2$, 804.3; found 787.3 (M–H$_2$O+H), 805.3 (M+H), 827.3 (M+Na). $^1$H-NMR (500 MHz, CDCl$_3$): δ 6.89-6.84 (m, 3H), 6.77 (d, 1H, J=11 Hz), 6.49-6.41 (m, 2H), 6.24 (s, 1H), 5.72 (dd, 1H, J=16 Hz, 9 Hz), 5.47 (q, 1H, J=7 Hz), 4.87 (dd, 1H, J=12 Hz, 3 Hz), 4.30 (td, 1H, J=12 Hz, 2 Hz), 4.00 (m, 5H), 3.71 (d, 1H, J=13 Hz), 3.52 (d, 1H, J=9 Hz), 3.36 (s, 3H), 3.33 (br s, 1H), 3.13 (d, 1H, J=13 Hz), 3.06 (s, 3H), 3.02 (d, 1H, J=10 Hz), 2.83 (d, 3H, J=2 Hz), 2.66 (dd, 1H, J=15 Hz, 12 Hz), 2.18 (dd, 1H, J=14 Hz, 3 Hz), 1.67 (s, 3H), 1.63 (d, 1H, J=14 Hz), 1.51-1.45 (m, 1H), 1.43 (d, 3H, J=7 Hz), 1.31 (d, 3H, J=6 Hz), 1.27 (m, 1H), 0.84 (s, 3H).

Example 12

Figure 17:
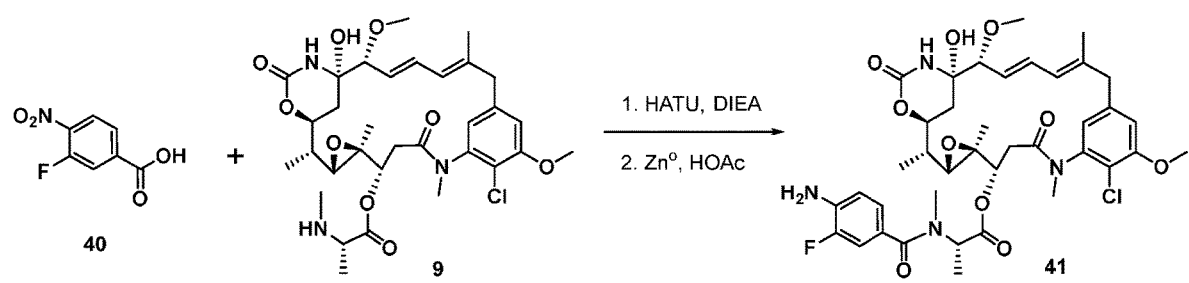
FIG. 17 depicts a synthetic sequence for preparing maytansin-N-methyl-L-alanine-(3-fluoro-4-amino)benzamide

Compound 41 was synthesized as described below and as depicted in FIG. 17.

Maytansin-N-methyl-L-alanine-(3-fluoro-4-amino)benzamide (41)

Step A: Maytansin-N-methyl-L-alanine-(3-fluoro-4-nitro)benzamide

The title compound was prepared from maytansin-N-methyl-L-alanine (9, 47 mg, 0.072 mmol) and 3-fluoro-4-nitrobenzoic acid (40) (24 mg, 0.130 mmol), using the method from Step A of Example 5, to give a yellow solid (40 mg, 68%). MS (ESI, pos.): calc'd for $C_{39}H_{46}N_4O_{12}ClF$, 816.3; found 799.2 (M–H$_2$O+H), 817.2 (M+H), 839.2 (M+Na).

Step B: Maytansin-N-methyl-L-alanine-(3-fluoro-4-amino)benzamide (41)

The title compound was prepared from the product of the preceding step (39 mg, 0.048 mmol), using the method from Step B of Example 5, to give a white solid (24 mg, 60%). MS (ESI, pos.): calc'd for $C_{39}H_{48}N_4O_{10}ClF$, 786.3; found 769.2 (M–H$_2$O+H), 787.2 (M+H), 809.2 (M+Na). $^1$H-NMR (500 MHz, CDCl$_3$): δ 7.11-7.04 (m, 2H), 6.89 (s, 1H), 6.83 (d, 1H, J=2 Hz), 6.72 (d, 1H, J=11 Hz), 6.68 (t, 1H, J=8 Hz), 6.45 (dd, 1H, J=15 Hz, 11 Hz), 6.25 (s, 1H), 5.72 (dd, 1H, J=15 Hz, 9 Hz), 5.43 (m, 1H), 4.86 (dd, 1H, J=12 Hz, 3 Hz), 4.31 (t, 1H, J=11 Hz), 3.99 (s, 3H), 3.92 (m, 2H), 3.62 (d, 1H, J=13 Hz), 3.51 (d, 1H, J=9 Hz), 3.40 (bs s, 1H), 3.36 (s, 3H), 3.12 (m, 1H), 3.08 (s, 3H), 3.04 (d, 1H, J=10 Hz), 2.92 (s, 3H), 2.68 (t, 1H, J=13 Hz), 2.20 (dd, 1H, J=15 Hz, 3 Hz), 1.66 (s, 3H), 1.63 (m, 1H), 1.49-1.46 (m, 1H), 1.44 (d, 3H, J=7 Hz), 1.31 (d, 3H, J=7 Hz), 1.27 (m, 1H), 0.84 (s, 3H).

Example 13

Figure 18:
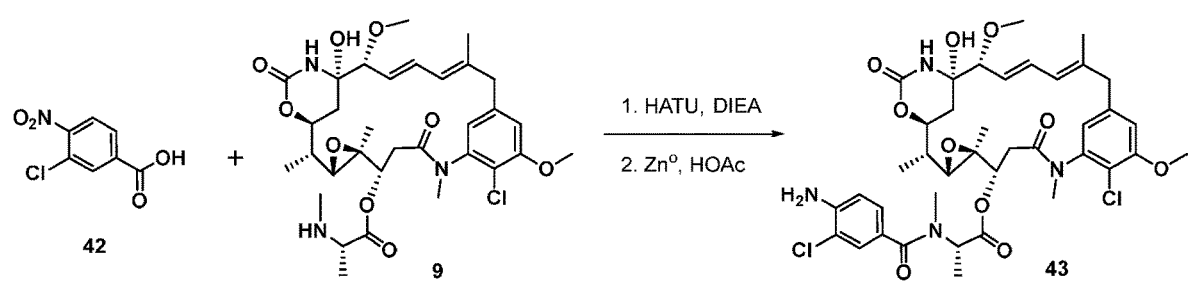
FIG. 18 depicts a synthetic sequence for preparing maytansin-N-methyl-L-alanine-(3-chloro-4-amino)benzamide.

Compound 43 was synthesized as described below and as depicted in FIG. 18.

Maytansin-N-methyl-L-alanine-(3-chloro-4-amino)benzamide (43)

Step A: Maytansin-N-methyl-L-alanine-(3-chloro-4-amino)benzamide

The title compound was prepared from maytansin-N-methyl-L-alanine (9, 45 mg, 0.069 mmol) and 3-chloro-4-nitrobenzoic acid (42) (26 mg, 0.129 mmol), using the method from Step A of Example 5, to give a yellow solid (36 mg, 62%). MS (ESI, pos.): calc'd for $C_{39}H_{46}N_4O_{12}Cl_2$, 832.2; found 815.2 (M–$H_2O$+H), 833.2 (M+H), 855.2 (M+Na).

Step B: Maytansin-N-methyl-L-alanine-(3-chloro-4-amino)benzamide (43)

The title compound was prepared from the product of the preceding step (35 mg, 0.042 mmol), using the method from Step B of Example 5, to give a white solid (24 mg, 67%). MS (ESI, pos.): calc'd for $C_{39}H_{48}N_4O_{10}Cl_2$, 802.3; found 785.2 (M–$H_2O$+H), 803.2 (M+H), 825.1 (M+Na). $^1$H-NMR (500 MHz, $CDCl_3$): δ 7.35 (s, 1H), 7.17 (d, 1H, J=8 Hz), 6.90 (s, 1H), 6.83 (d, 1H, J=2 Hz), 6.68 (m, 2H), 6.44 (dd, 1H, J=15 Hz, 11 Hz), 6.30 (s, 1H), 5.73 (dd, 1H, J=15 Hz, 9 Hz), 5.42 (m, 1H), 4.87 (dd, 1H, J=12 Hz, 3 Hz), 4.32-4.27 (m, 3H), 3.99 (s, 3H), 3.60 (d, 1H, J=13 Hz), 3.51 (d, 1H, J=10 Hz), 3.44 (bs s, 1H), 3.36 (s, 3H), 3.10 (m, 4H), 3.03 (d, 1H, J=10 Hz), 2.92 (s, 3H), 2.69 (m, 1H), 2.21 (dd, 1H, J=15 Hz, 3 Hz), 1.65 (s, 3H), 1.63 (m, 1H), 1.52-1.45 (m, 1H), 1.43 (d, 3H, J=7 Hz), 1.31 (d, 3H, J=7 Hz), 1.27 (m, 1H), 0.83 (s, 3H).

Example 14

Figure 19:
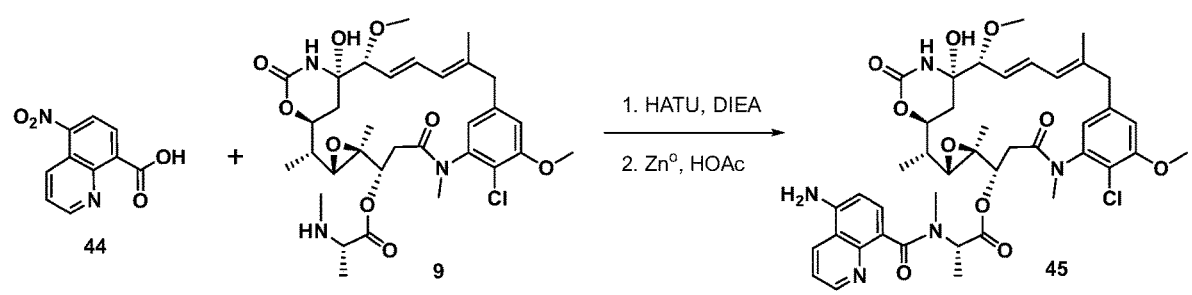
FIG. 19 depicts a synthetic sequence for preparing maytansin-N-methyl-L-alanine-(5-amino-8-carboxyquinoline)carboxamide.

Compound 45 was synthesized as described below and as depicted in FIG. 19.

Maytansin-N-methyl-L-alanine-(5-amino-8-carboxyquinoline)carboxamide (45)

Step A: Maytansin-N-methyl-L-alanine-(5-nitro-8-carboxyquinoline)carboxamide The title compound was prepared from maytansin-N-methyl-L-alanine (9, 45 mg, 0.069 mmol) and 5-nitro-8-carboxyquinoline (44) (24 mg, 0.110 mmol), using the method from Step A of Example 5, to give a pale yellow solid (26 mg, 44%). MS (ESI, pos.): calc'd for $C_{42}H_{48}N_5O_{12}Cl$, 849.3; found 832.2 (M–$H_2O$+H), 850.2 (M+H), 872.2 (M+Na).

Step B: Maytansin-N-methyl-L-alanine-(5-amino-8-carboxyquinoline)carboxamide (45)

The title compound was prepared from the product of the preceding step (25 mg, 0.029 mmol), using the method from Step B of Example 5, to give a pale yellow solid (8 mg, 31%). MS (ESI, pos.): calc'd for $C_{42}H_{50}N_5O_{10}Cl$, 819.3; found 802.3 (M–$H_2O$+H), 820.3 (M+H). $^1$H-NMR (500 MHz, DMSO-$d_6$): δ 8.80 (br s, 1H), 8.54 (d, 1H, J=10 Hz), 7.39 (br s, 1H), 7.28 (s, 1H), 7.05-7.00 (br m, 2H), 6.90 (s, 1H), 6.84 (m, 1H), 6.62 (dd, 1H, J=15 Hz, 11 Hz), 6.52 (br m, 1H), 6.22 (s, 2H), 5.98 (s, 1H), 5.62 (br m, 2H), 4.56 (br m, 1H), 4.11 (m, 1H), 3.98 (s, 3H), 3.64 (d, 1H, J=13 Hz), 3.53 (d, 1H, J=9 Hz), 3.27 (s, 3H), 2.92-2.88 (m, 3H), 2.81 (d, 1H, J=10 Hz), 2.42 (br s, 2H), 2.07-2.04 (m, 1H), 1.75 (m, 2H), 1.66 (s, 3H), 1.55-1.45 (m, 3H), 1.42 (d, 3H, J=7 Hz), 1.32 (d, 1H, J=14 Hz), 1.24 (s, 1H), 1.14 (d, 3H, J=7 Hz), 0.84 (s, 3H).

Example 15

Figure 20:
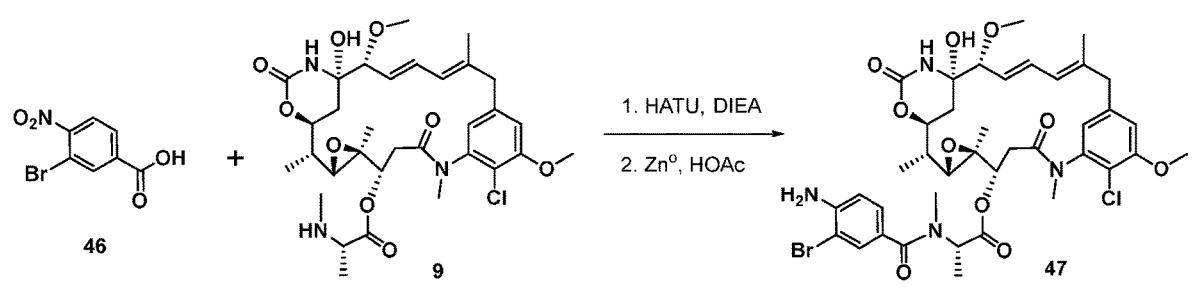
FIG. 20 depicts a synthetic sequence for preparing maytansin-N-methyl-L-alanine-(3-bromo-4-amino)benzamide.

Compound 47 was synthesized as described below and as depicted in FIG. 20.

Maytansin-N-methyl-L-alanine-(3-bromo-4-amino)benzamide (47)

Step A: Maytansin-N-methyl-L-alanine-(3-bromo-4-nitro)benzamide

The title compound was prepared from maytansin-N-methyl-L-alanine (9, 49 mg, 0.075 mmol) and 3-bromo-4-nitrobenzoic acid (46) (30 mg, 0.122 mmol), using the method from Step A of Example 5, to give a yellow solid (38 mg, 58%). MS (ESI, pos.): calc'd for $C_{39}H_{46}N_4O_{12}BrCl$, 876.2/878.2; found 861.1 (M–$H_2O$+H), 879.1 (M+H), 901.1 (M+Na) for the most abundant isotopes.

Step B: Maytansin-N-methyl-L-alanine-(3-bromo-4-amino)benzamide (47)

The title compound was prepared from the product of the preceding step (37 mg, 0.042 mmol), using the method from Step B of Example 5, to give a white solid (28 mg, 74%). MS (ESI, pos.): calc'd for $C_{39}H_{48}N_4O_{10}BrCl$, 846.2/848.2; found 831.1 (M–$H_2O$+H), 849.1 (M+H), 871.2 (M+Na) for the most abundant isotopes. $^1$H-NMR (500 MHz, $CDCl_3$): δ 7.51 (s, 1H), 7.20 (d, 1H, J=8 Hz), 6.90 (s, 1H), 6.83 (s, 1H), 6.68 (m, 2H), 6.44 (dd, 1H, J=15 Hz, 11 Hz), 6.33 (s, 1H), 5.74 (dd, 1H, J=15 Hz, 10 Hz), 5.42 (m, 1H), 4.88 (dd, 1H, J=12 Hz, 3 Hz), 4.31 (m, 3H), 3.99 (s, 3H), 3.60 (d, 1H, J=13 Hz), 3.51 (d, 1H, J=9 Hz), 3.46 (br s, 1H), 3.36 (s, 3H), 3.10 (s, 3H), 3.09 (m, 1H), 3.03 (d, 1H, J=10 Hz), 2.70 (t, 1H, J=13 Hz), 2.21 (dd, 1H, J=15 Hz, 3 Hz), 1.65 (s, 3H), 1.51-1.45 (m, 2H), 1.43 (d, 3H, J=7 Hz), 1.30 (d, 3H, J=6 Hz), 1.27 (m, 1H), 0.85 (s, 3H).

Example 16

Figure 21:
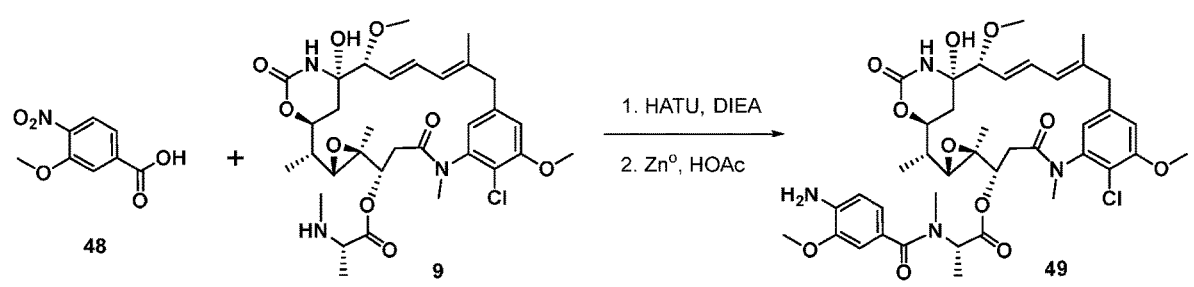
FIG. 21 depicts a synthetic sequence for preparing maytansin-N-methyl-L-alanine-(3-methoxy-4-amino)benzamide.

Compound 49 was synthesized as described below and as depicted in FIG. 21.

Maytansin-N-methyl-L-alanine-(3-methoxy-4-amino)benzamide (49)

Step A: Maytansin-N-methyl-L-alanine-(3-methoxy-4-nitro)benzamide

The title compound was prepared from maytansin-N-methyl-L-alanine (9, 49 mg, 0.075 mmol) and 3-methoxy-4-nitrobenzoic acid (48) (23 mg, 0.117 mmol), using the method from Step A of Example 5, to give a yellow solid (34 mg, 55%). MS (ESI, pos.): calc'd for $C_{40}H_{49}N_4O_{13}Cl$, 828.3; found 811.2 (M–$H_2O$+H), 829.3 (M+H), 851.3 (M+Na).

Step B: Maytansin-N-methyl-L-alanine-(3-methoxy-4-amino)benzamide (49)

The title compound was prepared from the product of the preceding step (33 mg, 0.040 mmol), using the method from Step B of Example 5, to give a white solid (25 mg, 74%).

MS (ESI, pos.): calc'd for $C_{40}H_{51}N_4O_{11}Cl$, 798.3; found 781.2 (M–H$_2$O+H), 799.2 (M+H). $^1$H-NMR (500 MHz, CDCl$_3$): d 6.94 (s, 1H), 6.92 (s, 1H), 6.85 (d, 1H, J=8 Hz), 6.81 (s, 1H), 6.74 (br d, 1H, J=10 Hz), 6.54 (d, 1H, J=10 Hz), 6.44 (dd, 1H, J=15 Hz, 11 Hz), 6.33 (s, 1H), 5.76 (m, 1H), 5.43 (br s, 1H), 4.87 (dd, 1H, J=12 Hz, 3 Hz), 4.31 (t, 1H, J=11 Hz), 3.98 (s, 3H), 3.70 (s, 3H), 3.64 (br d, 1H, J=13 Hz), 3.36 (s, 3H), 3.11-3.02 (m, 5H), 2.94 (s, 3H), 2.68 (m, 1H), 2.20 (dd, 1H, J=14 Hz, 3 Hz), 1.67 (m, 1H), 1.65 (s, 3H), 1.49 (dd, 1H, J=9 Hz, 7 Hz), 1.44 (d, 3H, J=7 Hz), 1.30 (d, 3H, J=7 Hz), 1.27 (m, 1H), 0.85 (s, 3H).

Example 17

Figure 22:
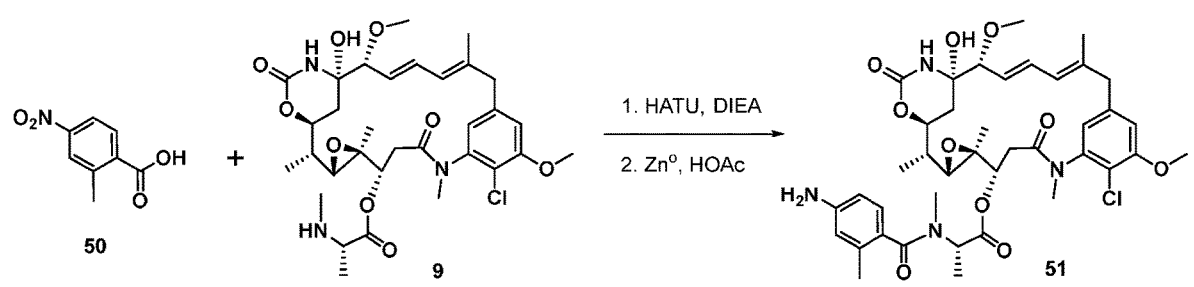
FIG. 22 depicts a synthetic sequence for preparing maytansin-N-methyl-L-alanine-(2-methyl-4-amino)benzamide.

Compound 51 was synthesized as described below and as depicted in FIG. 22.

Maytansin-N-methyl-L-alanine-(2-methyl-4-amino) benzamide (51)

Step A: Maytansin-N-methyl-L-alanine-(2-methyl-4-nitro)benzamide

The title compound was prepared from maytansin-N-methyl-L-alanine (9, 49 mg, 0.075 mmol) and 2-methyl-4-nitrobenzoic acid (50) (24 mg, 0.132 mmol), using the method from Step A of Example 5, to give a pale yellow solid (32 mg, 52%). MS (ESI, pos.): calc'd for $C_{40}H_{49}N_4O_{12}Cl$, 812.3; found 795.3 (M–H$_2$O+H), 813.3 (M+H), 835.3 (M+Na).

Step B: Maytansin-N-methyl-L-alanine-(2-methyl-4-amino)benzamide (51)

The title compound was prepared from the product of the preceding step (30 mg, 0.037 mmol), using the method from Step B of Example 5, to give a white solid (17 mg, 55%). MS (ESI, pos.): calc'd for $C_{40}H_{51}N_4O_{10}Cl$, 782.3; found 765.2 (M–H$_2$O+H), 783.2 (M+H). $^1$H-NMR (500 MHz, CDCl$_3$): d 6.93 (s, 1H), 6.85 (s, 1H), 6.81 (d, 1H, J=8 Hz), 6.77 (d, 1H, J=11 Hz), 6.49 (s, 1H), 6.45 (dd, 1H, J=15 Hz, 11 Hz), 6.34 (d, 1H, J=7 Hz), 6.28 (s, 1H), 5.74 (dd, 1H, J=15 Hz, 9 Hz), 5.38 (m, 1H), 4.90 (m, 1H), 4.32 (t, 1H, J=11 Hz), 4.00 (s, 3H), 3.69 (d, 1H, J=13 Hz), 3.51 (d, 1H, J=9 Hz), 3.36 (s, 3H), 3.15 (m, 1H), 3.12 (s, 3H), 3.01 (d, 1H, J=10 Hz), 2.73 (s, 3H), 2.69 (m, 1H), 2.22 (m, 1H), 2.18 (s, 3H), 1.68 (m, 1H), 1.66 (s, 3H), 1.51 (m, 1H), 1.47 (d, 3H, J=7 Hz), 1.30 (d, 3H, J=6 Hz), 1.28 (m, 1H), 0.87 (s, 3H).

Example 18

Figure 23:
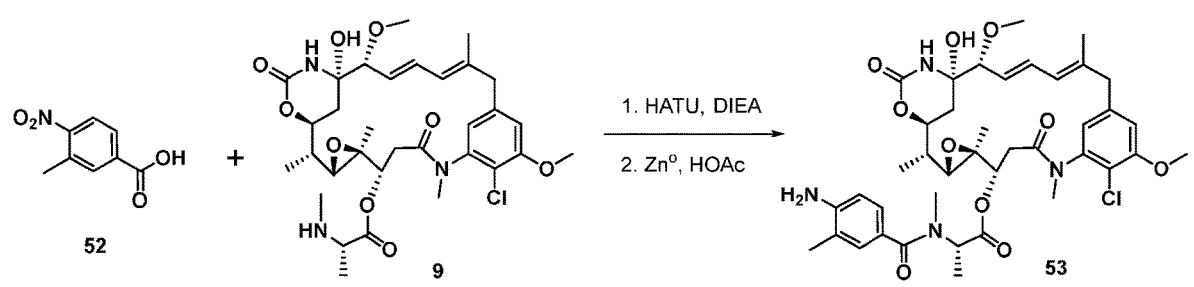
FIG. 23 depicts a synthetic sequence for preparing maytansin-N-methyl-L-alanine-(3-methyl-4-amino)benzamide.

Compound 53 was synthesized as described below and as depicted in FIG. 23.

Maytansin-N-methyl-L-alanine-(3-methyl-4-amino) benzamide (53)

Step A: Maytansin-N-methyl-L-alanine-(3-methyl-4-nitro)benzamide

The title compound was prepared from maytansin-N-methyl-L-alanine (9, 49 mg, 0.075 mmol) and 3-methyl-4-nitrobenzoic acid (52) (26 mg, 0.143 mmol), using the method from Step A of Example 5, to give a yellow solid (34 mg, 56%). MS (ESI, pos.): calc'd for $C_{40}H_{49}N_4O_{12}Cl$, 812.3; found 795.2 (M–H$_2$O+H), 813.2 (M+H).

Step B: Maytansin-N-methyl-L-alanine-(3-methyl-4-amino)benzamide (53)

The title compound was prepared from the product of the preceding step (33 mg, 0.041 mmol), using the method from Step B of Example 5, to give a white solid (24 mg, 71%). MS (ESI, pos.): calc'd for $C_{40}H_{51}N_4O_{10}Cl$, 782.3; found 765.2 (M–H$_2$O+H), 783.2 (M+H). $^1$H-NMR (500 MHz, CDCl$_3$): d 7.15 (s, 1H), 7.09 (d, 1H, J=8 Hz), 6.94 (s, 1H), 6.82 (s, 1H), 6.72 (br d, 1H, J=10 Hz), 6.54 (d, 1H, J=8 Hz), 6.44 (dd, 1H, J=15 Hz, 12 Hz), 6.33 (s, 1H), 5.75 (dd, 1H, J=14 Hz, 9 Hz), 5.42 (m, 1H), 4.87 (dd, 1H, J=12 Hz, 10 Hz), 4.31 (t, 1H, J=11 Hz), 3.98 (s, 3H), 3.63 (br d, 1H, J=13 Hz), 3.50 (d, 1H, J=9 Hz), 3.36 (s, 3H), 3.10 (m, 1H), 3.07 (s, 3H), 3.03 (d, 1H, J=10 Hz), 2.91 (s, 3H), 2.68 (t, 1H, J=13 Hz), 2.19 (dd, 1H, J=14 Hz, 3 Hz), 2.06 (s, 3H), 1.66 (m, 1H), 1.65 (s, 3H), 1.48 (dd, 1H, J=11 Hz, 7 Hz), 1.43 (d, 3H, J=7 Hz), 1.29 (d, 3H, J=7 Hz), 1.27 (m, 1H), 0.84 (s, 3H).

Example 19

Figure 24:
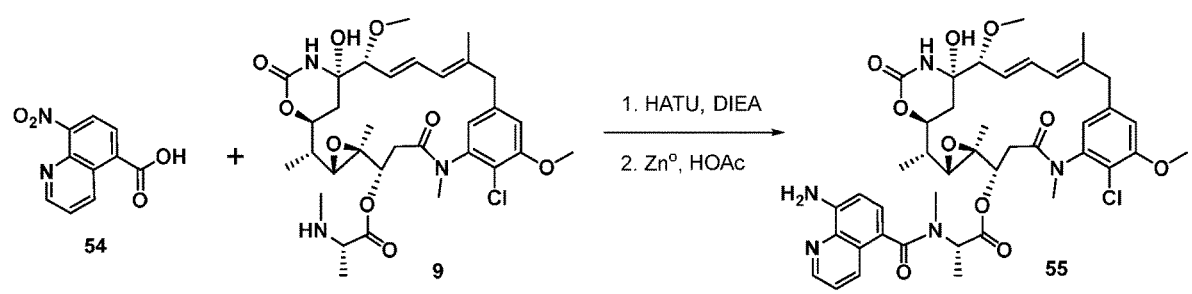
FIG. 24 depicts a synthetic sequence for preparing maytansin-N-methyl-L-alanine-(8-amino-5-carboxyquinoline)carboxamide.

Compound 55 was synthesized as described below and as depicted in FIG. 24.

Maytansin-N-methyl-L-alanine-(8-amino-5-carboxyquinoline)carboxamide (55)

Step A: Maytansin-N-methyl-L-alanine-(8-nitro-5-carboxyquinoline)carboxamide

The title compound was prepared from maytansin-N-methyl-L-alanine (9, 47 mg, 0.072 mmol) and 8-nitro-5-carboxyquinoline (54) (35 mg, 0.160 mmol), using the method from Step A of Example 5, to give a pale yellow solid (30 mg, 49%). MS (ESI, pos.): calc'd for $C_{42}H_{48}N_5O_{12}Cl$, 849.3; found 832.6 (M–H$_2$O+H), 850.7 (M+H).

Step B: Maytansin-N-methyl-L-alanine-(8-amino-5-carboxyquinoline)carboxamide (55)

The title compound was prepared from the product of the preceding step (29 mg, 0.034 mmol), using the method from Step B of Example 5, to give a pale yellow solid (18 mg, 60%). MS (ESI, pos.): calc'd for $C_{42}H_{50}N_5O_{10}Cl$, 819.3; found 802.0 (M–H$_2$O+H), 820.0 (M+H). $^1$H-NMR (500 MHz, CDCl$_3$): d 8.77 (dd, 1H, J=4 Hz, 2 Hz), 8.18 (d, 1H, J=8 Hz), 7.40 (dd, 1H, J=9 Hz, 4 Hz), 7.23 (m, 1H), 6.99 (s, 1H), 6.87 (s, 1H), 6.73 (d, 1H, J=8 Hz), 6.68 (d, 1H, J=11 Hz), 6.47 (dd, 1H, J=15 Hz, 11 Hz), 6.26 (s, 1H), 5.77 (dd, 1H, J=15 Hz, 9 Hz), 5.32 (br m, 1H), 5.21 (br s, 2H), 4.99 (d, 1H, J=9 Hz), 4.34 (t, 1H, J=11 Hz), 4.01 (s, 3H), 3.78 (br m, 1H), 3.67 (d, 1H, J=13 Hz), 3.51 (d, 1H, J=10 Hz), 3.37 (s, 3H), 3.16 (d, 1H, J=13 Hz), 3.12 (s, 3H), 3.00 (d, 1H, J=10 Hz), 2.79 (s, 3H), 2.73 (m, 1H), 2.24 (dd, 1H, J=14 Hz, 3 Hz), 1.76 (d, 1H, J=14 Hz), 1.68 (s, 3H), 1.61 (d, 3H, J=7 Hz), 1.33 (m, 1H), 1.30 (d, 3H, J=7 Hz), 1.25 (s, 1H), 0.90 (s, 3H).

Example 20

Figure 25:
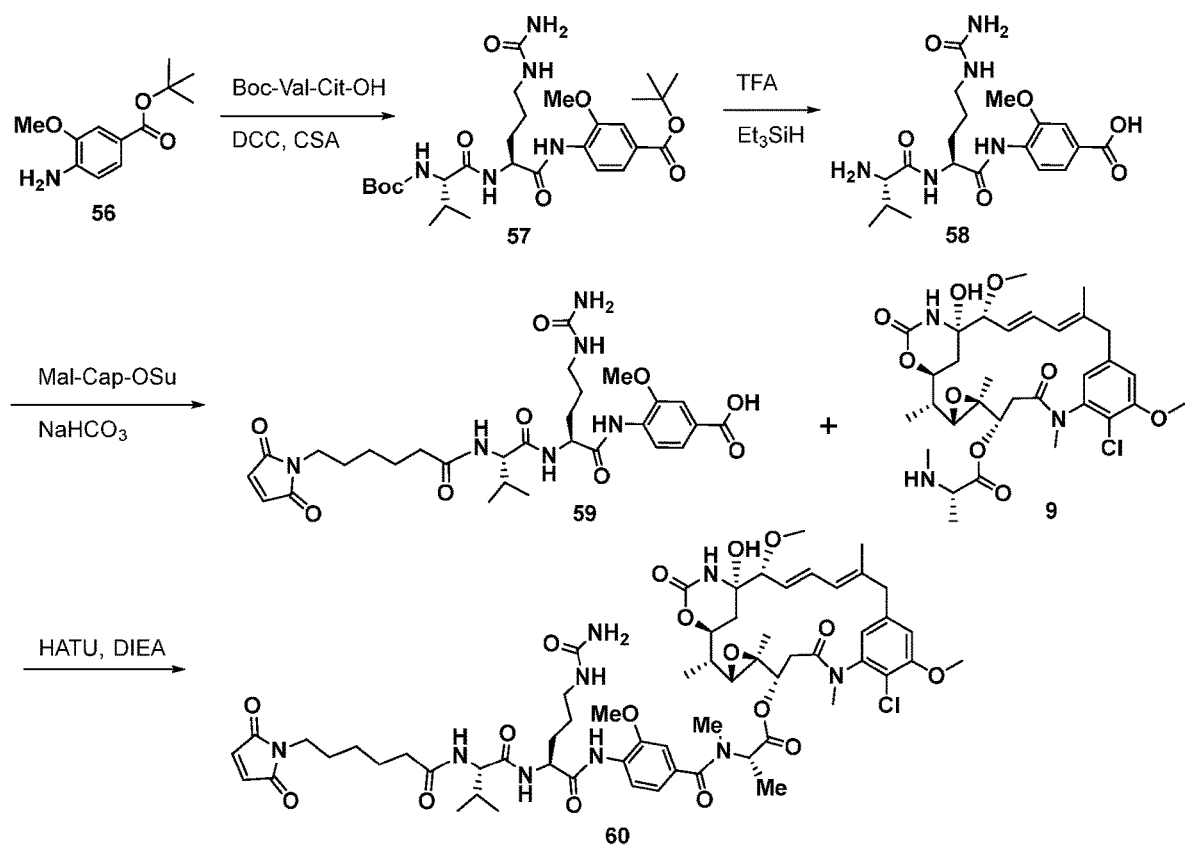
FIG. 25 depicts a synthetic sequence for preparing maytansin-N-methyl-L-alanine-(3-methoxy-4-amino)benzamido-Cit-Val-Cap-Mal.

Compound 60 was synthesized as described below and as depicted in FIG. 25.

Maytansin-N-methyl-L-alanine-(3-methoxy-4-amino)benzamido-Cit-Val-Cap-Mal (60)

Step A: Boc-L-valine-L-citrulline-(3-methoxy-4-amino)benzoic acid t-butyl ester (57)

The title compound was prepared from Boc-L-valine-L-citrulline (3, 100 mg, 0.267 mmol) and 4-amino-3-methoxybenzoic acid tert-butyl ester (56, 61 mg, 0.273 mmol), using the method from Step A of Example 2, to give a white solid (74 mg, 48%). MS (ESI, pos.): calc'd for $C_{28}H_{45}N_5O_8$, 579.3; found 580.4 (M+H), 602.6 (M+Na).

Step B: L-valine-L-citrulline-(3-methoxy-4-amino)benzoic acid (58)

The title compound was prepared from the product of the preceding step (57, 72 mg, 0.124 mmol), using the method from Step C of Example 1, to give an off-white solid (68 mg, 100%). MS (ESI, pos.): calc'd for $C_{19}H_{29}N_5O_6$, 423.2; found 424.4 (M+H), 847.4 (2M+H).

Step C: 6-(Maleimidyl-caprolyl)-L-valine-L-citrulline-(3-methoxy-4-amino)benzoic acid (59)

The title compound was prepared from the product of the preceding step (58, 67 mg, 0.124 mmol), using the method from Step D of Example 1, to give a white solid (45 mg, 59%). MS (ESI, pos.): calc'd for $C_{29}H_{40}N_6O_9$, 616.3; found 617.5 (M+H), 639.6 (M+Na).

Step D: Maytansin-N-methyl-L-alanine-(3-methoxy-4-amino)benzamido-Cit-Val-Cap-Mal (60)

The title compound was prepared from the product of the preceding step (59, 44 mg, 0.071 mmol) and maytansin-N-methyl-L-alanine (9, 49 mg, 0.075 mmol), using the method from Step E of Example 1, to give a white solid (14 mg, 16%). MS (ESI, pos.): calc'd for $C_{61}H_{82}N_9O_{17}Cl$, 1247.6; found 1231.1 (M–H$_2$O+H), 1249.1 (M+H), 1271.1 (M+Na). $^1$H-NMR (500 MHz, CDCl$_3$): d 8.48 (s, 1H), 8.24 (d, 1H, J=8 Hz), 7.11 (d, 1H, J=8 Hz), 6.96-6.93 (m, 3H), 6.83 (s, 1H), 6.72-6.68 (m, 3H), 6.45 (dd, 1H, J=16 Hz, 11 Hz), 6.25 (s, 1H), 6.18 (d, 1H, J=9 Hz), 5.77 (dd, 1H, J=15 Hz, 10 Hz), 5.44 (m, 1H), 5.03 (br s, 1H), 4.90 (d, 1H, J=10 Hz), 4.62 (m, 1H), 4.54 (br s, 2H), 4.33-4.28 (m, 2H), 3.99 (s, 3H), 3.75 (s, 3H), 3.61 (d, 1H, J=13 Hz), 3.52-3.48 (m, 3H), 3.36 (s, 3H), 3.24 (m, 2H), 3.11 (d, 1H, J=13 Hz), 3.07 (s, 3H), 3.03 (d, 1H, J=10 Hz), 2.90 (s, 3H), 2.70 (m, 1H), 2.26-2.20 (m, 3H), 2.12 (m, 1H), 2.00 (m, 1H), 1.78 (m, 1H), 1.63-1.57 (m, 6H), 1.46 (d, 2H, J=7 Hz), 1.33-1.25 (m, 6H), 0.95 (m, 6H), 0.86 (s, 3H).

Example 21

Figure 26:
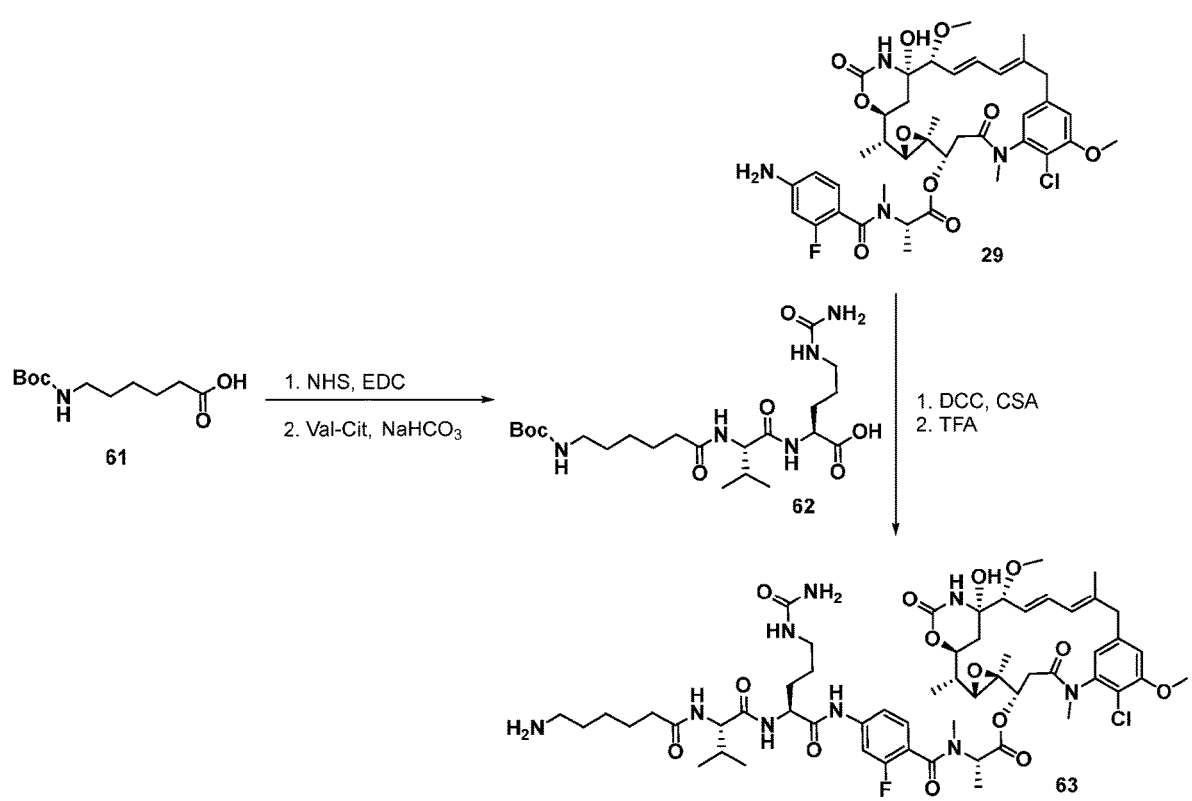
FIG. 26 depicts a synthetic sequence for preparing maytansin-N-methyl-L-alanine-(2-fluoro-4-amino)benzamido-Cit-Val-Cap-6-amine.

Compound 63 was synthesized as described below and as depicted in FIG. 26.

Maytansin-N-methyl-L-alanine-(2-fluoro-4-amino)benzamido-Cit-Val-Cap-6-amine (63)

Step A: Boc-6-aminohexanoic acid succinate ester

The title compound was prepared from Boc-6-aminohexanoic acid (64, 502 mg, 2.17 mmol), using the method from Step A of Example 1, to give a white solid (712 mg, 99%). MS (ESI, pos.): calc'd for $C_{15}H_{24}N_2O_6$, 328.2; found 351.2 (M+Na).

Step B: Boc-(6-amino-caprolyl)-L-valine-L-citrulline (62)

The title compound was prepared from the product of the preceding steps (710 mg, 2.16 mmol) and L-valine-L-citrulline TFA salt (970 mg, 2.51 mmol), using the method from Step D of Example 1, to give a pale gold solid (720 mg, 69%). MS (ESI, pos.): calc'd for $C_{22}H_{41}N_5O_7$, 487.3; found 488.3 (M+H), (M+H).

Step C: Maytansin-N-methyl-L-alanine-(2-fluoro-4-amino)benzamido-Cit-Val-Cap-6-Boc-amine The title compound was prepared from the product of the preceding step (62, 25 mg, 0.051 mmol) and Maytansin-N-methyl-L-alanine-(2-fluoro-4-amino)benzamide (29, 35 mg, 0.041 mmol), using the method from Step A of Example 2, to give a white solid (17 mg, 33%). MS (ESI, pos.): calc'd for $C_{61}H_{87}N_9O_{16}ClF$, 1255.6; found 1238.5 (M–H$_2$O+H), 1256.6 (M+H), 1278.6 (M+Na).

Step D: Maytansin-N-methyl-L-alanine-(2-fluoro-4-amino)benzamido-Cit-Val-Cap-6-amine (63)

The product of the preceding step (16 mg, 0.013 mmol) was dissolved in acetonitrile (MeCN, 3 mL) and water (1 mL), treated with trifluoroacetic acid (TFA, 1.0 mL, 13.0 mmol), the flask sealed with a rubber septum, purged with argon, and the reaction stirred at ambient temperature. After 24 h, the reaction was partially concentrated in vacuo at ambient temperature, diluted with water (ca. 1 mL), and purified twice on C18 Aq RediSep Gold columns via ISCO system (20-80% MeCN in water, 0.1% TFA both phases). The purest fractions by LCMS were combined, partially concentrated in vacuo at ambient temperature, frozen at –78° C., and lyophilized to give the title compound as a white solid (9 mg, 56%). MS (ESI, pos.): calc'd for $C_{56}H_{79}N_9O_{14}ClF$, 1155.5; found 1156.6 (M+H), 1178.6 (M+Na). $^1$H-NMR (500 MHz, CD$_3$OD): d 8.72 (d, 1H, J=12 Hz), 8.39 (d, 1H, J=13 Hz), 8.14 (d, 1H, J=10 Hz), 7.84 (dd, 1H, J=21 Hz, 3 Hz), 7.75 (dd, 1H, J=21 Hz, 3 Hz), 7.60 (dd, 1H, J=15 Hz, 3 Hz), 7.33 (dd, 1H, J=14 Hz, 3 Hz), 7.25 (m, 1H), 7.21 (s, 1H), 6.97 (s, 1H), 6.75 (m, 1H), 6.72 (s, 1H), 6.67 (m, 1H), 5.78-5.60 (m, 3H), 4.77 (m, 1H), 4.45 (m, 2H), 4.26 (m, 1H), 4.20 (d, 1H, J=13 Hz), 4.05-4.00 (m, 2H), 4.03 (s, 3H), 3.69 (dd, 1H, J=21 Hz, 5 Hz), 3.64 (d, 1H, J=16 Hz), 3.41 (s, 3H), 3.30-3.26 (m, 2H), 3.23-3.09 (m, 2H), 3.05 (m, 3H), 2.97 (dd, 1H, J=16 Hz, 5 Hz), 2.92 (d, 1H, J=13 Hz), 2.86 (m, 3H), 2.82 (d, 1H, J=13 Hz), 2.75 (m, 1H), 2.36-2.29 (m, 2H), 2.25-2.20 (m, 1H), 2.08-2.02 (m, 2H), 1.76 (s, 3H), 1.73-1.50 (m, 10H), 1.45 (m, 2H), 1.36-1.32 (m, 2H), 1.28 (d, 3H, J=11 Hz), 1.05 (d, 3H, J=11 Hz), 1.03-0.98 (m, 4H), 0.93 (s, 3H).

Example 22

Figure 27:
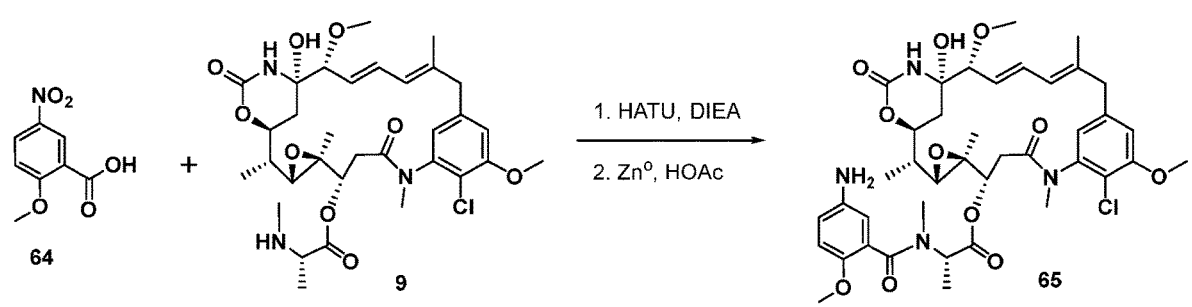
FIG. 27 depicts a synthetic sequence for preparing maytansin-N-methyl-L-alanine-N-(2-methoxy-5-amino)benzamide.

Compound 65 was synthesized as described below and as depicted in FIG. 27.

Maytansin-N-methyl-L-alanine-N-(2-methoxy-5-amino)benzamide (65)

Step A: Maytansin-N-methyl-L-alanine-(2-methoxy-5-nitro)benzamide

The title compound was prepared from maytansin-N-methyl-L-alanine (9, 50 mg 0.077 mmol) and 2-methoxy- 5-nitrobenzoic acid (64) (25 mg, 0.127 mmol), using the method from Step A of Example 5, to give a white solid (51 mg, 80%). MS (ESI, pos.): calc'd for $C_{40}H_{49}ClN_4O_{13}$, 829.3; found 812.0 (M–$H_2$O+H), 830.0 (M+H), 852.0 (M+Na).

Step B: Maytansin-N-methyl-L-alanine-N-(2-methoxy-5-amino)benzamide (65)

The title compound was prepared from the product of the preceding step (50 mg, 0.060 mmol), using the method from Step B of Example 5, to give a white solid (19 mg, 40%). MS (ESI, pos.): calc'd for $C_{40}H_{51}ClN_4O_{11}$, 798.3; found 781.3 (M–$H_2$O), 799.3 (M+H), 822.3 (M+Na).

Example 23

Figure 28:
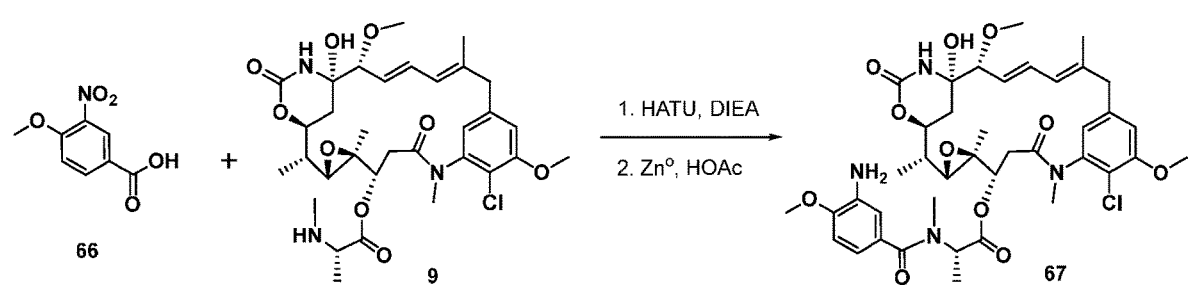
FIG. 28 depicts a synthetic sequence for preparing maytansin-N-methyl-L-alanine-N-(3-amino-4-methoxy)benzamide.

Compound 67 was synthesized as described below and as depicted in FIG. 28.

Maytansin-N-methyl-L-alanine-N-(3-amino-4-methoxy)benzamide (67)

Step A: Maytansin-N-methyl-L-alanine-(3-nitro-4-methoxy)benzamide

The title compound was prepared from maytansin-N-methyl-L-alanine (9, 50 mg 0.077 mmol) and 3-nitro-4-methoxybenzoic acid (66) (25 mg, 0.127 mmol), using the method from Step A of Example 5, to give a white solid (46 mg, 72%). MS (ESI, pos.): calc'd for $C_{40}H_{49}ClN_4O_{13}$, 829.3; found 812.0 (M–$H_2$O+H), 830.0 (M+H), 852.0 (M+Na).

Step B: Maytansin-N-methyl-L-alanine-N-(3-amino-4-methoxy)benzamide (67)

The title compound was prepared from the product of the preceding step (45 mg, 0.054 mmol), using the method from Step B of Example 5, to give a white solid (23 mg, 53%). MS (ESI, pos.): calc'd for $C_{40}H_{51}ClN_4O_{11}$, 798.3; found 781.3 (M–$H_2$O), 799.3 (M+H), 822.3 (M+Na).

Example 24

Figure 29:
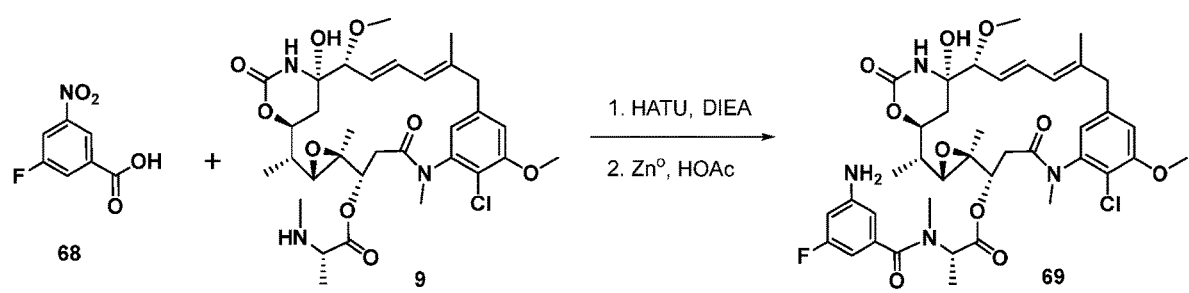
FIG. 29 depicts a synthetic sequence for preparing maytansin-N-methyl-L-alanine-N-(3-amino-5-fluoro)benzamide.

Compound 69 was synthesized as described below and as depicted in FIG. 29.

Maytansin-N-methyl-L-alanine-N-(3-amino-5-fluoro)benzamide (69)

Step A: Maytansin-N-methyl-L-alanine-(3-nitro-5-fluoro)benzamide

The title compound was prepared from maytansin-N-methyl-L-alanine (9, 50 mg, 0.077 mmol) and 3-nitro-5-fluorobenzoic acid (68) (24 mg, 0.127 mmol), using the method from Step A of Example 5, to give a yellow solid (37 mg, 59%). MS (ESI, pos.): calc'd for $C_{39}H_{46}ClFN_4O_{12}$, 816.3; found 817.2 (M+H).

Step B: Maytansin-N-methyl-L-alanine-N-(3-amino-5-fluoro)benzamide (69)

The title compound was prepared from the product of the preceding step (37 mg, 0.045 mmol), using the method from Step B of Example 5, to give a white solid (9.1 mg, 24%). MS (ESI, pos.): calc'd for $C_{39}H_{49}ClFN_4O_{10}$, 786.3; found 769.3 (M–$H_2$O), 787.3 (M+H).

Example 25

Figure 30:
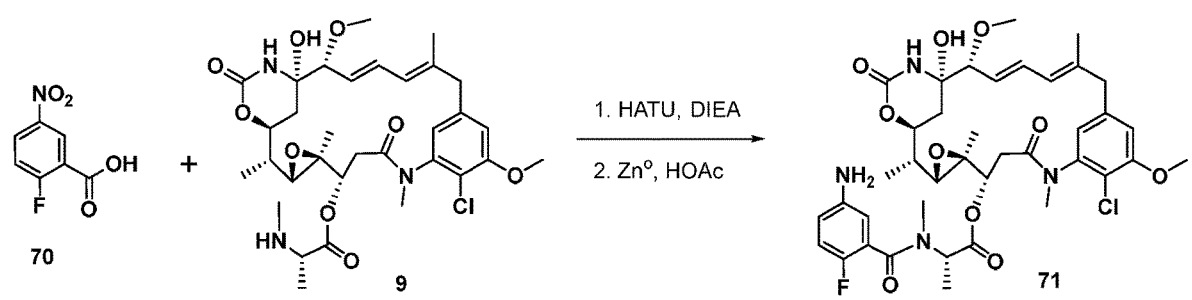
FIG. 30 depicts a synthetic sequence for preparing maytansin-N-methyl-L-alanine-N-(2-fluoro-5-amino)benzamide.

Compound 71 was synthesized as described below and as depicted in FIG. 30.

Maytansin-N-methyl-L-alanine-N-(2-fluoro-5-amino)benzamide (71)

Step A: Maytansin-N-methyl-L-alanine-(2-fluoro-5-nitro)benzamide

The title compound was prepared from maytansin-N-methyl-L-alanine (9, 50 mg, 0.077 mmol) and 2-fluoro-5-nitrobenzoic acid (70) (24 mg, 0.127 mmol), using the method from Step A of Example 5, to give a yellow solid (37 mg, 59%). MS (ESI, pos.): calc'd for $C_{39}H_{46}ClFN_4O_{12}$, 816.3; found 799.3 (M–$H_2$O), 817.2 (M+H).

Step B: Maytansin-N-methyl-L-alanine-N-(2-fluoro-5-amino)benzamide (71)

The title compound was prepared from the product of the preceding step (37 mg, 0.045 mmol), using the method from Step B of Example 5, to give a white solid (2.2 mg, 6%). MS (ESI, pos.): calc'd for $C_{39}H_{49}ClFN_4O_{10}$, 786.3; found 769.3 (M–$H_2$O), 787.3 (M+H).

Example 26

Figure 31:
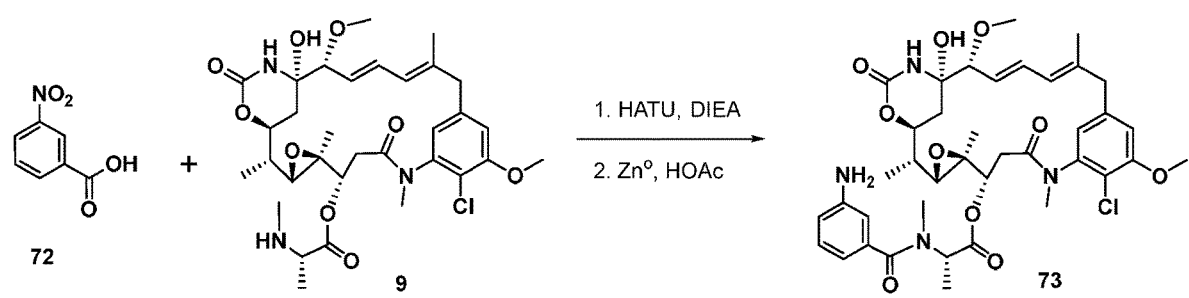
FIG. 31 depicts a synthetic sequence for preparing maytansin-N-methyl-L-alanine-N-(3-amino)benzamide.

Compound 73 was synthesized as described below and as depicted in FIG. 31.

Maytansin-N-methyl-L-alanine-N-(3-amino)benzamide (73)

Step A: Maytansin-N-methyl-L-alanine-(3-nitro)benzamide

The title compound was prepared from maytansin-N-methyl-L-alanine (9, 50 mg, 0.077 mmol) and 3-nitrobenzoic acid (72) (21 mg, 0.127 mmol), using the method from Step A of Example 5, to give a white solid (34 mg, 56%). MS (ESI, pos.): calc'd for $C_{39}H_{47}ClN_4O_{12}$, 798.3; found 781.2 (M–$H_2$O), 799.3 (M+H).

Step B: Maytansin-N-methyl-L-alanine-N-(3-amino)benzamide (73)

The title compound was prepared from the product of the preceding step (34 mg, 0.043 mmol), using the method from Step B of Example 5, to give a white solid (9.3 mg, 27%). MS (ESI, pos.): calc'd for $C_{39}H_{49}ClN_4O_{10}$, 768.3; found 751.2 (M–$H_2$O), 769.2 (M+H).

Example 27

Figure 32:
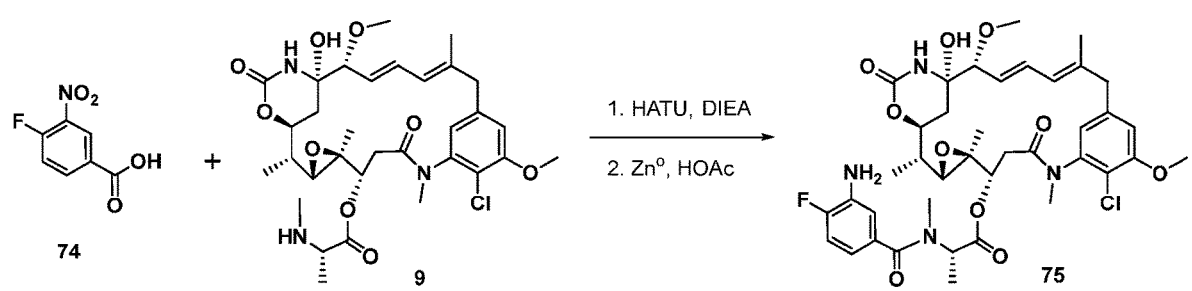
FIG. 32 depicts a synthetic sequence for preparing maytansin-N-methyl-L-alanine-N-(3-amino-4-fluoro)benzamide.

Compound 75 was synthesized as described below and as depicted in FIG. 32.

Maytansin-N-methyl-L-alanine-N-(3-amino-4-fluoro)benzamide (75)

Step A: Maytansin-N-methyl-L-alanine-(3-nitro-4-fluoro)benzamide

The title compound was prepared from maytansin-N-methyl-L-alanine (9, 50 mg, 0.077 mmol) and 3-nitro-4- fluorobenzoic acid (74) (24 mg, 0.127 mmol), using the method from Step A of Example 5, to give a white solid (34 mg, 54%). MS (ESI, pos.): calc'd for $C_{39}H_{46}ClFN_4O_{12}$, 816.3; found 799.3 (M–$H_2O$), 817.2 (M+H).

Step B: Maytansin-N-methyl-L-alanine-N-(3-amino-4-fluoro)benzamide (75)

The title compound was prepared from the product of the preceding step (34 mg, 0.042 mmol), using the method from Step B of Example 5, to give a white solid (12 mg, 37%). MS (ESI, pos.): calc'd for $C_{39}H_{49}ClFN_4O_{10}$, 786.3; found 769.3 (M–$H_2O$), 787.3 (M+H).

Example 28

Figure 33:
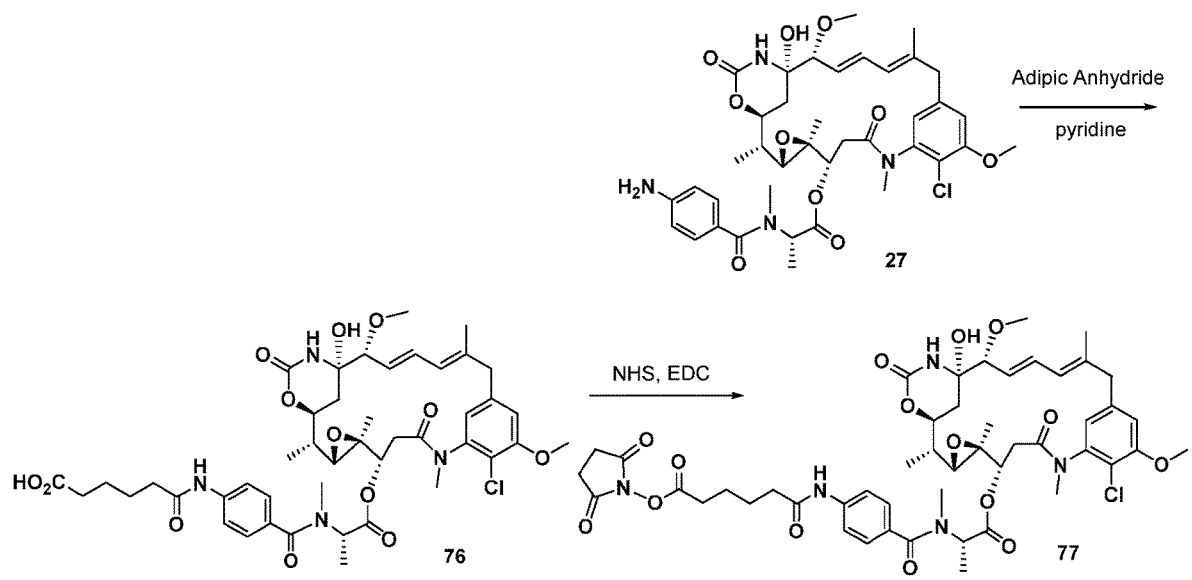
FIG. 33 depicts a synthetic sequence for preparing maytansin-N-methyl-L-alanine-N-4-aminobenzamide-adipic-NHS.

Compound 77 was synthesized as described below and as depicted in FIG. 33.

Maytansin-N-methyl-L-alanine-N-4-aminobenzamide-adipic-NHS (77)

Step A: Maytansin-N-methyl-L-alanine-N-(4-amino)benzamide-adipic acid (76)

The title compound was prepared from 27 (20 mg, 0.026 mmol) and adipic anhydride (17 mg, 0.133 mmol) were weighed into a round-bottom flask and dissolved in pyridine (1.5 mL). The flask was sealed via rubber septum, purged with nitrogen, and the reaction was stirred at ambient temperature. After 4 h the reaction was purified directly on a 30 g C18 RediSep Gold Aq column via ISCO system (gradient elution: 20-90% MeCN in water, 0.05% acetic acid in both, over 20 min). The product-containing fractions were combined, partially concentrated invacuo, frozen on dry ice, and lyophilized to give an off-white solid (16 mg, 67%). MS (ESI, pos.): calc'd for $C_{45}H_{57}ClN_4O_{13}$, 896.4; found 879.4 (M–$H_2O$), 897.4 (M+H).

Step B: Maytansin-N-methyl-L-alanine-N-(4-amino)benzamide-adipic-NHS (77)

The title compound was prepared from the product of the preceding step (76, 16 mg, 0.017 mmol), using the method from Step A of Example 1, to give a white solid (10 mg, 58%). MS (ESI, pos.): calc'd for $C_{49}H_{60}ClN_5O_{15}$, 993.5; found 976.0 (M–$H_2O$), 994.0 (M+H). $^1$H-NMR (500 MHz, $CDCl_3$): δ 7.92 (s, 1H), 7.57 (d, 2H, J=8 Hz), 7.36 (d, 2H, J=8 Hz), 6.93 (s, 1H), 6.86 (s, 1H), 6.75 (d, 1H, J=12 Hz), 6.47 (dd, 1H, J=15 Hz, 11 Hz), 6.29 (s, 1H), 5.74 (dd, 1H, J=16 Hz, 9 Hz), 5.47 (m, 1H), 4.90 (dd, 1H, J=12 Hz, 3 Hz), 4.32 (t, 1H, J=11 Hz), 4.02 (s, 4H), 3.63 (d, 1H, J=13 Hz), 3.62 (br s, 1H), 3.53 (d, 1H, J=9 Hz), 3.38 (s, 3H), 3.13 (d, 1H, J=13 Hz), 2 (s, 3H), 2.80 (d, 2H, J=10 Hz), 2.73 (s, 3H), 2.60 (m, 1H), 2.27 (t, 2H, J=10 Hz), 2.11 (br s, 1H), 2.07 (s, 2H), 1.62 (s, 3H), 1.58-1.52 (m, 2H), 1.51-1.46 (m, 2H), 1.34-1.29 (m, 3H), 1.25-1.20 (m, 2H), 1.13 (d, 3H, J=7 Hz), 0.82 (s, 3H).

Example 29

Figure 34:
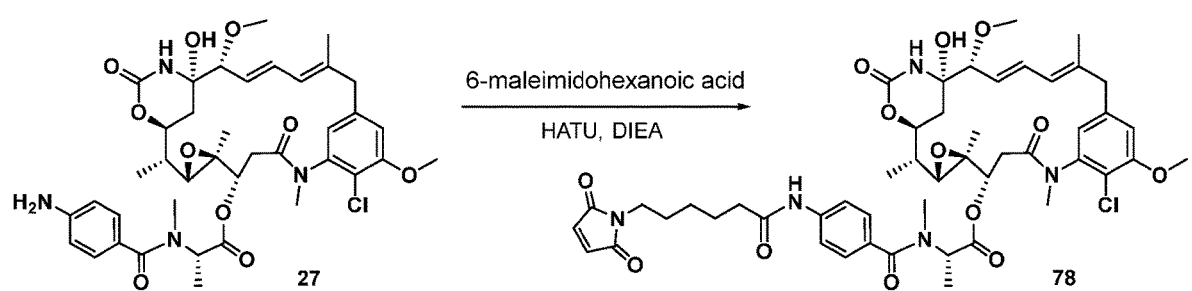
FIG. 34 depicts a synthetic sequence for preparing maytansin-N-methyl-L-alanine-4-aminobenzamide-Cap-Mal.

Compound 78 was synthesized as described below and as depicted in FIG. 34.

Maytansin-N-methyl-L-alanine-4-aminobenzamide-Cap-Mal (78)

The title compound was prepared from 27 (15 mg, 0.019 mmol) and 6-maleimidohexanoic acid (6 mg, 0.029 mmol), using the method from Step A of Example 5, to give an off-white solid (9.8 mg, 52%). MS (ESI, pos.): calc'd for $C_{49}H_{60}ClN_5O_{13}$, 962.5; found 944.8 (M–$H_2O$), 962.8 (M+H). $^1$H-NMR (500 MHz, DMSO-$d_6$): δ 10.01 (s, 1H), 7.56 (d, 2H, J=9 Hz), 7.29 (d, 2H, J=9 Hz), 7.21 (s, 1H), 6.99 (s, 2H), 6.91 (s, 1H), 6.83 (s, 1H), 6.62-6.56 (m, 2H), 5.97 (s, 1H), 5.61 (dd, 1H, J=15 Hz, 10 Hz), 5.44 (m, 1H), 4.59 (d, 1H, J=12 Hz), 4.10 (t, 1H, J=12 Hz), 3.94 (s, 3H), 3.51 (d, 1H, J=9 Hz), 3.40-3.36 (m, 2H), 3.26 (s, 3H), 3.23-3.21 (m, 2H), 2.94 (s, 3H), 2.80 (d, 1H, J=10 Hz), 2.73 (s, 3H), 2.64-2.57 (m, 1H), 2.27 (t, 2H, J=10 Hz), 2.11-2.09 (m, 1H), 2.07 (s, 2H), 1.62 (s, 3H), 1.57-1.52 (m, 2H), 1.51-1.46 (m, 2H), 1.34-1.29 (m, 3H), 1.25-1.19 (m, 2H), 1.13 (d, 3H, J=7 Hz), 0.82 (s, 3H).

Example 30

Figure 35:
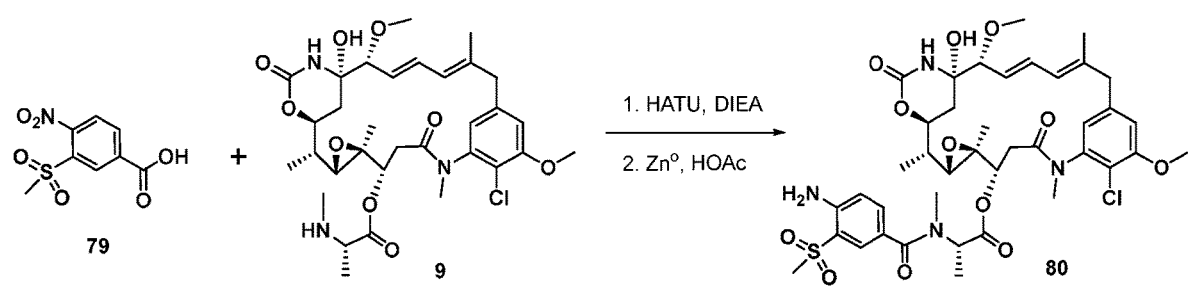
FIG. 35 depicts a synthetic sequence for preparing maytansin-N-methyl-L-alanine-N-(3-methylsulfonyl-4-amino)benzamide.

Compound 80 was synthesized as described below and as depicted in FIG. 35.

Maytansin-N-methyl-L-alanine-N-(3-methylsulfonyl-4-amino)benzamide (80)

Step A: Maytansin-N-methyl-L-alanine-(3-methylsulfonyl-4-nitro)benzamide

The title compound was prepared from maytansin-N-methyl-L-alanine (9, 40 mg, 0.062 mmol) and 3-methylsulfonyl-4-nitrobenzoic acid (79) (25 mg, 0.102 mmol), using the method from Step A of Example 5, to give a yellow solid (37 mg, 69%). MS (ESI, pos.): calc'd for $C_{50}H_{49}N_4O_{14}ClS$, 876.3; found 857.6 (M–$H_2O$+H), 875.6 (M+H), 897.6 (M+Na).

Step B: Maytansin-N-methyl-L-alanine-(3-methylsulfonyl-4-amino)benzamide (80)

The title compound was prepared from the product of the preceding step (36 mg, 0.041 mmol), using the method from Step B of Example 5, to give a white solid (28 mg, 76%). MS (ESI, pos.): calc'd for $C_{40}H_{51}N_4O_{12}ClS$, 846.3; found 829.1 (M–$H_2O$+H), 847.1 (M+H), 869.1 (M+Na). $^1$H-NMR (500 MHz, $CDCl_3$): δ 7.85 (s, 1H), 7.44 (d, 1H, J=9 Hz), 6.90 (s, 1H), 6.84 (s, 1H), 6.71 (d, 1H, J=9 Hz), 6.66 (d, 1H, J=11 Hz), 6.45 (dd, 1H, J=15 Hz, 11 Hz), 6.23 (s, 1H), 5.72 (dd, 1H, J=15 Hz, 10 Hz), 5.32-5.25 (m, 2H), 4.89 (dd, 1H, J=12 Hz, 3 Hz), 4.31 (t, 1H, J=11 Hz), 3.99 (s, 3H), 3.65 (d, 1H, J=13 Hz), 3.51 (d, 1H, J=9 Hz), 3.36 (s, 3H), 3.14 (d, 1H, J=13 Hz), 3.05 (s, 3H), 3.01 (m, 1H), 2.99 (s, 3H), 2.95 (s, 3H), 2.68 (t, 2H, J=14 Hz), 2.20 (dd, 1H, J=15 Hz, 3 Hz), 1.70 (m, 1H), 1.67 (s, 3H), 1.55 (s, 3H), 1.52 (m, 1H), 1.47 (d, 1H, J=7 Hz), 1.31 (d, 1H, J=7 Hz), 1.28 (m, 1H), 0.85 (s, 3H).

Example 31

Figure 36:
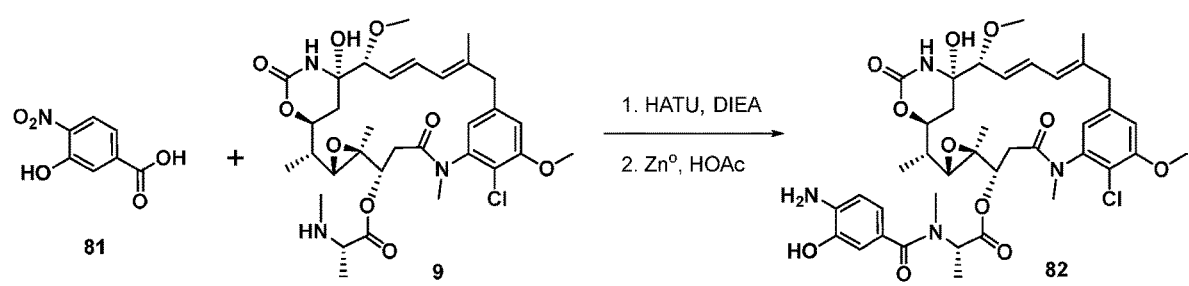
FIG. 36 depicts a synthetic sequence for preparing maytansin-N-methyl-L-alanine-N-(3-hydroxy-4-amino)benzamide.

Compound 82 was synthesized as described below and as depicted in FIG. 36.

Maytansin-N-methyl-L-alanine-N-(3-hydroxy-4-amino)benzamide (82)

Step A: Maytansin-N-methyl-L-alanine-(3-hydroxy-4-nitro)benzamide

The title compound was prepared from maytansin-N-methyl-L-alanine (9, 47 mg, 0.072 mmol) and 3-hydroxy- 4-nitrobenzoic acid (81) (20 mg, 0.109 mmol), using the method from Step A of Example 5, to give a yellow solid (29 mg, 49%). MS (ESI, pos.): calc'd for $C_{39}H_{47}N_4O_{13}Cl$, 814.3; found 796.8 (M–$H_2O$+H), 814.8 (M+H), 836.8 (M+Na).

Step B: Maytansin-N-methyl-L-alanine-(3-hydroxy-4-amino)benzamide (82)

The title compound was prepared from the product of the preceding step (28 mg, 0.034 mmol), using the method from Step B of Example 5, to give a pale yellow solid (20 mg, 69%). MS (ESI, pos.): calc'd for $C_{40}H_{51}N_4O_{12}ClS$, 784.3; found 767.7 (M–$H_2O$+H), 785.7 (M+H). $^1$H-NMR (500 MHz, $CDCl_3$): δ 9.19 (s, 1H), 7.17 (s, 1H), 6.88 (s, 1H), 6.79 (br s, 2H), 6.63-6.56 (m, 3H), 6.47 (m, 1H), 5.93 (s, 1H), 4.93 (s, 2H), 4.57 (d, 1H, J=11 Hz), 4.09 (t, 1H, J=12 Hz), 3.93 (s, 3H), 3.50 (d, 1H, J=9 Hz), 3.26 (s, 3H), 3.18 (br m, 1H), 2.99 (s, 3H), 2.79 (d, 1H, J=10 Hz), 2.76 (s, 3H), 2.06 (dd, 1H, J=14 Hz, 2 Hz), 1.60 (s, 3H), 1.48-1.46 (m, 2H), 1.33-1.27 (m, 4H), 1.13 (d, 3H, J=6 Hz), 0.80 (s, 3H).

Example 32

Figure 37:
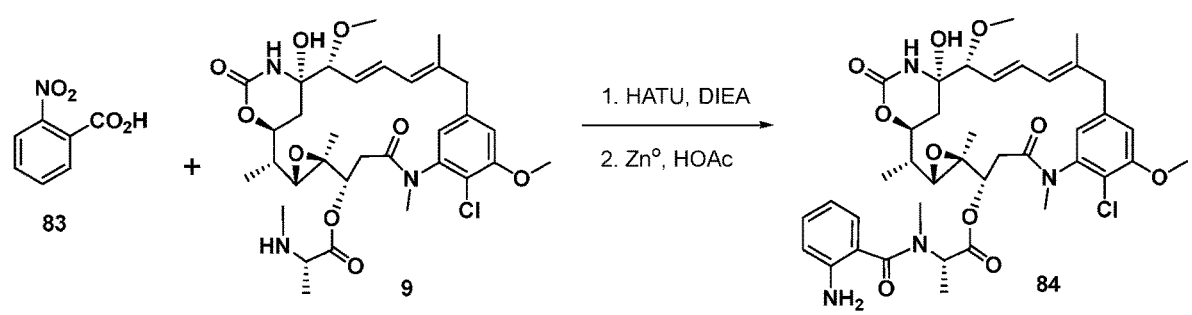
FIG. 37 depicts a synthetic sequence for preparing maytansin-N-methyl-L-alanine-N-(2-amino)benzamide.

Compound 84 was synthesized as described below and as depicted in FIG. 37.

Maytansin-N-methyl-L-alanine-N-(2-amino)benzamide (84)

Step A: Maytansin-N-methyl-L-alanine-(2-nitro)benzamide

The title compound was prepared from maytansin-N-methyl-L-alanine (9, 30 mg, 0.046 mmol) and 2-nitrobenzoic acid (83) (15 mg, 0.092 mmol), using the method from Step A of Example 5, to give a yellow solid (26 mg, 71%). MS (ESI, pos.): calc'd for $C_{39}H_{47}N_4O_{12}Cl$, 798.3; found 799.3 (M+H), 821.3 (M+Na).

Step B: Maytansin-N-methyl-L-alanine-(2-amino)benzamide (84)

The title compound was prepared from the product of the preceding step (24 mg, 0.038 mmol), using the method from Step B of Example 5, to give a white solid (13 mg, 54%). MS (ESI, pos.): calc'd for $C_{39}H_{49}N_4O_{10}Cl$, 768.3; found 769.0 (M+H). $^1$H-NMR (500 MHz, $CDCl_3$): δ 7.16 (m, 1H), 7.08 (d, 1H, J=6 Hz), 6.92 (s, 1H), 6.84 (d, 1H, J=2 Hz), 6.71 (d, 1H, J=8 Hz), 6.63 (t, 1H, J=7 Hz), 6.57 (m, 1H), 6.47 (dd, 1H, J=15 Hz, 11 Hz), 6.27 (s, 1H), 5.76 (m, 1H), 5.20 (br s, 1H), 4.99 (m, 1H), 4.39-4.32 (m, 3H), 4.01 (s, 3H), 3.74 (br s, 1H), 3.59 (d, 1H, J=13 Hz), 3.52 (d, 1H, J=9 Hz), 3.39 (s, 3H), 3.20 (s, 3H), 3.15 (d, 1H, J=12 Hz), 2.99 (d, 1H, J=12 Hz), 2.94 (s, 3H), 2.73 (t, 1H, J=14 Hz), 2.26 (m, 1H), 1.75 (d, 1H, J=12 Hz), 1.69 (s, 3H), 1.55 (d, 3H, J=7 Hz), 1.50 (m, 1H), 1.35-1.30 (m, 4H), 0.90 (s, 3H).

Example 33

Figure 38:
FIG. 38 depicts a synthetic sequence for preparing maytansin-N-methyl-L-alanine-N-(4-methoxy-2-amino)benzamide.

Compound 86 was synthesized as described below and as depicted in FIG. 38.

Maytansin-N-methyl-L-alanine-N-(4-methoxy-2-amino)benzamide (86)

Step A: Maytansin-N-methyl-L-alanine-(4-methoxy-2-nitro)benzamide

The title compound was prepared from maytansin-N-methyl-L-alanine (9, 30 mg, 0.046 mmol) and 4-methoxy-2-nitrobenzoic acid (85) (18 mg, 0.092 mmol), using the method from Step A of Example 5, to give a yellow solid (18 mg, 47%). MS (ESI, pos.): calc'd for $C_{40}H_{49}N_4O_{13}Cl$, 828.3; found 829.4 (M+H), 851.3 (M+Na).

Step B: Maytansin-N-methyl-L-alanine-(4-methoxy-2-amino)benzamide (86)

The title compound was prepared from the product of the preceding step (18 mg, 0.022 mmol), using the method from Step B of Example 5, to give a white solid (15 mg, 84%). MS (ESI, pos.): calc'd for $C_{40}H_{51}N_4O_{11}Cl$, 798.3; found 799.1 (M+H). $^1$H-NMR (500 MHz, $CDCl_3$): δ 6.94 (s, 1H), 6.85 (d, 1H, J=2 Hz), 6.79 (dd, 1H, J=9 Hz, 3 Hz), 6.67 (d, 1H, J=9 Hz), 6.65 (m, 1H), 6.60 (d, 1H, J=11 Hz), 6.48 (dd, 1H, J=15 Hz, 12 Hz), 6.27 (s, 1H), 5.76 (m, 1H), 5.22 (br s, 1H), 4.98 (m, 1H), 4.36 (t, 1H, J=11 Hz), 4.01 (s, 3H), 3.93 (br s, 1H), 3.72 (br s, 1H), 3.65 (m, 1H), 3.61 (s, 3H), 3.52 (d, 1H, J=9 Hz), 3.39 (s, 3H), 3.18 (s, 3H), 3.16 (m, 1H), 2.99 (d, 1H, J=10 Hz), 2.94 (s, 3H), 2.72 (t, 1H, J=13 Hz), 2.26 (dd, 1H, J=15 Hz, 3 Hz), 1.74 (d, 1H, J=14 Hz), 1.70 (s, 3H), 1.55 (d, 3H, J=7 Hz), 1.52-1.48 (m, 1H), 1.35-1.30 (m, 4H), 0.90 (s, 3H).

Example 34

Figure 39:
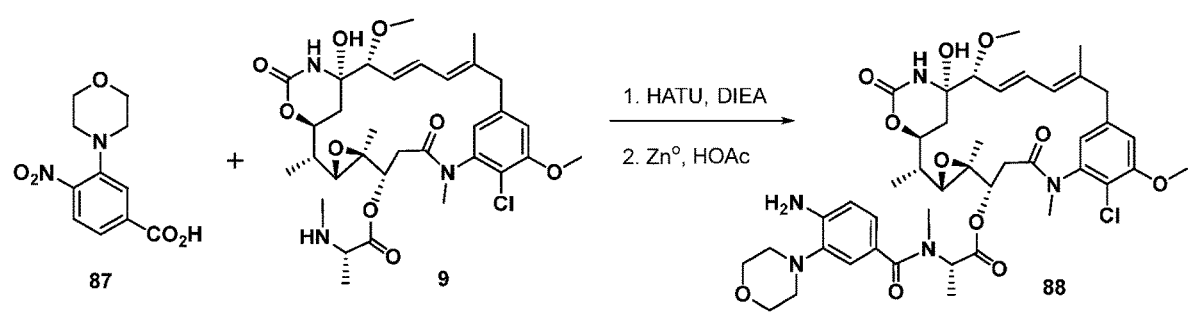
FIG. 39 depicts a synthetic sequence for preparing maytansin-N-methyl-L-alanine-N-(3-morpholino-4-amino)benzamide.

Compound 88 was synthesized as described below and as depicted in FIG. 39.

Maytansin-N-methyl-L-alanine-N-(3-morpholino-4-amino)benzamide (88)

Step A: Maytansin-N-methyl-L-alanine-(3-morpholino-4-nitro)benzamide

The title compound was prepared from maytansin-N-methyl-L-alanine (9, 30 mg, 0.046 mmol) and 3-morpholino-4-nitrobenzoic acid (87) (23 mg, 0.092 mmol), using the method from Step A of Example 5, to give a yellow solid (28 mg, 70%). MS (ESI, pos.): calc'd for $C_{43}H_{54}N_5O_{13}Cl$, 883.3; found 884.5 (M+H), 906.3 (M+Na).

Step B: Maytansin-N-methyl-L-alanine-(3-morpholino-4-amino)benzamide (88)

The title compound was prepared from the product of the preceding step (28 mg, 0.032 mmol), using the method from Step B of Example 5, to give an off-white solid (12 mg, 52%). MS (ESI, pos.): calc'd for $C_{43}H_{56}N_5O_{11}Cl$, 853.4; found 853.9 (M+H), 875.9 (M+Na). $^1$H-NMR (500 MHz, $CDCl_3$): δ 7.12 (s, 1H), 7.02 (d, 1H, J=8 Hz), 6.98 (s, 1H), 6.86 (d, 1H, J=2 Hz), 6.81 (d, 1H, J=11 Hz), 6.61 (d, 1H, J=8 Hz), 6.48 (dd, 1H, J=16 Hz, 12 Hz), 6.29 (s, 1H), 5.77 (dd, 1H, J=15 Hz, 9 Hz), 5.48 (m, 1H), 4.89 (dd, 1H, J=12 Hz, 3 Hz), 4.34 (t, 1H, J=12 Hz), 4.19 (br m, 1H), 4.01 (s, 3H), 3.80-3.75 (m, 5H), 3.53 (m, 2H), 3.39 (s, 3H), 3.15 (d, 1H, J=13 Hz), 3.07 (d, 1H, J=10 Hz), 3.03 (s, 3H), 2.96 (s, 3H), 2.73 (m, 5H), 2.22 (dd, 1H, J=14 Hz, 3 Hz), 1.71 (m, 1H), 1.69 (s, 3H), 1.54-1.49 (m, 1H), 1.47 (d, 3H, J=8 Hz), 1.33 (d, 3H, J=7 Hz), 1.30 (m, 1H), 0.88 (s, 3H).

Example 35

Figure 40:
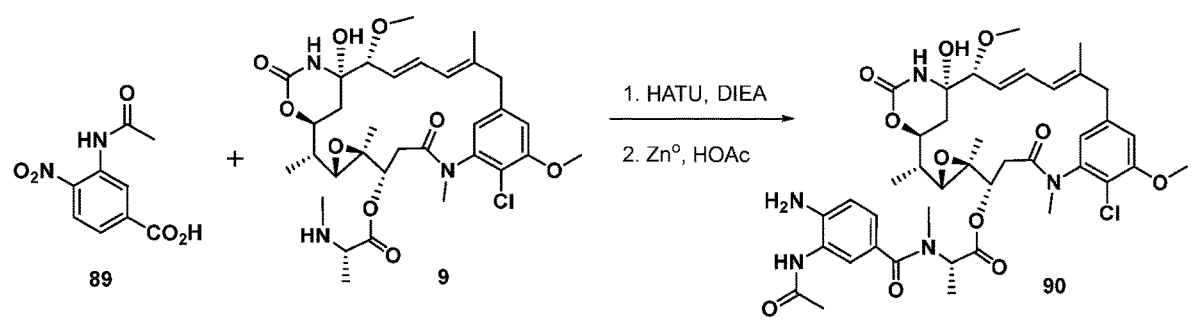
FIG. 40 depicts a synthetic sequence for preparing maytansin-N-methyl-L-alanine-N-(3-acetamido-4-amino)benzamide.

Compound 90 was synthesized as described below and as depicted in FIG. 40.

Maytansin-N-methyl-L-alanine-N-(3-acetamido-4-amino)benzamide (90)

Step A: Maytansin-N-methyl-L-alanine-(3-acetamido-4-nitro)benzamide

The title compound was prepared from maytansin-N-methyl-L-alanine (9, 50 mg, 0.077 mmol) and 3-acetamido-4-nitrobenzoic acid (89) (29 mg, 0.129 mmol), using the method from Step A of Example 5, to give a fluffy pale yellow solid (36 mg, 54%). MS (ESI, pos.): calc'd for $C_{41}H_{50}N_5O_{13}Cl$, 855.3; found 839.1 (M−H$_2$O), 857.1 (M+H), 879.1 (M+Na).

Step B: Maytansin-N-methyl-L-alanine-(3-acetamido-4-amino)benzamide (90)

The title compound was prepared from the product of the preceding step (35 mg, 0.042 mmol), using the method from Step B of Example 5, to give a white solid (19 mg, 57%). MS (ESI, pos.): calc'd for $C_{41}H_{52}N_5O_{11}Cl$, 825.3; found 808.4 (M−H$_2$O), 826.4 (M+H). $^1$H-NMR (500 MHz, DMSO-d$_6$): δ 9.05 (s, 1H), 7.30 (s, 1H), 7.17 (s, 1H), 6.98 (d, 1H, J=9 Hz), 6.91 (s, 1H), 6.79 (s, 1H), 6.58 (m, 3H), 5.97 (s, 1H), 5.64 (br s, 1H), 5.34 (m, 3H), 4.60 (d, 1H, J=12 Hz), 4.10 (t, 1H, J=12 Hz), 3.93 (s, 3H), 3.50 (d, 1H, J=9 Hz), 3.33 (s, 3H), 3.29 (m, 1H), 3.26 (s, 3H), 3.16 (d, 1H, J=12 Hz), 2.97 (s, 3H), 2.79 (m, 4H), 2.07 (d, 1H, J=13 Hz), 1.95 (s, 2H), 1.59 (s, 3H), 1.51-1.42 (m, 2H), 1.29 (m, 3H), 1.13 (d, 3H, J=6 Hz), 0.81 (s, 3H).

Example 36

Figure 41:
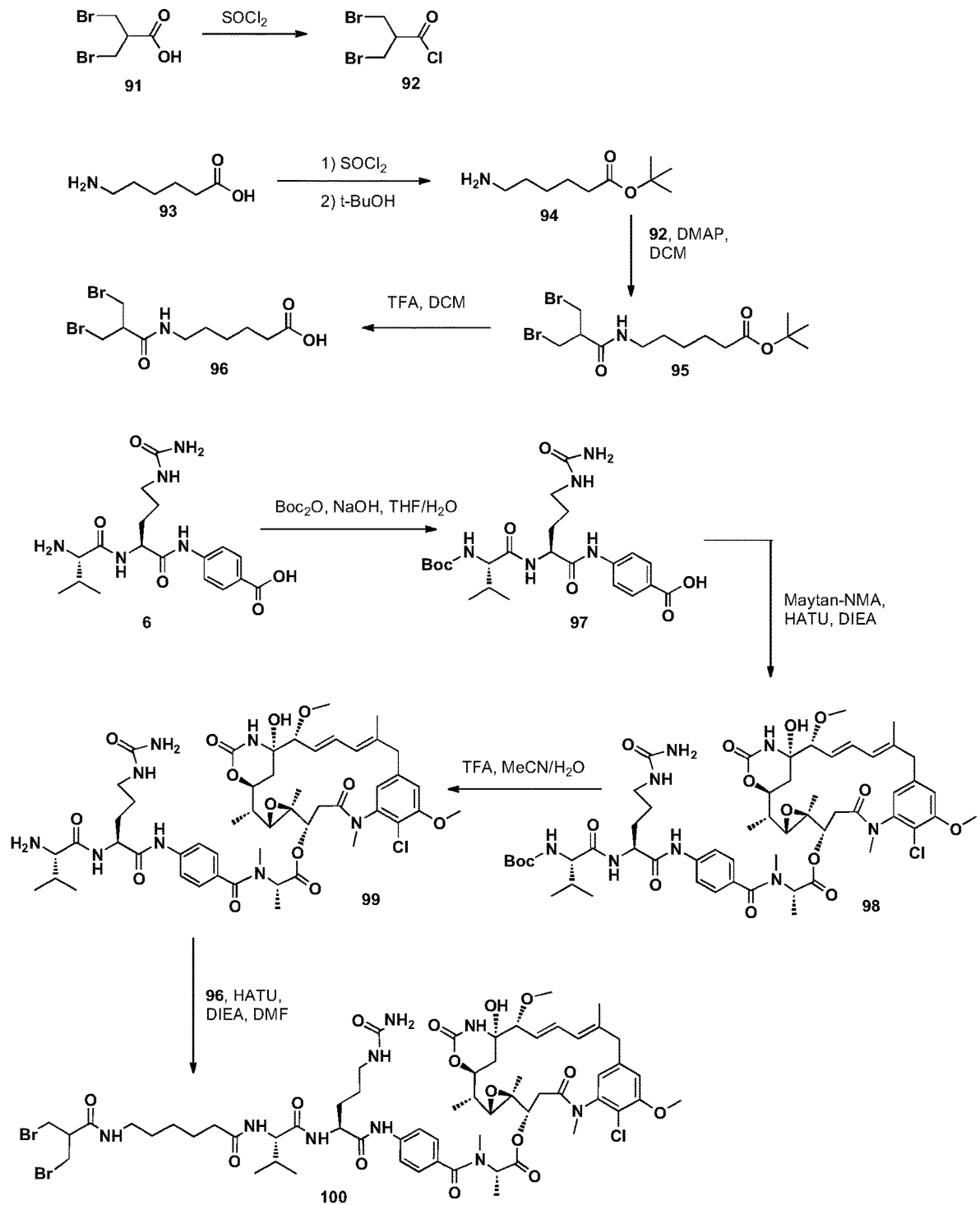
FIG. 41 depicts a synthetic sequence for preparing maytansin-N-methyl-L-alanine-N-4-aminobenzamide-Cit-Val-cap-diBromomethylacryl.

Compound 100 was synthesized as described below and as depicted in FIG. 41.

Maytansin-N-methyl-L-alanine-N-4-aminobenzamide-Cit-Val-cap-diBromomethylacryl (100)

Step A: 3-Bromo-2-bromomethyl-propionyl chloride (92)

To a 10 mL round bottom flask equipped with a magnetic stirrer and nitrogen inlet was charged 3-romo-2-bromomethyl-propionic acid (91, 1.0 g; 4.1 mmol) and thionyl chloride (3.0 mL). This solution was heated to reflux for 3 hours and concentrated to 0.90 g (84% yield) as a brown oil. $^1$H-NMR (300 MHz, CDCl$_3$): δ 3.85-3.75 (m, 4H), 3.60 (pentet, 1H, J=9 Hz).

Step B: 6-Amino-hexanoic acid tert-butyl ester (94)

To a 50 mL round bottom flask equipped with a magnetic stirrer and nitrogen inlet was charged 6-aminohexanoic acid (93, 2.0 g; 15 mmol) and thionyl chloride (5.0 mL; 69 mmol; 4.5 equiv.). This solution was stirred at or below 30° C. for 2 hours and concentrated in vacuo to dryness. To the tan semi-solid a slurry of sodium bicarbonate (2.6 g; 30 mmol; 2.0 equiv.) in t-BuOH (5.0 mL; 87 mmol; 5.7 equiv.) was added and the slurry was stirred at ambient temperature for another 2 h. The butanol was removed in vacuo at 40° C. The thick white slurry was diluted with ethyl acetate and washed with 4 portions of 1 N NaOH, 3 portions of H$_2$O, 1 portion of brine. The organics were dried over Na$_2$SO$_4$, filtered and concentrated to afford 2.2 g (77% yield) as a colorless oil. MS (ESI, pos.): calc'd for $C_{10}H_{21}NO_2$, 187.3; found 188.4 (M+H), $^1$H-NMR (300 MHz, CDCl$_3$): δ 2.68-2.64 (m, 2H), 2.21-2.16 (m, 2H), 1.62-1.52 (m, 2H), 1.48-1.38 (m, 9H), 1.36-1.20 (m, 2H), 1.09 (m, 2H).

Step C: 6-(3-Bromo-2-bromomethyl-propionylamino)-hexanoic acid tert-butyl ester (95)

To a 50 mL round bottom flask equipped with a magnetic stirrer and nitrogen inlet was charged 6-aminohexanoic acid tert-butyl ester (94, 0.50 g; 2.7 mmol) and dimethylaminopyridine (0.03 g; 0.27 mmol; 0.10 equiv.) in DCM (5.0 mL). This solution was chilled to 0° C. via an ice bath. 3-Bromo-2-bromomethyl-propionyl chloride (92, 0.90 g; 3.4 mmol; 1.2 equiv.) was dissolved in DCM (5 mL) and slowly added to the reaction mixture at 0° C. Stir and slowly warm to ambient temperature overnight. Dilute reaction mixture with ethyl acetate, wash the organic mixture with H$_2$O, 5% NaHCO$_3$ and brine. The organics were dried over Na$_2$SO$_4$, filtered, concentrated and purified on a silica gel column eluting with 0-100% ethyl acetate in hexanes to afford 0.49 g (42% yield) as a clear yellow oil. $^1$H-NMR (300 MHz, CDCl$_3$): δ 5.92 (br s, 1H), 3.64-3.58 (m, 2H), 3.54-3.48 (m, 2H), 3.36-3.29 (m, 2H), 2.89-2.83 (m, 1H), 2.24-2.20 (m, 2H), 1.65-1.51 (m, 4H), 1.44-1.35 (m, 11H).

Step D: 6-(3-Bromo-2-bromomethyl-propionylamino)-hexanoic acid (96)

To a 50 mL round bottom flask equipped with a magnetic stirrer and nitrogen inlet was charged 6-(3-Bromo-2-bromomethyl-propionylamino)-hexanoic acid tert-butyl ester (95, 0.26 g; 0.62 mmol) and trifluoroacetic acid (0.70 mL; 9.3 mmol; 15 equiv.) in DCM (10 mL). This solution was stirred at ambient temperature overnight, concentrated to dryness, dissolved in acetonitrile and H$_2$O (1.0 mL each), frozen and lyophilized to afford 0.22 g (100%) as a solid. MS (ESI, pos.): calc'd for $C_{10}H_{17}Br_2NO_3$, 359.0 found 358.0, 360.0, 362.0 (M+H), 380.0, 382.0, 384.0 (M+Na), 356.0, 358.0, 360.0 (M−H). $^1$H-NMR (300 MHz, CDCl$_3$): δ 11.97 (s, 1H), 8.20-8.16 (m, 1H), 3.58-3.56 (d, 4H), 3.11-3.04 (m, 2H), 3.02-2.97 (m, 1H), 2.21-2.16 (m, 2H), 1.54-1.37 (m, 4H), 1.33-1.29 (m, 2H).

Step E: Boc-Val-Cit-4-aminobenzoic acid (97)

The title compound was prepared from the product of Example 1, Step D (6, 100 mg, 0.254 mmol) and di-tert-butyl dicarbonate (61 mg, 0.279 mmol), which were weighed into a round-bottom flask and treated with 1 M NaOH (2 mL) in THF (3 mL) and H$_2$O (1.5 mL). The flask was sealed via rubber septum and the reaction was stirred at ambient temperature overnight, concentrated in vacuo and neutralized to pH 7 with dropwise addition of 1 M HCl (2 mL). The aqueous the reaction with ethyl acetate, dried the organic layer over Na$_2$SO$_4$, filter and concentrated to give an off-white solid (93 mg, 74%). MS (ESI, pos.): calc'd for $C_{23}H_{35}N_5O_7$, 493.5; found 394.2 (M+1-Boc), 494.2 (M+H), 516.2 (M+Na).

Step F: Maytansin-N-methyl-L-alanine-N-4-amino-benzamide-Cit-Val-Boc (98)

The title compound was prepared from the product of the preceding step Boc-Val-Cit-4-aminobenzoic acid (97, 76 mg, 0.154 mmol) and maytansin-N-methyl-L-alanine (9, 50 mg, 0.077 mmol) using the method from Step A of Example 5, to give a white solid (22 mg, 26%). MS (ESI, pos.): calc'd for $C_{55}H_{77}ClN_8O_{15}$, 1124.5; found 1107.2 (M–H$_2$O), 1125.3 (M+H), 1147.2 (M+Na).

Step G: Maytansin-N-methyl-L-alanine-N-4-amino-benzamide-Cit-Val (99)

The title compound was prepared from the product of the preceding step (98, 20 mg, 0.018 mmol) weighed into a round-bottom flask dissolved in ACN (3 mL) and H$_2$O (1 mL) and treated with TFA (1 mL). The flask was sealed via rubber septum, purged with nitrogen, and the reaction was stirred at ambient temperature. After 48 h the reaction was purified directly on a 30 g C18 RediSep Gold Aq column via ISCO system (gradient elution: 10-65% MeCN in water, 0.05% acetic acid in both, over 20 min). The product-containing fractions were combined, partially concentrated in vacuo, frozen on dry ice, and lyophilized to give an off-white solid (8 mg, 46%). MS (ESI, pos.): calc'd for $C_{50}H_{69}ClN_8O_{13}$, 1024.5; found 1007.2 (M–H$_2$O), 1026.2 (M+H).

Step H: Maytansin-N-methyl-L-alanine-N-4-amino-benzamide-Cit-Val-capryl-bis(BrMe)acrylamide (100)

The title compound was prepared from the product of the preceding step (99, 8 mg, 0.008 mmol) and 6-(3-Bromo-2-bromomethyl-propionylamino)-hexanoic acid (96), using the method from Step A of Example 5, to give a white solid (8 mg, 75%). MS (ESI, pos.): calc'd for $C_{60}H_{84}Br_2ClN_9O_{15}$, 1363.4; found 1363.1 (M+H). $^1$H-NMR (500 MHz, CDCl$_3$): δ 9.32 (s, 1H), 8.72 (m, 1H), 8.37 (m, 1H), 7.65 (m, 2H), 7.45 (m, 1H), 7.34 (m, 1H), 7.32 (m, 2H), 7.22-7.18 (m, 2H), 6.89-6.84 (m, 2H), 6.70-6.60 (m, 2H), 6.44 (m, 1H), 6.32 (br s, 1H), 6.12 (s, 1H), 5.76-5.71 (m, 1H), 5.65 (s, 1H), 5.37-5.29 (m, 3H), 4.86-4.70 (m, 3H), 4.52 (br s, 1H), 4.31-4.25 (m, 1H), 4.12 (m, 1H), 3.99 (s, 3H), 3.65-3.58 (m, 1H), 3.51 (m, 1H), 3.34-3.21 (m, 8H), 3.13-3.02 (m, 5H), 2.88 (s, 3H), 2.68 (m, 1H), 2.28-2.17 (m, 3H), 2.11-1.83 (m, 2H), 1.80-1.70 (m, 2H), 1.66 (s, 3H), 1.57-1.49 (m, 4H), 1.47-1.43 (m, 3H), 1.30-1.26 (m, 7H), 1.00-0.91 (m, 6H), 0.85 (s, 3H).

Example 37

Conjugate Preparation and Characterization

Five antibodies were conjugated to the linker-payload compounds of the disclosure using the procedures below. The four targeting antibodies used in these experiments were: (1) a PSMA antibody having the heavy and light chain variable domains of clone AB-PG1-XG1-006 as set forth in WO2007002222A2, (2) anti-MUC16 antibody having variable regions derived from clone 3A5 from WO2007001851, and (3) two PRLR antibodies having the heavy and light chain variable domains of clone H1H6765P and H1H6958N2 as set forth in WO2015026907A1. All the monoclonal antibodies were expressed in CHO cells and purified by Protein A. A non-binding isotype control derived from an antigen having no relation to oncology was also used.

Example 38

Conjugation Method for Compound 10

Conjugation Method for Maleimides

The antibody (1-10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative 10, 15, 20, 25, 60, and 78 (1.2 equivalents/SH group) in DMSO (10 mg/ml) was added to the reduced antibody and the mixture adjusted to pH 7.0 with 1M HEPES (pH 7.4). After 1 h the reaction was quenched with excess N-ethyl maleimide. The conjugates were purified by size exclusion chromatography and sterile filtered. Protein concentrations and payload to antibody ratios were determined by UV spectral analysis. Size exclusion HPLC established that all conjugates used were >95% monomeric, and RP-HPLC established that there was <0.5% unconjugated linker payload. All conjugated antibodies were analyzed by UV for linker payload loading values according to Hamblett et al, Cancer Res 2004 10 7063. Yields and payload to antibody ratios are reported in Table 1.

Example 39

Conjugation Method for Active Esters

The antibodies (1-10 mg/ml) in 50 mM HEPES, 150 mM NaCl, pH 8.0, and 15% (v/v) DMA were conjugated with a 6 fold excess of compound 77 for 1-2 hours at ambient temperature. The conjugates were purified by size exclusion chromatography and sterile filtered. Protein and linker payload concentrations were determined by UV spectral analysis. Size-exclusion HPLC established that all conjugates used were >95% monomeric, and RP-HPLC established that there was <0.5% unconjugated linker payload. Yields are reported in Table 1 based on protein. All conjugated antibodies were analyzed by UV for linker payload loading values according to Hamblett et al, Cancer Res 2004 10 7063. Yields and payload to antibody ratios are reported in Table 1.

TABLE 1

|  | ε252 nm (cm$^{-1}$ M$^{-1}$) | ε280 nm (cm$^{-1}$ M$^{-1}$) |
|---|---|---|
| Compound |  |  |
| 10 | 45990 | 20600 |
| 15 | 68900 | 26500 |
| 20 | 65000 | 33000 |
| 25 | 64550 | 25550 |
| 60 | 32000 | 8600 |
| 63 | 53500 | 22300 |
| 77 | 44500 | 17166 |
| 78 | 47600 | 15600 |
| Antibody |  |  |
| PSMA | 77652 | 224320 |
| MUC16 | 85888 | 247360 |
| PRLR | 80673 | 220420 |
| PRLR-Q | 82000 | 195400 |

TABLE 1-continued

| Isotype Control | 75113 | 218360 |
|---|---|---|
| Isotype Control-Q | 68741 | 203757 |

| Antibody Conjugate | Payload:Antibody (UV) | Yield % |
|---|---|---|
| PSMA-10 | 2.4 | 70 |
| MUC16-10 | 1.5 | 50 |
| Isotype Control-10 | 2.4 | 75 |
| PSMA-25 | 2.5 | 65 |
| MUC16-25 | 2.0 | 40 |
| Isotype Control-25 | 2.5 | 65 |
| PSMA-60 | 3.9 | 60 |
| MUC16-60 | 1.5 | 40 |
| PRLR-60 | 3.8 | 70 |
| Isotype Control-60 | 3.1 | 70 |
| PRLR-Q-63 | 2.9 (3.3 ESI-MS) | 60 |
| Isotype Control-Q-63 | 3.2 (3.1 ESI-MS) | 60 |
| PSMA-77 | 4.0 | 55 |
| MUC16-77 | 2.8 | 40 |
| PRLR-77 | 4.3 | 70 |
| Isotype Control-77 | 3.9 | 65 |
| PSMA-78 | NA | NA |
| MUC16-78 | 2.0 | 40 |
| PRLR-78 | 2.8 | 50 |
| Isotype Control-78 | 4.0 | 70 |

Example 40

In Vitro Linker-Payload Cell-Free Enzymatic Assays

Cathepsin B Incubation

In vitro cell-free enzymatic assay procedure was adopted from Dubowchik, et al. Bioconjugate Chem. 2002 13 855. The linker payload 10 was set at 100 μg/mL final in 25 mM sodium acetate buffer, 1 mM EDTA, pH 5.0 and pre-incubated at 37° C. Cathepsin B (Sigma #C8571) was activated at room temperature for 15 minutes with 1 equivalent of 30 mM DTT, 15 mM EDTA to 2 equivalents of cathepsin B stock. The activated cathepsin B solution was added to the substrate solutions at a 1:20 molar ratio (purified $H_2O$, instead of activated cathepsin B was added for the control sample.) Samples were incubated at 37° C. overnight and the resulting samples are detected by LC-MS through Q1 Scan.

LC-MS Detection

Samples are centrifuged at 12,000 g for 5 min. Supernatant was recovered and analyzed by liquid chromatography-mass spectrometry (Thermo Quantiva) by combined infusion of 0.3 ml/min of 30:70 mobile phase B:A (Mobile Phase A: 0.1% FA in $H_2O$; Mobile Phase B: 0.1% FA in Acetonitrile) at 20 l/min from supernatant. MS1 is set at an appropriate range for detection of molecular ion of either linker payload or payload. The supernatant contained the predicted payload, p-amino-benzamide maytansinoid (27), with a mass of 791.27 M+Na (calc'd monoisotopic mass for $C_{39}H_{49}ClN_4O_{10}$, 768.31) and the control samples without cathepsin B contained 10 with a mass of 1240.50 M+Na (calc'd monoisotopic mass for $C_{60}H_{80}ClN_9O_{16}$, 1217.54). No predicted payload molecular ion was detected in the control samples.

The results of this Example are significant in part because cathepsin B proteolysis of 10 should only occur after internalization of the ADC in the cell where the enzyme exists. Off target effects should be reduced since the antibody delivers the cytotoxic payload directly to targeted cells.

Example 41

In Vitro Cytotoxicity Assays

In this Example, the ability of various antibody-drug conjugates or their associated payloads to kill antigen-expressing tumor cells in vitro was assessed.

Ovcar3 (Muc16+) or C4-2 (PSMA+) cells were seeded in 96 well plates at 3000 (C42) cells per well in complete growth media and grown overnight. For cell viability curves, serially diluted conjugates or payloads were added to the cells at final concentrations ranging from 300 nM to 5 pM and incubated for 3 days. To measure viability, cells were incubated with CCK8 (Dojindo) for the final 1-3 hours and the absorbance at 450 nm ($OD_{450}$) was determined on a Victor (Perkin Elmer). Background $OD_{450}$ levels determined from digitonin (40 nM) treated cells were subtracted from all wells and viability is expressed as a percentage of the untreated controls. $IC_{50}$ values were determined from a four-parameter logistic equation over a 10-point response curve (GraphPad Prism). All conjugate curves and $IC_{50}$ values are corrected for payload equivalents.

In C4-2 cells (prostate cancer line), natively expressing PSMA at 271 fold above isotype control binding, the maytansinoid conjugates PSMA-10 and PSMA-25 possessed $IC_{50}$ values of 0.11 and 0.59 nM, respectively (FIGS. 2-5). The payloads 27 and 33 alone had $IC_{50}$ values of 0.20 and 0.55 nM, respectively. The naked PSMA antibody and isotype control were devoid of any anti-proliferation activity at the concentrations assayed.

In Ovcar-3 cells (ovarian cancer line), natively expressing MUC16 at 320 fold above isotype control binding, the maytansinoid conjugates MUC16-10 and MUC16-25 possessed $IC_{50}$ value of 0.74 and 0.63 nM, respectively (FIGS. 2-5). The payloads 27 and 33 alone had $IC_{50}$ values of 0.06 and 0.11 nM, respectively. The naked MUC16 antibody and isotype control were devoid of any anti-proliferation activity at the concentrations assayed.

Table 2 lists the anti-proliferating ability of the payloads only in both Ovcar3 (Muc16+) or C4-2 (PSMA+) cells. All compounds possess sub-nanomolar activities with compounds 35 and 37 at or near single digit picomolar $IC_{50}s$.

TABLE 2

| | C4-2 | | Ovcar3 | |
|---|---|---|---|---|
| Compound # | IC50 (nM) | % kill | IC50 (nM) | % kill |
| 29 | 0.27 | 83 | 0.13 | 93 |
| 33 | 0.45 | 86 | 0.20 | 93 |
| 31 | 0.10 | 82 | 0.04 | 93 |
| 27 | 0.20 | 84 | 0.09 | 92 |
| 35 | 0.004 | 84 | <0.01 | 93 |
| 37 | 0.01 | 86 | <0.01 | 94 |

Example 42

Antibody Expression

Assay/Experiment Type. Cloning, Expression and Purification of Antibodies Modified to Contain Site-Specific Conjugation Motifs This Example provides the generation of antibodies with amino acids sequences that allow site-specific conjugation by transglutaminase reactions.

To generate antibodies, mutagenesis was performed on a plasmid encoding the CH1, CH2, and CH3 domains of human IgG1 (amino acids 1 through 330 of UniprotKB accession no. P01857) to generate an N to Q mutation at position 180 using a QuikChange Lightning Multi Site-Directed Mutagenesis Kit (Agilent, #210516). Two antibody variable region heavy (VH) fragments, one encoding the VH of an anti-human PRLR antibody, H1H6958N2 (international patent application WO 2015026907 A1) and another encoding the VH of the isotype control antibody recognizing an exogenous antigen, were selected. Primers were designed (idtdna.com) to amplify the VH regions of these two antibodies using Kapa HiFi DNA polymerase (Kapa Biosciences; #KK2102). While PCR amplification was proceeding, a plasmid containing the human IgG1 N180Q mutation was digested with LguI enzyme (Fermentas, #FD1934) at 37° C. for 30 minutes. Once the amplification was complete, the digested human IgG1 plasmid and both PCR products were run out on a 1% agarose gel containing SYBR Safe stain (Life Technologies, #S33102). Bands of the appropriate size were identified and excised from the gel using a clean razor blade. All excised products were purified using a Gel Extraction kit (Qiagen, #28704). An In-Fusion cloning reaction (Clontech, #638911) was then performed using a ratio of 3:1 of digested human IgG1 vector to VH PCR product and then incubated for 15 minutes at 50° C. After incubation, each reaction was transformed into Mix and Go competent cells (Zymo, #T3007), incubated on ice for 5 minutes, and competent cells were plated on LB+Carbenicillin plates (Teknova, VWR, #101320-126), which were incubated overnight at 37° C.

The following day, single colonies were inoculated from the plate into LB broth containing 100 μg/mL Carbenicillin and grown overnight shaking in a table top incubator at 37° C. Cells were then pelleted by centrifugation and mini-prepped on a Hamilton Starlet robot using a PureLink HiPure Plasmid miniprep kit (Thermo Fisher, #K210003). Purified DNA was sequenced and results were analyzed using Sequencher software (GeneCodes). A clone from each ligation reaction was selected for re-transformation into Mix and Go competent cells, incubated on ice for 5 minutes and competent cells were plated on LB plates containing Carbenicillin, which were incubated overnight at 37° C.

The following day, a single colony was picked from each plate and grown in LB broth containing 100 μg/mL Carbenicillin for 3 to 4 hours. The sample was then diluted into LB broth containing 100 μg/ml Carbenicillin and transferred to a 37° C. shaking incubator to grow overnight. A maxiprep DNA extraction was then performed on both plasmids and the full DNA open reading frames were sequenced. Once the sequences were confirmed, the heavy chain DNA along with previously cloned affiliated light chain DNA was stably transfected into a CHO cell line to produce each antibody.

The H1H6958N2 (international patent application WO 2015026907 A1) containing the N180Q Fc mutation is referred to as PRLR-Q, and the isotype control antibody recognizing an exogenous antigen also containing the N180Q Fc mutation is referred to as ISOTYPE CONTROL-Q.

Example 43

Bacterial Transglutaminase Conjugation

Figure 42:
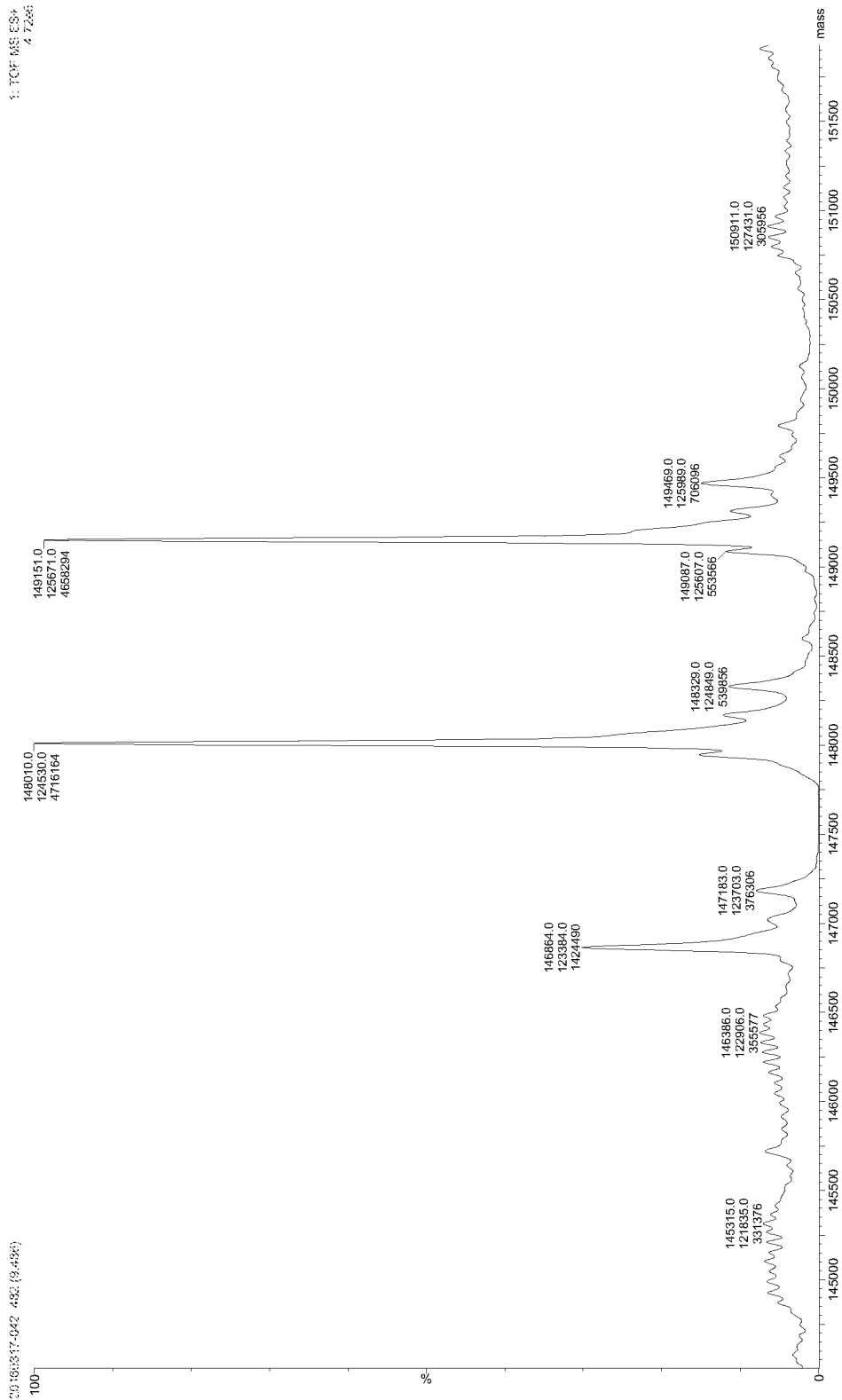
FIG. 42 depicts the deconvoluted mass spectroscopy (MS) spectrum of the antibody drug conjugate, PRLR-Q-63 conjugate from EXAMPLE 43.
Figure 43:
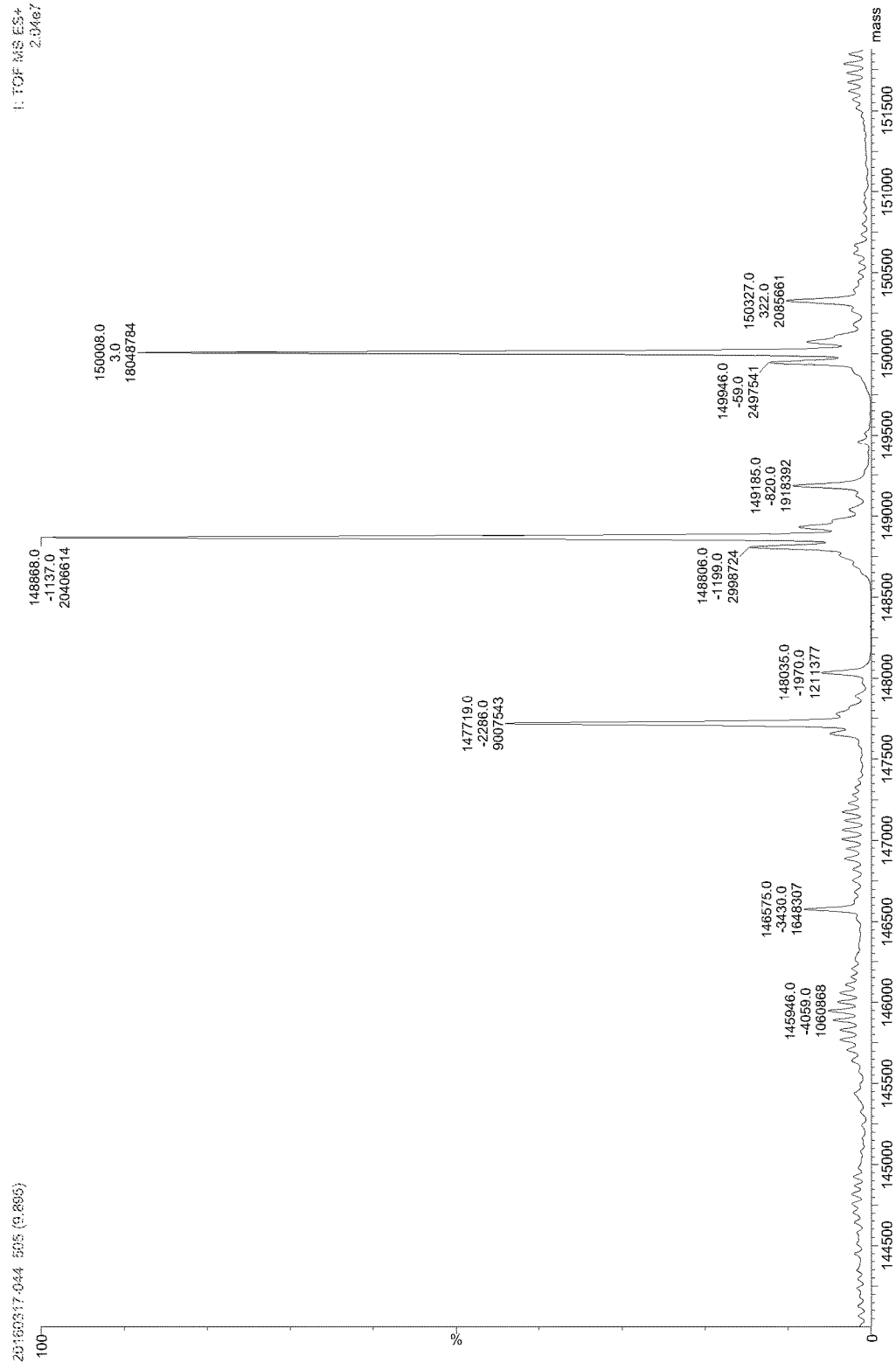
FIG. 43 depicts the deconvoluted MS spectrum of the Isotype Control-Q-63 conjugate from EXAMPLE 43.

PRLR-Q (MW 145438 Da) and Isotype Control-Q (MW 144602 Da) antibodies were conjugated at 1-10 mg/mL in PBS pH 7.4. Linker payload 63 was added in a 10 to 25-fold molar excess over antibody and the enzymatic reaction was initiated by addition of 1-5 units of bacterial transglutaminase (Zedira, T1001) per mg antibody and incubated with shaking at 37° C. for 4-16 hours. The conjugates were purified by size exclusion chromatography and sterile filtered. Protein and linker payload concentrations were determined by UV spectral analysis. Size-exclusion HPLC established that all conjugates used were >95% monomeric. Yields are reported in Table 1 based on protein. All conjugated antibodies were analyzed by UV for linker payload loading values according to Hamblett et al, Cancer Res 2004 10 7063. In addition, the conjugates were analyzed by ESI-MS for linker payload loadings using a Waters Synapt G2-Si QTOF mass spectrometry coupled with Acquity UPLC. The chromatographic separation was achieved on a C4 column (Waters protein BEH C4, 50 mm×1 mm, 1.7 μm) in a 25 minute gradient (minute:percentage of mobile phase B; 0:20%, 1:20%, 18:40%, 18.1:90, 20:95%, 20.8:95%, 20.9:20% 25:20%). The mobile phase A was 0.1% formic acid in water and mobile phase B was 0.1% formic acid in acetonitrile. The flow rate was set at 100 l/min. The detector TOF scan was set from m/z 700-5000 for 25 minutes with major parameters as listed (Capillary voltage 3.2 kV; Sampling Cone 150; Source Offset at 80; Source temperatures 120° C.; Desolvation temperature 500° C.; Trap collision Energy 30; Transfer Collision Energy Off, Gas controls OFF; Resolving Quadrupole: LM resolution at 4.7). The combined spectra were deconvoluted with MaxEnt function within MassLynx software. The resulting molecular ions which when weighted according to intensities corresponded to the loadings listed in Table 3. The actual mass spec spectra are listed in FIGS. 42 and 43.

TABLE 3

The summary of intensity-weighted average linker-payload loadings in PRLR-Q and Isotype Control-Q conjugates for compound 63.

| PRLR-Q-63 | | | | Isotype Control-Q-63 | | | |
|---|---|---|---|---|---|---|---|
| Molecular Ion MW (Da) | Corresponding linker payload loading | Relative intensity | Intensity weighted average loading | Molecular Ion MW (DA) | Corresponding linker payload loading | Relative intensity | Intensity weighted average loading |
| | | | 3.3 | 146575 | 1 | 1648307 | 3.1 |
| 146864 | 2 | 1424490 | | 147719 | 2 | 9007543 | |
| 148010 | 3 | 4716164 | | 148868 | 3 | 20406614 | |
| 149151 | 4 | 4658294 | | 150008 | 4 | 18048784 | |

Example 44

Equilibrium dissociation constants ($K_D$ values) for human PRLR binding to purified anti-PRLR antibodies that were either unmodified H1H6958N2, PRLR-Q, and PRLR-Q-63 were determined using a real-time surface plasmon resonance biosensor using a Biacore 3000 instrument. The Biacore sensor surface was first derivatized by amine coupling with a monoclonal mouse anti-human Fc antibody (GE, #BR-1008-39) to capture anti-PRLR monoclonal antibodies. All binding studies were performed in 0.01M HEPES pH 7.4, 0.15M NaCl, 3 mM EDTA, and 0.05% v/v Surfactant Tween-20 (HBS-ET running buffer) at 25° C. and 37° C. Different concentrations of human PRLR extracellular domain expressed with a C-terminal myc-myc-hexa-histidine tag (hPRLR-MMH; SEQ ID NO: 401 as described in patent application WO 2015026907 A1), in HBS-ET running buffer (ranging from 40 nM to 3.33 nM) were injected over the anti-PRLR antibody captured surface for 4 minutes at a flow rate of 50 μL/minute and their dissociation in HBS-ET running buffer was monitored for 8 minutes. Kinetic association rate constant ($k_a$) and dissociation rate constant ($k_d$) were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ka}, \text{ and } t1/2(\min) = \frac{\ln(2)}{60 * kd}$$

Binding kinetic parameters for hPRLR-MMH binding to different anti-PRLR antibodies at 25° C. are shown in Table 4. At 25° C., hPRLR-MMH bound to the parental antibody H1H6958N2 with a $K_D$ value of 1.09 nM. Human PRLR-MMH bound to the PRLR-Q with a $K_D$ value of 850 pM and to PRLR-Q-63 with a $K_D$ value of 1.50 nM.

TABLE 4

Binding Kinetics parameters of anti-PRLR antibodies binding to hPRLR-MMH at 25° C.

| Antibody | mAb Capture Level (RU) | 100 nM hPRLR-MMH Bound (RU) | $k_a$ (1/Ms) | $k_d$ (1/s) | $K_D$ (M) | t½ (min) |
|---|---|---|---|---|---|---|
| H1H6958N2 | 141.3 ± 0.8 | 38 | 4.17E+05 | 4.54E−04 | 1.09E−09 | 25 |
| PRLR-Q | 148.5 ± 0.6 | 46 | 4.48E+05 | 3.79E−04 | 8.50E−10 | 30 |
| PRLR-Q-63 | 153.7 ± 0.7 | 45 | 3.80E+05 | 5.69E−04 | 1.50E−09 | 20 |

Example 45

The present example provides cytotoxicity assays for conjugates provided herein. To evaluate the ability of anti-PRLR antibodies conjugated with 63, 60, 77, and 78 to kill a PRLR expressing cell line, an in vitro cytotoxicity assay using a T47D ductal carcinoma line (ATCC, #HTB-133), which was previously determined to express >27,000 copies of human PRLR at its cell surface, was utilized.

For the assay, T47D cells were seeded onto white 96 well plates at 2,000 cells/well in media containing DMEM supplemented with 10% FBS, NEAA, and pencillin/streptomycinin (complete media). They were grown overnight at 37° C. in 5% $CO_2$. To determine cell viability curves, the following day antibody drug conjugates, unconjugated antibodies, or free payloads were added to the cells at final serial dilutions ranging from 100 nM to 0.01 nM in complete medium and then incubated for an additional 5 days. Luciferase activity was detected after the addition of Cell-Titer-Glo™ reagent (Promega, G7571) to each well, which contains reagents to lyse the remaining viable cells to release their ATP, ATPase inhibitors to prevent degradation of the ATP, as well as luciferin and luciferase to catalyse the luminescent reaction. Viable cells prior to addition of Cell-Titer-Glo will be the only source of ATP since the dead cells in culture will not synthesis ATP and any of their released ATP will be destroyed via endogenous ATPases. Relative light units (RLUs) were measured on a Victor luminometer (PerkinElmer) and the results were determined using a four-parameter logistic equation over a 10-point response curve (GraphPad Prism). All measured values and calculated $IC_{50}$ values were corrected for payload equivalents. All $IC_{50}$ values are expressed in nM concentration and percent kill is reported for the highest concentration tested. The results are summarized in FIGS. 45 through 48.

Figure 44:
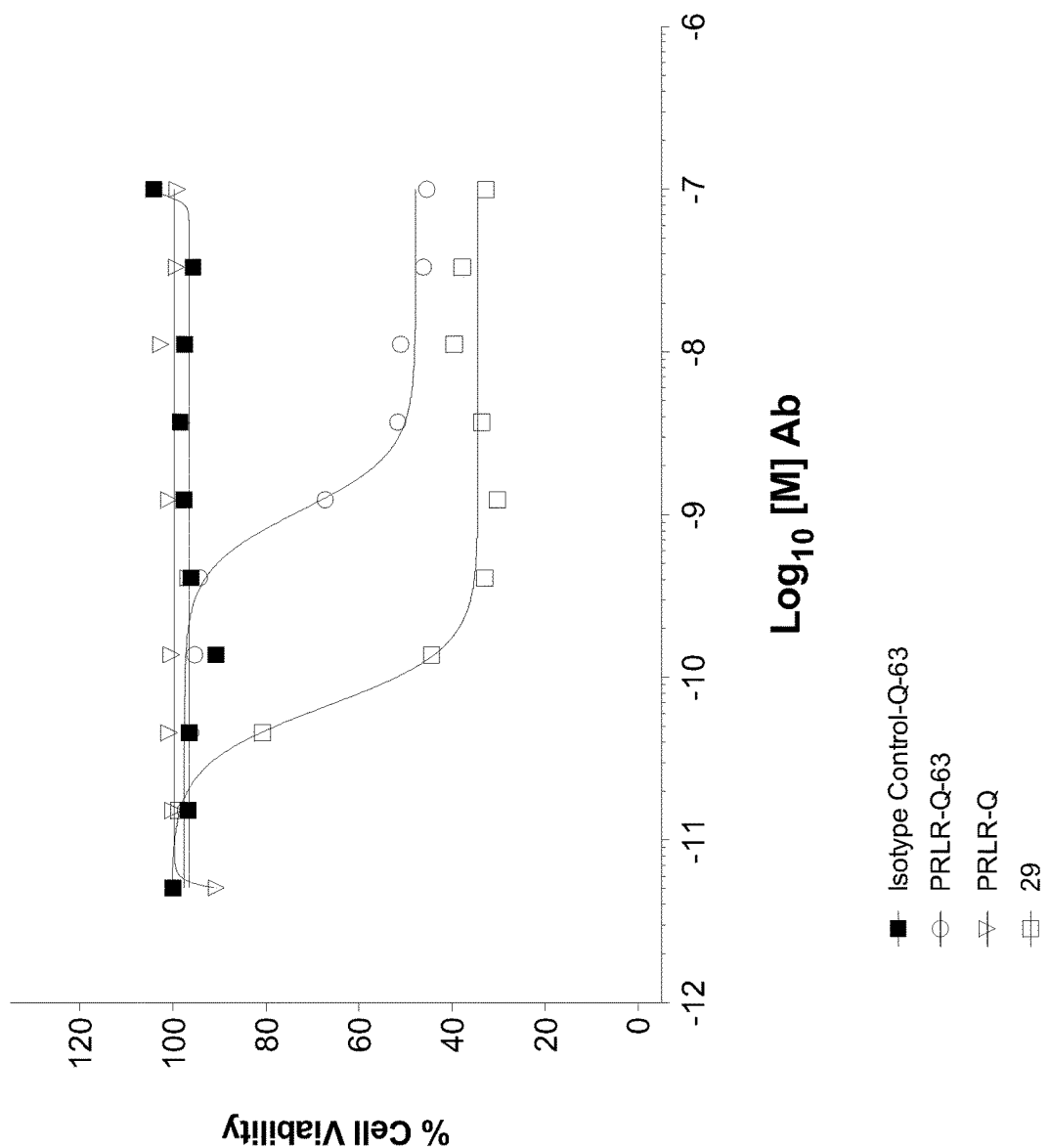
FIG. 44 depicts the plot of % Cell Viability vs. $\text{Log}_{10}$ [M] of certain compounds tested in EXAMPLE 45.

As shown in FIG. 44, the anti-PRLR antibody site-specifically conjugated with 63 (PRLR-Q-63) demonstrated cytotoxicity of T47D cells with an $IC_{50}$ of 1.1 nM and a maximum percent killing of 55%. The free payload, 29, demonstrated cytotoxicity of T47D cells with an $IC_{50}$ of 0.07 nM and a maximum percent killing of 67%. An isotype control antibody conjugated with 63 (ISOTYPE CONTROL-Q-63) did not demonstrate any killing of T47D cells, and the unconjugated anti-PRLR antibody (PRLR-Q) did not demonstrate any killing of T47D cells.

Figure 45:
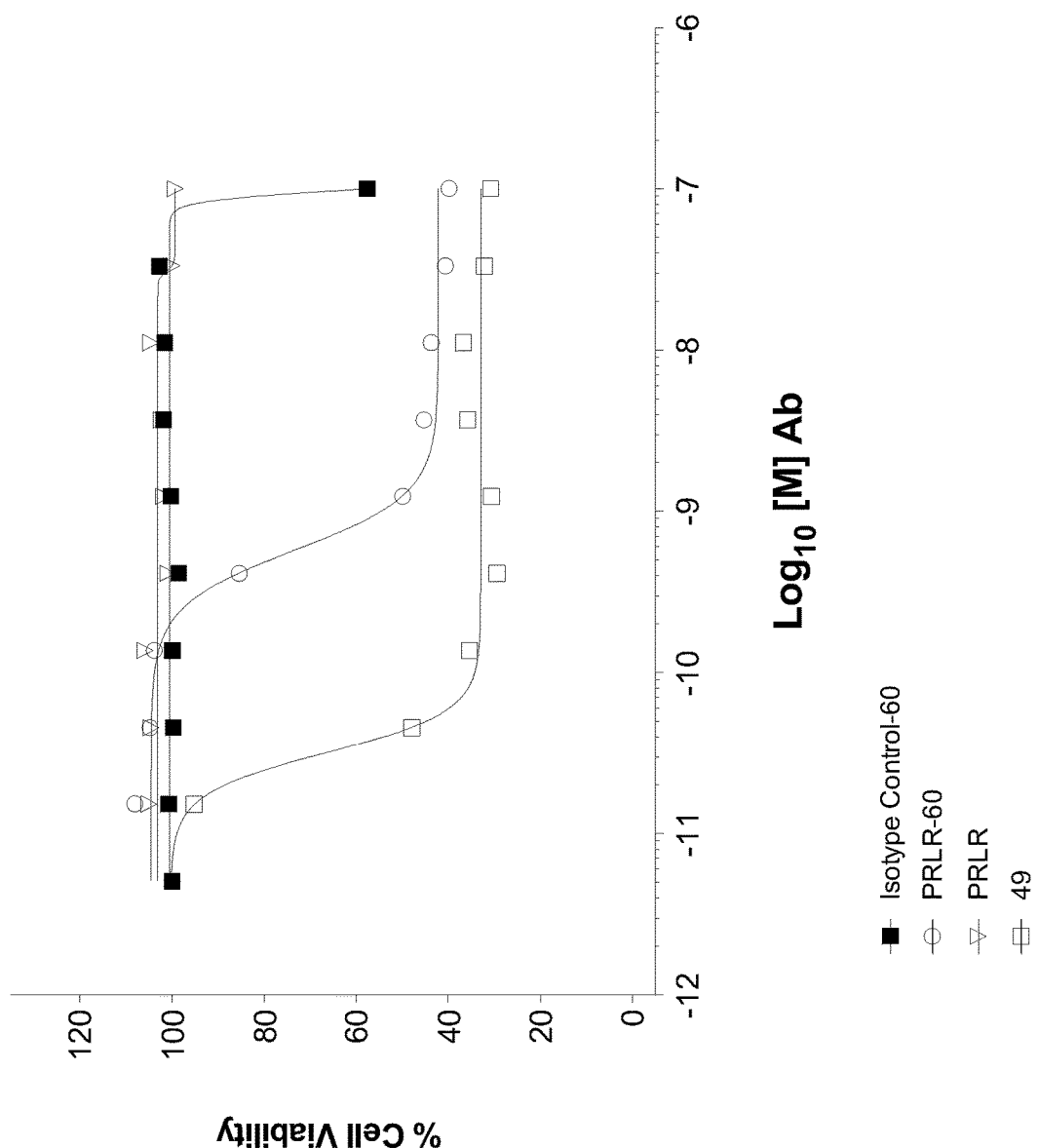
FIG. 45 depicts the plot of % Cell Viability vs. $\text{Log}_{10}$ [M] of certain compounds tested in EXAMPLE 45.

As shown in FIG. 45, the anti-PRLR antibody conjugated with 60 (PRLR-60) demonstrated cytotoxicity of T47D cells with an $IC_{50}$ of 0.6 nM and a maximum percent killing of 60%. The free payload, 49, demonstrated cytotoxicity of T47D cells with an $IC_{50}$ of 0.03 nM and a maximum percent killing of 69%. An isotype control antibody conjugated with 60 (ISOTYPE CONTROL-60) did not demonstrate any killing of T47D cells, and the unconjugated anti-PRLR antibody (PRLR) did not demonstrate any killing of T47D cells.

Figure 46:
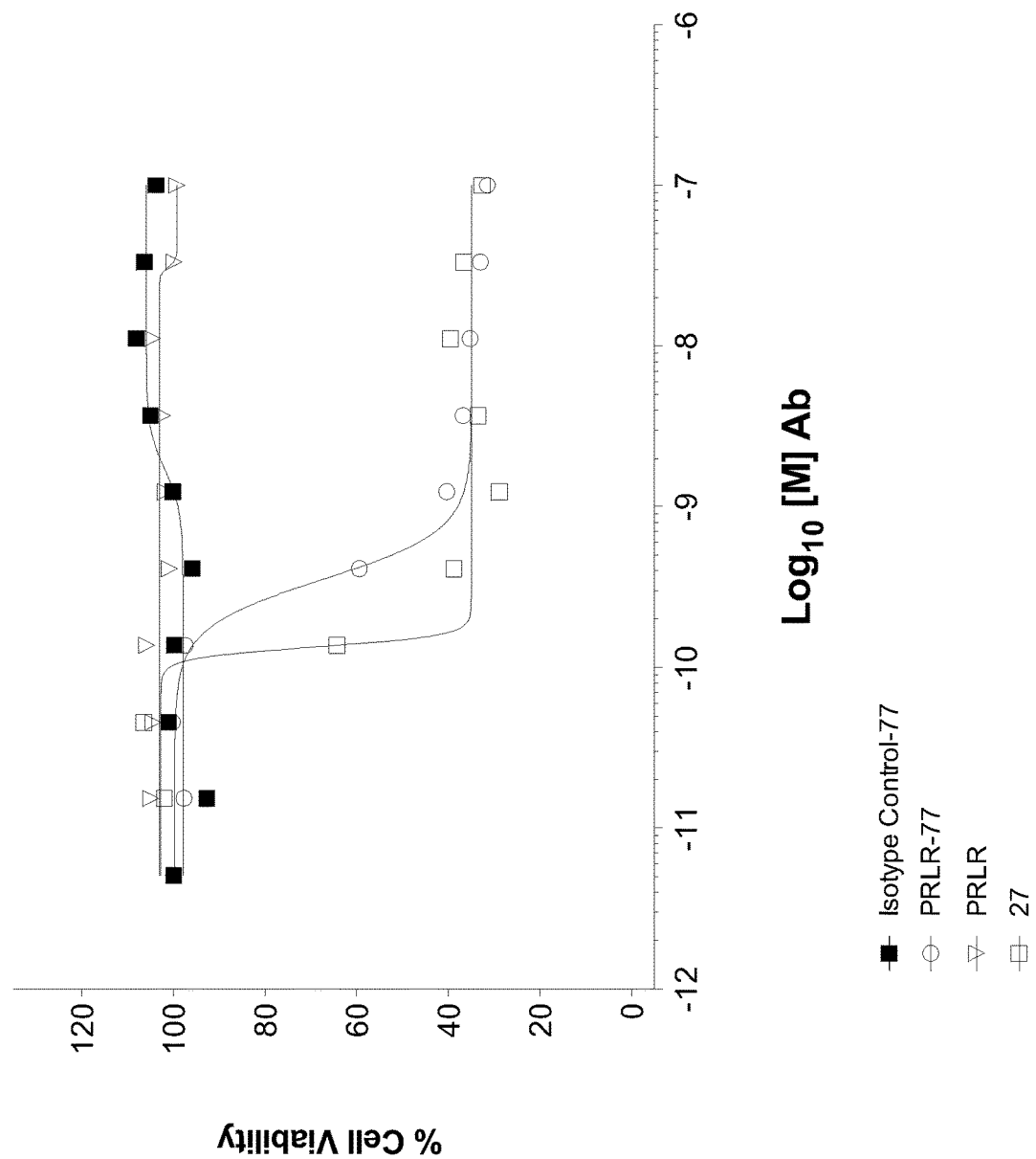
FIG. 46 depicts the plot of % Cell Viability vs. Log 10 [M] of certain compounds tested in EXAMPLE 45.

As shown in FIG. 46, the anti-PRLR antibody conjugated with 77 (PRLR-77) demonstrated cytotoxicity of T47D cells with an $IC_{50}$ of 0.4 nM and a maximum percent killing of 69%. The free payload, 27, demonstrated cytotoxicity of T47D cells with an $IC_{50}$ of 0.1 nM and a maximum percent killing of 67%. An isotype control antibody conjugated with 77 (ISOTYPE CONTROL-77) did not demonstrate any killing of T47D cells, and the unconjugated anti-PRLR antibody (PRLR) did not demonstrate any killing of T47D cells.

Figure 47:
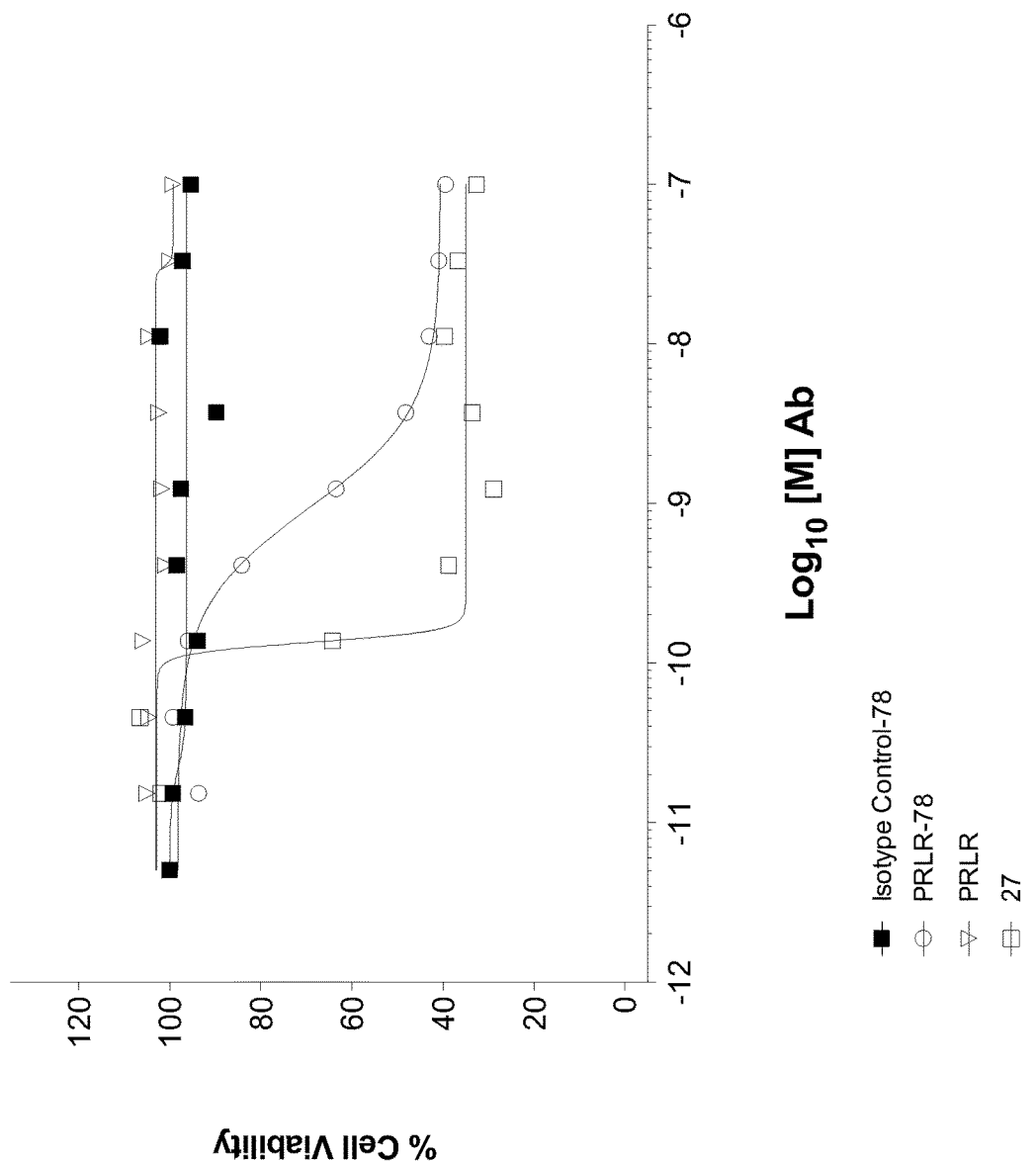
FIG. 47 depicts the plot of % Cell Viability vs. Log 10 [M] of certain compounds tested in EXAMPLE 45.

As shown in FIG. 47, the anti-PRLR antibody conjugated with 78 (PRLR-78) demonstrated cytotoxicity of T47D cells with an $IC_{50}$ of 0.9 nM and a maximum percent killing of 61%. The free payload, 27, demonstrated cytotoxicity of T47D cells with an $IC_{50}$ of 0.1 nM and a maximum percent killing of 67%. An isotype control antibody conjugated with 78 (ISOTYPE CONTROL-78) did not demonstrate any killing of T47D cells, and the unconjugated anti-PRLR antibody (PRLR) did not demonstrate any killing of T47D cells.

Table 5 lists the anti-proliferating ability of the payloads only in Ovcar3 (Muc16+), C4-2 (PSMA+), and T47D (PRLR+) cells.

TABLE 5

| Compound # | C4-2 IC50 (nM) | C4-2 % kill | Ovcar3 IC50 (nM) | Ovcar3 % kill | T47D IC50 (nM) | T47D % kill |
|---|---|---|---|---|---|---|
| 29 | 0.27 | 83 | 0.13 | 93 | 0.07 | 67 |
| 33 | 0.45 | 86 | 0.20 | 93 | | |
| 31 | 0.10 | 82 | 0.04 | 93 | | |
| 27 | 0.20 | 84 | 0.09 | 92 | | |
| 35 | 0.004 | 84 | <0.01 | 93 | | |
| 37 | 0.01 | 86 | <0.01 | 94 | | |
| 39 | | | 0.02 | 70 | | |
| 41 | | | 0.03 | 72 | | |
| 43 | | | 0.01 | 71 | | |
| 45 | | | 3.73 | 72 | | |
| 47 | | | 0.01 | 72 | | |
| 49 | | | 0.06 | 70 | | |
| 51 | | | 0.49 | 72 | | |
| 53 | | | 0.2 | 72 | | |
| 55 | | | 0.18 | 75 | | |
| 65 | | | 1.13 | 72 | | |
| 67 | | | 0.19 | 71 | | |
| 69 | | | 0.39 | 73 | | |
| 71 | | | 0.73 | 68 | | |
| 73 | | | 0.57 | 73 | | |
| 75 | | | | | | |
| 86 | 0.73 | 90 | | | | |
| 84 | 0.07 | 88 | | | | |
| 90 | >100 | 86 | | | | |
| 80 | 1.3 | 91 | | | | |
| 88 | 0.05 | 89 | | | | |
| 82 | 19.95 | 93 | | | | |

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A compound of Formula (I):

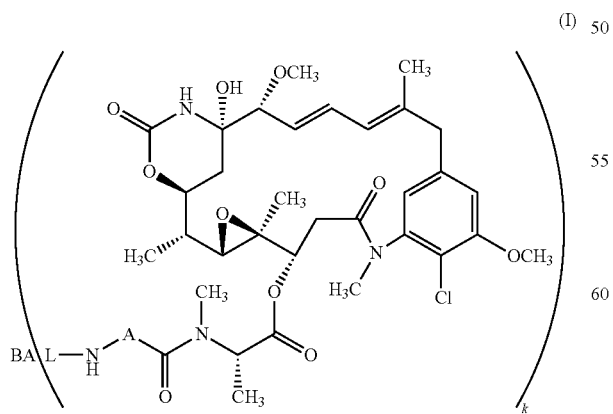

or a pharmaceutically acceptable salt thereof, wherein:

A is

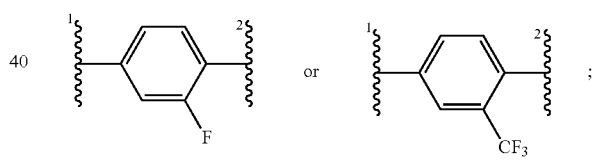

;

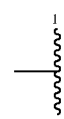

is the bond linking A to the nitrogen, and

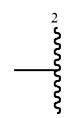

is the bond linking A to the carbonyl;

BA is an antibody or antigen binding fragment thereof;

L is

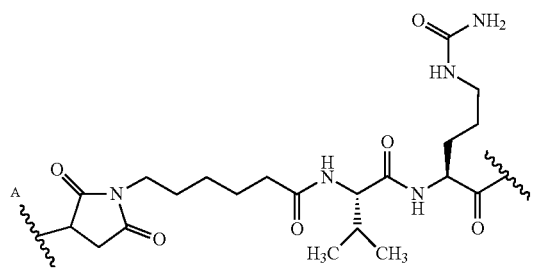   or

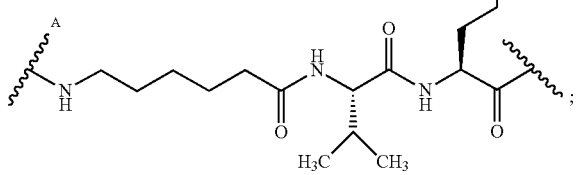 ;

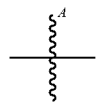

is a bond to the antibody or antigen binding fragment thereof; and k is an integer from 1 to 6.

2. The compound of claim 1, wherein A is

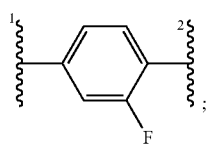 ;

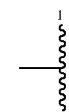

is the bond linking A to the nitrogen, and

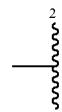

is the bond linking A to the carbonyl.

3. The compound of claim 1, wherein A is

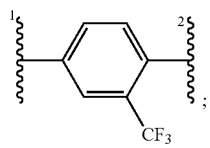 ;

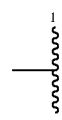

is the bond linking A to the nitrogen, and

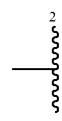

is the bond linking A to the carbonyl.

4. A pharmaceutical composition comprising the compound of claim 1 and a pharmaceutically acceptable diluent, excipient, or carrier.

5. The compound of claim 1, wherein the compound is

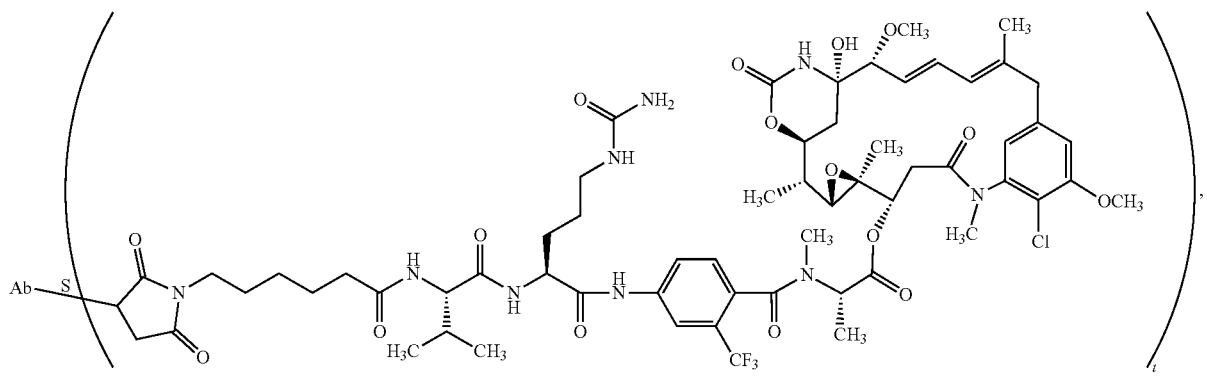

wherein
Ab is an antibody or antigen binding fragment thereof; and
S is a bond to a cysteine on said antibody or antigen binding fragment thereof.
6. The compound of claim 1, wherein the compound is
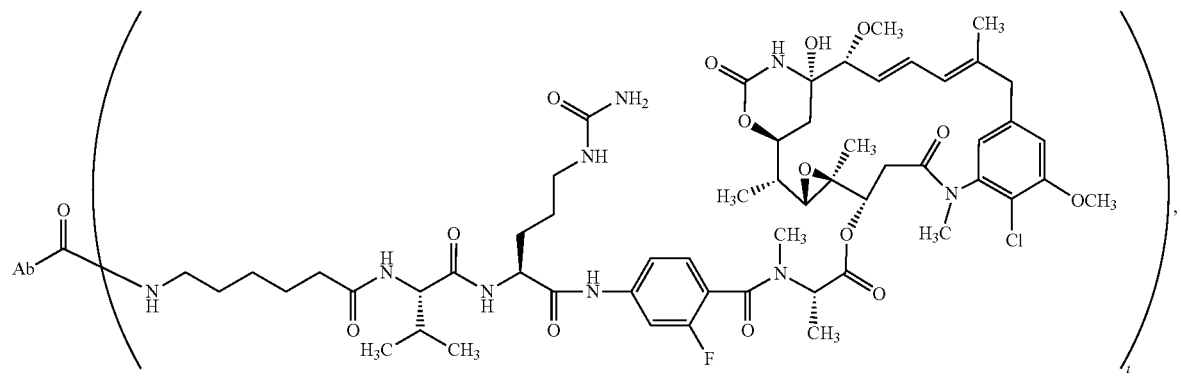
and Ab is an antibody or antigen binding fragment thereof.
7. The compound of claim 1, wherein k is an integer from 1 to 4.
8. The compound of claim 1, wherein k is an integer from 1 to 3.
* * * * *